(12) United States Patent
Coghlan et al.

(10) Patent No.: US 6,506,766 B1
(45) Date of Patent: Jan. 14, 2003

(54) GLUCOCORTIOCOID-SELECTIVE ANTINFLAMMATORY AGENTS

(75) Inventors: Michael J. Coghlan, Grayslake, IL (US); James P. Edwards, San Diego, CA (US); Steven W. Elmore, Gurnee, IL (US); Todd K. Jones, Solana Beach, CA (US); Michael E. Kort, Lake Bluff, IL (US); Philip R. Kym, Grayslake, IL (US); Jimmie L. Moore, Redwood City, CA (US); John K. Pratt, Kenosha, WI (US); Alan X. Wang, Guilford, CT (US)

(73) Assignees: Abbott Laboratories, Abbott Park, IL (US); Ligand Pharmaceuticals Incorporated, San Diego, CA (US)

( * ) Notice: Subject to any disclaimer, the term of this patent is extended or adjusted under 35 U.S.C. 154(b) by 0 days.

(21) Appl. No.: 09/610,638

(22) Filed: Jul. 5, 2000

Related U.S. Application Data

(63) Continuation-in-part of application No. 09/247,831, filed on Feb. 10, 1999, now abandoned
(60) Provisional application No. 60/074,666, filed on Feb. 13, 1998.

(51) Int. Cl.[7] .................. A61K 31/4741; C07D 491/02
(52) U.S. Cl. .......................................... 514/285; 546/62
(58) Field of Search ............................. 514/285; 546/62

(56) References Cited

U.S. PATENT DOCUMENTS

| | | |
|---|---|---|
| 3,719,667 A | 3/1973 | Gutowski et al. |
| 3,840,556 A | 10/1974 | Kukolja et al. |
| 5,688,808 A | 11/1997 | Jones et al. |
| 5,688,810 A | 11/1997 | Jones et al. |
| 5,693,133 A | 12/1997 | Largent et al. |
| 5,693,646 A | 12/1997 | Jones et al. .................. 514/285 |
| 5,693,647 A | 12/1997 | Jones et al. .................. 514/285 |
| 5,696,127 A | 12/1997 | Jones et al. .................. 514/285 |
| 5,696,130 A | 12/1997 | Jones et al. |

FOREIGN PATENT DOCUMENTS

| | | | |
|---|---|---|---|
| WO | WO-96/19458 | 6/1996 | ......... C07D/215/06 |
| WO | 9619458 | 6/1996 | |
| WO | WO-99/41256 | 8/1999 | ......... C07D/491/04 |

OTHER PUBLICATIONS

Berg, S.M., et al., "Review Artice—Pharmaceutical Salts", *Journal of Pharmaceutical Sciences*, 1977, 66:1–19.

Edwards, J.P. et al., "5–Aryl–1,2–dihydro–5H–chromeno [3,4–f]quinolines as Potent, Orally Active, Nonsteroidal Progesterone Receptor Angonists: The Effect of D–Ring Substituents," *J. Med. Chem.*, 41(1998) 303–310.

T. Erdos, et al., "A rapid essay for binding estradiol to uterine receptor(s)", *Analytical Biochemistry*, 37(1970) 244–252.

*Primary Examiner*—Charanjit S. Aulakh
(74) *Attorney, Agent, or Firm*—Schwegman, Lundberg, Woessner & Kluth, P.A.

(57) ABSTRACT

Compounds having Formula I

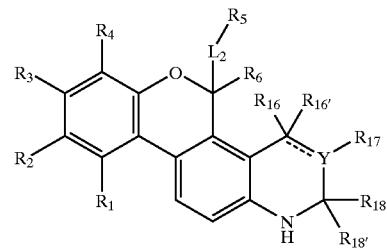

are useful for partially or fully antagonizing, repressing, agonizing, or modulating the glucocorticoid receptor and treating immune, autoimmune and inflammatory diseases in a mammal. Also disclosed are pharmaceutical compositions comprising compounds of Formula I and methods of inhibiting immune or autoimmune diseases in a mammal.

35 Claims, No Drawings

GLUCOCORTIOCOID-SELECTIVE ANTINFLAMMATORY AGENTS

This application is a continuation-in-part of U.S. Ser. No. 09/247,831 filed Feb. 10, 1999, now abandoned which, in turn, is a continuation in part of copending U.S. Provisional Application Ser. No. 60/074,666, filed Feb. 13, 1998.

TECHNICAL FIELD

The present invention relates to glucocorticoid receptor-selective benzopyrano[3,4-f]quinolines that are useful for treating immune or autoimmune diseases, to pharmaceutical compositions comprising these compounds, and to methods of inhibiting inflammation, inflammatory disease, immune, and autoimmune diseases in a mammal.

BACKGROUND OF THE INVENTION

Intracellular receptors (IR's) are a class of structurally related proteins involved in the regulation of gene expression. The steroid hormone receptors are a subset of this superfamily whose natural ligands are typically comprised of endogenous steroids such as estradiol, progesterone, and cortisol. Man-made ligands to these receptors play an important role in human health and, of these receptors, the glucocorticoid receptor (GR) has an essential role in regulating human physiology and immune response. Steroids which interact with GR have been shown to be potent antiinflammatory agents. Despite this benefit, steroidal GR ligands are not selective. Side effects associated with chronic dosing are believed to be the result of cross-reactivity with other steroid receptors such as estrogen, progesterone, androgen, and mineralocorticoid receptors which have somewhat homologous ligand binding domains.

Selective GR modulators (e.g. repressors, agonists, partial agonists and antagonists) of the present disclosure can be used to influence the basic, life-sustaining systems of the body, including carbohydrate, protein and lipid metabolism, and the functions of the cardiovascular, kidney, central nervous, immune, skeletal muscle, and other organ and tissue systems, In this regard, prior art GR modulators have proven useful in the treatment of inflammation, tissue rejection, auto-immunity, various malignancies, such as leukemias and lymphomas, Cushing's syndrome, acute adrenal insufficiency, congenital adrenal hyperplasia, rheumatic fever, polyarteritis nodosa, granulomatous polyarteritis, inhibition of myeloid cell lines, immune proliferation/apoptosis, HPA axis suppression and regulation, hypercortisolemia, modulation of the Th1/Th2 cytokine balance, chronic kidney disease, stroke and spinal cord injury, hypercalcemia, hypergylcemia, acute adrenal insufficiency, chronic primary adrenal insufficiency, secondary adrenal insufficiency, congenital adrenal hyperplasia, cerebral edema, thrombocytopenia, and Little's syndrome.

GR modulators are especially useful in disease states involving systemic inflammation such as inflammatory bowel disease, systemic lupus erythematosus, polyartitis nodosa, Wegener's granulomatosis, giant cell arteritis, rheumatoid arthritis , osteoarthritis, hay fever, allergic rhinitis, urticaria, angioneurotic edema, chronic obstructive pulmonary disease, asthma, tendonitis, bursitis, Crohn's disease, ulcerative colitis, autoimmune chronic active hepatitis, organ transplantation, hepatitis, and cirrhosis. GR active compounds have also been used as immunostimulants and repressors, and as wound healing and tissue repair agents.

GR modulators have also found use in a variety of topical diseases such as inflammatory scalp alopecia, panniculitis, psoriasis, discoid lupus erythematosus, inflamed cysts, atopic dermatitis, pyoderma gangrenosum, pemphigus vulgaris, bullous pemphigoid, systemic lupus erythematosus, dermatomyositis, herpes gestationis, eosinophilic fasciitis, relapsing polychondritis, inflammatory vasculitis, sarcoidosis, Sweet's disease, type 1 reactive leprosy, capillary hemangiomas, contact dermatitis, atopic dermatitis, lichen planus, exfoliative dermatitus, erythema nodosum, acne, hirsutism, toxic epidermal necrolysis, erythema multiform, cutaneous T-cell lymphoma.

Selective antagonists of the glucocorticoid receptor have been unsuccessfully pursued for decades. These agents would potentially find application in several disease states associated with Human Immunodeficiency Virus (HIV), cell apoptosis, and cancer including, but not limited to, Kaposi's sarcoma, immune system activation and modulation, desensitization of inflammatory responses, IL-1 expression, anti-retroviral therapy, natural killer cell development, lymphocytic leukemia, and treatment of retinitis pigmentosa. Cogitive and behavioral processes are also susceptible to glucocorticoid therapy where antagonists would potentially be useful in the treatment of processes such as cognitive performance, memory and learning enhancement, depression, addiction, mood disorders, chronic fatigue syndrome, schizophrenia, stroke, sleep disorders, and anxiety.

Reference is made to U.S. Pat. No. 5,696,127 and U.S Pat. No. 5,693,646, the disclosures of which are hereinafter incorporated by reference into this specification. These references, while showing certain quinolines as useful for the modulation progesterone receptors, and even disclosing the use of the compounds therein for the purpose of modulation of glucocorticoid receptors, do not show the surprising selectivity exhibited by the compounds of the instant invention.

SUMMARY OF THE INVENTION

In one embodiment of the instant invention, therefore, are glucocorticoid-selective compounds represented by Formula I

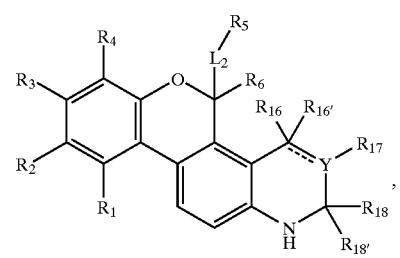

or a pharmaceutically acceptable salt or prodrug thereof, where the symbol === represents a single bond or a double bond, $R_1$ is $—L_1—R_A$ where $L_1$ is selected from
  (1) a covalent bond,
  (2) —O—,
  (3) —S(O)$_t$— where t is 0, 1, or 2,
  (4) —C(X)—, where X is O or S,
  (5) —N(R$_7$)— where $R_7$ is selected from
    (a) hydrogen,
    (b) aryl
    (c) cycloalkyl of three to twelve carbons,
    (d) alkanoyl where the alkyl part is one to twelve carbons, (e) alkoxycarbonyl where the alkyl part is one to twelve carbons,
(f) alkoxycarbonyl where the alkyl part is one to twelve carbons and is substituted by 1 or 2 aryl groups,
(g) alkyl of one to twelve carbons,
(h) alkyl of one to twelve carbons substituted with 1 or 2 substituents independently selected from
  (i) aryl and
  (ii) cycloalkyl of three to twelve carbons,
(i) alkenyl of three to twelve carbons,
  provided that a carbon of a carbon-carbon double bond is not attached directly to nitrogen,
(j) alkynyl of three to twelve carbons,
  provided that a carbon of a carbon-carbon triple bond is not attached directly to nitrogen,
(6) —N($R_8$)C(X)N($R_9$)— where X is O or S and $R_8$ and $R_9$ are independently selected from
  (a) hydrogen,
  (b) aryl,
  (c) cycloalkyl of three to twelve carbons,
  (d) alkyl of one to twelve carbons,
  (e) alkyl of one to twelve carbons substituted with 1 or 2 substituents independently selected from aryl or cycloalkyl of three to twelve carbons,
  (f) alkenyl of three to twelve carbons,
    provided that a carbon of a carbon-carbon double bond is not attached directly to nitrogen,
  (g) alkynyl of three to twelve carbons,
    provided that a carbon of a carbon-carbon triple bond is not attached directly to nitrogen,
(7) —X'C(X)— where X is previously defined and X' is O or S,
(8) —C(X)X'—,
(9) —X'C(X)X"— where X and X' are previously defined and X' is O or S,
  provided that when X is O, at least one of X' or X" is O,
(10) —N($R_8$)C(X)—,
(11) —C(X)N($R_8$)—,
(12) —N($R_8$)C(X)X'—,
(13) —X' C(X)N($R_8$)—,
(14) —SO$_2$N($R_8$)—,
(15) —N($R_8$)SO$_2$—, and
(16) —N($R_8$)SO$_2$N($R_9$)—
  where (6)–(16) are drawn with their right ends attached to $R_A$, and $R_A$ is selected from
(1) —OH,
(2) —OG where G is a —OH protecting group,
(3) —SH,
(4) —CO$_2$R$_{20}$ where $R_{20}$ is hydrogen or alkyl of one to twelve carbons,
(5) alkoxylcarbonyl,
(6) —CN,
(7) halo,
(8) haloalkoxy of one to twelve carbons,
(9) perfluoroalkoxy of one to twelve carbons,
(10) —CHO,
(11) —NR$_7$R$_{7'}$ where $R_{7'}$ is the same as defined for $R_7$,
(12) —C(X)NR$_8$R$_9$,
(13) —OSO$_2$R$_{11}$ where $R_{11}$ is selected from
  (a) aryl,
  (b) cycloalkyl of three to twelve carbons,
  (c) alkyl of one to twelve carbons,
  (d) alkyl of one to twelve carbons substituted with 1, 2, 3, or 4 halo substituents, and
  (e) perfluoroalkyl of one to twelve carbons,
  provided that when $R_A$ is (1)–(13), $L_1$ is a covalent bond,
(14) alkyl of one to twelve carbons,
(15) alkenyl of two to twelve carbons,
  provided that a carbon of a carbon-carbon double bond is not attached directly to $L_1$ when $L_1$ is other than a covalent bond,
(16) alkynyl of two to twelve carbons,
  provided that a carbon of a carbon-carbon triple bond is not attached directly to $L_1$ when $L_1$ is other than a covalent bond,
  where (14), (15), and (16) can be substituted with 1, 2, or 3 substituents independently selected from
  (a) alkoxy of one to twelve carbons,
  (b) —OH,
  provided that no two —OH groups are attached to the same carbon,
  (c) —SH,
  (d) thioalkoxy of one to twelve carbons,
    provided that no two —SH groups are attached to the same carbon,
  (e) —CN,
  (f) halo,
  (g) —CHO,
  (h) —NO$_2$,
  (i) haloalkoxy of one to twelve carbons,
  (j) perfluoroalkoxy of one to twelve carbons,
  (k) —NR$_7$R$_{7'}$,
  (l) =NNR$_7$R$_{7'}$,
  (m) —NR$_7$NR$_{7'}$R$_{7''}$ where $R_{7''}$ is the same as defined for $R_7$,
  (n) —CO$_2$R$_{10}$ where $R_{10}$ is selected from
    (i) hydrogen,
    (ii) aryl,
    (iii) aryl substituted with 1, 2, or 3 alkyl of one to twelve carbon substituents,
    (iv) cycloalkyl of three to twelve carbons,
    (v) alkyl of one to twelve carbons, and
    (vi) alkyl of one to twelve carbons substituted with aryl or cycloalkyl of three to twelve carbons,
  (o) —C(X)NR$_8$R$_9$,
  (p) =N—OR$_{10}$,
  (q) =NR$_{10}$,
  (r) —S(O)$_r$R$_{10}$,
  (s) —X'C(X)R$_{10}$,
  (t) (=X),
  (u) —OSO$_2$R$_{11}$, and
  (v) aryl,
(17) cycloalkyl of three to twelve carbons,
(18) cycloalkenyl of four to twelve carbons,
  provided that a carbon of a carbon-carbon double bond is not attached directly to $L_1$ when $L_1$ is other than a covalent bond,
  where (17) and (18) can be substituted with 1, 2, 3, or 4 substituents independently selected from
  (a) alkyl of one to twelve carbons,
  (b) aryl,
  (c) alkoxy of one to twelve carbons,
  (d) halo,
  (e) alkoxycarbonyl where the alkyl group is one to twelve carbons, and (f) —OH,
provided that no two —OH groups are attached to the same carbon,
(19) perfluoroalkyl of one to twelve carbons,
(20) aryl, and
(21) heterocycle
where (20) and (21) can be substituted with 1, 2, 3, 4, or 5 substituents independently selected from
(a) alkyl of one to twelve carbons,
(b) alkanoyloxy where the alkyl part is one to twelve carbons,
(c) alkoxycarbonyl where the alkyl part is one to twelve carbons,
(d) alkoxy of one to twelve carbons,
(e) halo,
(f) —OH,
provided that no two —OH groups are attached to the same carbon,
(g) thioalkoxy of one to twelve carbons,
(h) perfluoroalkyl of one to twelve carbons,
(i) —$NR_7R_{7'}$,
(j) —$CO_2R_{10}$,
(k) —$OSO_2R_{11}$, and
(l) (=X);

$R_2$, $R_3$, and $R_4$ are independently hydrogen or $R_1$; or
$R_1$ and $R_2$ together are —X*—Y*—Z*— where X* is —O— or —$CH_2$—, Y* is —C(O)— or —$(C(R_{12})(R_{13}))_v$— where $R_{12}$ and $R_{13}$ are independently hydrogen or alkyl of one to twelve carbons and v is 1, 2, or 3, and Z* is selected from —$CH_2$—, —$CH_2S(O)_t$—, —$CH_2O$—, —$CH_2N(R_7)$—, —$N(R_7)$—, and —O—;

$L_2$ is selected from
(1) a covalent bond,
(2) alkylene of one to twelve carbons,
(3) alkylene of one to twelve carbons substituted with 1 or 2 substituents independently selected from
(a) spiroalkyl of three to eight carbon atoms,
(b) spiroalkenyl of five or eight carbon atoms,
(c) oxo,
(d) halo, and
(e) —OH,
provided that no two —OH groups are attached to the same carbon,
(4) alkynylene of two to twelve carbons,
(5) —$N(R_7)$—,
(6) —C(X)—,
(7) —O—, and
(8) —$S(O)_t$—; and $R_5$ is selected from
(1) halo,
(2) hydrogen,
(3) —$C(=NR_7)OR_{10}$,
(4) —CN,
provided that when $R_5$ is (1), (2), or (3), $L_2$ is a covalent bond,
(5) alkyl of one to twelve carbons,
(6) alkynyl two to twelve carbons,
provided that a carbon of a carbon-carbon triple bond is not attached directly to $L_2$ when $L_2$ is other than a covalent bond,
(7) cycloalkyl of three to twelve carbons,
(8) heterocycle,
(9) aryl provided that when $R_5$ is (9), $L_2$ is other than —$N(R_7)$— or —O—, and where (5)—(9) can be substituted with 1, 2, 3, 4, or 5 substituents independently selected from
(a) —OH,
provided that no two —OH groups are attached to the same carbon,
(b) —SH,
provided that no two —SH groups are attached to the same carbon,
(c) —CN,
(d) halo,
(e) —CHO,
(f) —$NO_2$,
(g) haloalkoxy of one to twelve carbons,
(h) perfluoroalkoxy of one to twelve carbons,
(i) —$NR_{8'}R_{9'}$ where $R_{8'}$ and $R_{9'}$ are selected from
(i) hydrogen,
(ii) alkanoyl where the alkyl part is one to twelve carbons,
(iii) alkoxycarbonyl where the alkyl part is one to twelve carbons,
(iv) alkoxycarbonyl where the alkyl part is one to twelve carbons and is substituted with 1 or 2 phenyl substituents,
(v) cycloalkyl of three to twelve carbons,
(vi) alkyl of one to twelve carbons,
(vii) alkyl of one to twelve carbons substituted with 1, 2, or 3 substituents independently selected from
alkoxy of one to twelve carbons,
cycloalkyl of three to twelve carbons,
aryl, and
alkoxycarbonyl where the alkyl group is one to twelve carbons,
(viii) alkenyl of three to twelve carbons,
provided that a carbon of a carbon-carbon double bond is not directly attached to nitrogen,
(ix) alkynyl of three to twelve carbons,
provided that a carbon of a carbon-carbon triple bond is not directly attached to nitrogen,
(x) —$C(O)NR_XR_Y$ where $R_X$ and $R_Y$ are independently selected from hydrogen and alkyl of one to twelve carbons,
(xi) alkoxy of one to twelve carbons,
(xii) aryl, and
(xiii) aryl substituted with 1, 2, 3, 4, or 5 substituents independently selected from
alkyl of one to twelve carbons,
alkanoyloxy where the alkyl part is one to twelve carbons,
alkoxycarbonyl where the alkyl part is one to twelve carbons,
alkoxy of one to twelve carbons,
halo,
—OH
provided that no two —OH groups are attached to the same carbon,
thioalkoxy of one to twelve carbons,
perfluoroalkyl of one to twelve carbons,
—$NR_7R_{7'}$,
—$CO_2R_{10}$,
—$OSO_2R_{11}$, and
(=X), or $R_{8'}$ and $R_{9'}$ together with the nitrogen atom to which they are attached form a ring selected from
(i) aziridine,
(ii) azetidine, (iii) pyrrolidine,
(iv) piperidine,
(v) pyrazine,
(vi) morpholine,
(vii) phthalimide,
(viii) thiomorpholine, and
(ix) thiomorpholine sulfone
   where (i)–(ix) can be substituted with 1, 2, or 3 alkyl of one to twelve carbon substituents,
(j) =$NR_8 R_9$,
(k) —$N(R_7)NR_8 R_9$,
(l) —$CO_2 R_8$,
(m) —$C(X)NR_8 R_9$,
(n) =N—$OR_8$,
(o) =$NR_8$,
(p) —$S(O)_t R_{10}$,
(q) —X'C(X)$R_8$,
(r) (=X),
(s) —O—$(CH_2)_q$—Z—$R_{10}$ where $R_{10}$ is defined previously, q is 1, 2, or 3, and Z is O or —$S(O)_t$—,
(t) —$OC(X)NR_8 R_9$,
(u) —$OSO_2 R_{11}$,
(v) alkanoyloxy where the alkyl group is one to twelve carbons,
(w) —$L_B R_{30}$ where $L_B$ is selected from
   (i) a covalent bond,
   (ii) —O—,
   (iii) —$S(O)_t$—, and
   (iv) —C(X)— and
   $R_{30}$ is selected from
   (i) alkyl of one to twelve carbons,
   (ii) alkenyl of one to twelve carbons, provided that a carbon of a carbon-carbon double bond is not attached directly to $L_B$ when $L_B$ is other than a covalent bond,
   (iii) alkynyl of one to twelve carbons, provided that a carbon of a carbon-carbon triple bond is not attached directly to $L_B$ when $L_B$ is other than a covalent bond, where (i), (ii), and (iii) can be substituted with
      cycloalkyl of three to twelve carbons,
      —OH,
      provided that no two —OH groups are attached to the same carbon,
      halo,
      alkoxy of one to twelve carbons,
      thioalkoxy of one to twelve carbons,
      —$NR_8 R_9$,
      —O—$(CH_2)_q$—Z—$R_{10}$,
      alkoxycarbonyl where the alkyl group is one to twelve carbons, alkanoyloxy where the alkyl group is one to twelve carbons,
      —$N(R_7)SO_2$-(alkyl of one to twelve carbons),
      —$OSO_2$-(alkyl of one to twelve carbons),
      aryl, and
      heterocycle,
   (iv) aryl,
   (v) aryl substituted with 1, 2, 3, 4, or 5 substituents independently selected from
      alkyl of one to twelve carbons,
      halo,
      —$NO_2$, and
      —OH,
      provided that no two —OH groups are attached to the same carbon,
   (vi) heterocycle, and
   (vii) heterocycle substituted with 1, 2, 3, 4, or 5 substituents independently selected from
      alkyl of one to twelve carbons,
      halo,
      —$NO_2$, and
      —OH,
      provided that no two —OH groups are attached to the same carbon,
(x) —X'C(X)X''$R_{10}$,
(y) —N(H)C(O)N(H)$NH_2$,
(z) alkenyl of two carbons,
(aa) —C(=$NR_7$)$OR_{10}$, and
(bb) —$N(R_7)C(X)NR_8 R_9$, (10)

where the carbon-carbon double bond is in the Z or E configuration, and $R_{19}$, $R_{20}$, and $R_{21}$ are independently selected from
(a) hydrogen,
(b) halo,
(c) alkoxycarbonyl where the alkyl group is of one to twelve carbons,
(d) alkyl of one to twelve carbons, and
(e) alkyl of one to twelve carbons substituted with
   (i) alkoxy of one to twelve carbons,
   (ii) —OH,
      provided that no two —OH groups are attached to the same carbon,
   (iii) —SH,
      provided that no two —SH groups are attached to the same carbon,
   (iv) —CN,
   (v) halo,
   (vi) —CHO,
   (vii) —$NO_2$,
   (viii) haloalkoxy of one to twelve carbons,
   (ix) perfluoroalkoxy of one to twelve carbons,
   (x) —$NR_8 R_9$,
   (xi) =$NNR_8 R_9$,
   (xii) —$N(R_7)NR_8 R_9$,
   (xiii) —$CO_2 R_{10}$,
   (xiv) —$C(X)NR_8 R_9$,
   (xv) =N—$OR_{10}$,
   (xvi) =$NR_{10}$,
   (xvii) —$S(O)_t R_{10}$,
   (xviii) —X'C(X)$R_{10}$,
   (xix) (=X),
   (xx) —O—$(CH_2)_q$—Z—$R_{10}$,
   (xxi) —$OC(X)NR_8 R_9$,
   (xxii) —$L_B R_{30}$,
   (xxiii) alkanoyloxy where the alkyl group is one to twelve carbons,
   (xxiv) —$OSO_2 R_{11}$, and
   (xxv) —$N(R_7)C(X)NR_8 R_9$, or
   $R_{20}$ and $R_{21}$ together are selected from
(a) cycloalkyl of three to twelve carbon atoms,
(b) cycloalkenyl of four to twelve carbon atoms, and (c)

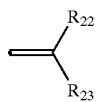

(allene) where $R_{22}$ and $R_{23}$ are independently hydrogen or alkyl of one to twelve carbons, and
(11) cycloalkenyl of four to twelve carbons
where the cycloalkenyl group or the ring formed by $R_{20}$ and $R_{21}$ together can be substituted with one or two substituents independently selected from
(a) alkoxy of one to twelve carbons,
(b) —OH,
provided that no two —OH groups are attached to the same carbon,
(c) —SH,
provided that no two —SH groups are attached to the same carbon,
(d) —CN,
(e) halo,
(f) —CHO,
(g) —$NO_2$,
(h) haloalkoxy of one to twelve carbons,
(i) perfluoroalkoxy of one to twelve carbons,
(j) —$NR_8R_9$,
(k) =$NNR_8R_9$,
(l) —$N(R_7)NR_8R_9$,
(m) —$CO_2R_{10}$,
(n) —$C(X)NR_8R_9$,
(o) =N-$OR_{10}$,
(p) =$NR_{10}$,
(q) —$S(O)_rR_{10}$,
(r) —X'C(X)$R_{10}$,
(s) (=X),
(t) —O—$(CH_2)_q$—Z—$R_{10}$,
(u) —OC(X)$NR_8R_9$,
(v) —$L_BR_{30}$,
(w) alkanoyloxy where the alkyl group is one to twelve carbons,
(x) —$OSO_2R_{11}$, and
(y) —$N(R_7)C(X)NR_8R_9$;
$R_6$ is hydrogen or alkyl of one to twelve carbon atoms; or
—$L_2$—$R_5$ and $R_6$ together are selected from
(1) =O,
(2)

where d is 1, 2, 3, or 4 and A is selected from
(a) —$CH_2$—,
(b) —O—,
(c) —$S(O)_r$, and
(d) —$N(R_7)$—, and
(3)

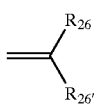

where the carbon-carbon double bond can be in the E or Z configuration and $R_{26}$ and $R_{26'}$ are independently selected from (a) hydrogen,
(b) alkenyl of three to twelve carbons,
(c) aryl,
(d) heterocycle,
(e) alkyl of one to twelve carbons,
(f) cycloalkyl of three to twelve carbons,
(g) cycloalkenyl of four to twelve carbons, and
(h) cycloalkenyl of four to twelve carbons where (a)–(f) can be substituted with 1, 2, 3, 4, or 5 substituents independently selected from
(i) alkoxy of one to twelve carbons,
(ii) —OH,
provided that no two —OH groups are attached to the same carbon,
(iii) —SH,
provided that no two —SH groups are attached to the same carbon,
(iv) —CN,
(v) halo,
(vi) —CHO,
(vii) —$NO_2$,
(viii) haloalkoxy of one to twelve carbons,
(ix) perfluoroalkoxy of one to twelve carbons,
(x) —$NR_8R_9$,
(Xi) =$NNR_8R_9$,
(xii) —$N(R_7)NR_8R_9$,
(xiii) —$CO_2R_{10}$,
(xiv) —$C(X)NR_8R_9$,
(xv) =N—$OR_{10}$,
(xvi) =$NR_{10}$,
(xvii) —$S(O)_rR_{10}$,
(xviii) —X'C(X)$R_{10}$,
(xix) (=X),
(xx) —O—$(CH_2)_q$—Z—$R_{10}$,
(xxi) —OC(X)$NR_8R_9$,
(xxii) —$L_BR_{30}$,
(xxiii) alkanoyloxy where the alkyl group is one to twelve carbons,
(xxiii) —$OSO_2R_{11}$, and
(xxiv) —$N(R_7)(X)NR_8R_9$;
$R_{16}$ and $R_{16'}$ are independently hydrogen or alkyl of one to six carbons; or
$R_{16}$ and $R_{16'}$ together are =$CH_2$;
a broken line represents the optional presence of a double bond, provided that when $R_{16}$ and $R_{16'}$ together are alkenyl of two carbons, the double bond is not present;
Y is selected from carbon, nitrogen, and $N^+(=O^-)$;
$R_{17}$ is absent or hydrogen or alkyl of one to six carbons, provided that when the double bond is present, and Y is nitrogen or $N^+(=O^-)$, $R_{17}$ is absent; and
$R_{18}$ and $R_{18'}$ are independently hydrogen or alkyl of one to six carbons; or
$R_{18}$ and $R_{18'}$ together are a cycloheteroalkyl ring or a cycloalkyl ring of three to eight carbons.
In another embodiment of the invention are disclosed compounds of Formula II

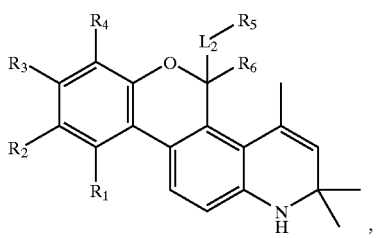

or a pharmaceutically acceptable salt or prodrug thereof, where $R_1$, $R_2$, $R_3$, $R_4$, $R_5$, $R_6$, and $L_2$, are defined above.

In another embodiment of the invention are disclosed compounds of Formula III

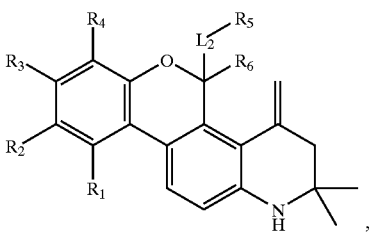

or a pharmaceutically acceptable salt or prodrug thereof, where $R_1$, $R_2$, $R_3$, $R_4$, $R_5$, $R_6$, and $L_2$, are defined above.

In another embodiment of the invention are disclosed compounds of Formula IV

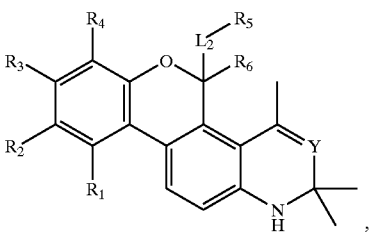

or a pharmaceutically acceptable salt or prodrug thereof, where Y is nitrogen or $N^+(=O^-)$, and $R_1$, $R_5$, $R_6$, and $L_2$, are defined above.

In another embodiment of the invention are disclosed compounds of Formula V

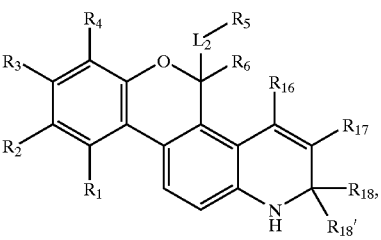

or a pharmaceutically acceptable salt or prodrug thereof, where $R_1$, $R_5$, and $L_2$, are defined above;

$R_{16}$ and $R_{17}$ are independently hydrogen or alkyl of one to six carbons; and $R_{18}$ and $R_{18'}$ are independently hydrogen or alkyl of one to six carbons; or $R_{18}$ and $R_{18'}$ together are a cycloheteroalkyl ring or a cycloalkyl ring of three to eight carbons;

In a preferred embodiment of the invention, $R_1$ is a substituent group having from about 1 to about 15 atoms, preferably from about 1 to about 10 atoms. Most preferably $R_1$ is a substituent group having from about 1 to about 6 atoms. Specific preferred substituent groups at $R^1$ include, but are not limited to, amino, $C_1$–$C_3$-alkyl, carbaldehyde oxime, $C_2$–$C_4$-alkoxycarbonyloxy, $C_1$–$C_3$-aminoalkyl, $C_3$-alkenylamino, $C_2$–$C_4$-alkanoyloxy, $C_1$–$C_3$-alkylamine, cyano, $C_3$–$C_4$-cycloalkyl, $C_2$–$C_3$-alkenyl, $C_2$–$C_3$-alkynyl, $C_3$-alkenyloxy $C_3$-alkynyloxy, $C_1$–$C_3$-alkoxy, $C_2$–$C_3$-alkoxycarbonyl, $C_2$–$C_4$-alkoxyalkyl, benzyloxy, $C_1$–$C_3$-dialkylamine, carboxy, furan-2-yl, halo, hydroxyl, $C_1$–$C_3$-hydroxyalkyl, formyl, $C_1$–$C_3$-thioalkoxy, and the like.

In each of the above substituent groups, protons may be substituted by halogen, so that, for instance, and by way of example only, difluoromethoxy, and bromodifluromethoxy are within the scope of the preferred substituents of this invention.

An especially preferred $R_1$ group is alkoxy, preferably methoxy.

Thus, taking the listing of preferred substituents, and the limitation on the number of atoms in the substituents, it will be seen by those skilled in the art that $R_1$ may vary considerably among the classes enumerated above having no more than 15 atoms in any one substituent.

Accordingly, in a preferred embodiment of this invention, $R_1$ is selected from the group consisting of $C_1$–$C_3$ alkyl, $C_1$–$C_3$ haloalkyl, $C_1$–$C_3$ alkenyl, $C_1$–$C_3$ haloalkenyl, $C_1$–$C_3$ alkynyl, $C_1$–$C_3$ alkoxy, $C_1$–$C_3$-haloalkoxy, $C_3$-alkynyloxy, benzyloxy, amino, methylamine, dimethylamine, substituted substituted amino, methylamine, thiomethoxy, substituted thiomethoxy, and the like.

$R_2$ may likewise may vary considerably without departing from the intent of this invention. It is believed that a preferred substituent at $R^2$ is hydroxy and that prodrugs can be made therefrom.

Accordingly, in a preferred embodiment of this invention, $R_1$ is $—L_1—R_A$ where $L_1$ is selected from (1) a covalent bond,
(2) —O—,
(3) —S(O)$_t$— where t is 0, 1, or 2,
(4) —C(X)—,
(5) —N(R$_7$)— where R$_7$ is selected from
  (a) hydrogen,
  (b) aryl
  (c) cycloalkyl of three to four carbons,
  (d) alkanoyl where the alkyl part is one to three carbons,
  (e) alkoxycarbonyl where the alkyl part is one to three carbons,
  (f) alkyl of one to three carbons,
  (h) alkyl of one to three carbons substituted with 1 or 2 substituents independently selected from
    (i) halo and
    (ii) cycloalkyl of three to twelve carbons,
  (i) alkenyl of three to four carbons,
    provided that a carbon of a carbon-carbon double bond is not attached directly to nitrogen,
  (j) alkynyl of three to four carbons,
    provided that a carbon of a carbon-carbon triple bond is not attached directly to nitrogen,
(6) —X'C(X)— where X is previously defined and X' is O or S,
(7) —C(X)X'—,
(8) —X'C(X)X"— where X and X' are previously defined and X" is O or S, provided that when X is O, at least one of X' or X" is O, (9) —N(R$_8$)C(X)—,
(10) —C(X)N(R$_8$)—,
(11) —N(R$_8$)C(X)X'—,
(12) —X' C(X)N(R$_8$)—,
(13) —SO$_2$N(R$_8$)—,
(14) —N(R$_8$)SO$_2$—, and
(15) —N(R$_8$)SO$_2$N(R$_9$)—
where (7)–(15) are drawn with their right ends attached to R$_A$ and R$_A$ is selected from
(1) —OH,
(2) —OG where G is a —OH protecting group,
(3) —SH,
(4) —CO$_2$R$_{20}$ where R$_{20}$ is hydrogen or alkyl of one to three carbons,
(5) alkoxylcarbonyl,
(6) —CN,
(7) halo,
(8) haloalkoxy of one to three carbons,
(9) perfluoroalkoxy of one to three carbons,
(10) —CHO,
(11) —NR$_7$ R$_{7'}$ where R$_7$ is defined previously and R$_{7'}$ is selected from
  (a) hydrogen,
  (c) cycloalkyl of three to four carbons,
  (d) alkanoyl where the alkyl part is one to three carbons,
  (e) alkoxycarbonyl where the alkyl part is one to three carbons,
  (f) alkyl of one to twelve carbons,
  (g) alkyl of one to four carbons substituted with 1 or 2 substituents independently selected from
    (i) halo and
    (ii) hydroxyl,
  (i) alkenyl of three to four carbons,
    provided that a carbon of a carbon-carbon double bond is not attached directly to nitrogen, and
  (j) alkynyl of three to four carbons,
    provided that a carbon of a carbon-carbon triple bond is not attached directly to nitrogen,
(12) —C(X)NR$_8$R$_9$,
(13) —OSO$_2$R$_{11}$ where R$_{11}$ is selected from
  (a) aryl,
  (b) cycloalkyl of three to four carbons,
  (c) alkyl of one to three carbons,
  (d) alkyl of one to twelve carbons substituted with 1, 2, 3, or 4 halo substituents, and
  (e) perfluoroalkyl of one to three carbons,
  provided that when R$_A$ is (1)–(13), L$_1$ is a covalent bond,
(14) alkyl of one to three carbons,
(15) alkenyl of two to four carbons,
  provided that a carbon of a carbon-carbon double bond is not attached directly to L$_1$ when L$_1$ is other than a covalent bond,
(16) alkynyl of two to four carbons,
  provided that a carbon of a carbon-carbon triple bond is not attached directly to L$_1$ when L$_1$ is other than a covalent bond,
  where (14), (15), and (16) can be substituted with 1, 2, or 3 substituents independently selected from
  (a) alkoxy of one to twelve carbons,
  (b) —OH,
    provided that no two —OH groups are attached to the same carbon,
  (c) —SH,
  (d) thioalkoxy of one to twelve carbons,
    provided that no two —SH groups are attached to the same carbon,
  (e) —CN,
  (f) halo,
  (g) —CHO,
  (h) —NO$_2$,
  (i) haloalkoxy of one to twelve carbons,
  (j) perfluoroalkoxy of one to twelve carbons,
  (k) —NR$_7$R$_{7'}$,
  (l) =NNR$_7$R$_{7'}$,
  (m) —N(R$_7$)NR$_7$R$_{7''}$ where R$_7$ and R$_{7'}$ are defined previously and R$_{7''}$ is selected from
    (i) hydrogen,
    (ii) aryl,
    (iii) cycloalkyl of three to four carbons,
    (vi) alkanoyl where the alkyl part is one to three carbons,
    (v) alkoxycarbonyl where the alkyl part is one to three carbons,
    (vi) alkoxycarbonyl where the alkyl part is one to three carbons substituted by 1 or 2 aryl groups,
    (vii) alkyl of one to three carbons,
    (viii) alkyl of one to three carbons substituted with 1 or 2 substituents independently selected from halo or cycloalkyl of three to four carbons,
    (ix) alkenyl of three to four carbons,
      provided that a carbon-carbon double bond is not attached directly to nitrogen, and
    (x) alkynyl of three to four carbons,
      provided that a carbon-carbon triple bond is not attached directly to nitrogen,
  (n) —CO$_2$R$_{10}$ where R$_{10}$ is selected from
    (i) hydrogen
    (ii) cycloalkyl of three to four carbons,
    (iii) alkyl of one to three carbons, and
    (iv) alkyl of one to three carbons substituted with halo or cycloalkyl of three to twelve carbons,
  (o) —C(X)NR$_8$R$_9$,
  (p) =N—OR$_{10}$,
  (q) =NR$_{10}$,
  (r) —S(O)$_r$R$_{10}$,
  (s) —X'C(X)R$_{10}$,
  (t) (=X),
  (u) —OSO$_2$R$_{11}$, and
  (v) aryl,
(18) cycloalkyl of three to four carbons,
(19) cycloalkenyl of four to four carbons,
  provided that a carbon of a carbon-carbon double bond is not attached directly to L$_1$ when L$_1$ is other than a covalent bond,
  where (18) and (19) can be substituted with 1, 2, 3, or 4 substituents independently selected from
  (a) alkyl of one to twelve carbons,
  (c) alkoxy of one to three carbons,
  (d) halo,
  (e) alkoxycarbonyl where the alkyl group is one to three carbons, and
  (f) —OH,
  provided that no two —OH groups are attached to the same carbon, and

(20) perfluoroalkyl of one to three carbons; and $R_2$, $R_3$, and $R_4$ are independently hydrogen or $R_1$.

In another embodiment of the invention are disclosed methods of selectively partially antagonizing, antagonizing, agonizing or modulating the glucocorticoid receptor.

In another embodiment of the invention are disclosed methods of treating diseases comprising administering an effective amount of a compound having Formula I.

In yet another embodiment of the invention are disclosed pharmaceutical compositions containing compounds of Formula I.

Compounds of this invention include, but are not limited to, 2,5-dihydro-10-methoxy-2,2,4-trimethyl-5-phenyl-1H-[1]benzopyrano[3,4-f]quinoline-2,5-dihydro-10-methoxy-2,2,4-trimethyl-5-(2-propenyl)-1H-[1]benzopyrano[3,4-f]quinoline, 2,5-dihydro-2,2,4,N-tetramethyl-5-(2-propenyl)-1H-[1]benzopyrano[3,4-f]quinolin-10-amine, methyl 2,5-dihydro-2,2,4-trimethyl-5-(2-propenyl)-1H-[1]benzopyrano[3,4-f]quinoline-10-carboxylate, 10-ethenyl-2,5-dihydro-2,2,4-trimethyl-5-(2-propenyl)-1H-[1]benzopyrano[3,4f]quinoline, 10-ethynyl-2,5-dihydro-10-methoxy-2,2,4-trimethyl-5-(2-propenyl)-1H-[1]benzopyrano[3,4-f]quinoline, 2,5-dihydro-2,2,4-trimethyl-5-phenyl-1H-[1]benzopyrano[3,4-f]quinolin-10-ol, 10-(difluoromethoxy)-2,5-dihydro-2,2,4-trimethyl-5-(2-propenyl)-1H-[1]benzopyrano[3,4f]quinoline, 10-ethoxy-2,5-dihydro-2,2,4-trimethyl-5-phenyl-1H-[1]benzopyrano[3,4-f]quinoline, 2,5-dihydro-2,2,4-trimethyl-5-phenyl-1H-[1]benzopyrano[3,4-f]quinoline-10-ol acetate (ester), 5-(3-bromo-5-methylphenyl)-2,5-dihydro-10-methoxy-2,2,4-trimethyl-1H-[1]benzopyrano[3,4-f]quinoline, 3-(2,5-dihydro-10-methoxy-2,2,4-trimethyl-1H-[1]benzopyrano[3,4-f]quinolin-5-yl)phenol, acetate (ester), 3-(2,5-dihydro-10-methoxy-2,2,4-trimethyl-1H-[1]benzopyrano[3,4-f]quinolin-5-yl)phenol, 2,5-dihydro-10-methoxy-2,2,4-trimethyl-5-[[3-(methylthio)methoxy]phenyl]-1H-[1]benzopyrano[3,4-f]quinoline, [3-(2,5-dihydro-10-methoxy-2,2,4-trimethyl-1H-[1]benzopyrano[3,4-f]quinolin-5-yl)phenyl]dimethylcarbamate, 5-[3-(2-furanyl)-5-methylphenyl]-2,5-dihydro-10-methoxy-2,2,4-trimethyl-1H-[1]benzopyranol[3,4-f]quinoline, 2,5-dihydro-10-methoxy-2,2,4-trimethyl-5-[3-methyl-5-(1-morpholinyl)phenyl]-1H-[1]benzopyrano[3,4-f]quinoline, 2,5-dihydro-10-methoxy-2,2,4-trimethyl-5-(phenylmethylene)-1H-[1]benzopyrano[3,4-f]quinoline, 5-(3,5-dichlorophenyl)-2,5-dihydro-10-methoxy-2,2,4-trimethyl-1H-[1]benzopyrano[3,4-f]quinoline, 5-butyl-2,5-dihydro-10-methoxy-2,2,4-trimethyl-1H-[1]benzopyrano[3,4-f]quinoline, 2,5-dihydro-10-methoxy-2,2,4-trimethyl-5-[3-(trifluoromethyl)phenyl]-1H-[1]benzopyrano[3,4-f]quinoline, 2,5-dihydro-10-methoxy-5-(4-methoxyphenyl)-2,2,4-trimethyl-1H-[1]benzopyrano[3,4-f]quinoline, 5-(3-chlorophenyl)-2,5-dihydro-10-methoxy-2,2,4-trimethyl-1H-[1]benzopyrano[3,4-f]quinoline, 2,5-dihydro-10-methoxy-2,2,4-trimethyl-5-(3-methylphenyl)-1H-[1]benzopyrano[3,4-f]quinoline, (±)-2,5-dihydro-10-methoxy-2,2,4-trimethyl-5-phenyl-1H-[1]benzopyrano[3,4-f]quinoline, (±)-2,5-dihydro-10-methoxy-2,2,4-trimethyl-5-phenyl-1H-[1]benzopyrano[3,4-f]quinoline, 5-(3,5-dimethylphenyl)-2,5-dihydro-10-methoxy-2,2,4-trimethyl-1H-[1]benzopyrano[3,4-f]quinoline, 5-(4-chlorophenyl)-2,5-dihydro-10-methoxy-2,2,4-trimethyl-1H-[1]benzopyrano[3,4-f]quinoline, 5-(3,4-dimethylphenyl)-2,5-dihydro-10-methoxy-2,2,4-trimethyl-1H-[1]benzopyrano[3,4-f]quinoline, 5-(4-fluorophenyl)-2,5-dihydro-10-methoxy-2,2,4-trimethyl-1H-[1]benzopyrano[3,4-f]quinoline, 5-[3,5-bis(trifluoromethyl)phenyl]-2,5-dihydro-10-methoxy-2,2,4-trimethyl-1H-[1]benzopyrano[3,4-f]quinoline, (−)-5-(3,5-dichlorophenyl)-2,5-dihydro-10-methoxy-2,2,4-trimethyl-1H-[1]benzopyrano[3,4-f]quinoline, (+)-5-(3,5-dichlorophenyl)-2,5-dihydro-10-methoxy-2,2,4-trimethyl-1H-[1]benzopyrano[3,4-f]quinoline, 5-(3,5-difluorophenyl)-2,5-dihydro-10-methoxy-2,2,4-trimethyl-1H-[1]benzopyrano[3,4-f]quinoline, 2,5-dihydro-10-methoxy-2,2,4,N-tetramethyl-N-phenyl-1H-[1]benzopyrano[3,4-f]quinolin-5-amine, (−)-2,5-dihydro-10-methoxy-2,2,4-trimethyl-5-(2-propenyl)-1H-[1]benzopyrano[3,4-f]quinoline, (+)-2,5-dihydro-10-methoxy-2,2,4-trimethyl-5-(2-propenyl)-1H-[1]benzopyrano[3,4-f]quinoline, 2,5-dihydro-10-methoxy-2,2,4-trimethyl-1H-[1]benzopyrano[3,4-f]quinoline, 4-(2,5-dihydro-10-methoxy-2,2,4-trimethyl-1H-[1]benzopyrano[3,4-f]quinolin-5-yl)-N,N-dimethylbenzenamine, 2,5-dihydro-10-methoxy-2,2,4-trimethyl-5-(5-methoxy-2-thienyl)-1H-[1]benzopyrano[3,4-f]quinoline, 2,5-dihydro-10-methoxy-2,2,4-trimethyl-5-(5-propyl-2-thienyl)-1H-[1]benzopyrano[3,4-f]quinoline, 2,5-dihydro-10-methoxy-2,2,4-trimethyl-5-[4-(1-morpholinyl)phenyl]-1H-[1]benzopyrano[3,4-f]quinoline, 1-(2,5-dihydro-10-methoxy-2,2,4-trimethyl-1H-[1]benzopyrano[3,4-f]quinolin-5-yl)-3,3-dimethyl-2-butanone, 2,5-dihydro-10-methoxy-2,2,4-trimethyl-1H-[1]benzopyrano[3,4-f]quinoline-5-carbonitrile, 1-(2,5-dihydro-10-methoxy-2,2,4-trimethyl-1H-[1]benzopyrano[3,4-f]quinolin-5-yl)-2-propanone, methyl-2,5-dihydro-10-methoxy-2,2,4-trimethyl-1H-[1]benzopyrano[3,4-f]quinoline-5-acetate, 2-(2,5-dihydro-10-methoxy-2,2,4-trimethyl-1H-[1]benzopyrano[3,4-f]quinolin-5-yl)-1-phenylethanone, 5-[2-(chloromethyl)-2-propenyl]-2,5-dihydro-10-methoxy-2,2,4-trimethyl-1H-[1]benzopyrano[3,4-f]quinoline, 2,5-dihydro-10-methoxy-2,2,4-trimethyl-(-methylene-1H-[1]benzopyrano[3,4-f]quinoline-5-propanol, acetate (ester), 2,5-dihydro-10-methoxy-2,2,4-trimethyl-5-(4-methylphenyl)-1H-[1]benzopyrano[3,4-f]quinoline, 5-(3-fluorophenyl)-2,5-dihydro-10-methoxy-2,2,4-trimethyl-1H-[1]benzopyrano[3,4-f]quinoline, 5-(3-bromophenyl)-2,5-dihydro-10-methoxy-2,2,4-trimethyl-1H-[1]benzopyrano[3,4-f]quinoline, 2,5-dihydro-10-methoxy-2,2,4-trimethyl-5-(phenylmethyl)-1H-[1]benzopyrano[3,4-f]quinoline, 2,5-dihydro-10-methoxy-2,2,4-trimethyl-5-propyl-1H-[1]benzopyrano[3,4-f]quinoline, 5-(4-fluorophenyl)-2,5-dihydro-10-methoxy-2,2,4-trimethyl-1H-[1]benzopyrano[3,4-f]quinoline, 5-(3-fluorophenyl)-2,5-dihydro-10-methoxy-2,2,4-trimethyl-1H-[1]benzopyrano[3,4-f]quinoline, 2,5-dihydro-10-methoxy-2,2,4,5-tetramethyl-1H-[1]benzopyrano[3,4-f]quinoline, 2,5-dihydro-10-methoxy-2,2,4-trimethyl-5-(1-methylethyl)-1H-[1]benzopyrano[3,4-f]quinoline, 2,5-dihydro-10-methoxy-2,2,4-trimethyl-5-(2-methylpropyl)-1H-[1]benzopyrano[3,4-f]quinoline, 5-ethyl-2,5-dihydro-10-methoxy-2,2,4-trimethyl-1H-[1]benzopyrano[3,4-f]quinoline, 2,5-dihydro-10-methoxy-2,2,4-trimethyl-1H-[1]benzopyrano[3,4-f]quinoline-5-carboximidic acid ethyl ester, 2,5-dihydro-10-methoxy-2,2,4-trimethyl-(-methylene 1H-[1]benzopyrano[3,4-f]quinoline-5-propanol, 2,5-dihydro-10-methoxy-2,2,4,N,N-pentamethyl-1H-[1]benzopyrano[3,4-f]quinoline-5-acetamide, 2,5-dihydro-10-methoxy-2,2,4,N,N-pentamethyl-1H-[1]benzopyrano[3,4-f]quinoline-5-ethanamine, N-cyclopropyl-2,5-dihydro-10-methoxy-2,2,4-trimethyl-1H-[1]benzopyrano[3,4-f]quinoline-5-acetamide, 2,5-dihydro-10-methoxy-2,2,4-trimethyl-5-(2-propynyl)-1H-[1]benzopyrano[3,4-f]quinoline, 5-(2,5-dihydro-10-methoxy-2,2,4-trimethyl-1H-[1]benzopyrano[3,4-f]quinolin-5-yl)-2(5H)-furanone, 5-(3-butenyl)-2,5-dihdyro-10-methoxy-2,2,4-trimethyl-1H-[1]benzopyrano[3,4-f]quinoline, 2,5-dihydro-10-methoxy-2,2,4-trimethyl-1H-[1]

benzopyrano[3,4-f]quinoline-5-propanol, 10-ethyl-2,5-dihydro-2,2,4-trimethyl-5-phenyl-1H-[1]benzopyrano[3,4-f]quinoline, 2,5-dihydro-2,2,4,10-tetrametnyl-5-phenyl-1H-[1]benzopyrano[3,4-f]quinoline, 5-(3,5-dichlorophenyl)-10-ethyl-2,5-dihydro-2,2,4-trimethyl-1H-[1]benzopyrano[3,4-f]quinoline, 5-(3,5-dichlorophenyl)-2,5-dihydro-2,2,4,N-tetramethyl-1H-[1]benzopyrano[3,4-f]quinolin-10-amine, 5-(3,5-dichlorophenyl)-2,5-dihydro-2,2,4-trimethyl-N-(2-propenyl)-1H-[1]benzopyrano[3,4-f]quinolin-10-amine, 2,5-dihydro-2,2,4-trimethyl-5-phenyl-10-(2-propynyloxy)-1H-[1]benzopyrano[3,4-f]quinoline, 2,5-dihydro-2,2,4-trimethyl-5-phenyl-10-(2-propenyloxy)-1H[1]benzopyrano[3,4-f]quinoline, 2,5-dihydro-2,2,4-trimethyl-5-(2-propenyl)-1H-[1]benzopyrano[3,4-f]quinoline-10-methanol, 2,5-dihydro-2,2,4-trimethyl-5-(2propenyl)-1H-[1]benzopyrano[3,4-f]quinoline-10-carboxylic acid, 5-(3,5-dichlorophenyl)-10-ethoxy-2,5-dihydro-2,2,4-trimethyl-1H-[1]benzopyrano[3,4-f]quinoline, 5-(3,5-dichlorophenyl)-2,5-dihydro-2,2,4-trimethyl-1H-[1]benzopyrano[3,4-f]quinolin-10-ol, 5-(3,5-dichlorophenyl)-2,5-dihydro-2,2,4-trimethyl-1H-[1]benzopyrano[3,4-f]quinolin-10-yl]methylcarbonate, 2,5-dihydro-2,2,4-trimethyl-5-(2-propenyl)-1H-[1]benzopyrano[3,4-f]quinolin-10-ol, 10-(bromodifluoromethoxy)-2,5-dihyro-2,2,4-trimethyl-5-(2-propenyl)-1H-[1]benzopyrano[3,4-f]quinoline, [3-(2,5-dihydro-10-methoxy-2,2,4-trimethyl-1H-[1]benzopyrano[3,4-f]quinolin-5-yl)phenyl] methylcarbonate, 2,5-dihydro-10-methoxy-5-(3-methoxyphenyl)-2,2,4-trimethyl-1H-[1]benzopyrano[3,4-f]quinoline, 2,5-dihydro-10-methoxy-2,2,4-trimethyl-5-[3-(2-propenyloxy)phenyl]-1H-[1]benzopyrano[3,4-f]quinoline, 2,5-dihydro-10-methoxy-2,2,4-trimethyl-5-[3-(phenylmethoxy)phenyl]-1H-[1]benzopyrano[3,4-f]quinoline, 5-[3-(cyclopropylmethoxy)phenyl]-2,5-dihydro-10-methoxy-2,2,4-trimethyl-1H-[1]benzopyrano[3,4-f]quinoline, 2,5-dihydro-10-methoxy-2,2,4-trimethyl-5-[3-[2-(1-piperidinyl)ethoxy]phenyl-1H-[1]benzopyrano[3,4-f]quinoline, 5-(3-hexyloxyphenyl)-2,5-dihydro-10-methoxy-2,2,4-trimethyl-1H-[1]benzopyrano[3,4-f]quinoline, 5-[3-(2,4-dinitrophenoxy)phenyl]-2,5-dihydro-10-methoxy-2,2,4-trimethyl-1H-[1]benzopyrano[3,4-f]quinoline, 2,5-dihydro-10-methoxy-2,2,4-trimethyl-5-[3-(2-propynyloxy)phenyl]-1H-[1]benzopyrano[3,4-f]quinoline, 3-(2,5-dihydro-10-methoxy-2,2,4-trimethyl-1H-[1]benzopyrano[3,4-f]quinolin-5-yl)phenol, 4-methylbenzenesulfonate (ester), 4-(2,5-dihydro-10-methoxy-2,2,4-trimethyl-1H-[1]benzopyrano[3,4-f]quinolin-5-yl)phenolacetate (ester), 4-(2,5-dihydro-10-methoxy-2,2,4-trimethyl-1H-[1]benzopyrano[3,4-f]quinolin-5-yl)phenol, 2,5-dihydro-10-methoxy-2,2,4-trimethyl-5-[[4-(methylthio)methoxy]phenyl]-1H-[1]benzopyrano[3,4-f]quinoline, [4-(2,5-dihydro-10-methoxy-2,2,4-trimethyl-1H-[1]benzopyrano[3,4-f]quinolin-5-yl)phenyl]dimethylcarbamate, 2,5-dihydro-10-methoxy-2,2,4-trimethyl-5-[4-(phenylmethoxy)phenyl]-1H-[1]benzopyrano[3,4-f]quinoline, 2,5-dihydro-10-methoxy-2,2,4-trimethyl-5-[3-(methoxymethoxy)phenyl]-1H-[1]benzopyrano[3,4-f]quinoline, [(2,5-dihydro-10-methoxy-2,2,4-trimethyl-1H-[1]benzopyrano[3,4-f]quinolin-5-yl)phenyl]1-morpholinecarboxylate, 2,5-dihydro-10-methoxy-2,2,4-trimethyl-5-[3-[(methylsulfinyl)methoxy]phenyl]-1H-[1]benzopyrano[3,4-f]quinoline, O-[3-(2,5-dihydro-10-methoxy-2,2,4-trimethyl-1H-[1]benzopyrano[3,4-f]quinolin-5-yl)phenyl]ester, 2,5-dihydro-10-methoxy-2,2,4-trimethyl-5-[3-(methylthio)phenyl]-1H-[1]benzopyrano[3,4-f]quinoline, O-[3-(2,5-dihydro-10-methoxy-2,2,4-trimethyl-1H-[1]benzopyrano[3,4-f]quinolin-5-yl)phenyl] methylcarbonothioate, [3-(2,5-dihydro-10-methoxy-2,2,4-trimethyl]-1H-[1]benzopyrano[3,4-f]quinolin-5-yl)phenyl] trifluoromethanesulfonate, 5-[3-(4,5-dihydro-4,4-dimethyl-2-oxazolyl)phenyl]-2,5-dihydro-10-methoxy-2,2,4-trimethyl-1H-[1]benzopyrano[3,4-f]quinoline, ethyl 3-(2,5-dihydro-10-methoxy-2,2,4-trimethyl-1H-[1]benzopyrano[3,4-f]quinolin-5-yl)benzoate, 3-(2,5-dihydro-10-methoxy-2,2,4-trimethyl-1H-[1]benzopyrano[3,4-f]quinolin-5-yl) benzoic acid, 2,5-dihydro-10-methoxy-2,2,4-trimethyl-5-[3-methyl-5-(2-propenyl)phenyl]-1H-[1]benzopyrano[3,4-f]quinoline, 1-[3-(2,5-dihydro-10-methoxy-2,2,4-trimethyl-1H-[1]benzopyrano[3,4-f]quinolin-5-yl)-5-methylphenyl] ethanone, 3-(2,5-dihydro-10-methoxy-2,2,4-trimethyl-1H-[1]benzopyrano[3,4-f]quinolin-5-yl)-5-trimethylbenzenemethanol, 5-[3-(2-furanyl)phenyl]-2,5-dihydro-10-methoxy-2,2,4-trimethyl-1H-[1]benzopyrano[3,4-f]quinoline, 2,5-dihydro-10-methoxy-2,2,4-trimethyl-5-[3-methyl-5-(1H-pyrrolidin-1-yl)phenyl]-1H-[1]benzopyrano[3,4-f]quinoline, 3-(2,5-dihydro-10-methoxy-2,2,4-trimethyl-1H-[1]benzopyrano[3,4-f]quinolin-5-methyl)-5,N-dimethylbenzenamine, 3-(2,5-dihydro-10-methoxy-2,2,4-trimethyl-1H-[1]benzopyrano[3,4-f]quinolin-5-yl)-5-methyl-N-(2-propenyl)benzamide, 3-(2,5-dihydro-10-methoxy-2,2,4-trimethyl-1H-[1]benzopyrano[3,4-f]quinolin-5-yl)-N-(2-methoxyethyl)-5-methylbenzenamine, 3-(2,5-dihydro-10-methoxy-2,2,4-trimethyl-1H-[1]benzopyrano[3,4-f]quinolin-5-yl)-N-(2-propenyl)benzenamine, N'-[3-(2,5-dihydro-10-methoxy-2,2,4-trimethyl-1H-[1]benzopyrano[3,4-f]quinolin-5-yl)-5-methylphenyl]-N,N-dimethylurea, N-[3-(2,5-dihydro-10-methoxy-2,2,4-trimethyl-1H-[1]benzopyrano[3,4-f]quinolin-5-yl)phenyl]benzenemethanamine, 5-[(3,5-dichlorphenyl)methylene]-2,5-dihydro-10-methoxy-2,2,4-trimethyl-1H-[1]benzopyrano[3,4-f]quinoline, 5-[(4-chlorophenyl)methylene]-2,5-dihydro-10-methoxy-2,2,4-trimethyl-1H-[1]benzopyrano[3,4-f]quinoline, 2,5-dihydro-10-methoxy-2,2,4-trimethyl-5-[[3-(trifluoromethyl)phenyl]methylene]-1H-[1]-benzopyrano[3,4-f]quinoline, 5-[(2,6-difluorophenyl)methylene]-2,5-dihydro-10-methoxy-2,2,4-trimethyl-1H-[1]benzopyrano[3,4-f]quinoline, 5-[(2-chlorophenyl)methylene]-2,5-dihydro-10-methoxy-2,2,4-trimethyl-1H-[1]benzopyrano[3,4-f]quinoline, 5-[(2,6-dichlorophenyl)methylene]-2,5-dihydro-10-methoxy-2,2,4-trimethyl-1H-[1]benzopyrano[3,4-f]quinoline, 5-[(2-fluorophenyl)methylene]-2,5-dihydro-10-methoxy-2,2,4-trimethyl-1H-[1]benzopyrano[3,4-f]quinoline, 2,5-dihydro-10-methoxy-2,2,4-trimethyl-5-[(4,5-dihydro-4,4-dimethyl-2-oxazolyl)methylene]-1H-[1]benzopyrano[3,4-f]quinoline, 2,5-dihydro-10-methoxy-2,2,4-trimethyl-5-(2-pyridinylmethylene)-1H-[1]benzopyrano[3,4-f]quinoline, 2,5-dihydro-10-methoxy-2,2,4-trimethyl-5-(2-thienyl)-1H-[1]benzopyrano[3,4-f]quinoline, 2,5-dihydro-9,10-dimethoxy-2,2,4-trimethyl-5-(2-propenyl)-1H-[1]benzopyrano[3,4-f]quinoline, 5-(2-cyclohexen-1-yl)-2,5-dihydro-9,10-dimethoxy-2,2,4-trimethyl-1H-[1]benzopyrano[3,4-f]quinoline, 2,5-dihydro-10-methoxy-5-(3-methyl-3-butenyl)-2,2,4-trimethyl-1H-[1]benzopyrano[3,4-f]quinoline, 2,5-dihydro-10-methoxy-5-(5,5-dimethyl-3-cyclohexenyl)-2,2,4-trimethyl-1H-[1]benzopyrano[3,4-f]quinoline, rel(5R,2'R)-2,5-dihydro-10-methoxy-5-(2-oxo-3-tetrahydropyranyl)-2,2,4-trimethyl-1H-[1]benzopyrano[3,4-f]quinoline, anti(5R,2'S)-2,5-dihydro-10-methoxy-5-(2-oxo-3-tetrahydropyranyl)-2,2,4-trimethyl-1H-[1]benzopyrano[3,4-f]quinoline, 2,5-dihydro-10-methoxy-5-(3-cyclopentenyl)-2,2,4-trimethyl-1H-[1]benzopyrano[3,4-f]quinoline, 2,5-dihydro-10-methoxy-5-(3-cyclohexenyl)-2,2,4-trimethyl-1H-[1]benzopyrano[3,4-f]quinoline, 2,5-dihydro-10-methoxy-5-(3-butenyl)-2,2,4-trimethyl-1H-[1]

benzopyrano[3,4-f]quinoline, 2,5-dihydro-10-methoxy-5-(1-ethenyl-1-cyclohexyl)-2,2,4-trimethyl-1H-[1]benzopyrano[3,4-f]quinoline, 2,5-dihydro-10-methoxy-5-(4,4-dimethyl-3-cyclohexenyl)-2,2,4-trimethyl-1H-[1]benzopyrano[3,4-f]quinoline, 2,5-dihydro-10-methoxy-5-(1-methylene-2-cyclohexyl)-2,2,4-trimethyl-1H-[1]benzopyrano[3,4-f]quinoline, 2,5-dihydro-10-methoxy-5-(1-oxo-2-cyclohexyl)-2,2,4-trimethyl-1H-[1]benzopyrano[3,4-f]quinoline, 2,5-dihydro-10-methoxy-5-(3-cyclooctenyl)-2,2,4-trimethyl-1H-[1]benzopyrano[3,4-f]quinoline, 2,5-dihydro-10-methoxy-5-(3-cycloheptenyl)-2,2,4-trimethyl-1H-[1]benzopyrano[3,4-f]quinoline, 2,5-dihydro-10-methoxy-5-(1-cyclohexenylmethyl)-2,2,4-trimethyl-1H-[1]benzopyrano[3,4-f]quinoline, 2,5-dihydro-10-methoxy-5-(3,3-dimethyl-6-cyclohexenyl)-2,2,4-trimethyl-1H-[1]benzopyrano[3,4-f]quinoline, 2,5-dihydro-10-methoxy-5-(2-bromo-3-propenyl)-2,2,4-trimethyl-1H-[1]benzopyrano[3,4-f]quinoline, rel(5R,3'R)-2,5-dihydro-10-methoxy-5-(1-hydroxymethyl-3-cyclohexenyl)-2,2,4-trimethyl-1H-[1]benzopyrano[3,4-f]quinoline, rel(5R,3'S)-2,5-dihydro-10-methoxy-5-(1-hydroxymethyl-3-cyclohexenyl)-2,2,4-trimethyl-1H-[1]benzopyrano[3,4-f]quinoline, 2,5-dihydro-10-methoxy-5-(3-hydroxymethyl-3-cyclohexenyl)-2,2,4-trimethyl-1H-[1]benzopyrano[3,4-f]quinoline, 2,5-dihydro-10-methoxy-5-(3-indolyl)-2,2,4-trimethyl-1H-[1]benzopyrano[3,4-f]quinoline, rel(5S,3'S)-2,5-dihydro-10-methoxy-5-(1-methyl-3-cyclohexenyl)-2,2,4-trimethyl-1H-[1]benzopyrano[3,4-f]quinoline, rel(5R,3'S)-2,5-dihydro-10-methoxy-5-(1-methyl-3-cyclohexenyl)-2,2,4-trimethyl-1H-[1]benzopyrano[3,4-f]quinoline, (−)(5S,3'S)-2,5-dihydro-10-methoxy-5-(1-methyl-3-cyclohexenyl)-2,2,4-trimethyl-1H-[1]benzopyrano[3,4-f]quinoline, (−)(5S,3'R)-2,5-dihydro-10-methoxy-5-(1-hydroxymethyl-3-cyclohexenyl)-2,2,4-trimethyl-1H-[1]benzopyrano[3,4-f]quinoline, (+)(5R,3'S)-2,5-dihydro-10-methoxy-5-(1-hydroxymethyl-3-cyclohexenyl)-2,2,4-trimethyl-1H-[1]benzopyrano[3,4-f]quinoline, (−)-(5S,3'R)-2,5-dihydro-10-methoxy-5-(1-methyl-3-cyclohexenyl)-2,2,4-trimethyl-1H-[1]benzopyrano[3,4-f]quinoline, (+)-(5R,3'S)-2,5-dihydro-10-methoxy-5-(1-methyl-3-cyclohexenyl)-2,2,4-trimethyl-1H-[1]benzopyrano[3,4-f]quinoline, 2,5-dihydro-10-methoxy-5-(1-chloromethyl-3-cyclohexenyl)-2,2,4-trimethyl-1H-[1]benzopyrano[3,4-f]quinoline, rel(5R,3'R)-2,5-dihydro-10-methoxy-5-(1-methoxymethyl-3-cyclohexenyl)-2,2,4-trimethyl-1H-[1]benzopyrano[3,4-f]quinoline, rel(5R,3'R)-2,5-dihydro-10-methoxy-5-(1-methylthiomethyl-3-cyclohexenyl)-2,2,4-trimethyl-1H-[1]benzopyrano[3,4-f]quinoline, rel(5R,3'S)-2,5-dihydro-10-methoxy-5-(1-acetoxymethyl-3-cyclohexenyl)-2,2,4-trimethyl-1H-[1]benzopyrano[3,4-f]quinoline, rel(5R,3'R)-2,5-dihydro-10-methoxy-5-(1-acetoxymethyl-3-cyclohexenyl)-2,2,4-trimethyl-1H-[1]benzopyrano[3,4-f]quinoline, rel(5R,3'R)-2,5-dihydro-10-methoxy-5-(1-methoxymethyl-3-cyclohexenyl)-2,2,4-trimethyl-1H-[1]benzopyrano[3,4-f]quinoline, rel(5R,3'R)-2,5-dihydro-10-methoxy-5-(1-(N,N-dimethylamino)methyl-3-cyclohexenyl)-2,2,4-trimethyl-1H-[1]benzopyrano[3,4-f]quinoline, rel(5R,3'S)-2,5-dihydro-10-methoxy-5-(1-methylthiomethyl-3-cyclohexenyl)-2,2,4-trimethyl-1H-[1]benzopyrano[3,4-f]quinoline, rel(5R,3'R)-2,5-dihydro-10-methoxy-5-(1-(N-morpholino)methyl-3-cyclohexenyl)-2,2,4-trimethyl-1H-[1]benzopyrano[3,4-f]quinoline, rel(5R,3'R)-2,5-dihydro-10-methoxy-5-(1-(N-methyl-N-methylsulfonylamino)methyl-3-cyclohexenyl)-2,2,4-trimethyl-1H-[1]benzopyrano[3,4-f]quinoline, rel(5R,3'S)-2,5-dihydro-10-methoxy-5-(1-(N,N-dimethylamino)methyl-3-cyclohexenyl)-2,2,4-trimethyl-1H-[1]benzopyrano[3,4-f]quinoline, rel(5R,3'R)-2,5-dihydro-10-methoxy-5-(1-(N-methylamino)methyl-3-cyclohexenyl)-2,2,4-trimethyl-1H-[1]benzopyrano[3,4-f]quinoline, 2,5-dihydro-10-methoxy-5-(2-methyl-3-propenyl)-2,2,4-trimethyl-1H-[1]benzopyrano[3,4-f]quinoline, 2,5-dihydro-10-methoxy-5-(1,3-butadien-2-yl)-2,2,4-trimethyl-1H-[1]benzopyrano[3,4-f]quinoline, 2,5-dihydro-10-methoxy-5-(2-carbomethoxy-3-propenyl)-2,2,4-trimethyl-1H-[1]benzopyrano[3,4-f]quinoline, 2,5-dihydro-10-methoxy-5-(1,2-dihydroxy-3-propyl)-2,2,4-trimethyl-1H-[1]benzopyrano[3,4-f]quinoline, 2,5-dihydro-10-methoxy-5-(1,2-epoxy-3-propenyl)-2,2,4-trimethyl-1H-[1]benzopyrano[3,4-f]quinoline, 2,5-dihydro-10-methoxy-5-(1-(N-phthalimido)-3-propyl)-2,2,4-trimethyl-1H-[1]benzopyrano[3,4-f]quinoline, 2,5-dihydro-10-methoxy-5-(1-amino-3-propyl)-2,2,4-trimethyl-1H-[1]benzopyrano[3,4-f]quinoline, 2,5-dihydro-10-methoxy-5-(1-(hydrazinocarbonylamino)-3-propyl)-2,2,4-trimethyl-1H-[1]benzopyrano[3,4-f]quinoline, (E)2,5-dihydro-10-methoxy-5-(2-carbomethoxy-1-ethenyl)-2,2,4-trimethyl-1H-[1]benzopyrano[3,4-f]quinoline, (Z)-2,5-dihydro-10-methoxy-5-(1-propenyl)-2,2,4-trimethyl-1H-[1]benzopyrano[3,4-f]quinoline, (E) 2,5-dihydro-10-methoxy-5-(3-hydroxy-1-propenyl)-2,2,4-trimethyl-1H-[1]benzopyrano[3,4-f]quinoline, (E) 2,5-dihydro-10-methoxy-5-(3-(N,N-dimethylaminocarbonyloxy)-1-propenyl)-2,2,4-trimethyl-1H-[1]benzopyrano[3,4-f]quinoline, (E) 2,5-dihydro-10-methoxy-5-(3-methoxymethoxy-1-propenyl)-2,2,4-trimethyl-1H-[1]benzopyrano[3,4-f]quinoline, 2,5-dihydro-10-methoxy-5-(3-hydroxy-3-propenyl)-2,2,4-trimethyl-1H-[1]benzopyrano[3,4-f]quinoline, methyl 2-(2,5-dihydro-10-methoxy-2,2,4-trimethyl-1H-[1]benzopyrano[3,4-]quinolin-5-yl)acetyl hydroxamate, 2-(2,5-dihydro-10-methoxy-2,2,4-trimethyl-1H-[1]benzopyrano[3,4-f]quinolin-5-yl)acetaldehyde, 2,5-dihydro-10-methoxy-5-(2-cyclohexylidenylethyl)-2,2,4-trimethyl-1H-[1]benzopyrano[3,4-f]quinoline, 2,5-dihydro-10-methoxy-5-(2-cyclopentylidenylethyl)-2,2,4-trimethyl-1H-[1]benzopyrano[3,4-f]quinoline, 2,5-dihydro-10-methoxy-5-(2-cycloheptylidenylethyl)-2,2,4-trimethyl-1H-[1]benzopyrano[3,4-f]quinoline, 2,5-dihydro-10-methoxy-5-(3-methyl-2-butenyl)-2,2,4-trimethyl-1H-[1]benzopyrano[3,4-f]quinoline, trans 2,5-dihydro-10-methoxy-5-(2-butenyl)-2,2,4-trimethyl-1H-[1]benzopyrano[3,4-f]quinoline, trans 2,5-dihydro-10-methoxy-5-(2-penten-1-yl)-2,2,4-trimethyl-1H-[1]benzopyrano[3,4-]quinoline, 2,5-dihydro-10-methoxy-5-(1,1-difluoro-1-propen-3-yl)-2,2,4-trimethyl-1H-[1]benzopyrano[3,4-f]quinoline, (E) methyl 2-(2,5-dihydro-10-methoxy-2,2,4-trimethyl-1H-[1]benzopyrano[3,4-f]quinolin-5-yl)2-butenoate, (E) 2,5-dihydro-10-methoxy-5-(4-hydroxy-2-buten-1-yl)-2,2,4-trimethyl-1H-[1]benzopyrano[3,4-f]quinoline, (E) 2,5-dihydro-10-methoxy-5-(4-(N,N-dimethylaminocarbonyloxy)-2-buten-1-yl)-2,2,4-trimethyl-1H-[1]benzopyrano[3,4-f]quinoline, (E) 2,5-dihydro-10-methoxy-5-(4-(N-methylaminocarbonyloxy)-2-buten-1-yl)-2,2,4-trimethyl-1H-[1]benzopyrano[3,4-f]quinoline, (E) 2,5-dihydro-10-methoxy-5-(2-butenyl)-2,2,4-trimethyl-1H-[1]benzopyrano[3,4-f]quinoline, 2,5-dihydro-10-methoxy-5-(2-hydroxyethyl)-2,2,4-trimethyl-1H-[1]benzopyrano[3,4-f]quinoline, 2,5-dihydro-10-methoxy-5-(2-(N-benzylcarbonyloxy)ethyl)-2,2,4-trimethyl-1H-[1]benzopyrano[3,4-f]quinoline, 2,5-dihydro-10-methoxy-5-(2-(N-morpholinocarbonyloxy)ethyl)-2,2,4-trimethyl-1H-[1]benzopyrano[3,4-f]quinoline, 2,5-dihydro-10-methoxy-5-(2-(N-(2-methoxyethyl)aminocarbonyloxy)ethyl)-2,2,4-trimethyl-1H-[1]benzopyrano[3,4-f]quinoline, 2,5-dihydro- 10-methoxy-5-(2(N-methyaminocarbonyloxyoxy)ethyl)-2,2,4-trimethyl-1H-[1]benzopyrano[3,4-f]quinoline, 2,5-dihydro-10-methoxy-5-(2-,N-dimethylaminocarbonyloxy)ethyl)-2,2,4-trimethyl-1H-[1]benzopyrano-[3,4-f]quinoline, 2,5-dihydro-10-methoxy-5-(2-methoxymethoxyethyl)-2,2,4-trimethyl-1H-[1]benzopyrano[3,4-f]quinoline, 2,5-dihydro-10-methoxy-5-(2,2-dimethylethoxycarbonylamino)methyl)-2,2,4-trimethyl-1H-[1]benzopyrano[3,4-f]quinoline, 2,5-dihydro-10-methoxy-5-(aminomethyl)-2,2,4-trimethyl-1H-[1]benzopyrano[3,4-f]quinoline, 2,5-dihydro-10-methoxy-5-(ethoxycarbonylamino)methyl)-2,2,4-trimethyl-1H-[1]benzopyrano[3,4-f]quinoline, 2,5-dihydro-10-methoxy-5-(carboethoxy)-2,2,4-trimethyl-1H-[1]benzopyrano[3,4-f]quinoline, 2,5-dihydro-10-methoxy-5-(cyclopentyl)-2,2,4-trimethyl-1H-[1]benzopyrano[3,4-f]quinoline, 2,5-dihydro-10-methoxy-5-(1-methylpropa-1,2-dienyl)-2,2,4-trimethyl-1H-[1]benzopyrano[3,4-f]quinoline, 2,5-dihydro-10-methoxy-5-(3,4,5-trifluorophenyl)-2,2,4-trimethyl-1H-[1]benzopyrano[3,4-f]quinoline, 2,5-dihydro-10-methoxy-5-(cyclohexyl)-2,2,4-trimethyl-1H-[1]benzopyrano[3,4-f]quinoline, 2,5-dihydro-10-methoxy-5-(2-pyridyl)-2,2,4-trimethyl-1H-[1]benzopyrano[3,4-f]quinoline, 2,5-dihydro-10-methoxy-5-(3-pyridyl)-2,2,4-trimethyl-1H-[1]benzopyrano[3,4-f]quinoline, 2,5-dihydro-10-methoxy-5-(4-pyridyl)-2,2,4-trimethyl-1H-[1]benzopyrano[3,4-f]quinoline, (10-chloro-9-hydroxy-5-(3-propenyl)-2,2,4-trimethyl-1H-2,5-dihydro-[1]benzopyrano[3,4-f]benzopyrano[3,4-f]quinoline, 10-chloro-9-hydroxy-5-phenyl-2,2,4-trimethyl-1H-2,5-dihydro-[1]benzopyrano[3,4-f]quinoline, 10-chloro-9-hydroxy-5-(3-trifluoromethylphenyl)-2,2,4-trimethyl-1H-2,5-dihydro[1]benzopyrano[3,4-f]quinoline, 10-chloro-9-hydroxy-5-(3,5-dimethylphenyl)-2,2,4-trimethyl-1H-2,5-dihydro[1]benzopyrano[3,4-f]quinoline, rel-(5S,3'R)-9-hydroxy-10-methoxy-5-[1-hydroxymethyl-3-cyclohexenyl]-2,2,4-trimethyl-2,5-dihydro-1H-[1]benzopyrano[3,4-f]quinoline, (−)2,5(S)-dihydro-9-hydroxy-10-chloro-2,2,4-trimethyl-5-(3S-cyclopentenyl)-1H-[1]benzopyrano[3,4-f]quinoline, (−)2,5(S)-4-dihydro-9-hydroxy-10-chloro-2,2,4-trimethyl-5-(3R-cyclopentenyl)-1H-[1]benzopyrano[3,4-f]quinoline, 10-chloro-9-hydroxy-5-(3,5-dichlorophenyl)-2,2,4-trimethyl-1H-2,5-dihydro[1]benzopyrano[3,4-f]quinoline, (+)-(5R,3'S)-2,5-dihydro-9-hydroxy-10-chloro-2,2,4-trimethyl-5-(3-cyclopentenyl)-1H-[1]benzopyrano[3,4-f]quinoline, (+)-(5R,3'R)-2,5-dihydro-9-hydroxy-10-chloro-2,2,4-trimethyl-5-(3-cyclopentenyl)-1H-[1]benzopyrano[3,4-f]quinoline, 10-chloro-9-hydroxy-5-(3,4-difluorophenyl)-2,2,4-trimethyl-1H-2,5-dihydro[1]benzopyrano[3,4-f]quinoline, 9-10-methylenedioxy-5-phenyl-2,2,4-trimethyl-1H-2,5-dihydro-[1]benzopyrano[3,4-f]quinoline, 5-(3-propenyl)-9-chloro-10-ethenyl-2,2,4-trimethyl-2,5-dihydro-1H-[1]benzopyrano[3,4-f]quinoline, 9-chloro-10-methoxy-5-phenyl-2,2,4-trimethyl-2,5-dihydro-1H-[1]benzopyrano[3,4-f]quinoline, 5-(3-propenyl)-9-chloro-10-difluoromethoxy-2,2,4-trimethyl-2,5-dihydro-1H-[1]benzopyrano[3,4-f]quinoline, 9-chloro-10-difluoromethoxy-5-phenyl-2,2,4-trimethyl-2,5-dihydro-1H-[1]benzopyrano[3,4-f]quinoline, 8-fluoro-10-methoxy-5-phenyl-2,2,4-trimethyl-2,5-dihydro-1H-[1]benzopyrano[3,4-f]quinoline, 5-(3-propenyl)-8-fluoro-10-methoxy-2,2,4-trimethyl-2,5-dihydro-1H-[1]benzopyrano[3,4-f]quinoline, (10-methoxy-9-fluoro-5-(3-propenyl)-2,2,4-trimethyl-1H-2,5-dihydro-[1]benzopyrano[3,4-f]quinoline, 10-methoxy-9-hydroxy-5-(3-propenyl)-2,2,4-trimethyl-1H-2,5-dihydro[1]benzopyrano[3,4-f]quinoline, (+/−)2,5-dihydro-9-hydroxy-10-methoxy-2,2,4-trimethyl-5-(3-cyclohexenyl)-1H-[1]benzopyrano[3,4-f]quinoline, (+/−)2,5-dihydro-9-hydroxy-10-methoxy-2,2,4-trimethyl-5-(1-methylcyclohexen-3-yl)-1H-[1]benzopyrano[3,4-f]quinoline, (−)(5S,3'S)-9-hydroxy-5-[1-methyl-3-cyclohexenyl]-10-methoxy-2,2,4-trimethyl-2,5-dihydro-1H-[1]benzopyrano[3,4-f]quinoline, (+)(5R,3'R)-9-hydroxy-5-[1-methyl-3-cyclohexenyl]-10-methoxy-2,2,4-trimethyl-2,5-dihydro-1H-[1]benzopyrano[3,4-f]quinoline, (+)(5R,3'S)-9-hydroxy-5-[1-methyl-3-cyclohexenyl]-10-methoxy-2,2,4-trimethyl-2,5-dihydro-1H-[1]benzopyrano[3,4-f]quinoline, (−)(5S,3'R)-9-hydroxy-5-[1-methyl-3-cyclohexenyl]-10-methoxy-2,2,4-trimethyl-2,5-dihydro-1H-[1]benzopyrano[3,4-f]quinoline, rel-(5S,3'R)-9-hydroxy-5-[1-hydroxymethyl-3-cyclohexenyl]-10-methoxy-2,2,4-trimethyl-2,5-dihydro-1H-[1]benzopyrano[3,4-f]quinoline, (+/−)(5S,3'R)-2,5-dihydro-9-hydroxy-10-methoxy-2,2,4-trimethyl-5-(1-methylcyclohexen-3-yl)-1H-[1]benzopyrano[3,4-f]quinoline, rel-(5S,3'R)-9-hydroxy-5-[1-methoxymethyl-3-cyclohexenyl]-10-methoxy-2,2,4-trimethyl-2,5-dihydro-1H-[1]benzopyrano[3,4-f]quinoline, 2,5-dihydro-9-hydroxy-10-methoxy-5-propyl-2,2,4-trimethyl-1H-[1]benzopyrano[3,4-f]quinoline, (−)(5S,3'S)-2,5-dihydro-9-hydroxy-10-methoxy-2,2,4-trimethyl-5-(3-cycloheptenyl)-1H-[1]benzopyrano[3,4-f]quinoline, (−)(5S,3'R)-2,5-dihydro-9-hydroxy-10-methoxy-2,2,4-trimethyl-5-(3-cycloheptenyl)-1H-[1]benzopyrano[3,4-f]quinoline, 2,5-dihydro-9-hydroxy-10-methoxy-2,2,4-trimethyl-5-phenyl-1H-[1]benzopyrano[3,4-f]quinoline, 2,5-dihydro-9-hydroxy-10-methoxy-2,2,4-trimethyl-5-(3,5-difluorophenyl)-1H-[1]benzopyrano[3,4-f]quinoline, 2,5-dihydro-9-hydroxy-10-methoxy-2,2,4-trimethyl-5-(3,4,5-trifluorophenyl)-1H-[1]benzopyrano[3,4-f]quinoline, 5-butyl-2,5-dihydro-9-hydroxy-10-methoxy-2,2,4-trimethyl-1H-[1]benzopyrano[3,4-f]quinoline, (−)(5S,3'S)-2,5-dihydro-9-hydroxy-10-methoxy-2,2,4-trimethyl-5-(3-cyclopentenyl)-1H-[1]benzopyrano[3,4-f]quinoline, (−)(5S,3'R)-2,5-dihydro-9-hydroxy-10-methoxy-2,2,4-trimethyl-5-(3-cyclopentenyl)-1H-[1]benzopyrano[3,4-f]quinoline, 2,5-dihydro-9-hydroxy-10-methoxy-2,2,4-trimethyl-5-(3,4-difluorophenyl)-1H-[1]benzopyrano[3,4-f]quinoline, 2,5-dihydro-9-hydroxy-10-methoxy-2,2,4-trimethyl-5-(4-fluorophenyl)-1H-[1)benzopyrano[3,4-f]quinoline, 2,5-dihydro-9-hydroxy-10-methoxy-2,2,4-trimethyl-5-(3-trifluoromethylphenyl)-1H-[1]benzopyrano[3,4-f]quinoline, 2,5-dihydro-9-hydroxy-10-methoxy-2,2,4-trimethyl-5-(3-5-bistrifluoromethylphenyl)-1H-[1]benzopyrano[3,4-f]quinoline, 2,5-dihydro-9-hydroxy-10-methoxy-2,2,4-trimethyl-5-(3-trifluoromethylchlorophenyl)-1H-[1]benzopyrano[3,4-f]quinoline, 2,5-dihydro-9-hydroxy-10-methoxy-2,2,4-trimethyl-5-(2-methylpropyl)-1H-[1]benzopyrano[3,4-f]quinoline, 2,5-dihydro-9-hydroxy-1-methoxy-2,2,4-trimethyl-5-(3-fluoro-4-chlorophenyl)-1H-[1]benzopyrano[3,4-f]quinoline, 2,5-dihydro-9-hydroxy-10-methoxy-2,2,4-trimethyl-5-(3-butenyl)-1H-[1]benzopyrano[3,4-f]quinoline, 2,5-dihydro-9-hydroxy-10-methoxy-5-(phenylmethyl)-2,2,4-trimethyl-1H-[1]benzopyrano[3,4-f]quinoline, (−)(5S,3'R)2,5-dihydro-9-hydroxy-10-methoxy-2,2,4-trimethyl-5-[1-ethyl-3-cyclohexexyl]-1H-[1]benzopyrano[3,4-f]quinoline, (−)(S) 5-cyclopentyl-2,5-dihydro-9-hydroxy-10-methoxy-2,2,4-trimethyl-1H-[1]benzopyrano[3,4-f]quinoline, (+)(R) 5-cyclopentyl-2,5-dihydro-9-hydroxy-10-methoxy-2,2,4-trimethyl-1H-[1]benzopyrano[3,4-f]quinoline, 2,5-dihydro-9-hydroxy-10-methoxy-5-(3-propynyl)-2,2,4-trimethyl-1H-[1]benzopyrano[3,4-f]quinoline, 2,5-dihydro-9-hydroxy-10-methoxy-2,2,4-trimethyl-5-(2-propyl)-1H-[1]benzopyrano[3,4-f]quinoline, 2,5-dihydro-9-hydroxy-10-methoxy-2,2,4-trimethyl-5-(5-methoxy-2-thienyl)-1H-[1]benzopyrano[3,4- f]quinoline, (±)2,5-dihydro-9-hydroxy-10-methoxy-2,2,4-trimethyl-5-(2,3,4,5,6-pentafluorophenyl)-1H-[1]benzopyrano[3,4-f]quinoline, (+/−)2,5-dihydro-9-hydroxy-10-methoxy-2,2,4-trimethyl-5(S)-(3(S)-1-hydroxymethylcyclopenten-3-yl)-1H-[1]benzopyrano[3,4-f]quinoline, (+/−)2,5-dihydro-9-hydroxy-10-methoxy-2,2,4-trimethyl-5(S)-(3(S)-1-methylcarboxylatecyclopenten-3-yl)-1H-[1]benzopyrano[3,4-f]quinoline, (−)(5S,3'S)2,5-dihydro-9-hydroxy-10-methoxy-2,2,4-trimethyl-5-(3-cyclohexenyl)-1H-[1]benzopyrano[3,4-f]quinoline, (−)(5S,3'R)-2,5-dihydro-9-hydroxy-10-methoxy-2,2,4-trimethyl-5-(3-cyclohexenyl)-1H-[1]benzopyrano[3,4-f]quinoline, 2,5-dihydro-9-hydroxy-10-methoxy-2,2,4-trimethyl-5-(2-thienyl)-1H-[1]benzopyrano[3,4-f]quinoline, (±)2,5-dihydro-9-hydroxy-10-methoxy-2,2,4-trimethyl-5-(2-methylphenyl)-1H-[1]benzopyrano[3,4-f]quinoline, 2,5-dihydro-9-hydroxy-10-methoxy-2,2,4-trimethyl-5-(2-acetoxymethyl-3-propenyl)-1H-[1]benzopyrano[3,4-f]quinoline, (+)(5R,3'S)2,5-dihydro-9-hydroxy-10-methoxy-2,2,4-trimethyl-5-[1-ethyl-3-cyclohexenyl]-1H-[1]benzopyrano[3,4-f]quinoline, 2,5-dihydro-9-hydroxy-10-methoxy-2,2,4-trimethyl-5-cyclohexyl-1H-[1]benzopyrano[3,4-f]quinoline, 2,5,5-trihydro-9-hydroxy-10-methoxy-2,2,4-trimethyl-1H-[1]benzopyrano[3,4-f]quinoline, 2,5-dihydro-9-hydroxy-10-methoxy-2,2,4-trimethyl-5-(2-hydroxymethyl-3-propenyl)-1H-[1]benzopyrano[3,4-f]quinoline, methyl 2-[2,5-dihydro-9-hydroxy-10-methoxy-2,2,4-trimethyl-1H-[1]benzopyrano[3,4-f]-5-quinolinyl]acetate, (Z) 2,5-dihydro-9-hydroxy-10-methoxy-2,2,4-trimethyl-5-(2-butenyl)-1H-[1]benzopyrano[3,4-f]quinoline, 2,5-dihydro-9-hydroxy-10-methoxy-2,2,4-trimethyl-5-(3-methyl-2-butenyl)-1H-[1]benzopyrano[3,4-f]quinoline, (+)(5S,3'S)2,5-dihydro-9-hydroxy-10-methoxy-2,2,4-trimethyl-5-(3-cyclohexenyl)-1H-[1]benzopyrano[3,4-f]quinoline, (+)(5R,3'R)2,5-dihydro-9-hydroxy-10-methoxy-2,2,4-trimethyl-5-(3-cyclohexenyl)-1H-[1]benzopyrano[3,4-f]quinoline, (+)(5R,3'S)2,5(R)-dihydro-9-hydroxy-10-methoxy-2,2,4-trimethyl-5-(3-cyclopentenyl)-1H-[1]benzopyrano[3,4-f]quinoline, (+)(5R,3'R)2,5(R)-dihydro-9-hydroxy-10-methoxy-2,2,4-trimethyl-5-(3-cyclopentenyl)-1H-[1]benzopyrano[3,4-f]quinoline, rel-(5S)-9-hydroxy-5-[(3R)-(1-methoxycarbonyl)cyclohexen-3-yl]-10-methoxy-2,2,4-trimethyl-2,5-dihydro-1H-[1]benzopyrano[3,4-f]quinoline, 2,5-dihydro-9-hydroxy-10-methoxy-2,2,4-trimethyl-5-(2-methyl-3-propenyl)-1H-[1]benzopyrano[3,4-f]quinoline, 9,10-Dimethoxy-5-(3-propenyl)-2,2,4-trimethyl-2,5-dihydro-1H-[1]benzopyrano[3,4-f]quinoline, 9,10-Dimethoxy-5-[3-cyclohexenyl]-methoxy-2,2,4-trimethyl-2,5-dihydro-1H-[1]benzopyrano[3,4-f]quinoline, 10-methoxy-9-ethoxy-5-(3-propenyl)-2,2,4-trimethyl-1H-2,5-dihydro[1]benzopyrano[3,4-f]quinoline, 10-methoxy-9-(3-propenyloxy)-5-(3-propenyl)-2,2,4-trimethyl-1H-2,5dihydro-[1]benzopyrano[3,4-f]quinoline, 10-methoxy-9-(3-propynyloxy)-5-(3-propenyl)-2,2,4-trimethyl-1H-2,5-dihydro-[1]benzopyrano[3,4-f]quinoline, 2,5-dihydro-9-acetoxy-10-methoxy-2,2,4-trimethyl-5-(2-propenyl)-1H-[1]benzopyrano[3,4-f]quinoline, 2,5-dihydro-9-(4-N,N-dimethylamino-4-oxobutanoyloxy)-10-methoxy-2,2,4-trimethyl-5-(2-propenyl)-1H-[1]benzopyrano[3,4-f]quinoline, 7-bromo-5-[3-cyclohexenyl]-10-methoxy-2,2,4-trimethyl-2,5-dihydro-1H-[1]benzopyrano[3,4-f]quinoline, 10-methoxy-7-bromo-5-(3-propenyl)-2,2,4-trimethyl-1H-2,5-dihydro-[1]benzopyrano[3,4-f]quinoline, 7-bromo-5-[1-methyl-3-cyclohexenyl]-10-methoxy-2,2,4-trimethyl-2,5-dihydro-1H-[1]benzopyrano[3,4-f]quinoline, 10-methoxy-9-bromo-5-(3-propenyl)-2,2,4-trimethyl-1H-2,5-dihydro-[1]benzopyrano[3,4-f]quinoline, 7,9-Dibromo-10-methoxy-5-(3-propenyl)-2,2,4-trimethyl-1H-2,5-dihydro-[1]benzopyrano[3,4-f]quinoline, 7,9-Dibromo-5-[cyclohexen-3-yl]-10-methoxy-2,2,4-trimethyl-2,5-dihydro-1H-[1]benzopyrano[3,4-f]quinoline, 7,9-Dibromo-5-[1-methyl-3-cyclohexenyl]-10-methoxy-2,2,4-trimethyl-2,5-dihydro-1H-[1]benzopyrano[3,4-f]quinoline, 10-methoxy-7-(2-ethenyl)-5-(3-propenyl)-2,2,4-trimethyl-1H-2,5-dihydro-[1]benzopyrano[3,4-f]quinoline, 10-methoxy-7-methyl-5-(3-propenyl)-2,2,4-trimethyl-1H-2,5-dihydro-[1]benzopyrano[3,4-f]quinoline, 10-methoxy-7-acetyl-5-(3-propenyl)-2,2,4-trimethyl-1H-2,5-dihydro-[1]benzopyrano[3,4-f]quinoline, (+/−)2,5-dihydro-9-methyl-10-methoxy-2,2,4-trimethyl-5-(1-methylcyclohexen-3-yl)-1H-[1]benzopyrano[3,4-f]quinoline, 10-methoxy-7-methyl-9-methyl-5-(3-propenyl)-2,2,4-trimethyl-1H-2,5-dihydro-[1]benzopyrano[3,4-f]quinoline, 10-chloro-5-(3-propenyl)-2,2,4-trimethyl-2,5-dihydro-1H-[1]benzopyrano[3,4-f]quinoline, (+/−)2,5-dihydro-10-dichloro-2,2,4-trimethyl-5-phenyl-1H-[1]benzopyrano[3,4-f]quinoline, 2,5-dihydro-10-methoxy-5-(3-(N-methyl-N-carbomethoxymethyl)aminocarbonyloxy)phenyl)-2,2,4-trimethyl-1H-[1]benzopyrano[3,4-f]quinoline, 2,5-dihydro-10-methoxy-5-(3-(N-methyl-N-(N-methylcarbonyl)aminocarbonyloxy)phenyl)-2,2,4-trimethyl-1H-[1]benzopyrano[3,4-f]quinoline, 2,5-dihydro-10-methoxy-5-(3-(N-methylaminocarbonyloxy)phenyl)-2,2,4-trimethyl-1H-[1]benzopyrano[3,4-f]quinoline, 2,5-dihydro-10-methoxy-5-(3-(2-hydroxyethyl)phenyl)-2,2,4-trimethyl-1H-[1]benzopyrano[3,4-f]quinoline, 2,5-dihydro-10-methoxy-5-(3-(2-methanesulfonyloxyethyl)phenyl)-2,2,4-trimethyl-1H-[1]benzopyrano[3,4-f]quinoline, 2,5-dihydro-10-methoxy-5-(3-(2-methythioethyl)phenyl)-2,2,4-trimethyl-1H-[1]benzopyrano[3,4-f]quinoline, 2,5-dihydro-10-methoxy-5-(3-(2-(N,N-dimethylaminocarbonyloxy)ethyl)phenyl)-2,2,4-trimethyl-1H-[1]benzopyrano[3,4-f]quinoline, 2,5-dihydro-10-methoxy-5-(3-(2-(N,N-dimethylamino)ethyl)phenyl)-2,2,4-trimethyl-1H-[1]benzopyrano[3,4-f]quinoline, 2,5-dihydro-10-methoxy-5-cyclopropyl-2,2,4-trimethyl-1H-[1]benzopyrano[3,4-f]quinoline, 2,5-dihydro-10-methoxy-5-ethenyl-2,2,4-trimethyl-1H-[1]benzopyrano[3,4-f]quinoline, trans 2,5-dihydro-10-methoxy-5-(2-phenylethenyl)-2,2,4-trimethyl-1H-[1]benzopyrano[3,4-f]quinoline, 2,5-dihydro-10-methoxy-5-(2-phenylethynyl)-2,2,4-trimethyl-1H-[1]benzopyrano[3,4-f]quinoline, cis 2,5-dihydro-10-methoxy-5-(2-phenylethenyl)-2,2,4-trimethyl-1H-[1]benzopyrano[3,4-f]quinoline, 2,5-dihydro-10-methoxy-5-(2-methylpropenyl)-2,2,4-trimethyl-1H-[1]benzopyrano[3,4-f]quinoline, trans 2,5-dihydro-10-methoxy-5-(1-cyclohexenyl)-2,2,4-trimethyl-1H-[1]benzopyrano[3,4-f]quinoline, 2,5-dihydro-10-(2-furanyl)-5-(3-propenyl)-2,2,4-trimethyl]-1H-[1]benzopyrano[3,4-f]quinoline, 2,5-dihydro-10-cyano-5-(3-propenyl)-2,2,4-trimethyl-1H-[1]benzopyrano[3,4-f]quinoline, 2,5-dihydro-10-carboxy-5-(3-propenyl)-2,2,4-trimethyl-1H-[1]benzopyrano[3,4-f]quinoline, 2,5-dihydro-10-(2-hydroxymethyl-5-(3-propenyl)-2,2,4-trimethyl-1H-[1]benzopyrano[3,4-f]quinoline, 2,5-dihydro-10-formyl-5-(3-propenyl)-2,2,4-trimethyl-1H-[1]benzopyrano[3,4-f]quinoline, 2,5-dihydro-10-aminomethyl-5-(3-propenyl)-2,2,4-trimethyl-1H-[1]benzopyrano[3,4-f]quinoline, 2,5-dihydro-10-methoxymethyl-5-(3-propenyl)-2,2,4-trimethyl-1H-[1]benzopyrano[3,4-f]quinoline, 2,5-dihydro-10-ethenyl-5-phenyl-2,2,4-trimethyl-1H-[1]benzopyrano[3,4-f]quinoline, 2,5-dihydro-10-ethynyl-5-phenyl-2,2,4-trimethyl-1H-[1]benzopyrano[3,4-f]quinoline, methyl 2,5-dihydro-5-phenyl-2,2,4-trimethyl-1H-[1]benzopyrano[3,4-f]quinoline-10- carboxylate, 2,5-dihydro-10-(hydroxymethyl)-5-phenyl-2,2,4-trimethyl-1H-[1]benzopyrano[3,4-f]quinoline, 2,5-dihydro-10-formyl-5-phenyl-2,2,4-trimethyl-1H-[1]benzopyrano[3,4-f]quinoline, 2,5-dihydro-10-(methoxymethyl)-5-phenyl-2,2,4-trimethyl-1H-[1]benzopyrano[3,4-f]quinoline, 2,5-dihydro-10-ethenyl-5-oxo-2,2,4-trimethyl-1H-[1]benzopyrano[3,4-f]quinoline, 5-(3-cyclohexenyl)-2,5-dihydro-10-ethenyl-2,2,4-trimethyl-1H-[1]benzopyrano[3,4-f]quinoline, 2,5-dihydro-10-ethenyl-5-[1-methyl-3-cyclohexenyl]-2,2,4-trimethyl-1H-[1]benzopyrano[3,4-f]quinoline, 2,5-dihydro-5-(3-propenyl)-10-methylthio-2,2,4-trimethyl-1H-[1]benzopyrano[3,4-f]quinoline, 2,5-dihydro-5-(3-propenyl)-10-methylthio-2,2,4-trimethyl-1H-[1]benzopyrano[3,4-f]quinoline, (+/−)2,5-dihydro-9-(4-acetamidobutanoyloxy)-10-methoxy-2,2,4-trimethyl-5-allyl-1H-[1]benzopyrano[3,4-f]quinoline, 10-(difluoromethoxy)-2,5-dihydro-5-phenyl-2,2,4-trimethyl-1H-[1]benzopyrano[3,4-f]quinoline, 10-(bromodifluoromethoxy)-2,5-dihydro-5-phenyl-2,2,4-trimethyl-1H-[1]benzopyrano[3,4-f]quinoline, 10-(bromodifluoromethoxy)-5-phenyl-2,2-dimethyl-4-methylene-2,3,4,5-tetrahydro-1H-chromeno[3,4-f]quinoline, 2,5-dihydro-9-hydroxy-10-methoxy-2,2,4-trimethyl-5-((2-fluorophenyl)methyl)-1H-[1]benzopyrano[3,4-f]quinoline, 10-methoxy-5-(5-methylisoxazol-3-yl)methyidene-2,5-dihydro-5-phenyl-2,2,4-trimethyl-1H-[1]benzopyrano[3,4-f]quinoline, 10-methoxy-5-(3-methylisoxazol-5-yl)methyidene-2,5-dihydro-5-phenyl-2,2,4-trimethyl-1H-[1]benzopyrano[3,4-f]quinoline, 10-methoxy-5-(4,5-dimethyl-1,3-oxazol-2-yl)methyidene-2,5-dihydro-5-phenyl-2,2,4-trimethyl-1H-[1]benzopyrano[3,4-f]quinoline, 10-methoxy-5-(6-chloropyridin-2-yl)methyidene-2,5-dihydro-5-phenyl-2,2,4-trimethyl-1H-[1]benzopyrano[3,4-f]quinoline, 10-methoxy-5-(pyridin-2-yl)methyidene-2,5-dihydro-5-phenyl-2,2,4-trimethyl-1H-[1]benzopyrano[3,4-f]quinoline, 10-methoxy-5-(but-3-enylidene)-2,5-dihydro-5-phenyl-2,2,4-trimethyl-1H-[1]benzopyrano[3,4-f]quinoline, 10-methoxy-5-(1-methylpropylidene)-2,5-dihydro-5-phenyl-2,2,4-trimethyl-1H-[1]benzopyrano[3,4-f]quinoline, 10-methoxy-5-(1-butylidene)-2,5-dihydro-5-phenyl-2,2,4-trimethyl-1H-[1]benzopyrano[3,4-f]quinoline, 2,5-dihydro-10-methoxy-2,2,4-trimethyl-3-oxide-5-phenyl-1H-[1]benzopyrano[3,4-f]quinazoline, 2,5-dihydro-10-methoxy-2,2,4-trimethyl-5-phenyl-1H-[1]benzopyrano[3,4-f]quinazoline, 2,5-dihydro-10-methoxy-2,2-[spiro(tetrahydro-4-pyranyl)]4-methyl-5-allyl-1H-[1]benzopyrano[3,4-f]quinoline, 2,5-dihydro-10-methoxy-2,2-[spiro(hexyl)]-5-allyl-1H-[1]benzopyrano[3,4-f]quinoline, 2,5-dihydro-10-methoxy-2,2-diethyl-4-methyl-5-allyl-1H-[1]benzopyrano[3,4-f]quinoline, 2,5-dihydro-10-methoxy-2,2,3,4-tetramethyl-5-allyl-1H-[1]benzopyrano[3,4-f]quinoline, 2,5-dihydro-10-methoxy-2,2-dimethyl-4-ethyl-5-allyl-1H-[1]benzopyrano[3,4-f]quinoline, 2,5-dihydro-10-methoxy-2,2,3-trimethyl-5-allyl-1H-[1]benzopyrano[3,4-f]quinoline, Z-5-(benzylidenyl)-9-hydroxy-10-methoxy-2,2,4-trimethyl-1H-2,5-dihydro-[1]benzopyrano[3,4-f]quinoline, Z-5-(2,5-difluorobenzylidenyl)-9-hydroxy-10-methoxy-2,2,4-trimethyl-1H-2,5-dihydro-[1]benzopyrano[3,4-f]quinoline, Z-5-(3-fluorobenzylidenyl)-10-chloro-9-hydroxy-2,2,4-trimethyl-2,5-dihydro-1H-[1]benzopyrano[3,4-f]quinoline, Z-10-chloro-9-hydroxy-5-(2-picolinylidenyl)-2,2,4-trimethyl-2,5-dihydro-1H-[1]benzopyrano[3,4-f]quinoline, Z-9-hydroxy-10-methoxy-5-(2-picolinylidenyl)-2,2,4-trimethyl-2,5-dihydro-1H-[1]benzopyrano[3,4-f]quinoline, 9-hydroxy-10-methoxy-5-(3,5-difluorophenyl)methylidene-2,5-dihydro-5-phenyl-2,2,4-trimethyl-1H-[1]benzopyrano[3,4-f]quinoline, 9-hydroxy-10-methoxy-5-(3,4-difluorophenyl)methylidene-2,5-dihydro-5-phenyl-2,2,4-trimethyl-1H-[1]benzopyrano[3,4-f]quinoline, (Z) 9-hydroxy-10-methoxy-5-((4-fluorophenyl)methylene)-2,2,4-trimethyl-1H-2,5-dihydro-[1]benzopyrano[3,4-f]quinoline, (Z)-9-hydroxy-10-methoxy-5-([2,3-difluorophenyl]methylene)-2,2,4-trimethyl-1H-2,5-dihydro-[1]benzopyrano[3,4-f]quinoline, Z-5-(3-fluorobenzylidenyl)-10-methoxy-9-hydroxy-2,2,4-trimethyl-2,5-dihydro-1H-[1]benzopyrano[3,4-f]quinoline, rel-(5S,3'R)-9-hydroxy-5-[1-methoxymethyl-3-cyclohexenyl]-10-chloro-2,2,4-trimethyl-2,5-dihydro-1H-[1]benzopyrano[3,4-f]quinoline, 9-hydroxy-10-methoxy-5-ethyl-2,2,4-trimethyl-2,5-dihydro-1H-[1]benzopyrano[3,4-f]quinoline, (+/−)2,5-dihydro-9-cyanomethoxy-10-methoxy-2,2,4-trimethyl-5-allyl-1H-[1]benzopyrano[3,4-f]quinoline, 2,5-dihydro-9-(4-N,N-diethylamino-4-oxo-butanoyloxy)-10-methoxy-2,2,4-trimethyl-5-(2-propenyl)-1H-[1]benzopyrano[3,4-f]quinoline, 2,5-dihydro-9-(4-N-piperidino-4-oxo-butanoyloxy)-10-methoxy-2,2,4-trimethyl-5-(2-propenyl)-1H-[1]benzopyrano[3,4-f]quinoline, 2,5-dihydro-9-(4-N-morpholino-4-oxo-butanoyloxy)-10-methoxy-2,2,4-trimethyl-5-(2-propenyl)-1H-[1]benzopyrano[3,4-f]quinoline, 2,5-dihydro-9-(4-N,N-dimethylamino-4-oxo-butanoyloxy)-10-methoxy-2,2,4-trimethyl-5-(3,4,5-trifluorophenyl)-1H-[1]benzopyrano[3,4-f]quinoline, 2,5-dihydro-9-hydroxy-10-methoxy-2,2,4-trimethyl-5-(3-5-difluorophenylmethyl)-1H-[1]benzopyrano[3,4-f]quinoline, 2,5-dihydro-9-hydroxy-10-chloro-2,2,4-trimethyl-5-(2-thienyl)-1H-[1]benzopyrano[3,4-f]quinoline, 2,5-dihydro-9-hydroxy-10-methoxy-2,2,4-trimethyl-5-cyclopentyl-1H-[1]benzopyrano[3,4-f]quinoline, 2,5-dihydro-9-hydroxy-10-methoxy-2,2,4-trimethyl-5-((2-fluorophenyl)methyl)-1H-[1]benzopyrano[3,4-f]quinoline, 2,5-dihydro-9-hydroxymethyl-10-methoxy-2,2,4-trimethyl-5-allyl-1H-[1]benzopyrano[3,4-f]quinoline, 2,5-dihydro-9-hydroxy-10-methoxy-2,2,4-trimethyl-5-(1-pentenyl)-1H-[1]benzopyrano[3,4-f]quinoline, 2,5-dihydro-9-methylcarboxylate-10-methoxy-2,2,4-trimethyl-5-allyl-1H-[1]benzopyrano[3,4-f]quinoline, 2,5-dihydro-9-hydroxy-10-methoxy-2,2,4-trimethyl-5-allenyl-1H-[1]benzopyrano[3,4-f]quinoline, (−)(5S,3'S)2,5-dihydro-10-methoxy-2,2,4-trimethyl-5-(cyclopenten-3-yl)-1H-[1]benzopyrano[3,4-f]quinoline, (−)(5S,3'S)2,5-dihydro-10-methoxy-2,2,4-trimethyl-5-(cyclohexen-3-yl)-1H-[1]benzopyrano[3,4-f]quinoline, (−)(5S,3'R)2,5-dihydro-10-methoxy-2,2,4-trimethyl-5-(cyclohexen-3-yl)-1H-[1]benzopyrano[3,4-f]quinoline, (−)(5S,3'R)2,5-dihydro-10-methoxy-2,2,4-trimethyl-5-(cyclopenten-3-yl)-1H-[1]benzopyrano[3,4-f]quinoline, 2,5-dihydro-9-hydroxy-10-methoxy-2,2,4-trimethyl-5-(3(Z)-pentenyl)-1H-[1]benzopyrano[3,4-f]quinoline, 2,5-dihydro-9-hydroxy-10-methoxy-2,2,4-trimethyl-5-(3-acetoxyphenyl)-1H-[1]benzopyrano[3,4-f]quinoline, 10-difluoromethoxy-5-[[3-(methylthio)methoxylphenyl]-2,2,4-trimethyl-1H-2,5-dihydro-[1]benzopyrano[3,4-f]quinoline, 2,5-dihydro-7-bromo-9-hydroxy-10-chloro-2,2,4-trimethyl-5-allyl-1H-[1]benzopyrano[3,4-f]quinoline, 2,5-dihydro-9-hydroxy-10-methoxy-2,2,4-trimethyl-5-(3-hydroxyphenyl)-1H-[1]benzopyrano[3,4-f]quinoline, 2,5-dihydro-9-methylthiomethoxy-10-methoxy-2,2,4-trimethyl-5-(3(methylthio)methoxyphenyl)-1H-[1]benzopyrano[3,4-f]quinoline, 2,5-dihydro-9-hydroxy-10-methoxy-2,2,4-trimethyl-5-(3-(methylthiomethoxy)phenyl)-1H-[1]benzopyrano[3,4-f]quinoline, 9-hydroxy-10-chloro-5-(phenylmethylene)-2,2,4-trimethyl-1H-2,5-dihydro-[1]benzopyrano[3,4-f]quinoline, 2,5-dihydro-9-hydroxy-10- methoxy-2,2,4-trimethyl-5-([2-N,N-dimethylcarbamoyloxy]phenyl)-1H-[1]benzopyrano[3,4-f]quinoline, 2,5-dihydro-9-N,N-dimethylcarbamoyloxy-10-methoxy-2,2,4-trimethyl-5-([2-N,N-dimethylcarbamoyloxy]phenyl)-1H-[1]benzopyrano[3,4-f]quinoline, 2,5-dihydro-9-hydroxy-10-chloro-2,2,4-trimethyl-5-ethyl-1H-[1]benzopyrano[3,4-f]quinoline, 2,5-dihydro-9-hydroxy-10-chloro-2,2,4-trimethyl-5-isopropyl-1H-[1]benzopyrano[3,4-f]quinoline, 9-hydroxy-10-methoxy-5-(phenylmethylene)-2,2,4-trimethyl-1H-2,5-dihydro-[1]benzopyrano[3,4-f]quinoline, 2,5-dihydro-9-hydroxy-10-chloro-2,2,4-trimethyl-5-butyl-1H-[1]benzopyrano[3,4-f]quinoline, 2,5-dihydro-9-hydroxy-10-methoxy-2,2,4-trimethyl-5-(1-thiazol-2-yl)-1H-[1]benzopyrano[3,4-f]quinoline, 2,5-dihydro-9-hydroxy-10-chloro-2,2,4-trimethyl-5-(2-methylpropyl)-1H-[1]benzopyrano[3,4-f]quinoline, 2,5-dihydro-9-hydroxymethyl-10-chloro-2,2,4-trimethyl-5-allyl-1H-[1]benzopyrano[3,4-f]quinoline, 2,5-dihydro-9-hydroxy-10-chloro-2,2,4-trimethyl-5-propyl-1H-[1]benzopyrano[3,4-f]quinoline, 9-hydroxy-1-methoxy-5-([3-fluorophenyl]methylene)-2,2,4-trimethyl-1H-2,5-dihydro-[1]benzopyrano[3,4-f]quinoline, 9-hydroxy-10-chloro-5-([2-pyridyl]methylene)-2,2,4-trimethyl-1H-2,5-dihydro-[1]benzopyrano[3,4-f]quinoline, rel-(5S)-9-hydroxy-5-[(3S)-(1-hydroxymethyl)cyclohexen-3-yl]-10-methoxy-2,2,4-trimethyl-2,5-dihydro-1H-[1]benzopyrano[3,4-f]quinoline, rel-(5S)-9-hydroxy-5-[(3S)-(1-methoxycarbonyl)cyclohexen-3-yl]-10-methoxy-2,2,4-trimethyl-2,5-dihydro-1H-[1]benzopyrano[3,4-f]quinoline, 2,5-dihydro-9-hydroxy-10-methoxy-2,2,4-trimethyl-5-(3,5-dichlorophenyl)-1H-[1]benzopyrano[3,4-f]quinoline, (−)(5S,3'S)-2,5-dihydro-9-hydroxy-10-chloro-2,2,4-trimethyl-5-(1-methylcyclohexen-3-yl)-1H-[1]benzopyrano[3,4-f]quinoline, (−)(5S,3'R)-2,5-dihydro-9-hydroxy-10-chloro-2,2,4-trimethyl-5-(1-methylcyclohexen-3-yl)-1H-[1]benzopyrano[3,4-f]quinoline, (+)(5R,3'S)-2,5-dihydro-9-hydroxy-10-chloro-2,2,4-trimethyl-5-(1-methylcyclohexen-3-yl)-1H-[1]benzopyrano[3,4-f]quinoline, (+)(5R,3'R)-2,5-dihydro-9-hydroxy-10-chloro-2,2,4-trimethyl-5-(1-methylcyclohexen-3-yl)-1H-[1]benzopyrano[3,4-f]quinoline, (+/−)2,5-dihydro-9-(4-N,N-dimethylamino-4-oxo-butanoyloxy)-10-chloro-2,2,4-trimethyl-5-allyl-1H-[1]benzopyrano[3,4-f]quinoline, (−)2,5-dihydro-9-hydroxy-10-chloro-2,2,4-trimethyl-5-cyclopentyl-1H-[1]benzopyrano[3,4-f]quinoline, 2,5-dihydro-9-(4-N,N-dimethylamino-4-oxo-butanoyloxy)-10-methoxy-2,2,4-trimethyl-5-(1-methylethyl)-1H-[1]benzopyrano[3,4-f]quinoline, 2,5-dihydro-9-(4-N,N-dimethylamino-4-oxo-butanoyloxy)-10-methoxy-5-(phenylmethyl)-2,2,4-trimethyl-1H-[1]benzopyrano[3,4-f]quinoline, 2,5-dihydro-9-(4-N,N-dimethylamino-4-oxo-butanoyloxy)-10-methoxy-2,2,4-trimethyl-5(2-thienyl) 2,5-dihydro-9-(4-N,N-dimethylaminobutanoyloxy)-10-methoxy-2,2,4-trimethyl-5-(2 propenyl)-1H-[1]benzopyrano[3,4-f]quinoline, 9-(2 ethoxy-2-oxo-ethylaminocarbonyl)oxy-10-methoxy-5-(3-propenyl)-2,2,4-trimethyl-1H-2,5-dihydro-[1]benzopyrano[3,4-f]quinoline, (+/−)2,5-dihydro-9-(3-acetamidopropanoyloxy)-10-methoxy-2,2,4-trimethyl-5-allyl-1H-[1]benzopyrano[3,4-f]quinoline, (+/−)2,5-dihydro-9-hydroxy-10-chloro-2,2,4-trimethyl-5-benzyl-1H-[1]benzopyrano[3,4-f]quinoline, 9-hydroxy-10-methoxy-5-(phenylmethylene)-2,2,4-trimethyl-1H-2,5-dihydro-[1]benzopyrano[3,4-f]quinoline, 9-(dimethylaminothiocarbonyl)-oxy-10-methoxy-5-(3-propenyl)-2,2,4-trimethyl-1H-2,5-dihydro-[1]benzopyrano[3,4-f]quinoline, (+/−)2,5-dihydro-9-(N-carbamoyl-2-aminoacetoxy)-10-methoxy-2,2,4-trimethyl-5-allyl-1H-[1]benzopyrano[3,4-f]quinoline, (+/−)2,5-dihydro-9-(4-ethoxy-4-oxo-butoxy)-10-methoxy-2,2,4-trimethyl-5-allyl-1H-[1]benzopyrano[3,4-f]quinoline, (+/−)2,5-dihydro-9-(4-oxo-pentanoyloxy)-10-methoxy-2,2,4-trimethyl-5-allyl-1H-[1]benzopyrano[3,4-f]quinoline, 2,5-dihydro-9-hydroxy-10-chloro-2,2,4-trimethyl-5-(3,4,5-trifluorophenyl)-1H-[1]benzopyrano[3,4-f]quinoline, 2,5-dihydro-9-methylthiomethoxy-10-methoxy-2,2,4-trimethyl-5-allyl-1H-[1]benzopyrano[3,4-f]quinoline, 2,5-dihydro-9-(4-N,N-diethylamino-4-oxo-pentanoyloxy)-10-methoxy-2,2,4-trimethyl-5(2-propenyl)-1H-[1]benzopyrano[3,4-f]quinoline, 2,5-dihydro-9-(4-N,N-dimethylamino-4-oxo-pentanoyloxy)-10-methoxy-2,2,4-trimethyl-5(2-propenyl)-1H-[1]benzopyrano[3,4-f]quinoline, 2,5-dihydro-9-(4-N-piperidino-4-oxo-pentanoyloxy)-10-methoxy-2,2,4-trimethyl-5-(2-propenyl)-1H-[1]benzopyrano[3,4-f]quinoline, 2,5-dihydro-9-(4-N-morpholino-4-oxo-pentanoyloxy)-10-methoxy-2,2,4-trimethyl-5-(2-propenyl)-1H-[1]benzopyrano[3,4-f]quinoline, (−)2,5-dihydro-9-(4-N,N-dimethyamino-4-oxo-butanoyloxy)-10-methoxy-2,2,4-trimethyl-5(S)-(3(S)-1-cyclopenten-3-yl)-1H-[1]benzopyrano[3,4-f]quinoline, 10-methoxy-9-(allylaminocarbonyl)oxy-5-(3-propenyl)-2,2,4-trimethyl-1H-2,5-dihydro-[1]benzopyrano[3,4-f]quinoline, 10-methoxy-9-(cyclohexylaminocarbonyl)-oxy-5-(3-propenyl)-2,2,4-trimethyl-1H-2,5-dihydro-[1]benzopyrano[3,4-f]quinoline, 2,5-dihydro-9-hydroxy-10-methoxy-2,2,4-trimethyl-5-(3-thienyl)-1H-[1]benzopyrano[3,4-f]quinoline, 2,5-dihydro-9-hydroxy-10-methoxy-2,2,4-trimethyl-5-(4-(fluorophenyl)methyl)-1H-[1]benzopyrano[3,4-f]quinoline, 10-carbaldehydeoxime-5-(2-propenyl)-2,5-dihydro-2,2,4-trimethyl-1H-[1]benzopyrano[3,4-f]quinoline, and 10-benzyloxy-5-(2-propenyl)-2,5-dihydro-2,2,4-trimethyl-1H-[1]benzopyrano[3,4-f]quinoline.

DETAILED DESCRIPTION OF THE INVENTION

Definition of Terms

Generally, when groups are represented as $C_x$—$C_y$—, x and y represent the minimum and maximum number of carbon atoms, respectively, in the group.

The term "alkanoyl" refers to an alkyl group attached to the parent molecular group through a carbonyl group.

The term "alkanoyloxy" refers to an alkanoyl group attached to the parent molecular group through an oxygen atom.

The term "alkenyl" refers to a monovalent straight or branched chain group of two to twelve carbons derived from a hydrocarbon having at least one carbon-carbon double bond. The term "alkenyloxy" refers to an alkenyl group attached to the parent molecular group through an oxygen atom.

The term "alkoxy" refers to an alkyl group attached to the parent molecular group through an oxygen atom.

The term "alkoxyalkyl" refers to an alkoxy group attached to the parent molecular moiety through an alkyl group.

The term "alkoxycarbonyl" refers to an ester group, i.e. an alkoxy group attached to the parent molecular moiety through a carbonyl group.

The term "alkoxycarbonyloxy" refers to a carbonate; e.g., an alkoxycarbonyl group connected to the parent molecular group through an oxygen atom.

The term "alkyl" refers to a monovalent, saturated, straight or branched chain group of one to twelve carbons derived from a saturated hydrocarbon.

The term "alkylamine" refers to an amino group wherein one of the hydrogen atoms has been replaced by an alkyl group.

The term "alkenyamino" refers to an amino group wherein one of the hydrogen atoms has been replaced by an alkenyl group.

The term "alkylene" refers to a divalent straight or branched chain group of one to twelve carbons derived from an alkane.

The term "alkynyl" refers to a monovalent straight or branched chain hydrocarbon of two to twelve carbons with at least one carbon-carbon triple bond.

The term "alkynyloxy" refers to an alkynyl group attached to the parent molecular group through an oxygen atom.

The term "alkynylene" refers to a divalent straight or branched chain group of two to twelve carbons derived from an alkyne.

The term "amino refers to —NH$_2$.

The term "aminoalkyl" refers to an amino group, as defined herein, attached to the parent molecular group through an alkyl group.

The term "aryl" refers to a mono- or bicyclic carbocyclic ring system having one or two aromatic rings. The aryl group can also be fused to a cyclohexane, cyclohexene, cyclopentane or cyclopentene ring.

The term "benzy" refers to a methyl group to which is attached a phenyl ring.

The term "benzyloxy" refers to a benzyl group attached to the parent molecular group through an oxygen atom.

The term "carbaldehyde oxime," refers to —C(H)=N—OH.

The term "carboxy" refers to —CO$_2$H.

The term "cycloalkenyl" refers to a monovalent group derived from a cyclic or bicyclic hydrocarbon of three to twelve carbons that has at least one carbon-carbon double bond.

The term "cycloalkyl" refers to saturated, monovalent group three to twelve carbons derived from a saturated cyclic or bicyclic hydrocarbon.

The term "dialkylamine," refers to an amino group wherein both of the hydrogen atoms have been replaced by an alkyl group.

The terms "formyl" or "carboxaldehyde" refer to —CHO.

The term "halo" refers to F, Cl, Br, or I.

The term "haloalkoxy" refers to an alkoxy group to which is attached one, two, or three halogen atoms.

The term "haloalkyl" refers to an alkyl group to which is attached one, two, or three halogen atoms.

The term "haloalkenyl" refers to an alkenyl group to which is attached one, two, or three halogen atoms.

The term "haloalkynyl" refers to an alkynyl group to which is attached one, two, or three halogen atoms.

The term "heterocycle" represents a represents a 4-, 5-, 6- or 7-membered ring containing one, two or three heteroatoms independently selected from the group consisting of nitrogen, oxygen and sulfur. The 4- and 5-membered rings have zero to two double bonds and the 6- and 7-membered rings have zero to three double bonds. The term "heterocycle" also includes bicyclic, tricyclic and tetracyclic groups in which any of the above heterocyclic rings is fused to one or two rings independently selected from an aryl ring, a cyclohexane ring, a cyclohexene ring, a cyclopentane ring, a cyclopentene ring or another monocyclic heterocyclic ring. Heterocycles include acridinyl, benzimidazolyl, benzofuryl, benzothiazolyl, benzothienyl, benzoxazolyl, biotinyl, cinnolinyl, dihydrofuryl, dihydroindolyl, dihydropyranyl, dihydrothienyl, dithiazolyl, furyl, homopiperidinyl, imidazolidinyl, imidazolinyl, imidazolyl, indolyl, isoquinolyl, isothiazolidinyl, isothiazolyl, isoxazolidinyl, isoxazolyl, morpholinyl, oxadiazolyl, oxazolidinyl, oxazolyl, piperazinyl, piperidinyl, pyranyl, pyrazolidinyl, pyrazinyl, pyrazolyl, pyrazolinyl, pyridazinyl, pyridyl, pyrimidinyl, pyrimidyl, pyrrolidinyl, pyrrolinyl, pyrrolyl, quinolinyl, quinoxaloyl, tetrahydrofuryl, tetrahydroisoquinolyl, tetrahydroquinolyl, tetrazolyl, thiadiazolyl, thiazolidinyl, thiazolyl, thienyl, thiomorpholinyl, triazolyl, and the like.

Heterocyclics also include bridged bicyclic groups where a monocyclic heterocyclic group is bridged by an alkylene group such as

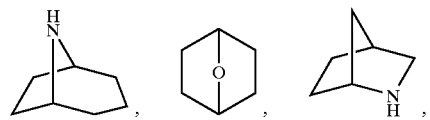

and the like.

Heterocyclics also include compounds of the formula

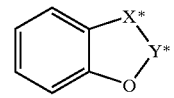

where X* is selected from —CH$_2$—, —CH$_2$O— and —O—, and Y* is selected from —C(O)— and —(C(R")$_2$)$_v$—, where R" is hydrogen or alkyl of one to four carbons, and v is 1–3. These heterocycles include 1,3-benzodioxolyl, 1,4-benzodioxanyl, and the like.

The term "heterocycloalkyl" as used herein, refers to a non-aromatic, partially unsaturated or fully saturated 4- to 8-membered ring having from one or two heteroatoms independently selected from oxygen, sulfur and nitrogen, in which the nitrogen and sulfur heteroatoms can be oxidized and the nitrogen heteroatom can be quaternized.

The term "hydroxy" refers to —OH. The term "hydroxyalkyl" refers to a hydroxy group attached to the parent molecular group through an alkyl group.

The term "N-protected amino" refers to groups intended to protect an amino group against undersirable reactions during synthetic procedures. Commonly used N-protecting groups are disclosed in Greene, "Protective Groups In Organic Synthesis," (John Wiley & Sons, New York (1981)). Preferred N-protecting groups are formyl, acetyl, benzoyl, pivaloyl, t-butylacetyl, phenylsulfonyl, benzyl, t-butyloxycarbonyl (Boc), and benzyloxycarbonyl (Cbz).

The term "O-protected carboxy" refers to a carboxylic acid protecting ester or amide group typically employed to block or protect the carboxylic acid functionality while the reactions involving other functional sites of the compound are performed. Carboxy protecting groups are disclosed in Greene, "Protective Groups in Organic Synthesis" (1981). Additionally, a carboxy protecting group can be used as a prodrug whereby the carboxy protecting group can be readily cleaved in vivo, for example by enzymatic hydrolysis, to release the biologically active parent. Such carboxy protecting groups are well known to those skilled in the art, having been extensively used in the protection of carboxyl groups in the penicillin and cephalosporin fields as described in U.S. Pat. No. 3,840,556 and 3,719,667.

The term "oxo" refers to (=O).

The term "pharmaceutically acceptable prodrugs" represents those prodrugs of the compounds of the present invention which are, within the scope of sound medical judgement, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the invention.

The term "prodrug" represents compounds which are rapidly transformed in vivo to the parent compound of the above formula, for example, by hydrolysis in blood. A thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference.

The term "pharmaceutically acceptable salt" represents those salts which are, within the scope of sound medical judgement, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describe pharmaceutically acceptable salts in detail in *J. Pharmaceutical Sciences*, 1977, 66:1–19. The salts can be prepared in situ during the final isolation and purification of the compounds of the invention, or separately by reacting the free base function with a suitable organic acid. Representative acid addition salts include acetate, adipate, alginate, ascorbate, aspartate, benzenesulfonate, benzoate, bisulfate, borate, butyrate, camphorate, camphersulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like.

The term "thioalkoxy," as used herein represents an alkyl group attached to the parent molecular group through a sulfur atom.

Compounds of the present invention can exist as stereoisomers where asymmetric or chiral centers are present. These compounds are designated by the symbols "R" or "S," depending on the configuration of substitiuents around the chiral carbon atom. The present invention contemplates various stereoisomers and mixtures thereof. Stereoisomers include enantiomers and diastereomers, and equal mixtures of enantiomers are designated (±). Individual stereoisomers of compounds of the present invention can be prepared synthetically from commercially available starting materials which contain asymmetric or chiral centers or by preparation of racemic mixtures followed by resolution well-known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary or (2) direct separation of the mixture of enantiomers on chiral chromatographic columns.

Geometric isomers can also exist in the compounds of the present invention. The present invention contemplates the various geometric isomers and mixtures thereof resulting from the arrangement of substituents around a carbon-carbon double bond or arrangement of substituents around a ring. Substituents around a carbon-carbon double bond are designated as being in the Z or E configuration where the term "Z" represents substituents on the same side of the carbon-carbon double bond and the term "E" represents substituents on opposite sides of the carbon-carbon double bond. The arrangement of substituents around a ring are designated as cis or trans where the term "cis" represents substituents on the same side of the plane of the ring and the term "trans" represents substituents on opposite sides of the plane of the ring. Mixtures of compounds where the substitutients are disposed on both the same and opposite sides of plane of the ring are designated cis/trans.

Methods for Radioligand Binding Studies with Human Glucocorticoid and Progesterone Receptor Cytosol The procedure described in Anal. Biochem. 1970, 37, 244–252, hereby incorporated by reference, was used. Briefly, cytosol preparations of human glucocorticoid receptor-α [GRX] isoform and human progesterone receptor-A [PRA] isoform were obtained from Ligand Pharmaceuticals (San Diego, Calif.). Both receptor cDNAs were cloned into baculovirus expression vectors and expressed in insect SF21 cells. [$^3$H]-dexamethasone (Dex, specific activity 82–86 Ci/mmole) and [$^3$H]-progesterone (Prog, specific activity 97–102 Ci/mmol) were purchased from Amersham Life Sciences (Arlington Heights, Ill.). Glass fiber type C multiscreen MAFC NOB plates were from Millipore (Burlington, Mass.). Hydroxyapatide Bio-Gel HTP gel was from Bio-Rad Laboratories (Hercules, Calif.). Tris (hydroxymethyl)aminomethane (Tris), ethylenediaminetetraacetic acid (EDTA), glycerol, dithiothreitol (DTT) and sodium moylybdate were obtained from Sigma Chemicals (St. Louis, Mo.). Microscint-20 scintillation fluid was from Packard Instrument (Meriden, Conn.).

Stock solutions (32 mM) of compounds were prepared in dimethylsulfoxide (DMSO), and 50× solutions of test compounds were prepared from the 32 mM solution with a 50:50 mixture of DMSO/ethanol. The 50× solution was then diluted with binding buffer that contained 10 mM Tri-HCl, 1.5 mM EDTA, 10% glycerol, 1 mM DTT, 20 mM sodium molybdate, pH 7.5 @4° C. 1% DMSO/ethanol was present in the binding assay.

GRX and PRA binding reactions were performed in Millipore Multiscreen plates. For GR binding assays, [$^3$H]-Dex (~35,000 dpm (~0.9 nM)), GRX cytosol (~35 μg protein), test compounds and binding buffer were mixed in a total volume of 200 μL and incubated at 4° C. overnight in a plate shaker. Specific binding was defined as the difference between binding of [$^3$H]Dex in the absence and in the presence of 1 μM unlabelled Dex.

For PR binding assays, [$^3$H]Prog (~36,000 dpm (~0.8 nM)), PRA cytosol (~40 μg protein), test compounds and binding buffer were mixed in a total volume of 200 μL and incubated at 4° C at overnight in a plate shaker. Specific binding was defined as the difference between binding of [$^3$H]Prog in the absence and in the presence of 3 μM unlabelled Prog.

After an overnight incubation, 50 μL of hydroxyapatite (25% weight/volume) slurry were added to each well and plates were incubated for 10 min at 0° C. in a plate shaker. Plates were suctioned with a Millipore vacuum manifold and each well was rinsed with 300 μL of ice-cold binding buffer. A 250 μL aliquot of Packard Microscint-20 was added to each well and the wells were shaken at room temperature for 20 minutes. The amount of radioactivity was determined with a Packard TopCount plate reader.

Determination of Inhibition Constant (Ki)

The concentration of test compounds that inhibited 50% of specific binding (IC$_{50}$) was determined from a Hill analysis of the competitive binding experiments. The Ki of test compounds was determined using the Cheng-Prusoff equation Ki=IC$_{50}$/(1+[L*]/[K$_L$]) where L* is the concentration of radioligand and K$_L$ is the dissociation constant of the radioligand determined from saturation analysis. For GRX, K$_L$ was ~1.5 nM, and for PRA, K$_L$ was ~4.5 nM. The inhibitory potencies of compounds of this invention and their selectivity for GR and PR receptors are shown in Table 1.

TABLE 1

| Example Number | Ki (nM) GR | Ki (nM) PR |
| --- | --- | --- |
| 1 | 8.6 | 10000 |
| 2 | 7.6 | 1702 |
| 3 | 4.8 | 2654 |
| 4 | 7 | 2960 |
| 5 | 357.5 | 10000 |
| 6 | 3.8 | 321 |
| 7 | 4.3 | 5676 |
| 8 | 167.9 | 6007 |
| 9 | 60.5 | 10000 |
| 10 | 179.1 | 10925 |
| 11 | 4.4 | 288 |
| 12 | 8.6 | 10000 |
| 13 | 11.1 | 10000 |
| 14 | 5.2 | 10000 |
| 15 | 2.5 | 10000 |
| 16 | 8 | 10000 |
| 17 | 39 | 10000 |
| 18 | 10.5 | 1035 |
| 19 | 6.7 | 4967 |
| 20 | 3.7 | 1684 |
| 21 | 10.7 | 4017 |
| 22 | 6.5 | 10000 |
| 23 | 8.2 | 6153 |
| 24 | 3.5 | 14837 |
| 25 | 240.4 | 10000 |
| 26 | 2.1 | 13390 |
| 27 | 5.2 | 3580 |
| 28 | 4.7 | 3271 |
| 29 | 7.7 | 7763 |
| 30 | 13 | 7924 |
| 31 | 12.2 | 10000 |
| 32 | 3.3 | 1559 |
| 33 | 95.2 | 8318 |
| 34 | 4 | 4706 |
| 35 | 260 | 10000 |
| 36 | 1.4 | 1704 |
| 37 | 20 | 10000 |
| 38 | 207 | 10000 |
| 39 | 31 | 10000 |
| 40 | 18 | 18132 |
| 41 | 9.5 | 3303 |
| 42 | 99 | 10000 |
| 43 | 72 | 10000 |
| 44 | 190 | 19524 |
| 45 | 15 | 10000 |
| 46 | 2.7 | 3436 |
| 47 | 174 | 10000 |
| 48 | 5.8 | 2769 |
| 49 | 13 | 10000 |
| 50 | 4.9 | 9449 |
| 51 | 18 | 7333 |
| 52 | 3 | 2269 |
| 53 | 8.1 | 2912 |
| 54 | 6.6 | 7344 |
| 55 | 8.2 | 10000 |
| 56 | 6.2 | 10000 |
| 57 | 50 | 4275 |
| 58 | 9 | 8572 |
| 59 | 9.5 | 16582 |
| 60 | 14 | 10493 |
| 61 | 62 | 14393 |
| 62 | 12 | 10000 |
| 63 | 511 | 10000 |
| 64 | 62 | 1671 |
| 65 | 591 | 10000 |
| 66 | 2.7 | 502 |
| 67 | 21.7 | 10000 |
| 68 | 8 | 9054 |
| 69 | 15 | 17331 |
| 70 | 25.5 | 7301 |
| 71 | 7.7 | 484 |
| 72 | 17.8 | 1454 |
| 73 | 10.3 | 4500 |
| 74 | 11.9 | 4877 |
| 75 | 7.3 | 13800 |
| 76 | 152 | 10000 |
| 77 | 1.6 | 173 |
| 78 | 80.5 | 10000 |
| 79 | 19.2 | 10000 |
| 80 | 168.2 | 10000 |
| 81 | 155.3 | 10000 |
| 82 | 22.9 | 327 |
| 83 | 54.8 | 2210 |
| 84 | 17.3 | 10000 |
| 85 | 3.5 | 10000 |
| 86 | 2.1 | 10000 |
| 87 | 4.7 | 10000 |
| 88 | 6 | 15327 |
| 89 | 275 | 10000 |
| 90 | 7.6 | 10000 |
| 91 | 17 | 10000 |
| 92 | 12 | 10000 |
| 93 | 148 | 10000 |
| 94 | 43 | 10000 |
| 95 | 31 | 10000 |
| 96 | 10 | 9163 |
| 97 | 320 | 10000 |
| 98 | 9.8 | 10000 |
| 99 | 3.6 | 10000 |
| 100 | 7.8 | 10000 |
| 101 | 11.4 | 10000 |
| 102 | 17.7 | 10000 |
| 103 | 5.2 | 10000 |
| 104 | 8.9 | 10000 |
| 105 | 9 | >10000 |
| 106 | 62 | >10000 |
| 107 | 215 | >10000 |
| 108 | 638 | >10000 |
| 109 | 6.1 | 10000 |
| 110 | 5.6 | 10000 |
| 111 | 7.2 | 10000 |
| 112 | 31 | 10000 |
| 113 | 9.7 | 10000 |
| 114 | 12 | 10000 |
| 115 | 17 | 10000 |

TABLE 1-continued

| Example Number | Ki (nM) GR | Ki (nM) PR |
|---|---|---|
| 116 | 7.2 | 10000 |
| 117 | 12 | 10000 |
| 118 | 43 | 10000 |
| 119 | 6.9 | 10000 |
| 120 | 30.3 | 6235 |
| 121 | 11.3 | 672 |
| 122 | 11.8 | 1409 |
| 123 | 6.1 | 9568 |
| 124 | 3.2 | 1611 |
| 125 | 36.6 | 10000 |
| 126 | 2.9 | 1407 |
| 127 | 29.3 | 10000 |
| 128 | 5.9 | 10000 |
| 129 | 5.5 | 3621 |
| 130 | 11.9 | 1054 |
| 131 | 7.71 | 996 |
| 132 | 230 | 9890 |
| 133 | 3.6 | 4867 |
| 134 | 238 | 10000 |
| 135 | | |
| 136 | 37 | 2700 |
| 137 | 5.5 | 2410 |
| 138 | 2.2 | 5600 |
| 139 | 235 | 4800 |
| 140 | 13 | 10000 |
| 141 | 10 | 10000 |
| 142 | 51 | 10000 |
| 143 | 91 | 8100 |
| 144 | 7.7 | 10000 |
| 145 | 78 | 10000 |
| 146 | 8.3 | 8300 |
| 147 | 15 | 9300 |
| 148 | 2.8 | 10000 |
| 149 | 2.7 | 4063 |
| 150 | 106 | 10000 |
| 151 | 298 | 10000 |
| 152 | 1.8 | 10000 |
| 153 | 1.9 | 10000 |
| 154 | 0.7 | 10000 |
| 155 | 0.86 | 10000 |
| 156 | 0.9 | 4100 |
| 157 | 1.5 | 433 |
| 158 | 48 | 10000 |
| 159 | 3.8 | 1837 |
| 160 | 1.8 | 10000 |
| 161 | 3.3 | 10000 |
| 162 | 6.5 | 10000 |
| 163 | 2.6 | 10000 |
| 164 | 36 | 10000 |
| 165 | 14 | 10000 |
| 166 | 8.16 | 5631 |
| 167 | 21 | 10000 |
| 168 | 2.5 | 10000 |
| 169 | 300 | 10000 |
| 170 | 82 | 10000 |
| 171 | 3.3 | 7429 |
| 172 | 7 | 9900 |
| 173 | 32 | 10000 |
| 174 | 270 | 10000 |
| 175 | 44 | 7700 |
| 176 | 88 | >10000 |
| 177 | | |
| 178 | 468 | 10000 |
| 179 | 9.5 | 2750 |
| 180 | 18 | 733 |
| 181 | 207 | 10000 |
| 182 | 23 | 10000 |
| 183 | 38 | 10000 |
| 184 | 40 | 10000 |
| 185 | 288 | 10000 |
| 186 | 90 | 10000 |
| 187 | 46 | 3900 |
| 188 | 4.9 | 5300 |
| 189 | 6.4 | 1700 |
| 190 | 6.25 | 1586 |
| 191 | 2.9 | 1190 |
| 192 | 3.1 | 10000 |
| 193 | 2.0 | 2184 |
| 194 | 7.7 | 10000 |
| 195 | 25 | 10000 |
| 196 | 1.1 | 10000 |
| 197 | 28 | 10000 |
| 198 | 0.65 | 2130 |
| 199 | 106 | 10000 |
| 200 | 45 | 10000 |
| 201 | 114 | 10000 |
| 202 | 134 | 10000 |
| 203 | 85 | 10000 |
| 204 | 74 | 10000 |
| 205 | 11.4 | 10000 |
| 206 | 201 | 10000 |
| 206A | 4192 | |
| 207 | 22 | 10000 |
| 208 | 25 | 970 |
| 209 | 2.0 | 5462 |
| 210 | 21 | 710 |
| 211 | 5.3 | 10000 |
| 212 | 13 | 10000 |
| 213 | 67 | 10000 |
| 214 | 5.7 | 10000 |
| 215 | 20 | 10000 |
| 216 | 0.58 | 7.6 |
| 217 | 1 | 65.1 |
| 218 | 1.6 | 227 |
| 219 | 2.4 | 178 |
| 220 | 0.66 | 527 |
| 221 | 0.66 | 4.2 |
| 222 | 0.47 | 9.9 |
| 223 | 2.6 | 297 |
| 224 | 57 | 786 |
| 225 | 155 | 5010 |
| 226 | 2.6 | 220 |
| 227 | 8.4 | 1930 |
| 228 | 5.4 | 29.5 |
| 229 | 34.7 | 1338 |
| 230 | 2.4 | 50.3 |
| 231 | 30.2 | 1870 |
| 232 | 1.6 | 230 |
| 233 | 2.5 | 350 |
| 234 | 3.8 | 202 |
| 235 | 0.94 | 155 |
| 236 | 0.89 | 36.2 |
| 237 | 1.5 | 18 |
| 238 | 1.2 | 11.5 |
| 239 | 16.8 | 240 |
| 240 | 52.2 | 2173 |
| 241 | 0.69 | 61.1 |
| 242 | 0.53 | 3420 |
| 243 | 1.6 | 21.2 |
| 244 | 6.3 | 804 |
| 245 | 0.95 | 119 |
| 246 | 0.87 | 113 |
| 247 | 0.86 | 195 |
| 248 | 1 | 870 |
| 249 | 0.80 | 488 |
| 250 | 2.4 | 1475 |
| 251 | 0.87 | 163 |
| 252 | 0.39 | 102 |
| 253 | 0.38 | 42 |
| 254 | 2.2 | 1824 |
| 255 | 1.5 | 1434 |
| 256 | 3.8 | 266 |
| 257 | 10 | 1624 |
| 258 | 10.7 | 879 |
| 259 | 1.2 | 938 |
| 260 | 3.3 | 250 |
| 261 | 0.75 | 161 |
| 262 | 1.1 | 150 |
| 263 | 2.2 | 59.6 |
| 264 | 0.51 | 307 |
| 265 | 767 | 1499 |

TABLE 1-continued

| Example Number | Ki (nM) GR | Ki (nM) PR |
|---|---|---|
| 266 | 0.71 | 102 |
| 267 | 0.79 | 938 |
| 268 | 0.84 | 486 |
| 269 | 17.1 | 2467 |
| 270 | 0.66 | 4756 |
| 271 | 0.82 | 2288 |
| 272 | 0.39 | 66.4 |
| 273 | 0.56 | 35.8 |
| 274 | 0.69 | 386 |
| 275 | 11.7 | 2873 |
| 276 | | |
| 277 | 11.3 | 272 |
| 278 | 1.1 | 533 |
| 279 | 12.4 | 1900 |
| 280 | 1.6 | 10000 |
| 281 | 0.84 | 526 |
| 282 | 0.5 | 42 |
| 283 | 1.1 | 60.4 |
| 284 | 110 | 2097 |
| 285 | 436 | 3757 |
| 286 | 64 | 3029 |
| 287 | 346 | 3502 |
| 288 | 0.86 | 4080 |
| 289 | 0.73 | 260 |
| 290 | 12.1 | 611 |
| 291 | 8.1 | 592 |
| 292 | 487 | 8338 |
| 293 | 12 | 3742 |
| 294 | 13.8 | 1807 |
| 295 | 0.67 | 59.3 |
| 296 | 0.63 | 476 |
| 297 | 4.7 | 4844 |
| 298 | 4.1 | 10000 |
| 298 | 4.1 | 10000 |
| 299 | 5.4 | 2900 |
| 300 | 5.3 | 34.4 |
| 301 | 16 | 113 |
| 302 | 5.9 | 99 |
| 303 | 4.9 | 58.5 |
| 304 | 34.5 | 681 |
| 305 | 2 | 6919 |
| 306 | 717 | 4455 |
| 307 | 4.6 | 27.8 |
| 308 | 50.8 | 960 |
| 309 | 1.9 | 60.7 |
| 310 | 4.4 | 382 |
| 311 | 15 | 10000 |
| 312 | 8.4 | 10000 |
| 313 | 6.4 | 10000 |
| 314 | 1.7 | 10000 |
| 315 | 13 | 10000 |
| 316 | 11 | 10000 |
| 317 | 6.5 | 10000 |
| 318 | 553 | 10000 |
| 319 | 16 | 492 |
| 320 | 49 | 3050 |
| 321 | 44 | 2880 |
| 322 | 107 | 2300 |
| 323 | 428 | 10000 |
| 324 | 24 | 10000 |
| 325 | 24 | 10000 |
| 326 | 228 | 10000 |
| 327 | 9.3 | 1457 |
| 329 | 2.2 | 192 |
| 330 | 2.2 | 53 |
| 331 | 142 | 10000 |
| 332 | 18 | 10000 |
| 333 | 5.6 | 3670 |
| 334 | 9.5 | 10000 |
| 335 | 652 | 10000 |
| 336 | 9.5 | 1564 |
| 337 | 3.3 | 702 |
| 338 | 61 | 10000 |
| 339 | 112 | 10000 |
| 340 | 1.8 | 254 |
| 341 | 2.5 | 10000 |
| 342 | 2586 | 10000 |
| 343 | 5.2 | 4700 |
| 344 | 0.46 | 76.7 |
| 345 | 8.7 | 3000 |
| 346 | 44 | 5110 |
| 347 | 128 | 10000 |
| 348 | 0.89 | 171 |
| 349 | 10.5 | 10000 |
| 350 | 6.22 | 10000 |
| 351 | 93 | 10000 |
| 352 | 58 | 10000 |
| 353 | 20 | 10000 |
| 354 | 32 | 1500 |
| 355 | 27 | 4280 |
| 356 | 15 | 2968 |
| 357 | 59.8 | 10000 |
| 358 | 4.2 | 8963 |
| 359 | 11.3 | 2219 |
| 360 | 33.7 | 10000 |
| 361 | 95.7 | 9143 |
| 362 | 6.5 | 3370 |
| 363 | 5 | 3942 |
| 364 | 424 | 10000 |
| 365 | 2.2 | 98 |
| 366 | 2.1 | 83.9 |
| 367 | 2.2 | 7.6 |
| 368 | 0.21 | 61 |
| 369 | 0.41 | 2528 |
| 372 | 1.8 | 164 |
| 373 | 3.1 | 279 |
| 374 | 9.0 | 222 |
| 375 | 3 | 1093 |
| 376 | 0.78 | 156 |
| 377 | 51 | 3085 |
| 378 | 1.1 | 440 |
| 379 | 1.4 | 175 |
| 380 | 1.2 | 204 |
| 381 | 7.1 | 9825 |
| 382 | 2.2 | 150 |
| 383 | 4.8 | 46 |
| 384 | 0.67 | 197 |
| 385 | 0.9 | 170 |
| 386 | 6.5 | 105 |
| 387 | 0.65 | 169 |
| 388 | 2.8 | 199 |
| 389 | 0.58 | 27.5 |
| 390 | 0.96 | 520 |
| 391 | 1.7 | 1087 |
| 392 | 1.2 | 487 |
| 393 | 0.76 | 589 |
| 394 | 0.89 | 109 |
| 395 | 2.1 | 1213 |
| 396 | 6.3 | 2125 |
| 397 | 2.3 | 22.8 |
| 398 | 6.7 | 1085 |
| 399 | 24.4 | 10000 |
| 400 | 3.5 | 5962 |
| 401 | 134 | 6083 |
| 402 | 3.3 | 10063 |
| 403 | 131 | 10000 |
| 404 | 1.3 | 49.7 |
| 405 | 1.1 | 75.1 |
| 406 | 2.3 | 97.9 |
| 407 | 1.8 | 16.4 |
| 408 | 112 | 14138 |
| 409 | 2.7 | 42 |
| 410 | 1.1 | 25.7 |
| 411 | 0.68 | 8.4 |
| 412 | 9 | 222 |
| 413 | 0.22 | 60.8 |
| 414 | 93.2 | 21805 |
| 415 | 9.9 | 3741 |
| 416 | 3.1 | 394 |
| 417 | 3 | 10.5 |

TABLE 1-continued

| Example Number | Ki (nM) GR | PR |
|---|---|---|
| 418 | 1.4 | 2.1 |
| 419 | 56.9 | 286 |
| 420 | 125 | 2396 |
| 421 | 0.66 | 11.6 |
| 422 | 0.28 | 2.9 |
| 423 | 0.67 | 8184 |
| 424 | 0.84 | 1952 |
| 425 | 0.35 | 3942 |
| 426 | 0.85 | 110 |
| 427 | 7.8 | 2205 |
| 428 | 0.91 | 204 |
| 429 | 4.1 | 29.1 |
| 430 | 4.8 | 281 |
| 431 | 113 | 10000 |
| 432 | 1.4 | 207 |
| 433 | 30.2 | 1413 |
| 434 | 0.96 | 123 |
| 435 | 120 | 734 |
| 436 | 18.8 | 5919 |
| 437 | 0.97 | 449 |
| 438 | 0.89 | 129 |
| 439 | 1.2 | 202 |
| 440 | 0.70 | 390 |
| 441 | 0.42 | 328 |
| 442 | 9.1 | 8863 |
| 443 | 63.5 | 10000 |
| 444 | 1.6 | 406 |
| 445 | 4 | 3471 |
| 446 | 33 | 8991 |
| 447 | 7097 | 24,5148 |

As seen in from the data in Table 1, the compounds of the invention have surprising selectivity for the glucocorticoid receptor over the progesterone receptor. The present invention also provides pharmaceutical compositions which comprise compounds of the present invention formulated together with one or more non-toxic pharmaceutically acceptable carriers. The pharmaceutical compositions may be specially formulated for oral administration in solid or liquid form, for parenteral injection, or for rectal administration.

The pharmaceutical compositions of this invention can be administered to humans and other animals orally, rectally, parenterally, intracisternally, intravaginally, intraperitoneally, topically (as by powders, ointments, or drops), bucally, or as an oral or nasal spray. The term "parenteral" administration refers to modes of administration which include intravenous, intramuscular, intraperitoneal, intrasternal, subcutaneous and intraarticular injection and infusion.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants. Conversely, reduced particle size may maintain biological activity.

These compositions may also contain adjuvants such as preservative, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents which delay absorption such as aluminum monostearate and gelatin.

In some cases, in order to prolong the effect of the drug, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides) Depot injectable formulations are also prepared by entrapping the drug in liposomes or microemulsions which are compatible with body tissues.

The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may contain opacifying agents and can also be of a composition that they release the active ingredient(s) only, or preferentially, in a certain part of the intestinal tract in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Compositions for rectal or vaginal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multilamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and the phosphatidyl cholines (lecithins), both natural and synthetic.

Methods to form liposomes are known in the art. See, for example, Prescott, Ed., *Methods in Cell Biology*, Volume XIV, Academic Press, New York, N.Y. (1976), p. 33 et seq.

Dosage forms for topical administration of a compound of this invention include powders, sprays, ointments and inhalants. The active compound is mixed under sterile conditions with a pharmaceutically acceptable carrier and any needed preservatives, buffers, or propellants which may be required. Opthalmic formulations, eye ointments, powders and solutions are also contemplated as being within the scope of this invention.

Actual dosage levels of active ingredients in the pharmaceutical compositions of this invention may be varied so as to obtain an amount of the active compound(s) that is effective to achieve the desired therapeutic response for a particular patient, compositions, and mode of administration. The selected dosage level will depend upon the activity of the particular compound, the route of administration, the severity of the condition being treated, and the condition and prior medical history of the patient being treated. However, it is within the skill of the art to start doses of the compound at levels lower than required for to achieve the desired therapeutic effect and to gradually increase the dosage until the desired effect is achieved.

Generally dosage levels of about 1 to about 50, more preferably of about 5 to about 20 mg of active compound per kilogram of body weight per day are administered orally to a mammalian patient. If desired, the effective daily dose may be divided into multiple doses for purposes of administration, e.g. two to four separate doses per day.

Abbreviations

Abbreviations that have been used in the descriptions of the scheme and the examples that follow are: $BF_3.OEt_2$ for boron trifluoride diethyl ether complex; DMF for N,N-dimethylformamide, DMSO for dimethylsulfoxide; and THF for tetrahydrofuran.

Synthetic Methods

The compounds and processes of the present invention will be better understood in connection with the following synthetic schemes which illustrate the methods by which the compounds of the invention can be prepared.

Syntheses of the compounds of the present invention are described in Schemes 1–21.

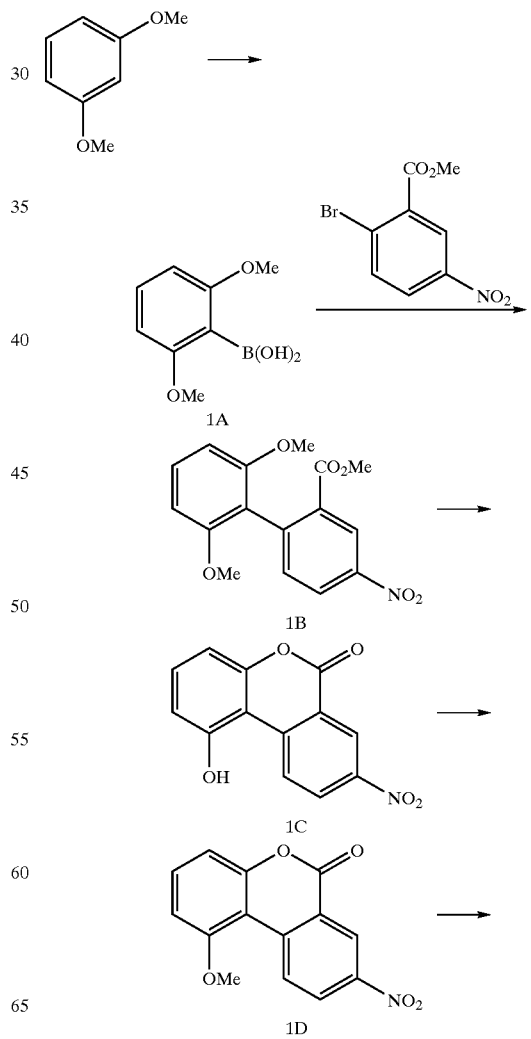

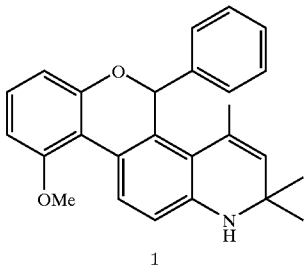

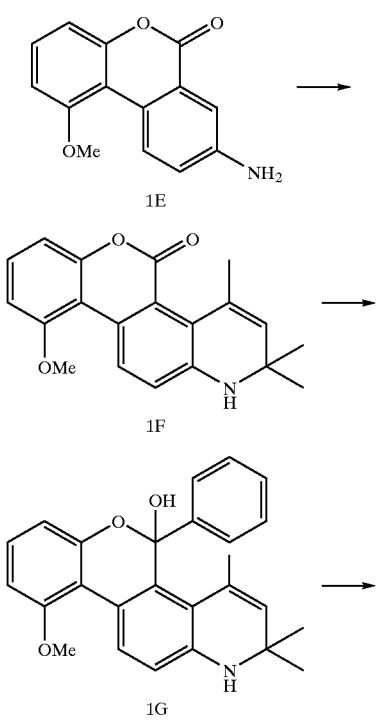

As exemplified in Scheme 1, resorcinol dimethyl ether was metallated with a strong base such as n- or sec-butyllithium, treated with a trialkoxyborate such as trimethyl- or triisopropylborate and hydrolyzed with acid such as 2M HCl to provide boronic acid 1A. Treatment of 1A with methyl 5-nitro-2-bromobenzoate in the presence of a palladium catalyst such as tetrakis(triphenylphosphine)palladium(0) or dichlorobis(triphenylphosphine)palladium (II) provided biphenyl 1B. Demethylation of 1B was accomplished with reagents such as BBr₃, to provide hydroxylactone 1C, which was treated with alkylating agents such as methyl iodide to provide 1D. Conversion of 1D to amine 1E was accomplished using hydrogen gas and a palladium catalyst such as 10% palladium on carbon. 1E was converted to quinoline 1F by a Skraup ring annulation reaction. Introduction of functionalization at the C-5 position of 1F to provide 1 was achieved through addition of organometallic reagents such as phenyllithium to the C-5 carbonyl to provide 1G, followed by deoxygenation with Lewis acids such as BF₃.OEt₃ and reducing agents such as triethylsilane to provide 1.

Scheme 2

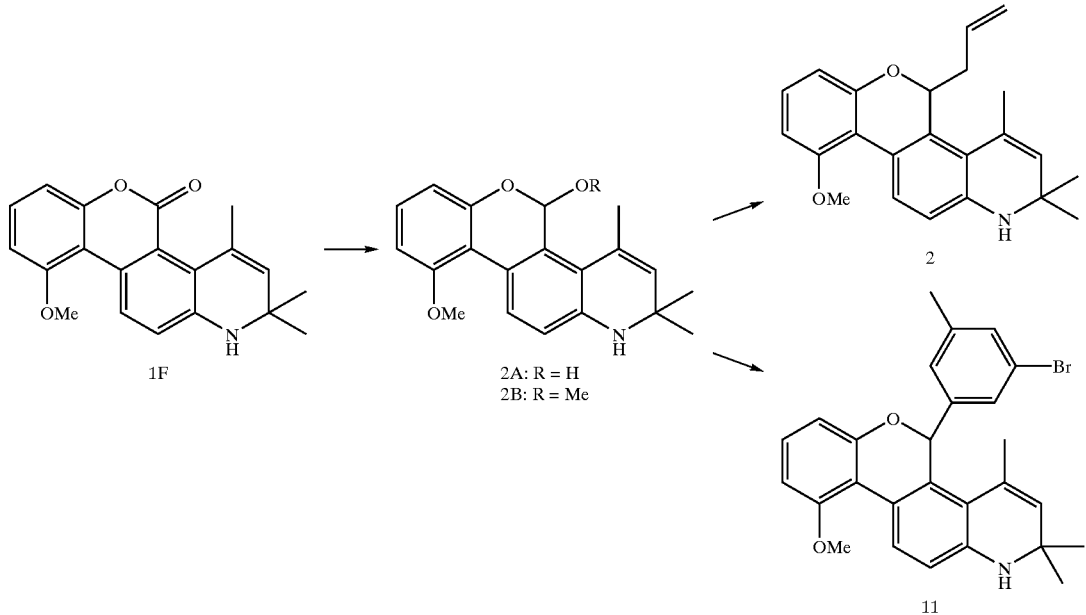

A more preferred route to compounds of this invention is exemplified in Scheme 2. 1F was converted to methyl acetal 2B, via hemiacetal 2A, using a two-step procedure comprising conversion of 1F to 2A with reagents such as diisobutylaluminum hydride in an aprotic solvent such as dichloromethane followed by acid-catalyzed acetal formation with acids such as p-toluenesulfonic acid monohydrate and alcohols such as methanol to provide 2B. 2B was treated with nucleophiles such as allyltrimethylsilane in the presence of a Lewis acid such as boron trifluoride diethyl etherate to form C-5 allyl analogs such as Example 2. The Lewis acid/methyl acetal complex was also condensed with organomagnesium chlorides, bromides or iodides to provide compounds of this invention such as Example 11.

Scheme 3

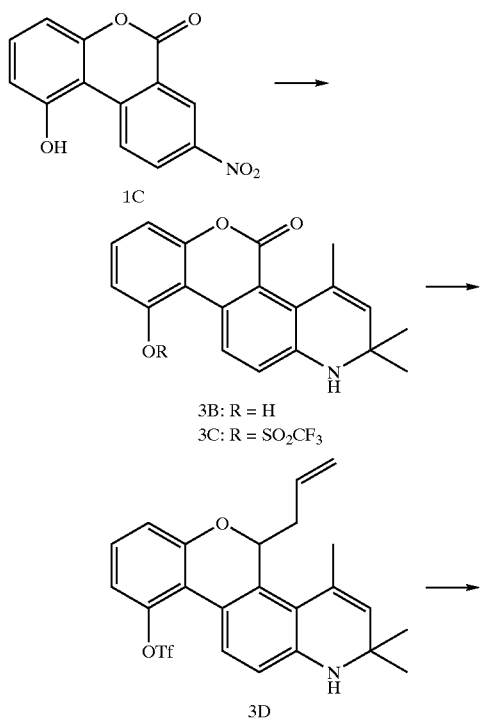

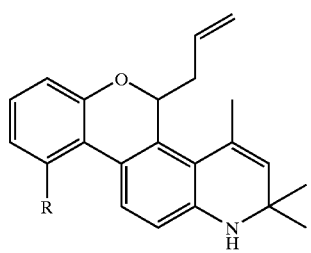

3: R = NHMe
4: R = CO₂Me
5: R = CH═CH₂
6: R = C≡CH

As exemplified in Scheme 3, the C-10 position of 1C was subjected the same reduction/Skraup conditions described in Scheme 1 to afford hydroxyquinoline 3B. 3B was converted to triflate derivative 3C with reagents such as trifluoromethanesulfonic anhydride then derivatized at the C-5 position as described in schemes 1 and 2 to provide analogs such as 3D. The functionalized C-10 triflates were used in coupling reactions mediated by palladium catalysts for aminations, carbonylations, Stille couplings and modified Sonagashira reactions and provided aminomethyl, carbomethoxy, vinyl and acetylenic derivatives of 3D such as the C-5 allyl-substituted examples 3, 4, 5, and 6, respectively.

Scheme 4

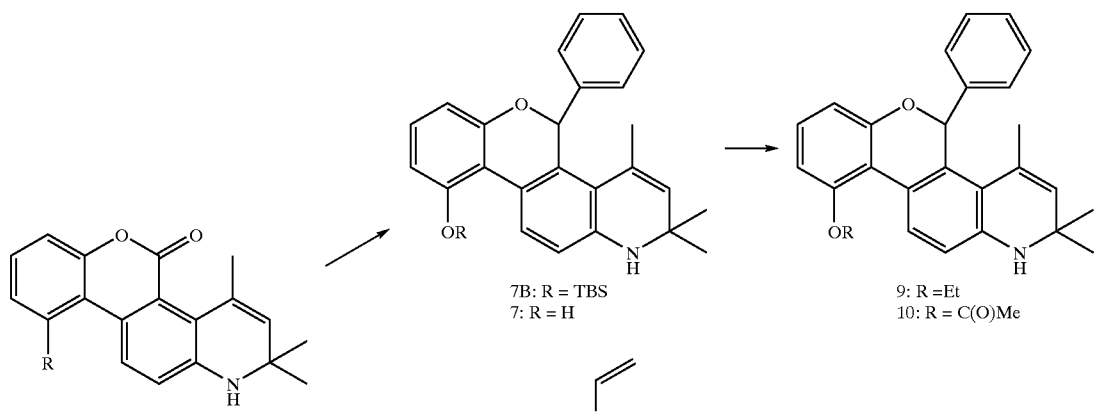

3B: R = OH
7A: R = OTBS
8A: R = OCF$_2$H

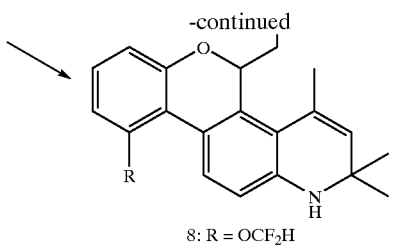

8: R = OCF$_2$H

As shown in Scheme 4, treatment of 3B with tert-butyl dimethylsilyl (TBS) ether and a base such as imidazole, triethylamine or diisopropylethylamine and functionalization of the C-5 position as described in schemes 1–3 provided silane 7B. Removal of the silane group with reagents such as tetra n-butylammonium fluoride in THF, to provide phenol 7, and treatment with R—X or RC(O)X, where R is an alkyl group and X is a leaving group such as halogen, provided alkoxy and carboxy compounds such as examples 9 and 10. Halo alkoxy analogs were prepared from 3B by nucleophillic displacement using a polyhalogenated alkylating agent such as CF$_2$HCl to provide 8A followed by functionalization at the C-5 position of 8A, as described in Schemes 1–3, to provide 8.

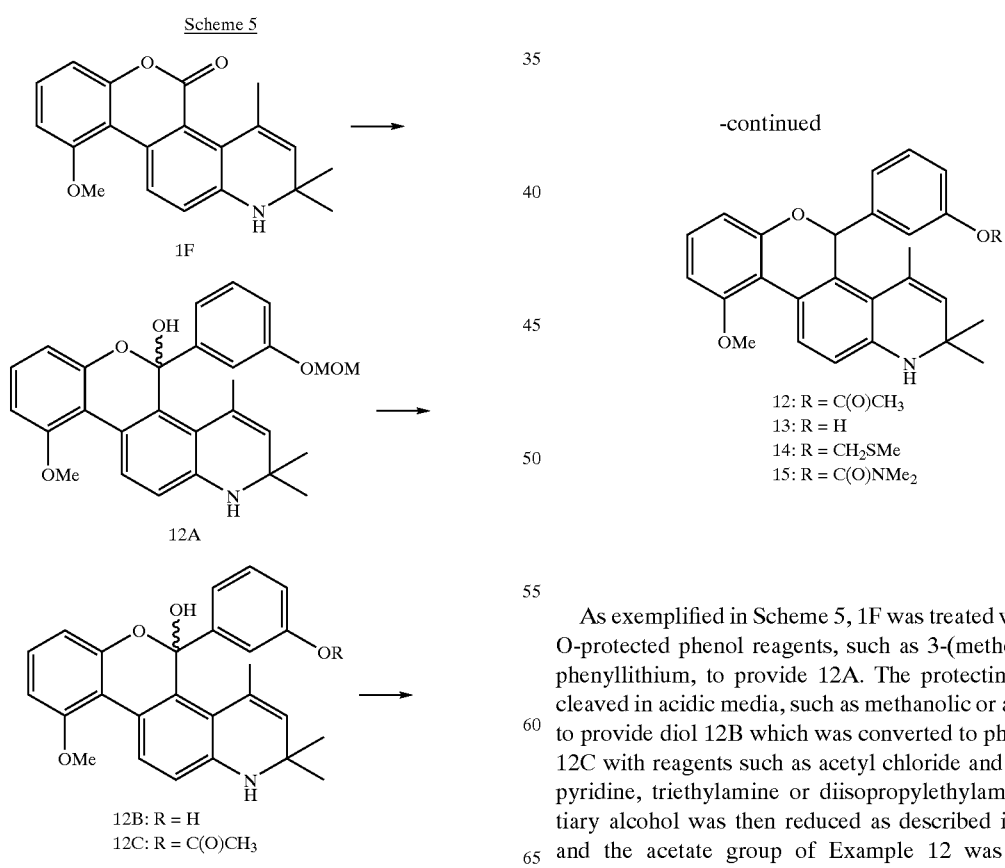

As exemplified in Scheme 5, 1F was treated with lithiated, O-protected phenol reagents, such as 3-(methoxymethoxy) phenyllithium, to provide 12A. The protecting group was cleaved in acidic media, such as methanolic or aqueous HCl, to provide diol 12B which was converted to phenyl acetates 12C with reagents such as acetyl chloride and base such as pyridine, triethylamine or diisopropylethylamine. The tertiary alcohol was then reduced as described in Scheme 1, and the acetate group of Example 12 was removed to provide Example 13. Example 13 was alkylated or acylated as described in Scheme 4 to provide examples 14 and 15.

Scheme 6

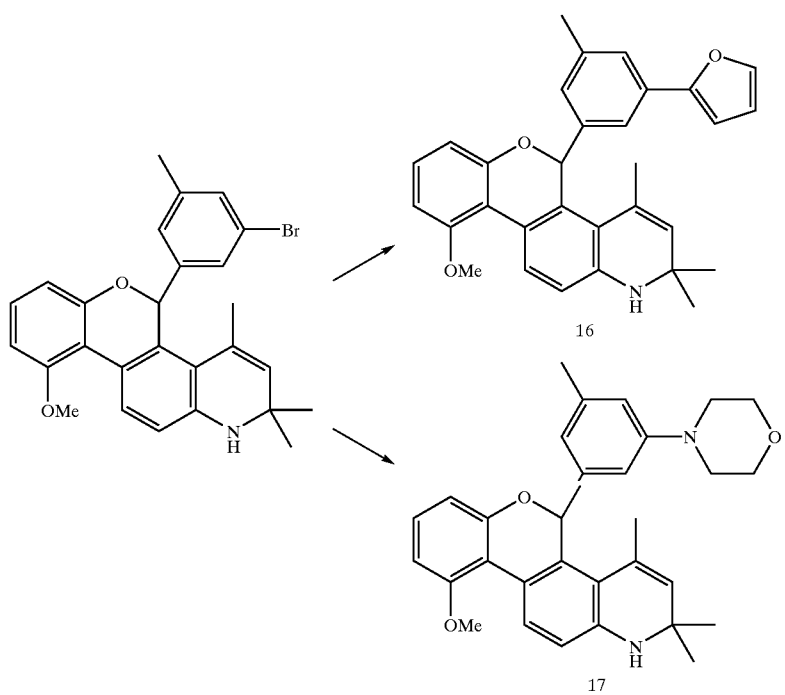

As shown in Scheme 6, functionality in the meta position of the phenyl ring in the C-5 position was introduced using meta-halophenyl analogs such as Example 11, prepared as described in Scheme 2. Stille or Suzuki couplings or aminations with palladium catalysts such as [1,1-bis(diphenylphosphino)ferrocene]dichloropalladium(II) or tetrakis(triphenylphosphine)palladium(0) in the presence of ligands such as tributyistannylfuran or morpholine provided carbon- or nitrogen-bound groups in the meta position of the aromatic ring at the C-5 position as exemplified in examples 16 and 17, respectively.

Scheme 7

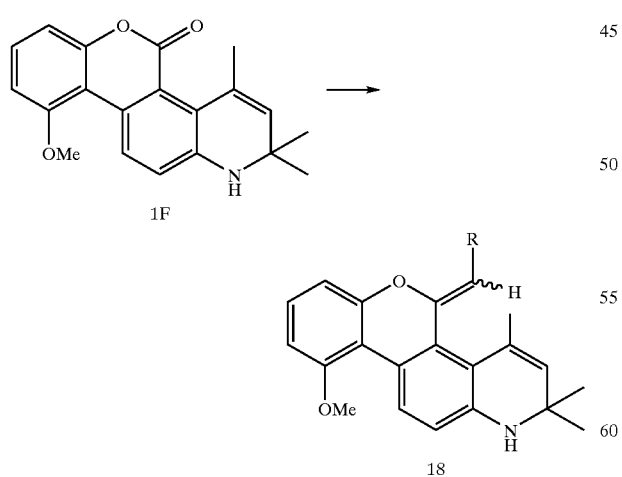

As shown in Scheme 7, 1F was treated with magnesium halides, preferably bromides, to provide an intermediate hemiketal which was treated with acid catalysts such as para-toluenesulfonic acid, methanesulfonic acid or aqueous hydrochloric acid to provide substituted analogs such as 18 as mixtures of E and Z isomers.

The chemistry shown in Scheme 1 was found to be general. Thus, a variety of tetracyclic cores could be prepared from an assortment of substituted anisoles via their corresponding boronic acids according to Scheme 8.

Scheme 8

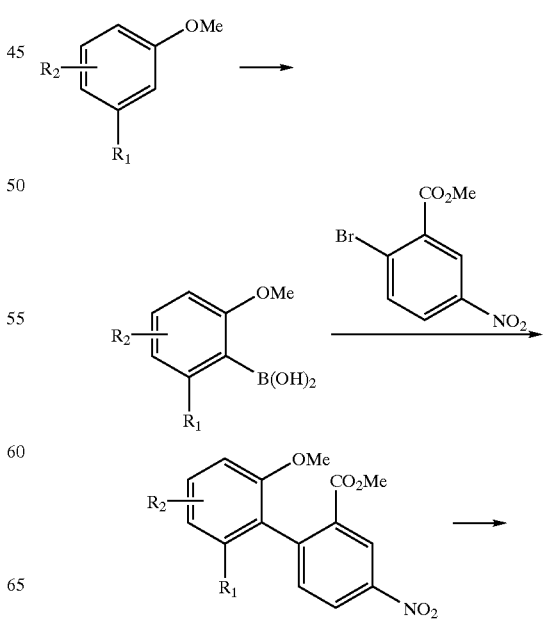

-continued

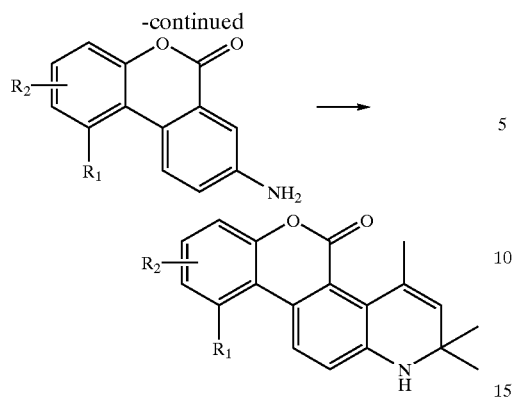

-continued

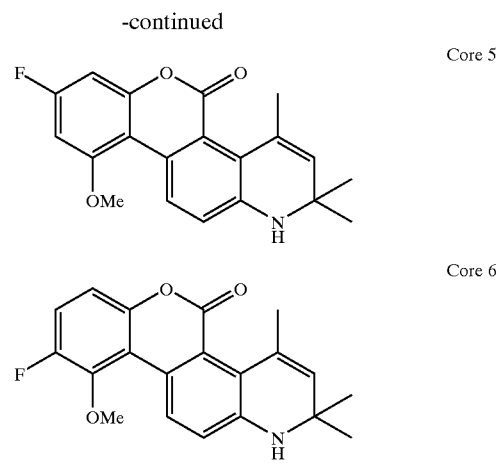

Core 5

Core 6

Scheme 8 shows the applicability of the chemistry described in Scheme 1 and Examples 1–131 to the synthesis of new cores with substituents other than alkoxy at the C-10 position. Ortho metallation of substituted anisoles with a strong base such as n- or sec-butyllithium, followed by sequential treatment with a trialkoxyborate such as trimethyl- or triisopropylborate and hydrolysis with acid, as described in Scheme 1, provided the appropriately substituted boronic acids which were then elaborated to compounds of Formula I using chemistry described above. Further elaboration of the ring to provide Cores 1–17 is described below.

Examples of novel tetracyclic cores prepared using the chemistry described in Scheme 8 are shown below.

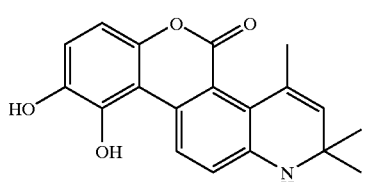

Core 1

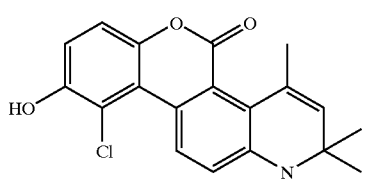

Core 2

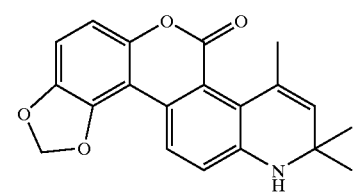

Core 3

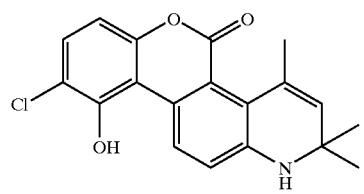

Core 4

Scheme 9

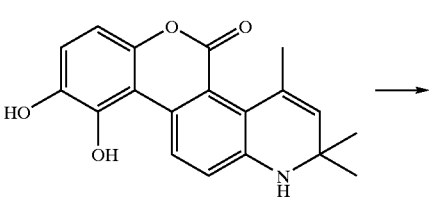

Core 1

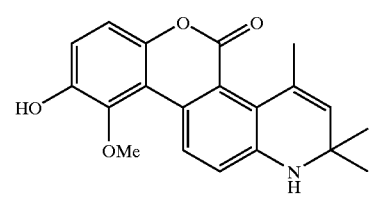

Core 7

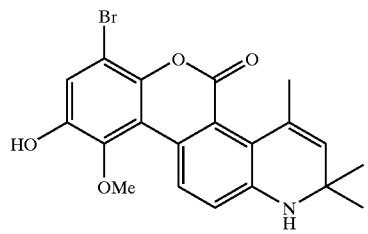

Core 8

Further derivatization of Core 1 using methods well-known in the art provide additional tetracyclic coumarins for subsequent elaboration at the C-5 position, as shown in Scheme 9. For example, selective alkylation of the C-10 hydroxyl of Core 1 with alkylating agents (e.g., methyl iodide) and base, such as potassium carbonate, provided Core 7. Selective derivitization of Core 1 at the C-7 position with halogenating agents such as bromine or N-bromosuccinimide provided the compound of Formula I precursor Core 8.

Scheme 10

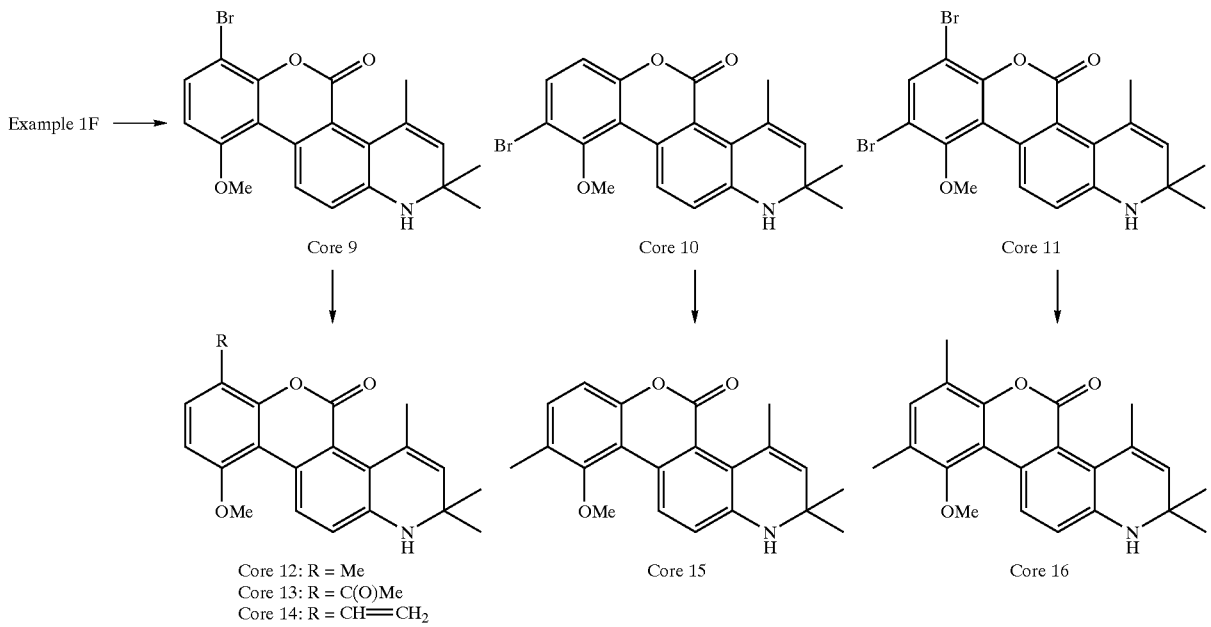

Scheme 10 shows additional selective bromination chemistry. Regiochemical bromination of Example 1F, as directed by the C-10 methoxy group and choice of brominating agent, provided Cores 9, 10, and 11. These brominated rings were further derivatized at the brominated position(s) by transition metal-catalyzed introduction of a variety of functional groups.

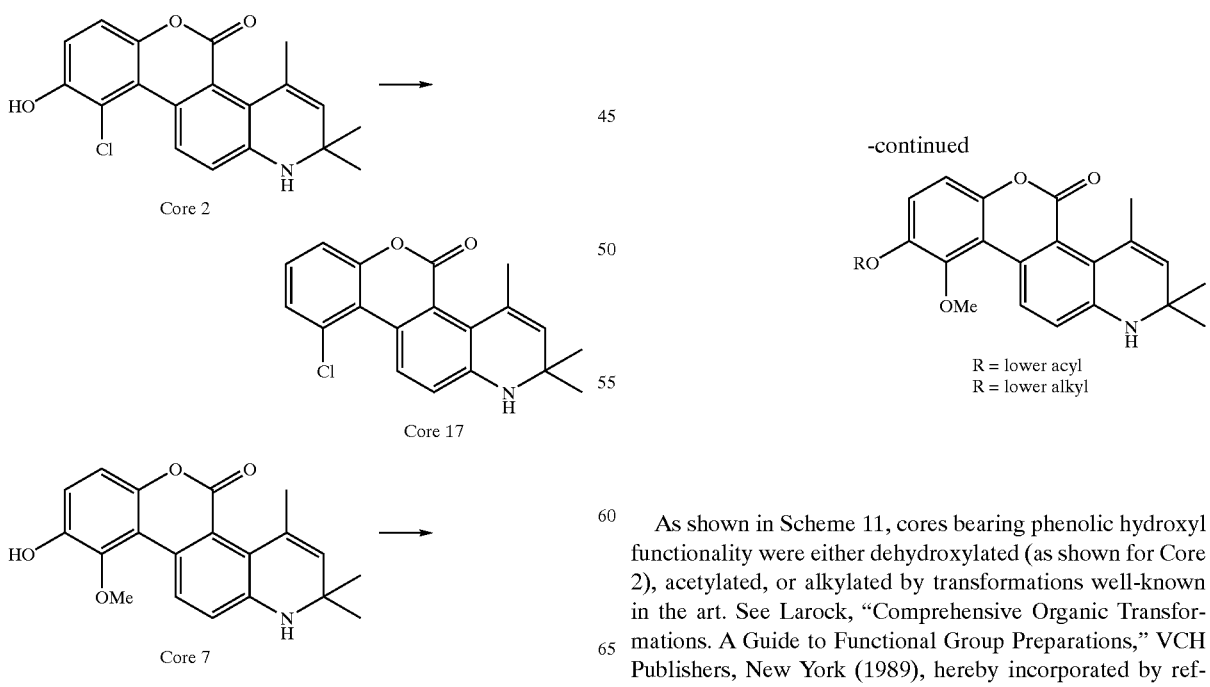

As shown in Scheme 11, cores bearing phenolic hydroxyl functionality were either dehydroxylated (as shown for Core 2), acetylated, or alkylated by transformations well-known in the art. See Larock, "Comprehensive Organic Transformations. A Guide to Functional Group Preparations," VCH Publishers, New York (1989), hereby incorporated by reference.

Scheme 12

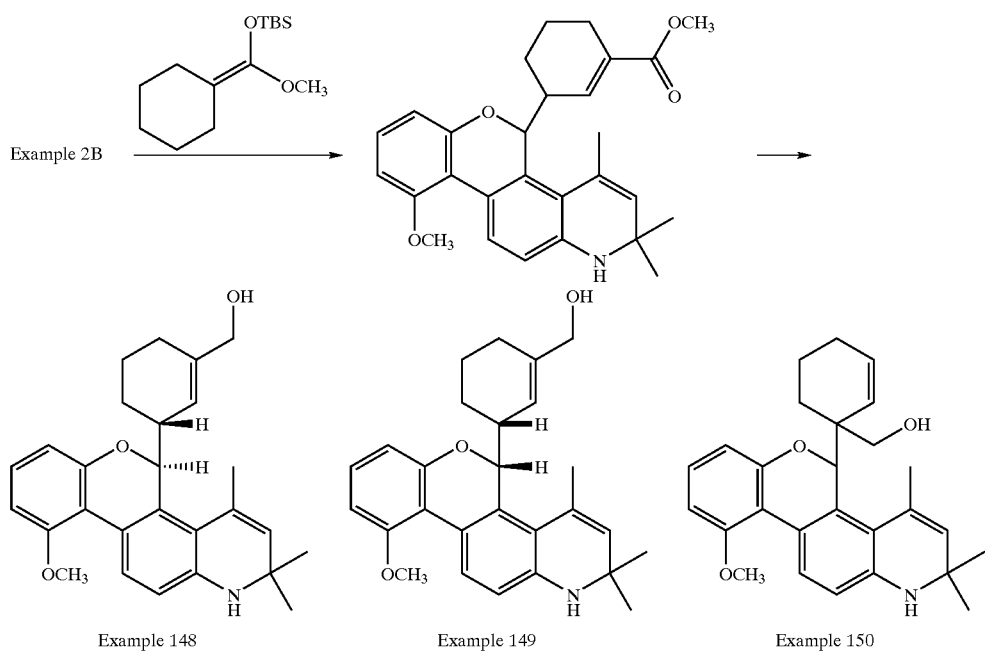

Scheme 12 shows the introduction of the substituted cyclohexenyl group by Lewis acid catalyzed addition of the tert-butyldimethylsilyl-protected enol ether to the C-5 position of Example 2B. Once introduced, the diastereomers and rearrangement products were separated, and the alkoxycarbonyl group was optionally reduced to a hydroxyalkyl group.

Scheme 13

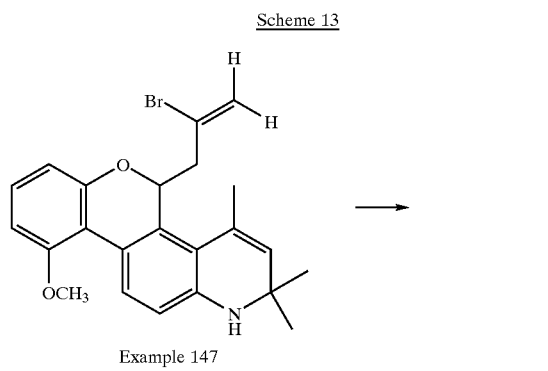

As shown in Scheme 13, the vinylic bromide group of compounds such as Example 147 were further derivatized at the brominated position(s) to provide a number of $R_{19}$ substituents by transition metal-catalyzed introduction of a variety of functional groups such as those described in Scheme 10.

Scheme 14

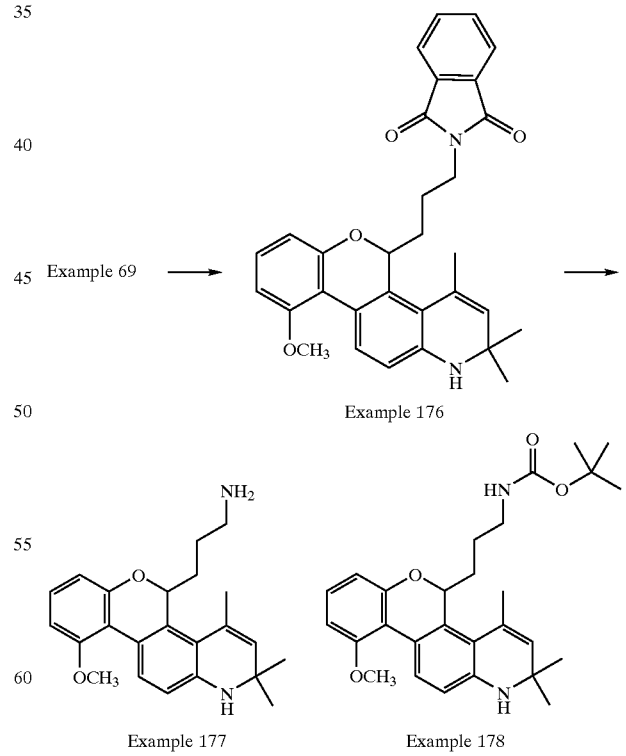

As shown in Scheme 14, Mitsunobu introduction of phthalimide to Example 69 and removal of the imide group with hydrazine provided alkylamino Example 177 which was further derivatized to Example 178 by treatment with di(tert-butyl)dicarbonate.

As shown in Scheme 15, elaboration of the C-5 nitrile of Example 44 to the α,β-unsaturated ester Example 179 followed by selective reduction of the alkoxycarbonyl group to the alkeneyl alcohol ($X_1$ is H) provided precursors for carbamates and methoxymethyl ethers Examples 182 and 183, respectively.

Scheme 15

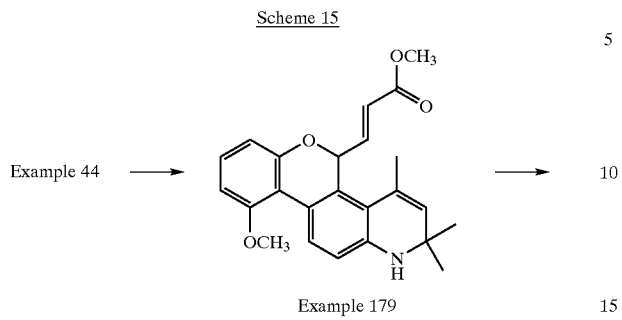

Example 44 →

Example 179

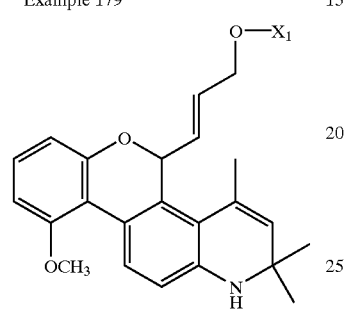

$X_1$ = CON(CH$_3$)$_2$ (Example 182)
$X_1$ = CH$_2$OCH$_3$ (Example 183)

Scheme 16

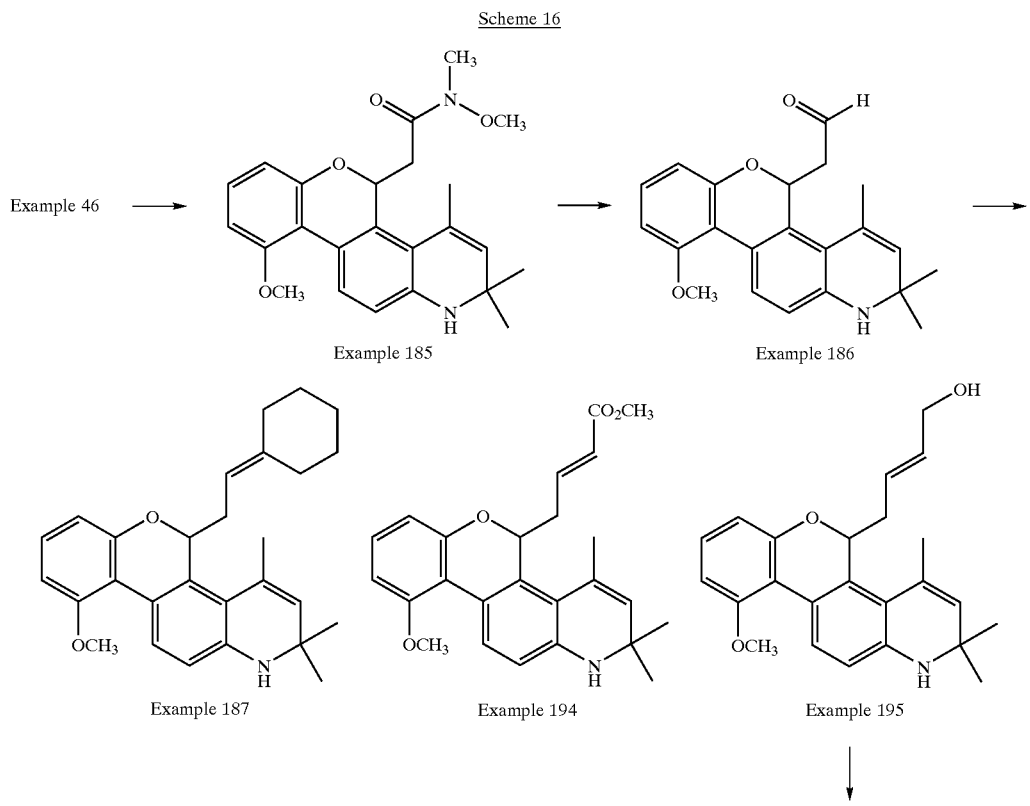

Example 46 →

Example 185

Example 186

Example 187

Example 194

Example 195

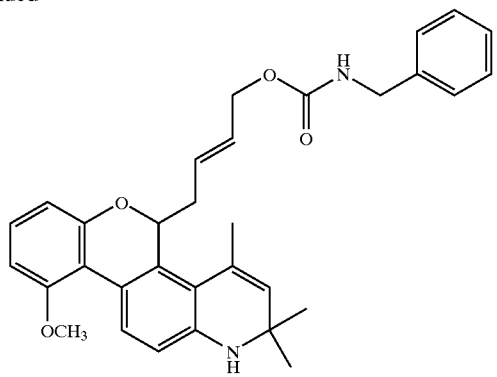

Example 200

As shown in Scheme 16, conversion of ester Example 46 to its Weinreb amide derivative Example 185 and subsequent reduction to aldehyde Example 186 provided precursors for alkene Examples 187, 194, 195, and 200 by treatment of the aldehydes with a number of commercially available Wittig of Homer-Wadsworth-Emmons reagents.

Scheme 17

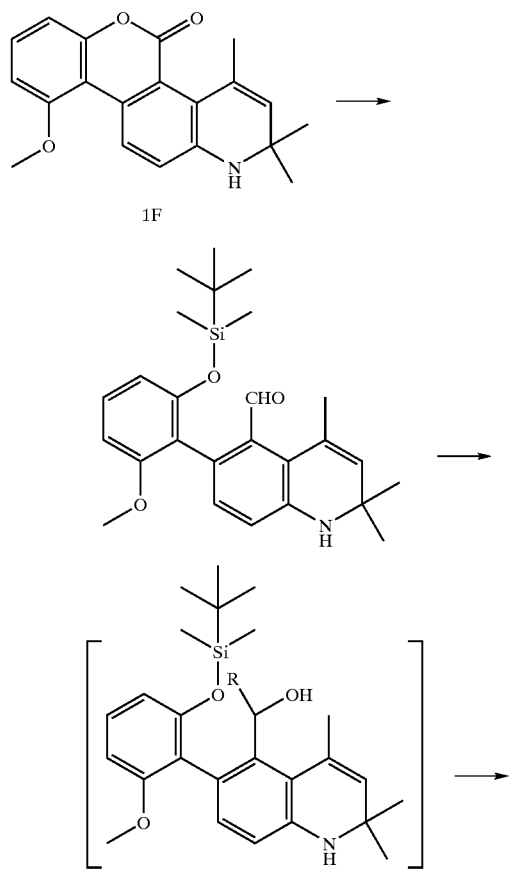

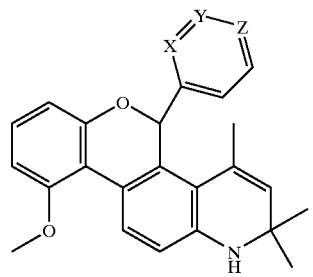

Example 213: X = N; Y, Z = C
Example 214: Y = N; X, Z = C
Example 215: Z = N; X, Y = C As shown in Scheme 17, Example 1F was converted to a ring-opened aldehyde using a two-step sequence involving treatment with a reducing agent such as diisobutylaluminum hydride in an aprotic solvent such as dichloromethane followed by treatment with a silylating reagent such as tert-butyldimethylsilyl chloride in the presence of a base such as potassium tert-butoxide. Addition of organolithium reagents such as lithiopyridines to the aldehyde produced benzylic alcohols (R=pyridyl) which could then be converted to analogs such as Examples 213–215 using a two-step sequence comprising removal of the silicon group with reagents such as tetrabutylammonium fluoride and subsequent cyclization using reagent combinations such as triethylphosphine and 1,1'-(azodicarbonyl)dipiperidine.

Scheme 18

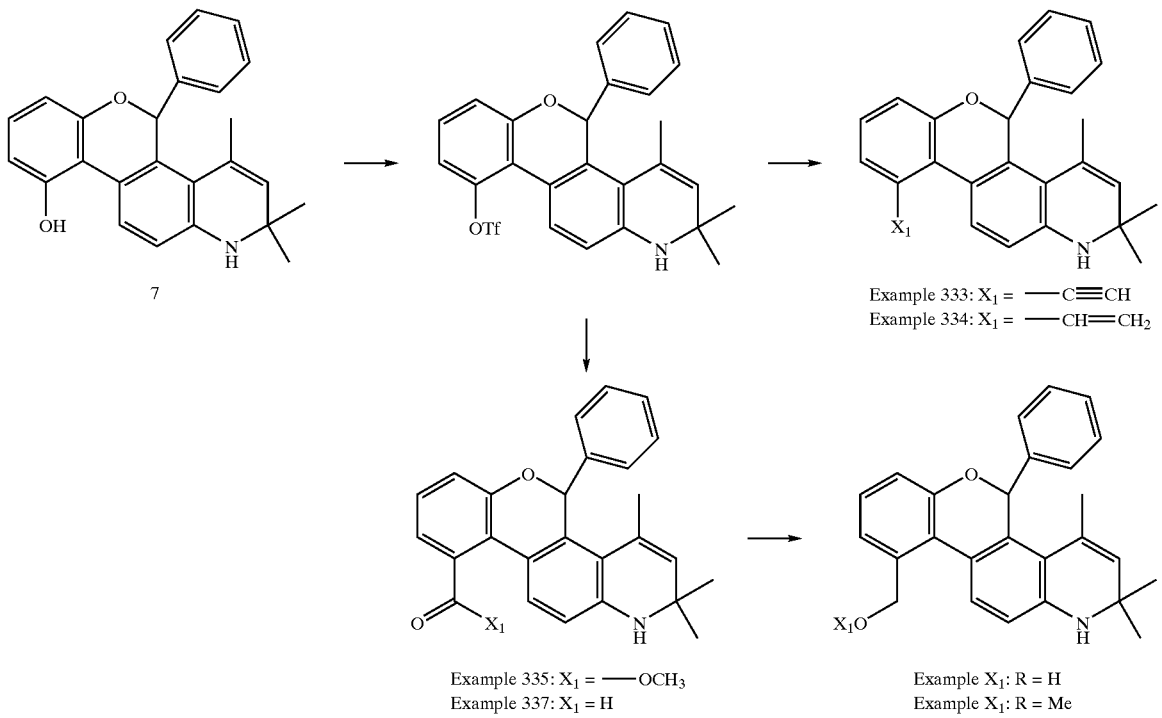

As shown in Scheme 18, Example 7 was converted to the triflate derivative with reagents such as trifluoromethanesulfonic anhydride, then derivatized at the C-10 position using the methods described in Scheme 3. Reduction of Example 335 with reagents such as diisobutylaluminum hydride provided Example 336. Treatment of Example 336 with oxidizing reagents such as tetrapropylammonium perruthenate afforded Example 337. Alkylation of Example 336 could be accomplished with reagents such as iodomethane in the presence of a base such as potassium bis(trimethylsilyl)amide to provide analogs such as Example 338.

Scheme 19

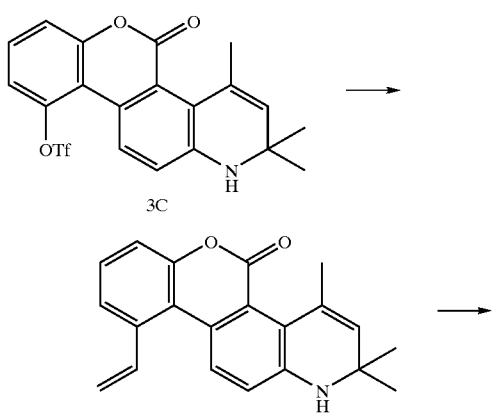

-continued

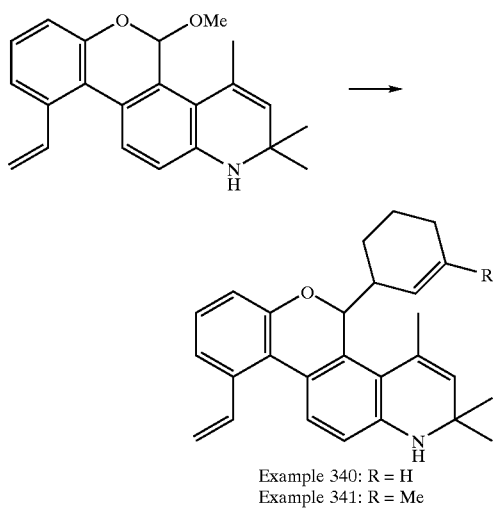

As shown in Scheme 19, triflate 3C was also converted to a C-10 vinyl derivative Example 339 and subsequently to its methyl acetal using the methods described in Schemes 3 and 2, respectively. The acetal was treated with nucleophiles such as 3-(trimethylsilyl)cyclohexene or 3-(dimethylphenylsilyl)-3-methylcyclohexene in the presence of a Lewis acid such as boron trifluoride etherate to provide analogs such as Examples 340 and 341, respectively.

Scheme 20

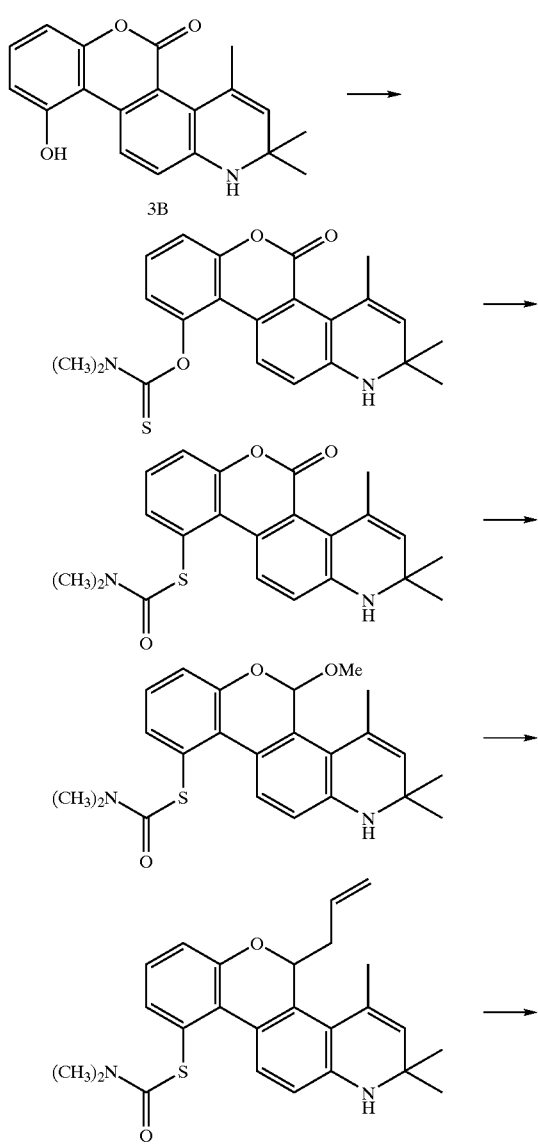

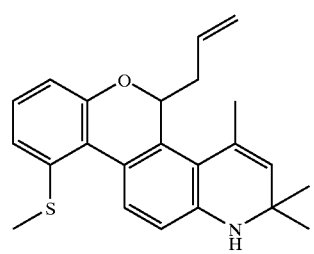

Example 343

Introduction of sulfur at C-10 position of Example 3B is shown in Scheme 20. Example 3B was treated with reagents such as dimethylcarbamoyl chloride to give a thionocarbamate which underwent thermal rearrangement to provide the sulfur-carbon bond at C-10. The allyl group at C-5 was introduced as described in Scheme 2. Hydrolysis with a strong base such as potassium hydroxide and alkylation of sulfur with electrophiles such as iodomethane in the presence of a base such as cesium carbonate provided analogs bearing thioalkoxy functionality at C-10, such as Example 343.

Scheme 21

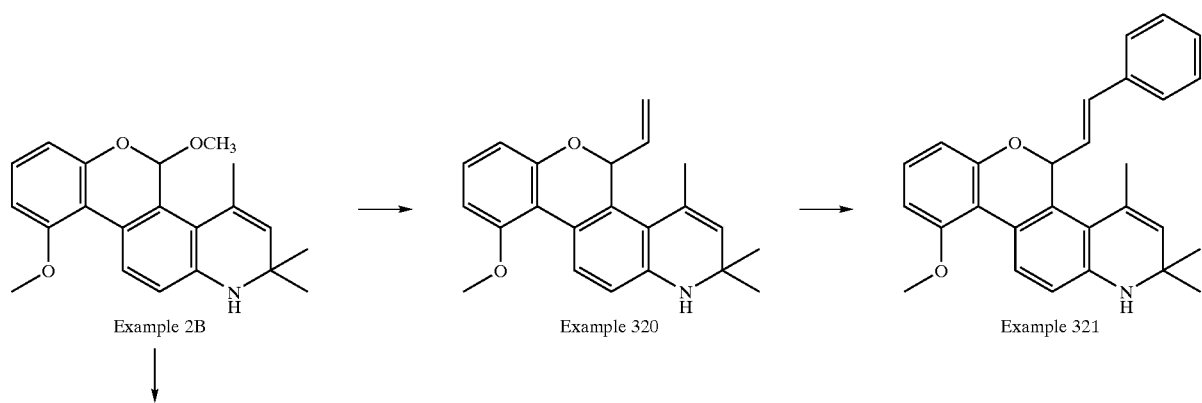

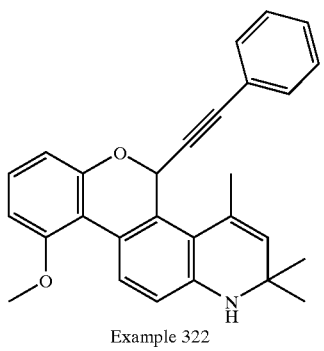

Example 322

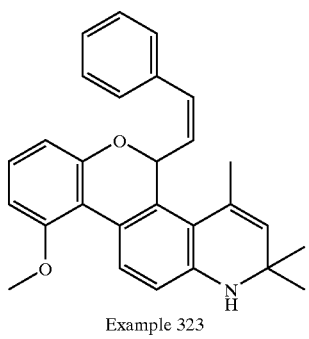

Example 323

A route to make Examples 320–323 is shown in Scheme 21. Example 2B was treated with nucleophiles such as tributylvinyltin in the presence of Lewis acids such as boron trifluoride diethyl etherate to provide Example 320 which was then coupled with aryl halides such as iodobenzene in the presence of catalysts such as palladium (II) acetate to provide trans isomer Example 321. The Lewis acid/methyl acetal complex was also condensed with tributylphenylacetylenyltin to provide Example 322 which was then partially hydrogenated in the presence of catalysts such as palladium on BaSO$_4$ to provide cis isomer Example 323.

It is understood from the preceeding schemes and the following examples that the substituents $R_1$, $R_2$, $R_3$, $R_4$, $R_5$, $R_6$, $R_{16}$, $R_{16'}$, $R_{17}$, $R_{18}$, $R_{18'}$, Y, $R_2$, and $L_2$ can be determined by selection of the appropriate commercially available or known starting materials (e.g., substituted methoxybenzenes) or introduced synthetically by known chemical methods such as those disclosed in Larock, "Comprehensive Organic Transformations. A Guide to Functional Group Preparations," VCH Publishers, New York (1989), hereby incorporated by reference.

Also, it will be appreciated by one skilled in the art that selective protection and deprotection steps depending on the nature of $R_1$, $R_2$, $R_3$, $R_4$, $R_5$, $R_6$, $R_{16}$, $R_{16'}$, $R_{17}$, $R_{18}$, $R_{18'}$, Y, $R_2$, and $L_2$ can be carried out in varying order or number of steps to successfully complete the synthetic sequences. Commonly used protecting groups are disclosed in Greene, "Protective Groups In Organic Synthesis," John Wiley & Sons, New York (1981), hereby incorporated by reference.

EXAMPLE 1

2,5-Dihydro-10-methoxy-2,2,4-trimethyl-5-phenyl-1H-[1]benzopyrano[3,4-f]quinoline1H-[1]benzopyrano[3,4-f]quinoline

EXAMPLE 1A

A solution of 1,3-dimethoxybenzene (33.2 g, 240 mmol) in hexanes (20 mL) at −20° C. was treated sequentially with n-butyllithium (100 mL of a 2.4 M solution in hexanes, 240 mmol) and N,N,N',N'-tetramethylethylenediamine (1.81 mL, 12 mmol), stirred at 23° C. for 1.5 hours, cooled to −78° C., treated with triisopropylborate (60.9 mL, 264 mmol) in diethyl ether (60 mL) over 1.5 hours with additional diethyl ether (150 mL) added to maintain stirring, stirred at 23° C. for 2 hours, poured into ice (150 mL) and 3M HCl (150 mL), and extracted with ethyl acetate. The extract was dried (Na$_2$SO$_4$), filtered, and concentrated, during which a white solid precipitated from solution. The solid was collected by filtration and washed with hexanes to provide the desired compound.

MS (DCI/NH$_3$) m/z 200 (M+NH$_4$)$^+$.

EXAMPLE 1B

A mixture of Example 1A, methyl 5-nitro-2-bromobenzoate (25.8 g, 99.2 mmol), (21.7 g, 119 mmol), cesium carbonate (97.1 g, 298 mmol), and dichlorobis(triphenylphosphine)palladium(II) (3.5 g, 5.0 mmol) in DMF (300 mL) was stirred for 24 hours at 80° C., cooled to 23° C., treated with water (600 mL), and extracted with ethyl acetate (800 mL). The extract was dried (Na$_2$SO$_4$) and concentrated, during which a light yellow solid precipitated from solution. The mixture was placed in a freezer (−20° C.) for 2 hours then filtered to provide the desired compound.

MS (DCI/NH$_3$) m/z 318 (M+H)$^+$ and 335 (M+NH$_4$)$^+$.

EXAMPLE 1C

A solution of Example 1B (11.1 g, 35.1 mmol) in dichloromethane (60 mL) at −78° C. was treated with boron tribromide (25.0 g, 99.8 mmol), warmed to 23° C. for 1 hour, recooled to −78° C., and treated with methanol (100 mL). The mixture was warmed to 0° C., and the precipitate was collected by filtration and recrystallized from methanol to provide the desired compound.

MS (DCI/NH$_3$) m/z 275 (M+NH$_4$)$^+$.

EXAMPLE 1D

A mixture of Example 1C (10.7 g, 41.6 mmol) and Cs$_2$CO$_3$ (20.0 g, 61.4 mmol) in DMF (130 mL) at 23° C. was treated dropwise with methyl iodide (22.8 g, 161 mmol), stirred for 4 hours, treated with water, and extracted with 1:1 ethyl acetate/hexane. The extract was concentrated, and the resulting solid was filtered, washed with water (100 mL), and dried under vacuum to provide the desired compound.

MS (DCI/NH$_3$) m/z 289 (M+NH$_4$)$^+$.

EXAMPLE 1E

A suspension of Example 1D (11.2 g, 41.3 mmol) in dioxane (400 mL) at 23° C. was treated with 10% palladium on carbon (580 mg), heated at 65° C., treated with hydrogen, stirred under atmospheric pressure for 60 hours, filtered through powdered sea shells (Celite®) while hot, and concentrated during which a precipitate formed. The product was filtered and dried under vacuum to provide the desired compound. Concentration of the mother liquor to half of its original volume afforded a second crop of desired compound.

MS (DCI/NH$_3$) m/z 242 (M+H)$^+$ and 259 (M+NH$_4$)$^+$.

EXAMPLE 1F

A solution of Example 1E (4.0 g, 16.6 mmol) and iodine (1.7 g, 6.64 mmol) in acetone (380 mL) in a 1L sealed ACE glass high pressure vessel at 105° C. was stirred for 48 hours, cooled to room temperature, and concentrated. The residue was purified by flash chromatography on silica gel with 0 to 12% ethyl acetate/hexanes to provide the desired compound.

MS (DCI/NH$_3$) m/z 322 (M+H)$^+$.

EXAMPLE 1G

A solution of Example 1F (1.02 g, 3.18 mmol) in THF (20 mL) at −78° C. was treated with a solution of phenyllithium (10.9 mL, 19.6 mmol) in cyclohexanes/diethyl ether, warmed to −50° C., stirred for 2 hours, treated with saturated NH$_4$Cl, warmed to 25° C., and extracted with ethyl acetate. The extract was dried (Na$_2$SO$_4$), filtered, and concentrated. The residue was purified by flash chromatography on silica gel with 20% ethyl acetate/hexanes to provide the desired compound.

MS (DCI/NH$_3$) m/z 400 (M+H)$^+$.

EXAMPLE 1

2,5-Dihydro-10-methoxy-2,2,4-trimethyl-5-phenyl-1H-[1]benzopyrano[3,4-f]quinoline1H-[1]benzopyrano[3,4-f]quinoline A solution of Example 1G (0.67 g, 1.67 mmol) in dichloromethane (30 mL) at -78°C. was treated with triethylsilane (2.91 g,25.05mmol) and BF$_3$OEt$_2$ (0.95 g, 6.66mmol), warmed to room temperature, stirred for 16hours, and traeted with saturated NaHCO$_3$. The organic layer was dried (Na$_2$SO$_4$), filtered, and concentrated. The residue was purified by flash chromatography on silica gel with 5% ethyl acetate/hexanes to provide the desired compound.

MS (DCI/NH$_3$) m/z 384 (M+H)$^+$; $^1$H NMR (300 MHz, DMSO-d$_6$) δ 8.00 (d, 1H), 7.19 (m, 5H), 6.9 (dd, 1H), 6.76 (s, 1H), 6.69 (dd, 1H), 6.55 (d, 1H), 6.43 (d, 1H), 6.2 (s, 1H), 5.38 (s, 1H), 3.8 (s, 3H), 1.83 (s, 3H), 1.22 (s, 3H), 1.14 (s, 3H); Anal. calcd for C$_{26}$H$_{25}$NO$_2$: C, 81.42; H, 6.58; N, 3.65. Found C, 81.28; H, 6.30; N, 3.47.

EXAMPLE 2

2,5-Dihydro-10-methoxy-2,2,4-trimethyl-5-(2-propenyl)-1H-[1]benzopyrano[3,4-f]quinoline

EXAMPLE 2A

A solution of Example 1F (6.65 g, 20.69 mmol) in dichloromethane (500 mL) at −78° C. was treated dropwise with 1M diisobutylaluminum hydride in hexanes (47.6 mL, 47.6 mmol), stirred for 2 hours, treated sequentially with saturated aqueous sodium potassium tartrate (300 mL) and ethyl acetate (600 mL), and stirred vigorously for 4 hours. The extract was washed with brine, dried (Na$_2$SO$_4$), filtered, and concentrated to provide the desired compound.

MS (DCI/NH$_3$) m/z 306 (M−OH)$^+$.

EXAMPLE 2B

A solution of Example 2A (4.20 g, 12.99 mmol) in methanol (150 mL) at 0° C. was treated with p-toluenesulfonic acid.H$_2$O (1.2 g, 20 wt %), stirred for 30 minutes, stirred at room temperature for 1 hour, cooled to 0° C. for 30 minutes, and filtered. The solid was rinsed with hexanes and dried under vacuum to provide the desired compound. The filtrate was poured into saturated NaHCO$_3$ and extracted with ethyl acetate. The extract was washed with brine, dried (Na$_2$SO$_4$), filtered, and concentrated. The residue was purified by flash chromatography on silica gel with 10–20% ethyl acetate/hexanes to provide additional desired compound.

MS (DCI/NH$_3$) m/z 306 (M−OCH$_3$)$^+$.

EXAMPLE 2

2,5-Dihydro-10-methoxy-2,2,4-trimethyl-5-(2-propenyl)-1H-[1]benzopyrano[3,4-f]quinoline A solution of Example 2B (2.50 g, 7.41 mmol) in dichloromethane (225 mL) was treated with allyltrimethylsilane (4.0 mL, 25.2 mmol), cooled to −78° C., treated dropwise with BF$_3$.OEt$_2$ (3.1 mL, 25.2 mmol), stirred for 15 minutes at −78° C., warmed to 0° C. for 30 minutes, treated with saturated NaHCO$_3$, and extracted with ethyl acetate. The extract was washed with brine, dried (MgSO$_4$), filtered, and concentrated. The residue was purified by flash chromatography on silica gel with 5–20% ethyl acetate/hexanes to provide the desired compound.

MS (DCI/NH$_3$) m/z 348 (M+H)$^+$; $^1$H NMR (300 MHz, DMSO-d$_6$) δ 7.96 (d, 1H), 7.07 (t, 1H), 6.71 (d, 1H), 6.60 (d, 1H), 6.52 (d, 1H), 6.12 (br s, 1H), 5.82 (m, 1H), 5.76 (dd, 1H), 5.44 (br s, 1H), 5.01 (m, 2H), 3.86 (s, 3H), 2.44 (m, 1H), 2.20 (m, 1H), 2.16 (s, 3H), 1.17 (s, 3H), 1.16 (s, 3H); Anal. calcd for C$_{23}$H$_{25}$NO$_2$: C, 79.51; H, 7.25; N, 4.03. Found: C, 79.35; H, 7.30; N, 3.89.

EXAMPLE 3

2,5-Dihydro-2,2,4,N-tetramethyl-5-(2-propenyl)-1H-[1]benzopyrano[3,4-f]quinolin-10-amine

EXAMPLE 3A

A solution of Example 1C was processed as in Example 1E to provide the desired compound.

MS (DCI/NH$_3$) m/z 227 (M+H)$^+$.

EXAMPLE 3B

A solution of Example 3A was processed according to the procedure in Example 1F to provide the desired compound.

MS (DCI/NH$_3$) m/z 308 (M+H)$^+$.

EXAMPLE 3C

A solution of Example 3B (1.38 g, 4.49 mmol), triethylamine (1.92 mL, 13.77 mmol) and 4-dimethylaminopyridine (100 mg) in dichloromethane (50 mL) at −78° C., was treated dropwise with trifluoromethanesulfonic anhydride (1.39 g, 4.94 mmol), stirred 30 minutes at −78° C., warmed slowly to room temperature over 1.5 hours, poured into saturated NH$_4$Cl, and extracted with ethyl acetate. The extract was washed with water, dried (MgSO$_4$), filtered, and concentrated. The residue was purified by flash chromatography on silica gel with 10% ethyl acetate/hexanes to provide the desired compound.

MS (DCI/NH$_3$) m/z 440 (M+H)$^+$.

EXAMPLE 3D

Example 3C was processed according to the procedures in examples 2A, 2B and 2 to provide the desired compound.

MS (DCI/NH$_3$) m/z 466 (M+H)$^+$.

EXAMPLE 3

2,5-Dihydro-2,2,4,N-tetramethyl-5-(2-propenyl)-1H-[1]benzopyrano[3,4-f]quinolin-10-amine A solution of Example 3D (0.165 g, 0.36 mmol), palladium(II) acetate (0.0016 g, 0.007 mmol), (S)-(−)-2,2'- bis(phenylphosphino)-1,1'-binapthyl (0.0055, 0.008 mmol), sodium tert-butoxide (0.051 g, 0.53 mmol), methylamine (0.44 mL of a 2.0M solution in THF, 0.88 mmol) in toluene (0.5 mL) was heated at 90° C. for 4 hours in a sealed ACE-glass high pressure vessel, cooled to 0° C., diluted with ethyl acetate (5 mL), and washed with 0.5M HCl. The organic extract was dried ($Na_2SO_4$), filtered, and concentrated. The residue was purified by flash chromatography on silica gel with 5–12% ethyl acetate/hexanes to provide the desired compound.

MS (DCI/$NH_3$) m/z 347 (M+H)$^+$; $^1$H NMR (300 MHz, DMSO-$d_6$) δ 7.83 (d, 1H), 6.94 (dd, 1H), 6.62 (d, 1H), 6.28 (dd, 1H), 6.25 (dd, 1H), 6.05 (d, 1H), 5.86–5.74 (m, 2H), 5.67 (dd, 1H), 5.45 (s, 1H), 5.40 (q, 1H), 5.03 (dd, 1H), 4.98 (dd, 1H), 2.72 (d, 3H), 2.16 (s, 3H), 1.17, (s, 3H), 1.15 (s, 3H); HRMS m/z calcd for $C_{23}H_{26}N_2O$: 346.2045 (M+H)$^+$. Found: 346.2049.

EXAMPLE 4

Methyl 2,5-Dihydro-2,2,4-trimethyl-5-(2-propenyl)-1H-[1]benzopyrano[3,4-f]quinoline-10-carboxylate A solution of Example 3D (263 mg, 0.565 mmol), triethylamine (0.10 mL, 0.717 mmol), 1,3-bis(diphenylphosphino)propane (26 mg, 0.063 mmol) and DMSO (1.5 mL) in methanol (8 mL) was treated with palladium acetate (12.7 mg, 0.056 mmol), saturated with carbon monoxide, stirred under carbon monoxide (1 atm) for 20 minutes, heated at 65° C. for 3 hours, cooled, diluted with ethyl acetate (100 mL), and filtered. The filtrate was washed with brine, dried ($MgSO_4$), filtered, and concentrated. The residue was purified by flash chromatography on silica gel with 5–10% ethyl acetate/hexanes to provide the desired compound.

MS (DCI/$NH_3$) m/z 376 (M+H)$^+$; $^1$H NMR δ 7.19 (m, 2H), 7.03 (dd, 1H), 6.78 (d, 1H), 6.60 (d, 1H), 6.30 (m, 1H), 5.85 (m, 2H), 5.46 (m, 1H), 5.05 (dm, 1H), 4.98 (dm, 1H), 3.77 (s, 3H), 2.30 (m, 2H), 2.19 (d, 3H), 1.21 (s, 3H), 1.15 (s, 3H); HRMS m/z calcd for $C_{24}H_{25}NO_3$: 375.1834 (M+H)$^+$. Found: 375.1841.

EXAMPLE 5

10-Ethenyl-2,5-dihydro-2,2,4-trimethyl-5-(2-propenyl)-1H-[1]benzopyrano[3,4-f]quinoline A solution of Example 3D (103 mg, 0.221 mmol) and (1,3-bis(diphenylphosphino)ferrocene)palladium (II) chloride-dichloromethane (22 mg, 0.027 mmol) in 1-methyl-2-pyrrolidinone (2 mL) was treated with vinyl tributylstannane (0.110 mL, 119 mg, 0.376 mmol), heated at 65° C. for 24 hours, cooled to room temperature, treated with saturated KF, and extracted with ethyl acetate. The extract was washed with brine, dried ($MgSO_4$), filtered, and concentrated. The residue was purified by flash chromatography on silica gel with 5% ethyl acetate/hexanes to provide the desired compound.

MS (DCI/$NH_3$) m/z 344 (M+H)$^+$; $^1$H NMR δ 7.22 (d, 1H), 7.15 (m, 2H), 6.99 (dd, 1H), 6.83 (dd, 1H), 6.63 (d, 1H), 6.23 (m, 1H), 5.87 (ddm, 1H), 5.73 (dd, 1H), 5.76 (dd, 1H), 5.47 (m, 1H), 5.33 (dd, 1H), 5.03 (dd, 1H), 4.98 (dm, 1H), 3.77 (s, 3H), 2.44 (m, 1H), 2.28 (m, 1H), 2.18 (d, 3H), 1.21 (s, 3H), 1.15 (s, 3H); HRMS m/z calcd for $C_{24}H_{26}NO$: 344.2014 (M+H)$^+$. Found: 344.2011.

EXAMPLE 6

10-Ethynyl-2,5-dihydro-10-methoxy-2,2,4-trimethyl-5-(2-propenyl)-1H-[1]benzopyrano[3,4-f]quinoline

EXAMPLE 6A

A solution of Example 3D (25 mg, 0.054 mmol), tetra-n-butylammonium iodide (40 mg, 0.108 mmol), bis(triphenylphosphine)palladium chloride (7.0 mg, 0.010 mmol), copper(I) iodide (3.8 mg, 0.020 mmol) and triethylamine (0.15 mL, 0.717 mmol) in DMF (0.75 mL) was treated with trimethylsilylacetylene (174 mg, 1.76 mmol), heated at 55° C. for 3 hours, diluted with ethyl acetate (20 mL), and filtered. The filtrate was washed with saturated $NH_4Cl$, and the aqueous layer was extracted with ethyl acetate. The combined extracts were dried ($MgSO_4$), filtered, and concentrated. The residue was applied to a 10×20 cm, 0.25 mm silica gel TLC plate and eluted twice with 10% ethyl acetate/hexane. Extraction of the silica gel with ethyl acetate provided the desired compound.

MS (DCI/$NH_3$) m/z 414 (M+H)$^+$; $^1$H NMR (300 MHz, DMSO-$d_6$) δ 8.36 (d, 1H), 7.07 (m, 2H), 6.90 (dd, 1H), 6.60 (d, 1H), 6.34 (m, 1H), 5.80 (m, 2H), 5.46 (m, 1H), 5.04 (dm, 1H), 4.97 (dm, 1H), 2.35 (m, 1H), 2.26 (m, 1H), 2.17 (d, 3H), 1.18 (s, 3H), 1.17 (s, 3H), 0.26 (s, 9H).

EXAMPLE 6

10-Ethynyl-2,5-dihydro-2,2,4-trimethyl-5-(2-propenyl)-1H-[1]benzopyrano[3,4-f]quinoline A solution of Example 6A in THF (2.5 mL) was treated sequentially with glacial acetic acid (0.005 mL) and 1M tetra-n-butylammonium fluoride in THF (0.050 mL, 0.050 mmol), stirred at room temperature for 18 hours, and purified according to the procedure in Example 6A to provide the desired compound.

MS (DCI/$NH_3$) m/z 342 (M+H)$^+$; $^1$H NMR (300 MHz, DMSO-$d_6$) δ 8.27 (dd, 1H), 7.15 (t, 1H), 7.07 (d, 1H), 6.91 (dm, 1H), 6.62 (d, 1H), 6.34 (m, 1H), 5.80 (m, 1H), 5.46 (m, 1H), 5.03 (dm, 1H), 4.98 (dm, 1H), 4.41 (s, 1H), 2.44 (m, 2H), 2.17 (s, 3H), 1.18 (s, 6H); HRMS calcd m/z for $C_{24}H_{23}NO$: 341.1780 (M+H)$^+$. Found: 341.1788.

EXAMPLE 7

2,5-Dihydro-2,2,4-trimethyl-5-phenyl-1H-[1]benzopyrano[3,4-f]quinolin-10-ol

EXAMPLE 7A

A solution of Example 3B (569 mg, 1.85 mmol) in DMF (8 mL) at 23° C. was treated sequentially with imidazole (379 mg, 5.55 mmol) and t-butyldimethylsilyl chloride (418 mg, 2.78 mmol), stirred for 3 hours, poured into water, and extracted with 2:1 hexane/ethyl acetate (22 mL). The extract was washed with water and brine, dried ($Na_2SO_4$), filtered, and concentrated. The residue was purified by flash chromatography on silica gel with 25% ethyl acetate/hexanes to provide the desired compound.

MS (DCI/$NH_3$) m/z 422 (M+H)$^+$.

EXAMPLE 7B

Example 7A was processed as in examples 1G and 1 to provide the desired compound.

EXAMPLE 7

2,5-Dihydro-2,2,4-trimethyl-5-phenyl-1H-[1]benzopyrano[3,4-f]quinolin-10-ol

A solution of Example 7B (0.90 g, 1.87 mmol) in THF (12 mL) at 0° C. was treated with 1M tetra-n-butylammonium fluoride in THF (3.37 mL, 3.37 mmol), warmed to 23° C. with over 1 hour, treated with water, and extracted with ethyl acetate. The extract was washed with brine, dried ($Na_2SO_4$), filtered, and concentrated. The residue was purified by flash chromatography on silica gel with 10–30% ethyl acetate/hexanes to provide the desired compound.

MS (DCI/NH$_3$) m/z 370 (M+H)$^+$; $^1$H NMR (300 MHz, DMSO-d$_6$) δ 9.63 (s, 1H), 9.16 (d, 1H), 7.13–7.24 (m, 5H), 6.74 (s, 1H), 6.70 (d, 1H), 6.8 (d, 1H), 6.39 (dd, 1H), 6.26 (dd, 1H), 6.11 (d, 1H), 5.37 (s, 1H), 1.85 (d, 3H), 1.22 (s, 3H), 1.11 (s, 3H); HRMS calcd m/z for C$_{25}$H$_{23}$NO$_2$: 369.1729 (M+H)$^+$. Found 369.1736.

EXAMPLE 8

10-(Difluoromethoxy)-2,5-dihydro-2,2,4-trimethyl-5-(2-propenyl)-1H-[1]benzopyrano[3,4-f]quinoline

EXAMPLE 8A

A solution of Example 3B (1.11 g, 3.6 mmol) in DMF (10 mL) at 0° C. was treated sequentially with sodium t-butoxide (0.38 g, 3.6 mmol) and bromodifluoromethane (10 mL), stirred at 0° C. for 6 hours, warmed to room temperature for 1 hour, treated with saturated NaHCO$_3$, and extracted with ethyl acetate. The extract was dried (Na$_2$SO$_4$), filtered and concentrated. The residue was purified by flash chromatography on silica gel with 5% ethyl acetate/hexanes to provide the desired compound.

MS (DCI/NH$_3$) m/z 436 (M+H)$^+$.

EXAMPLE 8

10-(Difluoromethoxy)-2,5-dihydro-2,2,4-trimethyl-5-(2-propenyl)-1H-[1]benzopyrano[3,4-f]quinoline Example 8A was processed as in examples 2B and 2 to provide the desired compound.

MS (DCI/NH$_3$) m/z 384 (M+H)$^+$; $^1$H NMR (300 MHz, DMSO-d$_6$) δ 7.75 (d, 1H), 7.20 (t, 1H), 7.15 (t, 1H), 6.83 (dd, 1H), 6.81 (dd, 1H), 6.63 (d, 1H), 6.28 (s, 1H), 5.89–5.75 (m, 2H), 5.46 (s, 1H), 5.04 (dd, 1H), 4.96 (dd, 1H), 2.48–2.40 (m, 1H), 2.29–2.20 (m, 1H), 2.18 (s, 3H), 1.17 (s, 6H); HRMS calcd for C$_{23}$H$_{23}$F$_2$NO$_2$: 383.1697 (M+H)$^+$. Found 383.1693.

EXAMPLE 9

10-Ethoxy-2,5-dihydro-2,2,4-trimethyl-5-phenyl-1H-[1]benzopyrano [3,4-f]quinoline

EXAMPLE 9A

A solution of Example 3B (28 mg, 0.09 mmol) in DMF (1.0 mL) at 0° C. was treated with sodium hydride (2.4 mg of a 60% dispersion in mineral oil, 0.01 mmol), stirred for 1 hour, treated with ethyl bromide (20 mg, 0.182 mmol), stirred for 30 minutes at room temperature, treated with saturated NaHCO$_3$, and extracted with ethyl acetate. The extract was dried (Na$_2$SO$_4$), filtered, and concentrated. The residue was purified by flash chromatography on silica gel with 5% ethyl acetate/hexanes to provide the desired compound.

EXAMPLE 9

10-Ethoxy-2,5-dihydro-2,2,4-trimethyl-5-phenyl-1H-[1]benzopyrano[3,4-f]quinoline Example 9A was processed as in examples 1G and 1 to provide the desired compound.

MS (DCI/NH$_3$) m/z 398 (M+H)$^+$; $^1$H NMR (300 MHz, DMSO-d$_6$) δ 8.09 (d, 1H), 7.20–7.15 (m, 5H), 6.78 (dd, 2H), 6.77 (s, 1H), 6.69 (d, 1H), 6.53 (dd, 1H), 6.43 (dd, 1H), 6.18 (d, 1H), 5.39 (d, 1H), 3.99–4.06 (m, 1H), 1.85 (d, 3H), 1.38 (t, 3H), 1.22 (s, 3H), 1.16 (s, 3H); HRMS calcd m/z for C$_{27}$H$_{27}$NO$_2$: 397.2042 (M+H)$^+$. Found 397.2034.

EXAMPLE 10

2,5-Dihydro-2,2,4-trimethyl-5-phenyl-1H-[1]benzopyrano[3,4-f]quinoline-10-ol Acetate (Ester)

A solution of Example 7 (20 mg, 0.05 mmol) in pyridine (1 mL) at 0° C. was treated with acetic anhydride (0.1 mL, 1.05 mmol), stirred at room temperature 14 hours, and concentrated. The residue was purified by flash chromatography on silica gel with 20% ethyl acetate/hexanes to provide the desired compound.

MS (DCI/NH$_3$) m/z 412 (M+H)$^+$; $^1$H NMR (300 MHz, DMSO-d$_6$) δ 7.62 (d, 1H), 7.21–7.16 (m, 5H), 6.93 (t, 1H), 6.77 (s, 1H), 6.73 (d, 1H), 6.65 (dd, 1H), 6.62 (dd, 1H), 6.32 (s, 1H), 5.37 (s, 1H), 2.30 (s, 3H), 1.79 (s, 3H), 1.22 (s, 3H), 1.14 (s, 3H); HRMS calcd m/z for C$_{27}$H$_{25}$NO$_3$: 411.1834 (M+H)$^+$. Found: 411.1842.

EXAMPLE 11

5-(3-Bromo-5-methylphenyl)-2,5-dihydro-10-methoxy-2,2,4-trimethyl-1H-[1]benzopyrano[3,4-f]quinoline A solution of Example 2B and (0.520 g, 1.54 mmol) in dichloromethane (50 mL) was cooled to −10° C., treated dropwise with BF$_3$.OEt$_2$ (0.57 mL, 4.62 mmol), stirred for 30 minutes at −10° C., treated dropwise with a 0.49 M solution of 3-bromo-5-methylphenylmagnesium bromide in diethyl ether (12.6 mL), stirred for 15 minutes, treated with saturated NaHCO$_3$, and extracted with ethyl acetate. The extract was washed with brine, dried (Na$_2$SO$_4$), filtered, and concentrated. The residue was purified by flash chromatography on silica gel with 5% ethyl acetate/hexanes to provide the desired compound.

$^1$H NMR (300 MHz, DMSO-d$_6$) δ 8.02 (d, 1H), 7.22 (s, 1H), 7.03 (br d, 1H), 6.95 (t, 1H), 6.74 (s, 1H), 6.71 (d, 1H), 6.59 (d, 1H), 6.50 (d, 1H), 6.26 (d, 1H), 5.42 (s, 1H), 4.04 (s, 1H), 3.80 (s, 3H), 2.18 (s, 3H), 1.85 (s, 3H), 1.23 (s, 3H), 1.16 (s, 3H); HRMS m/z calculated for C$_{27}$H$_{26}$NO$_2$Br: 475.1147 (M+H)$^+$. Found 475.1143.

EXAMPLE 12

3-(2,5-Dihydro-10-methoxy-2,2,4-trimethyl-1H-[1]benzopyrano[3,4-f]quinolin-5-yl)phenol, Acetate (Ester)

EXAMPLE 12A

A solution of 3-methoxymethoxyphenyl bromide (10.85 g, 50.00 mmol) in THF (300 mL) at −78° C. was treated with n-butyllithium (2.5 M in hexane, 20 mL), warmed to −30° C., recooled to −78° C., treated with Example 1F, warmed to −50° C., quenched with saturated NH$_4$Cl, warmed to ambient temperature, decanted, and concentrated. The residue was treated with water and extracted with ethyl acetate. The extract was washed with water and brine, dried (Na$_2$SO$_4$), filtered, and concentrated. The residue was purified by flash chromatography on silica gel with 20–25% ethyl acetate/hexanes to provide the desired compound.

MS (DCI/NH$_3$) m/z 460 (M+H)$^+$.

EXAMPLE 12B

A solution of Example 12A (2.30 g, 5.00 mmol) in methanol (10 mL) was treated with HCl-saturated methanol (50 mL), stirred for 18 hours, poured into 1:1 ethyl acetate/ saturated $NH_4Cl$, and extracted with ethyl acetate. The extract was washed with water and brine, dried ($Na_2SO_4$), filtered, and concentrated to provide the desired compound.

MS (DCI/$NH_3$) m/z 416 (M+H)$^+$.

EXAMPLE 12C

A solution of Example 12B (2.45 g, 5.89 mmol) and pyridine (2.33 g, 29.4 mmol) in THF (100 mL) was treated with acetyl chloride (0.51 g, 6.48 mmol), stirred for 4 hours, allowed to settle, decanted, and concentrated. The residue was treated with saturated $NaHCO_3$ and extracted with ethyl acetate. The extract was washed with water and brine, dried ($Na_2SO_4$), filtered, and concentrated. The residue was purified by flash chromatography on silica gel with 25–33% ethyl acetate/hexanes to provide the desired compound.

MS (DCI/$NH_3$) m/z 458 (M+H)$^+$.

EXAMPLE 12

3-(2,5-Dihydro-10-methoxy-2,2,4-trimethyl-1H-[1] benzopyrano[3,4-f]quinolin-5-yl)phenol, Acetate (Ester)

Example 12C was processed as in Example 1 to provide the desired compound.

MS (DCI/$NH_3$) m/z 442 (M+H)$^+$; $^1$H NMR (300 MHz, DMSO-$d_6$) δ 8.01 (d, 1H), 7.26 (t, 1H), 7.07 (d, 1H), 6.98–6.90 (m, 2H), 6.85 (s, 1H), 6.77 (s, 1H), 6.71 (d, 1H), 6.58 (d, 1H), 6.46 (dd, 1H), 6.23 (s, 1H), 5.40 (s, 1H), 3.79 (s, 3H), 2.19 (s, 3H), 1.85 (s, 3H), 1.23 (s, 3H), 1.14 (s, 3H); Anal. calcd for $C_{28}H_{27}NO_4$.0.25$H_2O$: C, 75.40; H, 6.21; N, 3.14. Found: C, 75.76; H, 6.21; N, 2.84.

EXAMPLE 13

3-(2,5-Dihydro-10-methoxy-2,2,4-trimethyl-1H-[1] benzopyrano[3,4-f]quinolin-5-yl)phenol A solution of Example 12 (0.81 g, 1.84 mmol) in THF (20 mL) and methanol (20 mL) was treated with $K_2CO_3$ (2.00 g, 14.5 mmol) in water (6 mL), stirred for 12 hours, quenched with saturated $NH_4Cl$, decanted, concentrated, treated with saturated $NaHCO_3$, and extracted with ethyl acetate. The extract was washed with water and brine, dried ($Na_2SO_4$), filtered, and concentrated to provide the desired compound.

MS (DCI/$NH_3$) m/z 400 (M+H)$^+$; $^1$H NMR (300 MHz, DMSO-$d_6$) δ 9.26 (s, 1H), 8.00 (d, 1H), 7.00 (t, 1H), 6.92 (t, 1H), 6.71–6.66 (m, 2H), 6.63 (d, 1H), 6.58–6.51 (m, 3H), 6.44 (dd, 1H), 6.15 (s, 1H), 5.38 (s, 1H), 3.80 (s, 3H), 1.88 (s, 3H), 1.24 (s, 3H), 1.15 (s, 3H); Anal. calcd for $C_{26}H_{25}NO_3$: C, 78.17; H, 6.30; N, 3.50. Found: C, 77.82; H, 6.42; N, 3.26.

EXAMPLE 14

2,5-Dihydro-10-methoxy-2,2,4-trimethyl-5-[[3-(methylthio)methoxy]phenyl]-1H-[1]benzopyrano[3, 4-f]quinoline A solution of Example 13 (420 mg, 1.05 mmol) in DMF (40 mL) at 0° C. was treated with NaH (50 mg, 2.10 mmol) portionwise over 5 minutes, stirred for 10 minutes, treated with chloromethyl methyl sulfide (152 mg, 1.58 mmol), warmed to room temperature, treated with saturated $NH_4Cl$, and extracted with ethyl acetate. The extract was washed sequentially with 1M NaOH and brine, dried ($Na_2SO_4$), filtered, and concentrated. The residue was purified by flash chromatography on silica gel with 5–17% ethyl acetate/ hexanes to provide the desired compound.

MS (DCI/$NH_3$) m/z 460 (M+H)$^+$; $^1$H NMR (300 MHz, DMSO-$d_6$) δ 8.01 (d, 1H), 7.14 (t, 1H), 6.92 (t, 1H), 6.83–6.68 (m, 5H), 6.56 (d, 1H), 6.47 (d, 1H), 6.21 (s, 1H), 5.40 (s, 1H), 5.13 (s, 2H), 3.80 (s, 3H), 2.09 (s, 3H), 1.97 (s, 3H), 1.24 (s, 3H), 1.16 (s, 3H); Anal. calcd for $C_{28}H_{29}NO_3S.0.5H_2O$: C, 71.76; H, 6.45; N, 2.98. Found: C, 71.93; H, 6.61; N, 2.68.

EXAMPLE 15

[3-(2,5-Dihydro-10-methoxy-2,2,4-trimethyl-1H-[1] benzopyrano[3,4-f]quinolin-5-yl)phenyl] dimethylcarbamate Example 13 and N,N-dimethylcarbamoyl chloride were processed as in Example 14 to provide the desired compound.

MS (DCI/$NH_3$) m/z 471 (M+H)$^+$; $^1$H NMR (300 MHz, DMSO-$d_6$) δ 8.01 (d, 1H), 7.22 (t, 1H), 7.05 (d, 1H), 6.93 (t, 2H), 6.83 (s, 1H), 6.77 (s, 1H), 6.71 (d, 1H), 6.57 (d, 1H), 6.48 (d, 1H), 6.23 (d, 1H), 5.40 (s, 1H), 3.80 (s, 3H), 2.97 (s, 3H), 2.85 (s, 3H), 1.86 (s, 3H), 1.24 (s, 3H), 1.14 (s, 3H), Anal. calcd for $C_{29}H_{30}N_2O_4$: C, 74.02; H, 6.42; N, 5.95. Found: C, 74.05; H, 6.36; N, 5.86.

EXAMPLE 16

5-[3-(2-Furanyl)-5-methylphenyl]-2,5-dihydro-10-methoxy-2,2,4-trimethyl-1H-[1]benzopyrano[3,4-f] quinoline A solution of Example 11 (0.253 g, 0.531 mmol) in 1-methyl-2-pyrrolidinone (25 mL) was deoxygenated with nitrogen, treated with 2-(tributylstannyl)furan (0.33 mL, 1.06 mmol), [1,1'-bis(diphenylphosphino)ferrocene] dichloropalladium(II) dichloromethane complex (0.045 g, 0.005 mmol), heated to 85° C. for 13 hours, cooled to room temperature, diluted with ethyl acetate and saturated KF, stirred for 3 hours, and extracted with ethyl acetate. The extract was washed with brine, dried ($MgSO_4$), filtered, and concentrated. The residue was purified by flash chromatography on silica gel with 5–10% ethyl acetate/hexanes to provide the desired compound.

MS (DCI/$NH_3$) m/z 464 (M+H)$^+$; $^1$H NMR (300 MHz, DMSO-$d_6$) δ 8.02 (d, 1H), 7.67 (m, 1H), 7.31 (d, 2H), 6.92 (t, 1H), 6.92 (s, 1H), 6.75 (m, 2H), 6.72 (d, 1H), 6.57–6.50 (m, 3H), 6.23 (m, 1H), 5.41 (s, 1H), 3.78 (s, 3H), 2.20 (s, 3H), 1.89 (s, 3H), 1.24 (s, 3H), 1.17 (s, 3H); Anal. calcd for $C_{31}H_{29}NO_3$: C, 80.32; H, 6.31; N, 3.02. Found: C, 80.08; H, 6.25; N, 2.83.

EXAMPLE 17

2,5-Dihydro-10-methoxy-2,2,4-trimethyl-5-[3-methyl-5-(1-morpholinyl)phenyl]-1H-[1] benzopyrano[3,4-f]quinoline A solution of Example 11 (0.055 g, 0.115 mmol) in toluene (5 mL) was treated sequentially with bis (dibenzylideneacetone)palladium(0) (0.007 g, 0.012 mmol), (S)-(−)-bis(diphenylphospino)-1,1'-binaphthyl (0.022 g, 0.035 mmol), morpholine (15 μL, 0.173 mmol), and sodium tert-butoxide (0.028 g, 0.289 mmol), stirred at 85° C. for 4 hours, cooled to room temperature, diluted with ethyl acetate and water, and filtered through powdered sea shells (Celite®). The extract was washed with brine, dried ($Na_2SO_4$), filtered, and concentrated. The residue was purified by flash chromatography on silica gel with 10–33% ethyl acetate/hexanes to provide the desired compound.

MS (DCI/NH$_3$) m/z 483 (M+H)$^+$; $^1$H NMR (300 MHz, DMSO-d$_6$) δ 7.97 (d, 1H), 6.93 (t, 1H), 6.68 (m, 2H), 6.54–6.60 (m, 3H), 6.49 (d, 1H), 6.40 (s, 1H), 6.18 (br s, 1H), 5.40 (s, 1H), 3.78 (s, 3H), 3.65 (m, 4H), 2.91 (m, 4H), 2.09 (s, 3H), 1.89 (s, 3H), 1.21 (s, 3H), 1.16 (s, 3H); Anal. calcd for C$_{31}$H$_{34}$N$_2$O$_3$.0.25H$_2$O: C, 76.44; H, 7.14; N, 5.75. Found: C, 76.61; H, 7.35; N, 5.47.

EXAMPLE 18

2,5-Dihydro-10-methoxy-2,2,4-trimethyl-5-(phenylmethylene)-1H-[1]benzopyrano[3,4-f]quinoline A solution of Example 1F (0.100 g, 0.31 mmol) in THF (5 mL) at −78° C. was treated with a solution of benzylmagnesium bromide (10 mL of 0.44 M solution in ether, 4.4 mmol) dropwise over 10 minutes, warmed to room temperature, stirred for 14 hours, treated with saturated NH$_4$Cl, and extracted with ethyl acetate. The extract was dried (Na$_2$SO$_4$) and concentrated. The residue was dissolved in dichloromethane (10 mL), treated with p-toluenesulfonic acid.H$_2$O (0.059 g, 0.31 mmol), stirred for 14 hours at room temperature, treated with 2% NaOH (10 mL), and extracted with ethyl acetate. The residue was purified by flash chromatography on silica gel with 10% ethyl acetate/hexanes to provide the desired compound as a mixture of regioisomers. The regioisomers were separated by HPLC (Microsorb, 5% acetone/hexanes) but rapidly interconverted at room temperature to a 1:1 regioisomeric mixture.

MS (DCI/NH$_3$) m/z 396 (M+H)$^+$; $^1$H NMR (300 MHz, DMSO-d$_6$) isomer 1: δ 8.12 (d, 1H), 7.16–7.03 (m, 5H), 6.80–6.66 (m, 4H), 6.45 (s, 1H), 6.34 (s, 1H), 5.0 (s, 1H), 3.90 (s, 3H), 1.84 (s, 3H), 1.20 (s, 3H), 0.91 (s, 3H); isomer 2: δ 8.23 (d, 1H), 7.70 (d, 2H), 7.37 (t, 2H), 7.22 (m, 1H), 7.03–7.16 (m, 3H), 6.86 (d, 1H), 6.55 (s, 1H), 5.53 (s, 1H), 5.45 (s, 1H), 3.90 (s, 3H), 1.97 (s, 3H), 1.25 (s, 6H); HRMS calcd m/z for C$_{27}$H$_{25}$NO$_2$: 395.1885 (M+H)$^+$. Found: 395.1884.

EXAMPLE 19

5-(3,5-Dichlorophenyl)-2,5-dihydro-10-methoxy-2,2,4-trimethyl-1H-[1]benzopyrano[3,4-f]quinoline Example 1F and 3,5-dichlorophenyl magnesium bromide were processed as in examples 1G and 1 to provide the desired compound.

MS (DCI/NH$_3$) m/z 452 (M+H)$^+$; $^1$H NMR (300 MHz, DMSO) δ 8.10 (d, 1H), 7.51 (t, Hz, 1H), 7.19 (d, 2H), 7.03 (dd, 1H), 6.87 (s, 1H), 6.80 (d, 1H), 6.67 (d, 1H), 6.59 (d, 1H), 6.36 (s, 1H), 5.50 (s, 1H), 3.87 (s, 3H), 1.93 (s, 3H), 1.29 (s, 3H), 1.22 (s, 3H); $^{13}$C NMR (75 MHz, DMSO) 156.1, 151.1, 145.6, 143.8, 133.8, 133.8, 133.5, 128.1, 127.6, 127.3, 127.2, 127.1, 126.7, 126.7, 117.8, 116.9, 114.1, 113.4, 110.2, 105.9, 73.3, 55.6, 49.7, 29.2, 28.5, 23.2; HRMS calcd for C$_{26}$H$_{23}$NO$_2$Cl$_2$: 451.1106 (M+H)$^+$. Found 451.1113.

EXAMPLE 20

5-Butyl-2,5-dihydro-10-methoxy-2,2,4-trimethyl-1H-[1]benzopyrano[3,4-f]quinoline Example 1F and n-butyllithium were processed as in examples 1G and 1 to provide the desired compound.

MS (DCI/NH$_3$) m/z 364 (M+H)$^+$; $^1$H NMR (300 MHz, DMSO-d$_6$) δ 7.94 (d, 1H), 7.06 (dd, 1H), 6.68 (dd, 1H), 6.58 (d, 1H), 6.54 (dd, 1H), 6.08 (s, 1H), 5.67 (m, 1H), 5.44 (s, 1H), 3.85 (s, 3H), 2.15 (s, 3H), 1.68 (m, 1H), 1.41–1.22 (m, 5H), 1.17 (s, 3H), 1.14 (s, 3H), 0.78 (t, 3H); Anal. calcd for C$_{24}$H$_{29}$NO$_2$: C, 79.30; H, 8.04; N, 3.85. Found C, 79.10; H, 8.14; N, 3.72.

EXAMPLE 21

2,5-Dihydro-10-methoxy-2,2,4-trimethyl-5-[3-(trifluoromethyl)phenyl]-1H-[1]benzopyrano[3,4-f]quinoline Example 1F and 3-trifluoromethylphenyl-magnesium bromide were processed as in examples 1G and 1 to provide the desired compound.

MS (DCI/NH$_3$) m/z 452 (M+H)$^+$; $^1$H NMR (300 MHz, DMSO-d$_6$) δ 8.03 (d, 1H), 7.55 (m, 1H), 7.47 (m, 3H), 6.93 (dd, 1H), 6.88 (s, 1H), 6.73 (d, 1H), 6.58 (d, 1H), 6.48 (d, 1H), 6.29 (s, 1H), 5.43 (s, 1H), 3.79 (s, 3H), 1.85 (s, 3H), 1.23 (s, 3H), 1.17 (s, 3H); Anal. calcd for C$_{27}$H$_{24}$F$_3$NO$_2$: C, 71.82; H, 5.35; N, 3.10. Found: C, 71.73; H, 5.44; N, 3.05.

EXAMPLE 22

2,5-Dihydro-10-methoxy-5-(4-methoxyphenyl)-2,2,4-trimethyl-1H-[1]benzopyrano[3,4-f]quinoline Example 2B and anisole were processed as in Example 2C to provide the desired compound.

MS (DCI/NH$_3$) m/z 414 (M+H)$^+$; $^1$H NMR (300 MHz, DMSO-d$_6$) δ 8.00 (d, 1H), 7.04 (d, 2H), 6.90 (dd, 1H), 6.78 (dd, 2H), 6.70 (dd, 2H), 6.60 (dd, 1H), 6.41 (dd, 1H), 6.18 (s, 1H), 5.37 (s, 1H), 3.79 (s, 3H), 3.65 (s, 3H), 1.83 (s, 3H), 1.22 (s, 3H), 1.13 (s, 3H); HRMS calcd m/z for C$_{27}$H$_{27}$NO$_3$: 413.1991 (M+H)$^+$. Found: 413.1987.

EXAMPLE 23

5-(3-Chlorophenyl)-2,5-dihydro-10-methoxy-2,2,4-trimethyl-1H-[1]benzopyrano[3,4-f]quinoline Example 1F and 3-chlorophenylmagnesium bromide were processed as in examples 1G and 1 to provide the desired compound.

MS (DCI/NH$_3$) m/z 418 (M+H)$^+$; $^1$H NMR (300 MHz, DMSO-d$_6$) δ 8.01 (d, 1H), 7.23–7.12 (m, 4H), 6.90 (dd, 1H), 6.77 (s, 1H), 6.70 (d, 1H), 6.55 (dd, 1H), 6.44 (dd, 1H), 6.18 (d, 1H), 5.38 (s, 1H), 3.79 (s, 3H), 1.84 (s, 3H), 1.22 (s, 3H), 1.15 (s, 3H); HRMS calcd m/z for C$_{26}$H$_{24}$NO$_2$Cl: 417.1496 (M+H)$^+$. Found: 417.1490.

EXAMPLE 24

2,5-Dihydro-10-methoxy-2,2,4-trimethyl-5-(3-methylphenyl)-1H-[1]benzopyrano[3,4-f]quinoline Example 1F and 3-methylphenylmagnesium bromide were processed as in examples 1G and 1 to provide the desired compound.

MS (DCI/NH$_3$) m/z 398 (M+H)$^+$; $^1$H NMR (300 MHz, DMSO-d$_6$) δ 7.94 (d, 1H), 7.01–6.91 (m, 4H), 6.84 (dd, 1H), 6.66 (s, 1H), 6.62 (d, 1H), 6.48 (dd, 1H), 6.38 (dd, 1H), 6.11 (d, 1H), 5.31 (d, 1H), 3.72 (s, 3H), 2.10 (s, 3H), 1.78 (d, 3H), 1.15 (s, 3H), 1.09 (s, 3H); Anal. calcd for C$_{28}$H$_{27}$NO$_2$: C, 81.58; H, 6.85; N, 3.52. Found: C, 81.23; H, 7.18; N, 3.36.

EXAMPLE 25

(±)-2,5-Dihydro-10-methoxy-2,2,4-trimethyl-5-phenyl-1H-[1]benzopyrano-[3,4-f]quinoline Enantiomer of Example 1.
Spectral data are identical to Example 1.

$[\alpha]_D$=+85.1;

Retention time=11.68 minutes on a Chiralcel OJ 4.6×250 mm HPLC column;

Solvent: 95:5 hexane:ethanol;

Flow rate: 1 mL/minute.

EXAMPLE 26

(±)-2,5-Dihydro-10-methoxy-2,2,4-trimethyl-5-phenyl-1H-[1]benzopyrano[3,4-f]quinoline Enantiomer of Example 1. Spectral data are identical to Example 1.

$[\alpha]_D$=−84.9;

Retention time=15.27 minutes on a Chiralcel OJ 4.6×250 mm HPLC column;

Solvent: 95:5 hexane:ethanol;

Flow rate: 1 mL/minute.

EXAMPLE 27

5-(3,5-Dimethylphenyl)-2,5-dihydro-10-methoxy-2,2,4-trimethyl-1H-[1]benzopyrano[3,4-f]quinoline Example 1F (0.052 g, 0.162 mmol) in THF (5 mL) was cooled to 0° C., treated dropwise with 0.38 M 3,5-dimethylphenyl magnesium bromide in dimethylether (4.4 mL, 1.68 mmol), warmed to room temperature, stirred for 14 hours, partitioned between saturated $NH_4Cl$ and ethyl acetate, and extracted with ethyl acetate. The extract was washed with brine, dried ($MgSO_4$), filtered, and concentrated. The residue was purified by flash chromatography on silica gel with a gradient from 10–25% ethyl acetate/hexanes to provide the desired lactol.

The lactol (0.043 g, 0.101 mmol) was dissolved in dichloromethane (7 mL), treated with triethylsilane (0.16 mL, 1.01 mmol), cooled to 0° C., treated with $BF_3.OEt_2$ (0.12 mL, 1.01 mmol), warmed to room temperature, stirred for 19 hours, and treated with $NaHCO_3$, and extracted with ethyl acetate. The extract was washed with brine, dried ($MgSO_4$), and concentrated. The residue was purified by flash chromatography on silica gel with 5–10% ethyl acetate/hexanes to provide the desired compound.

MS (DCI/$NH_3$) m/z 412 (M+H)$^+$; $^1$H NMR (300 MHz, DMSO-$d_6$) δ 8.00 (d, 1H), 6.92 (t, 1H), 6.78 (m, 3H), 6.70 (d, 1H), 6.69 (s, 1H), 6.56 (dd, 1H), 6.47 (dd, 1H), 6.19 (d, 1H), 5.39 (s, 1H), 3.79 (s, 3H), 2.11 (s, 6H), 1.85 (s, 3H), 1.22 (s, 3H), 1.15 (s, 3H); Anal. calcd for $C_{28}H_{29}NO_2$: C, 81.72; H, 7.10; N, 3.40. Found: C, 81.59; H, 7.54; N, 3.16.

EXAMPLE 28

5-(4-Chlorophenyl)-2,5-dihydro-10-methoxy-2,2,4-trimethyl-1H-[1]benzopyrano[3,4-f]quinoline Example 1F and 4-chlorophenylmagnesium bromide were processed as in examples 1G and 1 to provide the desired compound.

MS (DCI/$NH_3$) m/z 418 (M+H)$^+$; $^1$H NMR (300 MHz, DMSO-$d_6$) δ 8.01 (d, 1H), 7.24 (q, 4H), 6.92 (t, 1H), 6.76 (s, 1H), 6.70 (d, 1H), 6.57 (d, 1H), 6.43 (d, 1H), 6.24 (br s, 1H), 5.20 (br s, 1H), 3.79 (s, 3H), 1.83 (s, 3H), 1.24 (s, 3H), 1.14 (s, 3H); Anal. calcd for $C_{26}H_{24}NO_2Cl$: C, 74.72; H, 5.79; N, 3.35. Found: C, 74.73; H, 5.68; N, 3.29.

EXAMPLE 29

5-(3,4-Dimethylphenyl)-2,5-dihydro-10-methoxy-2,2,4-trimethy-1H-[1]benzopyrano[3,4-f]quinoline Example 1F and 3,4-dimethylphenylmagnesium bromide were processed as in examples 1G and 1 to provide the desired compound.

MS (DCI/$NH_3$) m/z 412 (M+H)$^+$; $^1$H NMR (300 MHz, DMSO-$d_6$) δ 7.98 (d, 1H), 6.94 (s, 1H), 6.82 (q, 2H), 6.78 (d, 1H), 6.67 (d, 1H), 6.53 (d, 1H), 6.42 (d, 1H), 6.17 (s, 1H), 5.37 (s, 1H), 3.78 (s, 3H), 2.08 (s, 6H), 1.84 (s, 3H), 1.22 (s, 3H), 1.14 (s, 3H); Anal. calcd for $C_{28}H_{29}O_2N.0.5H_2O$: C, 79.97; H, 7.19; N, 3.33. Found: C, 79.94; H, 7.25; N, 2.98.

EXAMPLE 30

5-(4-Fluorophenyl)-2,5-dihydro-10-methoxy-2,2,4-trimethyl-1H-[1]benzopyrano[3,4-f]quinoline Example 2B and 4-fluorophenylmagnesium bromide were processed as in Example 11 to provide the desired compound.

MS (DCI/$NH_3$) m/z 402 (M+H)$^+$; $^1$H NMR (300 MHz, DMSO-$d_6$) δ 8.03 (d, 1H), 7.16 (m, 2H), 7.03 (t, 2H), 6.88 (t, 1H), 6.71 (s, 1H), 6.68 (d, 1H), 6.55 (d, 1H), 6.41 (d, 1H), 6.22 (s, 1H), 5.38 (s, 1H), 3.79 (s, 3H), 1.82 (s, 3H), 1.23 (s, 3H), 1.14 (s, 3H).

EXAMPLE 31

5-[3,5-bis(Trifluoromethyl)phenyl]-2,5-dihydro-10-methoxy-2,2,4-trimethyl-1H-[1]benzopyrano[3,4-f]quinoline Example 2B and 4-fluorophenylmagnesium bromide were processed as in Example 11 to provide the desired compound.

$^1$H NMR (300 MHz, DMSO-$d_6$) δ 8.02 (d, 1H), 7.98 (s, 1H), 7.00 (s, 1H), 6.93 (d, 1H), 6.75 (d, 1H), 6.59 (d, 1H), 6.49 (d, 1H), 6.38 (s, 1H), 5.46 (s, 1H), 3.79 (s, 3H), 1.87 (s, 3H), 1.21 (s, 3H), 1.19 (s, 3H); HRMS calcd m/z for $C_{28}H_{23}O_2F_6N$: 519.1633 (M+H)$^+$. Found: 519.1646; Anal. calcd for $C_{28}H_{23}NO_2F_6.1.25H_2O$: C, 62.05; H, 4.74; N, 2.58. Found: C, 61.96; H, 4.70; N, 2.35.

EXAMPLE 32

(−)-5-(3,5-Dichlorophenyl)-2,5-dihydro-10-methoxy-2,2,4-trimethyl-1H-[1]benzopyrano[3,4-f]quinoline Enantiomer of Example 19.

Spectal data are identical to Example 19.

$[\alpha]_D$=−208.0;

Retention time=6.89 minutes on a Regis (R,R)-WhelkO1 Kromasil 4.6×250 mm HPLC column;

Solvent: 86:10:3 hexane:dichloromethane:ethanol;

Flow rate: 1 mL/minute.

EXAMPLE 33

(+)-5-(3,5-Dichlorophenyl)-2,5-dihydro-10-methoxy-2,2,4-trimethyl-1H-[1]benzopyrano[3,4-f]quinoline Enantiomer of Example 19. Spectal data are identical to Example 19.

$[\alpha]_D$=+210.7;

Retention time=8.63 min on a Regis (R,R)-WhelkO1 Kromasil 4.6×250 mm HPLC column;

Solvent: 86:10:3 hexane:dichloromethane:ethanol;

Flow rate: 1 mL/minute.

EXAMPLE 34

5-(3,5-Difluorophenyl)-2,5-dihydro-10-methoxy-2,2,4-trimethyl-1H-[1]benzopyrano[3,4-f]quinoline Example 2B and 3,5-difluorophenylmagnesium bromide were processed as in Example 11 to provide the desired compound.

$^1$H NMR (300 MHz, DMSO-d$_6$) δ 8.01 (d, 1H), 7.05 (m, 1H), 6.93 (t, 1H), 6.79 (s, 3H), 6.71 (d, 1H), 6.59 (9, 1H), 6.50 (d, 1H), 6.30 (s, 1H), 5.43 (s, 1H), 3.81 (s, 3H), 1.87 (s, 3H), 1.23 (s, 3H), 1.16 (s, 3H); HRMS calcd m/z for C$_{26}$H$_{23}$O$_2$F$_2$N: 419.1697 (M+H)$^+$. Found: 419.1702; Anal. calcd for C$_{26}$H$_{23}$O$_2$F$_2$N.0.5H$_2$O: C, 72.88; H, 5.65; N, 3.27. Found: C, 72.62; H, 5.58; N, 3.06.

EXAMPLE 35

2,5-Dihydro-10-methoxy-2,2,4,N-tetramethyl-N-phenyl-1H-[1]benzopyrano[3,4-f]quinolin-5-amine Example 1F and N-methylaniline were processed as in Example 2 to provide the desired compound.

MS (DCI/NH$_3$) m/z 306 (M−NMePh)$^+$; $^1$H NMR (300 MHz, DMSO-d$_6$) δ 8.03 (d, 1H), 7.25 (t, 2H), 7.08 (m, 2H), 6.99 (t, 1H), 6.86 (s, 1H), 6.80 (t, 1H), 6.70–6.65 (m, 2H), 6.41 (d, 1H), 6.26 (br s, 1H), 5.39 (br s, 1H), 3.87 (s, 3H), 2.47 (s, 3H), 1.74 (s, 3H), 1.24 (s, 3H), 1.11 (s, 3H).

EXAMPLE 36

(−)2,5-Dihydro-10-methoxy-2,2,4-trimethyl-5-(2-propenyl)-1H-[1]benzopyrano[3,4-f]quinoline Example 2 was purified by flash chromatography on Chiralcel OJ with 10% ethanol/hexanes to provide the desired compound.

[α]$_D$32 1.8 (c 1.2, CHCl$_3$); MS (DCI/NH$_3$) m/z 348 (M+H)$^+$; $^1$H NMR (300 MHz, DMSO-d$_6$) δ 7.96 (d, 1H), 7.07 (t, 1H), 6.71 (d, 1H), 6.60 (d, 1H), 6.52 (d, 1H), 6.12 (br s, 1H), 5.82 (m, 1H), 5.76 (dd, 1H), 5.44 (br s, 1H), 5.01 (m, 2H), 3.86 (s, 3H), 2.44 (m, 1H), 2.20 (m, 1H), 2.16 (s, 3H), 1.17 (s, 3H), 1.16 (s, 3H); Anal. calcd for C$_{23}$H$_{25}$NO$_2$: C, 79.51; H, 7.25; N, 4.03. Found: C, 9.34; H, 7.00; N, 4.07.

EXAMPLE 37

(+)-2,5-Dihydro-10-methoxy-2,2,4-trimethyl-5-(2-propenyl)-1H-[1]benzopyrano[3,4-f]quinoline Example 2 was purified by flash chromatography on Chiralcel OJ with 10% ethanol/hexanes to provide the desired compound.

[α]$_D$=+2.1(c 1.1, CHCl$_3$); MS (DCI/NH$_3$) m/z 348 (M+H)$^+$; $^1$H NMR (300 MHz, DMSO-d$_6$) δ 7.96 (d, 1H), 7.07 (t, 1H), 6.71 (d, 1H), 6.60 (d, 1H), 6.52 (d, 1H), 6.12 (br s, 1H), 5.82 (m, 1H), 5.76 (dd, 1H), 5.44 (br s, 1H), 5.01 (m,2H), 3.86 (s, 3H), 2.44 (m, 1H), 2.20 (m, 1H), 2.16 (s, 3H), 1.17 (s, 3H), 1.16 (s, 3H); Anal. calcd for C$_{23}$H$_{25}$NO$_2$: C, 79.51; H, 7.25; N, 4.03. Found: C, 79.29; H, 7.01; N, 3.92.

EXAMPLE 38

2,5-Dihydro-10-methoxy-2,2,4-trimethyl-1H-[1]benzopyrano[3,4-f]quinoline

Example 2B and triethylsilane were processed as in Example 2 to provide the desired compound.

MS (DCI/NH$_3$) m/z 308 (M+H)$^+$; $^1$H NMR (300 MHz, DMSO-d$_6$) δ 7.82 (d, 1H), 7.05 (t, 1H), 6.72 (dd, 1H), 6.58 (d, 1H), 6.57 (dd, 1H), 6.13 (d, 1H), 5.39 (t, 1H), 5.10 (s, 2H), 3.84 (s, 3H), 2.02 (d, 3H), 1.18 (s, 6H); Anal. calcd for C$_{20}$H$_{21}$NO$_2$.0.1H$_2$O: C, 77.69; H, 6.91; N, 4.53. Found: C, 77.60; H, 7.15; N, 4.33.

EXAMPLE 39

4-(2,5-Dihydro-10-methoxy-2,2,4-trimethyl-1H-[1]benzopyrano[3,4-f]quinolin-5-yl)-N,N-dimethylbenzenamine Example 2B and N,N-dimethylaniline were processed as in Example 2 to provide the desired compound.

MS (DCI/NH$_3$) m/z 427 (M+H)$^+$; $^1$H NMR (300 MHz, DMSO-d$_6$) δ 7.98 (d, 1H), 6.95 (d, 2H), 6.88 (t, 1H), 6.57 (d, 1H), 6.64 (s, 1H), 6.53 (m, 3H), 6.39 (d, 1H), 6.14 (d, 1H), 5.35 (s, 1H), 3.79 (s, 3H), 2.80 (s, 6H), 1.84 (s, 3H), 1.21 (s, 3H), 1.13 (s, 3H); Anal. calcd for C$_{28}$H$_{30}$N$_2$O$_2$.0.25H$_2$O: C, 78.02; H, 7.13; N, 6.50. Found: C, 78.29; H, 7.38; N, 6.01.

EXAMPLE 40

2,5-Dihydro-10-methoxy-2,2,4-trimethyl-5-(5-methoxy-2-thienyl)1H-[1]benzopyrano[3,4-f]quinoline Example 2B and 2-methoxythiophene were processed as in Example 2 to provide the desired compound.

MS (DCI/NH$_3$) m/z 420 (M+H)$^+$; $^1$H NMR (500 MHz, DMSO-d$_6$) δ 7.98 (d, 1H), 6.97 (d, 1H), 6.73 (s, 1H), 6.67 (d, 1H), 6.63 (d, 1H), 6.46 (d, 1H), 6.20 (d, 1H), 6.18 (s, 1H), 5.96 (d, 4H), 5.39 (s, 1H), 3.82 (s, 3H), 3.72 (s, 3H), 1.98 (s, 3H), 1.21 (s, 3H), 1.13 (s, 3H); Anal. calcd for C$_{25}$H$_{25}$NO$_3$S: C, 71.57; H, 6.01; N, 3.34. Found: C, 71.54; H, 5.99; N, 3.17.

EXAMPLE 41

2,5-Dihydro-10-methoxy-2,2,4-trimethyl-5-(5-propyl-2-thienyl)-1H-[1]benzopyrano[3,4-f]quinoline Example 2B and 2-propylthiophene were processed as in Example 2 to provide the desired compound.

$^1$H NMR (300 MHz, DMSO-d$_6$) δ 8.01 (d, 1H), 6.95 (t, 1H), 6.84 (s, 1H), 6.67 (d, 1H), 6.61 (d, 1H), 6.51 (d, 1H), 6.46 (d, 1H), 6.41 (d, 1H), 6.18 (m, 1H), 5.39 (s, 1H), 3.82 (s, 3H), 2.59 (t, 2H), 1.96 (s, 3H), 1.50 (h, 2H), 1.20 (s, 3H), 1.14 (s, 3H), 0.83 (t, 3H); HRMS calcd m/z for C$_{27}$H$_{29}$NO$_2$S: 431.1919 (M+H)$^+$. Found: 431.1911.

EXAMPLE 42

2,5-Dihydro-10-methoxy-2,2,4-trimethyl-5-[4-(1-morpholinyl)phenyl]1H-[1]benzopyrano[3,4-f]quinoline Example 2B and 4-phenylmorpholine were processed as in Example 2 to provide the desired compound.

MS (DCI/NH$_3$) m/z 469 (M+H)$^+$; $^1$H NMR (300 MHz, DMSO-d$_6$) δ 8.00 (d, 1H), 7.00 (d, 2H), 6.92 (t, 1H), 6.76 (d, 2H), 6.68 (d, 2H), 6.55 (d, 1H), 6.40 (d, 1H), 6.16 (m, 1H), 5.36 (s, 1H), 3.79 (s, 3H), 3.62 (m, 4H), 3.05 (m, 4H), 1.81 (s, 3H), 1.22 (s, 3H), 1.13 (s, 3H); Anal. calcd for C$_{30}$H$_{32}$N$_2$O$_2$.0.5H$_2$O: C, 75.45; H, 6.96; N, 5.87. Found: C, 75.46; H, 6.69; N, 5.31.

EXAMPLE 43

1-(2,5-Dihydro-10-methoxy-2,2,4-trimethyl-1H-[1]benzopyrano[3,4-f]quinolin-5yl)-3,3-dimethyl-2-butanone Example 2B and (2,2-dimethyl-1-methylenepropoxy)trimethylsilane were processed as in Example 2 to provide the desired compound.

MS (DCI/NH$_3$) m/z 406 (M+H)$^+$; $^1$H NMR (300 MHz, DMSO-d$_6$) δ 7.95 (d, 1H), 7.04 (t, 1H), 6.71 (d, 1H), 6.60 (d, 1H), 6.41 (d, 1H), 6.33 (d, 1H), 6.15 (br s, 1H), 5.43 (s, 1H), 3.87 (s, 3H), 3.26 (m, 1H), 2.36 (m, 1H), 2.13 (s, 3H), 1.16 (s, 3H), 1.15 (s, 3H), 0.89 (s, 9H); Anal. calcd for C₂₆H₃₁NO₃0.33H₂O: C, 75.90; H, 7.76; N, 3.40. Found: C, 75.91; H, 8.17; N, 3.62.

EXAMPLE 44

2,5-Dihydro-10-methoxy-2,2,4-trimethyl-1H-[1]benzopyrano[3,4-f]quinoline-5-carbonitrile Example 2B and cyanotrimethylsilane were processed as in Example 2 to provide the desired compound.

MS (DCI/NH₃) m/z 333 (M+H)⁺; ¹H NMR (300 MHz, DMSO-d₆) δ 7.96 (d, 1H), 7.20 (t, 1H), 6.89 (s, 1H), 6.84 (s, 1H), 6.74 (d, 8H), 6.73 (d, 1H), 6.46 (s, 1H), 5.51 (s, 1H), 3.90 (s, 3H), 2.22 (s, 3H), 1.29 (s, 3H), 1.09 (s, 3H); Anal. calcd for C₂₁H₂₀N₂O₂.0.25H₂O: C, 74.87; H, 6.13; N, 8.31. Found: C, 75.00; H 6.23; N, 8.34.

EXAMPLE 45

1-(2,5-Dihydro-10-methoxy-2,2,4-trimethyl-1H-[1]benzopyrano[3,4-f]quinolin-5-yl)-2-propanone Example 2B and 2-(trimethylsiloxy)-propene were processed as in Example 2 to provide the desired compound.

¹H NMR (300 MHz, DMSO-d₆) δ 7.96 (t, 1H), 7.04 (t, 1H), 6.71 (d, 1H), 6.58 (d, 1H), 6.48 (d, 1H), 6.20 (dd, 1H), 6.16 (s, 1H), 5.4 (s, 1H), 3.87 (s, 3H), 2.91 (q, 1H), 2.16 (s, 3H), 2.04 (s, 3H), 1.15 (d, 6H); HRMS calcd m/z for C₂₃H₂₅O₃N: 363.1834 (M+H)⁺. Found: 363.1843; Anal. calcd for C₂₃H₂₅NO₃.0.33H₂O: C, 74.79; H, 7.00; N, 3.79. Found: C, 74.77; H, 7.14; N, 3.67.

EXAMPLE 46

Methyl 2,5-Dihydro-10-methoxy-2,2,4-trimethyl-1H-[1]benzopyrano[3,4-f]quinoline-5-acetate Example 2B and 1-methoxy-1-(tert-butyldimethylsiloxy)ethylene were processed as in Example 2 to provide the desired compound.

MS (DCI/NH₃) m/z 380 (M+H)⁺; ¹H NMR (300 MHz, DMSO-d₆) δ 8.01 (d, 1H), 7.11 (t, 1H), 6.78 (d, 1H), 6.66 (d, 1H), 6.53 (d, 1H), 6.27 (d, 1H), 6.22 (s, 2H), 5.52 (s, 1H), 3.93 (s, 3H), 3.67 (s, 3H), 2.70 (dd, 1H), 2.64 (d, 1H), 2.27 (s, 3H), 1.22 (d, 6H); Anal. calcd for C₂₃H₂₅O₄N.0.5H₂O: C, 71.12; H, 6.75; N, 3.61. Found: C, 71.46; H, 6.81; N, 3.45.

EXAMPLE 47

2-(2,5-Dihydro-10-methoxy-2,2,4-trimethyl-1H-[1]benzopyrano[3,4-f]quinolin-5-yl)-1-phenylethanone Example 2B and 1-phenyl-1-(trimethylsiloxy)ethylene were processed as in Example 2 to provide the desired compound.

¹H NMR (300 MHz, DMSO-d₆) δ 8.01 (d, 1H), 7.72 (d, 2H), 7.59 (t, 1H), 7.40 (t, 2H), 6.93 (t, 1H), 6.70 (d, 1H), 6.61 (d, 1H), 6.43 (d, 1H), 6.25 (d, 1H), 6.18 (s, 1H), 5.44 (s, 1H), 3.90 (s, 3H), 3.66 (q, 1H), 2.95 (d, 1H), 2.16 (s, 3H), 1.16 (s, 6H); HRMS calcd m/z for C₂₈H₂₇O₃N: 425.1991 (M+H)⁺. Found: 425.2005.

EXAMPLE 48

5-[2-(Chloromethyl)-2-propenyl]-2,5-dihydro-10-methoxy-2,2,4-trimethyl-1H-[1]benzopyrano[3,4-f]quinoline Example 2B and 2-chloromethyl-3-trimethylsilyl-1-propene were processed as in Example 2 to provide the desired compound.

¹H NMR (300 MHz, DMSO-d₆) δ 7.96 (d, 1H), 7.03 (t, 1H), 6.69 (d, 1H), 6.59 (d, 1H), 6.44 (d, 1H), 6.15 (s, 1H), 5.96 (dd, 1H), 5.45 (s, 1H), 5.27 (s, 1H), 4.95 (s, 1H), 4.17 (q, 2H), 3.87 (s, 3H), 2.55 (d, 1H), 2.26 (dd, 1H), 2.20 (s, 3H), 1.15 (d, 6H); HRMS m/z calcd for C₂₄H₂₆O₂ClN: 395.1652 (M+H)⁺. Found: 395.1645; Anal. calcd for C₂₄H₂₆O₂ClN.0.333H₂O: C, 71.73; H, 6.69; N, 3.49. Found: C, 71.71; H, 6.32; N, 3.35.

EXAMPLE 49

2,5-Dihydro-10-methoxy-2,2,4-trimethyl-(-methylene-1H-[1]benzopyrano[3,4-f]quinoline-5-propanol, Acetate (Ester)

Example 2B and 2-[(trimethylsilyl)methyl]-2-propen-1-yl acetate were processed as in Example 2 to provide the desired compound.

¹H NMR (300 MHz, DMSO-d₆) δ 8.02 (d, 1H), 7.10 (t, 1H), 6.75 (dd, 1H), 6.65 (d, 1H), 6.50 (d, 1H), 6.18 (s, 1H), 5.98 (dd, 1H), 5.51 (s, 1H), 5.16 (s, 1H), 4.98 (s, 1H), 4.48 (q, 2H), 3.93 (s, 3H), 2.25 (s, 3H), 1.22 (s, 6H); HRMS calcd m/z for C₂₆H₂₉O₄N₄N: 419.2097 (M+H)⁺. Found: 419.2095; Anal. calcd for C₂₆H₂₉O₄N.0.25H₂O: C, 73.65; H, 7.01; N, 3.30. Found: C, 73.83; H, 6.91; N, 3.20.

EXAMPLE 50

2,5-Dihydro-10-methoxy-2,2,4-tnimethyl-5-(4-methylphenyl)-1H-[1]benzopyrano[3,4-f]quinoline Example 1F and 4-methylphenylmagnesium bromide were processed as in examples 1G and 1 to provide the desired compound.

MS (DCI/NH₃) m/z 398 (M+H)⁺; ¹H NMR (300 MHz, DMSO-d₆) δ 8.00 (d, 1H), 7.02 (q, 4H), 6.89 (t, 1H), 6.72 (s, 1H), 6.69 (d, 1H), 6.55 (d, 1H), 6.41 (d, 1H), 6.18 (br s, 1H), 5.37 (br s, 1H), 3.79 (s, 3H), 2.18 (s, 3H), 1.83 (s, 3H), 1.23 (s, 3H), 1.14 (s, 3H); Anal. calcd for C₂₇H₂₇NO₂: C, 81.58; H, 6.85; N, 3.52. Found: C, 81.56; H, 7.25; N, 3.29.

EXAMPLE 51

5-(3-Fluoro-4-methylphenyl)-2,5-dihydro-10-methoxy-2,2,4-trimethyl-1H-[1benzopyrano[3,4-f]quinoline Example 2B and 3-fluoro-4-methylphenylmagnesium bromide were processed as in Example 11 to provide the desired compound.

MS (DCI/NH₃) m/z 416 (M+H)⁺; ¹H NMR (300 MHz, DMSO-d₆) δ 8.01 (d, 1H), 7.11 (t, 1H), 6.95–6.84 (m, 3H), 6.74 (s, 1H), 6.71 (d, 1H), 6.57 (d, 1H), 6.46 (d, 1H), 6.23 (s, 1H), 5.39 (s, 1H), 3.79 (s, 3H), 2.11 (s, 3H), 1.85 (s, 3H), 1.22 (s, 3H), 1.14 (s, 3H); Anal. calcd for C₂₇H₂₆NO₂F: C, 78.05; H. 6.31; N, 3.37. Found: C, 77.80; H. 6.51; N, 3.06.

EXAMPLE 52

5-(3-Bromophenyl)-2,5-dihydro-10-methoxy-2,2,4-trimethyl-1H-[1]benzopyrano[3,4-f]quinoline Example 1F and 3-bromophenylmagnesium bromide were processed as in examples 1G and 1 to provide the desired compound.

MS (DCI/NH₃) m/z 462 (M+H)⁺; ¹H NMR (300 MHz, DMSO-d₆) δ 8.02 (d, 1H), 7.36 (m, 1H), 7.30 (m, 1H), 7.17 (m, 2H), 6.93 (t, 1H), 6.79 (s, 1H), 6.72 (d, 1H), 6.58 (d, 1H), 6.48 (d, 1H), 6.24 (br s, 1H), 5.41 (br s, 1H), 3.80 (s, 1H), 1.85 (s, 3H), 1.23 (s, 1H), 1.16 (s, 1H).

EXAMPLE 53

2,5-Dihydro-10-methoxy-2,2,4-trimethyl-5-(phenylmethyl)-1H-[1]benzopyrano[3,4-f]quinoline Example 2B and benzylmagnesium bromide were processed as in Example 11 to provide the desired compound.

MS (DCI/NH$_3$) m/z 398 (M+H)$^+$; 1H NMR (300 MHz, DMSO-d$_6$) δ 8.02 (d, 1H), 7.31–7.18 (m, 3H), 7.12 (m, 3H), 6.75 (d, 1H), 6.63 (d, 1H), 6.46 (d, 1H), 6.15 (d, 1H), 5.93 (dd, 1H), 5.43 (s, 1H), 3.89 (s, 3H), 2.98 (dd, 1H), 2.74 (dd, 1H), 2.23 (s, 3H), 1.16 (s, 3H), 1.15 (s, 3H); Anal. calcd for C$_{27}$H$_{27}$NO$_2$.0.25H$_2$O: C, 80.67; H, 6.89; N, 3.48. Found: C, 80.78; H, 7.08; N, 3.26.

EXAMPLE 54

2,5-Dihydro-10-methoxy-2,2,4-trimethyl-5-propyl-1H-[1]benzopyrano[3,4-f]quinoline Example 2B and propylmagnesium bromide were processed as in Example 11 to provide the desired compound.

MS (DCI/NH$_3$) m/z 350 (M+H)$^+$; $^1$H NMR (300 MHz, DMSO-d$_6$) δ 7.94 (d, 1H), 7.05 (t, 1H), 6.69 (d, 1H), 6.58 (d, 1H), 6.54 (d, 1H), 6.10 (d, 1H), 5.70 (m, 1H), 5.44 (s, 1H), 3.85 (s, 3H), 2.16 (s, 3H), 1.70 (m, 1H), 1.43–1.31 (m, 3H), 1.16 (s, 3H), 1.14 (s, 3H), 0.83 (t, 3H); Anal. calcd for C$_{23}$H$_{27}$NO$_2$: C, 79.05; H, 7.79; N, 4.01. Found: C, 78.76; H, 7.86; N, 3.84.

EXAMPLE 55

5-(4-Fluorophenyl)-2,5-dihydro-10-methoxy-2,2,4-trimethyl-1H-[1]benzopyrano[3,4-f]quinoline Example 2B and 4-fluorophenylmagnesium bromide were processed as in Example 11 to provide the desired compound.

$^1$H NMR (300 MHz, DMSO-d$_6$) δ 7.99 (d, 1H), 7.11 (d, 1H), 6.92 (m, 2H), 6.71 (s, 1H), 6.68 (s, 1H), 6.55 (d, 1H), 6.43 (d, 1H), 6.21 (s, 1H), 5.39 (s, 1H), 3.99 (s, 3H), 2.11 (s, 3H), 1.84 (s, 3H), 1.22 (s, 3H), 1.14 (s, 3H); HRMS calcd m/z for C$_{27}$H$_{26}$O$_2$NF: 415.1948 (M+H)$^+$. Found: 415.1947.

EXAMPLE 56

5-(3-Fluorophenyl)-2,5-Dihydro-10-methoxy-2,2,4-trimethyl-1H-[1]benzopyrano[3,4-f]quinoline Example 2B and 3-fluorophenylmagnesium bromide were processed as in Example 11 provide the desired compound.

$^1$H NMR (300 MHz, DMSO-d$_6$) δ 8.03 (d, 1H), 7.22 (q, 1H), 6.90 (m, 4H), 6.78 (s, 1H), 6.73 (d, 1H), 6.56 (d, 1H), 6.46 (d, 1H), 6.24 (s, 1H), 5.40 (s, 1H), 3.79 (s, 3H), 1.85 (s, 3H), 1.20 (s, 3H), 1.15 (s, 3H); HRMS calcd m/z for C$_{26}$H$_{24}$O$_2$NF: 402.1869 (M+H)$^+$. Found: 402.1865; Anal. calcd for C$_{26}$H$_{24}$O$_2$FN.2.25H$_2$O: C, 70.65; H, 6.50; N, 3.17. Found: C, 70.56; H 6.18; N, 2.83.

EXAMPLE 57

2,5-Dihydro-10-methoxy-2,2,4,5-tetramethyl-1H-[1]benzopyrano[3,4-f]quinoline

Example 2B and methylmagnesium iodide were processed as in Example 11 to provide the desired compound.

$^1$H NMR (300 MHz, DMSO-d$_6$) δ 7.91 (d, 1H), 7.02 (t, 1H), 6.67 (d, 1H), 6.54 (s, 1H), 6.52 (d, 1H), 6.08 (s, 1H), 5.87 (q, 1H), 5.43 (s, 1H), 3.85 (s, 3H), 2.16 (s, 3H), 1.25 (d, 3H), 1.18 (s, 3H), 1.13 (s, 3H); HRMS calcd m/z for C$_{21}$H$_{23}$O$_2$N: 321.1729 (M+H)$^+$. Found: 321.1728.

EXAMPLE 58

2,5-Dihydro-10-methoxy-2,2,4-trimethyl-5-(1-methylethyl)-1H-[1]benzopyrano[3,4-f]quinoline Example 2B and 2-propylmagnesium chloride were processed as in Example 11 to provide the desired compound.

$^1$H NMR (300 MHz, DMSO-d$_6$) δ 7.99 (d, 1H), 7.03 (t, 1H), 6.57 (d, 1H), 6.45 (d, 1H), 6.53 (d, 1H), 6.18 (s, 1H), 5.45 (s, 1H), 5.31 (d, 1H), 3.85 (s, 1H), 2.16 (s, 3H), 1.79 (m, 1H), 1.30 (s, 3H), 1.01 (s, 3H), 0.93 (d, 3H), 0.62 (d, 3H); HRMS calcd m/z for C$_{23}$H$_{27}$O$_2$N: 349.2042 (M+H)$^+$. Found: 349.2041.

EXAMPLE 59

2,5-Dihydro-10-methoxy-2,2,4-trimethyl-5-(2-methlpropyl)-1H-[1]benzopyrano[3,4-f]quinoline Example 2B and sec-butylmagnesium chloride were processed as in Example 11 to provide the desired compound.

$^1$H NMR (300 MHz, DMSO-d$_6$) δ 7.93 (d, 1H), 7.03 (t, 1H), 6.67 (d, 1H), 6.51 (q, 2H), 6.08 (s, 1H), 5.77 (dd, 1H), 5.43 (s, 1H), 3.85 (s, 3H), 2.18 (s, 3H), 1.72 (m, 2H), 1.76 (d, 6H), 0.86 (d, 3H), 0.74 (d, 3H); HRMS calcd m/z for C$_{24}$H$_{29}$O$_2$N: 363.2198 (M+H)$^+$. Found: 363.2208; Anal. calcd for C$_{24}$H$_{29}$NO$_2$: C, 79.30; H, 8.04; N, 3.85. Found: C, 79.63; H, 7.83; N, 3.89.

EXAMPLE 60

5-Ethyl-2,5-dihydro-10-methoxy-2,2,4-trimethyl-1H-[1]benzopyrano[3,4-f]quinoline Example 2B and ethylmagnesium bromide were processed as in Example 11 to provide the desired compound.

MS (DCI/NH$_3$) m/z 336 (M+H)$^+$; $^1$H NMR (300 MHz, DMSO-d$_6$) δ 7.92 (d, 1H), 7.03 (t, 1H), 6.67 (d, 1H), 6.54 (t, 2H), 6.10 (s, 1H), 5.55 (dd, 1H), 5.44 (s, 1H), 3.84 (s, 3H), 2.16 (s, 3H), 1.63 (m, 1H), 1.44 (m, 1H), 1.15 (s, 6H), 0.84 (t, 3H); Anal. calcd for C$_{22}$H$_{25}$O$_2$N.2.25H$_2$O: C, 77.73; H, 7.56; N, 4.12. Found: C, 77.95; H, 7.60; N, 4.07.

EXAMPLE 61

2,5-Dihydro-10-methoxy-2,2,4-trimethyl-1H-[1]benzopyrano[3,4-f]quinoline-5-carboximidic Acid Ethyl Ester A solution of Example 44 (0.040 g, 0.120 mmol) in ethanol (5 mL) was cooled to −5° C., saturated with hydrogen chloride gas, stirred for 10 minutes at −5° C., stirred 14 hours at room temperature, neutralized with NaHCO$_3$, and extracted with diethyl ether. The extract was dried (Na$_2$SO$_4$), filtered, and concentrated to provide the desired compound.

MS (DCI/NH$_3$) m/z 379 (M+H)$^+$; $^1$H NMR (300 MHz, DMSO-d$_6$) δ 7.95 (d, 1H), 7.32 (s, 1H), 7.05 (t, 1H), 6.69 (t, 2H), 6.61 (d, 1H), 6.22 (s, 1H), 6.14 (s, 1H), 5.44 (s, 1H), 3.92 (m, 2H), 3.82 (s, 3H), 2.06 (s, 3H), 1.20 (s, 3H), 1.12 (s, 3H), 1.02 (t, 3H).

EXAMPLE 62

2,5-Dihydro-10-methoxy-2,2,4-trimethyl-(-methylene 1H-[1]benzopyrano[3,4-f]quinoline5-propanol A solution of Example 49 (0.060 g, 0.143 mmol) in 1:1 methanol/water (10 mL) was treated with K$_2$CO$_3$ (0.080 g, 1.0 mmol), stirred for 24 hours at room temperature, neutralized with 10% HCl, and extracted with ethyl acetate. The extract was washed with brine, dried ($MgSO_4$), filtered, and concentrated. The residue was purified by flash chromatography on silica gel with 25% dichloromethane/ethyl acetate to provide the desired compound.

$^1$H NMR (300 MHz, DMSO-$d_6$) δ 8.01 (d, 1H), 7.72 (d, 2H), 7.59 (t, 1H), 7.40 (t, 2H), 6.93 (t, 1H), 6.70 (d, 1H), 6.61 (d, 1H), 6.43 (d, 1H), 6.25 (d, 1H), 6.18 (s, 1H), 5.44 (s, 1H), 3.90 (s, 3H), 3.66 (q, 1H), 2.95 (d, 1H), 2.16 (s, 3H), 1.16 (s, 6H); HRMS calcd m/z for $C_{28}H_{27}O_3N$: 425.1991 (M+H)$^+$. Found: 425.2005.

EXAMPLE 63

2,5-Dihydro-10-methoxy-2,2,4,N,N-pentamethyl-1H-[1]benzopyrano[3,4-f]quinoline-5-acetamide Example 46 was hydrolyzed with lithium hydroxide in THF to provide the corresponding acid which was then coupled to N,N-dimethylamine with 1-(3-dimethylaminopropyl)-3-ethylcarbodiimide to provide the desired compound.

$^1$H NMR (300 MHz, DMSO-$d_6$) δ 7.94 (d, 1H), 7.04 (t, 1H), 6.70 (d, 1H), 6.59 (d, 1H), 6.46 (d, 1H), 6.26 (d, 1H), 6.15 (s, 1H), 5.44 (s, 1H), 3.86 (s, 3H), 2.88 (q, 1H), 2.81 (s, 3H), 2.55 (s, 3H), 2.25 (s, 1H), 2.19 (s, 3H), 1.15 (s, 6H); HRMS calcd m/z for $C_{24}H_{28}O_3N_2$: 392.2100 (M+H)$^+$. Found: 392.2104; Anal. calcd for $C_{24}H_{28}N_2O_3$: C, 73.44; H 7.19, 7.35; N, 7.14. Found: C, 73.17; H, 7.19; N, 6.85.

EXAMPLE 64

2,5-Dihydro-10-methoxy-2,2,4,N,N-pentamethyl-1H-[1]benzopyrano[3,4-f]quinoline5-ethanamine A solution of Example 63 in diethyl ether was reduced at room temperature with lithium aluminum hydride to provide the desired compound.

$^1$NMR (300 MHz, DMSO-$d_6$) δ 7.93 (d, 1H), 7.03 (t, 1H), 6.68 (t, 1H), 6.54 (t, 1H), 6.12 (s, 1H), 5.76 (dd, 1H), 5.44 (s, 1H), 3.85 (s, 3H), 2.18 (s, 3H), 2.05 (s, 6H), 1.18 (s, 3H), 1.14 (s, 3H); HRMS m/z calcd for $C_{24}H_{30}O_2N_2$: 378.2307 (M+H)$^+$. Found: 378.2307.

EXAMPLE 65

N-Cyclopropyl-2,5-Dihydro-10-methoxy-2,2,4-trimethyl-1H-[1]benzopyrano[3,4-f]quinoline-5-acetamide Example 46 and cyclopropylmethylamine were processed as in Example 63 to provide the desired compound.

$^1$H NMR (300 MHz, DMSO-$d_6$) δ 7.94 (d, 1H), 7.70 (d, 1H), 7.03 (t, 1H), 6.68 (d, 1H), 6.58 (d, 1H), 6.43 (d,), 6.23 (dd, 1H), 6.13 (s, 1H), 5.43 (s, 1H), 3.85 (s, 3H), 2.51 (m, 2H), 2.07 (d, 1H), 2.03 (s, 3H), 1.17 (s, 3H), 1.13 (s, 3H), 0.60 (m, 2H), 0.31 (s, 2H); HRMS m/z calcd for $C_{25}H_{28}O_3N_2$: 404.2100 (M+H)$^+$. Found: 404.2092.

EXAMPLE 66

2,5-Dihydro-10-methoxy-2,2,4-trimethyl-5-(2-propynyl)-1H-[1]benzopyrano[3,4-f]quinoline Example 2B and 2-propynylmagnesium bromide were processed as in Example 11 to provide the desired compound.

$^1$H NMR (300 MHz, DMSO-$d_6$) δ 7.97 (d, 1H), 7.06 (t, 1H), 6.71 (d, 1H), 6.56 (q, 2H), 6.16 (s, 1H), 5.88 (q, 1H), 5.44 (s, 1H), 3.86 (s, 3H), 2.82 (q, 1H), 2.41 (q, 1H), 2.19 (s, 3H), 1.16 (s, 3H); HRMS m/z calcd for $C_{23}H_{23}O_2N$: 345.1729 (M+H)$^+$. Found: 345.1738.

EXAMPLE 67

5-(2,5-Dihydro-10-methoxy-2,2,4-trimethyl-1H-[1]benzopyrano[3,4-f]quinolin-5-yl)2(5H)-furanone Example 2B and 2-trimethylsiloxyfuran were processed as in Example 2C to provide the desired compound.

MS (DCI/$NH_3$) m/z 390 (M+H)$^+$; $^1$NMR (300 MHz, DMSO-$d_6$) δ 8.11 (d, 1H), 7.13 (dd, 1H), 6.75 (d, 1H), 6.72 (d, 1H), 6.64 (d, 1H), 6.37 (d, 1H), 6.25 (dd, 1H), 6.23 (d, 1H), 5.83 (d, 1H), 5.47 (s, 1H), 5.12 (dd, 1H), 3.87 (s, 3H), 2.03 (s, 3H), 1.30 (s, 3H), 1.09 (s, 3H); Anal. calcd for $C_{24}H_{23}NO_4$: C, 74.02; H, 5.95; N, 3.60. Found: C, 73.89; H, 5.94; N, 3.51.

EXAMPLE 68

5-(32-Butenyl)-2,5-dihdro-10-methoxy-2,2,4-trimethyl-1H -1H-[1]benzopyrano[3,4-f]quinoline Example 2B and 3-butenylmagnesium bromide were processed as in Example 11 to provide the desired compound.

MS (DCI/$NH_3$) m/z 362 (M+H)$^+$; $^1$H NMR (300 MHz, DMSO-$d_6$) δ 7.94 (d, 1H), 7.05 (t, 1H), 6.68 (d, 1H), 6.58 (d, 1H), 6.57 (d, 1H), 6.10 (s, 1H), (5.78 (dddd, 1H), 5.65 (dd, 1H), 5.44 (s, 1H), 5.00 (dd, 1H), 4.93 (dd, 1H), 3.85 (s, 3H), 2.16 (s, 3H), 2.10 (m, 2H), 1.78 (m, 1H), 1.45 (bm, 1H), 1.16 (s, 3H), 1.14 (s, 3H); HRMS calcd m/z for $C_{24}H_{27}NO_2$: 361.2042 (M+H)$^+$. Found: 361.2039.

EXAMPLE 69

2,5-Dihydro-10-methoxy-2,2,4-trimethyl-1H-[1]benzopyrano[3,4-f]quinoline-5-propanol Example 2 (52.0 mg, 0.15 mmol) in THF (4 mL) at 0° C. was treated dropwise with 0.5M 9-BBN (600 μL, 0.30 mmol), stirred overnight at room temperature, cooled to 0° C., treated sequentially with 2.5M NaOH (400 μL, 1.0 mmol), and 30% $H_2O_2$ (250 μL), stirred for 2 hours at room temperature, partitioned between 1:1 ethyl acetate/water, and extracted with ethyl acetate. The extract was washed with brine, dried ($Na_2SO_4$), filtered, and concentrated. The residue was purified by flash chromatography on silica gel with 30% ethyl acetate/hexanes to provide the desired compound.

MS (DCI/$NH_3$) m/z 366 (M+H)$^+$; $^1$H NMR (300 MHz, DMSO-$d_6$) δ 7.94 (d, 1H), 7.05 (t, 1H), 6.68 (d, 1H), 6.58 (d, 1H), 6.53 (d, 1H), 6.10 (s, 1H), 5.70 (dd, 1H), 5.44 (s, 1H), 4.36 (t, 1H), 3.85 (s, 3H), 3.33 (m, 2H), 2.16 (s, 3H), 1.40–1.75 (bm, 4H), 1.17 (s, 3H), 1.14 (s, 3H); HRMS calcd m/z for $C_{23}H_{27}NO_3$: 365.1991 (M+H)$^+$. Found: 365.1991.

EXAMPLE 70

10-Ethyl-2,5-dihydro-2,2,4-trimethyl-5-phenyl-1H-[1]benzopyrano[3,4-f]quinoline

EXAMPLE 70A

Example 3C (0.208 g, 0.493 mmol) and tetraethyltin (0,444 g, 1.89 mmol) were combined with (1,3-bis(diphenylphosphino)ferrocene)palladium(II)-chloride.dichloromethane (0.039 g, 0.047 mmol) in 1-methyl-2-pyrrolidinone (3 mL) at 80° C. for 16 hours and concentrated to provide the desired compound.

EXAMPLE 70

10-Ethyl-2,5-dihydro-2,2,4-trimethyl-5-phenyl-1H-[1]benzopyrano[3,4-f]quinoline

Example 70A was processed as in examples 1F, 1G, and 1 to provide the desired compound.

MS (DCI/NH$_3$) m/z 382 (M+H)$^+$; $^1$H NMR (300 MHz, DMSO) δ 7.37 (d, 1H), 7.21–7.16 (m, 5H), 6.85, (dd, 1H), 6.75 (s, 1H), 6.73 (dd, 1H), 6.68 d, 1H), 6.58 (dd, 1H), 6.21 (s, 1H), 5.39 (s, 1H), 3.02–2.75 (m, 2H), 1.79 (s, 3H), 1.24 (s, 3H), 1.15 (s, 3H), 1.15 (m, 3H); HRMS calcd for C$_{27}$H$_{27}$NO: 381.2093 (M+H)$^+$. Found 381.2096.

EXAMPLE 71

2,5-Dihydro-2,2,4,10-tetrametnyl-5-phenyl-1H-[1]benzopyrano[3,4-f]quinoline

Example 3C and tetramethyltin were processed as in Example 70 to provide the desired compound.

MS (DCI/NH$_3$) m/z 368 (M+H)$^+$; $^1$H NMR (300 MHz, DMSO-d$_6$) δ 7.44 (d, 1H), 7.21–7.12 (m, 5H), 6.82 (dd, 1H), 6.74 (d, 1H), 6.71 (s, 1H), 6.69 (dd, 1H), 6.59 (dd, 1H), 6.21 (s, 1H), 5.39 (s, 1H), 2.51 (s, 3H), 1.80 (s, 3H), 1.25 (s, 3H), 1.16 (s, 3H); HRMS calcd m/z for C$_{26}$H$_{25}$NO: 367.1936 (M+H)$^+$. Found: 367.1931.

EXAMPLE 72

5-(3,5-Dichlorophenyl)-10-ethyl-2,5-dihydro-2,2,4-trimethyl-1H-[1]benzopyrano[3,4-f]quinoline Example 70A and 3,5-dichlorophenylmagnesium bromide were processed as in examples 1G and 1 to provide the desired compound.

MS (DCI/NH$_3$) m/z 450 (M+H)$^+$; $^1$NMR (300 MHz, DMSO-d$_6$) δ 7.43 (d, 1H), 7.43 (t, 1H), 7.18 (d, 2), 6.91 (dd, 1H), 6.80 (dd, 1H), 6.78 (d, 1H), 6.72 (s, 1H), 6.62 (dd, 1H), 6.35 (s, 1H), 5.42 (s, 1H), 3.15–2.75 (m, 2H), 1.79 (s, 3H), 1.27 (s, 3H), 1.14 (s, 3H), 1.13 (t, 3H); HRMS calcd m/z for C$_{27}$H$_{25}$NOCl$_2$:449.1313 (M+H)$^+$. Found: 449.1330.

EXAMPLE 73

5-(3,5-Dichlorophenyl)-2,5-dihydro-2,2,4,N-tetramethyl-1H-[1]benzopyrano[3,4-f]quinolin-10-amine

EXAMPLE 73A

Example 3C and 3,5-dichlorophenylmagnesium bromide were processed as in Example 72 to provide the desired compound.

MS (DCI/NH$_3$) m/z 539 (M+H)$^+$.

EXAMPLE 73

5-(3,5-Dichlorophenyl)-2,5-dihydro-2,2,4,N-tetramethyl-1H[1]benzopyrano[3,4-f]quinolin-10-amine Example 73A was processed as in Example 3 to provide the desired compound.

MS (DCI/NH$_3$) m/z 451 (M+H)$^+$; $^1$H NMR (300 MHz, DMSO-d$_6$) δ 7.91 (d, 1H), 7.45 (dd, 1H), 7.20 (m, 2H), 6.83 (dd, 1H), 6.75 (d, 1H), 6.71 (s, 1H), 6.22 (s, 1H), 6.18 (s, 1H), 6.17 (dd, 1H), 5.57 (d, 1H), 5.44 (s, 1H), 2.65 (d, 3H), 1.85 (s, 3H), 1.24 (s, 3H), 1.15 (s, 3H); HRMS calcd m/z for C$_{26}$H$_{24}$N$_2$OCl$_2$: 450.1266 (M+H)$^+$. Found: 450.1267.

EXAMPLE 74

5-(3,5-Dichlorophenyl)-2,5-dihydro-2,2,4-trimethyl-N-(2-propenyl)-1H-[1]benzopyrano[3,4-f]quinolin-10-amine Example 73A and allylamine were processed as in Example 3 to provide the desired compound.

MS (DCI/NH$_3$) m/z 477 (M+H)$^+$; $^1$H NMR (300 MHz, DMSO-d$_6$) δ 7.99 (d, 3H), 7.49 (dd, 1H), 7.27 (d, 2H), 6.82 (dd, 1H), 6.77 (d, 1H), 6.75 (s, 1H), 6.25 (dd, 1H), 6.21 (s, 1H), 6.20 (dd, 1H), 5.95–5.86 (m, 1H), 5.69–5.65 (m, 1H), 5.48 (s, 1H), 5.18–5.12 (m, 1H), 5.11–5.06 (m, 1H), 3.78–3.70 (m, 2H), 1.88 (s, 3H), 1.30 (s, 3H ), 1.20 (s, 3H); HRMS calcd m/z for C$_{28}$H$_{26}$N$_2$OCl$_2$: 476.1422 (M+H)$^+$. Found: 476.1428.

EXAMPLE 75

2,5-Dihydro-2,2,4-trimethyl-5-phenyl-10-(2-propynyloxy)-1H-[1]benzopyrano[3,4-f]quinoline Example 7 and propargyl bromide were processed as in Example 9A to provide the desired compound.

MS (DCI/NH$_3$) m/z 408 (M+H)$^+$; $^1$H NMR (300 MHz, DMSO-d$_6$) δ 1.12 (s, 3H), 1.23 (s, 3H), 1.83 (s, 3H), 3.59 (t, 1H), 4.81 (d, 2H), 5.39 (br s, 1H), 6.19 (br s, 1H), 6.47 (d, 1H), 6.61 (d, 1H), 6,71 (d, 1H), 6.78 (s, 1H), 6.90 (t, 1H), 7.14–7.22 (m, 5H), 8.02 (d, 1H); Anal. calcd for C$_{28}$H$_{25}$NO$_2$: C, 82.53; H, 6.18; N, 3.44. Found: C, 82.64; H 6.31; N, 3.38.

EXAMPLE 76

2,5-Dihydro-2,2,4-trimethyl-5-phenyl-10-(2-prenyloxy)-1H-[1]benzopyrano[3,4-f]quinoline Example 7 and allyl bromide were processed as in Example 9A to provide the desired compound.

MS (DCI) m/z 410 (M+H)$^+$; $^1$H NMR (300 MHz, DMSO-d$_6$) δ 1.15 (s, 3H), 1.23 (s, 3H), 1.84 (s, 3H), 4.51–4.64 (m, 2H), 5.26 (dq, 1H ), 5.39 (br s, 1H), 5.40 (dq, 1H), 6.12 (ddt, 1H), 6.21 (br s, 1H), 6.44 (dd, 1H), 6.55 (dd, 1H), 6.69 (d, 1H), 6.77 (s, 1H), 6.88 (t, 1H), 7.15–7.24 (m, 5H), 8.06 (d, 1H); HRMS calcd m/z for C$_{28}$H$_{27}$NO$_2$: 409.2042 (M+H)$^+$. Found: 409.2039.

EXAMPLE 77

2,5-Dihydro-2,2,4-trimethyl-5-(2-propenyl)-1H-[1]benzopyrano[3,4-f]quinoline-10-methanol A solution of Example 4 (32 mg, 0.085 mmol) in dichloromethane (3 mL) under argon, at −78° C., was treated dropwise with diisobutylaluminum hydride (1.0 M) in cyclohexanes (0.400 mL, 0.40 mmol), warmed to 0° C. for 3.5 hours, treated with Rochelle's salt, separated, and extracted with ethyl acetate. The extract was dried (MgSO$_4$), filtered, and concentrated. The residue was applied to two 10×20 cm, 0.25 mm thick silica gel plates which were eluted three times with hexane, then ethyl acetate/hexanes (10:90). The product band was scraped off and extracted with ethyl acetate to provide the desired compound.

MS (DCI/NH$_3$) m/z 348 (M+H)$^+$; $^1$H NMR δ 7.47 (d, 1H), 7.14 (m, 2H), 6.80 (dd, 1H), 6.64 (d, 1H), 6.17 (m, 1H), 5.81 (ddm, 1H), 5.73 (dd, 1H), 5.46 (m, 1H), 5.32 (dd, 1H), 5.02

(dm, 1H), 4.94 (dm, 1H), 4.62 (m, 2H), 2.30 (m, 2H), 2.17 (s, 3H), 1.19 (s, 3H), 1.16 (s, 3H); HRMS Calcd m/z for $C_{23}H_{25}NO_2$: 347.1885 (M+H)⁺. Found: 347.1897.

EXAMPLE 78

2,5-Dihydro-2,2,4-trimethyl-5-(2propenyl)-1H-[1] benzopyrano[3,4-f]quinoline-10-carboxylic Acid Example 74 and chlorotris(triphenylphosphate)rhodium (I) chloride were processed as in Example 3 to provide the desired compound.

MS (DCI/NH₃) m/z 437 (M+H)⁺; ¹H NMR (300 MHz, DMSO-d₆) δ 7.91 (d, 1H), 7.44 (dd, 1H), 7.19 (d, 2H), 6.74 (d, 1H), 6.70 (s, 1H), 6.69 (dd, 1H), 6.26 (dd, 1H), 6.22 (s, 1H), 6.11 (dd, 1.0 Hz, 1H), 5.43 (s, 1H), 5.15 (s, 2H), 1.84 (s, 3H), 1.23 (s, 3H), 1.15 (s, 3H).

EXAMPLE 79

5-(3,5-Dichlorophenyl)-10-ethoxy-2,5-dihydro-2,2, 4-trimethyl-1H-[1]benzopyrano[3,4-f]quinoline Example 9A and 3,5-dichlorophenylmagnesium bromide were processed as in examples 1G and 1 to provide the desired compound.

MS (DCI) m/z 466 (M+H)⁺; ¹H NMR (300 MHz, DMSO-d₆) δ 8.10 (d, 1H), 7.46 (t, 1H), 7.13 (d, 2H), 6.95 (dd, 1H), 6.81 (s, 1H), 6.72 (d, 1H), 6.60 (d, 1H), 6.51 (d, 1H), 6.32 (d, 1H), 5.44 (s, 1H), 3.99–4.12 (m, 1H), 1.87 (s, 3H), 1.37 (t, 3H), 1.23 (s, 3H), 1.20 (s, 3H); HRMS calcd m/z for $C_{27}H_{25}NO_2Cl_2$: 465.1262 (M+H)⁺. Found 465.1277.

EXAMPLE 80

5-(3,5-Dichlorophenyl)-2,5-dihydro-2,2,4-trimethyl-1H-[1]benzopyrano[3,4-f]quinolin-10-ol Example 7A and 3,5-dichlorobenzylmagnesium bromide were processed as in examples 7B and 7 to provide the desired compound.

MS (DCI) m/z 438, 440 (M+H)⁺; ¹H NMR (300 MHz, DMSO-d₆) δ 9.79 (s, 1H), 8.18 (d, 1H), 7.44 (t, 1H), 7.12 (dd, 2H), 6.79 (d, 1H), 6.77 (s, 1H), 6.73 (d, 1H), 6.45 (d, 1H), 6.28 (dd, 1H), 6.23 (d, 1H), 5.43 (s, 1H), 1.87 (d, 3H), 1.22 (s, 3H), 1.16 (s, 3H); HRMS calcd m/z for $C_{25}H_{21}Cl_2NO_2$: 437.0949 (M+H)⁺. Found: 437.0955.

EXAMPLE 81

5-(3,5-Dichlorophenyl)-2,5-dihydro-2,2,4-trimethyl-1H-[1]benzopyrano[3,4-f]quinolin-10-yl] methylcarbonate Example 80 and methylchloroformate were processed as in examples 7B and 7 to provide the desired compound.

MS (DCI/NH₃) m/z 496 (M+H)⁺; ¹H NMR (300 MHz, DMSO-d₆) δ 7.58 (d, 1H), 7.45 (t, 1H), 7.24 (m, 2H), 7.02 (t, 1H), 6.82 (s, 1H), 6.80 (dd, 1H), 6.75 (dd, 1H), 6.74 (d, 1H), 6.48 (s, 1H), 5.43 (s, 1H), 3.79 (s, 3H), 1.79 (s, 3H), 1.25 (s, 3H), 1.13 (s, 3H); Anal. calcd for $C_{27}H_{23}NO_4C_{12}$ C, 65.33; H, 4.67; N, 2.82. Found: C, 65.12; H, 4.55, N, 2.79.

EXAMPLE 82

2,5-Dihydro-2,2,4-trimethyl-5-(2-propenyl)-1H-1benzopyrano[3,4-f]quinolin-10-ol

Example 7A and allylmagnesium bromide were processed as in examples 7B and 7 to provide the desired compound.

MS (DCI/NH₃) m/z 334 (M+H)⁺; ¹H NMR (300 MHz, DMSO-d₆) δ 9.77 (s, 1H), 8.10 (d, 1H), 6.88 (t, 1H), 6.58 (d, 1H), 6.53 (d, 1H), 6.35 (d, 1H), 6.05 (s, 1H), 5.89–5.72 (m, 2H), 5.44 (s, 1H), 5.03 (d, 1H), 4.99 (d, 1H), 2.50–2.40 (m, 1H), 2.25–2.18 (m, 1H), 2.16 (s, 3H), 1.16, (s, 3H), 1.15 (s, 3H); HRMS calcd m/z for $C_{22}H_{23}NO_2$: 333.1729 (M+H)⁺. Found 333,1734.

EXAMPLE 83

10-(Bromodifluoromethoxy)-2,5-dihyro-2,2,4-trimethyl-5-(2-propenyl)-1H-[1]benzopyrano[3,4-f] quinoline Example 82 and dibromodifluoromethane were processed as in examples 7B and 7 to provide the desired compound.

MS (DCI/NH₃) m/z 462 (M+H)⁺; ¹H NMR (300 MHz, DMSO-d₆) δ 7.60 (d, 1H), 7.21 (t, 1H), 7.0 (m, 1H), 6.95 (dd, 1H), 6.64 (d, 1H), 6.35 (s, 1H), 5.89–5.76 (m, 2H), 5.46 (s, 1H), 5.04 (dd, 1H), 4.96 (dd, 1H), 2.55–2.44 (m, 1H), 2.33–2.25 (m, 1H), 2.18 (s, 3H), 1.19 (s, 3H), 1.17 (s, 3H); HRMS calcd m/z for $C_{23}H_{22}F_2NO_2Br$: 461.0802 (M+H)⁺. Found 461.0815.

EXAMPLE 84

[3-(2,5-Dihydro-10-methoxy-2,2,4-trimethyl-1H-[1] benzopyrano[3,4-f]quinolin-5-yl)phenyl] methylcarbonate Example 13 and methylchloroformate were processed as in Example 10 to provide the desired compound.

MS (DCI/NH₃) m/z 458 (M+H)⁺; ¹H NMR (300 MHz, DMSO-d₆) δ 8.01 (d, 1H), 7.25 (t, 1H), 7.12 (d, 1H), 7.01 (q, 1H), 6.90 (q, 2H), 6.78 (s, 1H), 6.72 (d, 1H), 6.57 (q, 1H), 6.44 (q, 1H), 6.20 (d, 1H), 5.39 (s, 1H), 3.80 (s, 3H), 3.63 (s, 3H), 1.83 (s, 3H), 1.22 (s, 3H), 1.16 (s, 3H); Anal. calcd for $C_{28}H_{27}NO_5$: C, 73.50; H, 5.94; N, 3.06. Found: C, 73.63; H, 6.20; N, 2.86.

EXAMPLE 85

2,5-Dihydro-10-methoxy-5-(3-methoxyphenyl)-2,2, 4-trimethyl-1H-[1]benzopyrano[3,4-f]quinoline Example 13 and methyl iodide were processed as in Example 14 to provide the desired compound.

MS (DCI/NH₃) m/z 414 (M+H)⁺; ¹H NMR (300 MHz, DMSO-d₆) δ 8.01 (d, 1H), 7.13 (t, 1H), 6.92 (t, 1H), 6.75–6.67 (m, 5H), 6.57 (dd, 1H), 6.46 (dd, 1H), 6.20 (d, 1H), 5.39 (s, 1H), 3.80 (s, 3H), 3.63 (s, 3H), 1.88 (s, 3H), 1.22 (s, 3H), 1.16 (s, 3H); Anal. calcd for $C_{27}H_{27}NO_3$: C, 78.42; H, 6.58; N, 3.38. Found: C, 78.58; H, 6.55; N, 3.23.

EXAMPLE 86

2,5-Dihydro-10-methoxy-2,2,4-trimethyl-5-[3-(2-propenyloxy)phenyl]-1H-[1]benzopyrano[3,4-f] quionline Example 13 and allyl bromide were processed as in Example 14 to provide the desired compound.

MS (DCI/NH₃) m/z 440 (M+H)⁺; ¹H NMR (300 MHz, DMSO-d₆) δ 8.02 (d, 1H), 7.13 (t, 1H), 6.92 (t, 1H), 6.78–6.67 (m, 5H), 6.56 (d, 1H), 6.46 (d, 1H), 6.20 (d, 1H), 5.95 (m, 1H), 5.40 (s, 1H, 5.31 (dd, 1H), 5.21 (dd, 1H), 4.42 (d, 2H), 3.80 (s, 3H), 1.86 Cs, 3H), 1.23 (s, 3H), 1.16 Cs, 3H); Anal. calcd for $C_{29}H_{29}NO_3$: C, 79.24; H, 6.64; N, 3.18. Found: C, 78.87; H, 6.46; N, 3.07.

EXAMPLE 87

2,5-Dihydro-10-methoxy-2,2,4-trimethyl-5-[3-(phenylmethoxy)phenyl]-1H[1]benzopyrano[3,4-f]quinoline Example 13 and benzyl bromide were processed as in Example 14 to provide the desired compound.

MS (DCI/NH$_3$) m/z 490 (M+H)$^+$; $^1$H NMR (300 MHz, DMSO-d$_6$) δ 8.06 (d, 1H), 7.40 (m, 5H), 7.18 (t, 1H), 6.97 (t, 1H), 6.90–6.85 (m, 2H), 6.80–6.74 (m, 3H), 6.62 (d, 1H), 6.48 (d, 1H), 6.24 (d, 1H), 5.45 (s, 1H), 5.03 (d, 2H), 3.85 (s, 3H), 1.92 (s, 3H), 1.29 (s, 3H), 1.21 (s, 3H); Anal. calcd for C$_{33}$H$_{31}$NO$_3$: C, 80.95; H, 6.38; N, 2.86. Found: C, 80.81; H, 6.24; N, 2.96.

EXAMPLE 88

5-[3-(Cyclopropylmethoxy)phenyl]-2,5-dihydro-10-methoxy-2,2,4-trimethyl-1H-[1]benzopyrano[3,4-f]quinoline Example 13 and cyclopropylmethyl bromiode were processed as in Example 14 to provide the desired compound.

MS (DCI/NH$_3$) m/z 454 (M+H)$^+$; $^1$H NMR (300 MHz, DMSO-d$_6$) δ 8.01 (d, 1H), 7.12 (t, 1H), 6.92 (t, 1H), 6.74–6.68 (m, 5H), 6.55 (d, 1H), 6.46 (d, 1H), 6.20 (s, 1H), 5.39 (s, 3H), 3.79 (s, 3H), 3.66 (d, 2H), 1.86 (s, 3H), 1.23 (s, 3H), 1.16 (s, 3H), 1.12 (m, 1H), 0.50 (q, 2H), 0.24 (q, 2H); Anal. calcd for C$_{30}$H$_{31}$NO$_3$: C, 79.44; H, 6.88; N, 3.08. Found: C, 79.12; H, 6.72; N, 2.99.

EXAMPLE 89

2,5-Dihydro-10-methoxy-2,2,4-trimethyl-5-[3-[2-(1-piperidinyl)ethoxy]pheny]-1H-[1]benzopyrano[3,4-f]quinoline Example 13 and 1-(2-chloroethyl)piperidine were processed as in Example 14 to provide the desired compound.

MS (DCI/NH$_3$) m/z 511 (M+H)$^+$; $^1$H NMR (300 MHz, DMSO-d$_6$) δ 8.01 (d, 1H), 7.12 (t, 1H), 6.92 (t, 1H), 6.77–6.68 (m, 5H), 6.57 (d, 1H), 6.46 (d, 1H), 6.20 (d, 1H), 5.39 (s, 1H), 3.91 (t, 2H), 3.80 (s, 3H), 2.55 (t, 2H), 2.35 (b, 4H), 1.92 (s, 3H), 1.46 (b, 4H), 1.36 (b, 2H), 1.22 (s, 3H), 1.16 (s, 3H); Anal. calcd for C$_{33}$H$_{38}$N$_2$O$_3$·0.5H$_2$O: C, 76.27; H, 7.56; N, 5.39. Found: C, 76.26; H, 7.38; N, 5.28.

EXAMPLE 90

5-(3-Hexyloxyphenyl)-2,5-dihydro-10-methoxy-2,2,4-trimethyl-1H-[1]benzopyrano[3,4-f]quinoline Example 13 and hexyl iodide were processed as in Example 14 to provide the desired compound.

MS (DCI/NH$_3$) m/z 484 (M+H)$^+$; $^1$H NMR (300 MHz, DMSO-d$_6$) δ 8.01 (d, 1H), 7.09 (t, 1H), 6.92 (t, 1H), 6.75–6.67 (m, 5H), 6.56 (dd, 1H), 6.46 (dd, 1H), 6.18 (d, 1H), 5.40 (s, 1H), 3.81 (t, 2H), 3.79 (s, 3H), 1.87 (s, 3H), 1.60 (m, 2H), 1.36–1.23 (b, 6H), 1.22 (s, 3H), 1.16 (s, 3H), 0.86 (t, 3H); HRMS calcd m/z for C$_{32}$H$_{37}$NO$_3$: 483.2773 (M+H)$^+$. Found: 483.2776.

EXAMPLE 91

5-[3-(2,4-Dinitrophenoxy)phenyl]-2,5-dihydro-10-methoxy-2,2,4-trimethyl-1H-[1]benzopyrano[3,4-f]quinoline Example 13 and 1-fluoro-2,4-dinitrobenzene were processed as in Example 14 to provide the desired compound.

MS (DCI/NH$_3$) m/z 566 (M+H)$^+$; $^1$H NMR (300 MHz, DMSO-d$_6$) δ 8.87 (d, 1H), 8.38 (dd, 1H), 7.88 (d, 1H), 7.40 (t, 1H), 7.20–7.08 (m, 2H), 7.20–7.08 (m, 2H), 6.81 (s, 1H), 6.72 (d, 1H), 6.68 (d, 1H), 6.62 (d, 1H), 6.46 (dd, 1H), 6.24 (d, 1H), 5.40 (s, 1H), 3.78 (s, 3H), 1.90 (s, 3H), 1.19 (s, 3H), 1.13 (s, 3H); Anal. calcd for C$_{32}$H$_{27}$N$_3$O$_7$: C, 67.95; H, 4.81; N, 7.42. Found: C, 68.20; H, 5.05; N, 7.20.

EXAMPLE 92

2,5-Dihydro-10-methoxy-2,2,4-trimethyl-5-[3-(2-propynyloxy)phenyl]-1H-[1]benzopyrano[3,4-f]quinoline Example 13 and propargyl bromide were processed as in Example 14 to provide the desired compound.

MS (DCI/NH$_3$) m/z 566 (M+H)$^+$; $^1$H NMR (300 MHz, DMSO-d$_6$) δ 8.00 (d, 1H), 7.13 (t, 1H), 6.92 (t, 1H), 6.80–6.68 (m, 5H), 6.56 (d, 1H), 6.48 (d, 1H), 6.18 (d, 1H), 5.39 (s, 1H), 4.67 (d, 2H), 3.80 (s, 3H), 3.50 (t, 1H), 1.87 (s, 3H), 1.23 (s, 3H), 1.16 (s, 3H);

EXAMPLE 93

3-(2,5-Dihydro-10-methoxy-2,2,4-trimethyl-1H-[1]benzopyrano[3,4-f]quinolin-5-yl)phenol 4-Methylbenzenesulfonate (Ester)

Example 13 and p-toluenesulfonyl chloride were processed as in Example 15 to provide the desired compound.

MS (DCI/NH$_3$) m/z 554 (M+H)$^+$; $^1$H NMR (300 MHz, DMSO-d$_6$) δ 7.99 (d, 1H), 7.47 (d, 2H), 7.36 (d, 4H), 7.22 (t, 1H), 7.13 (d, 1H), 6.97 (t, 1H), 6.85–6.78 (m, 2H), 6.70 (d, 1H), 6.68 (s, 1H), 6.59 (dd, 1H), 6.37 (dd, 1H), 6.24 (d, 1H), 5.39 (s, 1H), 3.80 (s, 3H), 2.43 (s, 3H), 1.74 (s, 3H), 1.24 (s, 3H), 1.18 (s, 3H); Anal. calcd for C$_{33}$H$_{31}$NO$_5$S: C, 71.58; H, 5.64; N, 2.52. Found: C, 71.49; H, 5.75; N, 2.40.

EXAMPLE 94

4-(2,5-Dihydro-10-methoxy-2,2,4-trimethyl-1H-[1]benzopyrano[3,4-f]quinolin5-yl)phenolacetate (Ester)

Example 1F and 4-methoxymethoxyphenyl bromide were processed as in examples 12A–C to provide the desired compound.

MS (DCI/NH$_3$) m/z 442 (M+H)$^+$; $^1$H NMR (300 MHz, DMSO-d$_6$) δ 8.02 (d, 1H), 7.19 (d, 2H), 6.99 (d, 2H), 6.91 (t, 1H), 6.79 (s, 1H), 6.71 (d, 1H), 6.58 (d, 1H), 6.46 (dd, 1H), 6.21 (d, 1H), 5.39 (s, 1H), 3.79 (s, 3H), 2.19 (s, 3H), 1.83 (s, 3H), 1.22 (s, 3H), 1.15 (s, 3H); Anal. calcd for C$_{28}$H$_{27}$NO$_4$: C, 76.16; H, 6.16; N, 3.17. Found: C, 75.79; H, 6.24; N, 3.03.

EXAMPLE 95

4-(2,5-Dihydro-10-methoxy-2,2,4-trimethyl-1H-[1]benzopyrano[3,4-f]quinolin-5-yl)phenol Example 94 was processed as in Example 13 to provide the desired compound.

MS (DCI/NH$_3$) m/z 400 (M+H)$^+$; $^1$H NMR (300 MHz, DMSO-d$_6$) δ 9.29 (s, 1H), 8.05 (d, 1H), 7.00 (d, 2H), 6.95 (t, 1H), 6.74 (d, 2H), 6.72 (s, 1H), 6.63–6.58 (m, 3H), 6.44 (dd, 1H), 6.15 (s, 1H), 5.41 (s, 1H), 3.83 (s, 3H), 1.90 (s, 3H), 1.28 (s, 3H), 1.20 (s, 3H); Anal. calcd for C$_{26}$H$_{25}$NO$_3$: C, 78.17; H, 6.30; N, 3.50. Found: C, 78.59; H, 6.20; N, 3.12.

EXAMPLE 96

2,5-Dihydro-10-methoxy-2,2,4-trimethyl-5-[[4-(methylthio)methoxy]phenyl]-1H-[1]benzopyrano[3,4-f]quinoline Example 95 was processed as in Example 14 to provide the desired compound.

MS (DCI/NH$_3$) m/z 460 (M+H)$^+$; $^1$H NMR (300 MHz, DMSO-d$_6$) δ 8.01 (d, 1H), 7.17 (d, 2H), 6.90 (t, 1H), 6.82 (d, 2H), 6.72 (s, 1H), 6.69 (d, 1H), 6.56 (d, 1H), 6.42 (d, 1H), 6.17 (s, 1H), 5.38 (s, 1H), 5.16 (s, 2H), 3.80 (s, 3H), 2.11 (s, 3H), 1.85 (s 3H), 1.23 (s, 3H), 1.16 (s, 3H); Anal. calcd for C$_{28}$H$_{29}$NO$_3$S: C, 73.17; H, 6.35; N, 3.04. Found: C, 72.86; H, 6.62; N, 2.69.

EXAMPLE 97

[4-(2,5-Dihydro-10-methoxy-2,2,4-trimethyl-1H-1benzopyrano[3,4-f]quinolin-5-yl)phenyl] dimethylcarbamate Example 95 and dimethylcarbanoylchloride were processed as in Example 15 to provide the desired compound.

MS (DCI/NH$_3$) m/z 471 (M+H)$^+$; $^1$H NMR (300 MHz, DMSO-d$_6$) δ 8.01 (d, 1H), 7.15 (d, 2H), 6.98 (d, 2H), 6.90 (d, 1H), 6.76 (s, 1H), 6.70 (d, 1H), 6.57 (d, 1H), 6.44 (d, 1H), 6.22 (d, 1H), 5.40 (s, 1H), 3.80 (s, 3H), 2.98 (s, 3H), 2.85 (s, 3H), 1.86 (s, 3H), 1.23 (s, 3H), 1.15 (s, 3H).

EXAMPLE 98

2,5-Dihydro-10-methoxy-2,2,4-trimethyl-5-[4-(phenylmethoxy)phenyl]-1H-[1]benzopyranol[3,4-f]quinoline Example 95 and benzyl bromide were processed as in Example 14 to provide the desired compound.

MS (DCI/NH$_3$) m/z 490 (M+H)$^+$; $^1$H NMR (300 MHz, DMSO-d$_6$) δ 8.02 (d, 1H), 7.40–7.28 (m, 4H), 7.08 (d, 2H), 6.90 (t, 1H), 6.84 (d, 2H), 6.72 (s, 1H), 6.70 (d, 1H), 6.55 (d, 1H), 6.41 (d, 1H), 6.15 (s, 1H), 5.37 (s, 1H), 4.96 (s, 2H), 3.80 (s, 3H), 1.85 (s, 3H), 1.23 (s, 3H), 1.15 (s, 3H); Anal. calcd for C$_{33}$H$_{31}$NO$_3$: C, 80.95; H, 6.38; N, 2.86. Found: C, 81.02; H, 6.25; N, 2.76.

EXAMPLE 99

2,5-Dihydro-10-methoxy-2,2,4-trimethyl-5-[3-(methoxymethoxy)phenyl]-1H-[1benzopyrano[3,4-f]quinoline Example 13 and methoxymethyl chloride were processed as in Example 14 to provide the desired compound.

MS (DCI/NH$_3$) m/z 444 (M+H)$^+$; $^1$H NMR (300 MHz, DMSO-d$_6$) δ0 8.01 (d, 1H), 7.14 (t, 1H), 6.92 (t, 1H), 6.83–6.75 (m, 4H), 6.70 (d, 1H), 6.58 (d, 1H), 6.47 (q, 1H), 6.21 (s, 1H), 5.40 (s, 1H), 5.06 (s, 2H), 3.80 (s, 3H), 3.30 (s, 3H), 1.89 (s, 3H), 1.24 (s, 3H), 1.16 (s, 3H); HRMS calcd m/z for C$_{28}$H$_{29}$NO$_4$: 443.2097 (M+H)$^+$. Found: 443.2098.

EXAMPLE 100

[(2,5-Dihydro-10-methoxy-2,2,4-trimethyl-1H-[1]benzopyrano[3,4-f]quinolin-5-yl)phenyl]1-morpholinecarboxylate Example 13 and morpholine were processed as in Example 15 to provide the desired compound.

MS (DCI/NH$_3$) m/z 513 (M+H)$^+$; $^1$H NMR (300 MHz, DMSO-d$_6$) δ 8.01 (d, 1H), 7.22 (t, 1H), 7.05 (d, 1H), 6.93 (t, 2H), 6.83 (s, 1H), 6.77 (s, 1H), 6.71 (d, 1H), 6.57 (d, 1H), 6.48 (q, 1H), 6.23 (d, 1H, 5.40 (s, 1H), 3.80 (s, 3H), 3.60 (t, 4H), 3.50 (b, 4H), 1.86 (s, 3H), 1.24 (s, 3H), 1.14 (s, 3H); HRMS calcd m/z for C$_{31}$H$_{32}$N$_2$O$_5$: 512.2311 (M+H)$^+$. Found: 512.2328.

EXAMPLE 101

2,5-Dihydro-10-methoxy-2,2,4-trimethyl-5-[3-[(methylsulfinyl)methoxy]phenyl]-1H-[1]benzopyrano[3,4-f]quionline A solution of Example 14 (12 mg, 0.005 mmol) in methanol (1 mL) at 0° C. was treated sequentially with TeO$_2$ (1.6 mg, 0.01 mmol) and acetic acid (50 mg, 0.83 mmol), stirred at ambient temperature overnight, treated with saturated NaHCO$_3$ and extracted with dichloromethane. The extract was washed with water and brine, dried (MgSO$_4$), filtered, and concentrated to yield.

MS (DCI/NH$_3$) m/z 476 (M+H)$^+$; $^1$H NMR (300 MHz, DMSO-d$_6$) δ 8.01 (dd, 1H), 7.15 (dt, 1H), 6.92 (m, 3H), 6.78 (t, 1H), 6.74 (s, 1H), 6.70 (d, 1H), 6.58 (d, 1H), 6.47 (d, 1H), 6.19 (d, 1H), 5.40 (d, 1H), 5.12 (dd, 1H), 4.93 (q, 1H), 3.79 (d, 3H), 2.57 (d, 3H), 1.87 (d 3H), 1.24 (d, 3H), 1.16 (d, 3H); HRMS calcd m/z for C$_{28}$H$_{29}$NO$_4$S: 475.1817 (M+H)$^+$. Found: 475.1819.

EXAMPLE 102

O-[3-(2,5-Dihydro-10-methoxy-2,2,4-trimethyl-1H-[1]benzopyrano[3,4-f]quinolin-5-yl)phenyl]ester Example 13 and thiocarbanoyl chloride were processed as in Example 16 to provide the desired compound.

MS (DCI/NH$_3$) m/z 487 (M+H)$^+$; $^1$H NMR (300 MHz, DMSO-d$_6$) δ 8.01 (d, 1H), 7.22 (t, 1H), 7.13 (d, 1H), 6.92 (t, 1H), 6.85 (d, 1H), 6.78 (s, 1H), 6.72 (s, 1H), 6.59 (d, 1H), 6.57 (d, 1H), 6.45 (d, 1H), 6.21 (s, 1H), 5.39 (s, 1H), 3.80 (s, 3H), 3.29 (s, 3H), 3.22 (s, 3H), 1.86 (s, 3H), 1.24 (s, 3H), 1.24 (s, 3H), 1.14 (s, 3H).

EXAMPLE 103

2,5-Dihydro-10-methoxy-2,2,4-trimethyl-5-[3-(methylthio)phenyl]-1H-[1]benzopyrano[3,4-f]quinoline

EXAMPLE 103A

A solution of 3-bromophenylmethoxymethyl ether (3.50 g, 15.0 mmol) in THF (150 mL) at −78° C. was treated with n-butyllithium (2.5 M in hexanes, 6.00 mL) over 5 minutes, warmed to −30° C., cooled to −78° C., treated with Example 1F in one portion, warmed to −40° C., quenched with saturated NH$_4$Cl, warmed to ambient temperature, and allowed to settle. The supernatant was decanted and concentrated, and the residue was partitioned between water and ethyl acetate. The organic layer was washed sequentially with water and brine, dried (Na$_2$SO$_4$) and concentrated. Flash chromatography of the residue on silica gel with 20–25% ethyl acetate/hexane provided the desired compound. MS (DCI/NH$_3$) m/z 476 (M+H)$^+$.

EXAMPLE 103

2,5-Dihydro-10-methoxy-2,2,4-trimethyl-5-[3-(methylthio)phenyl]-1H-[1benzopyrano[3,4-f] quinoline A solution of Example 103A (20 mg, 0.042 mmol) and triethylsilane (49 mg, 0.42 mmol) in dichloromethane (1 mL) at ambient temperature was treated with BF$_3$.OEt$_2$ (60 mg, 0.42 mmol), stirred for 24 hours, and treated with saturated NaHCO$_3$. The aqueous layer was extracted with dichloromethane, and the combined extracts were washed sequentially with 1M NaOH and brine, dried (Na$_2$SO$_4$), filtered, and concentrated. Flash chromatography of the residue on silica gel with 10–25% ethyl acetate/hexane provided the desired compound.

MS (DCI/NH$_3$) m/z 430 (M+H)$^+$; $^1$H NMR (300 MHz, DMSO-d$_6$) δ 8.01 (d, 1H), 7.15 (t, 1H), 7.05 (s, 1H), 7.03 (d, 1H), 6.93 (t, 1H), 6.89 (s, 1H), 6.74 (s, 1H), 6.70 (d, 1H), 6.57 (d, 1H), 6.46 (d, 1H), 6.19 (d, 1H), 5.40 (s, 1H), 3.78 (s, 3H), 3.33 (s, 3H), 1.88 (s, 3H), 1.22 (s, 3H), 1.16 (s, 3H); HRMS calcd m/z for C$_{27}$H$_{27}$NO$_2$S: 429.1763 (M+H)$^+$. Found: 429.1764.

EXAMPLE 104

O-[3-(2,5-Dihydro-10-methoxy-2,2,4-trimethyl-1H-[1]benzopyrano[3,4-f]quinolin-5-yl)phenyl] methylcarbonothioate Example 95 and methyl thiochloroformate were processed as in Example 15 to provide the desired compound.

MS (DCI/NH$_3$) m/z 474 (M+H)$^+$; $^1$H NMR (300 MHz, DMSO-d$_6$) δ 8.00 (d, 1H), 7.26 (t, 1H), 7.12 (d, 1H), 7.01 (q, 1H), 6.89 (t, 1H), 6.87 (s, 1H), 6.78 (s, 1H), 6.72 (d, 1H), 6.57 (q, 1H), 6.44 (q, 1H), 6.20 (d, 1H), 5.39 (s, 1H), 3.78 (s, 3H), 2.35 (s, 3H), 1.83 (s, 3H), 1.22 (s, 3H), 1.16 (s, 3H); Anal. calcd for C$_{28}$H$_{27}$NO$_4$S: C, 71.01; H, 5.74; N, 2.95. Found: C, 70.77; H, 5.74; N, 2.79.

EXAMPLE 105

[3-(2,5-Dihydro-10-methoxy-2,2,4-trimethyl]-1H-1]benzopyrano[3,4-f]quinolin-5-yl)phenyl] trifluoromethanesulfonate A solution of Example 13 (100 mg, 0.25 mmol), triethylamine (70 μL, 0.5 mmol), and 4-dimethylaminopyridine (catalytic) in dichloromethane (10 mL) at −78° C. was treated dropwise with trifluoromethanesulfonic anhydride (50 μL, 0.30 mmol), stirred for 30 minutes at −78° C., poured into saturated NaHCO$_3$, and extracted with ethyl acetate. The extract was washed sequentially with water and brine, dried (Na$_2$SO$_4$), filtered, and concentrated. The residue was purified by flash chromatography on silica gel with 15–85% ethyl acetate/hexanes to provide the desired compound.

MS (DCI/NH$_3$) m/z 532 (M+H)$^+$; $^1$H NMR (300 MHz, DMSO-d$_6$) δ 8.02 (d, 1H), 7.44 (t, 1H), 7.30 (m, 2H), 7.17 (s, 1H), 6.93 (t, 1H), 6.83 (s, 1H), 6.71 (d, 1H), 6.57 (d, 1H), 6.43 (d, 1H), 6.28 (d, 1H), 5.40 (s, 1H), 3.78 (s, 3H), 1.83 (s, 3H), 1.22 (s, 3H), 1.15 (s, 3H); Anal. calcd for C$_{27}$H$_{24}$NO$_5$SF$_3$: C, 61.01; H, 4.55; N, 2.64. Found: C, 61.17; H, 4.60; N, 2.51.

EXAMPLE 106

5-[3-(4,5-Dihydro-4,4-dimethyl-2-oxazolyl)phenyl]-2,5-dihydro-10-methoxy-2,2,4-trimethyl-1H-[1benzopyrano[3,4-f]quinoline Example 52 (92.9 mg, 0.20 mmol), 2-trimethylstannyl-4,4-dimethyloxazoline (210 mg, 0.80 mmol), and [1,1'-is(diphenylphosphino)-ferrocene]dichloropalladium(II) (16 mg, 0.02 mmol) in 1-methyl-2-pyrrolidinone (2 mL) were purged with N$_2$, heated at 85° C. for 3 hours, partitioned between ethyl acetate (50 mL) and saturated KF (30 mL), stirred for 1 hour, and filtered through a pad of powdered sea shells (Celite®). The filtrate was washed with water, brine, dried (Na$_2$SO$_4$), filtered, and concentrated. The residue was purified by flash chromatography on silica gel with 0–30% ethyl acetate/hexanes to provide the desired compound.

MS (DCI/NH$_3$) m/z 481 (M+H)$^+$; $^1$H NMR (300 MHz, DMSO-d$_6$) δ 8.02 (d, 1H), 7.64 (d, 1H), 7.62 (s, 1H), 7.41 (d, 1H), 7.32 (t, 1H), 6.92 (t, 1H), 6.82 (s, 1H), 6.71 (d, 1H), 6.56 (dd, 1H), 6.47 (dd, 1H), 6.25 (d, 1H), 5.40 (s, 1H), 4.02 (s, 2H), 3.78 (s, 3H), 1.84 (s, 3H), 1.25 (s, 3H), 1.22 (s, 6H), 1.22 (s, 6H), 1.16 (s, 3H); Anal. calcd for C$_{31}$H$_{32}$N$_2$O$_3$.0.7H$_2$O: C, 75.49; H, 6.85; N, 5.68. Found: C, 75.83; H 6.88; N, 5.29.

EXAMPLE 107

Ethyl 3-(2,5-Dihydro-10-methoxy-2,2,4-trimethyl-1H-[1]benzopyrano3,4-f]quinolin-5-yl)benzoate Example 106 (48 mg, 0.1 mmol) in 1.5 M sulfuric acid in ethanol (5 mL) was refluxed for 16 hours, cooled, poured into saturated NaHCO$_3$, and extracted with ethyl acetate. The extract was washed with brine, dried (Na$_2$SO$_4$), filtered, and concentrated. The residue was purified by flash chromatography on silica gel with 30% ethyl acetate/hexanes to provide the desired compound.

MS (DCI/NH$_3$) m/z 456 (M+H)$^+$; $^1$H NMR (300 MHz, DMSO-d$_6$) δ 8.02 (d, 1H), 7.76 (m, 2H), 7.48 (d, 1H), 7.38 (t, 1H, 6.91 (t, 1H), 6.85 (s, 1H), (d, 1H), 6.56 (dd, 1H), 6.46 (dd, 1H), 6.26 (d, 1H), 5.40 (s, 1H), 4.23 (q, 2H), 3.78 (s, 3H), 1.84 (s, 3H), 1.25 (t, 3H), 1.24 (s, 3H), 1.16 (s, 3H); HRMS m/z calcd for C$_{29}$H$_{30}$NO$_4$: 456.2175 (M+H)$^+$. Found: 456.2175.

EXAMPLE 108

3-(2,5-Dihydro-10-methoxy-2,2,4-trimethyl-1H-[1]benzopyrano[3,4-f]quinolin-5-yl)benzoic Acid Example 107 (20 mg, 0.04 mmol) and LiOH.H$_2$O (16.8 mg, 0.4 mmol) in 1:1:1 THF/methanol/water (3 mL) was stirred for 48 hours, and concentrated. The residue was dissolved in 1M NaOH (2 mL, washed with diethyl ether, treated with 1M HCl to pH 3, concentrated to provide the desired compound.

MS (DCI/NH$_3$) m/z 428 (M+H)$^+$; $^1$H NMR (300 MHz, DMSO-d$_6$) δ 8.02 (d, 1H), 7.73 (m, 2H), 7.46 (d, 1H), 7.35 (t, 1H), 6.91 (t, 1H), 6.83 (s, 1H), 6.71 (d, 1H), 6.55 (dd, 1H), 6.46 (dd, 1H), 6.22 (d, 1H), 5.40 (s, 1H), 3.78 (s, 3H), 1.83 (s, 3H), 1.24 (s, 3H), 1.16 (s, 3H); Anal. calcd for C$_{27}$H$_{25}$NO$_4$: C, 72.86; H, 5.89; N, 3.28. Found: C, 72.89; H, 6.00; N, 2.94.

EXAMPLE 109

2,5-Dihydro-10-methoxy-2,2,4-trimethyl-5-[3-methyl-5-(2-propenyl)phenyl]-1H-[1]benzopyrano[3,4-f]quinoline Example 52 and allyltributylin were processed as in Example 16 to provide the desired compound.

MS (DCI/NH$_3$) m/z 438 (M+H)$^+$; $^1$H NMR (300 MHz, DMSO-d$_6$) δ 7.99 (d, 1H), 6.91 (t, 1H), 6.80 (m, 3H), 6.70 (s, 1H), 6.68 (d, 1H), 6.56 (dd, 1H), 6.44 (dd, 1H), 6.16 (d, 1H), 5.78 (ddt, 1H), 5.39 (s, 1H), 4.94 (dq, 1H), 4.88 (dq, 1H), 3.78 (s, 3H), 3.17 (d, 2H), 2.13 (s, 3H), 1.86 (s, 3H), 1.22 (s, 3H), 1.16 (s, 3H); Anal. calcd for C$_{30}$H$_{31}$NO$_2$: C, 82.35; H, 7.14; N, 3.20. Found: C, 81.99; H, 7.14; N, 2.98.

EXAMPLE 110

1-[3-(2,5-Dihydro-10-methoxy-2,2,4-trimethyl-1H-[1]benzopyrano[3,4-f]quinolin-5-yl)-5-methylphenyl]ethanone Example 52 and tributyl(1-ethoxyvinyl)tin in dichloroethane (20 mL) was treated with silica gel (1.0 g) and formic acid (10 drops), heated to 40° C. for 6 hours, treated with water, and extracted with ethyl acetate. The extract was washed with brine, dried (MgSO$_4$), filtered, and concentrated. The residue was purified by flash chromatography on silica gel with 5–10% ethyl acetate/hexanes to provide the desired compound.

MS (DCI/NH$_3$) m/z 440 (M+H)$^+$; $^1$H NMR (300 MHz, DMSO-d$_6$) δ 8.01 (d, 1H), 7.61 (s, 1H), 7.51 (s, 1H), 7.28 (s, 1H), 6.92 (t, 1H), 6.80 (s, 1H), 6.72 (d, 1H), 6.56 (dd, 1H), 6.49 (dd, 1H), 6.24 (m, 1H), 5.40 (s, 1H), 3.78 (s, 3H), 2.44 (s, 3H), 2.26 (s, 3H), 1.84 (s, 3H), 1.23 (s, 3H), 1.16 (s, 3H).

EXAMPLE 111

3-(2,5-Dihydro-10-methoxy-2,2,4-trimethyl-1H-[1benzopyrano3,4-f]quinolin-5-yl)5-trimethylbenzenemethanol A solution of Example 110 (0.022 g, 0.050 mmol) in THF (5 mL) at 0° C. was treated with methylmagnesium chloride (3 M in THF, 0.83 μL), warmed to room temperature, stirred for 1 hour, treated with saturated NH$_4$Cl, separated, and extracted with ethyl acetate. The extract was washed with brine and dried (MgSO$_4$), filtered, and concentrated to provide the desired compound.

MS (DCI/NH$_3$) m/z 456 (M+H)$^+$; $^1$H NMR (300 MHz, DMSO-d$_6$) δ 7.98 (d, 1H), 7.11 (s, 1H), 7.08 (s, 1H), 6.91 (t, 8H), 6.78–6.63 (m, 3H), 6.55 (d, 1H), 6.46 (d, 1H), 6.18 (m, 1H), 5.39 (s, 1H), 4.84 (s, 1H), 3.73 (s, 3H), 2.14 (s, 3H), 1.88 (s, 3H), 1.24 (s, 3H), 1.23 (s, 3H), 1.22 (s, 3H), 1.16 (s, 3H).

EXAMPLE 112

5-[3-(2-Furanyl)phenyl]-2,5-dihydro-10-methoxy-2,2,4-trimethyl-1H-[1]benzopyrano[3,4-f]quinoline Example 52 and 2-(tributylstannyl)furan were processed as in Example 16 to provide the desired compound.

MS (DCI/NH$_3$) m/z 456,450 (M+H)$^+$; $^1$H NMR (300 MHz, DMSO-d$_6$) δ 8.0 (d, 1H), 7.69 (s, 1H), 7.48 (d, 1H), 7.23 (t, 1H), 7.05 (d, 1H), 6.88 (t, 1H), 6.81 (s, 2H), 6.70 (d, 1H), 6.54 (m, 2H), 6.47 (d, 1H), 6.23 (s, 1H), 5.41 (s, 1H), 3.78 (s, 3H), 1.88 (s, 3H), 1.24 (s, 3H), 1.16 (s, 3H); Anal. calcd for C$_{30}$H$_{27}$NO$_3$.H$_2$O: C, 77.07; H, 6.25; N, 3.00. Found: C, 77.27; H, 5.97; N, 3.23.

EXAMPLE 113

2,5-Dihydro-10-methoxy-2,2,4-trimethyl-5-[3-methyl-5-(1H-pyrrolidin-1-yl)phenyl]1H-[1]benzopyrano[3,4-f]quinoline Example 11 and pyrrolidine were processed as in Example 17 to provide the desired compound.

MS (DCI/NH$_3$) m/z 467 (M+H)$^+$; $^1$H NMR (300 MHz, DMSO-d$_6$) δ 7.97 (d, 1H), 6.93 (t, 1H), 6.67 (s, 1H), 6.67 (d, 1H), 6.56 (d, 1H), 6.49 (d, 1H), 6.22 (s, 1H), 6.14 (m, 3H), 5.39 (s, 1H), 3.79 (s, 3H), 3.04 (m, 4H), 2.07 (s, 3H), 1.92 (s, 3H), 1.87 (m, 4H), 1.21 (s, 3H), 1.17 (s, 3H).

EXAMPLE 114

3-(2,5-Dihydro-10-methoxy-2,2,4-trimethyl-1H-[1]benzopyrano[3,4-f]quinolin-5-methyl)-5,N-dimethylbenzenamine Example 11 and methylamine were processed as in Example 17 to provide the desired compound.

MS (DCI/NH$_3$) m/z 427 (M+H)$^+$; $^1$H NMR (300 MHz, DMSO-d$_6$) δ 7.98 (d, 1H), 6.92 (t, 1H), 6.67 (d, 1H), 6.61 (s, 1), 6.56 (d, 1H), 6.46 (d, 1H), 6.18 (br s, 2H), 6.14 (br s, 1H), 6.10 (s, 1H), 5.58 (q, 1H), 5.38 (br s, 1H), 3.79 (s, 3H), 2.50 (d, 3H), 2.04 (s, 3H), 1.90 (s, 3H), 1.22 (s, 3H), 1.15 (s, 3H); Anal. calcd for C$_{28}$H$_{30}$N$_2$O$_2$.0.5H$_2$O: C, 77.21; H, 7.17; N, 6.43. Found: C, 77.65; H 7.13; N, 5.97.

EXAMPLE 115

3-(2,5-Dihydro-10-methoxy-2,2,4-trimethyl-1H-[1]benzopyrano[3,4-f]quinolin-5-yl)-5-methyl-N-(2-propenyl)benzamide Example 11 and allylamine were processed as in Example 17 to provide the desired compound.

MS (DCI/NH$_3$) m/z 453 (M+H)$^+$; $^1$H NMR (300 MHz, DMSO-d$_6$) δ 7.98 (d, 1H), 6.92 (t, 1H), 6.67 (d, 1H), 6.56 (d, H), 6.45 (d, 1H), 6.24 (br s, 1H), 6.14 (m, 3H), 5.76 (m, 1H), 5.63 (t, 1H), 5.37 (br s, 1H), 5.10 (qd, 1H), 5.02 (qd, 1H), 3.79 (s, 3H), 3.50 (m, 2H), 2.02 (s, 3H), 1.89 (s, 3H), 1.22 (s, 3H), 1.15 (s, 3H); Anal. calcd for C$_{23}$H$_{25}$NO$_2$: C, 79.51; H, 7.25; N, 4.03. Found: C, 79.35; H, 7.30; N, 3.89.

EXAMPLE 116

3-(2,5-Dihydro-10-methoxy-2,2,4-trimethyl-1H-[1]benzopyrano[3,4-f]quinolin-5-yl)-N-(2-methoxyethyl)-5-methylbenamine Example 11 and 2-methoxyethylamine were processed as in Example 17 to provide the desired compound.

$^1$H NMR (300 MHz, DMSO-d$_6$) δ 7.98 (d, 1H), 6.95 (t, 1H), 6.65 (d, 1H), 6.60 (s, 1H), 6.54 (d, 1H), 6.44 (d, 1H), 6.22 (s, 1H), 6.17 (s, 2H), 6.13 (s, 1H), 5.41 (t, 10H), 5.38 (s, 1H), 3.79 (s, 3H), 3.26 (q, 2H), 3.20 (s, 3H,), 2.98 (q, 2H), 2.03 (s, 3H), 1.90 (s, 3H), 1.22 (s, 3H), 1.15 (s, 3H).

EXAMPLE 117

3-(2,5-Dihydro-10-methoxy-2,2,4-trimethyl-1H-[1]benzopyrano[3,4-f]quinolin-5-yl)-N-(2-propenyl)benzenamine Example 52 and allylamine were processed as in Example 17 to provide the desired compound.

MS (DCI/NH$_3$) m/z 439 (M+H)$^+$; $^1$H NMR (300 MHz, DMSO-d$_6$) δ 7.99 (d, 1H), 6.91 (t, 1H), 6.86 (t, 1H), 6.67 (d, 1H), 6.63 (s, 1H), 6.55 (d, 1H), 6.44 (m, 2H), 6.33 (m, 2H), 6.14 (d, 1H), 5.78 (m, 2H, 5.37 (s, 1H), 5.12 (qd, 1H), 5.03 (qd, 1H), 3.79 (s, 3H), 3.51 (m, 2H), 1.88 (s, 3H), 1.22 (s, 3H), 1.14 (s, 3H); Anal. calcd for C$_{29}$H$_{30}$N$_2$O$_2$: C, 79.42; H, 6.89; N, 6.39. Found: C, 79.03; H, 7.05; N, 6.17.

EXAMPLE 118

N'-[3-(2,5-Dihydro-10-methoxy-2,2,4-trimethyl-1H-1benzopyrano[3,4-f]quinolin-5-yl)-5-methylphenyl]-N,N-dimethylurea A solution of Example 115 (0.112 g, 0.247 mmol) in 10% ethanol/water (10 mL) was treated with 1,4-diazabicyclo

[2.2.2]octane (0.056 g, 0.495 mmol) and chlorotris(triphenylphosphine)rhodium(I) (0.115 g, 0.124 mmol), refluxed for 15 hours, poured into 5% HCl, stirred 20 minutes, neutralized with NaHCO$_3$, and extracted with ethyl acetate. The extract was washed with brine, dried (Na$_2$SO$_4$), filtered, and concentrated. The residue was purified by flash chromatography on silica gel with 20–33% ethyl acetate/hexanes to provide the desired aniline.

The aniline (0.030 g, 0.073 mmol) was dissolved in 2:1/toluene:THF (7 mL), treated sequentially with diisopropylethylamine (38 µL, 0.218 mmol) and N,N-dimethylcarbamoyl chloride (20 µL, 0.218 mmol), refluxed for 18 hours, cooled, treated with water, and extracted with ethyl acetate. The extract was washed with brine, dried (MgSO$_4$), filtered, and concentrated. The residue was purified by flash chromatography on silica gel with 25–50% ethyl acetate/hexanes to provide the desired compound.

$^1$H NMR (300 MHz, DMSO-d$_6$) δ 8.15 (s, 1H), 7.98 (d, 1H), 7.10 (br s, 2H), 6.91 (t, 1H), 6.69 (d, 1H), 6.63 (s, 1H), 6.56 (d, 1H), 6.54 (s, 1H), 6.46 (d, 1H), 6.16 (br s, 1H), 5.38 (s, 1H), 2.85 (s, 6H), 2.09 (s, 3H), 1.86 (s, 3H), 1.24 (s, 3H), 1.14 (s, 3H); HRMS m/z calcd for C$_{30}$H$_{39}$N$_3$O$_3$: 484.2600 (M+H)$^+$. Found: 484.2601.

EXAMPLE 119

N-[3-(2,5-Dihydro-10-methoxy-2,2,4-trimethyl-1H-[1]benzopyrano[3,4-f]quinolin-5-yl)phenyl]benzenemethanamine Example 11 and benzylamine were processed as in Example 17 to provide the desired compound.

$^1$H NMR (300 MHz, DMSO-d$_6$) δ 7.97 (d, 1H), 7.23 (m, 5H), 6.80 (m, 2H), 6.65 (d, 1H), 6.59 (s, 1H), 6.53 (d, 2H), 6.49 (s, 1H), 6.20 (m, 3H), 6.16 (t, 1H), 6.12 (t, 1H), 6.12 (s, 1H), 5.35 (s, 1H), 4.10 (b, 2H), 3.78 (s, 3H), 1.83 (s, 3H), 1.22 (s, 3H), 1.14 (s, 3H); HRMS m/z calcd for C$_{33}$H$_{32}$O$_2$N$_2$: 488.2464 (M+H)$^+$. Found: 488.2468.

EXAMPLE 120

5-[(3,5-dichlorphenyl)methylen]-2,5-dihydro-10-methoxy-2,2,4-trimethyl-1H-[1]benzopyrano[3,4-f]puinoline Example 1F and 3,5-dichlorobenzylmagnesium bromide were processed as in Example 1B to provide the desired compound.

MS (DCI/NH$_3$) m/z 464 (M+H)$^+$; $^1$H NMR (300 MHz, DMSO-d$_6$) isomer 1: δ 8.17 (d, 1H), 7.32 (s, 1H), 6.96 (s, 2H), 6.81–6.74 (m, 4H), 6.45 (s, 2H), 5.11 (s, 1H), 3.93 (s, 3H), 1.88 (s, 3H), 1.22 (s, 3H), 0.89 (s, 3H); isomer 2: δ 8.29 (d, 1H), 7.78 (s, 2H), 7.45 (s, 1H), 7.23 (t, 1H), 7.18 (d, 1H), 7.16 (d, 1H), 6.84 (d, 1H), 6.66 (s, 1H), 5.59 (s, 1H), 5.47 (s, 1H), 3.93 (s, 3H), 1.96 (s, 3H), 1.27 (s, 6H); HRMS calcd m/z for C$_{27}$H$_{23}$Cl$_2$NO$_2$: 463.1106 (M+H)$^+$. Found: 463.1112.

EXAMPLE 121

5-[(4-chlorophenyl)methylene]-2,5-dihydro-10-methoxy-2,2,4-trimethyl-1H-[1]benzopyrano[3,4-f]quinoline Example 1F and 4-chlorobenzylmagnesium bromide were processed as in Example 1B to provide the desired compound.

MS (DCI/NH$_3$) m/z 430 (M+H)$^+$; $^1$H NMR (300 MHz, DMSO-d$_6$) isomer 1: δ 8.26 (d, 1H), 7.75 (d, Hz, 2H), 7.42 (d, 2H), 7.18 (t, 2H), 6.89 (d, 1H), 6.74 (d, 1H), 6.61 (s, 1H), 5.54 (s, 1H), 5.46 (s, 1H), 3.91 (s, 3H), 1.97 (s, 3H), 1.26 (s, 6H); isomer 2: δ 8.13 (s, 1H), 7.18 (t, 1H), 7.04 (d, 2H), 6.82–6.71 (m, 5H), 6.46 (s, 1H), 6.41 (s, 1H), 5.04 (s, 1H), 3.91 (s, 3H), 1.84 (s, 3H), 1.22 (s, 3H), 0.90 (s, 3H); HRMS calcd m/z for C$_{27}$H$_{24}$ClNO$_2$: 429.1496 (M+H)$^+$. Found: 429.1500.

EXAMPLE 122

2,5-Dihydro-10-methoxy-2,2,4-trimethyl-5-[[3-(trifluoromethyl)phenyl]methylene-]1H-[1]-benzopyrano[3,4-f]quinoline Example 1F and 3-trifluoromethylmagnesium bromide were processed as in Example 1B to provide the desired compound.

MS (DCI/NH$_3$) m/z 464 (M+H)$^+$; $^1$H NMR (300 MHz, DMSO-d$_6$) isomer 1: δ 8.28 (d, 1H), 8.13 (s, H), 7.98 (d, 6H), 7.65–7.56 (m, 1H), 7.33–7.39 (m, 1H), 7.21 (t, 1H), 6.83–6.78 (s , 2H), 6.75 (t, 1H, 6.64 (s, 1H), 5.68 (s, 1H), 5.48 (s, 1H), 3.92 (s, 3H), 1.99 (s, 3H), 1.27 (s, 6H); isomer 2: δ 8.17 (d, 1H), 7.65–7.56 (m, 6H), 7.45 (d, 1H), 7.39–7.33 (m, 7H), 7.27 (d, 1H), 7.17 (t, 1H), 6.83–6.78 (m, 2H), 6.75 (t, 1H), 6.56 (s, 1H), 6.40 (s, 1H), 5.01 (s, 1H), 3.92 (s, 3H), 1.88 (s, 3H), 1.19 (s, 3H), 0.78 (s, 3H); HRMS calcd m/z for C$_{28}$H$_{24}$F$_3$NO$_2$: 463.1759 (M+H)$^+$. Found: 463.1762.

EXAMPLE 123

5-[(2,6-Difluorophenyl)methylenel-2,5-dihydro-10-methoxy-2,2,4-trimethyl-1H-[1]benzopyrano[3,4-f]quinoline Example 1F and 2,6-difluorobenzylmagnesium bromide were processed as in Example 1B to provide the desired compound.

MS (DCI/NH$_3$) m/z 432 (M+H)$^+$; $^1$H NMR (300 MHz, DMSO-d$_6$) isomer 1: δ 8.32 (d, 1H), 7.19–7.08 (m, 3H), 6.92 (t, 1H), 6.81–6.76 (m, 2H), 6.64 (s, 1H), 6.54 (d, 1H), 5.49 (s, 1H), 5.46 (s, 1H), 3.92 (s, 3H), 2.11 (s, 3H), 1.25 (s, 6H); isomer 2: δ 8.18 (d, 1H), 7.38 (t, 1H), 7.19–7.08 (m, 3H), 6.81–6.76 (m, 2H), 6.67 (d, 1H), 6.21 (s, 1H), 6.19 (s, 1H), 4.96 (s, 3H), 3.93 (s, 3H), 1.91 (s, 3H), 1.16 (s, 3H), 0.61 (s, 3H); HRMS calcd m/z for C$_{27}$H$_{23}$F$_2$NO$_2$: 431.1697 (M+H)$^+$. Found: 431.1704.

EXAMPLE 124

5-[(2-Chlorophenyl)methylene]-2,5-dihydro-10-methoxy-2,2,4-trimethyl-1H-[1]benzopyrano 3,4-f]quinoline Example 1F and 2-chlorobenzylmagnesium bromide were processed as in Example 1B to provide the desired compound.

MS (DCI/NH$_3$) m/z 430 (M+H)$^+$; $^1$H NMR (300 MHz, DMSO-d$_6$) isomer 1: δ 8.11 (d, 1H), 7.47 (d, 1H), 7.40 (d, 1H), 7.23–7.10 (m, 3H), 6.84–6.74 (m, 2H), 6.71 (s, 1H), 6.66 (s, 1H), 6.01 (s, 1H), 5.47 (s, 1H), 3.93 (s, 3H), 2.02 (s, 3H), 1.25 (s, 6H); isomer 2: δ 8.27 (d, 1H), 8.18 (d, 1H), 7.41 (t, 1H), 7.26 (d, 1H), 7.01 (t, 1H), 6.84–6.74 (m, 4H), 6.47 (s, 1H), 6.37 (s, 1H), 5.00 (s, 1H), 3.93 (s, 3H), 1.88 (s, 3H), 1.18 (s, 3H), 0.73 (s, 3H); HRMS calcd m/z for C$_{27}$H$_{24}$ClNO$_2$: 429.1496 (M+H)$^+$. Found: 429.1497.

EXAMPLE 125

5-[(2,6-Dichlorophenyl)methylenel]-2,5-dihydro-10-methoxy-2,2,4-trimethyl-1H-[1]benzopyrano3,4-f]quinoline Example 1F and 2,6-dichlorobenzylmagnesium bromide were processed as in Example 1B to provide the desired compound.

MS (DCI/NH$_3$) m/z 464 (M+H)$^+$; $^1$H NMR (300 MHz, DMSO-d$_6$) isomer 1: δ 8.27 (d, 1H), 7.16 (m, 2H), 7.07 (t, 1H), 6.81–6.76 (m, 3H), 6.68 (d, 1H), 6.30 (s, 1H), 5.47 (s, 1H), 4.90 (s, 1H), 3.93 (s, 3H), 1.96 (s, 3H), 1.15 (s, 3H), 0.59 (s, 3H); isomer 2: δ 8.37 (d, 1H), 7.45 (d, 2H), 7.31 (t, 1H), 7.16 (m, 2H), 6.77 (m, 1H), 6.65 (s, 1H), 6.44 (d, 1H), 6.34 (s, 1H), 5.60 (s, 1H), 3.91 (s, 3H), 2.20 (s, 3H), 1.25 (s, 6H); HRMS calcd m/z for C$_{27}$H$_{23}$Cl$_2$NO$_2$: 463.1106 (M+H)$^+$. Found: 463.1114.

EXAMPLE 126

5-[(2-Fluorophenyl)methylene-2,5-dihydro-10-methoxy-2,2,4-trimethyl-1H-[1]benzopyrano[3,4-f]quinoline Example 1F and 2-fluorobenzylmagnesium bromide were processed as in Example 1B to provide the desired compound.

MS (DCI/NH$_3$) m/z 414 (M+H)$^+$; $^1$H NMR (300 MHz, DMSO-d$_6$) isomer 1: δ 8.30 (d, 1H), 8.23 (m, 1H), 7.28 (m, 1H), 7.19 (t, 1H), 7.18 (d, 1H), 6.93–6.75 (m, 3H), 6.76 (d, 1H), 6.65 (s, 1H), 5.77 (s 1H), 5.49 (s, 1H), 3.93 (s, 3H), 2.01 (s, 3H), 1.25 (s, 6H); isomer 2: δ 8.17 (d, 1H), 7.28 (m, 2H), 7.18 (d, 1H), 7.14–7.06 (m, 2), 6.79 (m, 2H), 6.72 (d, 1H), 6.41 (s, 1H), 6.38 (s, 1H), 5.00 (s, 1H), 3.93 (s, 3H), 1.87 (s, 3H), 1.18 (s, 3H), 0.76 (s, 3H); HRMS calcd m/z for C$_{27}$H$_{24}$FNO$_2$: 413.1791 (M+H)$^+$. Found: 413.1788.

EXAMPLE 127

2,5-Dihydro-10-methoxy-2,2,4-trimethyl-5-[(4,5-dihydro-4,4-dimethyl-2-oxazolyl)methylene]-1H-[1]benzopyrano[3,4-f]quinoline Example 1F and 4,4-dimethyl-2-oxazoline-2-methyllithium were processed as in Example 1B to provide the desired compound.

MS (DCI/NH$_3$) m/z 417 (M+H)$^+$; $^1$H NMR (300 MHz, DMSO-d$_6$) isomer 1: δ 8.34 (d, 1H), 7.19 (t, 1H), 6.83–6.78 (m, 2H), 6.74–6.70 (m, 2H), 5.48 (s, 1H), 5.08 (s, 1H), 3.98 (s, 2H), 3.92 (s, 3H), 1.99 (s, 3H), 1.22 (s, 3H), 1.20 (s, 9H); isomer 2: δ 8.06 (d, 1H), 7.14 (m, 1H), 6.80 (m, 1H), 6.76 (m, 1H), 6.72 (m, 1H), 6.42 (s, 1H), 5.96 (s, 1H), 5.35 (s, 1H), 3.90 (s, 3H), 3.72 (m, 2H), 1.93 (s, 3H), 1.32 (s, 3H), 1.20 (s, 6H), 1.11 (s, 3H); HRMS calcd m/z for C$_{26}$H$_{28}$N$_2$O$_3$: 417.2178 (M+H)$^+$. Found: 417.2176.

EXAMPLE 128

2,5-Dihydro-10-methoxy-2,2,4-trimethyl-5-(2-pyridinylmethylene)-1H-[1]benzopyrano[3,4-f]quinoline Example 1F and 2-methylpyridyl]ithium were processed as in Example 1B to provide the desired compound.

MS (DCI/NH$_3$) m/z 397 (M+H)$^+$; $^1$H NMR (300 MHz, DMSO-d$_6$) isomer 1: δ 8.50 (m, 1H), 8.31 (d, 1H), 8.25 (d, 1H), 7.83 (t, 1H), 7.20 (d, 1H), 7.19 (m, 1H), 6.95 (d, 1H), 6.83 (d, 1H,), 6.78 (d, 1H), 6.64 (s, 1H), 5.77 (s, 1H), 5.49 (s, 1H), 3.92 (s, 3H), 2.00 (s, 3H), 1.27 (s, 6H). isomer 2: δ 8.43 (m, 1H), 8.15 (d, 1H), 7.48 (t, 1H), 7.22 (d, 1H), 7.15 (d, 1H), 7.08 (m, 1H), 6.88 (d, 1H), 6.78 (d, 1H), 6.77 (t, 1H), 6.46 (s, 1H), 6.38 (s, 1H), 4.99 (s, 1H), 3.92 (s, 3H), 1.87 (s, 3H), 1.21 (s, 3H), 0.89 (s, 3H); HRMS calcd m/z for C$_{26}$H$_{24}$N$_2$O$_2$: 397.1916 (M+H)$^+$. Found: 397.1923.

EXAMPLE 129

2,5-Dihydro-10-methoxy-2,2,4-trimethyl-5-(2-thienyl)-1H-[1]benzopyrano[3,4-f]quinoline Example 1F and 2-thienyl]ithium were processed as in Example 1B to provide the desired compound.

MS (DCI/NH$_3$) m/z 391 (M+H)$^+$; $^1$H NMR (300 MHz, DMSO-d$_6$) δ 8.01 (d, 1H), 7.38 (d, 1H), 6.95 (dd, 1H), 6.93 (s, 1H), 6.81 (dd, 1H), 6.68 (d, 1H), 6.65 (d, 1H), 6.64 (d, 1H), 6.46 (d, 1H), 6.21 (d, 1H, 5.39 (s, 1H), 3.81 (s, 3H), 1.95 (d, 3H), 1.21 (s, 3H), 1.15 (s, 3H).

EXAMPLE 130

2,5-Dihydro-9,10-dimethoxy-2,2,4-trimethyl-5-(2-propenyl)-1H-[1]benzopyrano[3,4-f]quinoline 1,2,4-trimethoxybenzene was processed as described in Schemes 1 and 2 to provide the desired compound.

MS (DCI/NH$_3$) m/e 378 (M+H)$^+$; $^1$H NMR (300 MHz, DMSO-d$_6$) δ 7.93 (d, 1H), 6.82 (d, 1H), 6.61 (dd, 2H), 6.22 (d, 1H), 5.81 (ddt, 1H), 5.70 (dd, 1H), 5.44 (s, 1H), 5.01 (m, 2H), 3.76 (s, 3H), 3.67 (s, 3H), 2.35 (m, 2H), 2.16 (s, 3H), 1.17 (s, 3H), 1.16 (s, 3H).

EXAMPLE 131

5-(2-Cyclohexen-1-yl)-2,5-dihydro-9,10-dimethoxy-2,2,4-trimethyl-1H-[1]benzopyrano[3,4-f]quinoline 1,2,4-trimethoxybenzene was processed as described in Example 130 but substituting 3-trimethylsilylcyclohexene for allyltrimethylsilane to provide the desired compound.

MS (DCI/NH$_3$) m/e 418 (M+H)$^+$; $^1$H NMR (300 MHz, DMSO d$_6$) δ 8.03 (d, 1H), 8.01 (d, 1H), 6.83 (d, 1H), 6.82 (d, 1H), 6.60–6.69 (m, 4H), 6.31 (d, 1H), 6.27 (d, 1H), 5.6–5.8 (m, 4H), 5.35–5.52 (m, 4H), 5.11 (m, 1H), 5.09 (m, 1H), 3.77 (s, 6H), 3.69 (s, 3H), 3.68 (s, 3H), 2.25 (m, 4H), 2.13 (s, 3H), 2.10 (s, 3H), 1.95 (m, 4H), 1.6 (m, 4H), 1.31 (s, 3H), 1.29 (s, 3H), 1.07 (s, 3H), 1.04 (s, 3H).

EXAMPLE 132

2,5-Dihydro-10-methoxy-5-(3-methyl-3-butenyl)-2,2,4-trimethyl-1H-[1]benzopyrano[3,4-f]quinoline Example 2B and 3-methyl-1-trimethylsilyl-2-butene (prepared according to Fleming, et. al. *Synthesis* 1979, 446.) were processed as in example 2 to provide the desired compound.

MS (DCI/NH$_3$) m/e (M+H)$^+$376; $^1$H NMR (300 MHz, DMSO-d$_6$) δ 8.10 (d, J=8 Hz, 1H), 7.01 (t, J=8 Hz, 1H), 6.65 (d, J=8 Hz, 1H), 6.62 (d, J=8 Hz, 1H), 6.49 (d, J=8 Hz, 1H), 6.25 (br s, 1H), 5.57 (s, 1H), 5.55 (dd, J=17, 11 Hz, 1H), 5.41 (s, 1H), 4.64–4.56 (m, 2H), 3.83 (s, 3H), 2.14 (s, 3H), 1.31 (s, 3H), 1.01 (s, 3H), 0.86 (s, 3H), 0.83 (s, 3H); $^{13}$C NMR (100 MHz, DMSO-d$_6$) δ 156.31, 153.48, 145.02, 143.74, 133.05, 128.73, 127.10, 126.82, 126.27, 119.20, 118.15, 114.05, 113.11, 110.85, 109.36, 105.24, 78.33, 55.69, 49.12, 44.84, 29.53, 26.14, 23.53, 23.43, 23.35; Anal. calcd for C$_{25}$H$_{29}$NO$_2$.1/4H$_2$O: C, 79.02; H, 7.82; N, 3.69. Found: C, 79.09; H, 7.94; N, 3.59.

EXAMPLE 133

2,5-Dihydro-10-methoxy-5-(5,5-dimethyl-3-cyclohexenyl)-2,2,4-trimethyl-1H-[1]benzopyrano[3,4-f]quinoline Example 2B and 5,5-dimethyl-1-trimethylsilyl-2-cyclohexene (prepared from 5,5-dimethyl-2-cyclohexene-1-ol by the method of Tsuji, et. al. *J. Org. Chem.* 1996, 61, 5779) were processed as in example 2 to provide the desired compound as a 1.8:1 inseparable mixture of diastereomers. MAJOR:

MS (DCI/NH₃) m/e (M+H)⁺416; ¹H NMR (300 MHz, DMSO-d₆) δ 8.08 (d, J=8 Hz, 1H), 7.07 (t, J=8 Hz, 1H), 6.69 (d, J=8Hz, 1H), 6.64 (d, J=8 Hz, 1H), 6.25 (br s, 1H), 5.85 (m, 1H), 5.62–5.71 (m, 1H), 5.46 (s, 1H), 5.45 (d, J=10 Hz, 1H), 3.86 (s, 3H), 2.41–2.33 (m, 1H), 2.11 (s, 3H), 1.84–1.72 (m, 1H), 1.68–1.48 (m, 2H), 1.30 (s, 3H), 1.35–1.21 (m, 1H), 1.01 (s, 3H), 0.76 (s, 3H), 0.53 (s, 3H); Anal. calcd for C₂₈H₃₃NO₂.1/2H₂O: C, 79.21; H, 8.07; N, 3.30. Found: C, 79.31; H, 7.75; N, 3.11.

MINOR:

¹H NMR (300 MHz, DMSO-d₆) δ 8.02 (d, J=8 Hz, 1H), 7.09 (t, J=8 Hz, 1H), 6.70 (d, J=8Hz, 1H), 6.64 (d, J=8 Hz, 1H), 6.57 (d, J=8 Hz, 1H), 6.20 (br s, 1H), 5.60–5.52 (m, 1H), 5.50 (d, J=10 Hz, 1H), 5.14 (m, 1H), 5.41 (m, 1H), 3.86 (s, 3H), 2.41–2.33 (m, 1H), 2.09 (s, 3H), 1.91–1.78 (m, 1H), 1.68–1.48 (m, 2H), 1.35–1.21 (m, 1H), 1.28 (s, 3H), 1.07 (s, 3H), 0.92 (s, 3H), 0.51 (s, 3H).

EXAMPLE 134 rel (5R,2'R) 2,5-Dihydro-10-methoxy-5-(2-oxo-3-tetrahydropyranyl)-2,2,4-trimethyl-1H[1]benzopyrano[3,4-f]quinoline Example 2B and 3,4-dihydro-6-(trimethylsiloxy)-2H-pyran were processed as in Example 2 to give 41% Example 134 and 48% Example 135.

MS (DCI/NH₃) m/e 406 (M+H)⁺; ¹H NMR (300 MHz, DMSO-d₆) δ 8.12 (d, J=8 Hz, 1H), 7.05 (t, J=8 Hz, 1H), 6.67 (d, J=8Hz, 1H), 6.63 (d, J=9 Hz, 1H), 6.49 (d, J=8 Hz, 1H), 6.42 (d, J=5 Hz, 1H), 6.21 (d, J=2 Hz, 1H), 5.44 (br s, 1H), 4.35–4.00 (m, 2H), 3.86 (s, 3H), 2.77–2.67 (m, 1H), 2.17 (s, 3H), 2.01–1.50 (m, 4H), 1.27 (s, 3H), 1.01 (s, 3H); ¹³C NMR (100 MHz, DMSO-d₆) δ 169.93, 156.40, 152.16, 145.53, 133.80, 128.46, 127.75, 127.20, 126.66, 117.38, 116.74, 113.45, 112.07, 109.23, 109.19, 105.44, 98.19, 72.79, 69.09, 55.62, 49.44, 46.37, 29.45, 27.13, 23.20, 21.46, 20.22, 19.61; Anal. calcd for C₂₅H₂₇NO₄.1/2H₂O: C, 72.44; H, 6.81; N, 3.38. Found: C, 72.66; H, 6.92; N, 2.91.

EXAMPLE 135 anti (5R, 2'S) 2,5-Dihydro-10-methoxy-5-(2-oxo-3-tetrahydropyranyl)-2,2,4-trimethyl-1H-[1]benzopyrano[3,4-f]quinoline Example 2B and 3,4-dihydro-6-(trimethylsiloxy)-2H-pyran were processed as in Example 2 to give 41% Example 135 and 48% Example 135 A. MS (DCI/NH₃) m/e 406 (M+H)⁺; ¹H NMR (300 MHz, DMSO-d₆) δ 8.12 (d, J=8 Hz, 1H), 7.05 (t, J=8 Hz, 1H), 6.67 (d, J=8 Hz, 1H), 6.63 (d, J=9 Hz, 1H), 6.49 (d, J=8 Hz, 1H), 6.42 (d, J=5 Hz, 1H), 6.21 (d, J=2 Hz, 1H), 5.44 (br s, 1H), 4.35–4.00 (m, 2H), 3.86 (s, 3H), 2.77–2.67 (m, 1H), 2.17 (s, 3H), 2.01–1.50 (m, 4H), 1.27 (s, 3H), 1.01 (s, 3H); ¹³C NMR (100 MHz, DMSO-d₆) δ 169.93, 156.40, 152.16, 145.53, 133.80, 128.46, 127.75, 127.20, 126.66, 117.38, 116.74, 113.45, 112.07, 109.23, 109.19, 105.44, 98.19, 72.79, 69.09, 55.62, 49.44, 46.37, 29.45, 27.13, 23.20, 21.46, 20.22, 19.61; Anal. calcd for C₂₅H₂₇NO₄.1/2H₂O: C, 72.44; H, 6.81; N, 3.38. Found: C, 72.66; H, 6.92; N, 2.91.

EXAMPLE 135A anti (5R,2'S) 2,5-Dihydro-10-methoxy-5-(2-oxo-3-tetrahydropyranyl)-2,2,4-trimethyl-1H-[1]benzopyrano[3,4-f]quinoline MS (DCI/NH₃) m/e 406 (M+H)⁺; ¹H NMR (300 MHz, DMSO-d₆) δ 8.06 (d, J=9 Hz, 1H), 7.06 (t, J=8 Hz, 1H), 6.70 (d, J=8 Hz, 1H), 6.65 (d, J=9 Hz, 1H), 6.50 (d, J=8 Hz, 1H), 6.27 (d, J=8 Hz, 1H), 6.21 (d, J=2Hz, 1H), 5.46 (s, 1H), 4.01–4.10 (m, 2H), 3.87 (s, 3H), 2.81 (m, 1H), 2.14 (m, 3H), 1.68–1.61 (m, 2H), 1.27 (s, 3H), 1.16–1.36 (m, 2H), 1.03 (s, 3H); ¹³C NMR (100 MHz, DMSO-d₆) δ 172.14, 156.33, 150.95, 145.21, 134.18, 127.71, 127.38, 127.20, 126.73, 118.09, 116.66, 113.53, 112.78, 110.56, 105.45, 71.40, 66.76, 55.52, 49.49, 29.46, 27.38, 23.69, 21.05, 20.79; Anal. calcd for C₂₅H₂₇NO₄.1/4H₂O: C, 73.24; H, 6.76; N, 3.42. Found: C, 72.89; H; 7.07; N, 3.05.

EXAMPLE 136

2,5-Dihydro-10-methoxy-5-(3-cyclopentenyl)-2,2,4-trimethyl-1H-[1]benzopyrano[3,4-f]quinoline Example 2B and cyclopenten-2-yltrimethylsilane were processed as in Example 2 to provide the desired compound as an inseparable mixture of two diastereomers (1.5:1).

MS (DCI/NH₃) m/z 374 (M+H)⁺; ¹H NMR (300 MHz, DMSO-d₆) Major diastereomer: δ 8.05 (d, 1H), 7.09 (t, 1H), 6.72 (d, 1H), 6.66 (d, 1H), 6.58 (d, 1 H), 6.19 (s, 1H), 5.77 (ddd, 1H), 5.50 (d, 1H), 5.43 (s, 1H), 5.19 (ddd, 1H), 3.87 (s, 3H), 2.90 (m, 1H), 2.43–2.15 (m, 2H), 2.09 (s, 3H), 1.97–1.70 (m, 2H), 1.31 (s, 3H), 1.09 (s, 3H); Minor diastereomer: δ 8.07 (d, 1H), 7.08 (t, 1H), 6.70 (d, 1H), 6.66 (d, 1H), 6.61 (d, 1H), 6.22 (s, 1H), 5.82–5.70 (m, 2H), 5.48 (d, 1H), 5.41 (d, 1H), 3.88 (s, 3H), 2,92 (m, 1H), 2.30 (m, 1H), 2.20 (m, 1H), 2.15 (s, 3H), 1.50 (m, 2H), 1.33 (s, 3H), 1.05 (s, 3H); HRMS calcd m/z for C₂₅H₂₇NO₂: 373.2042. Found: 373.2049.

EXAMPLE 137

2,5-Dihydro-10-methoxy-5-(3-cyclohexenyl)-2,2,4-trimethyl-1H-[1]benzopyrano[3,4-f]quinoline Example 2B and cyclohexen-2-yltrimethylsilane were processed as in Example 2 to provide the desired compound as an inseparable mixture of two diastereomers (1.1:1).

MS (DCI/NH₃) m/z 388 (M+H)⁺; ¹H NMR (300 MHz, DMSO-d₆) Major diastereomer: δ 8.05 (d, 1H), 7.06 (t, 1H), 6.67 (d, 1H), 6.64 (d, 1H), 6.59 (d, 1H), 6.19 (s, 1H), 5.82 (m, 1H), 5.72 (m, 1H), 5.41 (s, 1H), 5.40 (d, 1H), 3.87 (s, 3H), 2.29 (m, 1H), 2.13 (s, 3H), 1.95–1.80 (m, 2H), 1.72–1.50 (m, 2H), 1.38–1.10 (m, 2H), 1.30 (s, 3H), 1.02 (s, 3H); Minor diastereomer: δ 8.03 (d, 1H), 7.07 (t, 1H), 6.68 (d, 1H), 6.63 (d, 1H), 6.57 (d, 1H), 6.15 (s, 1H), 5.62 (m, 1H), 5.54 (m, 1H), 5.46 (s, 1H), 5.09 (m, 1H), 3.85 (s, 3H), 2.29 (m, 1H), 2.10 (s, 3H), 1.95–1.80 (m, 2H), 1.72–1.50 (m, 2H), 1.38–1.10 (m, 2H), 1.28 (s, 3H), 1.05 (s, 3H); HRMS calcd m/z for C₂₆H₂₉NO₂: 387.2198. Found: 387.2206.

EXAMPLE 138

2,5-Dihydro-10-methoxy-5-(3-butenyl)-2,2,4-trimethyl-1H-[1]benzopyrano[3,4-f]quinoline Example 2B and 2-butenyltrimethylsilane were processed as in Example 2 to provide the desired compound as an inseparable mixture of two diastereomers (1.3:1).

MS (DCI/NH₃) m/z 362 (M+H)⁺; ¹H NMR (300 MHz, DMSO-d₆) Major diastereomer: δ 8.04 (d, 1H), 7.05 (t, 1H), 6.69 (d, 1H), 6.64 (d, 1H), 6.47 (d, 1H), 6.16 (s, 1H), 5.88 (ddd, 1H), 5.54 (d, 1H), 5.46 (s, 1H), 4.93 (ddd, 1H), 4.74 (ddd, 1H), 3.86 (s, 3H), 2.37 (bm, 1H), 2.17 (s, 3H), 1.30 (s, 3H), 1.02 (s, 3H), 0.71(d, 3H); Minor diastereomer: δ 8.03 (d, 1H), 7.08 (t, 1H), 6.67 (d, 1H), 6.64 (d, 1H), 6.58 (d, 1H), 6.10 (s, 1H), 5.51 (ddd, 1H), 5.47 (d, 1H), 5.40 (s, 1H, 4.78

(ddd, 1H), 4.74 (ddd, 1H), 3.86 (s, 3H), 2.38 (bm, 1H), 2.11 (s, 3H), 1.28 (s, 3H), 1.05 (s, 3H), 1.01(d, 3H); Anal. calcd for $C_{24}H_{27}NO_2$: C, 79.74; H, 7.53; N, 3.87. Found: C, 79.41; H, 7.63; N, 3.43.

EXAMPLE 139

2,5-Dihydro-10-methoxy-5-(1-ethenyl-1-cyclohexyl)-2,2,4-trimethyl-1H-[1]benzopyrano[3,4-f]quinoline Example 2B and 2-cyclohexylideneethyl trimethylsilane were processed as in Example 2 to provide the desired compound.

MS (DCI/NH$_3$) m/z 416 (M+H)$^+$; $^1$H NMR (300 MHz, DMSO-d$_6$) δ 8.10 (d, 1H), 7.00 (t, 1H), 6.63 (d, 1H), 6.60 (dd, 1H), 6.47 (dd, 1H), 6.20 (dd, 1H), 5.45 (s, 1H), 5.40 (s, 1H), 5.14 (dd, 1H), 4.81 (dd, 1H), 4.53 (dd, 1H), 3.85 (s, 3H), 2.15 (s, 3H), 1.78 (m, 1H), 1.45–0.80 (m, 9H), 1.32 (s, 3H), 1.03 (s 3H); Anal. calcd for $C_{28}H_{33}NO_2$: C, 80.93; H, 8.00; N, 3.37. Found: C, 80.57; H, 8.02; N, 3.22.

EXAMPLE 140

2,5-Dihydro-10-methoxy-5-(4,4-dimethyl-3-cyclohexenyl)-2,2,4-trimethyl-1H-[1]benzopyrano[3,4-f]quinoline Example 2B and (4,4-dimethylcyclohexen-2-yl)trimethylsilane were processed as in Example 2 to provide the desired compound as an inseparable mixture of diastereomers (2:1).

MS (DCI/NH$_3$) m/z 416 (M+H)$^+$; $^1$H NMR (300 MHz, DMSO-d$_6$) Major diastereomer δ 8.07 (d, 1H), 6.99 (t, 1H), 6.63 (d, 1H), 6.62 (d, 1H), 6.48 (d, 1H), 6.23 (s, 1H), 5.72 (d, 1H), 5.48 (m, 1H), 5.40 (m, 2H), 3.84 (s, 3H), 2.16 (s, 3H), 2.05 (m, 1H), 1.75 (bm, 2H), 1.30 (s, 3H), 1.12 (m, 2H), 1.02 (s, 6H), 0.51 (s, 3H), Minor diastereomer δ 8.04 (d, 1H), 7.06 (t, 1H), 6.68 (d, 1H), 6.62 (d, 1H), 6.57 (d, 1H), 6.19 (s, 1H), 5.68 (dd, 1H), 5.50–5.38 (m, 3H), 3.86 (s, 3H), 2.14 (s, 3H), 2.08 (m, 1H), 1.71 (m, 1H), 1.42 (m, 1H), 1.30 (s, 3H), 1.07 (m, 2H), 1.02 (s, 3H), 0.91 (s, 3H), 0.84 (s, 3H); HRMS calcd m/z for $C_{28}H_{33}NO_2$: 415.2511. Found: 415.2527.

EXAMPLE 141

2,5-Dihydro-10-methoxy-5-(1-methylene-2-cyclohexyl)-2,2,4-trimethyl-1H-[1]benzopyrano[3,4-f]quinoline Example 2B and 1-(trimethylsilylmethyl)cyclohexene were processed as in Example 2 to provide the desired compound as an inseparble mixture of diastereomers (4:1).

MS (DCI/NH$_3$) m/z 402 (M+H)$^+$; $^1$H NMR (300 MHz, DMSO-d$_6$) Major diastereomer δ 8.07 (d, 1H), 7.03 (t, 1H), 6.65 (d, 1H), 6.63 (d, 1H), 6.40 (d, 1H), 6.22 (s, 1H), 5.89 (d, 1H), 4.75 (d, 1H), 4.56 (d, 1H), 3.87 (s, 3H), 2.38 (m, 1H), 2.23 (m, 1H), 2.21 (s, 3H), 1.97 (bm, 2H), 1.55–1.05 (m, 6H), 1.34 (s, 3H), 1.01 (s, 3H); Minor diastereomer δ 8.09 (d, 1H), 7.05 (t, 1H), 6.68 (d, 1H), 6.57 (d, 1H), 6.56 (d, 1H), 6.11 (s, 1H), 5.86 (d, 1H), 5.40 (s, 1H), 4.33 (d, 1H), 3.91 (d, 1H), 3.87 (s, 3H), 2.48 (m, 1H), 2.22 (m, 1H), 2.20 (s, 3H), 1.94 (bm, 1H), 1.75–1.05 (m, 6H), 1.29 (s, 3H), 0.97 (s, 3H; HRMS calcd m/z for $C_{27}H_{31}NO_2$: 401.2355. Found: 401.2351.

EXAMPLE 142

2,5-Dihydro-10-methoxy-5-(1-oxo-2-cyclohexyl)-2,2,4-trimethyl-1H-[1]benzopyrano[3,4-f]quinoline Example 2B and 1-(trimethylsilyloxy)cyclohexene were processed as in Example 2 to provide the desired compound as single diastereomer.

MS (DCI/NH$_3$) m/z 404 (M+H)$^+$; $^1$H NMR (300 MHz, DMSO-d$_6$) δ 8.04 (d, 1H), 7.02 (t, 1H), 6.67 (d, 1H), 6.63 (d, 1H), 6.39 (d, 1H), 6.37 (d, 1H), 6.17 (s, 1H), 5.44 (s, 1H), 3.80 (s, 3H), 2.70 (ddd, 1H), 2.25 (m, 2H), 2.15 (s, 3H), 1.84 (bm, 1H), 1.62–1.25 (m, 4H), 1.28 (s, 3H), 1.09 (m, 1H), 1.00 (s, 3H). HRMS calcd m/z for $C_{26}H_{29}NO_3$: 403.2147. Found: 403.2142.

EXAMPLE 143

2,5-Dihydro-10-methoxy-5-(3-cyclooctenyl)-2,2,4-trimethyl-1H-[1]benzopyrano[3,4f]quinoline Example 2B and cyclooccten-2-yltrimethylsilane were processed as in Example 2 to provide the desired compound as an inseparable mixture of two diastereomers (7:5).

MS (DCI/NH$_3$) m/z 416 (M+H)$^+$; $^1$H NMR (300 MHz, DMSO-d$_6$) Major diastereomer: δ 8.03 (dd, 1H), 7.07 (t, 1H), 6.62 (d, 1H), 6.57 (d, 1H), 6.39 (d,1H), 6.17 (s, 1H), 5.59 (m, 2H), 5.44 (s, 1H), 5.14 (dd, 1H), 3.88 (s, 3H), 2.18 (s, 3H), 2.04–0.84 (m, 17H; Minor diastereomer: δ 8.00 (d, 1H), 7.00 (t, 1H), 6.70 (d, 1H), 6.66 (d, 1H), 6.58 (d, 1H), 6.12 (s, 1H), 5.59 (m, 2H), 5.48 (s, 1H), 5.38 (dd, 1H), 3.88 (s, 3H), 2.18 (s, 3H), 2.04–0.84 (m, 17H); HRMS calcd m/z for $C_{28}H_{33}NO_2$: 415.2511. Found: 415.2498.

EXAMPLE 144

2,5-Dihydro-10-methoxy-5-(3-cycloheptenyl)-2,2,4-trimethyl-1H-[1]benzopyrano[3,4-f]quinoline Example 2B and cyclohepten-2-yltrimethylsilane were processed as in Example 2 to provide the desired compound as an inseparable mixture of two diastereomers (1:1).

MS (DCI/NH$_3$) m/z 402 (M+H)$^+$; $^1$H NMR (300 MHz, DMSO-d$_6$) diastereomer A: δ 8.04 (d, 1H0, 7.04 (t, 1H), 6.68 (d, 1H), 6.63 (d, 1H), 6.51 (d, 1H), 6.22 (s, 1H), 5.97 (m, 1H), 5.73 (m, 1H), 5.58 (m, 1H), 5.47 (s, 1H), 3.87 (s, 3H), 2.42–0.98 (m, 18H); diastereomer B: δ 8.01 (d, 1H), 7.08 (t, 1H), 6.70 (d, 1H), 6.62 (d, 1H), 6.56 (d, 1H), 6.21 (s, 1H), 5.58 (m, 2H), 5.49 (s, 1H), 5.32 (m, 1H), 3.87 (s, 3H), 2.42–0.98 (m, 18H); HRMS calcd m/z for $C_{27}H_{31}NO_2$: 401.2355. Found: 401.2351.

EXAMPLE 145

2,5-Dihydro-10-methoxy-5-(1-cyclohexenylmethyl)-2,2,4-trimethyl-1H-[1]benzopyrano[3,4-f]quinoline Example 2B and 2-methylenecyclohexyldimethylphenylsilane were processed as in Example 2 to provide the desired compound.

MS (DCI/NH$_3$) m/z 402 (M+H)$^+$; $^1$H NMR (300 MHz, DMSO-d$_6$) δ 7.96 (d, 1H), 7.05 (t, 1H), 6.68 (d, 1H), 6.58 (d, 1H), 6.45 (d, 1H), 6.10 (s, 1H), 5.85 (dd, 1H), 5.43 (s, 1H), 5.18 (bs, 1H), 3.85 (s, 3H), 2.45–1.12 (m, 19H); HRMS calcd m/z for $C_{27}H_{31}NO_2$: 401.2355. Found: 401.2342; Anal. calcd for $C_{27}H_{31}NO_2$: C, 80.76; H, 7.78; N, 3.49. Found: C, 80.76; H, 8.00; N, 3.25.

EXAMPLE 146

2,5-Dihydro-10-methoxy-5-(3,3-dimethyl-6-cyclohexenyl)-2,2,4-trimethyl-1H-[1]benzopyrano[3,4-f]quinoline Example 2B and (6,6-dimethylcyclohexen-2-yl)dimethylphenylsilane were processed as in Example 2 to provide the desired compound as an inseparable mixture of diastereomers (5:1).

MS (DCI/NH$_3$) m/z 416 (M+H)$^+$; $^1$H NMR (300 MHz, DMSO-d$_6$) major diastereomer: δ 8.04 (d, 1H), 7.06 (t, 1H), 6.68 (d, 1H), 6.63 (d, 1H), 6.58 (d, 1H), 6.21 (s, 1H), 5.67 (dd, 1H), 5.49–5.38 (m, 3H), 3.86 (s, 3H), 2.29–0.82 (m, 20H); minor diastereomer: δ 8.01 (d, 1H), 7.07 (t, 1H), 6.68 (d, 1H), 6.63 (d, 1H), 6.57 (d, 1H), 6.16 (s, 1H), 5.56–5.33 (m, 3H), 4.97 (dd, 1H, 3.86 (s, 3H), 2.29–0.82 (m, 20H); HRMS calcd m/z for C$_{28}$H$_{33}$NO$_2$: 415.2511. Found: 415.2527; Anal. calcd for C$_{28}$H$_{33}$NO$_2$: C, 80.93; H, 8.00; N, 3.37. Found: C, 80.92; H, 7.98; N, 3.25.

EXAMPLE 147

2,5-Dihydro-10-methoxy-5-(2-bromo-3-propenyl)-2,2,4-trimethyl-1H-[1]benzopyrano[3,4-f]quinoline Example 2B and (2-bromoallyl)trimethylsilane were processed as in Example 2 to provide the desired compound. MS (DCI/NH$_3$) m/z 426 (M+H)$^+$; $^1$H NMR (300 MHz, DMSO-d$_6$) δ 8.00 (d, 1H), 7.08 (t, 1H), 6.72 (d, 1H), 6.62 (d, 1H), 6.47 (d, 1H), 6.17 (s, 1H), 6.02 (dd, 1H), 5.51 (d, 1H), 5.47 (s, 1H), 5.42 (s, 1H), 3.87 (s, 3H), 2.89 (dd, 1H), 2.44 (dd, 1H), 2.26 (s, 3H), 1.17 (s, 3H), 1.15 (s, 3H), Anal. calcd for C$_{23}$H$_{24}$NO$_2$Br: C, 64.79; H, 5.67; N, 3.29. Found: C, 64.70; H, 5.65; N, 3.09.

EXAMPLES 148–150

Example 2B (1.25 g, 3.70 mmol) and 1-[1'-t-butyldimethylsiloxy-1'-methoxyalkylidene]-2-cyclohexene were processed as in example 2 to provide a diastereomeric mixture of unsaturated ester adducts (1.21 g, 73%) that was carried on to the next step.

The mixture above (1.20 g, 2.69 mmol) was dissolved in THF (100 ml), cooled to 0° C., treated slowly with Dibal-H (13.5 ml of 1Mhex solution, 13.5 mmol) by syringe, stirred 30 minutes, diluted with 250 ml saturated aqueous sodium pottasium tartrate and 300 ml ethyl acetate and stirred overnight. The layers were separated, aqueous phase extracted twice with ethyl acetate, combined organics washed with brine and dried (MgSO$_4$). The resulting residue was purified by silica gel chromatography eluting with from 20% to 30% methyl t-butylether in hexanes to give Examples 148–150.

EXAMPLE 148 rel (5R,3'R) 2,5-Dihydro-10-methoxy-5-(1-hydroxymethyl-3-cyclohexenyl)-2,2,4-trimethyl-1H-[1]benzopyrano[3,4-f]quinoline MS (DCI/NH$_3$) m/l 418 (M+H)$^+$; $^1$H NMR (300 MHz, DMSO-d$_6$) δ 8.01 (d, J=8 Hz, 1H), 7.07 (t, J=8 Hz, 1H), 6.69 (d, J=8 Hz, 1H), 6.63 (d, J=9 Hz, 1H), 6.57 (d, J=8 Hz, 1H), 6.17 (d, J=2 Hz, 1H), 5.50 (d, J=10Hz, 1H), 5.39 (br s, 1H), 5.05 (br s, 1H), 4.42 (t, 1H), 3.85 (s, 3H), 3.64 (d, J=6 Hz, 2H), 2.27 (n, 1H), 2.05 (s, 3H), 1.95–1.86 (m, 2H), 1.78–1.21 (m, 4H), 1.28 (s, 3H), 1.09 (s, 3H); Anal. calcd for C$_{27}$H$_{31}$NO$_3$.1/2H$_2$O: C, 76.03; H, 7.56; N, 3.28. Found: C, 76.34; H, 7.71; N, 3.20.

EXAMPLE 149 rel (5R,3'S) 2,5-Dihydro-10-methoxy-5-(1-hydroxymethyl-3-cyclohexenyl)-2,2,4-trimethyl-1H-[1]benzopyrano[3,4-f]quinoline MS (DCI/NH$_3$) m/e 418 (M+H)$^+$; $^1$H NMR (300 MHz, DMSO-d$_6$) δ 8.40 (d, J=9 Hz, 1H), 7.07 (t, J=8 Hz, 1H), 6.67 (d, J=8 Hz, 1H), 6.63 (d, J=8 Hz, 1H), 6.59 (d, J=8 Hz, 1H), 6.20 (d, J=8 Hz, 1H), 6.20 (s, 1H), 5 (78, J=s Hz, 1H), 5.45 (s, 1H), 5.37 (d, J=10 Hz, 1H), 4.60 (dd, J=5 Hz, 1H),3.85 (s, 3H), 3.75 (s, 2H), 2.37 (m, 1H), 2.12 (s, 3H), 1.70 (m, 2H), 1.60 (m, 1H), 1.30 (s, 3H), 1.15 (m, 2H), 1.02 (s, 3H); $^{13}$C NMR (75 MHz, DMSO-d$_6$) δ 156.3, 151.5, 145.0, 139.6, 133.7, 130.2, 128.0, 127.1, 126.9, 120.8, 120.3, 118.5, 116.5, 113.0, 110.2, 105.2, 105.2, 76.2, 65.1, 55.6, 49.4, 36.9, 29.6, 26.8, 23.7, 21.3.

EXAMPLE 150

2,5-Dihydro-10-methoxy-5-(3-hydroxymethyl-3-cyclohexenyl)-2,2,4-trimethyl-1H-[1]benzopyrano[3,4-f]quinoline MS (DCI/NH$_3$) m/e 418 (M+H)$^+$; $^1$H NMR (300 MHz, DMSO-d$_6$) δ 8.06 (d, J=8 Hz, 1H), 7.01 (t, J=8 Hz, 1H), 6.59 (d, J=8 Hz, 1H), 6.52 (d, J=8 Hz, 1H), 6.27 (s, 1H), 6.03 (s, 1H), 5.38 (s, 1H), 5.23 (m, 1H), 4.75 (m, 2H), 3.81 (s, 3H), 3.47 (m, 1H), 2.95 (m, 1H), 2.19 (s, 3H), 1.70–1.35 (m, 6H), 1.31 (s, 3H), 1.03 (s, 3H); $^{13}$C NMR (75 MHz, DMSO-d$_6$) δ 156.4, 154.4 (145.1), 132.9, 129.2, 128.0, 127.6, 126.9, 126.1, 119.3, 118.6, 114.3, 113.1, 109.0, 105.5, 73.5, 64.4, 55.9, 49.2, 48.6, 29.7, 26.5, 25.6, 24.3, 23.5, 18.3; Anal. calcd for C$_{27}$H$_{31}$NO$_3$.1/4H$_2$O: C, 76.84; H17.52; N, 3.32. Found: C, 76.93; H, 7.73; N, 3.18.

EXAMPLE 151

2,5-Dihydro-10-methoxy-5-(3-indolyl)-2,2,4-trimethyl-1H-[1]benzopyrano[3,4-f]quinoline Example 2B and indole were processed as in Example 2 to provide the desired compound.

MS (DCI/NH$_3$) m/e 423 (M+H)$^+$; $^1$H NMR (300 MHz, DMSO-d$_6$) δ 10.89 (d, 1H), 8.01 (d, 1H), 7.83 (dd, 1H), 7.27 (dd, 1H), 7.04 (m, 3H), 6.80 (t, 1H), 6.68 (d, 1H), 6.54 (s, 1H), 6.53 (d, 1H), 6.28 (d, 1H), 6.12 (s, 1H), 5.35 (s, 1H), 3.83 (s, 3H), 1.89 (s, 3H), 1.22 (s, 3H), 1.14 (s, 3H) Anal. calcd for C$_{28}$H$_{26}$N$_2$O$_2$: C, 79.59; H, 6.20; N, 6.62. Found: C, 79.58; H, 6.28; N, 6.36.

EXAMPLE 152 rel (5S,3'S) 2,5-Dihydro-10-methoxy-5-(1-methyl-3-cyclohexenyl)-2,2,4-trimethyl-1H[1]benzopyrano[3,4-f]quinoline Example 148 (0.512 g, 1.23 mmol) was dissolved in CH$_2$Cl$_2$ (5 ml), cooled to 0° C., treated with (i-Pr)$_2$NEt (0.32 ml, 1.84 mmol), methanesulfonyl chloride (0.11 ml, 1.47 mmol) and stirred for 1 hour. The reaction mixture was treated dropwise with lithium triethylborohydride (4.70 ml of 1M/THF solution, 4.70 mmol), stirred 60 minutes, treated with 10 ml 1M NaOH, 0.6 ml 30% H$_2$O$_2$, stirred 2 hours and extracted with ethyl acetate. The organic layer was washed with H$_2$O, saturated aqueous NaHCO$_3$, brine, dried (MgSO$_4$) and concentrated. The residue was purified by silica gel chromatography eluting with 5% then 7% ethyl acetate in hexanes to give 0.362 g (74%) of the desired product as a colorless foam.

MS (DCI/NH$_3$) m/e 402 (M+H)$^+$; $^1$H NMR (300 MHz, DMSO-d$_6$) δ 8.02 (d, J=8 Hz, 1H), 7.06 (t, J=8 Hz, 1H), 6.68 (d, J=8 Hz, 1H), 6.64 (d, J=8 Hz, 1H), 6.56 (d, J=8 Hz, 1H), 6.16 (s, 1H), 5.49 (d, J=10 Hz, 1H), 5.41 (br s, 1H), 4.83 (br s, 1H), 3.85 (s, 3H), 2.31–2.17 (m, 1H), 2.06 (s, 3H), 1.99–1.21 (m, 6H), 1.49 (s, 3H), 1.29 (s, 3H), 1.08 (s, 3H).

EXAMPLE 153 rel (5R,3'S) 2,5-Dihydro-10-methoxy-5-(1-methyl-3-cyclohexenyl)-2,2,4-trimethyl-1H-[1]benzopyrano[3,4-f]quinoline Example 149 was processed as in Example 152 to provide the desired compound.

MS (DCI/NH$_3$) m/e 402 (M+H)$^+$; $^1$H NMR (300 MHz, DMSO-d$_6$) δ 8.04 (d, J=9 Hz, 1H), 7.07 (t, J=8 Hz, 1H), 6.68 (d, J=8 Hz, 1H), 6.63 (d, J=9 Hz, 1H), 6.61 (d, J=8 Hz, 1H), 6.22 (d, J=2 Hz, 1H), 5.55 (br s, 1H), 5.45 (br s, 1H), 5.35 (d, J=10 Hz, 1H), 3.86 (s, 3H), 2.34–2.18 (m, 1H), 2.12 (s, 3H), 1.97–0.88 (m, 6H), 1.61 (s, 3H), 1.30 (s, 3H), 1.02 (s, 3H); Anal. calcd for C$_{27}$H$_{31}$NO$_2$.1/4H$_2$O: C, 79.87; H, 7.82; N, 3.45. Found: C, 79.81; H, 8.28; N, 3.39.

EXAMPLE 154

(−) (5S,3'S) 2,5-Dihydro-10-methoxy-5-(1-methyl-3-cyclohexenyl)-2,2,4-trimethyl-1H-[1]benzopyrano[3,4-f]quinoline Example 152 was subjected to HPLC on an (R,R) WHELK-O 1 column eluting with 2% EtOH in hexanes to provide the desired compound.

[α]$_D^{20}$−155.9° (c 0.85, CHCl$_3$); MS (DCI/NH$_3$) m/e 402 (M+H)$^+$; $^1$H NMR (300 MHz, DMSO-d$_6$) δ 8.02 (d, J=9 Hz, 1H), 7.06 (t, J=8 Hz, 1H), 6.68 (d, J=8 Hz, 1H), 6.64 (d, J=9 Hz, 1H), 6.57 (d, J=8 Hz, 1H), 6.20 (d, J=2 Hz, 1H), 5.49 (d, J=10 Hz, 1H), 5.42 (br s, 1H), 4.83 (br s, 1H), 3.85 (s, 3H), 2.30–2.18 (m, 1H), 2.06 (s, 3H), 1.97–1.20 (m, 6H), 1.49 (s, 3H), 1.29 (s, 3H), 1.08 (s, 3H); Anal. calcd for C$_{27}$H$_{31}$NO$_2$.1/4H$_2$O: C, 79.87; H, 7.82; N, 3.45. Found: C, 79.80; H, 8.15; N, 3.41.

EXAMPLE 155

(−) (5S, 3'R) 2,5-Dihydro-10-methoxy-5-(1-hydroxymethyl-3-cyclohexenyl)-2,2,4-trimethyl-1H-[1]benzopyrano[3,4-f]quinoline Example 149 was subjected to HPLC on an (R,R) WHELK-O 1 column eluting with 6% EtOH in hexanes to provide the desired product.

[α]$_D^{20}$−233.9° (c 1.27, CHCl$_3$); MS (DCI/NH$_3$) m/e 418 (M+H)$^+$; $^1$H NMR (300 MHz, DMSO-d$_6$) δ 8.05 (d, J=9 Hz, 1H), 7.08 (d, J=8 Hz, 1H), 6.68 (d, J=8 Hz, 1H), 6.63 (d, J=9 Hz, 1H), 6.61 (d, J=8 Hz, 1H), 6.23 (br s, 1H), 5.78 (br s, 1H), 5.46 (br s, 1H), 5.37 (d, J=10 Hz, 1H), 4.65 (t, J=6 Hz, 1H), 3.86 (s, 3H), 3.76 (m, 2H), 2.36–2.22 (m, 2H), 2.12 (s, 3H), 1.87–1.77 (m, 2H), 1.65–1.53 (m, 1H), 1.30 (s, 3H), 1.27–0.92 (m, 2H), 1.02 (s, 3H),

EXAMPLE 156

(+) (5R,3'S) 2,5-Dihydro-10-methoxy-5-(1-hydroxymethyl-3-cyclohexenyl)-2,2,4-trimethyl-1H-[1]benzopyrano[3,4-f]quinoline Example 149 was subjected to HPLC on an (R,R) WHELK-O 1 column eluting with 6% EtOH in hexanes to provide the desired product.

[α]$_D^{20}$+234.6° (c 1.10, CHCl$_3$); MS (DCI/NH$_3$) m/e 418 (M+H)$^+$; $^1$H NMR (300 MHz, DMSO-d$_6$) δ 8.05 (d, J=9 Hz, 1H), 7.07 (t, J=8 Hz, 1H), 6.68 (d, J=8 Hz, 1H), 6.63 (d, J=9 Hz, 1H), 6.61 (d, J=8 Hz, 1H), 6.22 (br s, 1H), 5.78 (br s, 1H), 5.45 (br s, 1H), 5.37 (d, J=10 Hz, 1H), 4.63 (t, J=6 Hz, 1H), 3.86 (s, 3H), 3.78–3.73 (m, 2H), 2.36–2.22 (m, 2H), 2.12 (s, 3H), 1.87–1.77 (m, 2H), 1.65–1.52 (m, 1H), 1.34–0.93 (m, 2H), 1.30 (s, 3H), 1.02 (s, 3H).

EXAMPLE 157

(−)-(5S,3'R) 2,5-Dihydro-10-methoxy-5-(1-methyl-3-cyclohexenyl)-2,2,4-trimethyl-1H-[1]benzopyrano[3,4-f]quinoline Example 155 was processed as in Example 152 to provide the desired compound.

MS (DCI/NH$_3$) m/e (M+H)$^+$402; $^1$H NMR (300 MHz, DMSO-d$_6$) δ 8.04 (d, J=8 Hz, 1H), 7.07 (t, J=8 Hz, 1H), 6.68 (d, J=8 Hz, 1H), 6.63 (d, J=8 Hz, 1H), 6.62 (d, J=8 Hz, 1H), 6.23 (br s, 1H), 5.55 (br s, 1H), 5.45 (br s, 1H), 5.35 (d, J=10 Hz, 1H), 3.86 (s, 3H), 2.33–2.18 (m, 1H), 2.12 (s, 3H), 195–1.45 (m, 4H), 1.61 (s, 3H), 1.34–0.88 (m, 2H), 1.30 (s, 3H), 1.02 (s, 3H); [α]$_{20}$−224.1° (c 0.73, CHCl$_3$); Anal. calcd for C$_{27}$H$_{31}$NO$_2$.1/2H$_2$O: C, 78.99; H, 7.86; N, 3.41. Found: C, 79.14; H, 8.07; N, 3.03.

EXAMPLE 158

(+)-(5R, 3'S) 2,5-Dihydro-10-methoxy-5-(1-methyl-3-cyclohexenyl)-2,2,4-trimethyl-1H-[1]benzopyrano[3,4-f]quinoline Example 156 was processed as in Example 152 to provide the desired compound.

MS (DCI/NH$_3$) m/e 402 (M+H)$^+$; $^1$H NMR (300 MHz, DMSO-d$_6$) δ 8.04 (d, J=9 Hz, 1H), 7.07 (d, J=8 Hz, 1H), 6.67 (d, J=8 Hz, 1H), 6.63 (d, J=9 Hz, 1H), 6.59 (d, J=8 Hz, 1H), 6.22 (br s, 1H), 5.55 (m, 1H), 5.45 (br s, 1H), 5.35 (d, J=10 Hz, 1H), 3.86 (s, 3H), 2.27 (m, 1H), 2.12 (s, 3H), 1.94–1.05 (m, 6H), 1.61 (s, 3H), 1.30 (s, 3H), 1.02 (s, 3H).

EXAMPLE 159

2,5-Dihydro-10-methoxy-5-(1-chloromethyl-3-cyclohexenyl)-2,2,4-trimethyl-1H-[1]benzopyrano[3,4-f]quinoline Example 148 (0.110 g, 0.264 mmol) was combined with methanesulfonyl chloride (49 μl, 0.632 mmol), (i-Pr)2NEt (53 μL, 0.695 mmol), Lithium chloride (11 mg, 0.264 mmol) in 2 mL of THF containing 2 drops of DMF and the reaction mixture was stirred at room temperature for several hours. The reaction mixture was diluted with ethyl acetate and washed with saturated aqueous bicarbonate, brine, dried over MgSO$_4$ and purified by silica gel chromatography eluting with 20% ethyl acetate in hexane to give 106 mg (92%) of the desired compound as a foam.

MS (DCI/NH$_3$) m/e 436 (M+H)$^+$; $^1$H NMR (300 MHz, DMSO-d$_6$) δ 8.03 (d, J=8 Hz, 1H), 7.08 (t, J=8 Hz, 1H), 6.66 (dd, J=8 Hz, 2H), 6.55 (d, J=8 Hz, 1H), 6.25 (br s, 1H), 5.53 (d, J=10 Hz, 1H), 5.39 (s, 1H), 5.25 (s, 1H), 3.91 (s, 2H), 3.84 (s, 3H), 2.30 (m, 1H), 2.05 (s, 3H), 1.35–2.00 (m, 6H), 1.30 (s, 3H), 1.10 (s, 3H).

EXAMPLE 160 rel (5R, 3'R) 2,5-Dihydro-10-methoxy-5-(1-methoxymethyl-3-cyclohexenyl)-2,2,4-trimethyl-1H-[1]benzopyrano[3,4-f]quinoline Example 148 was processed according to Example 152 using sodium methoxide instead of lithium triethylborohydride to give the desired compound.

MS (DCI/NH$_3$) m/e 432 (M+H)$^+$; $^1$H NMR (400 MHz, DMSO-d$_6$) δ 8.02 (d, J=9 Hz, 1H), 7.07 (t, J=8 Hz, 1H), 6.69 (d, J=8 Hz, 1H), 6.64 (d, J=9 Hz, 1H), 6.57 (d, J=9 Hz, 1H), 5.53 (d, J=10 Hz, 1H), 5.11 (s, 1H), 3.85 (s, 3H), 3.58 (dd, J=12+32 Hz, 1H), 3.06 (s, 3H), 2.30 (br m, 1H), 2.07 (s, 3H), 1.50–2.00 (br m, 4H), 1.35 (m, 1H), 1.30 (s, 3H), 1.10 (s, 3H); $^{13}$C NMR (100 MHz, DMSO-d$_6$) δ 156.2, 150.9, 145.0, 137.0, 133.7, 133.6, 130.4, 128.1, 127.1, 127.1, 123.5, 117.9, 116.4, 113.5, 113.1, 110.1, 105.4, 105.3, 105.0, 76.2, 75.4, 56.4, 55.6, 49.5, 36.9, 29.7, 23.4, 25.5, 25.3, 25.2, 24.2, 20.2.

EXAMPLE 161 rel (5R, 3'R) 2,5-Dihydro-10-methoxy-5-(1-methylthiomethyl-3-cyclohexenyl)-2,2,4-trimethyl-1H-[1]benzopyrano[3,4-f]quinoline Example 148 was processed according to Example 152 using sodium thiomethoxide instead of lithium triethylborohydride to give the desired compound as a white foam.

MS (DCI/NH₃) m/e 448 (M+H)⁺; ¹H NMR (300 MHz, DMSO-d₆) δ 8.02 (d, J=8 Hz, 1H), 7.08 (t, J=8 Hz, 1H), 6.69 (d, J=8 Hz, 1H), 6.65 (d, J=9 Hz, 1H), 6.57 (d, J=9 Hz, 1H), 6.23 (s, 1H), 5.49 (d, J=10 Hz, 1H), 5.40 (s, 1H), 5.00 (s, 1H), 3.86 (s, 2H), 2.30 (br m, 2H), 2.07 (s, 3H), 1.81 (s, 3H), 1.40–1.78 (br m, 6H), 1.30 (s, 3H), 1.09 (s, 3H); ¹³C NMR (100 MHz, DMSO-d₆) δ 156.2, 151.0, 145.0, 135.7, 133.8, 130.3, 128.2, 127.1, 127.1, 123.5, 118.1, 116.5, 113.4, 113.1, 110.1, 105.3, 75.7, 55.5, 49.5, 40.8, 37.5, 29.7, 27.3, 26.2, 25.7 (24.2), 20.6, 13.7.

EXAMPLE 162 rel (5R, 3'S) 2,5-Dihydro-10-methoxy-5-(1-acetoxymethyl-3-cyclohexenyl)-2,2,4-trimethyl-1H-[1]benzopyrano[3,4-f]quinoline Example 149 (0.100 g, 0.239 mmol) was combined with acetic anhydride (27 μL, 0.288 mmol), DMAP (2 mg, catalytic), (i-Pr)₂NEt (50 μL, 0.288 mmol) in dichloromethane (6 ml). The reaction mixture was stirred for 1 hour at room temperature, diluted with ethyl acetate and washed with saturated aqueous bicarbonate, brine, dried (MgSO₄) and purified by silica gel chromatography eluting with 20% ethyl acetate in hexane to give 89 mg (81%) of the desired compound as a white solid.

MS (DCI/NH3) m/e 460 (M+H)⁺; ¹H NMR (300 MHz, DMSO-d₆) δ 8.05 (d, J=8 Hz, 1H), 7.08 (t, J=8 Hz, 1H), 6.68 (d, J=8 Hz, 1H), 6.64 (d, J=8 Hz, 1H), 6.62 (d, J=8 Hz, 1H), 6.23 (s, 1H), 5.82 (s, 1H), 5.46 (s, 1H), 5.40 (d, J=10 Hz, 1H), 4.38 (s, 2H), 3.86 (s, 3H), 2.33 (br m, 1H), 2.12 (s, 3H), 2.03 (s, 3H), 1.85 (br m, 2H), 1.60 (br m, 1H), 1.30 (s, 3H), 1.02–1.28 (br m, 3H), 1.02 (s, 3H); Anal. calcd for C₂₉H₃₃NO₄: C, 75.79; H, 7.24; N, 3.05. Found: C, 76.14; H, 7.47; N, 3.02.

EXAMPLE 163 rel (5R, 3'R) 2,5-Dihydro-10-methoxy-5-(1-acetoxymethyl-3-cyclohexenyl)-2,2,4-trimethyl-1H-[1]benzopyrano[3,4-f]quinoline Example 148 was processed as in Example 162 to provide the desired compound as a white solid.

MS (DCI/NH₃) m/e 460 (M+H)⁺; ¹H NMR (300 MHz, DMSO-d₆) δ 8.02 (d, J=8 Hz, 1H), 7.08 (t, J=8 Hz, 1H), 6.70 (d, J=8 Hz, 1H), 6.65 (d, J=8 Hz, 1H), 6.58 (d, J=8 Hz, 1H), 6.18 (s, 1H), 5.55 (d, J=10 Hz, 1H), 5.39 (s, 1H), 5.16 (s, 1H), 4.22 (s, 2H), 3.85 (s, 3H), 2.40 (br, J=8 Hz, 1H), 2.06 (s, 3H), 1.96 (s, 3H), 1.32–1.95 (br m, 3H), 1.28 (s, 3H), 1.06 (s, 3H); Anal. calcd for C₂₉H₃₃NO₄: C, 75.79; H, 7.24; N, 3.05. Found: C, 75.53; H, 7.32; N, 2.84.

EXAMPLE 164 rel (5R, 3'R) 2,5-Dihydro-10-methoxy-5-(1-methoxymethyl-3-cyclohexenyl)-2,2,4-trimethyl-1H-[1]benzopyrano[3,4-f]quinoline Example 149 was processed according to Example 152 using sodium methoxide instead of lithium triethylborohydride to give the desired compound as a white foam.

MS (DCI/NH₃) m/e 432 (M+H)⁺; ¹H NMR (300 MHz, DMSO-d₆) δ 8.05 (d, J=9 Hz, 1H), 7.07 (t, J=8 Hz, 1H), 6.67 (d, J=8 Hz, 1H), 6.64 (d, J=8 Hz, 1H), 6.60 (d, J=8 Hz, 1H), 6.59 (d, J=8 Hz, 1H), 6.20 (s, 1H), 5.78 (s, 1H), 5.45 (s, 1H), 5.39 (d, J=10 Hz, 1H), 3.70 (s, 2H), 3.14 (s, 3H), 2.30 (br m, 1H), 2.12 (s, 3H), 1.81 (br m, 2H), 1.60 (br m, 1H), 1.30 (s, 3H), 1.15 (br m, 2H), 1.02 (s, 3H); Anal. calcd for C₂₈H₃₃NO₃.1/4H₂O: C, 77.12; H, 7.74; N, 3.21. Found: C, 77.17; H, 7.55; N, 3.15.

EXAMPLE 165 rel (5R, 3'R) 2,5-Dihydro-10-methoxy-5-(1-(N,N-dimethylamino)methyl-3-cyclohexenyl)-2,2,4-trimethyl-1H-[1]benzopyrano[3,4-f]quinoline Example 148 was processed according to Example 152 using dimethylamine instead of lithium triethylborohydride to give the desired compound as a white foam. MS (DCI/NH₃) m/e 445 (M+H)⁺; ¹H NMR (300 MHz, DMSO-d₆) δ 8.01 (d, J=8 Hz, 1H), 7.07 (t, J=8 Hz, 1H), 6.69 (d, J=8 Hz, 1H), 6.64 (d, J=8 Hz, 1H), 6.57 (d, J=8 Hz, 1H), 6.22 (s, 1H), 5.50 (d, J=10 Hz, 1H), 5.39 (s, 1H), 5.03 (s, 1H), 3.85 (s, 3H), 2.62 (d, J=11 Hz, 1H), 2.50 (d, J=11 Hz, 1H), 2.25 (br s, 1H), 2.06 (s, 6H), 1.98 (s, 3H), 1.40–1.95 (br m, 6H), 1.30 (s, 3H), 1.25 (br m, 1H), 1.11 (s, 3H); Anal. calcd for C₂₉H₃₆N₂O₂.3/4H₂O: C, 76.03; H, 8.25; N, 6.11. Found: C, 75.90; H, 7.81; N, 5.90.

EXAMPLE 166 rel (5R, 3'S) 2,5-Dihydro-10-methoxy-5-(1-methylthiomethyl-3-cyclohexenyl)-2,2,4-trimethyl-1H-[1]benzopyrano[3,4-f]quinoline Example 149 was processed according to Example 152 using sodium thiomethoxide instead of lithium triethylborohydride to give the desired compound as a white foam.

MS (DCI/NH₃) m/e 448 (M+H)⁺; ¹H NMR (300 MHz, DMSO-d₆) δ 8.05 (d, J=9 Hz, 1H), 7.07 (t, J=8 Hz, 1H), 6.68 (d, J=8 Hz, 1H), 6.63 (d, J=8 Hz, 1H), 6.61 (d, J=8 Hz, 1H), 6.24 (s, 1H), 5.71 (s, 1H), 5.46 (s, 1H), 5.39 (d, J=10 Hz, 1H), 3.86 (s, 3H), 3.02 (s, 2H), 2.17–2.41 (br m, 2H), 2.11 (s, 3H), 1.91–2.10 (br m, 2H), 1.88 (s, 3H), 1.30 (s, 3H), 1.25 (s, 3H), 1.05–1.25 (br m, 3H), 1.02 (s, 3H); Anal. calcd for C₂₈H₃₃NO₂S.1/2H₂O: C, 73.65; H, 7.50; N, 3.07. Found: C, 73.37; H, 7.46; N, 2.97.

EXAMPLE 167 rel (5R, 3'R) 2,5-Dihydro-10-methoxy-5-(1-(N-morpholino)methyl-3-cyclohexenyl)-2,2,4-trimethyl-1H-[1]benzopyrano[3,4-f]quinoline Example 148 was processed according to Example 152 using morpholine instead of lithium triethylborohydride to give the desired compound as a white foam.

MS (DCI/NH₃) m/e 487 (M+H)⁺; ¹H NMR (300 MHz, DMSO-d₆) δ 8.01 (d, J=9 Hz, 1H), 7.07 (t, J=8 Hz, 1H), 6.68 (d, J=8 Hz, 1H), 6.65 (d, J=8 Hz, 1H), 6.56 (d, J=8 Hz, 1H), 6.22 (s, 1H), 5.49 (d, J=11 Hz, 1H), 5.41 (s, 1H), 5.04 (s, 1H), 3.85 (s, 3H), 3.52 (br s, 3H), 2.68 (d, J=12 Hz, 1H), 2.56 (d, J=12 Hz, 1H), 2.25 (br s, 1H), 2.15 (br s, 2H), 2.05 (s, 3H), 1.40–2.00 (br m, 6H), 1.32 (s, 3H), 1.20–1.28 (br m, 6H), 1.17 (s, 3H); Anal. calcd for C₃₁H₃₈N₂O₃: C, 76.51; H, 7.87; N, 5.76. Found: C, 76.24; H, 8.05; N, 5.52.

EXAMPLE 168 rel (5R, 3'R) 2,5-Dihydro-10-methoxy-5-(1-(N-methyl-N-methylsulfonylamino)methyl-3-cyclohexenyl)-2,2,4-trimethy-1H-[1]benzopyrano[3,4-f]quinoline Example 170 (0.80 g, 0.186 mmol) was combined with methanesulfonyl chloride (15 μL, 0.195 mmol), (i-Pr)₂NEt (48 μl, 0.279 mmol) and THF at 0° C. for 1.5 hours. The product was added directly to a silica gel plug and eluted with hexane then 40% ethyl acetate in hexane to give 88 mg (93%) of the desired compound as a white solid.

MS (DCI/NH$_3$) m/e 509 (M+H)$^+$; $^1$H NMR (300 MHz, DMSO-d$_6$) δ 8.02 (d, J=9 Hz, 1H), 7.08 (t, J=8 Hz, 1H), 6.69 (d, J=8 Hz, 1H), 6.65 (d, J=9 Hz, 1H), 6.58 (d, J=9 Hz, 1H), 6.20 (s, 1H), 5.53 (d, J=5 Hz, 1H), 5.41 (s, 1H), 5.11 (s, 1H), 3.85 (s, 3H), 3.46 (d, J=13 Hz, 1H), 3.24 (d, J=13 Hz, 1H), 2.82 (s, 3H), 2.53 (s, 3H), 2.30 (br, 1H), 2.08 (s, 2H), 1.5–2.0 (br m, 6H), 1.35 (br m, 1H), 1.30 (s, 3H), 1.25 (m, 1H), 1.11 (s, 3H); Anal. calcd for C$_{29}$H$_{36}$N$_2$O$_4$S: C, 68.47; H, 7.13; N, 5.51. Found: C, 68.20; H, 7.09; N, 5.36.

EXAMPLE 169 rel (5R, 3'S) 2,5-Dihydro-10-methoxy-5-(1-(N,N dimethylamino)methyl-3-cyclohexenyl)-2,2,4-trimethyl-1H-[1]benzopyrano[3,4-f]quinoline Example 149 was processed according to Example 152 using dimethylamine instead of lithium triethylborohydride to give the desired compound as a white foam.

MS (DCI/NH$_3$) m/e 445 (M+H)$^+$; $^1$H NMR (300 MHz, DMSO-d$_6$) 6 8.05 (d, J=9 Hz, 1H), 7.05 (t, J=8 Hz, 1H), 6.67 (d, J=8 Hz, 1H), 6.63 (d, J=8 Hz, 1H), 6.60 (d, J=8 Hz, 1H), 6.213 (s, 1H), 5.69 (s, 1H), 5.46 (s, 1H), 5.42 (d, J=10 Hz, 1H), 3.86 (s, 3H), 2.70 (br, 1H), 2.30 (br m, 1H), 2.11 (s, 3H), 2.05 (br, 4H), 1.85 (br, 2H), 1.56 (m, 1H), 1.30 (s, 3H), 1.10–1.25 (m, 3H), 1.02 (s, 3H); Anal. calcd for C$_{29}$H$_{36}$N$_2$O$_2$·1/2H$_2$O: C, 76.79; H, 8.22; N, 6.18. Found: C, 76.49; H, 8.23; N, 5.95.

EXAMPLE 170 rel (5R, 3'R) 2,5-Dihydro-10-methoxy-5-(1-(N-methylamino)methyl-3-cyclohexenyl)2,2,4-trimethyl-1H-[1]benzoppyrano[3,4-f]quinoline Example 148 was processed according to Example 152 using methylamine instead of lithium triethylborohydride to give the desired compound as a white foam.

MS (DCI/NH$_3$) m/e 431 (M+H)$^+$; $^1$H NMR (300 MHz, DMSO-d$_6$) δ 8.00 (d, J=8 Hz, 1H), 7.05 (t, J=8 Hz, 1H), 6.68 (d, J=7 Hz, 1H), 6.63 (d, J=7 Hz, 1H), 6.57 (d, J=7 Hz, 1H), 6.22 (s, 1H), 5.76 (s, 1H), 5.53 (d, J=10 Hz, 1H), 5.41 (s, 1H), 5.14 (br s, 1H), 3.85 (s, 3H), 3.02 (s, 2H), 2.30 (br m, 1H), 2.22 (s, 3H), 2.07 (s, 3H), 1.74 (br m, 2H), 1.80–1.4 (br m, 4H), 1.30 (s, 3H), 1.25 (s, 1H), 1.10 (s, 3H); Anal. calcd for C$_{28}$H$_{33}$N$_2$O$_2$·1.25H$_2$O: C, 74.22; H, 8.12; N, 6.18. Found: C, 74.05; H, 7.81; N, 6.00.

EXAMPLE 171

2,5-Dihydro-10-methoxy-5-(2-methyl-3-propenyl)-2,2,4-trimethyl-1H-[1]benzopyrano[3,4-f]quinoline A solution of Example 147 (51 mg, 0.12 mmol) and tetramethyltin (66.5 μl, 0.048 mmol) in 1 ml HMPA was degassed with N$_2$ for 20 minutes. Dichlorobis(triphenylphosphine)palladium(II) (9.8 mg, 0.012 mmol) was added and the reaction mix was heated at 85° C. for 60 hours, cooled to room temperature, and stirred vigorously with 30 ml of ethyl acetate and 30 ml of saturated KF aqueous solution for 3 hours. The mixture was then filtered through a plug of celite and the layers were separated. The organic layer was washed with water, brine and dried (Na$_2$SO$_4$). Concentration followed by silica gel chromatography (15% ethyl acetate/hexanes) provided the desired compound.

MS (DCI/NH$_3$) m/z 362 (M+H)$^+$; $^1$H NMR (300 MHz, DMSO-d$_6$) δ 7.94 (d, 1H), 7.05 (t, 1H), 6.68 (d, 1H), 6.58 (d, 1H), 6.42 (d, 1H), 6.12 (d, 1H), 5.91 (dd, 1H), 5.44 (s, 1H), 4.77 (s, 1H), 4.54 (s, 1H), 3.87 (s, 3H), 2.43 (m, 1H), 2.20 (s, 3H), 2.09 (m, 1H), 1.74 (s, 3H), 1.16 (s, 3H). HRMS calcd m/z for C$_{24}$H$_{27}$NO$_2$: 361.2042. Found: 361.2047.

EXAMPLE 172

2,5-Dihydro-10-methoxy-5-(1,3-butadien-2-yl)-2,2,4-trimethyl-1H-[1]benzopyrano[3,4-f]quinoline Example 147 and tributyl(vinyl)tin were processed as in the previous example to give the desired compound.

MS (DCI/NH$_3$) m/z 374 (M+H)$^+$; $^1$H NMR (300 MHz, DMSO-d$_6$) δ 8.00 (d, 1H), 7.05 (t, 1H), 6.70 (dd, 1H), 6.60 (d, 1H), 6.47 (dd, 1H), 6.36 (dd, 1H), 6.18 (d, 1H), 5.95 (dd, 1H), 5.43 (s, 1H), 5.16 (s, 1H), 5.12 (s, 1H), 5.05 (d, 1H), 5.00 (d, 1H), 3.87 (s, 3H), 2.55 (dd, 1H), 2.22 (dd, 1H), 2.10 (s, 3H), 1.20 (s, 3H), 1.12 (s, 3H).

EXAMPLE 173

2,5-Dihydro-10-methoxy-5-(2-carbomethoxy-3-propenyl)-2,2,4-trimethyl-1H-[1]benzopyrano[3,4-f]quinoline A mixture of Example 147 (64 mg, 0.15 mmol), bis(triphenylphosphine)dicarbonylnickel (144 mg, 0.225 mmol) and triethylamine (42 μL, 0.30 mmol) in 5 mL of MeOH was refluxed for 16 hours, cooled, and partitioned between ethyl acetate and water. The organic layer was washed with brine, dried (Na$_2$SO$_4$) and concentrated. The residue was purified by flash silica gel chromatography (15% ethyl acetate/hexanes) to give the desired compound.

MS (DCI/NH$_3$) m/z 406 (M+H)$^+$; $^1$H NMR (300 MHz, DMSO-d$_6$) δ 8.01 (d, 1H), 7.06 (t, 1H), 6.70 (dd, 1H), 6.60 (d, 1H), 6.41 (dd, 1H), 6.12 (dd, 1H), 6.01 (dd, 1H), 5.43 (s, 1H), 5.36 (s, 1H), 3.87 (s, 3H), 3.68 (s, 3H), 2.60 (dd, 1H), 2.43 (dd, 1H), 2.21 (s, 3H), 1.20 (s, 3H), 1.12 (s, 3H); Anal. calcd for C$_{25}$H$_{27}$NO$_4$: C, 74.05; H, 6.71; N, 3.45. Found: C, 73.81; H, 6.61; N, 3.38.

EXAMPLE 174

2,5-Dihydro-10-methoxy-5-(1,2-dihydroxy-3-propyl)-2,2,4-trimethyl-1H-[1]benzopyrano[3,4-f]quinoline A solution of Example 2 (50 mg, 0.144 mmol) in pyridine (3 mL) at 0° C. was treated with OSO$_4$ (370 μL, 0.144 mmol), stirred at ambient temperature for 48 hours, treated with saturated aqueous sodium bisulfite (3 mL), stirred for 4 hours and filtered through Celite. The Celite plug was washed repeatedly with EtOAc. The organic filtrate was washed with water, brine, dried (Na$_2$SO$_4$) and concentrated. The residue was purified by flash silica gel chromatography (95:5 methylene chloride/methanol) to give the desired compound as an inseparable mixture of two diastereomers (2:1).

MS (DCI/NH$_3$) m/z 382 (M+H)$^+$; $^1$H NMR (300 MHz, DMSO-d$_6$); Major diastereomer: δ 7.94 (d, 1H), 7.05 (t, 1H), 6.67 (d, 1H), 6.57 (d, 1H), 6.53 (d, 1H 6.13–6.05 (m, 2H), 5.42 (s, 1H), 4.80 (d, 1H), 4.38 (t, 1H), 3.85 (s, 3H), 3.65 (bm, 1H), 3.19–3.00 (m, 2H), 2.21 (s, 3H), 1.83 (m, 2H), 1.19 (s, 3H), 1.11 (s, 3H); Minor diastereomer: δ 7.96 (d, 1H), 7.07 (t, 1H), 6.68 (d, 1H), 6.58 (d, 1H), 6.55 (d, 1H), 6.13 (s, 1H), 5.97 (dd, 1H), 5.42 (s, 1H), 4.50 (t, 1H), 4.45 (d, 1H), 3.85 (s, 3H), 3.45–3.30 (m, 3H), 2.23 (s, 3H), 1.80–1.58 (m, 2H), 1.21 (s, 3H), 1.09 (s, 3H); Anal. calcd for C$_{23}$H$_{27}$NO$_4$.0.35H$_2$O: C,71.24; H, 7.20; N, 3.61. Found: C, 71.24; H, 7.28; N, 3.49.

EXAMPLE 175

2,5-Dihydro-10-methoxy-5-(1,2-epoxy-3-propenyl)-2,2,4-trimethyl-1H-[1]benzopyrano[3,4-f]quinoline A mixture of Example 174 (50 mg, 0.13 mmol), triphenylphosphine (38 mg, 0.14 mmol), diethyl azodicarboxylate (25 mg, 0.14 mmol) and 3 angstrom molecular sieves (50 mg) in benzene (5 mL) was refluxed for 48 hours, cooled and partitioned between EtOAc and water. The organic layer was washed with water, brine, dried (Na$_2$SO$_4$) and concentrated. The residue was purified by flash silica gel chromatography (8:2 hexane/EtOAc) to give the desired compound as an inseparable mixture of two diastereomers (1.3:1).

MS (DCI/NH$_3$) m/z 364 (M+H)$^+$; $^1$H NMR (300 MHz, DMSO-d$_6$); Major diastereomer: δ 7.93 (d, 1H), 7.09 (t, 1H), 6.72 (d, 1H), 6.60 (d, 1H), 6.58 (d, 1H), 6.14 (s 1H), 5.95 (m, 1H), 5.44 (s, 1H), 3.85 (s, 3H), 3.04 (m, 1H), 2.72 (dd, 1H), 2.35 (dd, 1H), 2.17 (s, 3H), 2.05–1.35 (m, 2H), 1.16 (s, 3H), 1.14 (s, 3H); Minor diastereomer: δ 7.95 (d, 1H), 7.08 (t, 1H), 6.71 (d, 1H), 6.59 (d, 1H), 6.57 (d, 1H), 6.15 (s 1H), 5.93 (m, 1H), 5.44 (s, 1H), 3.85 (s, 3H), 2.90 (m, 1H), 2.65 (dd, 1H), 2.28 (m, 1H), 2.17 (s, 3H), 2.05–1.58 (m, 2H), 1.17 (s, 3H), 1.13 (s, 3H); HRMS calcd m/z for C$_{23}$H$_{35}$NO$_3$: 363.1834. Found: 363.1846.

EXAMPLE 176

2,5-Dihydro-10-methoxy-5-(1-(N-phthalimido)-3-propyl)-2,2,4-trimethyl-1H-[1]benzopyrano3,4-f]quinoline Example 69 (250 mg, 0.68 mmol), phthalimide (103 mg, 0.7 mmol), triphenylphosphine (184 mg, 0.7 mmol) and diethyl azodicarboxylate (110 μL, 0.7 mmol) in THF (15 mL) was stirred for 24 hours and partitioned between EtOAc and water. The organic layer was washed with water, brine, dried (Na$_2$SO$_4$) and concentrated. The residue was purified by flash silica gel chromatography (3:1 hexane/EtOAc) to give the desired compound.

MS (DCI/NH$_3$) m/z 495 (M+H)$^+$; $^1$H NMR (300 MHz, DMSO-d$_6$) δ 7.88 (d, 1H), 7.81 (s, 4H), 6.82 (t, 1H), 6.58 (d, 1H), 6.42 (d, 1H), 6.40 (d, 1H), 6.10 (s, 1H), 5.61 (dd, 1H), 5.40 (s, 1H), 3.78 (s, 3H), 3.48 (t, 2H), 2.16 (s, 3H), 1.75–1.40 (bm, 4H), 1.22 (s, 3H), 1.16 (s, 3H); HRMS calcd m/z for C$_{31}$H$_{30}$N$_2$O$_4$: 494.2206. Found: 494.2198.

EXAMPLE 177

2,5-Dihydro-10-methoxy-5-(1-amino-3-propyl)-2,2,4-trimethyl-1H-[1]benzopyrano[3,4-f]quinoline Example 176 (118 mg, 0.24 mmol) was treated with hydrazine (12.8 mg, 0.4 mmol) in refluxing ethanol (8 mL) for 16 hours, cooled and filtered to remove a solid. The filtrate was concentrated and purified by flash silica gel chromatography (9.5:0.5 methylene chloride/methanol) to give the desired compound.

MS (DCI/NH$_3$) m/z 365 (M+H)$^+$; $^1$H NMR (300 MHz, DMSO-d$_6$) δ 7.94 (d, 1H), 7.05 (t, 1H), 6.68 (d, 1H), 6.57 (d, 1H), 6.54(d, 1H), 6.08 (s, 1H), 5.66 (dd, 1H), 5.43 (s, 1H), 3.85 (s, 3H), 2.43 (t, 2H), 2.17 (s, 3H), 1.80–1.22 (m, 4H), 1.16 (s, 3H), 1.15 (s, 3H); Anal. calcd for C$_{23}$H$_{28}$N$_2$O$_2$.0.30H$_2$O: C,74.69; H, 7.79; N, 7.57. Found: C, 74.50; H, 7.78; N, 7.31.

EXAMPLE 178

2,5-Dihydro-10-methoxy-5-(1-(hydrazinocarbonylamino)-3-propyl)-2,2,4-trimethyl-1H-[1]benzopyrano[3,4-f]quinoline Example 177 (65 mg, 0.178 mmol) was treated with triphosgene (19 mg, 0.0646 mmol) and triethylamine (50 μL, 0.36 mmol) in refluxing THF (6 mL) for 3 hours, cooled and concentrated to give the crude isocyanate.

The crude isocyanate (0.089 mmol) in THF (10 mL) was treated with hydrazine (4.5 mmol), stirred for 2 hours under nitrogen, concentrated and the resulting residue was purified by flash silica gel chromatography(9:1 dichloromethane/methanol) to give the desired compound.

MS (DCI/NH$_3$) m/z 423 (M+H)$^+$; $^1$H NMR (300 MHz, DMSO-d$_6$) δ 7.94 (d, 1H), 7.06 (t, 1H), 6.79 (bs, 1H), 6.68 (dd, 1H), 6.57 (d, 1H), 6.54 (dd, 1H), 6.22 (bt, 1H), 6.10 (d, 1H), 5.63 (dd, 1H), 5.44 (s, 1H), 3.96 (bs, 2H), 3.85 (s, 3H), 2.92 (m, 2H), 2.15 (s, 3H), 1.58–1.20 (m, 4H), 1.16 (s, 3H), 1.15 (s, 3H); HRMS (M+H)$^+$ calcd m/z for C$_{24}$H$_{30}$N$_4$O$_3$: 423.2396. Found: 423.2413.

EXAMPLE 179

(E) 2,5-Dihydro-10-methoxy-5-(2-carbomethoxy-1-ethenyl)-2,2,4-trimethyl-1H-[1]benzopyrano[3,4-f]quinoline Example 44 (0.087 g, 0.26 mmol) was dissolved in CH$_2$Cl$_2$ (10 ml), cooled to −23° C., treated dropwise with 0.52 ml 1M Dibal-H/heptane solution (0.52 mmol) and stirred for 1 h. The reaction mixture was poured into 30 ml 0.5 M HCl, stirred 30 min, extracted with ethyl acetate, the combined organics washed with brine and dried (Na$_2$SO$_4$) to give the intermediate aldehyde as a yellow foam.

The resulting yellow foam was dissolved in THF (8 ml), cooled to 0° C., treated with methyl (triphenylphosphoranylidene)acetate (0.130 g, 0.39 mmol), stirred overnight at room temperature and then at 45° C. for 1 hour. The reaction mixture was allowed to cool, diluted with saturated aqueous NH$_4$Cl, extracted with ethyl acetate, and the combined organics washed with brine and dried (MgSO$_4$). The resulting residue was purified by column chromatography on silica gel eluting with 90:10-hexane:ethyl acetate to give 0.043 g (42%) the desired compound as a yellow foam.

MS (DCI/NH$_3$) m/e 392 (M+H)$^+$; $^1$H NMR (300 MHz, DMSO-d$_6$) δ 7.99 (d, J=9 Hz, 1H), 7.05 (t, J=8 Hz, 1H), 6.86 (dd, J=4, 16 Hz, 1H), 6.69 (d, J=7 Hz, 1H), 6.67 (d, J=9 Hz, 1H), 6.61 (d, J=8 Hz, 1H), 6.41 (dd, J=2, 4 Hz, 1H), 6.26 (d, J=2 Hz, 1H), 5.63 (dd, J=2, 16 Hz, 1H), 5.45 (br s, 1H), 3.84 (s, 3H), 3.56 (s, 3H), 2.08 (s, 3H), 1.19 (s, 3H), 1.15 (s, 3H); $^{13}$C NMR (100 MHz, DMSO-d$_6$) δ 165.19, 156.18, 151.64, 146.45, 145.59, 133.53, 128.39, 127.17, 123.57, 117.17, 116.54, 113.85, 109.82, 105.78, 71.93, 55.80, 55.59, 51.57, 49.75, 29.56, 29.15, 28.70, 23.45; Anal. calcd for C$_{24}$H$_{25}$NO$_4$.1/4H$_2$O: C, 72.80; H, 6.49; N, 3.54. Found: C, 73.00; H, 6.56; N, 3.34.

EXAMPLE 180

(Z)-2,5-Dihydro-10-methoxy-5-(1-propenyl)-2,2,4-trimethyl-1H-[1]benzopyrano[3,4-f]quinoline The intermediate aldehyde from Example 179 and ethyltriphenylphosphonium iodide were processed according to Example 187 to provide the desired compound.

MS (DCI/NH$_3$) m/e 348 (M+H)$^+$; $^1$H NMR (300 MHz, DMSO-d$_6$) δ 7.90 (d, J=8 Hz, 1H), 6.97 (t, J=6 Hz, 1H), 6.67 (d, J=8 Hz, 1H), 6.52 (d, J=8 Hz, 1H), 6.48 (d, J=12 Hz, 1H), 6.26 (d, J=7 Hz, 1H), 6.10 (s, 1H), 5.59 (m, 1H), 5.41 (s, 2H), 3.83 (s, 3H), 2.08 (s, 3H), 1.79 (d, J=7 Hz, 3H), 1.23 (s, 3H), 1.11 (s, 3H); $^{13}$C NMR (125 MHz, DMSO-d$_6$) δ 156.1, 152.4, 145.4, 132.4, 131.0, 130.2, 127.7, 127.2, 127.0, 126.7, 116.9, 116.4, 113.7, 113.0, 109.9, 105.4, 69.4, 55.6, 49.7, 29.6, 28.3, 23.0, 13.8; Anal. calcd for C$_{23}$H$_{25}$O$_2$N.1.0H$_2$O: C, 75.59; H, 7.45; N, 3.83. Found: C, 75.53; H, 7.20; N, 3.62.

EXAMPLE 181

(E) 2,5-Dihydro-10-methoxy-5-(3-hydroxy-1-propenyl)-2,2,4-trimethyl-1H-[1]benzopyrano[3,4-f]quinoline A 20 ml ethereal suspension of LiAlH$_4$ (0.200 g, 5.17 mmol) was treated dropwise at room temperature with a 15 ml ethereal solution of AlCl$_3$ (0.230 g, 1.72 mmol), stirred for 15 minutes and treated dropwise with a 20 ml ethereal solution of Example 179. After stirring 1 hour at room temperature, 2 ml H$_2$O was carefully added followed by the dropwise addition of 15% NaOH until a white paste deposited on the bottom of the vessel. The ether solution was decanted, the paste washed several times with ether and the combined organics washed with brine and dried (MgSO$_4$). The residue was purified by column chromatography on silica gel eluting with 25% then 33% ethyl acetate in hexanes to give 0.195 g (78%) of the desired compound as a colorless foam.

$^1$H NMR (300 MHz, DMSO-d$_6$) δ 7.95 (d, J=8 Hz, 1H), 7.01 (t, J=8 Hz, 1H), 6.64 (d, J=9 Hz, 1H), 6.61 (d, J=9 Hz, 1H), 6.52 (d, J=8 Hz, 1H), 6.18 (br d, J=4 Hz, 1H), 6.08 (s, 1H), 5.73–5.66 (m, 1H), 5.51 (5.43, J=m Hz, 1H), 5.41 (s, 1H), 4.65 (t, J=5 Hz, 1H), 3.83 (s, 3H), 3.77 (t, J=5 Hz, 2H), 2.12 (s, 3H), 1.19 (s, 3H), 1.13 (s, 3H); MS (FAB) m/e calcd for C$_{23}$H$_{25}$NO$_3$: 363.183. Found 363.1839.

EXAMPLE 182

(E) 2,5-Dihydro-10-methoxy-5-(3-(N,N-dimethylaminocarbonyloxy)-1-propenyl)-2,2,4-trimethyl-1H-[1]benzopyrano[3,4-f]quinoline Example 181 (0.035 g, 0.096 mmol) was dissoved in DMF (5 ml), treated with NaH (0.012 g 60% dispersion in oil, 0.289 mmol) at room temperature, stirred for 10 minutes, treated dropwise with N,N-dimethylcarbamoyl chloride (44 μl, 0.481 mmol) and stirred for 30 minutes. The reaction mixture was diluted with 10 ml saturated aqueous NH$_4$Cl, extracted with ethyl acetate, the organic layers washed with H$_2$O, brine, dried (MgSO$_4$), concentrated, and purified by silica gel chromatography eluting with 25% then 33% ethyl acetate in hexanes to give 0.033 g (79%) of the desired compound as a colorless foam.

MS (DCI/NH$_3$) m/e 509 (M+H)$^+$; $^1$H NMR (300 MHz, DMSO-d$_6$) δ 7.94 (d, J=9 Hz, 1H), 7.02 (t, J=8 Hz, 1H), 6.66 (d, J=8 Hz, 1H), 6.63 (d, J=9 Hz, 1H), 6.53 (d, J=8 Hz, 1H), 6.17 (m, 2H), 5.82 (dd, J=16, 4 Hz, 1H), 5.49–5.42 (m, 1H), 5.42 (s, 1H), 4.31 (d, J=6 Hz, 2H), 3.82 (s, 3H), 2.71 (m, 6H), 2.09 (s, 3H), 1.20 (s, 3H), 1.12 (s, 3H); $^{13}$C NMR (100 MHz, DMSO-d$_6$) δ 156.1, 155.1, 151.8, 145.4, 133.0, 131.5, 130.0, 129.8, 127.6, 127.0, 126.8, 117.3, 116.9, 113.7, 113.5, 110.0, 105.6, 72.9, 63.8, 55.7, 55.6, 49.7, 29.3, 28.5, 28.4, 23.3; MS (FAB) m/e calcd for C$_{26}$H$_{30}$N$_2$O$_4$: 434.2206. Found 434.2209.

EXAMPLE 183

(E) 2,5-Dihydro-10-methoxy-5-(3-methoxymethoxy-1-propenyl)-2,2,4-trimethyl-1H-[1]benzopyrano[3,4-f]quinoline Example 181 (0.026 g, 0.072 mmol) was dissolved in dichloroethane (5 ml), cooled to 0° C., treated with (i-Pr)$_2$NEt (62 μl, 0.358 mmol) followed by chloromethyl methyl ether (16 μl, 0.215 mmol) the bath removed and the mixture heated to 55° C. for 14 hours. The mixutre was partitioned between ethyl acetate and saturated aqueous NH$_4$Cl, the organic layer washed with brine, dried (MgSO$_4$) and purified by silica gel chromatography eluting with 10% ethyl acetate in hexanes to give 0.012 g (41%) of the desired compound as an amber oil.

$^1$H NMR (300 MHz, DMSO-d$_6$) δ 7.94 (d, J=8 Hz, 1H), 7.02 (t, J=8 Hz, 1H), 6.66 (d, J=9 Hz, 1H), 6.63 (d, J=9 Hz, 1H), 6.53 (d, J=8 Hz, 1H), 6.19 (br d, J=3 Hz, 1H), 6.14 (d, J=2 Hz, 1H), 5.78 (dd, J=16, 4 Hz, 1H), 5.42 (s, 1H), 4.31 (ABq, J=8, 6 Hz, 2H), 3.84 (m, 2H), 3.82 (s, 3H), 3.09 (s, 3H), 2.11 (s, 3H), 1.20 (s, 3H), 1.13 (s, 3H); MS (FAB) m/e calcd for C$_{25}$H$_{29}$NO$_4$: 407.2097. Found 407.2090.

EXAMPLE 184

2,5-Dihydro-10-methoxy-5-(3-hydroxy-3-propenyl)-2,2,4-trimethyl-1H-[1]benzopyrano[3,4-f]quinoline Example 44 (0.58 g, 1.74 mmol) was dissolved in CH$_2$Cl$_2$ (40 ml), cooled to −45° C., treated dropwise with 2.09 ml 1M Dibal-H/heptane solution (2.09 mmol) and stirred for 1 h. The reaction mixture was poured into 75 ml 0.5 M HCl, stirred 30 min, extracted with ethyl acetate, the combined organics washed with brine, dried (Na$_2$SO$_4$) and concentrated to give 0.55 g crude aldehyde as a yellow foam. The resulting aldehyde (0.048 g, 0.143 mmol) was dissolved in THF (5 ml) cooled to 0° C., and treated slowly with vinylmagnesium bromide (0.72 ml 1M/THF, 0.72 mmol). After stirring 15 minutes, the mixture was partitioned between ethyl acetate and brine, the aqueous layer extracted with ethyl acetate and combined organics washed with brine, dried (Na$_2$SO$_4$), concentrated and purified by silica gel chromatography eluting with 20% ethyl acetate in hexanes to give the desired compound (0.027 g, 53%) as an inseparable 1:1 mixture of diastereomers.

MAJOR:

$^1$H NMR (300 MHz, DMSO-d$_6$) δ 7.97 (d, J=8 Hz, 1H), 7.04 (t, J=8 Hz, 1H), 6.68 (d, J=8 Hz, 1H), 6.59 (d, J=8 Hz, 1H), 6.48 (d, J=8 Hz, 1H), 6.03 (br s, 1H), 5.61 (s, 1H), 5.46 (m, 1H), 5.36 (m, 1H), 4.97–5.10 (m, 1H), 4.87 (m, 1H), 3.94 (m, 1H), 3.85 (s, 3H), 2.19 (s, 3H), 1.23 (s, 3H), 1.10 (s, 3H);

MINOR:

MS (DCI/NH$_3$) m/e 364 (M+H)$^+$; $^1$H NMR (300 MHz, DMSO-d$_6$) δ 8.02 (d, J=8 Hz, 1H), 7.07 (t, J=8 Hz, 1H), 6.68 (d, J=8 Hz, 1H), 6.62 (d, J=8 Hz, 1H), 6.61 (d, J=8 Hz, 1H), 6.16 (br s, 1H), 5.95 (m, 1H), 5.58 (s, 1H), 5.41 (s, 1H), 4.97–5.10 (m, 2H), 3.94 (m, 1H), 3.85 (s, 3H), 2.11 (s, 3H), 1.27 (s, 3H), 1.01 (s, 3H); MS (DCI/NH$_3$) m/e (M+H)$^+$ 364; Anal. calcd for C$_{23}$H$_{25}$NO$_3$.3/4H$_2$O: C, 73.29; H, 7.09; N, 3.72. Found: C, 73.67; H, 6.80; N, 3.81.

EXAMPLE 185

Methyl 2-(2,5-Dihydro-10-methoxy-2,2,4-trimethyl-1H-[1]benzopyrano[3,4-f]quinolin-5-yl)acetyl Hydroxamate Example 46 (0.150 g, 0.395 mmol) was added dropwise to a solution of N,O-dimethylhydroxylamine hydrochloride (0.192 g, 1.98 mmol) and trimethylaluminium (1.0 mL, 2.0 mmol and the resulting mixture heated at 40° C. for 2 hours, quenched with methanol and partitioned between methylene chloride and saturated aqueous Rochelle's salt. The organic layer was washed with saturated aqueous sodium bicarbonate, brine, and dried (MgSO$_4$). The crude product was purified by flash chromatography on silica gel eluting with 4% then 10% ethyl acetate in methylene chloride to give the desired compound (62%) as a white foam.

MS (DCI/NH$_3$) m/e 409 (M+H)$^+$; $^1$H NMR (300 MHz, DMSO-d$_6$) δ 7.79 (d, J=8 Hz, 1H), 7.05 (dd, J=8 Hz, 1H), 6.73 (d, J=8 Hz, 1H), 6.61 (d, J=8 Hz, 1H), 6.48 (d, J=8 Hz, 1H), 6.25 (dd, J=2+10 Hz, 1H), 6.16 (s, 1H), 5.43 (s, 1H), 3.87 (s, 3H), 3.25 (br s, 3H), 3.04 (br s, 3H), 2.34 (m, 1H), 2.18 (s, 3H), 1.17 (s, 6H); Anal. calcd for C$_{24}$H$_{28}$N$_2$O$_4$: C, 70.57; H, 6.91; N, 6.86. Found: C, 70.74; H, 7.11; N, 6.59.

EXAMPLE 186

2-(2,5-Dihydro-10-methoxy-2,2,4-trimethyl-1H-[1]benzopyrano[3,4-f]quinolin-5-yl)acetaldehyde Example 185 (0.334 g, 0.817 mmol) was dissolved in THF (20 ml), cooled to −78° C., and treated with 1M Dibal-H in toluene (1.71 mL, 1.71 mmol) over 5 minutes and stirred for 1 hour. The reaction mixture was poured into saturated potassium sodium tartrate, the layers separated, the aqueous phase extracted with CH$_2$Cl$_2$, the combined organics washed with saturated aqueous sodium bicarbonate, brine, dried (MgSO$_4$), and purified by silica gel chromatography eluting with 30% ethyl acetate in hexane to give 0.265 g (93%) of the desired product as a colorless foam.

MS (DCI/NH$_3$) m/e 350 (M+H)$^+$; $^1$H NMR (300 MHz, DMSO-d$_6$) δ 9.65 (s, 1H), 7.95 (d, J=9 Hz, 1H), 7.05 (dd, J=8 Hz, 1H), 6.73 (d, J=8 Hz, 1H), 6.60 (d, J=8 Hz, 1H), 6.45 (d, J=8 Hz, 1H), 6.35 (dd, J=3+10 Hz, 1H), 6.20 (s, 1H), 5.45 (s, 1H), 3.85 (s, 3H), 2.85 (m, 1H), 2.60 (m, 1H), 2.15 (s, 3H), 1.17 (s, 3H), 1.15 (s, 3H); Anal. calcd for C$_{22}$H$_{23}$NO$_3$·1/4H$_2$O: C, 74.66; H, 6.69; N, 3.96. Found: C, 74.32; H, 6.30; N, 3.86.

EXAMPLE 187

2,5-Dihydro-10-methoxy-5-(2-cyclohexylidenylethyl)-2,2,4-trimethyl-1H-[1]benzopyrano[3,4-f]quinoline Cyclohexyltriphenylphosphonium bromide (Grim, S. O.; Ambrus, J. H.; *J. Org. Chem.* 1968, 33, 2993–2994.) (0.234 g, 0.55 mol) was suspended in (5:3) THF:Ether (8.0 ml), cooled to −10° C., treated with 220 μl of 2.5 M n-butyl lithium, stirred for 10 minutes. Example 186 was added as a solution in THF and the reaction was allowed to stir at room temperature 12 hours, refluxed for 15 minutes and allowed to cool. Diethyl ether was added and the reaction was filtered and concentrated. The resulting residue was purified by silica gel chromatography eluting with 10:1 to 5:1 hexanes:ethyl acetate to afford 0.033 g (51%) desired compound.: m.p. 130–135° C.;

MS (DCI/NH$_3$) m/e 416 (M+H)$^+$; $^1$H NMR (300 MHz, DMSO-d$_6$) δ 7.03 (t, J=9 Hz, 1H), 6.67 (d, J=8 Hz, 1H), 6.57 (d, J=9 Hz, 1H), 6.50 (d, J=8 Hz, 1H), 6.11 (s, 1H), 5.64 (dd, J=10, 10 Hz, 1H), 5.43 (s, 1H), 5.04 (t, J=7 Hz, 1H), 3.85 (s, 3H), 2.10 (s, 3H), 2.0 (b, 2H), 1.81 (t, J=7 Hz, 2H), 1.45 (b, 3H), 1.3 (b, 3H), 1.17 (s, 3H), 1.15 (s, 3H); $^{13}$C NMR (100 MHz, DMSO-d$_6$) δ 165.0, 151.1, 145.4, 140.5, 133.41, 132.2, 127.5, 127.0, 126.8, 116.5, 116.3, 116.0, 113.0, 110.3, 105.3, 73.9, 55.5, 49.6, 36.6, 30.5, 28.9, 28.7, 28.1, 27.9, 27.0, 26.2, 23.8.

EXAMPLE 188

2,5-Dihydro-10-methoxy-5-(2-cyclopentylidenylethyl)-2,2,4-trimethyl-1H-[1]benzopyrano[3,4-f]quinoline Example 186 and cyclopentyltriphenylphosphonium bromide (Ramirez, F.; Levy, S. *JACS* 1957, 79, 67–69.) were processed according to Example 187 to provide the desired compound.

$^1$H NMR (300 MHz, DMSO-d$_6$) δ 7.94 (d, J=9 Hz, 1H), 7.02 (t, J=8 Hz, 1H), 6.67 (d, J=8 Hz, 1H), 6.57 (d, J=9 Hz, 1H), 6.48 (d, J=7 Hz, 1H), 6.10 (s, 1H), 5.56 (d, J=10, 8 Hz, 1H), 5.43 (s, 1H), 5.22 (b, 1H), 3.85 (s, 3H), 2.14 (s, 6H), 1.77 (b, 2H), 1.49 (b, 4H), 1.17 (s, 3H), 1.14 (s, 3H); $^{13}$C NMR (75 MHz, DMSO-d$_6$) δ 156.1, 151.2, 145.4, 144.6, 133.4, 132.3, 127.6, 127.0, 126.8, 116.4, 116.1, 115.3, 113.3, 113.1, 110.3, 105.3, 73.6, 55.6, 49.6, 33.1, 29.0, 28.7, 28.0, 25.8, 25.7, 23.8; HRMS (FAB) m/e calcd for C$_{27}$H$_{32}$O$_2$N: 401.2355. Found 401.2342.

EXAMPLE 189

2,5-Dihydro-10-methoxy-5-(2-cycloheptylidenylethyl)-2,2,4-trimethyl-1H-[1]benzopyrano[3,4-f]quinoline Example 186 and cycloheptyltriphenylphoshonium bromide (Albright, T. A.; Freeman, W. J.; Schweizer, E. E. *JACS* 1974, 97, 2942–2943.) were processed according to example 186 to provide the desired compound.

MS (DCI/NH$_3$) m/e 430 (M+H)$^+$; $^1$H NMR (300 MHz, DMSO-d$_6$) δ 7.94 (d, J=9 Hz, 1H), 7.02 (t, J=8 Hz, 1H), 6.67 (d, J=8 Hz, 1H), 6.57 (d, J=9 Hz, 1H), 6.49 (d, J=8 Hz, 1H), 6.12 (s, 1H), 5.69 (dd, J=10, 9 Hz, 1H), 5.43 (s, 1H), 5.12 (t, J=7 Hz, 1H), 3.85 (s, 3H), 2.13 (s, 6H), 1.90 (b, 2H), 1.38 (b, 3H), 1.27 (m, 4H), 1.17 (s, 3H), 1.14 (s, 3H), 0.82 (m, 3H); $^{13}$C NMR (75 MHz, DMSO-d$_6$) δ 156.1, 151.1, 145.4, 142.2, 133.4, 132.2, 128.6, 127.6, 127.0, 126.8, 120.0, 116.3, 116.0, 113.0, 110.3, 105.3, 73.6, 65.7, 55.6, 49.6, 37.3, 33.2, 31.1, 29.8, 29.3, 29.2, 29.0, 28.6, 28.5, 26.2, 23.8, 23.2; Anal. calcd for C$_{29}$H$_{35}$O$_2$N$_2$·3/4H$_2$O: C, 72.70; H, 8.52; N, 2.92. Found: C, 72.50; H, 8.11; N, 2.47.

EXAMPLE 190

2,5-Dihydro-10-methoxy-5-(3-methyl-2-butenyl)-2,2,4-trimethyl-1H-[1]benzopyrano[3,4f-]quinoline Example 186 and isopropyltriphenylphosphonium iodide were processed according to Example 187 to provide the desired compound.

$^1$H NMR (300 MHz, DMSO-d$_6$) δ 7.94 (d, J=8 Hz, 1H), 7.37 (s, 1H), 7.03 (t, J=8 Hz, 1H), 6.67 (d, J=7 Hz, 1H), 6.57 (d, J=8 Hz, 1H), 6.49 (d, J=8 Hz, 1H), 6.11 (s, 1H), 5.65 (dd, J=10, 9 Hz, 1H), 5.43 (s, 1H), 5.12 (t, J=7 Hz, 1H), 3.85 (s, 3H), 2.14 (s, 3H), 1.63 (s, 3H), 1.31 (s, 3H), 1.17 (s, 3H), 1.15 (s, 3H); $^{13}$C NMR (100 MHz, DMSO-d$_6$) δ 156.1, 151.1, 145.4, 133.4, 132.8, 132.2, 127.6, 127.0, 126.9, 119.8, 116.4, 116.1, 113.3, 113.1, 110.3, 105.3, 73.7, 55.6, 49.6, 31.5, 29.0, 28.7, 25.6, 23.8, 17.5; HRMS (FAB) m/e calc'd for C$_{25}$H$_{29}$O$_2$N: 375.2198. Found 375.2189.

EXAMPLE 191 trans 2,5-Dihydro-10-methoxy-5-(2-butenyl)-2,2,4-trimethyl-1H-[1]benzopyrano[3,4-f]quinoline Example 186 and ethyltriphenylphosphonium bromide were processed according to example 186 to provide the desired compound.

MS (DCI/NH$_3$) m/e 362 (M+H)$^+$; $^1$H NMR (300 MHz, DMSO-d$_6$) δ 7.96 (d, J=8 Hz, 1H), 7.05 (dd, J=8 Hz, 1H), 6.70 (d, J=8 Hz, 1H), 6.60 (d, J=8 Hz, 1H), 6.51 (d, J=8 Hz, 1H), 6.10 (s, 1H), 5.72 (dd, J=4+10 Hz, 1H), 5.45 (m, 3H), 3.86 (s, 3H), 2.43 (m, 1H), 2.20 (m, 1H), 2.15 (s, 3H), 1.30 (d, J=5 Hz, 3H), 1.17 (s, 3H), 1.15 (s, 3H).

EXAMPLE 192 trans 2,5-Dihydro-10-methoxy-5-(2-penten-1-yl)-2, 2,4-trimethyl-1H-[1]benzopyrano[3,4-f]quinoline Example 186 (0.050 g, 0.143 mmol) and propyltriphenylphosphonium bromide (165.6 mg, 0.429 mmol) were processed as in example 187 to give the desired compound.

MS (DCI/NH$_3$) m/e 376 (M+H)$^+$; $^1$H NMR (300 MHz, DMSO-d$_6$) δ 7.95 (d, J=9 Hz, 1H), 7.05 (dd, J=8 Hz, 1H), 6.70 (d, J=8 Hz, 1H), 6.60 (d, J=8 Hz, 1H), 6.50 (d, J=8 Hz, 1H), 6.09 (s, 1H), 5.70 (dd, J=3, 10 Hz, 1H), 5.44 (s, 1H), 5.38 (ss, J=5 Hz, 2H), 3.86 (s, 3H), 2.41 (m, 1H), 2.19 (m, 1H), 2.15 (s, 3H), 1.70 (m, 2H), 1.15 (s, 6H), 0.75 (t, J=7 Hz, 3H).

EXAMPLE 193

2,5-Dihydro-10-methoxy-5-(1,1-difluoro-1-propen-3-yl)-2,2,4-trimethyl-1H-[1]benzopyrano[3,4-f]quinoline Example 186 (0.050 g, 0.143 mmol) and diphenylphosphoranyl difluromethane (Edwards, M. L., et. al. *Tet. Let.* 1990, 31, 5571–74) were processed as in example 187 to give the desired compound.

$^1$H NMR (300 MHz, DMSO-d$_6$) δ 7.98 (d, J=8 Hz, 1H), 7.08 (t, J=8 Hz, 1H), 6.71 (d, J=9 Hz, 1H), 6.62 (d, J=9 Hz, 1H), 6.57 (d, J=9 Hz, 1H), 6.17 (s, 1H), 5.73 (dd, J=4, 10 Hz, 1H), 5.46 (s, 1H), 4.53 (m, 1H), 3.86 (s, 3H), 2.32 (m, 1H), 2.16 (s, 3H), 2.11 (m, 1H), 1.17 (s, 3H), 1.15 (s, 3H); HRMS (FAB) m/e calc'd 383.1697. Found 383.1689.

EXAMPLE 194

(E) Methyl 2-(2,5-Dihydro-10-methoxy-2,2,4-trimethyl-1H-[1]benzopyrano[3,4-f]quinolin-5-yl) 2-Butenoate Example 186 (0.040 g, 0.115 mmol) and methyl (triphenylphosphoranylidene)acetate (115 mg, 0.344 mmol, Aldrich) were processed according to example 179 to give 0.037 g (80%) of the desired compound as a white foam.

MS (DCI/NH$_3$) m/e 406 (M+H)$^+$; $^1$H NMR (300 MHz, DMSO-d$_6$) δ 7.95 (d, J=9 Hz, 1H), 7.07 (dd, J=8 Hz, 1H), 6.85 (m, 1H), 6.72 (d, J=8 Hz, 1H), 6.60 (d, J=8 Hz, 1H), 6.50 (d, J=8 Hz, 1H), 6.15 (s, 1H), 5.87 (dd, J=3+10 Hz, 1H), 5.80 (d, J=14 Hz, 1H), 5.45 (s, 1H), 3.88 (s, 3H), 3.65 (s, 3H), 2.60 (m, 1H), 2.45 (m, 1H), 2.15 (s, 3H), 1.15 (br s, 6H); $^{13}$C NMR (75 MHz, DMSO-d$_6$) δ 165.8, 156.2, 150.5, 145.6, 144.8, 133.6, 131.3, 127.4, 127.2, 122.7, 116.3, 115.9, 113.4, 113.1, 110.2, 105.7, 72.4, 55.6, 51.3, 49.7, 34.9, 29.0, 28.9, 28.9, 23.9; Anal. calcd for C$_{25}$H$_{27}$NO$_4$.1/2H$_2$O: C, 72.44; H, 6.81; N, 3.38. Found: C, 72.55; H, 6.71; N, 3.22.

EXAMPLE 195

(E) 2,5-Dihydro-10-methoxy-5-(4-hydroxy-2-buten-1-yl)-2,2,4-trimethyl-1H-[1]benzopyrano[3,4-f]quinoline Example 194 (0.063 g, 0.155 mmol) in Et$_2$O was treated dropwise with a slurry containing LiAlH$_4$ (0.044 g, 1.16 mmol) and AlCl$_3$ (0.041 g, 0.308 mmol) for 1 hour. The reaction mixture was diluted with Et$_2$O and treated with 2 drops of H$_2$O followed by 15% NaOH until a white paste formed. The Et$_2$O was decanted and the paste washed 2 times with Et$_2$O. The combined organics were washed with saturated aqueous sodium bicarbonate, brine, dried (MgSO$_4$), and purified by silica gel chromatography eluting with 6% then 10% ethyl acetate in methylene chloride to give 0.031 g (53%) of the desired compound.

MS (DCI/NH$_3$) m/e 378 (M+H)$^+$; $^1$H NMR (300 MHz, DMSO-d$_6$) δ 7.94 (d, J=9 Hz, 1H), 7.07 (dd, J=8 Hz, 1H), 6.70 (d, J=8 Hz, 1H), 6.60 (d, J=8 Hz, 1H), 6.54 (d, J=8 Hz, 1H), 6.12 (s, 1H), 5.70 (dd, J=3+10 Hz, 1H), 5.4–5.69 (m, 3H), 4.63 (dd, J=6 Hz, 1H), 3.87 (m, 5H), 3.31 (s, 3H), 2.40 (m, 1H), 2.15 (s, 3H), 1.15 (s, 6H); Anal. calcd for C$_{24}$H$_{27}$NO$_3$.1/4H$_2$O: C, 75.47; H, 7.26; N, 3.67. Found: C, 75.62; H, 7.40; N, 3.59.

EXAMPLE 196

(E) 2,5-Dihydro-10-methoxy-5-(4-(N,N-dimethylaminocarbonyloxy)-2-buten-1-yl)-2,2,4-trimethyl-1H-[1]benzopyrano[3,4-f]quinoline Example 195 and disuccinimidyl carbonate were processed as in Example 200 to give the an intermediate succinate ester.

The intermediate succinate ester and N,N-dimethylamine were processed as in Example 200 to give the desired compound.

MS (DCI/NH$_3$) m/e 449 (M+H)$^+$; $^1$H NMR (400 MHz, DMSO-d$_6$) δ 7.95 (d, J=9 Hz, 1H), 7.07 (t, J=8 Hz, 1H), 6.70 (d, J=8 Hz, 1H), 6.59 (d, J=8 Hz, 1H), 6.52 (d, J=8 Hz, 1H), 6.09 (s, 1H), 5.74 (dd, J=3, 10 Hz, 1H), 5.65 (m, 1H), 5.48 (m, 1H), 5.43 (s, 1H), 3.85 (s, 3H), 3.79 (d, J=5 Hz, 2H), 2.45 (m, 1H), 2.20 (m, 1H), 2.15 (s, 3H), 1.17 (s, 3H), 1.16 (s, 3H); $^{13}$C NMR (100 MHz, DMSO-d$_6$) δ 156.1, 150.9, 145.5, 133.6, 132.0, 129.0, 128.6, 127.4, 127.1, 127.0, 116.2, 115.9, 113 (3), 113.2, 110.3, 105.4, 73.5, 72.0, 56.9, 55.6, 49.7, 35.0, 28.9, 23.3; Anal. calcd for C$_{27}$H$_{32}$N$_2$O$_4$: C, 72.30; H, 7.19; N, 6.25. Found: C, 72.10; H, 7.11; N 5.98.

EXAMPLE 197

(E) 2,5-Dihydro-10-methoxy-5-(4-(N-methylaminocarbonyloxy)-2-buten-1-yl)-2,2,4-trimethyl-1H-[1]benzopyrano[3,4-f]quinoline The intermediate succinate ester from Example 196 and methylamine were processed as in Example 200 to give the desired compound.

MS (DCI/NH$_3$) m/e 435 (M+H)$^+$; $^1$H NMR (300 MHz, DMSO-d$_6$) δ 7.95 (d, J=8 Hz, 1H), 7.05 (t, J=8 Hz, 1H), 6.95 (m, 1H), 6.70 (d, J=8 Hz, 1H), 6.57 (d, J=8 Hz, 1H), 6.52 (d, J=8 Hz, 1H), 6.08 (s, 1H), 5.70 (m, 2H), 5.50 (m, 1H), 5.43 (s, 1H), 4.35 (d, J=5 Hz, 2H), 3.85 (s, 3H), 2.56 (d, J=5 Hz, 3H), 2.42 (m, 1H), 2.20 (m, 1H), 2.15 (s, 3H), 1.15 (s, 6H); Anal. calcd for C$_{26}$H$_{30}$N$_2$O$_4$: C, 71.87; H, 6.96; N, 6.45. Found: C, 71.66; H, 7.25; N, 6.07.

EXAMPLE 198

(E) 2,5-Dihydro-10-methoxy-5-(2-butenyl)-2,2,4-trimethyl-1H-[1]benzopyrano[3,4-f]quinoline Example 195 (0.080 g, 0.212 mmol) was dissolved in CH$_2$Cl$_2$ (10 ml), cooled to −10° C., treated with (i-Pr)$_2$NEt (55 µL, 0.318 mmol) followed by methanesulfonyl chloride (20 μL, 0.255 mmol), stirred for 1 hr and allowed to warm to room temperature. The mixture was recooled to −10° C. and treated dropwise with lithium triethylborohydride (635 μL, 0.635 mmol), stirred for 1 hr, allowed to warm to room temperature, treated with 5.0 ml of 1N NaOH followed by 0.11 ml of 30% $H_2O_2$ and stirred for 30 minutes. The mixture was partitioned between water and ethyl acetate, the aqueous extacted with ethyl acetate and the combined organics washed with water, brine, and dried ($Na_2SO_4$). Purification by silica gel chromatography eluting with 15:1 then 7:1 hexanes:ethyl acetate provided 0.029 g (38%) desired compound.

$^1$H NMR (360 MHz, DMSO-$d_6$) δ 7.93 (d, J=9 Hz, 1H), 7.04 (t, J=8 Hz, 1H), 6.68 (d, J=8 Hz, 1H), 6.57 (d, J=8 Hz, 1H), 6.51 (d, J=7 Hz, 1H), 6.11 (s, 1H), 5.67 (dd, J=10 Hz, 1H), 5.41 (t, J=9 Hz, 1H), 5.34 (t, J=11 Hz, 1H), 3.85 (s, 3H), 2.34 (m, 1H), 2.15 (s, 3H), 1.59 (dd, J=5 Hz, 3H), 1.17 (s, 3H), 1.15 (s, 3H); $^{13}$C NMR (100 MHz, DMSO-$d_6$) δ 156.2, 151.0, 145.4, 133.4, 132.1, 127.1, 127.0, 126.9, 126.6, 125.5, 115.9, 113.2, 110.0, 105.3, 73.7, 55.5, 49.6, 35.4, 28.9, 28.8, 23.9, 17.8; HRMS (FAB) calc'd for $C_{24}H_{28}O_2N$: m/e 362.2120. Found 362.2119.

EXAMPLE 199

2,5-Dihydro-10-methoxy-5-(2-hydroxyethyl)-2,2,4-trimethyl-1H-[1]benzopyrano[3,4-f]quinoline Example 46 (0.100 g, 0.264 mmol) was treated with 1M Dibal-H in toluene (0.544 ml, 0.544 mmol) at −78° C., warmed to room temperature, quenched with methanol and the partitioned between methylene chloride and saturated aqueous Rochelle's salt. The organic layer was washed with 1HCl, saturated aqueous sodium bicarbonate, brine, and dried ($MgSO_4$). The resulting crude product was purified by flash chromatography on silica gel eluting with 10% ethyl acetate in methylene chloride to give (87%) of the desired compound as a white solid.

MS (DCI/$NH_3$) m/e 352 (M+H)$^+$; $^1$H NMR (300 MHz, DMSO-$d_6$) δ 7.95 (d, J=8 Hz, 1H), 7.05 (dd, J=8 Hz, 1H), 6.69 (d, J=8 Hz, 1H), 6.59 (d, J=8 Hz, 1H), 6.55 (d, J=8 Hz, 1H), 610 (s, 1H), 5.59 (dd, J=2, 10 Hz, 1H), 5.43 (s, 1H), 4.61 (t, J=6 Hz, 1H), 3.84 (s, 3H), 3.52 (m, 1H), 2.20 (s, 3H), 1.80 (m, 1H), 1.50 (m, 1H), 1.19 (s, 3H), 1.16 (s, 3H).

EXAMPLE 200

2,5-Dihydro-10-methoxy-5-(2-(N-benzylcarbonyloxy)ethyl)-2,2,4-trimethyl-1H-[1]benzopyrano[3,4-f]quinoline Example 199 (0.200 g, 0.57 mmol) was combined with N,N'-disuccinimidyl carbonate (0.217 g, 0.85 mmol), (i-Pr)$_2$NEt (0.30 ml, 1.71 mmol), and acetonitrile (2 mL), stirred at room temperature 2 hours and partitioned between $CH_2Cl_2$ and saturated aqueous sodium bicarbonate. The organic layer was washed with brine, dried ($MgSO_4$), and purified by silica gel chromatography eluting with 6% ethyl acetate in dichloromethane to give 0.252 g (90%) of the succinate ester as a white foam.

The succinate ester (0.020 g, 0.041 mmol), benzyl amine (6.6 μl, 0.061 mmol), and $CH_2Cl_2$ (3 ml) were combined and stirred for 20 minutes at room temperature. The reaction mixture was diluted with $CH_2Cl_2$ and the organic layers washed with $H_2O$, saturated aqueous sodium bicarbonate, brine, dried ($MgSO_4$) and purified by silica gel chromatography eluting with 20% ethyl acetate in hexane to give 19 mg (97%) of the desired compound as a white solid.

MS (DCI/$NH_3$) m/e 485 (M+H)$^+$; $^1$H NMR (400 MHz, DMSO-$d_6$) δ 7.95 (d, J=9 Hz, 1H), 7.68 (t, J=6 Hz, 1H), 7.25 (m, 3H), 7.07 (t, J=8 Hz, 1H), 6.71 (d, J=8 Hz, 1H), 6.59 (dd, J=8 Hz, 1H), 6.11 (s, 1H), 5.86 (d, J=8 Hz, 1H), 5.40 (s, 1H), 4.18 (m, 2H), 4.00 (m, 2H), 3.85 (s, 3H), 2.12 (s, 3H), 1.90 (m, 1H), 1.71 (m, 1H), 1.17 (s, 3H), 1.15 (s, 3H); $^{13}$C NMR (100 MHz, DMSO-$d_6$) δ 156.3, 156.1, 150.7, 145.6, 139.7, 133.5, 131.9, 128.2, 127.5, 127.2, 127.1, 127.0, 126.7, 116.3, 115.9, 113.2, 113.2, 110.2, 110.1, 105.6, 70.3, 60.2, 55.6, 49.6, 43.7, 31.5, 28.8, 28.7, 23.8; Anal. calcd for $C_{30}H_{32}N_2O_5 \cdot H_2O$: C, 71.69; H, 6.82; N, 5.57. Found: C, 71.45; H, N, 5.56.

EXAMPLE 201

2,5-Dihydro-10-methoxy-5-(2-(N-morpholinocarbonyloxy)ethyl)-2,2,4-trimethyl-1H-[1]benzopyrano[3,4-f]quinoline The intermediate succinate ester from Example 200 and morpholine were processed as in Example 200 to give the desired compound.

MS (DCI/$NH_3$) m/e 465 (M+H)$^+$; $^1$H NMR (400 MHz, DMSO-$d_6$) δ 7.95 (d, J=9 Hz, 1H), 7.07 (t, J=8 Hz, 1H), 6.71 (d, J=8 Hz, 1H), 6.60 (d, J=8 Hz, 1H), 6.57 (d, J=8 Hz, 1H), 6.10 (s, 1H), 5.88 (dd, J=3+10 Hz, 1H), 5.44 (s, 1H), 4.05 (m, 2H), 3.85 (s, 3H), 3.75 (m, 4H), 2.16 (s, 3H), 1.85 (m, 1H), 1.78 (m, 1H), 1.16 (s, 3H), 1.15 (s, 3H); $^{13}$C NMR (100 MHz, DMSO-$d_6$) δ 156.2, 154.4, 150.6, 145.6, 133.5, 131.8, 127.3, 127.2, 127.1, 116 (1), 115.9, 113.2, 113.2, 110.1, 105.6, 70.3, 65.8, 61 (2), 55.6, 49.7, 43.7, 43.6, 31.3, 29.0, 28.9, 23.8; Anal. calcd for $C_{27}H_{32}N_2O_5 \cdot 1/4H_2O$: C, 69.14; H, 6.98; N, 5.97. Found: C, 68.96; H, 7.05; N, 5.94.

EXAMPLE 202

2,5-Dihydro-10-methoxy-5-(2-(N-(2-methoxyethyl)aminocarbonyloxy)ethyl)-2,2,4-trimethyl-1H-[1]benzopyrano[3,4-f]quinoline The intermediate succinate ester from Example 200 and 2-methoxyethyl aminewere processed as in Example 200 to give the desired compound.

MS (DCI/$NH_3$) m/e 453 (M+H)$^+$; $^1$H NMR (500 MHz, DMSO-$d_6$) δ 7.95 (d, J=8 Hz, 1H), 7.13 (m, 1H), 7.04 (t, J=8 Hz, 1H), 6.70 (d, J=8 Hz, 1H), 6.60 (d, J=8 Hz, 1H), 6.56 (d, J=8 Hz, 1H), 6.08 (s, 1H), 5.85 d (10, 1H), 5.45 (s, 1H), 3.95 (m, 2H), 3.85 (s, 3H), 3.25 (s, 3H), 3.12 (m, 2H), 2.15 (s, 3H), 1.92 (m, 1H), 1.72 (m, 1H), 1.15 (d, 6H); $^{13}$C NMR (125 MHz, DMSO-$d_6$) δ 156.1, 156.1, 150.7, 145.6, 133.5, 131.9, 127.6, 127.1, 127.1, 116.3, 116.0, 113.2, 113.2, 110.2, 105.6, 70.7, 70.3, 60.0, 57.8, 55.6, 49.6, 31.5, 28.8, 28.8, 23.8.

EXAMPLE 203

2,5-Dihydro-10-methoxy-5-(2-(N-methyaminocarbonyloxyoxy)ethyl)-2,2,4-trimethyl-1H-[1]benzopyrano[3,4-f]quinoline The intermediate succinate ester from Example 200 and methylamine were processed as in Example 200 to give the desired compound.

MS (DCI/$NH_3$) m/e 409 (M+H)$^+$; $^1$H NMR (500 MHz, DMSO-$d_6$) δ 7.95 (d, J=8 Hz, 1H), 7.04 (t, J=8 Hz, 1H), 6.93 (m, 1H), 6.70 (d, J=8 Hz, 1H), 6.60 (d, J=8 Hz, 1H), 6.56 (d, J=8 Hz, 1H), 6.08 (s, 1H), 5.85 d (10, 1H), 5.45 (s, 1H), 3.95 (m, 2H), 3.85 (s, 3H), 2.59 (d, 3H), 2.15 (s, 3H), 1.92 (m, 1H), 1.72 (m, 1H), 1. 15 (d, 6H); $^{13}$C NMR (125 MHz,

DMSO-d$_6$) δ 156.6, 156.1, 150.7, 145.6, 133.5, 131.9, 127.5, 127.2, 127.1, 116.3 (116.0), 113.2, 113.2, 113.2, 105.6, 70.3, 60.0, 55.6, 49.6, 31.5, 28.8, 28.8, 26.9, 23.7; Anal. calcd for C$_{24}$H$_{28}$N$_2$O$_4$: C, 70.57; H, 6.91; N, 6.86. Found: C, 70.30; H, 6.91; N, 6.58.

EXAMPLE 204

2,5-Dihydro-10-methoxy-5-(2-(N,N-dimethylaminocarbonyloxy)ethyl)-2,2,4-trimethyl-1H-[1]benzopyrano[3,4-f]quinoline The intermediate succinate ester from Example 200 and N,N-dimethylamine were processed as in Example 200 to give the desired compound as a white solid.

MS (DCI/NH$_3$) m/e 423 (M+H)$^+$; $^1$H NMR (300 MHz, DMSO-d$_6$) δ 7.95 (d, J=8 Hz, 1H), 7.05 (t, J=8 Hz, 1H), 6.69 (d, J=8 Hz, 1H), 6.56 (dd, J=8 Hz, 2H), 6.12 (s, 1H), 5.86 (dd, J=3+10 Hz, 1H), 5.44 (s, 1H), 3.96 (m, 2H), 3.85 (s, 3H), 2.86 (s, 3H), 2.83 (s, 3H), 2.18 (s, 3H), 1.95 (m, 1H), 1.76 (m, 1H). 1.15 (s, 6H).

EXAMPLE 205

2,5-Dihydro-10-methoxy-5-(2-methoxymethoxyethyl)-2,2,4-trimethyl-1H-[1]benzopyrano[3,4-f]quinoline Example 199 (0.040 g, 0.114 mmol) was combined with chloromethyl methyl ether (13 μL, 0.171 mmol), (i-Pr)$_2$NEt (40 μL, 0.228 mmol), and methylene chloride (5 ml) and heated to reflux for 3 hours. The reaction was partitioned between H$_2$O and ethyl acetate, the aqueous layer extracted with ethyl acetate and the combined organic layers washed with saturated aqueous sodium bicarbonate, brine, dried over MgSO$_4$, and purified by silica gel chromatography eluting with 2% then 5% ethyl acetate in methylene chloride to give 45 mg (40%) of the desired product.

MS (DCI/NH$_3$) m/e 396 (M+H)$^+$; $^1$H NMR (300 MHz, DMSO-d$_6$) δ 7.95 (d, J=9 Hz, 1H), 7.05 (t, J=8 Hz, 1H), 6.70 (d, J=8 Hz, 1H), 6.60 (d, J=8 Hz, 1H), 6.55 (d, J=8 Hz, 1H), 6.14 (s, 1H), 5.89 (dd, J=3+10 Hz, 1H), 5.45 (s, 1H), 4.55 (s, 2H), 3.85 (s, 3H), 3.58 (m, 1H), 3.25 (s, 3H), 2.18 (s, 3H), 1.85 (m, 1H), 1.65 (m, 1H), 1.19 (s, 3H), 1.13 (s, 3H); Anal. calcd for C$_{24}$H$_{29}$NO$_4$.1/4H$_2$O: C, 72.07; H, 7.43; N, 3.50. Found: C, 71.90; H, 7.33; N, 3.24.

EXAMPLE 206

2,5-Dihydro-10-methoxy-5-(2,2-dimethylethoxycarbonylamino)methyl)-2,2,4-trimethyl-1H-[1]benzopyrano[3,4-f]quinoline

EXAMPLE 206A 2,5-Dihydro-10-methoxy-5-(aminomethyl)-2,2,4-trimethyl-1H-[1]benzopyrano[3,4-f]quinoline A 10 ml ethereal suspension of LiAlH$_4$ (0.050 g, 1.31 mmol) was treated dropwise at room temperature with a 5.0 ml ethereal solution of AlCl$_3$ (0.59 g, 4.4 mmol), strirred for 30 minutes and treated dropwise with a 4.0 ml ethereal solution of Example 44. After stirring for 1 hour at room temperature, 2.0 ml of H$_2$O carefully added followed by dropwise addition of 15% NaOH until a white paste formed. The ether solution was decanted, the paste washed several times with ether and combined organics washed with brine and dried (Na$_2$SO$_4$). The residue was purified by silica gel column chromatography eluting with CH$_2$Cl$_2$:CH$_3$OH (8:1) to give 0.031 g (69%) aminomethyl analog that was carried directly to the next step.

EXAMPLE 206

2,5-Dihydro-10-methoxy-5-(2,2-dimethylethoxycarbonylamino)methyl)-2,2,4-trimethyl-1H-[1]benzopyrano[3,4-f]quinoline The aminomethyl analog above (0.065 g, 0.19 mmol) was dissolved in dichloromethane (6.0 ml), cooled to 0° C., treated with BoC$_2$O (0.93 g, 0.42 mmol) Allowed to warm to room temperature overnight. 10 ml H$_2$O was added and the phases separated. The organic layer was washed with brine and dried (Na$_2$SO$_4$). The residue was purified by silica gel column chromatography eluting with CH$_2$Cl$_2$:CH$_3$OH (8:1) to give 0.080 g (95%) desired compound:

m.p. 130–135° C; $^1$H NMR (400 MHz, DMSO-d$_6$) δ 7.98 (d, J=9 Hz, 1H), 7.70 (t, J=9 Hz, 1H), 6.79 (t, J=5 Hz, 1H), 6.67 (d, J=9 Hz, 1H), 6.60 (d, J=9 Hz, 1H), 6.53 (d, J=8 Hz, 1H), 6.12 (s, 1H), 5.80 (dd, J=10, 10 Hz, 1H), 5.42 (s, 1H), 3.85 (s, 3H), 3.14 (m, 1H), 2.86 (m, 1H), 2.19 (s, 3H), 1.47 (s, 3H), 1.21 (s, 3H), 1.12 (s, 3H), 0.84 (m, 1H); $^{13}$C NMR (100 MHz, DMSO-d$_6$) δ 156.1, 155.5, 150.9, 145.4, 133.4, 131.5, 129.5, 128.6, 127.8, 126.9, 117.1, 116.4, 113.4, 112.7, 110.5, 105.3, 77.7, 72.3, 67.4, 55.6, 49.5, 41.5, 29.8, 29.2, 28.3, 28.2, 23.4, 23.2, 22.3; HRMS (FAB) m/e calc'd for C$_{26}$H$_{32}$N$_2$O$_4$: 436.2362. Found 436.2360.

EXAMPLE 207

2,5-Dihydro-10-methoxy-5-(ethoxycarbonylamino)methyl)-2,2,4-trimethyl-1H-[1]benzopyrano[3,4-f] quinoline Example 206A (0.047 g, 0.14 mmole) in THF (10 ml) was treated with triethylamine (21.0 μL, 0.14 mmol). Followed by dropwise addition of ethyl chloroformate (14.1 μL, 0.14 mmol.). After 30 minutes the reaction was poured into H$_2$O, the aqueous layer extracted with ethyl acetate and the combined organic layers washed 1× with H$_2$O, 1× with brine, and dried (Na$_2$SO$_4$). The residue was purified by silica gel column chromatography eluting with 3:2 hexanes:ethyl acetate to give 0.047 g (80%) of the desired compound as a solid.

$^1$H NMR (300 MHz, DMSO-d$_6$) δ 7.98 (d, J=8 Hz, 1H), 7.13 (t, 1H), 7.03 (t, J=8 Hz, 1H), 6.67 (d, J=8 Hz, 1H), 6.57 (d, J=8 Hz, 1H), 6.54 (d, J=8 Hz, 1H), 6.13 (s, 3H), 5.83 (dd, 1H), 5.43 (s, 1H), 3.94 (m, 2H), 3.85 (s, 3H), 3.13 (m, 1H), 2.94 (m, 1H), 2.21 (s, 3H), 1.20 (s, 3H), 1.17 (s, 3H), 1.11 (s, 3H); $^{13}$C NMR (75 MHz, DMSO-d$_6$) δ 156.1, 150.8, 145.5, 133.4, 129.4, 127.7, 127.0, 117.0, 116.4, 113.5, 112.7, 110.6, 105.4, 72.2, 59.7, 55.6, 49.6, 41.8, 29.2, 28.3, 23.5, 14.6; HRMS m/e calc'd for C$_{24}$H$_{28}$N$_2$O$_4$: 408.2049. Found 408.2044.

EXAMPLE 208

2,5-Dihydro-10-methoxy-5-(carboethoxy)-2,2,4-trimethyl-1H-[1]benzopyrano[3,4-f]quinoline To Example 61 was added 2.0 ml of 5% aqueous HCl, 5.0 ml H$_2$O, and enough ethanol to make the solution homogenous. This was warmed at 35° C. for 1 hour, quenched with saturated aqueous sodium bicarbonate to a pH of 7.0. The reaction was extracted with ethyl acetate. The organics were washed with H$_2$O, brine, and dried (Na$_2$SO$_4$). The residue was purified by silca gel column chromatography eluting with 7:1-5:1-3:2 hexanes:ethyl acetate to give 0.041 g (48%) of the desired compound as a solid.

MS (DCI/NH$_3$) m/e 380 (M+H)$^+$; $^1$H NMR (300 MHz, DMSO-d$_6$) δ 7.90 (d, J=9 Hz, 1H), 7.04 (t, J=8 Hz, 1H), 6.64 (d, J=8 Hz, 1H), 6.61 (m, 2H), 6.32 (s, 1H), 6.21 (s, 1H), 5.45 (s, 1H), 3.90 (m, 2H), 3.84 (s, 3H), 1.17 (s, 3H), 1.15 (s, 3H), 0.93 (t, J=7 Hz, 3H); $^{13}$C NMR (100 MHz, DMSO-d$_6$) δ 169.4, 156.2, 152.5, 145.4, 133.1, 127.6, 126.9, 126.0, 118.2, 117.7, 114.7, 109.8, 105.7, 73.0, 60.7, 55.6, 49.9, 28.9, 28.7, 22.8, 13.7; Anal. calcd for C$_{23}$H$_{25}$NO$_4$.1/4H$_2$O: C, 71.95; H, 6.68; N, 3.65. Found: C, 72.21; H, 6.41; N, 3.85.

EXAMPLE 209

2,5-Dihydro-10-methoxy-5-(cyclopentyl)-2,2,4-trimethyl-1H-[1]benzopyrano[3,4-f]quinoline Example 2B and cyclopentylmagnesium bromide were processed as in Example 11 to provide the desired compound.

MS (DCI/NH$_3$) m/e 376 (M+H)$^+$; $^1$H NMR (300 MHz, DMSO-d$_6$) δ 8.01 (d, J=8 Hz, 1H), 7.03 (t, J=8 Hz, 1H), 6.65 (d, J=8 Hz, 1H), 6.59 (d, J=9 Hz, 1H), 6.52 (d, J=8 Hz, 1H), 6.20 (s, 1H), 5.46 (s, 3H), 3.85 (s, 3H), 2.16 (s, 3H), 1.50 (m, 5H), 1.30 (s, 3H), 1.16 (m, 3H), 1.01 (s, 3H); $^{13}$C NMR (100 MHz, DMSO-d$_6$) δ 156.2, 151.7, 145.0, 133.7, 131.6, 128.1, 126.7, 117.7, 116.4, 113.3, 112.6, 109.9, 105.0, 76.5, 49.2, 42.5, 29.8, 29.5, 27.5, 26.6, 24.8, 24.6, 23.6; Anal. calcd for C$_{25}$H$_{29}$O$_2$N.1/2H$_2$O: C, 78.09; H, 7.86; N, 3.64. Found: C, 78.09; H, 7.52; N, 3.42.

EXAMPLE 210

2,5-Dihydro-10-methoxy-5-(-methylpropa-1,2-dienyl)-2,2,4-trimethyl-1H-[1]benzopyrano[3,4-f]quinoline Example 2B and proparhylmagnesium bromide (Gaoni, Y.; Leznoff, C. C.; Sondheimer, F. *J. Am. Chem. Soc.* 1968, 90, 4940–4945.) were processed as in example 11 to provide the desired compound.

m.p. 59–63°; $^1$H NMR (300 MHz, DMSO-d$_6$) δ 7.84 (d, J=8 Hz, 1H), 7.03 (t, J=6 Hz, 1H), 6.68 (d, J=6 Hz, 1H), 6.55 (d, J=8 Hz, 2H), 6.04 (s, 1H), 5.97 (s, 6H), 5.40 (s, 1H), 4.94 (m, 1H), 4.23 (m, 1H), 3.82 (s, 3H), 2.11 (s, 3H), 1.70 (s, 3H), 1.21 (s, 3H), 1.10 (s, 3H); $^{13}$C NMR (100 MHz, DMSO-d$_6$) δ 156.1, 151.2, 150.5, 145.1, 132.6, 130.5, 127.9, 127.1, 127.0, 126.7, 126.5, 117 (5), 117.1, 114.7, 113.3, 112.9, 110.1, 106.3, 98.6, 76.2, 75.6, 55.9, 49.6, 29.4, 28.4, 22.5, 16.0; MS m/e calc'd for C$_{24}$H$_{25}$O$_2$N: 359.1885. Found 359.1893.

EXAMPLE 211

2,5-Dihydro-10-methoxy-5-(3,4,5-trifluorophenyl)-2,2,4)-trimethyl-1H-[1]benzopyrano[3,4-f]quinoline Example 2B and 3,4,5-trifluorophenylmagnesium bromide were processed as in Example 11 to provide the desired compound.

MS (DCI/NH$_3$) m/e 438 (M+H)$^+$; $^1$H NMR (300 MHz, DMSO-d$_6$) δ 8.04 (d, J=8 Hz, 1H), 6.94–7.02 (m, 3H), 6.77 (s, 1H), 6.74 (d, J=9 Hz, 1H), 6.62 (d, J=8 Hz, 2H), 6.51 (d, J=8 Hz, 5H), 6.31 (br s, 1H), 5.43 (s, 1H), 3.81 (s, 3H), 1.85 (s, 3H), 1.23 (s, 3H), 1.15 (s, 3H); Anal. calcd for C$_{26}$H$_{22}$NO$_2$F$_3$.1/4H$_2$O: C, 70.66; H, 5.13; N, 3.17. Found: C, 70.89; H, 5.19; N, 2.93.

EXAMPLE 212

2,5-Dihydro-10-methoxy-5-(cyclohexyl)-2,2,4-trimethyl-1H-[1]benzopyrano[3,4-f]quinoline Example 2B and cyclohexylmagnesium bromide were processed as in Example 11 to provide the desired compound.

MS (DCI/NH$_3$) m/e 308 (M+H)$^+$; MAJOR: $^1$H NMR (300 MHz, DMSO-d$_6$) δ 8.03 (d, J=9 Hz, 1H), 7.05 (t, J=8 Hz, 1H), 6.72 (d, J=8 Hz, 1H), 6.61 (d, J=9 Hz, 1H), 6.59 (s, 1H), 6.15 (d, J=8 Hz, 1H), 5.40 (m, 2H), 3.86 (s, 3H), 2.01 (s, 3H), 1.61 (m, 1H), 1.56–1.41 (m, 2H), 1.35–0.96 (m, 6H), 1.29 (s, 3H), 1.18 (s, 3H), 0.95–0.77 (m, 2H); Anal. calcd for C$_{26}$H$_{31}$NO$_2$.1/2H$_2$O: C, 78.36; H, 8.09; N, 3.51. Found: C, 78.24; H, 7.72; N, 3.70.

EXAMPLE 213

2,5-Dihydro-10-methoxy-5-(2-pyridyl)-2,2,4-trimethyl-1H-[1]benzopyrano[3,4-f]quinoline

EXAMPLE 213A 2,5-Dihydro-10-methoxy-5-(2-pyridyl)-2,2,4-trimethyl-1H-[1]benzopyrano[3,4-f]quinoline To a solution of Example 2A (1.42 g, 4.39 mmol) in THF (40 mL) at 0° C. was added a solution of potassium tert-butoxide (1.48 g, 13.2 mmol) in THF (13 mL). The mixture was stirred 45 min at 0° C. then a solution of TBSCl (1.46 g, 9.66 mmol) in THF (9.5 mL) was introduced in dropwise fashion. The solution was stirred at 0° C. for 30 min then was quenched by addition of saturated aqueous NH$_4$Cl (10 mL) and was extracted with EtOAc (2×30 mL). The combined organic portions were washed with brine (8 mL) and were dried (Na$_2$SO$_4$). Filtration and concentration gave a brown residue which was purified via flash chromatography (elution with 2% EtOAc/CH$_2$Cl$_2$) to give the desired product as a yellow solid (994 mg, 2.28 mmol, 52%).

MS (DCI/NH$_3$) m/z 438 (M+H)$^+$.

EXAMPLE 213

2,5-Dihydro-10-methoxy-5-(2-pyridyl)-2,2,4-trimethyl-1H-[1]benzopyrano[3,4-f]quinoline A solution of the 2-lithiopyridine (nominally 1 M in THF) was formed by addition of n-BuLi (680 µL of a 2.5 M solution in hexane, 1.70 mmol) to a solution of 2-bromopyridine (285 mg, 1.80 mmol) in THF (17 mL) at −78° C. This solution was stirred for 20 min then a solution of the aldehyde prepared above (211 mg, 0.480 mmol) in THF (2.0 mL) was added in drop wise fashion at −78° C. The solution was stirred at −78° C. for 30 min then was quenched by addition of saturated aqueous NH$_4$Cl (7 mL) and was extracted with EtOAc (2×30 mL). The combined organic portions were washed with brine (10 mL) and were dried (Na$_2$SO$_4$). Filtration and concentration gave a brown residue which was used without further purification.

The crude material prepared above was dissolved in THF (10 mL) at 23° C. and was treated with tetrabutylammonium fluoride (500 µL of a 1 M solution in THF, 0.500 mmol). After 1 h, the reaction mixture was concentrated in vacuo, was resuspended in EtOAc (20 mL) and then was washed with water (5 mL) and brine (5 mL), and was dried (Na$_2$SO$_4$). Filtration and concentration gave a brown residue which was used without further purification.

This crude residue was dissolved in THF (10 mL), and the solution was cooled to 0° C. To this solution was added triethylphosphine (48 mg, 0.410 mmol) followed by a solution of 1,1'-(azodicarbonyl)dipiperidine (103 mg, 0.410 mmol) in THF (1.5 mL). The solution was stirred for 30 min at 0° C. then at 23° C. for 7 h. The reaction mixture was concentrated and was purified by flash chromoatography (elution with 25% EtOAc/hexane) to give the desired product (13 mg, 0.034 mmol, 8%) as a colorless solid.

MS (DCI/NH$_3$) m/z 385 (M+H)$^+$; $^1$H NMR (300 MHz, DMSO) δ 8.45 (br d, J=6.6 Hz, 1H), 7.98 (d, J=8.0 Hz, 1H), 7.61 (td, J=6.5, 1.8 Hz, 1H), 7.19–7.13 (m, 2H), 6.91 (t, J=6.6 Hz, 1H), 6.72 (s, 1H), 6.68 (d, J=7.9 Hz, 1H), 6.57 (br d, J=6.7 Hz, 1H), 6.44 (dd, J=6.5, 1.0 Hz, 1H), 6.17 (br s, 1H), 5.37 (br s, 1H), 3.80 (s, 3H), 1.80 (s, 3H), 1.23 (s, 3H), 1.13 (s, 3H); HRMS (FAB) calcd (M+H)$^+$ for C$_{25}$H$_{25}$N$_2$O$_2$: 385.1916. Found: 385.1910.

EXAMPLE 214

2,5-Dihydro-10-methoxy-5-(3-pyridyl)-2,2,4-trimethyl-1H-[1]benzopyrano[3,4-f]quinoline The desired compound was prepared as described in Example 213 in 49% yield.

MS (DCI/NH$_3$) m/z 385 (M+H)$^+$; $^1$H NMR (300 MHz, DMSO) δ 8.38 (d, J=2.4 Hz, 1H), 8.35 (dd, J=5.6, 2.0 Hz, 1H), 8.02 (d, J=8.0 Hz, 1H), 7.49 (br d, J=6.9 Hz, 1H), 7.25 (dd, J=6.9, 5.5 Hz, 1H), 6.92 (t, J=6.9 Hz, 1H), 6.86 (s, 1H), 6.72 (d, J=8.1 Hz, 1H), 6.58 (d, J=6.7 Hz, 1H), 6.45 (d, J=6.4 Hz, 1H), 6.38 (br s, 1H), 5.41 (br s, 1H), 3.80 (s, 3H), 1.83 (s, 3H), 1.23 (s, 3H), 1.15 (s, 3H); $^{13}$C NMR (125 MHz, DMSO) δ 156.0, 151.2, 149.4, 148.8, 145.6, 135.7, 134.7, 133.2, 128.5, 127.3, 127.2, 127.0, 123.2, 117.7, 117.2, 113.9, 113.7, 110.2, 105.7, 73.0, 55.5, 49.8, 29.5, 28.5, 23.4; HRMS (FAB) calcd m/z for C$_{25}$H$_{25}$N$_2$O$_2$: 385.1916 (M+H)$^+$. Found: 385.1915. Anal. calcd for C$_{25}$H$_{24}$N$_2$O$_2$: C, 78.09; H, 6.29; N, 7.28. Found: C, 76.98; H, 6.60; N, 6.93.

EXAMPLE 215

2,5-Dihydro-10-methoxy-5-(4-pyridyl)-2,2,4-trimethyl-1H-[1]benzopyrano[3,4-f]quinoline The desired compound was prepared as described in Example 213 in 20% yield.

MS (DCI/NH$_3$) m/z 385 (M+H)$^+$; $^1$H NMR (300 MHz, DMSO) δ 8.43 (br d, J=4.3 Hz, 2H), 8.04 (d, J=8.0 Hz, 1H), 7.15 (d, J=4.2 Hz, 2H), 6.96 (t, J=6.7 Hz, 1H), 6.81 (s, 1H), 6.75 (d, J=7.9 Hz, 1H), 6.59 (d, J=6.8 Hz, 1H), 6.53 (d, J=6.8 Hz, 1H), 6.37 (br s, 1H), 5.43 (br s, 1H), 3.79 (s, 3H), 1.88 (s, 3H), 1.26 (s, 3H), 1.18 (s, 3H); $^{13}$C NMR (125 MHz, DMSO) δ 156.1, 151.4, 149.4 (2), 148.2, 145.6, 133.4, 133.3, 128.3, 127.3 (2), 127.0, 122.9, 117.9, 117.0, 113.9, 110.2, 105.6, 105.0, 103.0, 73.4, 49.8, 29.4, 28.6, 23.2; HRMS (FAB) calcd m/z for C$_{25}$H$_{25}$N$_2$O$_2$: 385.1916 (M+H)$^+$. Found: 385.1906.

The chemistry described in Schemes 1–21 and Examples 1–215 was used with Core 2 to prepare Examples 216–226.

EXAMPLE 216

10-Chloro-9-hydroxy-5-(3-propenyl)-2,2,4-trimethyl-1H-2,5-dihydro-[1]benzopyrano[3,4-f]quinoline MS (DCI/NH$_3$) m/z 368 (M+H)$^+$; $^1$H NMR (300 MHz, DMSO) δ 9.34 (s, 1H), 7.87 (d, J=8 Hz, 1H), 6.72 (d, J=8 Hz, 1H), 6.66 (d, J=8 Hz, 1H), 6.58 (d, J=8 Hz, 1H), 6.21 (br s, 1H), 5.81–5.71 (m, 1H), 5.62 (dd, J=10, 3 Hz, 1H), 5.41 (br s, 1H), 4.98 (dd, J=10, 2 Hz, 1H), 4.93 (dd, J=17, 2 Hz, 1H), 2.42–2.34 (m, 1H), 2.26–2.20 (m, 1H), 2.11 (s, 3H), 1.16 (s, 3H), 1.11 (s, 3H); HRMS (FAB) calcd m/z for C$_{22}$H$_{22}$ClNO$_2$: 367.1339. Found: 367.1336.

EXAMPLE 217

10-Chloro-9-hydroxy-5-phenyl-2,2,4-trimethyl-1H-2,5-dihydro-[1]benzopyrano[3,4-f]quinoline MS (DCI/NH$_3$) m/z 404 (M+H)$^+$; $^1$H NMR (300 MHz, DMSO) δ 9.46 (s, 1H), 7.96 (d, J=8 Hz, 1H), 7.26–7.12 (m, 3H), 7.14–7.07 (m, 1H), 6.87 (dd, J=8, 2 Hz, 1H), 6.72 (d, J=8 Hz, 1H), 6.68 (s, 1H), 6.58 (app s, 2H), 6.37 (br s, 1H), 5.40 (br s, 1H), 1.80 (s, 3H), 1.26 (s, 3H), 1.17 (s, 3H); HRMS (FAB) calcd m/z for C$_{25}$H$_{22}$ClNO$_2$: 403.1339. Found: 403.1344.

EXAMPLE 218

10-Chloro-9-hydroxy-5-(3-trifluoromethylphenyl)-2,2,4-trimethyl-1H-2,5-dihydro-[1]benzopyrano[3,4-f]quinoline MS (DCI/NH$_3$) m/z 472 (M+H)$^+$; $^1$H NMR δ 9.45 (s, 1H), 7.98 (d, 1H, J=8.5 Hz), 7.54 (m, 4H), 6.85 (d, 1H, J=8.5 Hz), 6.75 (m, 2H), 6.57 (d, 1H, J=8.5 Hz), 6.42 (m, 1H), 5.39 (m, 1H), 1.91 (s, 3H), 1.24 (s, 3H), 1.11 (s, 3H); Anal. calcd for C$_{26}$H$_{21}$ClF$_3$NO$_2$: 471.1213. Found: 471.1216.

EXAMPLE 219

10-Chloro-9-hydroxy-5-(3,5-dimethylphenyl)-2,2,4-trimethyl-1H-2,5-dihydro-[1]benzopyrano[3,4-f]quinoline MS (DCI/NH$_3$) m/z 432 (M+H)$^+$; $^1$H NMR δ 9.52 (s, 1H), 7.95 (d, 1H, J=8.5 Hz), 6.82 (m, 2H), 6.71 (m, 2H), 6.61 (s, 2H), 6.36 (m, 1H), 6.42 (m, 1H), 5.40 (m, 1H), 2.31 (s, 6H), 1.92 (d, 3H, J=1.4 Hz), 1.24 (s, 2H), 1.14 (s, 2H); HRMS (FAB) calcd m/z for C$_{27}$H$_{26}$ClNO$_2$: 421.1652. Found: 431.1650.

EXAMPLE 220 rel-(5S,3'R)-9-Hydroxy-10-methoxy-5-[1-hydroxymethyl-3-cyclohexenyl]2,2,4-trimethyl-2,5-dihydro-1H-[1]benzopyrano[3,4-f]quinoline MS (DCI/NH$_3$) m/z 438 (M+H)$^+$; $^1$H NMR (300 MHz, DMSO) δ 9.56 (s, 1H), 8.01 (d, J=8 Hz, 1H), 6.77 (app s, 2H), 6.67 (d, J=8 Hz, 1H), 6.39 (br s, 1H), 5.48 (d, J=10 Hz, 1H), 5.42 (br s, 1H), 5.10 (br s, 1H), 4.42 (t, J=6 Hz, 1H), 3.65 (br d, J=6 Hz, 2H), 2.28–2.18 (m, 2H), 2.05 (br s, 3H), 1.94–187 (m, 2H), 1.75–1.64 (m, 1H), 1.52–1.42 (m, 1H), 1.36–1.27 (m, 1H), 1.29 (s, 3H), 1.10 (s, 3H); HRMS (FAB) calcd m/z for C$_{26}$H$_{28}$ClNO$_3$: 437.1758. Found: 437.1756.

The C-5 lactol-9-tert-butyldimethylsilyl ether of Core 2 and 3-cyclopentenyl trimethylsilane were processed as above to give a 2:1 diastereomeric product mixture which was subjected to HPLC on an (R,R) WHELK-O 1 column eluting with 2% ETOH in hexanes to provide the individual enantiomers.

EXAMPLE 221

(−)2,5(S)-Dihydro-9-hydroxy-10-chloro-2,2,4-trimethyl-5-(3S-cyclopentenyl)-1H-[1]benzopyrano[3,4-f]quinoline $[\alpha]^{23}_D$=−220° (c 0.012, CHCl$_3$); MS (DCI/NH$_3$) m/z 394 (M+H)$^+$; $^1$H NMR (300 MHz, DMSO-d$_6$) δ 9.55 (s, 1H), 8.00 (d, 1H), 6.75 (d, 1H), 6.72 (d, 1H), 6.63 (d, 1H), 6.36 (s, 1H), 5.73 (ddd, 1H), 5.44 (d, 1H), 5.40 (s, 1H), 5.17 (ddd, 1H), 2.78 (m, 1H), 2.35 (m, 1H), 2.15 (m, 1H), 2.05 (s, 3H), 1.80 (m, 1H), 1.72 (m, 1H), 1.27 (s, 3H), 1.05 (s, 3H); $^{13}$C NMR (400 MHz, DMSO-d$_6$) δ 148.7, 146.0, 144.0, 134.0, 133.6, 132.7, 129.9, 127.9, 127.0, 123.7, 116.6, 115.8, 115.4, 114.2, 112.4, 76.1, 49.6, 48.2, 31.7, 29.8, 27.8, 27.3, 24.4.

EXAMPLE 222

(−)2,5(S)-Dihydro-9-hydroxy-10-chloro-2,2,4-trimethyl-5-(3R-cyclopentenyl)-1H-[1]benzopyrano[3,4-f]quinoline $[\alpha]^{23}_D$=−232° (c 0.010, CHCl$_3$); MS (DCI/NH$_3$) m/z 394 (M+H)$^+$; $^1$H NMR (300 MHz, DMSO-d$_6$) δ 9.50 (bs, 1H), 8.02 (d, 1H), 6.75 (d, 1H), 6.72 (d, 1H), 6.63 (d, 1H), 6.39 (s, 1H), 5.74 (ddd, 1H), 5.60 (ddd, 1H), 5.46 (s, 1H), 5.39 (d, 1H), 2.83 (m, 1H), 2.26 (m, 1H), 2.14 (m, 1H), 2.09 (s, 3H), 1.55–1.40 (m, 2H), 1.27 (s, 3H), 1.01 (s, 3H); $^{13}$C NMR (400 MHz, DMSO-$d_6$) δ 148.7, 146.0, 144.6, 134.1, 132.8, 132.0, 131.7, 127.8, 126.8, 123.6, 117.4, 115.9, 115.8, 115.5, 114.2, 112.3, 76.4, 49.4, 48.0, 31.7, 29.5, 27.2, 24.5, 23.8.

EXAMPLE 223

10-Chloro-9-hydroxy-5-(3,5-dichlorophenyl)-2,2,4-trimethyl-1H-2,5-dihydro-[1]benzopyrano[3,4-f]quinoline MS (DCI/NH$_3$) m/z 472 (M+H)$^+$; $^1$H NMR δ 9.40 (s, 1H), 8.01 (d, 1H, J=8.5 Hz), 7.43 (m, 4H), 6.85 (d, 1H, J=8.5 Hz), 6.71 (m, 1H), 6.57 (d, 1H, J=8.5 Hz), 6.42 (m, 1H), 5.47 (m, 1H), 1.81 (s, 3H), 1.29 (s, 3H), 1.09 (s, 3H); HRMS (FAB) calcd m/z for $C_{25}H_{20}Cl_3NO_2$: 471.0559. Found: 471.0556.

EXAMPLE 224

(+)-(5R,3'S)2,5-Dihydro-9-hydroxy-10-chloro-2,2,4-trimethyl-5-(3-cyclopentenyl)-1H-[1]benzopyrano[3,4-f]quinoline $[α]^{23}_D$=+256° (c 0.046, CHCl$_3$). MS (DCI/NH$_3$) m/z 394 (M+H)$^+$; $^1$H NMR (300 MHz, DMSO-$d_6$) δ 9.50 (bs, 1H), 8.02 (d, 1H), 6.75 (d, 3H), 6.72 (d, 1H), 6.63 (d, 1H), 6.39 (s, 1H), 5.74 (ddd, 1H), 5.60 (ddd, 1H), 5.46 (s, 1H), 5.39 (d, 1H), 2.83 (m, Hz), 2.26 (m, 1H), 2.14 (m, 1H), 2.09 (s, 3H), 1.55–1.40 (m, 2H), 1.27 (s, 3H), 1.01 (s, 3H); $^{13}$C NMR (400 MHz, DMSO-$d_6$) δ 148.7, 146.0, 144.6, 134.1, 132.8, 132.0, 131.7, 127.8, 126.8, 123.6, 117.4, 115.9, 115.8, 115.5, 114.2, 112.3, 76.4, 49.4, 48.0, 31.7, 29.5, 27.2, 24.5, 23.8.

EXAMPLE 225

(+)-(5R,3'R)2,5-Dihydro-9-hydroxy-10-chloro-2,2,4-trimethyl-5-(3-cyclopentenyl)-1H-[1]benzopyrano[3,4-f]quinoline $[α]^{23}_D$=+244° (c 0.165, CHCl$_3$); MS (DCI/NH$_3$) m/z 394 (M+H)$^+$; $^1$H NMR (300 MHz, DMSO-$d_6$) δ 9.55 (s, 1H), 8.00 (d, 1H), 6.75 (d, 1H), 6.72 (d, 1H), 6.63 (d, 1H), 6.36 (s, 1H), 5.73 (ddd, 1H), 5.44 (d, 1H), 5.40 (s, 1H), 5.17 (ddd, 1H), 2.78 (m, 1H), 2.35 (m, 1H), 2.15 (m, 1H), 2.05 (s, 3H), 1.80 (m, (H), 1.72 (m, 1H), 1.27 (s, 3H), 1.05 (s, 3H); $^{13}$C NMR (400 MHz, DMSO-$d_6$) δ 148.7, 146.0, 144.0, 134.0, 133.6, 132.7, 129.9, 127.9, 127.0, 123.7, 116.6, 115.8, 115.4, 114.2, 112.4, 76.1, 49.6, 48.2, 31.7, 29.8, 27.8, 27.3, 24.4.

EXAMPLE 226

10-Chloro-9-hydroxy-5-(3,4-difluorophenyl)-2,2,4-trimethyl-1H-2,5-dihydro-[1]benzopyrano[3,4-f]quinoline MS (DCI/NH$_3$) m/z 440 (M+H)$^+$; $^1$H NMR δ 9.41 (s, 1H), 7.94 (d, 1H, J=8.5 Hz), 6.96 (m, 31), 6.75 (m, 3H), 6.57 (d, 1H), J=8.5 Hz), 6.45 (m, 1H), 5.47 (m, 1H), 1.81 (s, 3H), 1.29 (s, 3H), 1.09 (s, 3H); HRMS (FAB) calcd m/z for $C_{25}H_{20}ClF_2NO_2$: 429.1150. Found: 429.1152.

The chemistry described in Schemes 1–21 and Examples 1–215 was used with Core 3 to prepare Example 227.

EXAMPLE 227

9-10-Methylenedioxy-5-phenyl-2,2,4-trimethyl-1H-2,5-dihydro-[1]benzopyrano[3,4-f]quinoline MS (DCI/NH$_3$) m/z 298 (M+H)+; $^1$H NMR (200 MHz, DMSO-$d_6$) 7.72 (d, J=8.1 Hz, 1H), 7.20 (m, 5H), 6.82 (s, 1H), 6.75 (d, J=8.8 Hz, 1H), 6.50 (d, J=8.1 Hz, 1H), 6.26 (s, 1H), 6.27 (d, J=8.8 Hz, 1H), 6.05 (s, 1H), 5.98 (s, 1H), 5.4 (s, 1H), 1.87 (s, 2H), 1.20 (s, 2H), 1.17 (s, 2H), 1.17 (s, 2H).

The chemistry described in Schemes 1–21 and Examples 1–215 was used with Core 4 to prepare Examples 228–231.

EXAMPLE 228

5-(3-Propenyl)-9-chloro-10-ethenyl-2,2,4-trimethyl-2,5-dihydro-1H-[1]benzopyrano[3,4-f]quinoline $^1$H NMR δ 7.93 (d, 1H, J=8.5 Hz), 7.20 (d, 1H, J=8.5 Hz), 6.70 (d, 1H, J=8.5 Hz), 6.64 (d, 1H, J=8.5 Hz), 6.34 (m, 1H), 5.81 (m, 2H), 5.46 (m, 1H), 5.03 (dm, 1H, J=10.5 Hz), 4.98 (dm, 1H, J=17.1 Hz), 3.65 (s, 3H), 2.44 (m, 1H), 2.28 (m, 1H), 2.18 (s, 3H), 1.19 (s, 3H), 1.17 (s, 3H); HRMS (ESI) m/z calc'd for $C_{23}H_{25}ClNO_2$: 381.1495. Found: 381.1490.

EXAMPLE 229

9-Chloro-10-methoxy-5-phenyl-2,2,4-trimethyl-2,5-dihydro-1H[1]benzopyrano[3,4-f]quinoline $^1$H NMR δ 7.98 (d, 1H, J=8.5 Hz), 7.42 (m, 1H), 7.21 (m, 5H), 7.00 (d, 1H, J=8.5 Hz), 6.75 (m, 1H), 6.57 (d, 1H, J=8.5 Hz), 6.42 (m, 1H), 5.47 (m, 1H), 3.65 (s, 3H), 1.81 (s, 3H), 1.29 (s, 3H), 1.09 (s, 3H); HRMS (ESI) m/z calc'd for for $C_{26}H_{24}ClNO_2$: 417.1495. Found: 417.1497.

EXAMPLE 230

5-(3-Propenyl)-9-chloro-10-difluoromethoxy-2,2,4-trimethyl-2,5-dihydro-1H-[1]benzopyrano[3,4-f]quinoline $^1$H NMR δ 7.58 (d, 1H, J=8.5 Hz), 7.14 (m, 2H), 6.80 (dd, 1H, J=7.3 Hz), 6.64 (d, 1H), J=8.5 Hz), 6.24 (m, 1H), 5.81 (m, 2H), 5.46 (m, 1H), 5.02 (dm, 1H, J=10.5 Hz), 4.94 (dm, 1H, J=17.1 Hz), 2.30 (m, 2H), 2.17 (s, 3H), 1.19 (s, 3H), 1.16 (s, 3H); mass spectrum (ESI) m/z: 418 (M+H); Calcd for $C_{23}H_{22}ClF_2NO_2$: 417.1307. Found: 417.1304.

EXAMPLE 231

9-Chloro-10-difluoromethoxy-5-phenyl-2,2,4-trimethyl-2,5-dihydro-1H-[1]benzopyrano[3 4-f]quinoline $^1$H NMR δ 7.77 (d, 1H, J=8.5 Hz), 7.44 (m, 1H), 7.22 (m, 5H), 7.12 (d, 1H, J=8.5 Hz), 6.84 (s, 1H), 6.76 (t, 1H, J=75 Hz), 6.74 (d, 1H, J=8.5 Hz), 6.51 (m, 1H), 5.39 (m, 1H), 1.78 (s, 3H), 1.26 (s, 3H), 1.14 (s, 3H); mass spectrum (ESI) m/z: 454 (M+1); Calcd for $C_{26}H_{22}ClF_2NO_2$: 453.1307. Found: 453.1304.

The chemistry described in Schemes 1–21 and Examples 1–215 was used with Core 5 to prepare Examples 232–233.

EXAMPLE 232

8-Fluoro-10-methoxy-5-phenyl-2,2,4-trimethyl-2,5-dihydro-1H-[1]benzopyrano[3,4-f]quinoline $^1$H NMR δ 7.95 (d, 1H, J=8.5 Hz), 7.30 (m, 2H), 7.20 (m, 5H), 7.00 (d, 1H, J=8.5 Hz), 6.82 (s, 1H), 6.43 (m, 1H), 5.38 (m, 1H), 3.56 (s, 3H), 2.17 (s, 3H), 1.25 (s, 3H), 1.13 (s, 3H); mass spectrum (ESI) m/z: 402 (M+H); Calcd for $C_{26}H_{24}FNO_2$: 401.1791. Found: 401.1795. Anal. Calcd for $C_{26}H_{24}FNO_2$: C, 77.78; H, 6.02; N, 2.49. Found: C, 77.66; H, 5.90; N, 2.28.

EXAMPLE 233

5-(3-Propenyl)-8-fluoro-10-methoxy-2,2,4-trimethyl-2,5-dihydro-1H-[1]benzopyrano[3,4-f]quinoline $^1$H NMR δ 7.95 (d, 1H, J=8.5 Hz), 7.30 (m, 2H), 7.20 (m, 5H), 7.00 (d, 1H, J=8.5 Hz), 6.82 (s, 1H), 6.43 (m, 1H), 5.38

(m, 1H), 3.56 (s, 3H), 2.17 (s, 3H), 1.25 (s, 3H), 1.13 (s, 3H); mass spectrum (ESI) m/z: 402 (M+1); Calcd for $C_{26}H_{24}FNO_2$: 401.1791. Found: 401.1795.

The chemistry described in Schemes 1–21 and Examples 1–215 was used with Core 6 to prepare Example 234.

EXAMPLE 234

10-Methoxy-9-fluoro-5-(3-propenyl)-2,2,4-trimethyl-1H-2,5-dihydro-[1]benzopyrano[3,4-f]quinoline MS (DCI/NH$_3$) m/z 366 (M+H)$^+$; $^1$H NMR (300 MHz, DMSO) δ 7.87 (d, J=8.5 Hz, 1H), 7.00 (dd, J=8.8, 2.2 Hz, 1H), 6.64 (d, J=8.1 Hz, 1H), 6.63 (d, J=8.8 Hz, 1H), 6.31 (d, J=1.1 Hz, 1H), 5.90–5.80 (m, 1H), 5.79–5.75 (m, 1H), 5.46 (s, 1H), 5.05–4.95 (m, 2H), 3.79 (s, 3H), 2.17 (d, 1.1 Hz, 1H), 1.17 (s, 6H); HRMS calcd for $C_{23}H_{24}FNO_2$ is 366.1869. Found 366.1869.

The chemistry described in Schemes 1–21 and Examples 1–215 was used with Core 7 to prepare Examples 235–296.

EXAMPLE 235

10-Methoxy-9-hydroxy-5-(3-propenyl)-2,2,4-trimethyl-1H-2,5-dihydro-[1]benzopyrano[3,4-f]quinoline $^1$H NMR (300 MHz, DMSO) δ 8.69 (s, 1H), 7.92 (d, J=8.5, 1H), 6.62 (d, J=8.5 Hz, 1H), 6.62 (d, J=8.5 Hz, 1H), 6.48 (d, J=8.5, 1H), 6.16 (d, J=1.7 Hz, 1H), 5.81 (ddt, J=17.3, 10.3, 6.6 Hz, 1H), 5.67 (dd, J=9.8, 3.3 Hz), 5.44 (s, 1H), 5.02 (dd, J=10.3, 1.8 Hz, 1H), 4.98 (dd, J=17.3, 1.8 Hz, 1H), 2.47–2.41 (m, 1H), 2.34–2.27 (m, 1H), 2.16 (s, 3H), 1.18 (s, 3H), 1.16 (s, 3H); $^{13}$C NMR (75 MHz, DMSO) δ 145.8, 145.1, 143.9, 142.9, 134.4, 133.4, 132.7, 127.5, 126.5, 117.8, 117.0, 116.3, 116.1, 114.3, 113.6, 112.4, 73.3, 59.3, 49.7, 36.4, 29.2, 28.9, 23.9. MS (DCI/NH$_3$) m/z 364 (M+H)$^+$; Anal. calcd for $C_{23}H_{24}N_2O_2$: C, 76.01; H, 6.93; N, 3.85. Found C, 75.85; H, 7.18; N, 3.66.

EXAMPLE 236

(+/−)2,5-Dihydro-9-hydroxy-10-methoxy-2,2,4-trimethyl-5-(3-cyclohexenyl)-1H-[1]benzopyrano[3,4-f]quinoline MS (DCI/NH$_3$) m/z 404 (M+H)$^+$; $^1$H NMR (300 MHz, DMSO-d$_6$) δ 8.70 (s, 1H), 8.01 (d, 1H), 6.65 (d, 1H), 6.62 (d, 1H), 6.53 (d, 1H), 6.27 (d, 1H), 5.82–5.65 (m, 2H), 5.45 (s, 1H), 5.33 (d, 1H), 3.65 (s, 3H), 2.28 (m, 1H), 2.12 (s, 3H), 1.86 (m, 2H), 1.55 (m, 1H), 1.31 (s, 3H), 1.26–1.14 (m, 3H), 1.03 (s, 3H); $^{13}$C NMR (400 MHz, DMSO-d$_6$) δ 145.4, 145.0, 144.1, 143.5, 133.6, 130.7, 128.1, 127.9, 127.7, 126.1, 118.4, 117.8, 116.5, 114.4, 113.4, 112.1, 75.9, 59.3, 49.4, 37.2, 29.6, 27.1, 24.7, 24.6, 23.7, 21.2.

EXAMPLE 237

(+/−)2,5-Dihydro-9-hydroxy-10-methoxy-2,2,4-trimethyl-5-(1-methylcyclohexen-3-yl)-1H-[1]benzopyrano[3,4-f]quinoline MS (DCI/NH$_3$) m/z 718 (M+H)$^+$; $^1$H NMR (300 MHz, DMSO-d$_6$) δ 8.66 (s, 1H), 8.00 (d, J=8.5 Hz, 1H), 6.65 (d, J=8.5 Hz, 1H), 6.62 (d, J=8.5 Hz, 1H), 6.55 (d, J=8.5 Hz, 1H), 6.24 (d, J=1.5 Hz, 1H), 5.51 (br s, 1H), 5.44 (br s, 1H), 5.30 (d, J=9.5 Hz, 1H), 3.65 (s, 3H), 2.30–2.20 (m, 1H), 2.11 (s, 3H), 1.80–1.54 (m, 3H), 1.60, (s, 3H), 1.30 (s, 3H), 1.28–1.08 (m, 3H), 1.03 (s, 3H); $^{13}$C NMR (75 MHz, DMSO-d$_6$) δ 145.3, 144.9, 144.0, 143.6, 134.7, 133.5, 130.9, 128.0, 126.1, 121.8, 118.3, 117.9, 116.5, 114.3, 113.3, 112.1, 76.2, 59.3, 49.4, 37.5, 29.6, 29.5, 27.1, 24.5, 23.8, 23.7, 21.6.

EXAMPLE 238

(−)(5S,3'S)-9-Hydroxy-5-[1-methyl-3-cyclohexenyl]-10-methoxy-2,2,4-trimethyl-2,5-dihydro-1H-[1]benzopyrano[3,4-f]quinoline

[α]$_D$=−158.8°; MS (DCI/NH$_3$) m/z 718 (M+H)$^+$; $^1$H NMR (300 MHz, DMSO-d$_6$) δ 8.66 (s, 1H), 8.00 (d, J=8.5 Hz, 1H), 6.65 (d, J=8.5 Hz, Hz, 1H), 6.62 (d, J=8.5 Hz, 1H), 6.55 (d, J=8.5 Hz, 1H), 6.24 (d, J=1.5 Hz, 1H), 5.51 (br s, 1H), 5.44 (br s, 1H), 5.30 (d, J=9.5 Hz, 1H), 3.65 (s, 3H), 2.30–2.20 (m, 1H), 2.11 (s, 3H), 1.80–1.54 (m, 3H), 1.60, (s, 3H), 1.30 (s, 3H), 1.28–1.08 (m, 3H), 1.03 (s, 3H); $^{13}$C NMR (75 MHz, DMSO-d$_6$) δ 145.3, 144.9, 144.0, 143.6, 134.7, 133.5, 130.9, 128.0, 126.1, 121.8, 118.3, 117.9, 116.5, 114.3, 113.3, 112.1, 76.2, 59.3, 49.4, 37.5, 29.6, 29.5, 27.1, 24.5, 23.8, 23.7, 21.6. Anal. calcd for $C_{27}H_{31}NO_3$: C, 77.67; H, 7.48; N, 3.35. Found C, 77.65; H, 7.67; N, 3.36.

EXAMPLE 239

(+)(5R,3'R)-9-Hydroxy-5-[1-methyl-3-cyclohexenyl]-10-methoxy-2,2,4-trimethyl-2,5-dihydro-1H-[1]benzopyrano[3,4-f]quinoline

[α]$_D$=+157.9°; MS (DCI/NH$_3$) m/z 718 (M+H)$^+$; $^1$H NMR (300 MHz, DMSO-d$_6$) δ 8.66 (s, 1H), 8.00 (d, J=8.5 Hz, 1H), 6.65 (d, J=8.5 Hz, 1H), 6.62 (d, J=8.5 Hz, 1H), 6.55 (d, J=8.5 Hz, 1H), 6.24 (d, J=1.5 Hz, 1H), 5.51 (br s, 1H), 5.44 (br s, 1H), 5.30 (d, J=9.5 Hz, 1H), 3.65 (s, 3H), 2.30–2.20 (m, 1H), 2.11 (s, 3H), 1.80–1.54 (m, 3H), 1.60, (s, 3H), 1.30 (s, 3H), 1.28–1.08 (m, 3H), 1.03 (s, 3H); $^{13}$C NMR (75 MHz, DMSO-d$_6$) δ 145.3, 144.9, 144.0, 143.6, 134.7, 133.5, 130.9, 128.0, 126.1, 121.8, 118.3, 117.9, 116.5, 114.3, 113.3, 112.1, 76.2, 59.3, 49.4, 37.5, 29.6, 29.5, 27.1, 24.5, 23.8, 23.7, 21.6. Anal. calcd for $C_{27}H_{31}NO_3$: C, 77.67; H, 7.48; N, 3.35. Found C, 77.65; H, 7.67; N, 3.36.

EXAMPLE 240

(+)(5R,3'S)-9-Hydroxy-5-[1-methyl-3-cyclohexenyl]-10-methoxy-2,2,4-trimethyl-2,5-dihydro-1H-[1]benzopyrano[3,4-f]quinoline

[α]$_D$=+78.0°; MS (DCI/NH$_3$) m/z 718 (M+H)$^+$; $^1$H NMR (300 MHz, DMSO-d$_6$) δ 8.74 (s, 1H), 7.99 (d, J=8.8 Hz, 1H), 6.66 (d, J=8.8 Hz, 1H), 6.62 (d, J=8.5 Hz, 1H), 6.52 (d, J=8.5 Hz, 1H), 6.24 (d, J=1.5 Hz, 1H), 5.41 (br s, 1H), 5.41 (d, J=10.3 Hz, 1H), 4.84 (br s, 1H), 3.63 (s, 3H), 2.34–1.35 (m, 7H), 2.06 (s, 3H), 1.49, (s, 3H), 1.30 (s, 3H), 1.09 (s, 3H); $^{13}$C NMR (75 MHz, DMSO-d$_6$) δ 145.3, 145.0, 144.0, 143.2, 135.5, 133.3, 131.3, 128.4, 126.2, 120.5, 118.1, 117.9, 116.5, 114.4, 113.5, 112.0, 75.3, 59.3, 49.5, 36.8, 29.4, 27.5, 25.0, 24.1, 23.7, 20.2. HRMS calcd for $C_{27}H_{31}NO_3$ 417.2304. Found: 417.2305.

EXAMPLE 241

(−)(5S,3'R)-9-Hydroxy-5-[1-methyl-3-cyclohexenyl]-10-methoxy-2,2,4-trimethyl-2,5-dihydro-1H-[1]benzopyrano[3,4-f]quinoline

[α]$_D$=−79.4°; MS (DCI/NH$_3$) m/z 718 (M+H)$^+$; $^1$H NMR (300 MHz, DMSO-d$_6$) δ 8.74 (s, 1H), 7.99 (d, J=8.8 Hz,

1H), 6.66 (d, J=8.8 Hz, 1H), 6.62 (d, J=8.5 Hz, 1H), 6.52 (d, J=8.5 Hz, 1H), 6.24 (d, J=1.5 Hz, 1H), 5.41 (br s, 1H), 5.41 (d, J=10.3 Hz, 1H), 4.84 (br s, 1H), 3.63 (s, 3H), 2.34–1.35 (m, 7H), 2.06 (s, 3H), 1.49, (s, 3H), 1.30 (s, 3H), 1.09 (s, 3H); $^{13}$C NMR (75 MHz, DMSO-d$_6$) δ 145.3, 145.0, 144.0, 143.2, 135.5, 133.3, 131.3, 128.4, 126.2, 120.5, 118.1, 117.9, 116.5, 114.4, 113.5, 112.0, 75.3, 59.3, 49.5, 36.8, 29.4, 27.5, 25.0, 24.1, 23.7, 20.2. Anal. calcd for $C_{27}H_{31}NO_3$: C, 77.67; H, 7.48; N, 3.35. Found C, 77.55; H, 7.56; N, 3.34.

EXAMPLE 242 rel-(5S,3'R)-9-Hydroxy-5-[1-hydroxymethyl-3-cyclohexenyl]-10-methoxy-2,2,4-trimethyl-2,5-dihydro-1H-[1]benzopyrano[3,4-f]quinoline MS (DCI/NH$_3$) m/z 434 (M+H)$^+$; $^1$H NMR (300 MHz, DMSO-d$_6$) δ 8.72 (s, 1H), 7.98 (d, J=8.8 Hz, 1H), 6.65 (d, J=8.8 Hz, 1H), 6.62 (d, J=8.8 Hz, 1H), 6.52 (d, J=8.8 Hz, 1H), 6.23 (br s, 1H), 5.43–5.39 (m, 2H), 5.06 (br s, 1H), ), 4.44 (t, J=5.1 Hz, 1H), 3.69–3.67 (m, 1H), 3.67 (s, 3H), 2.32–2.22 (m, 1H), 2.05 (s, 3H), 1.94–1.88 (m, 2H), 1.74–1.61 (m, 2H), 1.55–1.45 (m, 2H), 1.29 (s, 3H), 1.10 (s, 3H); $^{13}$C NMR (75 MHz, DMSO-d$_6$) δ 145.4, 145.0, 144.0, 143.1, 140.4, 133.5, 131.2, 128.2, 126.2, 120.5, 118.0, 118.0, 116.5, 114.4, 113.5, 112.1, 75.4, 65.6, 59.4, 49.5, 37.0, 29.8, 27.8, 25.8, 25.1, 24.3, 20.3. Anal. calcd for $C_{27}H_{31}NO_4$: C, 74.80; H, 7.21; N, 3.23. Found: C, 74.59; H, 7.21; N, 3.22.

EXAMPLE 243

(+/−)(5S,3'R)2,5-Dihydro-9-hydroxy-10-methoxy-2,2,4-trimethyl-5-(1-methylcyclohexen-3-yl)-1H-[1]benzopyrano[3,4-f]quinoline MS (DCI/NH$_3$) m/z 718 (M+H)$^+$; $^1$H NMR (300 MHz, DMSO-d$_6$) δ 8.66 (s, 1H), 8.00 (d, J=8.5 Hz, 1H), 6.65 (d, J=8.5 Hz, 1H), 6.62 (d, J=8.5 Hz, 1H), 6.55 (d, J=8.5 Hz, 1H), 6.24 (d, J=1.5 Hz, 1H), 5.51 (br s, 1H), 5.44 (br s, 1H), 5.30 (d, J=9.5 Hz, 1H), 3.65 (s, 3H), 2.30–2.20 (m, 1H), 2.11 (s, 3H), 1.80–1.54 (m, 3H), 1.60, (s, 3H), 1.30 (s, 3H), 1.28–1.08 (m, 3H), 1.03 (s, 3H); $^{13}$C NMR (75 MHz, DMSO-d$_6$) δ 145.3, 144.9, 144.0, 143.6, 134.7, 133.5, 130.9, 128.0, 126.1, 121.8, 118.3, 117.9, 116.5, 114.3, 113.3, 112.1, 76.2, 59.3, 49.4, 37.5, 29.6, 29.5, 27.1, 24.5, 23.8, 23.7, 21.6.

EXAMPLE 244 rel-(5S,3'R)-9-Hydroxy-5-[1-methoxymethyl-3-cyclohexenyl]-10-methoxy-2,2,4-trimethyl-2,5-dihydro-1H-[1]benzopyrano[3,4-f]quinoline MS (DCI/NH$_3$) m/z 448 (M+H)$^+$; $^1$H NMR (300 MHz, DMSO-d$_6$) δ 8.75 (s, 1H), 8.00 (d, J=8.5 Hz, 1H), 6.67 (d, J=8.5 Hz, 1H), 6.62 (d, J=8.5 Hz, 1H), 6.54 (d, J=8.5 Hz, 1H), 6.27 (d, J=1.5 Hz, 1H), 5.46 (d, J=9.9 Hz, 1H), 5.38 (br s, 1H), 5.21 (br s, 1H), 4.33–4.29 (m, 1H), 3.66–3.63 (m, 1H), 3.65 (s, 3H), 3.64 (s, 3H), 2.32–1.45 (m, 7H), 2.04 (s, 3H), 1.29 (s, 3H), 1.07 (s, 3H); Anal. calcd for $C_{28}H_{33}NO_4$: C, 75.14; H, 7.43; N, 3.13. Found C, 74.81; H, 7.35; N, 3.05.

EXAMPLE 245

2,5-Dihydro-9-hydroxy-10-methoxy-5-propyl-2,2,4-trimethyl-1H-[1]benzopyrano[3,4-f]quinoline The C-5 lactol-9-TBS ether of core 7 and n-propylmagnesium chloride were processed as in example 251 to provide the desired compound:

$^1$H NMR (300 MHz, DMSO-d$_6$) δ 8.66 (s, 1H), 7.90 (d, J=9 Hz, 1H), 6.60 (d, J=8 Hz, 1H), 6.59 (s, 1H), 6.49 (d, J=9 Hz, 1H), 6.14 (br s, 1H), 5.57 (m, 1H), 5.44 (br s, 1H), 3.63 (s, 3H), 2.15 (s, 3H), 1.79–1.61 (m, 1H), 1.48–1.08 (m, 5H), 1.16 (s, 6H), 0.78 (t, J=7 Hz, 3H); $^{13}$C NMR (75 MHz, DMSO-d$_6$) δ 145.7, 144.9, 143.9, 143.1, 133.5, 127.5, 126.4, 117.9, 116.3, 116.2, 114.2, 113.4, 112.1, 73.6, 59.3, 49.7, 31.9, 29.1, 28.8, 27.7, 23.8, 21.7, 13.9; MS (DCI/NH$_3$) m/e (M+H)$^+$ 380; Anal. calcd for $C_{24}H_{29}NO_3$.1/4H$_2$O: CC, 75.07; H, 7.74; N, 3.65. Found: C, 74.78; H, 7.86; N, 3.29.

The C-5 lactol-9-TBS ether of core 7 and 3-cycloheptenyl trimethylsilane were processed as above to give a 5:1 diastereomeric product mixture which was subjected to HPLC on an (R,R) WHELK-O 1 column eluting with 2% ETOH in hexanes to provide two levaratory enantiomers.

EXAMPLE 246

(−)(5S,3'S)2,5-Dihydro-9-hydroxy-10-methoxy-2,2,4-trimethyl-5-(3-cycloheptenyl)-1H-[1]benzopyrano[3,4-f]quinoline MS (DCI/NH$_3$) m/z 418 (M+H)$^+$; $^1$H NMR (300 MHz, DMSO-d$_6$) δ 8.70 (s, 1H), 7.96 (d, 1H), 6.65 (d, 1H), 6.64 (d, 1H), 6.21 (s, 1H), 5.55 (ddd, 1H), 5.53 (d, 1H), 5.46 (s, 1H), 5.31 (ddd, 1H), 3.65 (s, 3H), 2.45 (m, 1H), 2.14 (m, 3H), 2.05–1.84 (m, 4H), 1.46 (m, 1H), 1.29 (s, 3H), 1.27–1.15 (m, 4H), 1.04 (s, 3H); $^{13}$C NMR (400 MHz, DMSO-d$_6$) δ 145.3, 144.9, 144.0, 143.1, 133.7, 132.1, 131.6, 131.2, 128.1, 126.1, 118.3, 117.9, 116.5, 114.4, 113.3, 112.1, 74.5, 59.3, 49.5, 38.9, 29.5, 29.0, 28.7, 27.8, 27.2, 26.3, 23.8; HRMS calcd m/z for $C_{27}H_{31}NO_3$: 417.2304 (M$^-$)$^+$. Found: 417.2319. $[\alpha]^{23}_D$=−134° (c 1.15, CHCl$_3$).

EXAMPLE 247

(−)(5S,3'R)2,5-Dihydro-9-hydroxy-10-methoxy-2,2,4-trimethyl-5-(3-cycloheptenyl)-1H-[1]benzopyrano[3,4-f]quinoline MS (DCI/NH$_3$) m/z 418 (M+H)$^+$; $^1$H NMR (300 MHz, DMSO-d$_6$) δ 8.66 (s, 1H), 7.97 (d, 1H), 6.65 (d, 1H), 6.59 (d, 1H), 6.45 (d, 1H), 6.22 (s, 1H), 5.93 (ddd, 1H), 5.72 (ddd, 1H), 5.50 (d, 1H), 5.45 (s, 1H), 3.65 (s, 3H), 2.38 (m, 1H), 2.13 (s, 3H), 2.04 (m, 1H), 1.82–1.70 (m, 2H), 1.50–1.05 (m, 5H), 1.30 (s, 3H), 1.02 (s, 3H); $^{13}$C NMR (400 MHz, DMSO-d$_6$) δ 145.2, 144.8, 143.8, 143.2, 133.9, 133.6, 131.1, 130.8, 128.0, 126.1, 118.6, 118.0, 116.5, 114.4, 113.4, 112.2, 75.3, 59.2, 49.4, 41.9, 30.0, 29.6, 28.3, 28.0, 27.3, 26.1, 23.9; HRMS calcd m/z for $C_{27}H_{31}NO_3$: 417.2304 (M$^-$)$^+$. Found: 417.2288. $[\alpha]^{23}_D$=−122° (c 0.74, CHCl$_3$).

EXAMPLE 248

2,5-Dihydro-9-hydroxy-10-methoxy-2,2,4-trimethyl-5-phenyl-1H-[1]benzopyrano[3,4-f]quinoline $^1$H NMR (300 MHz, DMSO), δ 8.53 (s, 1H), 7.93 (d, J=8.7 Hz, 1H), 7.20–7.14 (m, 5H), 6.73 (d, J=8.7 Hz, 1H), 6.66 (s, 1H), 6.42 (d, J=8.9 Hz, 1H), 6.33 (d, J=8.7 Hz, 1H), 6.22 (d, J=1.7 Hz, 1H), 5.37 (s, 1H), 3.55 (s, 3H), 1.80 (s, 3H), 1.24 (s, 3H), 1.14 (s, 3H); 13C NMR (300 MHz, DMSO), δ 145.7, 144.8, 143.8, 143.6, 139.3, 133.1, 132.7, 130.2, 128.3, 127.8, 127.6, 127.5, 126.4, 126.1, 123.8, 118.4, 117.8, 114.1, 114.0, 112.8, 112.2, 74.9, 59.0, 49.7, 29.7, 28.4, 23.2; MS ESI m/z 400 (M+H)+; HRMS calcd for $C_{26}H_{25}NO_2$ is 399.1834. Found 399.1839.

EXAMPLE 249

2,5-Dihydro-9-hydroxy-10-methoxy-2,2,4-trimethyl-5-(3,5-difluorophenyl)-1H-[1]benzopyrano[3,4-f]quinoline $^1$H NMR (300 MHz, DMSO), δ 8.68 (s, 1H), 7.95 (d, J=8.4 Hz, 1H), 7.06 (tt, J=9.2, 2.2 Hz, 1H), 6.82 (dd, J=8.1, 1.8 Hz, 2H); 6.77 (d, J=8.4 Hz, 1H), 6.70 (s, 1H), 6.48 (d, J=8.4 Hz, 1H), 6.42 (d, J=8.4 Hz, 1H), 6.32 (d, J=1.5 Hz), 5.42 (s, 1H), 3.56 (s, 3H), 1.84 (d, J=1.1 Hz, 3H), 1.25 (s, 3H), 1.15 (s, 3H); 13C NMR (300 MHz, DMSO), δ 163.6 (d, J=12.81 Hz), 160.4 (d, J=12.81 Hz), 145.9, 145.2, 144.5, 144.4 (t, J=7.93 Hz), 143.6, 143.3, 133.1, 129.0, 127.3, 126.6, 118.2, 117.9, 117.2, 114.5 (d, J=6.1 Hz), 112.4, 111.4, 103.5, 73.8, 64.9, 59.1, 49.9, 29.6, 28.5, 23.2; MS ESI m/z 436 (M+H)+; HRMS calcd for $C_{26}H_{22}F_2NO_2$ is 435.1646. Found 435.1657.

EXAMPLE 250

2,5-Dihydro-9-hydroxy-10-methoxy-2,2,4-trimethyl-5-(3,4,5-trifluorophenyl)-1H-[1]benzopyrano[3,4-f]quinoline $^1$H NMR (300 MHz, DMSO), δ 8.76 (s, 1H), 8.02 (d, J=8.4 Hz, 1H), 7.08 (dd, J=6.98, 1.8 Hz, 1H), 6.86 (dd, J=7.3, 2.2 Hz, 1H), 6.83 (d, J=8.8 Hz, 1H), 6.73 (s, 1H), 6.55 (d, J=8.8 Hz, 1H), 6.47 (d, J=8.8 Hz, 1H), 6.38 (d, J=1.5 Hz, 1H), 5.46 (s, 1H), 3.62 (s, 3H), 1.88 (d, J=1.1 Hz, 3H), 1.30 (s, 3H), 1.13 (s, 3H); 13C NMR (300 MHz, DMSO), δ 146.0, 145.3, 143.6, 143.1, 133.1, 128.7, 127.3, 126.7, 118.1 (d, J=15.87 Hz), 117.1, 116.0, 115.9, 115.8, 114.05 (d, J=9.16 Hz), 113.0, 112.7, 112.4, 73.5, 59.1, 49.8, 29.7, 28.4, 23.3, MS ESI m/z 454 (M+H)+; HRMS calcd for $C_{26}H_{22}F_2NO_2$ is 453.1552. Found 453.1571.

EXAMPLE 251

5-Butyl-2,5-dihydro-9-hydroxy-10-methoxy-2,2,4-trimethyl-1H-[1]benzopyrano[3,4-f]quinoline The C-5 lactol-9-tert-butyldimethylsilyl ether of core 7 (0.057 g, 0.122 mmol) was dissolved in 1,2-dichloroethane (5 ml), cooled to −10° C., and treated dropwise with $BF_3.OEt_2$ (46 mL, 0.366 mmol). The resulting deep green solution was treated dropwise with an ethereal solution of n-butylmagnesium chloride (0.19 ml of a 2M/Et$_2$O solution, 0.380 mmol). The color changed to yellow-brown. The reaction mixture was partitioned between saturated aqueous sodium bicarbonate and ethyl acetate, the aqueous layer extracted with ethyl acetate, the combined organics washed with brine, dried (MgSO$_4$), and concentrated to a yellow oil.

The resulting yellow oil was dissolved in THF (5 ml), cooled to 0° C., and treated with tetrabutylammonium fluoride solution (0.14 ml of a 1M/THF solution, 0.14 mmol). After 10 minutes, the mixture was quenched by the addition of saturated aqueous ammonium chloride and pH 7.0 buffer, and the layers were separated. The aqueous layer was extracted with ethyl acetate, the combined organics washed with brine, dried (MgSO$_4$), and concentrated. The residue was purified by silica gel chromatography eluting with 25% ethyl acetate in hexanes to give 0.032 g (72%) of the desired compound.

$^1$H NMR (300 MHz, DMSO-d$_6$) δ 8.70 (s, 1H), 7.90 (d, J=8 Hz, 1H), 6.60 (d, J=8 Hz, 1H), 6.59 (s, 1H), 6.49 (d, J=8 Hz, 1H), 6.16 (br s, 1H), 5.61 (m, 1H), 5.44 (br s, 1H), 3.63 (s, 3H), 2.16 (s, 3H), 1.77–1.63 (m, 1H), 1.47–1.26 (m, 3H), 1.17 (s, 3H), 1.16 (s, 3H), 0.83 (m, 3H); $^{13}$C NMR (75 MHz, DMSO-d$_6$) δ 145.7, 144.9, 143.9, 143.1, 133.5, 133.3, 127.5, 126.4, 117.9, 116.3, 114.2, 113.4, 112.1, 73.2, 59.3, 49.7, 34.1, 29.1, 28.9, 23.9, 18.6, 13.4; MS (DCI/NH$_3$) m/e (M+H)$^+$ 366; Anal. calcd for $C_{23}H_{27}NO_3·1.25H_2O$: C, 71.20; H, 7.66; N, 3.61. Found: C, 71.48; H, 7.32; N, 3.52.

The C-5 lactol-9-TBS ether of core 7 and 3-cyclopentenyl trimethylsilane were processed as above to give a 1:1 diastereomeric product mixture which was subjected to HPLC on an (R,R) WHELK-O 1 column eluting with 2% ETOH in hexanes to provide the individual enantiomers.

EXAMPLE 252

(−)(5S,3′S)2,5-Dihydro-9-hydroxy-10-methoxy-2,2,4-trimethyl-5-(3-cyclopentenyl)-1H-[1]benzopyrano[3,4-f]quinoline MS (DCI/NH$_3$) m/z 390 (M+H)$^+$; $^1$H NMR (300 MHz, DMSO-d$_6$) δ 8.68 (s, 1H), 8.01 (d, 1H), 6.65 (d, 1H), 6.62 (d, 1H), 6.51 (d, 1H), 6.22 (s, 1H), 5.72 (dd, 1H), 5.41 (d, 1H), 5.40 (s, 1H), 5.17 (dd, 1H), 3.63 (s, 3H), 2.90–2.80 (m, 1H), 2.41–2.32 (m, 1H), 2.23–2.10 (m, 1H), 2.06 (s, 3H), 1.89–1.71 (m, 2H), 1.30 (s, 3H), 1.08 (s, 3H); $^{13}$C NMR (400 MHz, DMSO-d$_6$) δ 145.5, 145.0, 143.9, 143.4, 133.5, 132.3, 132.2, 130.2, 128.1, 126.4, 117.8, 116.9, 116.4, 114.4, 113.4, 111.9, 75.7, 59.3, 49.5, 48.7, 31.6, 29.8, 27.6, 27.1, 24.2; HRMS calcd m/z for $C_{25}H_{27}NO_3$: 389.1991 (M$^-$)$^+$. Found: 389.1994. $[\alpha]^{23}_D = -120°$ (c 0.800, CHCl$_3$).

EXAMPLE 253

(−)(5S,3′R)2,5-Dihydro-9-hydroxy-10-methoxy-2,2,4-trimethyl-5-(3-cyclopentenyl)-1H-[1]benzopyrano[3,4-f]quinoline MS (DCI/NH$_3$) m/z 390 (M+H)$^+$; $^1$H NMR (300 MHz, DMSO-d$_6$) δ 8.67 (s, 1H), 8.02 (d, 1H), 6.65 (d, 1H), 6.62 (d, 1H), 6.53 (d, 1H), 6.25 (s, 1H), 5.77 (ddd, 1H), 5.69 (ddd, 1H), 5.47 (s, 1H), 5.37 (s, 1H), 3.66 (s, 3H), 2.90 (m, 1H), 2.34–2.13 (m, 2H), 2.10 (s, 3H), 1.55–1.41 (m, 2H), 1.31 (s, 3H), 1.04 (s, 3H); $^{13}$C NMR (400 MHz, DMSO-d$_6$) δ 145.5, 144.9, 144.0, 143.9, 133.6, 132.0, 131.7, 131.5, 127.9, 126.2, 117.7, 117.6, 116.5, 114.4, 113.3, 111.9, 76.1, 59.3, 49.4, 48.6, 31.7, 29.5, 27.1, 24.6, 23.7; HRMS calcd m/z for $C_{25}H_{27}NO_3$: 389.1991. Found: 389.1998. $[\alpha]^{23}_D = -132°$ (c 0.76, CHCl$_3$).

EXAMPLE 254

2,5-Dihydro-9-hydroxy-10-methoxy-2,2,4-trimethyl-5-(3,4-difluorophenyl)-1H-[1]benzopyrano[3,4-f]quinoline $^1$H NMR (300 MHz, DMSO-d$_6$), δ 8.65 (s, 1H), 7.96 (d, J=8.8 Hz, 1H), 7.31–7.17 (m, 2H), 6.98–6.95 (m, 1H), 6.76 (d, J=8.8 Hz, 1H), 6.67 (s, 1H), 6.48 (d, J=8.4 Hz, 1H), 6.38 (d, J=8.4 Hz, 1H), 6.29 (d, J=1.5 Hz, 1H), 5.40 (s, 1H), 3.57 (s, 3H), 1.82 (d, J=1.5 Hz, 3H), 1.25 (s, 3H), 1.14 (s, 3H); 12C-NMR (75 MHz, DMSO-d$_6$) δ 145.9, 145.1, 143.6, 143.3, 137.3, 132.9, 129.5, 127.4, 126.6, 125.2, 118.3, 117.8, 117.3, 117.1, 117.0, 116.8, 114.4, 114.3, 112.3, 73.8, 59.1, 49.8, 29.7, 28.4, 23.3; HRMS calcd for $C_{26}H_{22}NO_2F_2$ is 435.1646. Found 435.1638.

EXAMPLE 255

2,5-Dihydro-9-hydroxy-10-methoxy-2,2,4-trimethyl-5-(4-fluorophenyl)-1H-[1]benzopyrano[3,4-f]quinoline MS (DCI/NH$_3$) 418 (M+H)+; 1H NMR (300 MHz, DMSO-d$_6$), δ 8.58 (s, 1H), 7.95 (d, J=8.8 Hz, 1H), 7.23–7.19 (m, 2H), 7.03 (dd, J=8.8, 8.8 Hz, 2H), 6.74 (d, J=8.8 Hz, 1H), 6.66 (s, 1H), 6.44 (d, J=8.8 Hz, 1H), 6.34 (d, J=8.8 Hz, 1H), 6.24 (d, J=1.5 Hz, 1H), 5.38 (s, 1H), 3.57 (s, 3H), 1.80 (d, J=1.5 Hz, 3H), 1.24 (s, 3H), 1.14 (s, 3H); HRMS calcd for $C_{26}H_{24}NO_2F$ is 417.1740. Found 417.1745.

EXAMPLE 256

2,5-Dihydro-9-hydroxy-10-methoxy-2,2,4-trimethyl-5-(3-trifluoromethylphenyl)-1H-[1]benzopyrano[3,4-f]quinoline MS APCI m/z 468 (M+H)+; $^1$H NMR (300 MHz, DMSO), δ 8.62 (s, 1H), 7.97 (d, J=8.8 Hz, 1H), 7.61–7.41 (m, 3H), 7.36 (s, 1H), 6.75 (s, 1H), 6.44 (d, J=8.4 Hz, 1H), 6.35 (d, J=8.4, 1H), 6.30 (d, J=1.5 Hz, 1H), 5.40 (s, 1H), 3.52 (s, 3H), 1.80 (d, J=1.5 Hz, 3H), 1.24 (s, 3H), 1.15 (s, 3H); $^{13}$C NMR (300 MHz, DMSO), δ 145.9, 145.0, 143.5, 140.9 (d, J=17.01 Hz), 140.9, 133.0, 132.6, 129.3, 129.2, 127.4, 126.6, 124.4, 118.3, 118.0, 117.4, 114.5 (d, J=7.32 Hz), 112.3, 74.2, 58.9, 49.8, 29.5, 29.4, 23.3. HRMS calcd for $C_{27}H_{24}F_2NO_2$ is 467.1708. Found 467.1708.

EXAMPLE 257

2,5-Dihydro-9-hydroxy-10-methoxy-2,2,4-trimethyl-5-(3-5-bistrifluoromethylphenyl)-1H-[1]benzopyrano[3,4-f]quinoline MS APCI m/z 536 (M+H)+; 1H NMR (300 MHz, DMSO), δ 8.69 (s, 1H), 8.00 (d, J=8.8 Hz, 1H), 7.96 (s, 1H), 7.80 (s, 2H), 6.90 (s, 1H), 6.79 (d, J=8.4 Hz, 1H), 6.46 (d, J=8.8 Hz, 1H), 6.39 (d, J=1.3 Hz, 1H), 6.37 (d, J=8.4 Hz, 1H), 5.43 (s, 1H), 3.51 (s, 3H), 1.80 (d, J=0.73 Hz, 3H), 1.24 (s, 3H), 1.15 (s, 3H); 13C NMR (300 MHz, DMSO), δ 146.1, 145.3, 143.6, 142.9, 133.2, 130.1, 129.7, 129.5, 127.2, 126.7, 124.9, 118.2, 117.2, 114.8, 112.3, 73.5, 58.8, 49.8, 29.4, 28.3, 23.3. HRMS calcd for $C_{28}H_{22}F_6NO_2$ is 535.1582. Found 535.1573.

EXAMPLE 258

2,5-Dihydro-9-hydroxy-10-methoxy-2,2,4-trimethyl-5-(3-trifluoromethyl-4-chlorophenyl)-1H-[1]benzopyrano[3,4-f]quinoline MS (APCI) m/z 502 (M+H)+; $^1$H NMR (300 MHz, DMSO), δ 8.70 (s, 1H), 7.97 (d, J=8.8 Hz, 1H), 7.70–7.60 (m, 3H), 6.78 (s, 1H), 7.55 (s, 1H), 6.46 (d, J=8.8 Hz, 1H), 6.38 (s, 1H), 6.36 (d, J=8.8 Hz, 1H), 5.41 (s, 1H), 3.53 (s, 3H), 1.79 (s, 3H) 1.28 (s, 3H), 1.14 (s, 3H); $^{13}$C NMR (300 MHz, DMSO), δ 166.9, 146.0, 145.2, 143.6, 143.1, 139.6, 134.1, 133.0, 131.7, 131.5, 128.6, 127.3, 126.7, 114.6, 112.3, 73.7, 59.0, 49.8, 67.4, 29.6, 29.8, 28.3, 23.3, 23.2, 22.4, 13.8, 10.8. HRMS calcd for $C_{27}H_{22}ClF_2NO_2$ 501.1319. Found 501.1326.

EXAMPLE 259

2,5-Dihydro-9-hydroxy-10-methoxy-2,2,4-trimethyl-5-(2-methylpropyl)-1H-[1]benzopyrano[3,4-f]quinoline The C-5 lactol-9-tert-butyldimethylsilyl ether of core 7 and iso-butylmagnesium chloride were processed as in example 251 to provide the desired compound:

$^1$H NMR (300 MHz, DMSO-d$_6$) δ 8.69 (s, 1H), 7.90 (d, J=8 Hz, 1H), 6.61 (d, J=8 Hz, 1H), 6.59 (d, J=8 Hz, 1H), 6.48 (d, J=8 Hz, 1H), 6.16 (br s, 1H), 5.71 (m, 1H), 5.44 (br s, 1H), 3.63 (s, 3H), 2.17 (s, 3H), 1.82–1.60 (m, 2H), 1.43–1.18 (m, 1H), 1.17 (s, 3H), 1.16 (s, 3H), 0.97 (d, J=7 Hz, 3H), 0.76 (d, J=7 Hz, 3H); $^{13}$C NMR (75 MHz, DMSO-d$_6$) δ 144.8, 143.8, 143.0, 133.5, 133.3, 127.5, 126.4, 117.9, 116.3, 116.1, 114.2, 113.4, 112.1, 71.8, 59.3, 49.6, 29.1, 28.9, 24.6, 24.0, 23.3, 21.2; MS (FAB Hi Res) m/e calc'd for $C_{24}H_{29}NO_3$: 379.2147. Found 379.2159.

EXAMPLE 260

2,5-Dihydro-9-hydroxy-10-methoxy-2,2,4-trimethyl-5-(3-fluoro-4-chlorophenyl)-1H-[1]benzopyrano[3,4-f]quinoline The C-5 lactol-9-tert-butyldimethylsilyl ether of core 7 and 3-fluoro-4-chlorophenyl magnesium bromide were processed according to Example 251 to provide the desired compound.

$^1$H NMR (300 MHz, DMSO-d$_6$) δ 8.72 (s, 1H), 7.91 (d, J=8 Hz, 1H), 6.59 (d, J=8 Hz, 1H), 6.59 6.48 (d, J=8 Hz, 1H), 6.16 (br s, 1H), 5.71 (m, 1H), 5.44 (br s, 1H), 3.63 (s, 3H), 2.17 (s, 3H), 1.82–1.60 (m, 2H), 1.43–1.18 (m, 1H), 1.17 (s, 3H), 1.16 (s, 3H), 0.97 (d, J=7 Hz, 3H), 0.76 (d, J=7 Hz, 3H).

EXAMPLE 261

2,5-Dihydro-9-hydroxy-10-methoxy-2,2,4-trimethyl-5-(3-butenyl)-1H-[1]benzopyrano[3,4-f]quinoline The C-5 lactol-9-tert-butyldimethylsilyl ether of core 7 and 1-butenyl-4-magnesium bromide were processed according to Example 251 to provide the desired compound.

EXAMPLE 262

2,5-Dihydro-9-hydroxy-10-methoxy-5-(phenylmethyl)-2,2,4-trimethyl-1H-[1]benzopyrano[3,4-f]quinoline The C-5 lactol-9-TBS ether of core 7 and benzylmagnesium bromide were processed as in example 251 to provide the desired compound:

$^1$H NMR (300 MHz, DMSO-d$_6$) δ 8.77 (s, 1H), 7.97 (d, J=9 Hz, 1H), 7.34–7.13 (m, 3H), 7.11 (s, 1H), 7.10 (d, J=7 Hz, 1H), 6.67 (m, J=8 Hz, 1H), 6.65 (m, J=8 Hz, 1H), 6.42 (d, J=9 Hz, 1H), 6.20 (br s, 1H), 5.86 (dd, J=10, 3 Hz, 1H), 5.42 (br s, 1H), 3.69 (s, 3H), 2.29 (dd, J=10, 14 Hz, 1H), 2.77 (dd, J=3, 15 Hz, 1H), 2.23 (s, 3H), 1.16 (s, 3H), 1.15 (s, 3H); $^{13}$C NMR (125 MHz, DMSO-d$_6$) δ 145.8, 145.0, 144.0, 142.8, 138.0, 133.3, 132.4, 128.9 (2C), 121.1 (2C), 127.4, 126.4, 126.1, 117.9, 116.3, 116.2, 114.4, 113.7, 112.5, 74.5, 59.4, 49.7, 37.9, 29.2, 29.0, 24.3; MS (DCI/NH$_3$) m/e (M+H)$^+$ 414; Anal. calcd for $C_{27}H_{27}NO_3 \cdot 1/4H_2O$: C, 77.58; H, 6.63; N, 3.35. Found: C, 77.70; H, 7.07; N, 3.19.

EXAMPLE 263

(−)(5S,3'R)2,5-Dihydro-9-hydroxy-10-methoxy-2,2,4-trimethyl-5-[1-ethyl-3-cyclohexenyl]-1H-[1]benzopyrano[3,4-f]quinoline The mixture of diastereomers from example 277 were resolved on a Chiracel OJ HPLC column eluting with hexane:2-propanol (95:5) to give the desired product. $^1$H NMR (300 MHz, DMSO-d$_6$) δ 8.67 (s, 1H), 7.99 (d, J=9 Hz, 1H), 6.65 (d, J=9 Hz, 1H), 6.62 (d, J=9 Hz, 1H), 6.53 (d, J=8 Hz, 1H), 6.22 (s, 1H), 5.44 (d, J=12 Hz, 2H), 5.30 (d, J=10 Hz, 1H), 3.62 (s, 3H), 3.50–2.26 (m, 1H), 2.11 (s, 3H), 1.89–1.72 (m, 3H), 1.25–1.17 (m, 2H), 1.03 (2, 3H), 0.088 (t, J=7 Hz, 3H); $^{13}$C NMR (75 MHz, DMSO-d$_6$) δ 145.4 144.9, 144.0, 143.7, 140.1, 133.6, 130.9, 127.9, 126.1, 120.0, 118.2, 117.8, 116.6, 114.3, 113.3, 112.0, 76.2, 59.3, 49.4, 37.7, 30.2, 29.6, 27.7, 27.2, 24.9, 23.7, 21.6, 12.3.

EXAMPLE 264

(−)(S)5-Cyclopentyl-2,5-dihydro-9-hydroxy-10-methoxy-2,2,4-trimethyl-1H-[1]benzopyrano[3,4-f]quinoline The C-5 lactol-9-TBS ether of core 7 and cyclopentylmagnesium chloride were processed as in Example 251. The resulting racemic product was resolved into its constituent enantiomers by HPLC on a (R,R)-WHELK-O$_1$ column eluting with 2% EtOH in hexanes to give the desired compound as the first eluent:

$^1$H NMR (300 MHz, DMSO-d$_6$) δ 8.66 (s, 1H), 8.00 (d8, 1H), 6.63 (d8, 1H), 6.61 (d, J=8 Hz, 1H), 6.48 (d, J=8 Hz, 1H), 6.24 (br s, 1H), 5.45 (br s, 1H), 5.35 (d, J=10 Hz, 1H), 3.65 (s, 3H), 2.15 (s, 3H), 2.12–1.97 (m, 1H), 1.60–1.43 (m, 4H), 1.42–1.22 (m, 2H), 1.19–1.07 (m, 2H), 1.31 (s, 3H), 1.02 (s, 3H); MS (DCI/NH$_3$) m/e (M+H)$^+$ 392.

EXAMPLE 265

(+)(R)5-Cyclopentyl-2,5-dihydro-9-hydroxy-10-methoxy-2,2,4-trimethyl-1H-[1]benzopyrano[3,4-f]quinoline The racemic product from Example 264 was resolved into its constituent enantiomers by HPLC on a (R, R)-WHELK-O$_1$ column eluting with 2% EtOH in hexanes to give the desired compound as the second eluent:

$^1$H NMR (300 MHz, DMSO-d$_6$) δ 8.66 (s, 1H), 8.00 (d8, 1H), 6.63 (d8, 1H), 6.61 (d, J=8 Hz, 1H), 6.48 (d, J=8 Hz, 1H), 6.24 (br s, 1H), 5.45 (br s, 1H), 5.35 (d, J=10 Hz, 1H), 3.65 (s, 3H), 2.15 (s, 3H), 2.12–1.97 (m, 1H), 1.60–1.43 (m, 4H), 1.42–1.22 (m, 2H), 1.19–1.07 (m, 2H), 1.31 (s, 3H), 1.02 (s, 3H); MS (DCI/NH$_3$) m/e (M+H)$^+$ 392.

EXAMPLE 266

2,5-Dihydro-9-hydroxy-10-methoxy-5-(3-propynyl)-2,2,4-trimethyl-1H-[1]benzopyrano[3,4-f]quinoline The C-5 lactol-9-TBS ether of core 7 and propargylmagnesium bromide (Gaoni, Y:, Leznoff, C. C:, Sondheimer. *J. Am. Chem. Soc.* 1968, 90, 4940–4945.) were processed as in Example 251 to give the desired compound. $^1$H NMR (300 MHz, DMSO-d$_6$) δ 8.77 (s, 1H), 7.92 (d, J=9 Hz, 1H), 6.63 (dd, J=9, 8 Hz, 2H), 6.54 (m, 1H), 6.17 (s, 1H), 5.82 (dd, J=9, 9 Hz, 1H), 5.44 (s, 1H), 3.68 (s, 3H), 2.78 (t, 1H), 2.44–2.36 (m, 2H), 2.18 (s, 3H), 1.17 (d, J=5 Hz, 6H); $^{13}$C NMR (75 MHz, DMSO-d$_6$) δ 145.9, 145.5, 145.4, 145.2, 143.9, 142.3, 133.5, 132.6, 131.4, 127.4, 126.5, 117.4, 116.5, 115.8, 114.5, 114.0, 112.6, 91.4, 80.7, 72.5, 59.4, 49.8, 29.3, 29.0, 23.9, 23.3, 22.4.

EXAMPLE 267

2,5-Dihydro-9-hydroxy-10-methoxy-2,2,4-trimethyl-5-(2-propyl)-1H-[1]benzopyrano[3,4-f]quinoline The C-5 lactol-9-TBS ether of core 7 and isopropylmagnesium chloride were processed as in Example 251 to provide the desired compound.

$^1$H NMR (300 MHz, DMSO-d$_6$) δ 8.65 (s, 1H), 7.99 (d8, 1H), 6.64 (d, J=8 Hz, 1H), 6.61 (d, J=8 Hz, 1H), 6.51 (d, J=8 Hz, 1H), 6.22 (br s, 1H), 5.44 (br s, 1H), 2.56 (d, J=10 Hz, 1H), 3.64 (s, 3H), 2.16 (s, 3H), 1.85–1.67 (m, 1H), 1.30 (s, 3H), 1.02 (s, 3H), 0.93 (d, J=6 Hz, 3H), 0.64 (7, 3H); $^{13}$C NMR (75 MHz, DMSO-d$_6$) δ 145.3, 144.8, 144.0, 143.7, 133.5, 131.6, 128.2, 126.1, 118.4, 117.9, 116.5, 114.3, 113.2, 112.0, 77.7, 59.3, 49.4, 30.7, 29.7, 27.2, 23.9, 19.5, 17.9; MS (DCI/NH$_3$) m/e (M+H)$^+$ 366; Anal. calcd for C$_{23}$H$_{27}$NO$_3$.1/4H$_2$O: C, 74.67; H, 7.49; N, 3.79. Found: C, 74.81; H, 7.39; N, 3.67.

EXAMPLE 268

2,5-Dihydro-9-hydroxy-10-methoxy-2,2,4-trimethyl-5-(5-methoxy-2-thienyl)-1H-[1]benzopyrano[3,4-f]quinoline The C-5 lactol-9-TBS ether of core 7 and 2-methoxythiophene were processed according to Example 276 to provide the desired compound.

$^1$H NMR (300 MHz, DMSO-d$_6$) δ 8.63 (s, 1H), 7.93 (d, J=8 Hz, 1H), 6.70 (d, J=8 Hz, 1H), 6.65 (s, 1H), 6.50 (d, J=8 Hz, 1H), 6.39 (d, J=9 Hz, 1H), 6.28 (d, J=3 Hz, 1H), 6.23 (br s, 1H), 5.97 (d, J=3 Hz, 1H), 5.38 (br s, 1H), 3.72 (s, 3), 3.59 (s, 3H), 1.97 (s, 3H), 1.22 (s, 3H), 1.13 (s, 3H); $^{13}$C NMR (75 MHz, DMSO-d$_6$) δ 166.2, 145.7, 145.1, 143.6, 143.5, 132.9, 130.2, 128.7, 127.6, 126.4, 126.0, 118.3, 117.2, 117.2, 114.2, 112.4, 102.7, 71.5, 59.7, 59.1, 49.8, 29.8, 28.6, 22.9; MS (DCI/NH$_3$) m/e (M+H)$^+$ 436; Anal. calcd for C$_{25}$H$_{25}$NO$_4$S.1/4H$_2$O: C, 68.24; H, 5.84; N, 3.18. Found: C, 68.52; H, 6.19; N, 3.00.

EXAMPLE 269

(±)2,5-Dihydro-9-hydroxy-10-methoxy-2,2,4-trimethyl-5-(2,3,4,5,6-pentafluorophenyl)-1H-[1]benzopyrano[3,4-f]quinoline The C-5 lactol-9-TBS ether of core 7 and pentafluorophenylmagnesium bromide were processed to give the desired compound which was purified by flash chromatography eluting with 4:1 hexane/EtOAc.

MS (DCI/NH$_3$) m/z 490 (M+H)$^+$; $^1$H NMR (300 MHz, DMSO-d$_6$) δ 8.75 (s, 1H), 7.83 (d, 1H), 6.82 (S, 1H), 6.67 (d, 1H), 6.44 (d, 1H), 6.33 (d, 1H), 6.19 (s, 1H), 5.37 (s, 1H), 3.53 (s, 3H), 1.77 (s, 3H), 1.17 (s, 3H), 1.06 (s, 3H); $^{13}$C NMR (400 MHz, DMSO-d$_6$) δ 146.1, 145.8, 143.8, 142.9, 133.4, 128.4, 127.0, 126.2, 118.6, 118.1, 117.6, 114.5, 114.2, 113.3, 112.2, 105.0, 68.6, 58.9, 49.9, 29.8, 28.3, 23.1; Anal. calcd for C$_{26}$H$_{20}$NO$_3$F$_5$.0.5H$_2$O: C, 62.65; H, 4.25; N, 2.81. Found: C, 62.4; H, 4.28; N, 2.73.

EXAMPLE 270

(+/−)2,5-Dihydro-9-hydroxy-10-methoxy-2,2,4-trimethyl-5(S)-(3(S)-1-hydroxymethylcyclopenten-3-yl)-1H-[1]benzopyrano[3,4-f]quinoline MS (DCI/NH$_3$) m/z 420(M+H)+; $_1$H NMR (400 MHz, DMSO-d$_6$) 1H NMR (200 MHz, DMSO-d6) δ 8.77 (s, 1H), 8.04 (d, 1H), 6.67 (d, 1H), 6.62 (d, 1H), 6.52 (d, 1H), 6.24 (bs, 1H), 6.12 (dd, 1H), 5.50 (d, 1H), 5.42 (bs, 1H), 2.64 (s, 2H), 2.57 (s, 2H), 2.75–1.09 (m, 14H).

EXAMPLE 271

(+/−)2,5-Dihydro-9-hydroxy-10-methoxy-2,2,4-trimethyl-5(S)-(3(S)-1-methylcarboxylatecyclopenten-3-yl)-1H-[1]benzopyrano[3,4-f]quinoline The C-5 lactol-9-TBS ether of core 7 and 3-cyclohexenyl trimethylsilane were processed as above to give a 3:2 diastereomeric product mixture which was subjected to HPLC on an (R,R) WHELK-O 1 column eluting with 2% EtOH in hexanes to provide the individual enantiomers.

EXAMPLE 272

(−)(5S,3'S)2,5-Dihydro-9-hydroxy-10-methoxy-2,2,4-trimethyl-5-(3-cyclohexenyl)-1H-[1]benzopyrano[3,4-f]quinoline MS (DCI/NH$_3$) m/z 404 (M+H)$^+$; $^1$H NMR (300 MHz, DMSO-d$_6$) δ 8.70 (s, 1H), 7.99 (d, 1H), 6.65 (d, 1H), 6.62 (d, 1H), 6.52 (d, 1H), 6.20 (d, 1H), 5.61 (ddd, 1H), 5.46 (d, 1H), 5.41 (s, 1H), 5.10 (dd, 1H), 3.66 (s, 3H), 2.27 (m, 1H), 2.10 (s, 3H), 1.99–1.72 (m, 2H), 1.70–1.55 (m, 3H), 1.35 (m, 1H), 1.29 (s, 3H), 1.06 (s, 3H); $^{13}$C NMR (400 MHz, DMSO-d$_6$) δ 145.4, 145.0, 143.4, 143.0, 133.5, 131.0, 128.9, 128.1, 126.4, 126.3, 117.9, 116.5, 114.4, 113.5, 112.1, 75.2, 59.3, 49.5, 36.9, 29.7, 27.6, 25.5, 24.6, 24.3, 20.0; $[\alpha]^{23}_D = -162°$ (c 0.11, $CHCl_3$).

EXAMPLE 273

(−)(5S,3'R)2,5-Dihydro-9-hydroxy-10-methoxy-2,2,4-trimethyl-5-(3-cyclohexenyl)-1H-[1]benzopyrano[3,4-f]quinoline MS (DCI/$NH_3$) m/z 404 (M+H)$^+$; $^1$H NMR (300 MHz, DMSO-$d_6$) δ 8.70 (s, 1H), 8.01 (d, 1H), 6.65 (d, 1H), 6.62 (d, 1H), 6.53 (d, 1H), 6.27 (d, 1H), 5.82–5.65 (m, 2H), 5.45 (s, 1H), 5.33 (d, 1H), 3.65 (s, 3H), 2.28 (m, 1H), 2.12 (s, 3H), 1.86 (m, 2H), 1.55 (m, 1H), 1.31 (s, 3H), 1.26–1.14 (m, 3H), 1.03 (s, 3H); $^{13}$C NMR (400 MHz, DMSO-$d_6$) δ 145.4, 145.0, 144.1, 143.5, 133.6, 130.7, 128.1, 127.9, 127.7, 126.1, 118.4, 117.8, 116.5, 114.4, 113.4, 112.1, 75.9, 59.3, 49.4, 37.2, 29.6, 27.1, 24.7, 24.6, 23.7, 21.2; $[\alpha]^{23}_D = -158°$ (c 0.50, $CHCl_3$).

EXAMPLE 274

2,5-Dihydro-9-hydroxy-10-methoxy-2,2,4-trimethyl-5-(2-thienyl)-1H-[1]benzopyrano[3,4-f]quinoline A 0.24 M solution of 2-thienylzinc chloride was prepared by diluting 2-thienyl lithium (1.0 ml of a 1M/THF solution, 1.0 mmol) with ethyl ether (2 ml), cooling to 0° C., treating with $ZnCl_2$ (1.1 ml of a 1M/$Et_2O$ solution, 1.10 mmol), and allowing to come to room temperature. The resulting heterogeneous mixture was stirred vigorously.

The C-5 lactol-9-TBS ether of core 7 and the 2-thienylzinc chloride from above were processed according to Example 251 to provide the desired compound:

$^1$H NMR (300 MHz, DMSO-$d_6$) δ 8.65 (s, 1H), 7.95 (d, J=9 Hz, 1H), 7.39 (dd, J=5, 1 Hz, 1H), 6.85–6.82 (m, 2H), 6.74 (m, 1H), 6.72 (d, J=8 Hz, 1H), 6.48 (d, J=8 Hz, 1H), 6.37 (d, J=9 Hz, 1H), 6.28 (br s, 1H), 5.39 (br s, 1H), 3.59 (s, 3H), 1.93 (s, 3H), 1.22 (s, 3H), 1.14 (s, 3H); $^{13}$C NMR (75 MHz, DMSO-$d_6$) δ 145.7, 145.1, 143.7, 143.6, 143.5, 133.0, 130.8, 127.9, 127.5, 127.0, 126.5, 126.4, 118.3, 117.1, 114.4, 114.2, 112.4, 70.9, 59.0, 49.8, 29.7, 28.6, 23.0; MS (DCI/$NH_3$) m/e (M+H)$^+$ 406; Anal. calcd for $C_{24}H_{23}NO_3S$: C, 71.09; H, 5.72; N, 3.45. Found: C, 70.93; H, 6.00; N, 3.27.

EXAMPLE 275

(±)2,5-Dihydro-9-hydroxy-10-methoxy-2,2,4-trimethyl-5-(2-methylphenyl)-1H-[1]benzopyrano[3,4-f]quinoline The C-5 lactol-9-TBS ether of core 7 and o-tolylmagnesium bromide were processed to give the desired product which was purified by flash chromatography eluting with 4:1 hexane/EtOAc.

MS (DCI/$NH_3$) m/z 414 (M+H)$^+$; $^1$H NMR (300 MHz, DMSO-$d_6$) δ 8.43 (s, 1H), 7.79 (d, 1H), 7.02 (d, 1H), 6.92 (dt, 1H), 6.72 (t, 1H), 6.59 (d, 1H), 6.55 (s, 1H), 6.54 (d, 1H), 6.24 (d, 1H), 6.12 (d, 1H), 6.07 (s, 1H), 5.20 (s, 1H), 3.48 (s, 3H), 2.44 (s, 3H), 1.54 (s, 3H), 1.09 (s, 3H), 0.98 (s, 3H); $^{13}$C NMR (400 MHz, DMSO-$d_6$) δ 145.9, 145.0, 143.9, 143.6, 137.5, 136.6, 132.6, 130.6, 130.5, 128.8, 128.1, 127.6, 126.4, 124.9, 118.7, 118.2, 117.8, 114.1, 114.0, 111.7, 73.7, 59.2, 49.8, 30.0, 28.3, 22.5, 19.3; Anal. calcd for $C_{27}H_{27}NO_3$: C, 78.42; H, 6.58; N, 3.39. Found: C, 78.07; H, 6.85; N, 3.09.

EXAMPLE 276

2,5-Dihydro-9-hydroxy-10-methoxy-2,2,4-trimethyl-5-(2-acetoxymethyl-3-propenyl)-1H-[1]benzopyrano[3,4-f]quinoline The C-5 lactol-9-TBS ether of core 7 (0.150 g, 0.321 mmol) was dissolved in dichloromethane (15 ml), treated with 2-[(trimethylsilyl)methyl]-2-propene-1-yl acetate (0.180 g, 0.962 mmol), cooled to −78° C., treated dropwise with $BF_3.Et_2O$ and allowed to warm to 0° C. After 10 minutes, the reaction mixture was partitioned between saturated aqueous bicarbonate and ethyl acetate, layers separated, aqueous layer extracted with ethyl acetate, the combined organics washed with brine, dried ($MgSO_4$) and concentrated.

The resulting yellow oil was dissolved in THF (10 ml), cooled to 0° C., and treated with tetrabutylammonium fluoride solution (0.35 ml of a 1M/THF solution, 0.35 mmol). After 10 minutes, the mixture was quenched by the addition of saturated aqueous ammonium chloride and pH 7.0 buffer, and the layers were separated. The aqueous layer was extracted with ethyl acetate, the combined organics washed with brine, dried ($MgSO_4$), and concentrated. The residue was purified by silica gel chromatography eluting with 25% ethyl acetate in hexanes to provide 0.125 g (89%) of the desired compound.

$^1$H NMR (300 MHz, DMSO-$d_6$) δ 8.74 (s, 1H), 7.92 (d, J=8 Hz, 1H), 6.63 (d, J=8 Hz, 1H), 6.62 (d, J=8 Hz, 1H), 6.41 (d, J=9 Hz, 1H), 6.21 (br s, 1H), 5.85 (dd, J=2, 10 Hz, 1H), 5.44 (s, 1H), 5.08 (s, 1H), 4.92 (s, 1H), 4.58 (ABq, J=13, 30 Hz, 2H), 3.65 (s, 3H), 2.23 (m, 2H), 2.17 (s, 3H), 1.99 (s, 3H), 1.18 (s, 3H), 1.15 (s, 3H); MS (DCI/$NH_3$) m/e (M+H)$^+$ 436; Anal. calcd for $C_{26}H_{29}NO_5$: C, 71.71; H, 6.71; N, 3.22. Found: C, 71.34; H, 6.98; N, 3.12.

EXAMPLE 277

(+)(5R,3'S)2,5-Dihydro-9-hydroxy-10-methoxy-2,2,4-trimethyl-5-[1-ethyl-3-cyclohexenyl]-1H-[1]benzopyrano[3,4-f]quinoline To 77 ml of a 0.36 M THF solution of dimethylphenylsilyl methyl cuprate (27.7 mmol) (Fleming, I.; Newton, T. W. *J. Chem. Soc. Perkin TransI.* 1, 1984, 1805.) at −23° C. was added 3-ethyl-cyclohex-2-ene-1-one (2.73 g, 27.0 mmol). The mixture was stirred for 1 hr at −23° C., then for 2 hr at 0° C., treated with N-phenyl-bis-(trifluoromethanesulfonimide) (4.43 g, 26.4 mmol), allowed to warm to room temperature and stirred for 18 hr. The reaction mixture was quenched with saturated aqueous sodium bicarbonate, filtered through celite, and the layers were separated. The organic layer was washed with saturated aqueous sodium bicarbonate, brine, and dried ($Na_2SO_4$). The product was purified by silica gel column chromatography eluting with hexanes to give the intermediate triflate as a light yellow oil.

The above triflate (0.70 g, 1.28 mmol) was combined with tributyltin hydride (0.92 g, 2.13 mmol) in THF and added dropwise to a THF solution of tetrakistriphenylphosphinepalladium(0) (0.44 g, 3.5 mmol) and LiCl (0.45 g, 10.7 mmol) at room temperature. After the addition, the reaction was refluxed for 24 hr, cooled, filtered through a pad of celite, and stirred vigorously with saturated potassium fluoride solution for 2 hours. The mixture was filtered through celite, diluted with ethyl acetate, and the layers were separated. The organic layer was washed with saturated aqueous sodium bicarbonate, brine, and dried ($Na_2SO_4$). The product was purified by silica gel column chromatography eluting with hexanes to give 3-ethyl-3-dimethylphenylsilylcyclohexene as a colorless oil.

The C-5 lactol-9-TBS ether of core 7 and 3-ethyl-3-dimethylphenylsilylcyclohexene were processed according to example 276 to give the product as a mixture of diastereomers that was separated on a (R,R,)-Whelk-O1 HPLC column eluting with hexane:ethanol (98:2) to give the desired compound.: $^1$H NMR (500 MHz, DMSO-d$_6$) δ 8.01 (d, J=8 Hz, 1H), 6.63 (d, J=8 Hz, 1H), 6.61 (d, J=9 Hz, 1H), 6.53 (d, J=9 Hz, 1H), 6.20 (s, 1H), 5.48 (s, 1H), 5.44 (s, 1H), 5.32 (d, J=9 Hz, 1H), 3.64 (s, 3H), 2.26 (m, 1H), 1.90–1.73 (m, 3H), 1.60 (m, 1H), 1.26–1.18 (m, 2H), 1.03 (s, 3H), 0.088 (t, J=7 Hz, 3H); $^{13}$C NMR (50 MHz, DMSO-d$_6$) δ 145.3, 144.8, 144.0, 143.6, 140.3, 133.5, 130.8, 127.8, 126.0, 120.0, 118.1, 117.8, 116.5, 114.2, 113.2, 111.9, 76.1, 59.2, 49.4, 37.5, 30.1, 29.5, 27.7, 27.1, 24.8, 23.6, 21.6, 12.2; MS m/e calc'd for C28H33O3N: 431.2460. Found 431.2467.

The C-5 lactol-9-TBS ether of core 7 and cyclohexyl-magnesium chloride were processed to give a mixture of Examples 278 and 279 which were separated by flash chromatography eluting with 4:1 hexane/EtOAc.

EXAMPLE 278

2,5-Dihydro-9-hydroxy-10-methoxy-2,2,4-trimethyl-5-cyclohexyl-1H-[1]benzopyrano[3,4-f]quinoline MS (DCI/NH$_3$) m/z 406 (M+H)$^+$; $^1$H NMR (300 MHz, DMSO-d$_6$) δ 8.66 (s, 1H), 7.96 (d, 1H), 6.61 (d, 1H), 6.59 (d, 1H), 6.47 (d, 1H), 6.18 (d, 1H), 5.42 (s, 1H), 5.30 (d, 1H), 3.64 (s, 3H), 2.13 (s, 3H), 1.87 (m, 1H), 1.60–1.48 (m, 3H), 1.28 (s, 3H), 1.20–0.80 (m, 7H), 1.00 (s, 3H); $^{13}$C NMR (400 MHz, DMSO-d$_6$) δ 145.3, 144.8, 144.1, 143.8, 133.5, 131.1, 128.1, 126.1, 118.5, 117.9, 116.6, 114.4, 113.2, 112.0, 76.8, 59.3, 49.4, 29.7, 29.5, 28.0, 27.2, 25.8, 25.6, 25.3, 23.8;

EXAMPLE 279

2,5,5-Trihydro-9-hydroxy-10-methoxy-2,2,4-trimethyl-1H-[1]benzopyrano[3,4-f]quinoline MS (DCI/NH$_3$) m/z 324 (M+H)$^+$; $^1$H NMR (300 MHz, DMSO-d$_6$) δ 8.78 (s, 1H), 7.81 (d, 1H), 6.62 (d, 1H), 6.57 (d, 1H), 6.53 (d, 1H), 6.22 (s, 1H), 5.40 (s, 1H), 5.05 (s, 2H), 3.62 (s, 3H), 2.01 (s, 3H), 1.19 (s, 6H); $^{13}$C NMR (400 MHz, DMSO-d$_6$) δ 146.6, 145.4, 145.3, 144.0, 131.5, 130.8, 128.1, 126.2, 118.2, 118.0, 117.2, 113.9, 113.2, 111.2, 67.1, 59.4, 49.9, 29.0, 22.9;

EXAMPLE 280

2,5-Dihydro-9-hydroxy-10-methoxy-2,2,4-trimethyl-5-(2-hydroxymethyl-3-propenyl)-1H-[1]benzopyrano[3,4-f]quinoline Example 276 (0.032 g, 0.074 mmol) was dissolved in THF/MeOH/H$_2$O 5 ml/1 ml/0.5 ml), cooled to 0° C., treated with K$_2$CO$_3$ (0.051 g, 0.367 mmol), and allowed to warm to room temperature and stir for 12 h. The mixture was partitioned between saturated aqueous ammonium chloride and ethyl acetate, the aqueous layer extracted with ethyl acetate, the combined organics washed with brine, dried (MgSO$_4$), and concentrated. The residue was purified by silica gel chromatography eluting with 25% then 50% ethyl acetate in hexanes to give 0.022 g (76%) of the desired compound.

$^1$H NMR (300 MHz, DMSO-d$_6$) δ 8.71 (s, 1H), 7.92 (s, J=9 Hz, 1H), 6.62 (d, J=9 Hz, 1H), 6.61 (d, J=8 Hz, 1H), 6.41 (d, J=8 Hz, 1H), 6.18 (d, J=1 Hz, 1H), 5.86 (dd, J=11, 1 Hz, 1H), 5.43 (br s, 1H), 5.02 (m, 1H), 4.80 (t, J=6 Hz, 1H), 4.74 (br s, 1H), 3.90–3.78 (m, 2H), 3.65 (s, 3H), 2.50–2.36 (m, 1H), 2.23–2.10 (m, 1H), 2.19 (s, 3H), 1.17 (s, 3H), 1.16 (s, 3H); $^{13}$C NMR (125 MHz, DMSO-d$_6$) δ 145.9, 145.8, 144.9, 143.8, 142.8, 133.2, 132.8, 127.6, 126.4, 117.7, 116.2, 116.2, 114.2, 113.6, 112.6, 110.6, 72.1, 63.7, 59.4, 49.7, 35.4, 29.2, 28.9, 23.9; MS (DCI/NH$_3$) m/e (M+H)$^+$ 394.

EXAMPLE 281

Methyl 2-[2,5-Dihydro-9-hydroxy-10-methoxy-2,2,4-trimethyl-1H-[1]benzopyrano[3,4-f]-5-quinoline] acetate The C-5 lactol-9-TBS ether of core 7 was processed as in example 46 to provide the intermediate silylated product.

$^1$H NMR (300 MHz, DMSO-d$_6$) δ 7.94 (d, J=9 Hz, 1H), 6.64 (dd, J=9, 3 Hz, 1H), 6.49 (d, J=9 Hz, 1H), 6.27 (s, 1H), 6.14 (dd, J=10, 3 Hz, 1H), 4.45 (s, 1H), 3.63 (s, 3H), 3.61 (s, 3H), 2.76–2.55 (m, 2H), 2.20 (s, 3H), 1.18 (s, 3H), 1.16 (s, 3H), 1.00 (s, 9H), 0.21 (s, 3H), 0.16 (s, 3H); MS (APCI) m/e (M+H)$^+$ 510, (M–H)$^-$ 508.

The intermediate silylated compound above (0.030 g, 0.058) was dissolved THF (1 ml) cooled to 0° C., and treated with tetrabutylammonium fluoride (58 μL of a 1M/THF solution, 0.058 mmol). After 5 minutes, the mixture was poured over saturated aqueous NH$_4$Cl and extracted with ethyl acetate. The combined organic layers were washed with brine and dried (MgSO$_4$). The product was purified by silica gel chromatography eluting with 40% methyl t-butyl ether in hexane to provide the desired compound (0.019 g, 82%) as a white solid. $^1$H NMR (300 MHz, DMSO-d$_6$) δ 8.80 (s, 1H), 7.93 (d, J=9 Hz, 1H), 6.64 (d, J=9 Hz, 1H), 6.61 (d, J=9 Hz, 1H), 6.43 (d, J=9 Hz, 1H), 6.25 (s, 1H), 6.10 (dd, J=10, 3 Hz, 1H), 5.45 (s, 1H), 3.66 (s, 3H), 3.60 (s, 3H), 2.77–2.52 (m, 2H), 2.21 (s, 3H), 1.18 (s, 3H), 1.16 (s, 3H); MS (APCI) m/e (M+H)$^+$ 396, (M–H)$^-$ 394.

EXAMPLE 282

(Z)2,5-Dihydro-9-hydroxy-10-methoxy-2,2,4-trimethyl-5-(2-butenyl)-1H-[1]benzopyrano[3,4-f] quinoline The intermediate silylated product from example 281 (0.445 g, 0.87 mmol) was dissolved in THF (4 ml), cooled to 0° C., treated dropwise with Dibal-H (2.69 mL of a 1M/THF solution, 2.69 mmol), and stirred for 30 minutes. The reaction mixture was poured over a rapidly stirring mixture of 100 mL of saturated aqueous potassium sodium tartrate and 100 mL of ethyl acetate and stirred for 1 hour. The layers were separated, the aqueous layer extracted with ethyl acetate, the combined organic layers washed with saturated aqueous sodium bicarbonate, brine and dried (MgSO$_4$). The residue was purified by silica gel chromatography eluting with 20% then 30% methyl t-butyl ether in hexane followed by 6% ethyl acetate in dichloromethane to give the primary alcohol (0.293 g, 70%) as a white solid. $^1$H NMR (300 MHz, DMSO-d$_6$) δ 7.92 (d, J=9 Hz, 1H), 6.65 (d, J=9 Hz, 1H), 6.61 (d, J=9 Hz, 1H), 6.57 (d, J=9 Hz, 1H), 6.21 (s, 1H), 5.88 (dd, J=10, 3 Hz, 1H), 5.43 (s, 1H), 4.62 (t, J=5 Hz, 1H), 3.61 (s, 3H), 2.19 (s, 3H), 1.90–1.75 (m, 2H), 1.62–1.47 (m, 2H), 1.17 (s, 3H), 1.15 (s, 3H), 0.99 (s, 9H), 0.20 (s, 3H), 0.15 (s, 3H); MS (APCI) m/e (M+H)$^+$ 482, (M–H)$^-$ 480.

A stirring solution of oxalyl chloride (22 μL, 0.249 mmol) in THF (2 mL) was cooled to –78° C., treated with DMSO (24 μL, 0.332 mmol), stirred for 5 minutes and treated dropwise with a solution of the above primary alcohol (0.080 g, 0.166 mmol) in 2 mL of THF. The resulting mixture was stirred for 40 minutes, treated with triethylamine (92.5 μL, 0.664 mmol) stirred a further 10 minutes and allowed to warm to 0° C. After 30 minutes at 0° C. the reaction mixture was partitioned between water and dichloromethane, the aqueous layer extracted with dichloromethane, and the combined organic layers dried (MgSO$_4$). The product was purified by silica gel chromatography eluting with 20% then 30% ethyl acetate in hexane to give the aldehyde (0.059 g, 73%) as a white solid. $^1$H NMR (300 MHz, DMSO-d$_6$) δ 9.65 (s, 1H), 7.93 (d, J=9 Hz, 1H), 6.67 (d, J=9 Hz, 1H), 6.65 (d, J=9 Hz, 1H), 6.48 (d, J=9 Hz, 1H), 6.33 (m, 2H), 5.46 (s, 1H), 3.63 (s, 3H), 2.87 (m, 1H), 2.65 (m, 1H), 2.18 (s, 3H), 1.19 (s, 3H), 1.14 (s, 3H), 1.00 (s, 9H), 0.21 (s, 3H), 0.15 (s, 3H); MS (APCI) m/e (M+H)$^+$ 480, (M−H)$^−$ 478.

A solution of ethyltriphenylphosphonium bromide (0.130 g, 0.351 mmol) in THF:Et$_2$O (3 ml, 3:2) was cooled to 0° C. and treated dropwise with n-BuLi (140 μL of a 2.5 M/hexanes, 0.351 mmol). The resulting deep red solution was stirred for 30 minutes at 0° C., cooled to −78° C. and treated with the above aldehyde (0.056 g, 0.117 mmol) in THF (2 mL). The reaction mixture was stirred for 5 minutes at −78° C., warmed to 0° C. for 40 minutes and quenched by the addition of water. The layers were separated, the aqueous layer extracted with dichoromethane, the combined organic layers washed with brine and dried (MgSO$_4$). The product was purified by silica gel chromatography eluting with a gradient from 5% to 20% ethyl acetate in hexane to provide the intermediate silyl ether (0.050 g, 87%) as a white solid. $^1$H NMR (300 MHz, DMSO-d$_6$) δ 7.92 (d, J=9 Hz, 1H), 6.65 (d, J=9 Hz, 1H,), 6.63 (d, J=9 Hz, 1H), 6.20 (s, 1H,), 5.68 (dd, J=10, 3 Hz, 1H), 5.43 (m, 3H), 3.64 (s, 3H), 2.15 (s, 3H), 1.26 (d, J=5 Hz, 3H), 1.17 (s, 6H), 1.00 (s, 9H), 0.20 (s, 3H), 0.15 (s, 3H); MS (APCI) m/e (M+H)$^+$ 492, (M−H)$^−$ 490.

The intermediate silyl ether (0.038 g, 0.077 mmol) was dissolved in THF (3 ml), cooled to 0° C., treated with tetrabutylammonium fluoride (80 ml of a 1 M/THF solution, 0.080 mmol), and the mixture was partitioned between ethyl acetate and saturated ammonium chloride. The aqueous layer was extracted with ethyl acetate, the combined organics were washed with brine, dried (MgSO$_4$) and purified by silica gel chromatography eluting with 25% ethyl acetate in hexanes to give the desired compound (0.024 g, 83%). $^1$H NMR (300 MHz, DMSO-d$_6$) δ 8.71 (s, 1H), 7.93 (d, J=9 Hz, 1H), 6.62 (d, J=9 Hz, 1H), 6.60 (d, J=9 Hz, 1H), 6.47 (d, J=9 Hz, 1H), 6.18 (s, 1H), 5.62 (dd, J=10, 3 Hz, 1H), 5.43 (m, 3H), 3.64 (s, 3H), 2.45–2.18 (m, 2H), 2.15 (s, 3H), 1.30 (d, J=5 Hz, 3H), 1.15 (s, 6H); MS (APCI) m/e calc'd for: 377.20. Found; (M+H)$^+$ 378, (M−H)$^−$ 376.

EXAMPLE 283

2,5-Dihydro-9-hydroxy-10-methoxy-2,2,4-trimethyl-5-(3-methyl-2-butenyl)-1H-[1]benzopyrano[3,4-f]quinoline The intermediate aldehyde from Example 282 and isopropyltriphenylphosphonium iodide were processed according to Example 282 to give the desired compound. $^1$H NMR (300 MHz, DMSO-d$_6$) δ 8.65 (s, 1H), 7.91 (d, J=9 Hz, 1H), 6.62 (d, J=9 Hz, 1H), 6.60 (d, J=9 Hz, 1H), 6.46 (d, J=9 Hz, 1H), 6.14 (s, 1H), 5.60 (dd, J=9, 3 Hz, 1H), 5.43 (s, 1H), 5.15 (m, 1H), 3.64 (s, 3H), 2.45–2.18 (m, 2H), 2.15 (s, 3H), 1.63 (s, 3H), 1.32 (s, 3H), 1.17 (s, 3H), 1.16 (s, 3H); MS (APCI) m/e (M+H)$^+$ 392, (M−H)$^−$ 390.

EXAMPLE 284

(+)(5S,3'S)2,5-Dihydro-9-hydroxy-10-methoxy-2,2,4-trimethyl-5-(3-cyclohexenyl)-1H-[1]benzopyrano[3,4-f]quinoline MS (DCI/NH$_3$) m/z 404 (M+H)$^+$; $^1$H NMR (300 MHz, DMSO-d$_6$) δ 8.70 (s, 1H), 8.01 (d, 1H), 6.65 (d, 1H), 6.62 (d, 1H), 6.53 (d, 1H), 6.27 (d, 1H), 5.82–5.65 (m, 2H), 5.45 (s, 1H), 5.33 (d, 1H), 3.65 (s, 3H), 2.28 (m, 1H), 2.12 (s, 3H), 1.86 (m, 2H), 1.55 (m, 1H), 1.31 (s, 3H), 1.26–1.14 (m, 3H), 1.03 (s, 3H); $^{13}$C NMR (400 MHz, DMSO-d$_6$) δ 145.4, 145.0, 144.1, 143.5, 133.6, 130.7, 128.1, 127.9, 127.7, 126.1, 118.4, 117.8, 116.5, 114.4, 113.4, 112.1, 75.9, 59.3, 49.4, 37.2, 29.6, 27.1, 24.7, 24.6, 23.7, 21.2; [α]$^{23}_D$=+184° (c 0.33, CHCl$_3$).

EXAMPLE 285

(+)(5R,3'R)2,5-Dihydro-9-hydroxy-10-methoxy-2,2,4-trimethyl-5-(3-cyclohexenyl)-1H-[1]benzopyrano[3,4-f]quinoline MS (DCI/NH$_3$) m/z 404 (M+H)$^+$; $^1$H NMR (300 MHz, DMSO-d$_6$) δ 8.70 (s, 1H), 7.99 (d, 1H), 6.65 (d, 1H), 6.62 (d, 1H), 6.52 (d, 1H), 6.20 (d, 1H), 5.61 (ddd, 1H), 5.46 (d, 1H), 5.41 (s, 1H), 5.10 (dd, 1H), 3.66 (s, 3H), 2.27 (m, 1H), 2.10 (s, 3H), 1.99–1.72 (m, 2H), 1.70–1.55 (m, 3H), 1.35 (m, 1H), 1.29 (s, 3H), 1.06 (s, 3H); $^{13}$C NMR (400 MHz, DMSO-d$_6$) δ 145.4, 145.0, 143.4, 143.0, 133.5, 131.0, 128.9, 128.1, 126.4, 126.3, 117.9, 116.5, 114.4, 113.5, 112.1, 75.2, 59.3, 49.5, 36.9, 29.7, 27.6, 25.5, 24.6, 24.3, 20.0; [α]$^{23}_D$=+170° (c 0.23, CHCl$_3$).

EXAMPLE 286

(+)(5R,3'S)2,5(R)-Dihydro-9-hydroxy-10-methoxy-2,2,4-trimethyl-5-(3-cyclopentenyl)-1H-[1]benzopyrano[3,4-f]quinoline MS (DCI/NH$_3$) m/z 390 (M+H)$^+$; $^1$H NMR (300 MHz, DMSO-d$_6$) δ 8.67 (s, 1H), 8.02 (d, 1H), 6.65 (d, 1H), 6.62 (d, 1H), 6.53 (d, 1H), 6.25 (s, 1H), 5.77 (ddd, 1H), 5.69 (ddd, 1H), 5.47 (s, 1H), 5.37 (s, 1H), 3.66 (s, 3H), 2.90 (m, 1H), 2.34–2.13 (m, 2H), 2.10 (s, 3H), 1.55–1.41 (m, 2H), 1.31 (s, 3H), 1.04 (s, 3H); $^{13}$C NMR (400 MHz, DMSO-d$_6$) δ 145.5, 144.9, 144.0, 143.9, 133.6, 132.0, 131.7, 131.5, 127.9, 126.2, 117.7, 117.6, 116.5, 114.4, 113.3, 111.9, 76.1, 59.3, 49.4, 48.6, 31.7, 29.5, 27.1, 24.6, 23.7; [α]$^{23}_D$=+136° (c 0.355, CHCl$_3$).

EXAMPLE 287

(+)(5R,3'R)2,5(R)-Dihydro-9-hydroxy-10-methoxy-2,2,4-trimethyl-5-(3-cyclopentenyl)-1H-[1]benzopyrano[3,4-f]quinoline MS (DCI/NH$_3$) m/z 390 (M+H)$^+$; $^1$H NMR (300 MHz, DMSO-d$_6$) δ 8.68 (s, 1H), 8.01 (d, 1H), 6.65 (d, 1H), 6.62 (d, 1H), 6.51 (d, 1H), 6.22 (s, 1H), 5.72 (dd, 1H), 5.41 (d, 1H), 5.40 (s, 1H), 5.17 (dd, 1H), 3.63 (s, 3H), 2.90–2.80 (m, 1H), 2.41–2.32 (m, 1H), 2.23–2.10 (m, 1H), 2.06 (s, 3H), 1.89–1.71 (m, 2H), 1.30 (s, 3H), 1.08 (s, 3H); $^{13}$C NMR (400 MHz, DMSO-d$_6$) δ 145.5, 145.0, 143.9, 143.4, 133.5, 132.3, 132.2, 130.2, 128.1, 126.4, 117.8, 116.9, 116.4, 114.4, 113.4, 111.9, 75.7, 59.3, 49.5, 48.7, 31.6, 29.8, 27.6, 27.1, 24.2; [α]$^{23}_D$=+116° (c 0.800, CHCl$_3$).

EXAMPLE 288 rel-(5S)-9-Hydroxy-5-[(3R)-(1-methoxycarbonyl)cyclohexen-3-yl]-10-methoxy-2,2,4-trimethyl-2,5-dihydro-1H-[1]benzopyrano[3,4-f]quinoline MS (DCI/NH3) 462 (M+H)+; 1H NMR (200 MHz, DMSO-d6), δ 8.81 (s, 1H), 8.07 (d, J=8.5 Hz, 1H), 6.72 (d, J=8.5 Hz, 1H), 6.70 (d, J=8.5 Hz, 1H), 6.60 (d, J=8.5 Hz, 1H), 6.42–6.41 (m, 1H), 6.21 (d, J=1.2 Hz), 5.57 (d, J=10.2

Hz, 1H), 1H), 5.45 (s, 1H), 2.71 (s, 2H), 2.58 (s, 2H), 2.56–2.48 (m, 2H), 2.20–2.16 (m, 2H), 2.08 (d, J=1.2 Hz), 1.80–1.40 (m, 4H), 1.25 (s, 2H), 1.18 (s, 2H); HRMS calcd for $C_{28}H_{21}NO5$ is 461.2202. Found 461.2212.

EXAMPLE 289

2,5-Dihydro-9-hydroxy-10-methoxy-2,2,4-trimethyl-5-(2-methyl-3-propenyl)-1H-[1]benzopyrano[3,4-f]quinoline Example 276 (0.040 g, 0.092 mmol) and dichlorobis(triphenylphosphine)palladium(II) (0.006 g, 0.009 mmol) were dissolved in dioxane (5 ml), heated to 100° C. and treated with sodium borohydride (0.017 g, 0.460 mmol). The resulting black solution was allowed to cool to room temperature, diluted with water and ethyl acetate and filtered through celite. The layers were separated, the aqueous layer was extracted with ethyl acetate, the combined organics were washed with brine, dried ($MgSO_4$), and concentrated. Purification by silica gel chromatography eluting with 25% ethyl acetate in hexanes provided the desired product (0.028 g, 80%) as a colorless foam.

$^1$H NMR (300 MHz, DMSO-$d_6$) δ 8.71 (s, 1H), 7.92 (d, J=8 Hz, 1H), 6.62 (d, J=8 Hz), 1H), 6.61 (d, J=8 Hz, 1H), 6.41 (d, J=8 Hz, 1H), 6.18 (d, J=1 Hz, 1H), 5.83 (dd, J=3, 10 Hz, 1H), 5.44 (br s, 1H), 4.75 (br s, 1H), 4.56 (br s, 1H), 3.65 (s, 3H), 2.50–2.41 (m, 1H), 2.19 (s, 3H), 2.16–2.07 (m, 1H), 1.73 (s, 3H), 1.18 (s, 3H), 1.15 (s, 3H); $^{13}$C NMR (125 MHz, DMSO-$d_6$) δ 145.8, 144.9, 143.8, 142.8, 141.6, 133.3, 132.7, 127.5, 126.4, 117.8, 116.3, 116.2, 114.2, 113.6, 112.8, 112.7, 72.0, 59.4, 49.7, 29.2, 28.8, 24.0, 22.4; MS (DCI/$NH_3$) m/e (M+H)$^+$ 378; Anal. calcd for $C_{24}H_{27}NO_3$: C, 76.36; H, 7.21; N, 3.71. Found: C, 76.06; H, 7.17; N, 3.39.

EXAMPLE 290

9,10-Dimethoxy-5-(3-propenyl)-2,2,4-trimethyl-1H-2,5-dihydro-[1]benzopyrano[3,4-f]quinoline MS (ESI) m/z 378 (M+H)$^+$; $^1$H NMR (300 MHz, DMSO) δ 7.93 (d, J=8.5 Hz, 1H), 6.82 (d, J=8.8 Hz, 1H), 6.61 (dd, J=4.4, 4.4 Hz, 2H), 6.22 (d, J=1.4 Hz, 1H), 5.83 (ddt, J=16.9, 10.3, 3.1 Hz, 1H), 5.70 (dd, J=10.3, 3.3 Hz, 1H), 5.44 (s, 1H), 5.44–4.96 (m, 2H), 3.77 (s, 3H), 3.67 (s, 3H), 2.16 (s, 3H), 1.17 (s, 3H), 1.16 (s, 3H); HRMS calcd for $C_{24}H_{27}NO_3$ 377.1991. Found 377.2001.

EXAMPLE 291

9,10-Dimethoxy-5-[3-cyclohexenyl]-methoxy-2,2,4-trimethyl-2,5-dihydro-1H-[1]benzopyrano[3,4-f]quinoline MS (ESI) m/z 418 (M+H)$^+$; $^1$H NMR (300 MHz, DMSO), isomer 1: δ 8.02 (d, J=8.8 Hz, 1H), 6.84 (d, J=1.7 Hz, 1H), 6.70–6.60 (m, 2H), 6.27 (d, J=0.6 Hz, 1H), 5.80–5.60 (m, 2H), 5.16–5.15 (m, 2H), 3.77 (s, 3H), 3.69 (s, 3H), 2.13 (s, 3H), 1.31 (s, 3H), 1.07 (s, 3H); isomer 2: δ 8.01 (d, J=8.81 Hz, 1H), 6.80 (d, J=0.7 Hz, 1H), 6.64 (m, 2H), 6.26 (d, J=0.7 Hz, 1H), 5.60–5.30 (m, 2H), 5.09 (s, 1H), 3.77 (s, 3H), 3.68 (s, 3H), 2.10 (s, 3H), 1.29 (s, 3H), 1.04 (s, 3H); HRMS calcd for $C_{27}H_{31}NO_3$ 417.2304. Found 417.2299.

EXAMPLE 292

10-Methoxy-9-ethoxy-5-(3-propenyl)-2,2,4-trimethyl-1H-2,5-dihydro-[1]benzopyrano[3,4-f]quinoline $^1$H NMR (300 MHz, DMSO) δ 7.94 (d, J=8.8 Hz, 1H), 6.79 (d, J=8.8 Hz, 1H), 6.60 (d, J=8.8 Hz, 1H), 6.55 (d, J=8.8, 1H), 6.45 (s, 1H), 5.85 (ddt, J=17.3, 10.3, 6.6 Hz, 1H), 5.43 (d, J=9.2 Hz), 5.16 (s, 1H), 5.09 (dd, J=10.3, 1.1 Hz, 1H), 5.06 (dd, J=17.3, 11 Hz, 1H), 4.91 (s, 1H), 4.06–3.97 (m, 2H), 2.62–2.52 (m, 1H), 2.31–2.15 (m, 1H), 2.24 (s, 3H), 1.35 (t, J=7.0 Hz, 3H), 1.26 (s, 3H), 1.07 (s, 3H); MS (DCI/$NH_3$) m/z 392 (M+H)$^+$; HRMS calcd for $C_{26}H_{27}NO_3$ 391.2147. Found 391.2138.

EXAMPLE 293

10-Methoxy-9-(3-propenyloxy)-5-(3-propenyl)-2,2,4-trimethyl-1H-2,5-dihydro[1]benzopyrano[3,4-f]quinoline MS (DCI/$NH_3$) m/z 404 (M+H)$^+$. $^1$H NMR (300 MHz, DMSO) δ 7.93 (d, J=9.0 Hz, 1H), 6.83 (d, J=8.8 Hz, 1H), 6.61 (d, J=9.0 Hz, 1H), 6.59 (d, J=8.8 Hz, 1H), 6.23 (d, J=1.5 Hz, 1H), 6.15–6.02 (m, 1H), 5.81 (ddt, J=17.3, 10.3, 6.6 Hz, 1H), 5.67 (dd, J=9.8, 3.3 Hz), 5.45 (s, 1H), 5.44 (dd, J=16.0, 2.0 Hz, 1H), 5.27 (dd, 10.6, 2.0 Hz, 1H), 5.03 (dd, J=10.3, 1.8 Hz, 1H), 4.98 (dd, J=17.3, 1.8 Hz, 1H), 4.56–4.53 (m, 1H), 2.47–2.41 (m, 1H), 2.34–2.27 (m, 1H), 2.16 (s, 3H), 1.17 (s, 3H), 1.16 (s, 3H); HRMS calcd for $C_{26}H_{29}NO_3$ 403.2147. Found 403.2150.

EXAMPLE 294

10-Methoxy-9-(3-propynyloxy)-5-(3-propenyl)-2,2,4-trimethyl-1H-2,5-dihydro[1]benzopyrano[3,4-f]quinoline MS (DCI/$NH_3$) m/z 402 (M+H)$^+$; $^1$H NMR (300 MHz, DMSO) δ 7.92 (d, J=8.8 Hz, 1H), 6.88 (d, J=8.8 Hz, 1H), 6.62 (d, J=8.8 Hz, 1H), 6.61 (d, J=8.8, 1H), 6.24 (d, J=1.7 Hz, 1H), 5.81 (ddt, J=17.3, 10.3, 6.6 Hz, 1H), 5.72 (dd, J=9.8, 3.3 Hz), 5.44 (s, 1H), 5.03 (dd, J=10.3, 1.8 Hz, 1H), 4.99 (dd, J=17.3, 1.8 Hz, 1H), 4.79 (d, J=2.3 Hz, 2H), 3.57 (t, J=2.3 Hz, 1H), 2.47–2.41 (m, 1H), 2.34–2.27 (m, 1H), 2.16 (s, 3H), 1.17 (s, 3H), 1.16 (s, 3H); HRMS calcd for $C_{26}H_{27}NO_3$ 401.1991. Found 401.1978.

EXAMPLE 295

2,5-Dihydro-9-acetoxy-10-methoxy-2,2,4-trimethyl-5-(2-propenyl)-1H-[1]benzopyrano[3,4-f]quinoline $^1$H NMR (400 MHz, DMSO-d6) δ 7.78 (d, J=8.5, 1H), 6.81 (d, J=8.5, 1H), 6.60 (d, J=8.5, 1H), 6.57 (d, J=8.9, 1H), 6.18 (d, J=1.7, 1H), 5.80–5.70 (m, 2H), 5.39 (s, 1H), 4.99–4.90 (m, 2H), 3.55 (s, 3H), 2.39 (br dd, 2H), 2.23 (s, 3H), 2.10 (d, J=0.9, 3H), 1.11 (s, 3H), 1.10 (s, 3H); $^{13}$C NMR (100 MHz, DMSO-d6) δ 169.3, 148.5, 148.0, 146.4, 138.6, 134.1, 133.7, 132.2, 127.4, 126.3, 120.8, 118.3, 117.4, 116.3, 115.1, 113.9, 112.7, 73.7, 60.0, 49.9, 36.7, 29.4, 29.1, 23.9, 20.6; MS (DCI/NH3) m/e 406(M+H)+; Anal. Calcd for $C_{25}H_{27}NO_4$: C, 74.05, H, 6.71, N, 3.45. Found: C, 73.91, H, 6.79, N, 3.31.

EXAMPLE 296

2,5-Dihydro-9-(4-N,N-dimethylamino-4-oxo-butanoyloxy)-10-methoxy-2,2,4-trimethyl-5(2-propenyl)-1H-[1]benzopyrano[3,4-f]quinoline 1H NMR (300 MHz, DMSO-d6) δ 7.86 (d, J=8.8, 1H), 6.85 (d, J=8.8, 1H), 6.68–6.62 (m, 2H), 6.25 (d, J=1.5, 1H), 5.89–5.75 (m, 2H), 5.46 (s, 1H), 5.06–4.96 (m, 2H), 3.62 (s, 3H), 3.00 (s, 3H), 2.85 (s, 3H), 2.83–2.67 (m, 4H), 2.48 (m, 1H), 2.26 (m, 1H), 2.17 (s, 3H), 1.18 (s, 3H), 1.17 (s, 3H); 13C NMR (75 MHz, DMSO-d6) δ 171.5, 170.4, 148.3, 148.0, 146.2, 138.5, 134.1, 133.5, 132.1, 127.3, 126.2, 120.8, 118.1, 117.2, 116.2, 115.0, 113.8, 112.5, 73.6, 60.0, 49.8, 36.6, 36.5, 34.9, 29.3, 29.0, 27.6, 23.8; MS (DCI/NH3) m/e 491(M+H)+, 508(M+NH4)+; Anal. Calcd for $C_{29}H_{24}N_2O_5$: C, 71.00, H, 6.99, N, 5.71 Found: C, 70.88, H, 7.10, N, 5.49.

The chemistry described above was used with Core 9 to prepare Examples 297–299.

EXAMPLE 297

7-Bromo-5-[3-cyclohexenyl]-10-methoxy-2,2,4-trimethyl-2,5-dihydro-1H[1]benzopyrano[3,4-f]quinoline MS (APCI) m/z 466 (M+H)+; $^1$H NMR (300 MHz, DMSO), isomer 1: δ 8.03 (d, J=8.8 Hz, 1H), 7.33 (d, J=9.2 Hz, 1H), 6.65 (dd, J=8.8, 1.7 Hz, 2H), 6.35 (d, J=1.3 Hz, 1H), 5.91–5.43 (m, 4H), 3.86 (s, 3H), 2.14 (s, 3H), 1.99 (s, 3H), 1.31 (s, 3H), 1.06 (s, 3H); isomer 2: δ 8.00 (dd, J=8.8 Hz, 1H), 7.33 (d, J=9.2 Hz, 1H), 6.65 (dd, J=8.8, 1.7 Hz, 1H), 6.35 (d, J=1.3 Hz, 1H), 6.31 (d, J=1.3 Hz, 1H), 5.91–5.43 (m, 4H), 2.12 (s, 3H), 1.28 (s, 3H), 1.03 (s, 3H); $^{13}$C NMR (300 MHz, DMSO) δ 155.5, 145.5, 133.9, 133.7, 129.5, 129.4, 128.5, 127.9, 127.7, 127.2, 127.0, 125.6, 118.1, 115.5, 113.2, 113.1, 106.9, 102.3, 77.2, 76.5, 55.8, 49.4, 37.6, 36.7, 29.6, 29.5, 27.4, 26.9, 25.6, 24.6, 24.2, 23.6, 21.1, 19.8; HRMS cald for $C_{26}H_{28}NO_2{}^{79}Br$ 465.1303. Found 465.1284; Cald for $C_{26}H_{28}NO_2{}^{81}Br$ 467.1283. Found 467.1281. Anal. calcd for $C_{26}H_{28}BrNO_2$, C, 66.95; H, 6.05; N, 3.00; found C, 66.77; H, 6.20; N, 2.88.

EXAMPLE 298

10-Methoxy-7-bromo-5-(3-propenyl)-2,2,4-trimethyl-1H-2,5-dihydro-[1]benzopyrano[3,4-f]quinoline MS (APCI) m/z 426 (M+H)+; $^1$H NMR (300 MHz, DMSO) δ 7.93 (d, J=8.8 Hz, 1H), 7.33 (d, J=9.2 Hz, 1H), 6.71 (d, J=9.2 Hz, 1H), 6.60 (d, J=8.5 Hz, 1H), 6.25 (d, J=1.5 Hz, 1H), 5.94–5.80 (m, 2H), 5.45 (s, 1H), 5.0 (m, 2H), 3.86 (s, 3H), 2.17 (d, J=1.5 Hz, 3H), 1.17 (s, 6H). $^{13}$C NMR (300 MHz, DMSO) 155.3, 147.0, 146.0, 133.8, 133.6, 131.8, 129.5, 127.3, 127.2, 117.4, 116.0, 115.1, 113.2, 107.1, 102.6, 74.8, 55.9, 49.8, 29.0, 23.8. HRMS calcd for $C_{23}H_{24}{}^{79}BrNO_2$ 426.3502. Found 426.3496. Anal. calcd for $C_{23}H_{24}BrNO_2$: C, 64.79; H, 5.67; N, 3.29; found C, 65.08; H, 5.73; N, 3.18.

EXAMPLE 299

7-Bromo-5-[1-methyl-3-cyclohexenyl]-10-methoxy-2,2,4-trimethyl-2,5-dihydro-1H-[1]benzopyrano[3,4-f]quinoline MS (APCI) m/z 480 (M+H)+; $^1$H NMR (300 MHz, DMSO) isomer 1: δ 8.02 (d, J=8.5 Hz, 1H), 7.55 (d, J=5.9 Hz, 1H), 7.37 (d, J=2.6 Hz, 1H), 7.31 (d, J=1.8 Hz, 1H), 6.67 (dd, J=14.7, 8.8 Hz, 1H), 6.35 (d, J=1.5 Hz, 1H), 5.63 (d, J=5.9 Hz, 1H), 5.56–5.45 (m, 2H), 3.86 (s, 3H), 2.13 (s, 3H), 1.61 (s, 3H), 1.30 (s, 3H), 1.02 (s, 3H); isomer 2: δ 8.00 (d, J=8.5 Hz, 1H), 7.54 (d, J=5.9 Hz, 1H), 7.35 (d, J=1.8 Hz, 2H), 6.67 (dd, J=14.7, 8.8 Hz, 2H), 6.31 (d, J=1.5 Hz, 1H), 5.51 (m, 2 3.86 (s, 3H), 2.08 (s, 3H), 1.50 (s, 3H), 1.09 (s, 3H), 0.92 (s, 3H); HRMS calcd for $C_{27}H_{30}NO_2{}^{79}Br$ 479.1460. Found 479.1463; HRMS calcd for $C_{27}H_{30}NO_2{}^{81}Br$ 481.1439. Found 481.1456. Anal. calcd for $C_{27}H_{30}NO_2{}^{79}Br$: C, 67.5; H, 6.29; N, 2.92; found C, 67.08; H, 6.38; N, 2.54.

The chemistry described above was used with Core 10 to prepare Example 300.

EXAMPLE 300

10-Methoxy-9-bromo-5-(3-propenyl)-2,2,4-trimethyl-1H-2,5-dihydro-[1]benzopyrano[3,4-f]quinoline MS (DCI/NH$_3$) m/z 428 (M+H)+; 426; $^1$H NMR (300 MHz, DMSO) δ 7.93 (d, J=8.8 Hz, 1H), 7.33 (d, J=8.5 Hz, 1H), 6.67 (d, J=8.5 Hz, 1H), 6.65 (d, J=8.5 Hz, 1H), 6.36 (d, J=1.1 Hz, 1H), 5.88–5.74 (m, 2H), 5.46 (s, 1H), 5.05–4.95 (m, 2H), 3.62 (s, 3H), 2.18 (d, J=1.1 Hz, 3H), 1.19 (s, 3H), 1.16 (s, 3H); $^{13}$C NMR (300 MHz, DMSO) δ 152.7, 150.8, 146.5, 134.0, 133.6, 132.1, 130.0, 127.3, 126.1, 119.3, 117.4, 116.2, 115.0, 114.6, 114.0, 109.5, 73.7, 59.6, 49.9, 36.7, 29.4, 29.1, 23.9; HRMS calcd for $C_{23}H_{24}NO_2{}^{79}Br$ 425.0990. Found 425.0998; HRMS calcd for $C_{23}H_{24}NO_2{}^{81}Br$ 427.0970. Found 427.0974. Anal. calcd for $C_{23}H_{24}BrNO_2$: C, 64.79; H, 5.67; N, 3.29; found C, 64.99; H, 5.98; N, 3.13.

The chemistry detailed above was used with Core 11 to prepare Examples 301–303.

EXAMPLE 301

7,9-Dibromo-10-methoxy-5-(3-propenyl)-2,2,4-trimethyl-1H-2,5-dihydro[1]benzopyrano[3,4-f]quinoline MS (ESI) m/z 504 (M+H)+; $^1$H NMR (300 MHz, DMSO) δ 7.57 (d, J=8.9 Hz, 1H), 7.65 (s, 1H), 6.66 (d, J=8.8 Hz, 1H), 6.44 (s, 1H), 5.95 (dd, J=10.1, 3.1 Hz, 1H), 5.97–5.78 (m, 2H), 5.47 (s, 1H), 5.08–4.99 (m, 2H), 3.62 (s, 3H), 2.19 (s, 3H), 1.20 (s, 3H), 1.17 (s, 3H); $^{13}$C NMR (300 MHz, DMSO) δ 152.1, 147.4, 147.0, 133.6, 132.7, 132.0, 131.7, 128.3, 127.1, 126.3, 120.5, 117.6, 115.9, 115.3, 114.0, 113.8, 110.0, 106.6, 75.2, 59.7, 49.9, 36.8, 29.6, 29.2, 23.7; HRMS calcd for $C_{23}H_{23}{}^{79}Br_2NO_2$ 503.0096. Found 503.0086; HRMS calcd for $C_{23}H_{23}{}^{79}Br{}^{81}BrNO_2$ 505.0075. Found 505.0075.

EXAMPLE 302

7,9-Dibromo-5-[cyclohexen-3-yl]-10-methoxy-2,2,4-trimethyl-2,5-dihydro-1H-[1]benzopyrano[3,4-f]quinoline MS (ESI) m/z 544 (M+H)+; $^1$H NMR (300 Mhz, DMSO), 1st isomer: δ 8.81 (d, 1H, J=8.83 Hz), 7.67 (s, 1H), 6.70 (d, 1H, J=8.83 Hz), 6.59 (s, 1H), 5.82–5.59 (m, 4H), 5.50 (s, 1H), 3.61 (s, 3H), 2.49–2.27 (m, 2H), 2.15 (s, 3H), 2.04–1.81 (m, 2H), 1.79–1.41 (m, 2H), 1.32 (s, 3H), 1.08 (s, 3H); 2nd isomer δ 7.9 (d, 1H, J=8.83 Hz), 7.66 (s, 1H), 6.69 (d, 1H, J=8.83 Hz), 6.54 (s, 1H), 5.82–5.59 (m, 4H), 5.45 (s, 1H), 3.60 (s, 3H), 2.49–2.27 (m, 2H), 2.13 (s, 3H), 2.04–1.81 (m, 2H), 1.79–1.41 (m, 2H), 1.30 (s, 3H), 1.05 (s, 3H); HRMS calcd for $C_{26}H_{27}{}^{79}Br_2NO_2$ is 543.0409. Found 543.0385; HRMS calcd for $C_{26}H_{27}{}^{79}Br{}^{81}BrNO_2$ 545.0388. Found 545.0396.

EXAMPLE 303

7,9-Dibromo-5-[1-methyl-3-cyclohexenyl]-10-methoxy-2,2,4-trimethyl-2,5-dihydro-1H-[1]benzopyrano[3,4-f]quinoline MS (ESI) m/z 560 (M+H)+; 1H NMR (300 MHz, DMSO), isomer 1: δ 8.83 (d, J=8.0 Hz, 1H), 7.37 (s, 1H), 6.70 (d, J=8.8 Hz, 1H), 6.58 (s, 1H), 5.58 (d, J=9.2 Hz, 1H), 5.49 (s, 1H), 3.61 (s, 3H), 2.51–2.49 (m, 4H), 2.14 (s, 3H), 1.31 (s, 3H), 1.29–1.20 (m, 4H), 1.26 (s, 3H); isomer 2: δ 7.99 (d, J=8.0 Hz, 1H), 7.37 (s, 1H), 6.71 (d, J=8.8 Hz, 1H), 6.55 (s, 1H), 5.57 (d, J=9.2 Hz, 1H), 5.45 (s, 1H), 3.59 (s, 3H), 2.51–2.49 (m, 4H), 2.09 (s, 3H), 1.30 (s, 3H), 1.29–1.20 (m, 4H), 1.21 (s, 3H); HRMS calcd for $C_{27}H_{29}Br_2NO_2$ 557.0565. Found 557.0548.

The chemistry described above was used with Cores 12–17 to prepare Examples 304–310.

EXAMPLE 304

10-Methoxy-7-(2-ethenyl)-5-(3-propenyl)-2,2,4-trimethyl-1H-2,5-dihydro-[1]benzopyrano[3,4-f]quinoline MS (ESI) m/z 373 (M+H)+; $^1$H NMR (300 MHz, DMSO) δ 7.82 (d, J=8.9 Hz, 1H), 7.23 (d, J=8.9 Hz, 1H), 6.78 (dd, J=11.0, 6.8 Hz, 1H), 6.61 (d, J=8.9 Hz, 1H), 6.49 (d, J=8.5 Hz, 1H), 5.99 (d, J=1.7 Hz, 1H), 5.74 (dd, J=7.6, 3.0 Hz, 1H), 5.71–5.63 (m, 1H), 5.57 (dd, J=7.6, 1.7 Hz, 1H), 5.32 (s, 1H), 5.00 (dd, J=9.3, 1.7 Hz, 1H), 4.92 (dd, J=10.2, 1.7 Hz, 1H), 4.83 (dd, J=16.9, 1.7 Hz, 1H), 3.75 (s, 3H), 2.06 (s, 3H), 1.53–1.41 (m, 2H), 1.24–1.15 (m, 3H), 1.05 (d, J=2.1 Hz, 1H); $^{13}$C NMR (300 MHz, DMSO) δ 155.66, 147.91, 145.55, 134.17, 133.45, 131.98, 130.77, 127.37, 127.28, 123.88, 119.52, 117.21, 115.99, 115.80, 113.20, 113.18, 112.12, 105.59, 74.01, 55.59, 49.69, 36.40, 29.03, 28.83, 27.67, 26.19, 23.83, 13.55; HRMS calcd for $C_{25}H_{27}NO_2$ 373.2042. Found 373.2048.

EXAMPLE 305

10-Methoxy-7-methyl-5-(3-propenyl)-2,2,4-trimethyl-1H-2,5-dihydro-[1]benzopyrano[3,4-f]quinoline MS (ESI) m/z 362 (M+H)+; $^1$H NMR (300 MHz, DMSO) δ 7.92 (d, J=8.5 Hz, 1H), 6.93 (d, J=8.5 Hz, 1H), 6.59 (dd, J=5.5, 2.6 Hz, 1H), 6.10 (s, 1H), 5.90–5.76 (m, 2H), 5.44 (s, 1H), 5.07–4.90 (m, 2H), 3.82 (s, 3H), 2.17 (s, 3H), 2.08 (s, 3H), 1.99 (s, 3H), 1.16 (s, 3H), 1.15 (s, 3H); $^{13}$C NMR (300 MHz, DMSO), 154.2, 148.5, 145.4, 134.5, 133.4, 131.9, 127.8, 127.4, 127.1, 118.2, 117.0, 116.3, 116.0, 113.1, 112.9, 104.8, 73.6, 55.5, 49.6, 36.5, 28.9, 28.8, 23.8, 15.0; HRMS calcd for $C_{24}H_{27}NO_2$ 361.2042. Found 361.2045.

EXAMPLE 306

10-Methoxy-7-acetyl-5-(3-propenyl)-2,2,4-trimethyl-1H-2,5-dihydro-[1]benzopyrano[3,4-f]quinoline MS (ESI) m/z 390 (M+H)+. $^1$H NMR (300 MHz, DMSO), 7.88 (d, J=8.8 Hz, 1H), 7.59 (d, J=8.8 Hz, 1H), 6.84 (d, J=8.8 Hz, 1H), 6.62 (d, J=8.8 Hz, 1H), 6.22 (d, J=1.5 Hz, 1H), 6.01–5.97 (m, 1H), 5.90–5.69 (m, 1H), 5.46 (s, 1H), 5.03–4.83 (m, 2H), 3.93 (s, 3H), 2.53 (s, 3H), 2.20 (d, J=1.5 Hz, 3H), 1.19 (s, 3H), 1.16 (s, 3H).

EXAMPLE 307

(+/−)2,5-Dihydro-9-methyl-10-methoxy-2,2,4-trimethyl-5-(1-methylcyclohexen-3-yl)-1H-[1]benzopyrano[3,4-f]quinoline MS (DCI/NH$_3$) m/z 416 (M+H)+.

EXAMPLE 308

10-Methoxy-7-methyl-9-methyl-5-(3-propenyl)-2,2,4-trimethyl-1H-2,5-dihydro-[1]benzopyrano[3,4-f]quinoline MS (DCI/NH$_3$) m/z 376 (M+H)+; $^1$H NMR (300 MHz, DMSO-d$_6$) δ 7.95 (d, J=8.5 Hz, 1H), 6.81 (s, 1H), 6.62 (d, J=8.5 Hz, 1H), 6.17 (d, J=1.5 Hz, 1H), 5.89–5.76 (m, 2H), 5.44 (br s, 1H), 5.04 (dd, J=10.3, 1.8 Hz, 1H), 4.94 (dd, J=17.3, 1.8 Hz, 1H), 3.52 (s, 3H), 2.46–2.40 (m, 1H), 2.28–2.24 (m, 1H), 2.18 (s, 3H), 2.17 (s, 3H), 2.07 (s, 3H), 1.19 (s, 3H), 1.14 (s, 3H); HRMS calcd for $C_{25}H_{29}NO_2$ 375.2198. Found: 375.2214.

EXAMPLE 309

10-Chloro-5-(3-propenyl)-2,2,4-trimethyl-2,5-dihydro-1H-[1]benzopyrano[3,4-f]quinoline MS (DCI/NH$_3$) m/z 352 (M+H)+; $^1$H NMR (300 MHz, DMSO) δ 7.93 (d, J=8 Hz, 1H), 7.12–7.10 (m, 2H), 6.90–6.84 (m, 1H), 6.65 (10, 2 Hz, 1H), 4.97 (dd, J=17, 2 Hz, 1H), 2.47–2.26 (m, 2H), 2.16 (s, 3H), 1.23 (s, 3H), 1.17 (s, 3H); HRMS (FAB) calcd m/z for $C_{22}H_{22}ClNO$: 351.1390 (M)+. Found: 351.1385.

EXAMPLE 310

(+/−)2,5-Dihydro-10-chloro-2,2,4-trimethyl-5-phenyl-1H-[1]benzopyrano[3,4-f]quinoline MS (DCI/NH3) m/z 288 (M+H)+; 1H NMR (200 MHz, DMSO) δ 7.98 (d, J=8 Hz, 1H), 7.27–7.14 (m, 5H), 6.97–6.80 (m, 2H), 6.81 (br s, 1H), 6.78–6.72 (m, 2H), 6.44 (br s, 1H), 5.40 (br s, 1H), 1.81 (br s, 2H), 1.26 (s, 2H), 1.16 (s, 2H); HRMS (FAB) calcd m/z for $C_{25}H_{23}ClNO$: 387.1390 (M)+. Found: 287.1286.

EXAMPLE 311

2,5-Dihydro-10-methoxy-5-(3-(N-methyl-N-(carbomethoxymethyl)aminocarbonyloxy)phenyl)-2,2,4-trimethyl-1H-[1]benzopyrano[3,4-f]quinoline Example 13 and N-methyl-N-(methylglycinate) carbamoyl chloride were processed as in Example 14 to provide the desired compound.

MS (DCI/NH$_3$) m/e 529 (M+H)+; $^1$H NMR (300 MHz, DMSO-d$_6$) δ 8.00 (d, 1H), 7.21 (m, 1H), 7.03 (d, 1H), 6.92 (m, 3H), 6.72 (m, 3H), 6.55 (d, 1H), 6.45 (t, 1H), 5.40 (s, 1H), 4.15 (s, 1H), 4.05 (s, 1H), 3.78 (s, 3H), 3.65 (s, 3H), 3.00 (s, 1H), 2.88 (s, 2H), 1.84 (s, 3H), 1.22 (s, 3H), 1.13 (s, 3H). Anal. calcd for $C_{31}H_{32}N_2O_6$: C, 70.43; H, 6.10; N, 5.29. Found: C, 70.98; H, 6.33; N, 4.85.

EXAMPLE 312

2,5-Dihydro-10-methoxy-5-(3-(N-methyl-N-(N-methylcarbonyl)aminocarbonyloxy)phenyl)-2,2,4-trimethyl-1H-[1]benzopyrano[3,4-f]quinoline Example 13 and methylisocyanate were processed as in Example 14 to provide the desired compound.

MS (DCI/NH$_3$) m/e 514 (M+H)+; $^1$H NMR (300 MHz, DMSO-d$_6$) δ 8.18 (q, 1H), 8.01 (d, 1H), 7.27 (t, 1H), 7.06 (t, 2H), 6.98 (s, 1H), 6.91 (t, 1H), 6.77 (s, 1H), 6.70 (d, 1H), 6.56 (d, 1H), 6.46 (d, 1H), 6.19 (s, 1H), 5.38 (s, 1H), 3.78 (s, 3H), 3.19 (s, 3H), 2.70 (d, 3H), 1.84 (s, 3H), 1.22 (s, 3H), 1.14 (s, 3H). Anal. calcd for $C_{30}H_{31}N_3O_5$·2H$_2$O: C, 65.55; H, 6.41; N, 7.60. Found: C, 65.71; N, 7.05.

EXAMPLE 313

2,5-Dihydro-10-methoxy-5-(3-(N-methyl-N-(N-methylcarbonyl)aminocarbonyloxy)phenyl)-2,2,4-trimethyl-1H-[1]benzopyrano[3,4-f]quinoline Example 13 and methylisocyanate were processed as in Example 14 to provide the desired compound.

MS (DCI/NH$_3$) m/e 457 (M+H)$^+$; $^1$H NMR (300 MHz, DMSO-d$_6$) δ 8.01 (d, 1H), 7.50 (q, 1H), 7.21 (t, 1H), 7.02 (d, 1H), 6.92 (dd, 2H), 6.80 (s, 1H), 6.77 (s, 1H), 6.70 (dd, 1H), 6.56 (d, 1H), 6.46 (d, 1H), 6.18 (s, 1H), 5.40 (s, 1H), 3.80 (s, 3H), 2.60 (d, 3H), 1.86 (s, 3H), 1.23 (s, 3H), 1.15 (s, 3H); Anal. calcd for C$_{28}$H$_{28}$N$_2$O$_4$.0.50H$_2$O: C, 72.33; H, 6.27; N, 6.01. Found: C, 72.20; H, 6.38; N, 5.78.

EXAMPLE 314

2,5-Dihydro-10-methoxy-5-(3-(2-hydroxyethyl)phenyl)-2,2,4-trimethyl-1H-[1]benzopyrano[3,4-f]quinoline A solution of 3-(2'-methoxymethoxy)ethylphenyl bromide (3.55 g, 14.5 mmol) in THF (150 ml) at −78° C. was treated with n-butyllithium (2.5 M in hexane, 5.80 ml) over 15 minutes, warmed to −30° C., cooled down to −78° C., treated with compound 1F in one portion, warmed to −50° C., quenched with saturated ammonium chloride, and allowed to warm to ambient temperature and settle. The supernatant was decanted and concentrated, and the residue was partitioned between water and ethyl acetate. The organic layer was washed sequentially with water and brine, dried (Na$_2$SO$_4$) and concentrated. Flash chromatography of the residue on silica gel with 20–35% ethyl acetate/hexane provided 0.82 g (56%) of the title 5-(3'-MOMO-phenyl) hemiketal.

MS (DCI/NH$_3$) m/e 489 (M+H)$^+$.

A solution of of the hemiketal prepared above (0.70 g, 1.43 mmol) in methanol (10 ml) was treated with saturated hydrogen chloride in methanol (20 ml) at ambient temperature, stirred for 18 hours, poured into 1:1 ethyl acetate/saturated ammonium chloride. The separated aqueous layer was extracted with ethyl acetate, and the combined acetate layers were sequentially washed with water and brine, dried (Na$_2$SO$_4$) and concentrated to provide 0.52 g (82%) of the unmasked hemiketal.

MS (DCI/NH$_3$) m/e 444 (M+H)$^+$.

A solution of the unmasked hemiketal prepared above (0.45 g, 1.00 mmol) and triethylsilane (1.16 g, 10 mmol) in dichloromethane (20 mL) was treated with boron trifluoride etherate (1.42 g, 10 mmol) at ambient temperature, stirred for 18 hours, and poured into 1:1 ethyl acetate/saturated NaHCO$_3$. The separated aqueous layer was extracted with ethyl acetate, and the combined extracts were washed sequentially with water and brine, dried (Na$_2$SO$_4$) and concentrated. Flash chromatography of the residue on silica gel with 25–45% ethyl acetate in hexane provided 0.342 of the title compound.

MS (DCI/NH$_3$) m/e 428 (M+H)$^+$; $^1$H NMR (300 MHz, DMSO-d$_6$) δ 8.00 (d, 1H), 7.00 (m, 5H), 6.74 (s, 1H), 6.70 (d, 1H), 6.55 (d, 1H), 6.45 (d, 1H), 6.16 (s, 1H), 5.39 (s, 1H), 4.54 (t, 1H), 3.79 (s, 3H), 3.44 (q, 4H), 2.59 (t, 2H), 1.86 (s, 3H), 1.22 (s, 3H), 1.11 (s, 3H); Anal. calcd for C$_{28}$H$_{29}$NO$_3$: C, 78.66; H, 6.83; N, 3.27. Found: C, 78.48; H, 6.85; N, 3.29.

EXAMPLE 315

2,5-Dihydro-10-methoxy-5-(3-(2-methanesulfonyloxyethyl)phenyl)-2,2,4-trimethyl-1H-[1]benzopyrano[3,4-f]quinoline A solution of Example 314 (200 mg, 0.47 mmole) and triethylamine (94 mg, 0.94 mmol) in CH$_2$Cl$_2$ (6 ml) at 0° C. was treated with methanesulfonyl chloride (64 mg, 0.56 mmol), stirred for 30 minutes, and quenched with saturated NaHCO$_3$. The separated aqueous layer was extracted with CH$_2$Cl$_2$, and the combined organic layers were washed with brine, dried (Na$_2$SO$_4$) and concentrated. Flash chromatography of the residue on silica gel with 10–30% ethyl acetate/hexane provided 0.30 g (97%) of the title compound.

MS (DCI/NH$_3$) m/e 506 (M+H)$^+$; $^1$H NMR (300 MHz, DMSO-d$_6$) δ 8.00 (d, 1H), 7.18 (s, 1H), 7.14 (d, 1H), 7.09 (d, 1H), 6.96 (d, 1H), 6.90 (t, 1H), 6.75 (s, 1H), 6.70 (d, 1H), 6.55 (d, 1H), 6.45 (d, 1H), 6.21 (s, 1H), 5.39 (s, 1H), 4.27 (t, 2H), 3.79 (s, 3H), 2.88 (s, 3H), 2.87 (t, 2H), 1.84 (s, 3H), 1.24 (s, 3H), 1.14 (s, 3H); Anal. calcd for C$_{29}$H$_{31}$NO$_5$S: C, 68.88; H, 6.17; N, 2.77. Found: C, 69.08; H, 6.14; N, 2.63.

EXAMPLE 316

2,5-Dihydro-10-methoxy-5-(3-(2-methythioethyl)phenyl)-2,2,4-trimethyl-1H-[1]benzopyrano[3,4-f]quinoline A solution of Example 315 (10 mg, 0.02 mmol) in DMF (1 ml) was treated with NaSMe (14 mg, 0.20 mmol) at ambient temperature, stirred for 2 hr, quenched with saturated NaHCO$_3$, and extracted with ethyl acetate. The organic layer was washed with brine, dried (Na$_2$SO$_4$) and concentrated. Flash chromatography of the residue on silica gel with 10–30% ethyl acetate/hexane provided 9 mg (99%) of the title compound.

MS (DCI/NH$_3$) m/e 458 (M+H)$^+$; $^1$H NMR (300 MHz, DMSO-d$_6$) δ 8.00 (d, 1H), 7.11 (t, 1H), 7.07 (s, 1H), 7.02 (d, 1H), 6.96 (d, 1H), 6.90 (t, 1H), 6.75 (s, 1H), 6.70 (d, 1H), 6.54 (d, 1H), 6.44 (d, 1H0, 6.16 (s, 1H), 5.39 (s, 1H), 3.77 (s, 3H), 2.70 (t, 2H), 2.54 (t, 2H), 1.91 (s, 3H), 1.95 (s, 3H), 1.21 (s, 3H), 1.15 (s, 3H).

EXAMPLE 317

2,5-Dihydro-10-methoxy-5-(3-(2-(N,N-dimethylaminocarbonyloxy)ethyl)phenyl)-2,2,4-trimethyl-1H-[1]benzopyrano[3,4-f]quinoline Example 314 and N,N-dimethylcarbamoyl chloride were processed as in Example 14 to provide the desired compound.

MS (DCI/NH$_3$) m/e 499 (M+H)$^+$; $^1$H NMR (300 MHz, DMSO-d$_6$) δ 8.01 (d, 1H), 7.00 (m, 5H), 6.76 (s, 1H), 6.70 (d, 1H), 6.55 (s, 1H), 6.44 (d, 1H), 6.15 (s, 1H), 5.39 (s, 1H), 4.01 (t, 2H), 3.78 (s, 3H), 2.79 (t, 2H), 2.77 (s, 3H), 2.65 (s, 3H), 1.84 (s, s, 3H), 1.23 (s, 3H), 1.15 (s, 3H); Anal. calcd for C$_{31}$H$_{34}$N$_2$O$_4$: C, 74.67; H, 6.87; N, 5.61. Found: C, 74.45; H, 6.73; N, 5.45.

EXAMPLE 318

2,5-Dihydro-10-methoxy-5-(3-(2-(N,N-dimethylamino)ethyl)phenyl)-2,2,4-trimethyl-1H-[1]benzopyrano[3,4-f]quinoline Example 315 and dimethylamine were processed as in Example 316 to provide the desired compound.

MS (DCI/NH$_3$) m/e 455 (M+H)$^+$; $^1$H NMR (300 MHz, DMSO-d$_6$) δ 8.00 (d, 1H), 7.09 (t, 1H), 7.01 (d, 1H), 6.97 (m, 2H), 6.90 (t, 1H), 6.73 (s, 1H), 6.69 (d, 1H), 6.55 (d, 1H), 6.44 (d, 1H), 6.16 (s, 1H), 5.39 (s, 1H), 3.79 (s, 3H), 2.54 (t, 2H), 2.25 (t, 2H), 2.08 (s, 6H), 1.87 (s, 3H), 1.22 (s, 3H), 1.17 (s, 3H).

EXAMPLE 319

2,5-Dihydro-10-methoxy-5-cyclopropyl-2,2,4-trimethyl-1H-[1]benzopyrano[3,4-f]quinoline

EXAMPLE 319A

A mixture of Example 1F (4.43 g, 13.7 mmol), 4-chlorophenol (9.28 g, 72.1 mmol) and MgSO$_4$ (8.69 g, 72.1 mmol) in CH$_2$Cl$_2$ (100 ml) at ambient temperature was stirred for 12 hr, diluted with ethyl acetate (200 ml), washed with 1M aq NaOH twice and brine respectively, dried (Na$_2$SO$_4$) and concentrated. The residue was triturated with hot ethyl acetate (25 ml) to provide the desired phenyl acetal.

MS (DCI/NH$_3$) m/e 306 (M-4-Cl-ph)$^+$.

EXAMPLE 319B

A solution of the Example 319A (131 mg, 0.30 mmol) in toluene (20 ml) at 0° C. was treated with cyclopropylmagnesium bromide made by refluxing cyclopropyl bromide (363 mg, 3.0 mmol) and Mg (73 mg, 3.0 mmol) in THF (1.5 ml) for 30 min. The final solution was allowed to warm to ambient temperature and stirred for 12 hr, quenched with sat. NH$_4$Cl. The organic layer was washed with 1M aq NaOH twice and brine respectively, dried (Na$_2$SO$_4$) and concentrated. Flash chromatography of the residue on silica gel with 5–15% ethyl acetate/hexane provided 18 mg (17%) of the title compound.

MS (DCI/NH$_3$) m/e 348 (M+H)$^+$; $^1$H NMR (300 MHz, DMSO-d$_6$) δ 8.01 (d, 1H), 7.04 (t, 1H), 6.67 (d, 1H), 6.60 (d, 1H), 6.57 (d, 1H), 6.16 (s, 1H), 5.44 (s, 1H), 5.42 (d, 1H), 3.85 (s, 3H), 2.12 (s, 3H), 1.26 (s, 3H), 1.05 (s, 3H), 0.28 (m, 4H), 0.08 (m, 1H).

EXAMPLE 320

2,5-Dihydro-10-methoxy-5-ethenyl-2,2,4-trimethyl-1H-[1]benzopyrano[3,4-f]quinoline A solution of 2B (34 mg, 0.1 mmol) and tributylvinyltin (96 mg) in CH$_2$Cl$_2$ (2 ml) was treated with boron trifluoride etherate (43 mg, 0.3 mmol) at −78° C., and allowed to warm to ambient temperature with stirring for 2 hr. The reaction was then quenched with sat. NaHCO$_3$, and the organic layer was washed with sat. NaHCO$_3$ and brine respectively, dried (Na$_2$SO$_4$) and concentrated. Flash chromatography of the residue on silica gel with 5–15% ethyl acetate/hexane provided 27 mg (81%) of the title compound.

MS (DCI/NH$_3$) m/e 334 (M+H)$^+$; $^1$H NMR (300 MHz, DMSO-d$_6$) δ 7.93 (d, 1H), 7.02 (t, 1H), 6.63 (dd, 2H), 6.54 (d, 1H), 6.19 (d, 1H), 6.10 (s, 1H), 5.93 (m, 1H), 5.42 (s, 1H), 5.16 (dt, 1H), 4.91 (d, 1H), 3.83 (s, 3H), 2.11 (s, 3H), 1.21 (s, 3H), 1.13 (s, 3H).

EXAMPLE 321 trans 2,5-Dihydro-10-methoxy-5-(2-phenylethenyl)-2,2,4-trimethyl-1H-[1]benzopyrano[3,4-f]quinoline A mixture of Example 320 (13 mg, 0.039 mmol), iodobenzene (12 mg, 0.058 mmol), palladium (II) acetate (18 mg, 0.008 mmol), tri(o-tolyl)phosphine (3.6 mg, 0.012 mmol), triethylamine (12 mg, 0.12 mmol) in CH$_3$CN (1 ml) was heated to 80° C. for 4 hr in a sealed tube. After solvent removal, flash chromatography of the residue on silica gel with 5–15% ethyl acetate/hexane provided 7 mg (44%) of the title compound.

MS (DCI/NH$_3$) m/e 410 (M+H)$^+$; $^1$H NMR (300 MHz, DMSO-d$_6$) δ 7.99 (d, 1H), 7.22 (m, 4H), 7.19 (m, 1H), 7.00 (t, 1H), 6.67 (d, 1H), 6.63 (d, 1H), 6.57 (d, 1H), 6.38 (q, 1H), 6.34 (d, 1H), 6.27 (d, 1H), 6.14 (s, 1H), 5.43 (s, 1H), 3.82 (s, 1H), 2.12 (s, 3H), 1.22 (s, 3H), 1.13 (s, 3H).

EXAMPLE 322

2,5-Dihydro-10-methoxy-5-(2-phenylethynyl)-2,2,4-trimethyl-1H-[1]benzopyrano[3,4-f]quinoline Example 2B and tributylphenylacetylenyltin were processed as in Example 320 to provide the desired compound.

MS (DCI/NH$_3$) m/e 408 (M+H)$^+$; $^1$H NMR (300 MHz, DMSO-d$_6$) δ 7.92 (d, 1H), 7.29 (m, 3H), 7.16 (m, 2H), 7.10 (d, 1H), 6.78 (d, 1H), 6.65 (dd, 1H), 6.59 (s, 1H), 6.23 (s, 1H), 5.45 (s, 1H), 3.87 (s, 3H), 2.33 (s, 3H), 1.28 (s, 3H), 1.12 (s, 3H).

EXAMPLE 323 cis 2,5-Dihydro-10-methoxy-5-(2-phenylethenyl)-2,2,4-trimethyl-1H-[1]benzopyrano[3,4-f]quinoline A mixture of Example 322 (20 mg, 0.049 mmol), palladium/BaSO$_4$ (20 mg) in pyridine (2 ml) was stirred at ambient temperature for 12 hr, quenched with water, and extracted with ethyl acetate. The organic layer was washed with brine, dried(Na$_2$SO$_4$), and concentrated. Flash chromatography of the residue on silica gel with 5–15% ethyl acetate/hexane provided 13 mg (75%) of the title compound.

MS (DCI/NH$_3$) m/e 410 (M+H)$^+$; $^1$H NMR (300 MHz, DMSO-d$_6$) δ 7.97 (d, 1H), 7.62 (d, 2H), 7.48 (t, 2H), 7.39 (t, 1H), 7.03 (t, 1H), 6.72 (d, 1H), 6.63 (d, 1H), 6.61 (d, 1H), 6.52 (d, 1H), 6.12 (d, 1H), 6.10 (s, 1H), 5.70 (dd, 1H), 5.27 (s, 1H), 3.87 (s, 3H), 1.55 (s, 3H), 1.17 (s, 3H), 1.079 (s, 3H).

EXAMPLE 324

2,5-Dihydro-10-methoxy-5-(2-methylpropenyl)-2,2,4-trimethyl-1H-[1]benzopyrano[3,4-f]quinoline Example 2B and tributyl-(2-methylpropenyl)tin were processed as in Example 320 to provide the desired compound.

MS (DCI/NH$_3$) m/e 362 (M+H)$^+$; $^1$H NMR (300 MHz, DMSO-d$_6$) δ 7.92 (d, 1H), 6.99 (t, 1H), 6.65 (d, 1H), 6.58 (d, 1H), 6.44 (d, 1H), 6.24 (d, 1H), 6.21 (s, 1H), 5.40 (s, 1H), 5.18 (d, 1H), 3.85 (s, 3H), 2.07 (s, 3H), 1.84 (s, 3H), 1.58 (s, 3H), 1.23 (s, 3H), 1.10 (s, 3H); Anal. calcd for C$_{24}$H$_{27}$NO$_2$: C, 79.74; H, 7.52; N, 3.87. Found: C, 79.34; H, 7.25; N, 3.68.

EXAMPLE 325 trans 2,5-Dihydro-10-methoxy-5-(1-cyclohexenyl)-2,2,4-trimethyl-1H-[1]benzopyrano[3,4-f]quinoline Example 2B and tributyl-(1-cyclohexenyl)tin were processed as in Example 320 to provide the desired compound.

MS (DCI/NH$_3$) m/e 388 (M+H)$^+$; $^1$H NMR (300 MHz, DMSO-d$_6$) δ 7.91 (d, 1H), 7.00 (t, 1H), 6.64 (d, 1H), 6.60 (d, 1H), 6.49 (d, 1H), 6.02 (s, 1H), 5.85 (s, 1H), 5.39 (s, 1H), 5.14 (s, 1H), 3.81 (s, 3H), 2.18 (m, 1H), 2.03 (s, 3H), 1.98 (m, 1H), 1.81 (m, 1H), 1.64 (m, 1H), 1.42 (m, 3H), 1.24 (m, 1H), 1.22 (s, 3H), 1.13 (s, 3H); Anal. calcd for C$_{26}$H$_{29}$NO$_2$.1.25H$_2$O: C, 76.15; H, 7.74; N, 3.41. Found: C, 76.12; H, 7.34; N, 3.21.

EXAMPLE 326

2,5-Dihydro-10-(2-furanyl)-5-(3-propenyl)-2,2,4-trimethyl-1H-[1]benzopyrano[3,4-f]quinoline A magnetically stirred mixture of triflate 3C [from the original patent application] (196 mg, 0.421 mmol) and 2-(tributylstannyl)furan (0.250 mL, 0.79 mmol) and [1,1'-bis(diphenylphosphino)ferrocene]dichloropalladium(II) methylene chloride complex (25 mg, 0.031 mmol) and tetrabutylammonium iodide (25 mg, 0.068 mmol) in dry NMP (6.5 mL) was heated at 70° C. for 5 h under argon. The reaction was allowed to cool to room temperature, was diluted with satd aq NaCl and extracted with ethyl acetate (5×20 mL). The combined organic layer was dried (MgSO$_4$), filtered, and concentrated. The crude material was chromatographed on silica gel (16 g) using ethyl acetate-hexane (10:90) to give product contaminated with starting material. The material was applied to three 10×20 cm, 0.25 mm thick silica gel plates which were eluted four times with EtOAc-hexane (5:95). The product band was scraped off and extracted with ethyl acetate to furnish 23 mg (0.044 mmol, 14%) of desired furan as a viscous syrup: $^1$H NMR δ 7.67 (d, 1H, J=1.0 Hz), 7.18 (t, 1H, J=7.8 Hz), 7.08 (m, 1H), 6.91 (dd, 1H, J=8.1 Hz, J=1.4 Hz), 6.64 (m, 2H), 6.35 (d, 1H, J=8.5 Hz), 6.25 (d, 1H, J=8.5 Hz), 6.14 (m, 1H), 5.82 (m, 2H), 5.43 (s, 1H), 5.05 (dd, 1H, J=10.5 Hz, J=1.5 Hz), 4.99 (dd, 1H, J=17.3 Hz, J=1.5 Hz), 2.40 (m, 2H), 2.19 (s, 3H), 1.20 (s, 3H), 1.12 (s, 3H); mass spectrum (DCI) m/z 384 (M+1).

Anal. Calcd for $C_{26}H_{25}NO_2$: C, 81.43; H, 6.57; N, 3.65. Found: C, 81.24; H, 6.62; N, 35 3.66.

EXAMPLE 327

2,5-Dihydro-10-cyano-5-(3-propenyl)-2,2,4-trimethyl-1H-[1]benzopyrano[3,4-f]quinoline A magnetically stirred mixture of triflate 3C (195 mg, 0.419 mmol), 36 mg (0.031 mmol) of tetrakis(triphenylphosphine)palladium(0) and zinc cyanide (36 mg, 0.31 mmol) in dry dioxane (4.0 mL) and water (1.0 mL) was heated at 80° C. for 48 h under argon. The reaction was allowed to cool to room temperature, was diluted with ethyl acetate (25 mL) and washed with satd aq NaCl. The aqueous layer was extracted with ethyl acetate (2×20 mL). The combined organic layer was dried (MgSO$_4$), filtered, and concentrated. The crude material was chromatographed on silica gel (20 g) using ethyl acetate-hexane (10:90) to give product contaminated with starting triflate. The partially pure nitrile was applied to two 10×20 cm, 0.25 mm thick silica gel plates which were eluted five times with EtOAc-hexane (5:95). The product band was scraped off and extracted with ethyl acetate to furnish 17.3 mg (0.0505 mmol, 12%) of desired nitrile: $^1$H NMR δ 7.87 (d, 1H, J=8.5 Hz), 7.46 (dd, 1H, J=7.5 Hz, J=1.5 Hz), 7.27 (t, 1H, J=7.8 Hz), 7.19 (dd, 1H, J=8.1 Hz, J=1.4 Hz), 6.71 (d, 1H, J=8.5 Hz), 6.57 (m, 1H), 5.90 (dd, 1H, J=10 Hz, 5.82 (m, 1H), 5.49 (m, 1H), 5.04 (dm, 1H, J=10.5 Hz), 4.98 (dm, 1H, J=17.3 Hz), 2.38 (m, 1H), 2.30 (m, 1H), 2.19 (s, 3H), 1.20 (s, 3H), 1.19 (s, 3H); mass spectrum (APCI) m/z 343 (M+1); Calcd for $C_{23}H_{22}N_2O$: 342.1732. Found: 342.1730.

EXAMPLE 328

2,5-Dihydro-10-carboxy-5-(3-propenyl)-2,2,4-trimethyl-1H-[1]benzopyrano[3,4-f]quinoline A magnetically stirred mixture of the Example 4 (31 mg, 0.082 mmol) and sodium cyanide (51 mg, 0.78 mmol) in dry dimethylsulfoxide (2.5 mL) was heated at 110° C. for 5 h under argon. The reaction was allowed to cool to room temperature, was diluted with satd aq NaCl and extracted with ethyl acetate (5×20 mL). The combined organic layer was dried (MgSO$_4$), filtered, and concentrated. The crude material was applied to two 10×20 cm, 0.25 mm thick silica gel plates which were eluted twice with EtOAc-hexane (10:90), then EtOAc-hexane (50:50) three times. The product band was scraped off and extracted with ethyl acetate to furnish 16 mg (0.044 mmol, 54%) of desired carboxylic acid as a viscous syrup: $^1$H NMR δ 7.16 (m, 2H), 7.02 (d, 1H, J=8.5 Hz), 6.98 (dd, 1H, J=5.5 Hz, J=3.7 Hz), 6.58 (d, 1H, J=8.5 Hz), 6.29 (m, 1H), 5.82 (m, 2H), 5.45 (s, 1H), 5.05 (dd, 1H, J=10.5 Hz, J=1.5 Hz), 4.98 (dd, 1H, J=17.3 Hz, J=1.5 Hz), 2.30 (m, 2H), 2.18 (s, 3H), 1.20 (s, 3H), 1.16 (s, 3H); mass spectrum (APCI) m/z 362 (M+1).

Anal. Calcd for $C_{23}H_{23}NO_3$: C, 76.43; H, 6.41; N, 3.88. Found: C, 76.24; H, 6.46; N, 3.66.

EXAMPLE 329

2,5-Dihydro-10-(2-hydroxymethyl)-5-(3-propenyl)-2,2,4-trimethyl-1H-[1]benzopyrano[3,4-f]quinoline To a magnetically stirred solution of example 4 (32 mg, 0.085 mmol) in dry methylene chloride (3 mL), cooled to −78°, was added dropwise 1.0 M diisobutylaluminum hydride in cyclohexane (0.400 mL, 0.40 mmol) under dry argon. The temperature of the reaction was allowed to rise to 0° C. After 3.5 h, the reaction was quenched by addition to aqueous Rochelle's salt and the layers were separated. The aqueous layer was extracted with ethyl acetate (3×40 mL). The combined organic layer was dried (MgSO$_4$), filtered, and concentrated. The crude material was applied to two 10×20 cm, 0.25 mm thick silica gel plates which were eluted with hexane, then EtOAc-hexane (10:90) three times. The product band was scraped off and extracted with ethyl acetate to furnish 27 mg (0.078 mmol, 91%) of desired alcohol as a viscous syrup: $^1$H NMR δ 7.47 (d, 1H, J=8.5 Hz), 7.14 (m, 2H), 6.80 (dd, 1H, J=7.3 Hz, J=1.8 Hz), 6.64 (d, 1H, J=8.5 Hz), 6.17 (m, 1H), 5.81 (ddm, 1H, J=10.5 Hz, J=17.1 Hz), 5.73 (dd, 1H, J=3.4 Hz, J=10.5 Hz), 5.46 (m, 1H), 5.32 (dd, 1H, J=6.3 Hz, J=4.2 Hz), 5.02 (dm, 1H, J=10.5 Hz), 4.94 (dm, 1H, J=17.1 Hz), 4.62 (m, 2H), 2.30 (m, 2H), 2.17 (s, 3H), 1.19 (s, 3H), 1.16 (s, 3H); mass spectrum (ESI) m/z: 3.48 (M+1); Calcd for $C_{23}H_{25}NO_2$: 347.1885. Found: 347.1897.

EXAMPLE 330

2,5-Dihydro-10-formyl-5-(3-propenyl)-2,2,4-trimethyl-1H-[1]benzopyrano[3,4-f]quinoline A magnetically stirred mixture of the Example 329 (185 mg, 0.532 mmol) and tetrapropylammonium perruthenate (205 mg, 0.583 mmol) in dry methylene chloride (10 mL) was stirred for 1.5 h under argon. The reaction was filtered through celite, the filter pad was washed with ethyl acetate and the filtrate was concentrated. The crude material was chromatographed on silica gel (20 g) using EtOAc-hexane (10:90) to furnish 144 mg (0.417 mmol, 78%) of desired aldehyde: $^1$H NMR δ 10.11 (s, 1H), 7.45 (dd, 1H, J=7.8 Hz, J=1.2 Hz), 7.29 (t, 1H, J=7.8 Hz), 7.16 (dd, 1H, J=7.8 Hz, J=1.4 Hz), 6.84 (d, 1H, J=8.5 Hz), 6.70 (d, 1H, J=8.5 Hz), 6.53 (m, 1H), 5.91 (dm, 1H, J=10.0 Hz), 5.84 (m, 1H), 5.51 (s, 1H), 5.05 (dm, 1H, J=10.5 Hz), 4.97 (dm, 1H, J=17.3 Hz), 2.40 (m, 2H), 2.21 (s, 3H), 1.22 (s, 3H), 1.18 (s, 3H); mass spectrum (APCI) m/z 346 (M+1); Calcd for $C_{23}H_{23}NO_2$: 345.1729. Found: 345.1732.

EXAMPLE 331

2,5-Dihydro-10-aminomethyl-5-(3-propenyl)-2,2,4-trimethyl-1H-[1]benzopyrano[3,4-f]quinolione To a magnetically stirred solution of Example 330 (40 mg, 0.116 mmol) and ammonium acetate (77 mg, 1.0 mmol) in dry methanol (10 mL) was added sodium cyanoborohydride (14 mg, 0.23 mmol) under nitrogen. After 5 h, the reaction was quenched by addition to 10% sodium carbonate and extracted with ethyl acetate (3×40 mL). The combined organic layer was dried (MgSO$_4$), filtered, and concentrated. The crude material was applied to two 10×20 cm, 0.25 mm thick silica gel plates which were eluted with hexane, then EtOAc-hexane (20:80) four times. The product band was scraped off and extracted with ethyl acetate to furnish 8.0 mg (0.023 mmol, 20%) of desired amine as a viscous syrup: $^1$H NMR δ 7.55 (d, 1H, J=8.5 Hz), 7.14 (m, 2H), 6.80 (dd, 1H, J=7.3 Hz, J=1.8 Hz), 6.64 (d, 1H, J=8.5 Hz), 6.17 (m, 1H), 5.81 (ddm, 1H, J=10.5 Hz, J=17.1 Hz), 5.73 (dd, 1H, J=3.4 Hz, J=10.5 Hz), 5.46 (m, 1H), 5.02 (dm, 1H, J=10.5 Hz), 4.94 (dm, 1H, J=17.1 Hz), 4.62 (m, 2H), 3.88 (m, 2H), 2.30 (m, 2H), 2.17 (s, 3H), 1.19 (s, 3H), 1.16 (s, 3H); mass spectrum (ESI) m/z: 347 (M+1); Calcd for $C_{23}H_{26}N_2O$: 346.2045. Found: 346.2047.

EXAMPLE 332

2,5-Dihydro-10-methoxymethyl-5-(3-propenyl)-2,2,4-trimethyl-1H-[1]benzopyrano[3,4-f]quinoline To a magnetically stirred solution of Example 329 (26 mg, 0.075 mmol) in dry THF (2.0 mL), cooled in an ice bath, was added 0.14 mL of 1M potassium hexamethyldisilazide in hexane under argon. Methyl iodide (13.8 mg, 0.097 mmol) was added and the reaction was allowed to slowly come to room temperature. The reaction was quenched with satd aq NH$_4$Cl and extracted with ethyl acetate (3×10 mL). The extracts were dried (MgSO$_4$), filtered, and concentrated. The crude material was applied to three 10×20 cm, 0.25 mm thick silica gel plates which were eluted four times with EtOAc-hexane (5:95). The product band was extracted using EtOAc to furnish 25 mg (0.069 mmol, 92%) of desired methyl ether: $^1$H NMR δ 7.34 (d, 1H, J=8.5 Hz), 7.11 (m, 2H), 6.85 (dd, 1H, J=7.1 Hz, J=2.4 Hz), 6.64 (d, 1H, J=8.5 Hz), 6.20 (m, 1H), 5.81 (dm, 1H, J=10.2 Hz), 5.75 (m, 1H), 5.46 (s, 1H), 5.02 (dm, 1H, J=10.2 Hz), 4.93 (dm, 1H, J=17.3 Hz), 4.61 (d, 1H, J=11.2 Hz), 4.43 (d, 1H, J=11.2 Hz), 3.37 (s, 3H), 2.33 (m, 1H), 2.27 (m, 1H), 2.17 (s, 3H), 1.19 (s, 3H), 1.17 (s, 3H); mass spectrum (ESI) m/z 362 (M+1); Calcd for $C_{24}H_{27}NO_2$: 361.2042. Found: 361.2047.

EXAMPLE 333

2,5-Dihydro-10-ethenyl-5-phenyl-2,2,4-trimethyl-1H-[1]benzopyrano[3,4-f]quinoline

EXAMPLE 333A 2,5-Dihydro-10-ethenyl-5-phenyl-2,2,4-trimethyl-1H-[1]benzopyrano[3,4-f]quinoline Example 7 and trifluoromethanesulfonic anhydride were processed as in Example 3C to provide the desired triflate.
MS (ESI) m/z 502 (M+H)$^+$.

EXAMPLE 333

2,5-Dihydro-10-ethenyl-5-phenyl-2,2,4-trimethyl-1H-[1]benzopyrano[3,4-f]quinoline Example 333A and vinyl tributylstannane were processed as in Example 5 to provide the desired compound.
MS (DCI/NH$_3$) m/z 380 (M+H)$^+$; $^1$H NMR (300 MHz, CDCl$_3$) δ 7.30–7.11 (m, 6H), 7.02–6.89 (m, 3H), 6.78 (s, 1H), 6.76–6.68 (m, 2H), 6.32 (br s, 1H), 5.72 (br d, J=11.4 Hz, 1H), 5.40 (br s, 1H), 5.30 (br d, J=15.9 Hz, 1H), 1.81 (s, 3H), 1.26 (s, 3H), 1.15 (s, 3H); $^{13}$C NMR (125 MHz, DMSO) δ 151.3, 145.7, 138.8, 137.3, 133.3, 133.0, 131.2, 128.5 (2), 128.3, 128.2, 128.0 (2), 127.8, 127.4, 126.6, 123.9, 120.8, 118.1, 116.2, 114.5, 113.6, 75.3, 50.0, 30.0, 28.7, 23.2; HRMS (FAB) calcd m/z for $C_{27}H_{25}NO$: 379.1936 (M)$^+$. Found: 379.1924.

EXAMPLE 334

2,5-Dihydro-10-ethynyl-5-phenyl-2,2,4-trimethyl-1H-[1]benzopyrano[3,4-f]quinoline Example 333A and (trimethylsilyl)acetylene were processed as in Example 6A and Example 6 to provide the desired compound.
MS (DCI/NH$_3$) m/z 378 (M+H)$^+$; $^1$H NMR (300 MHz, DMSO) δ 8.32 (d, J=8.8 Hz, 1H), 7.27–7.16 (m, 5H), 7.01 (dd, J=8.7, 1.8 Hz, 1H), 6.83 (t, J=8.6 Hz, 1H), 6.84–6.79 (m, 1H), 6.81 (br s, 1H), 6.74 (d, J=8.6 Hz, 1H), 6.42 (br s, 1H), 5.41 (br s, 1H), 4.38 (s, 1H), 2.03 (s, 3H), 1.24 (s, 3H), 1.18 (s, 3H); $^{13}$C NMR (125 MHz, DMSO) δ 150.9, 146.4, 138.8, 133.1, 130.7, 128.6, 128.2 (2), 128.0 (2), 127.9, 127.4, 126.6, 126.5, 126.4, 126.3, 118.3, 117.6, 117.5, 115.7, 113.4, 84.3, 75.1, 50.0, 30.0, 28.8, 23.2; HRMS (FAB) calcd m/z for $C_{27}H_{23}NO$: 377.1780 (M)$^+$. Found: 377.1779.

EXAMPLE 335

Methyl 2,5-Dihydro-5-phenyl-2,2,4-trimethyl-1H-[1]benzopyrano[3,4-f]quinoline-10-carboxylate Example 333A was processed as in Example 4 to provide the desired compound.
mp 150–2° C.; MS (DCI/NH$_3$) m/z 412 (M+H)$^+$; $^1$H NMR (300 MHz, DMSO) δ 7.36–7.30 (m, 2H), 7.28–7.17 (m, 3H), 7.12–7.01 (m, 2H), 6.93–6.88 (m, 2H), 6.84 (d, J=8.7 Hz, 1H), 6.70 (d, J=8.9 Hz, 1H), 6.40 (br s, 1H), 5.40 (br s, 1H), 3.79 (s, 3H), 1.81 (s, 3H), 1.26 (s, 3H), 1.17 (s, 3H); $^{13}$C NMR (125 MHz, DMSO) δ 169.9, 151.2, 146.1, 138.3, 132.5, 130.3, 128.8 (2), 128.1, 128.0 (2), 127.7, 127.4, 127.0, 126.6, 124.9, 122.9, 119.6, 117.7, 117.5, 114.2, 75.7, 52.2, 50.0, 30.0, 28.6, 23.2; Anal. calcd for $C_{27}H_{25}NO_3$: C, 78.81; H, 6.12; N, 3.40. Found: C, 78.84; H, 6.25; N, 3.24.

EXAMPLE 336

2,5-Dihydro-10-(hydroxymethyl)-5-phenyl-2,2,4-trimethyl-1H-[1]benzopyrano[3,4-f]quinoline To a solution of Example 335 (136 mg, 0.330 mmol) in anhydrous CH$_2$Cl$_2$ (12 mL) at −50° C. was added Dibal-H (1.65 mL of a 1.0 M solution in heptane, 1.65 mmol). The resulting orange solution was warmed gradually to 0° C. over a 30 min period, then was stirred at 0° C. for 2 h. EtOAc (5 mL) was then added to the solution at 0° C. to quench the excess Dibal-H reagent (indicated by a color change of the solution from orange to light yellow) and the reaction mixture was then treated with saturated aqueous NH$_4$Cl (5 mL). The reaction mixture was partitioned between EtOAc (40 mL) and saturated aqueous Rochelle's salt (sodium potassium tartrate; 35 mL) and the resulting mixture was stirred vigorously until a clear separation of layers was observed (ca. 1 h). The layers were partitioned and the aqueous layer was extractedwith EtOAc (15 mL). The organics were combined and were washed with brine (10 mL) and then were dried (Na$_2$SO$_4$). Filtration and concentration gave the desired compound (116 mg, 0.302 mmol, 92%) as a colorless foamy solid.
MS (DCI/NH$_3$) m/z 384 (M+H)$^+$; $^1$H NMR (300 MHz, DMSO) δ 7.58 (d, J=8.9 Hz, 1H), 7.23–7.11 (m, 5H), 6.98 (dd, J=8.7, 1.7 Hz, 1H), 6.84 (t, J=8.7 Hz, 1H), 6.76 (br s, 1H), 6.75 (d, J=8.6 Hz, 1H), 6.69 (dd, J=8.7, 1.8 Hz, 1H), 6.26 (br s, 1H), 5.40 (br s, 1H), 5.37 (dd, J=6.0, 4.0 Hz, 1H), 4.65 (dd, J=11.5, 6.0 Hz, 1H), 4.54 (dd, J=11.6, 4.4 Hz, 1H), 1.80 (s, 3H), 1.24 (s, 3H), 1.17 (s, 3H); $^{13}$C NMR (125 MHz, DMSO) δ 151.0, 145.6, 139.0, 137.0, 133.1, 131.4, 128.4 (2), 128.1, 128.0 (2), 127.7, 127.6, 126.2, 124.8, 123.7, 118.6, 118.0, 116.0, 113.9, 75.1, 61.9, 49.9, 29.9, 28.7, 23.3; Anal. calcd for $C_{26}H_{25}NO_2$: C, 81.43; H, 6.57; N, 3.65. Found: C, 81.53; H, 6.86; N, 3.41.

EXAMPLE 337

2,5-Dihydro-10-formyl-5-phenyl-2,2,4-trimethyl-1H-[1]benzopyrano[3,4-f]quinoline To a solution of Example 336 (50 mg, 0.130 mmol) in $CH_2Cl_2$ (6 mL) at 23° C. was added a solution of tetrapropylammonium perruthenate (60 mg, 0.16 mmol) in $CH_2Cl_2$ (14 mL). After 15 min, the reaction mixture was filtered through a small plug of silica gel, rinsing with $CH_2Cl_2$ followed by 1:1 EtOAc-hexanes. The filtrate was concentrated to give a gold syrup which was purified by preparative thin layer chromatography (elution with 3% EtOAc/toluene) to afford the desired product (19 mg, 0.050 mmol, 38%) as a pale yellow foam.

MS (DCI/NH$_3$) m/z 382 (M+H)$^+$; $^1$H NMR (300 MHz, DMSO) δ 10.13 (s, 1H), 7.31 (dd, J=8.8, 1.9 Hz, 1H), 7.28–7.16 (m, 5H), 7.12 (d, J=8.7 Hz, 1H), 7.05 (dd, J=8.7, 2.0 Hz, 1H), 6.95 (d, J=8.8 Hz, 1H), 6.92 (br s, 1H), 6.81 (d, J=8.8 Hz, 1H), 6.59 (br s, 1H), 5.43 (br s, 1H), 1.85 (s, 3H), 1.27 (s, 3H), 1.18 (s, 3H); $^{13}$C NMR (125 MHz, DMSO) δ 191.4, 151.9, 146.8, 138.3, 133.2, 131.5, 131.4, 130.8, 128.6 (2), 128.1 (2), 128.0, 127.2, 126.6, 121.5, 121.4, 118.1, 115.5, 114.2 (2), 75.8, 50.2, 30.1, 29.0, 23.1; HRMS (FAB) calcd m/z for $C_{26}H_{24}NO$: 382.1807 (M+H)$^+$. Found: 382.1816.

EXAMPLE 338

2,5-Dihydro-10-(methoxymethyl)-5-phenyl-2,2,4-trimethyl-1H-[1]benzopyrano[3,4-f]quinoline To a solution of Example 336 (22 mg, 0.057 mmol) in THF (2.0 mL) at 0° C. was added KHMDS (110 mL of a 0.5 M solution in toluene, 0.057 mmol). After 15 min, a solution of iodomethane was added as a solution in DMF (100 mL of a solution of 81 mg iodomethane in 1.0 mL DMF, 0.057 mmol) was added and the solution was stirred additionally at 0° C. for 30 min, the cooling bath was removed, and the reaction was stirred additionally at 23° C. for 1.5 h. The reaction was then quenched with water (3 mL) and was extracted with EtOAc (2×20 mL). The combined organic layers were washed with brine (mL), then were dried (MgSO$_4$), and were concentrated in vacuo to provide a brown oil. Purification of this residue by preparative thin layer chromatography (elution with 10% EtOAc/hexanes) afforded the desired product (15 mg, 0.038 mmol, 66%) as a colorless foam.

MS (DCI/NH$_3$) m/z 98 (M+H)$^+$; $^1$H NMR (300 MHz, DMSO) δ 7.40 (d, J=8.9 Hz, 1H), 7.19–7.10 (m, 5H), 6.97–6.92 (m, 1H), 6.94 (s, 1H), 6.77–6.70 (m, 3H), 6.29 (br s, 1H), 5.39 (br s, 1H), 4.58 (d, J=11.1 Hz, 1H), 4.39 (d, J=11.1 Hz, 1H), 3.28 (s, 3H), 1.81 (s, 3H), 1.26 (s, 3H), 1.17 (s, 3H); $^{13}$C NMR (125 MHz, DMSO) δ 151.0, 145.7, 138.8, 132.9, 132.6, 131.5, 128.4 (2), 127.8 (2), 127.8, 127.7, 127.5, 126.1, 125.7, 124.4, 118.3, 117.9, 116.6, 113.9, 75.2, 72.5, 57.2, 49.9, 29.9, 28.7, 23.3; HRMS (FAB) calcd m/z for $C_{27}H_{27}NO_2$: 397.2042 (M)$^+$. Found: 397.2039.

EXAMPLE 339

2,5-Dihydro-10-ethenyl-5-oxo-2,2,4-trimethyl-1H-[1]benzopyrano[3,4-f]quinoline

Example 3C and vinyl tributylstannane were processed as in Example 5 to provide the desired compound.

mp 218–224° C.; MS (DCI/NH$_3$) m/z 318 (M+H)$^+$, 335 (M+NH4)$^+$; $^1$H NMR (300 MHz, DMSO) δ 7.88 (d, J=8.8 Hz, 1H), 7.38 (dd, J=8.8, 6.6 Hz, 1H), 7.29 (s, 1H), 7.28 (d, J=8.6 Hz, 1H), 7.19 (dd, J=17.3, 11.1 Hz, 1H), 7.13 (d, J=8.7 Hz, 1H), 7.03 (br s, 1H), 5.75 (dd, J=17.3, 1.2 Hz, 1H), 5.52–5.47 (m, 2H), 1.97 (s, 3H), 1.24 (s, 6H); $^{13}$C NMR (125 MHz, CDCl$_3$) δ 160.1, 150.0, 145.4, 138.5, 136.3, 132.2, 131.0, 127.1, 126.7, 126.6, 125.5, 124.1, 119.9, 118.5, 117.2, 115.9, 115.7, 50.0, 27.9 (2), 21.0; Anal. calcd for $C_{21}H_{19}NO_2$: C, 79.47; H, 6.03; N, 4.41. Found: C, 79.28; H, 5.97; N, 4.20.

EXAMPLE 340

5-(3-Cyclohexenyl)-2,5-dihydro-10-ethenyl-2,2,4-trimethyl-1H-[1]benzopyrano[3,4-f]quinoline To a magnetically stirred solution of Example 339 (100 mg, 0.300 mmol) and 3-(trimethylsilyl)cyclohexene (139 mg, 0.900 mmol) in $CH_2Cl_2$ (6 mL) at −78° C. was added freshly distilled BF$_3$.OEt$_2$ (80 mL, 0.600 mmol). The resulting greenish brown solution was stirred at −78° C. for 15 min then slowly warmed to 23° C. with continued stirring over period of 1 h. The reaction mixture was poured into 10% NaHCO$_3$ solution (10 mL) and extracted with EtOAc (2×20 mL). The combined organic portions were washed with brine (8 mL) and were dried (Na$_2$SO$_4$). Filtration and concentration gave a brown residue which was purified via flash chromatography (elution with 5% EtOAc/hexanes) to give the desired product as a tan foam (356 mg, 0.186 mmol, 62%).

MS (DCI/NH$_3$) m/z 384 (M+H)$^+$; $^1$H NMR (300 MHz, DMSO) (data for major syn diasteromer) δ 7.30 (d, J=8.0 Hz, 1H), 7.16–6.97 (m, 3H), 6.95–6.88 (m, 1H), 6.67 (d, J=8.0 Hz, 1H), 6.42 (br s, 1H), 5.82–5.60 (m, 3H), 5.52–5.44 (m, 2H), 5.33 (d, J=7.6 Hz, 1H), 2.40–2.26 (m, 1H), 2.17 (s, 3H), 2.05–1.82 (m, 2H), 1.70–1.53 (m, 2H), 1.32 (s, 3H), 1.31–1.07 (m, 2H), 1.05 (s, 3H); $^{13}$C NMR (125 MHz, CDCl$_3$) δ 138.8, 134.2, 129.3 (2), 128.1 (2), 127.9 (2), 126.7, 12.13, 116.4, 114.1, 37.2, 37.0, 34.7, 31.6, 30.2, 27.2, 26.1, 25.2, 24.7, 22.6, 24.1, 21.8 (2), 20.5, 14.1; Anal. calcd for $C_{27}H_{29}NO$: C, 83.57; H, 7.66; N, 3.60. Found: C, 83.55; H, 7.38; N, 3.45.

EXAMPLE 341

2,5-Dihydro-10-ethenyl-5-[1-methyl-3-cyclohexenyl]-2,2,4-trimethyl-1H-[1]benzopyrano[3,4-f]quinoline Example 339 and 3-(dimethylphenylsilyl)-3-methylcyclohexene were processed as in Example 339 to provide the desired compound.

mp 198–201° C.; MS (DCI/NH$_3$) m/z 398 (M+H)$^+$; $^1$H NMR (300 MHz, DMSO) (data for major syn diastereomer) δ 7.30 (d, J=7.9 Hz, 1H), 7.16–7.00 (m, 3H), 6.92 (dd, J=7.1, 2.6 Hz, 1H), 6.66 (d, J=8.0 Hz, 1H), 6.39 (br s, 1H), 5.73 (d, J=12.4 Hz, 1H), 5.52–5.41 (m, 3H), 5.32 (d, J=10.2 Hz, 1H), 2.33–2.2 (m, 1H), 2.14 (s, 3H), 1.91–1.70 (m, 1H), 1.87–1.65 (m, 1H), 1.63–1.51 (m, 1H), 1.60 (s, 3H), 1.34–1.15 (m, 2H), 1.31 (s, 3H), 1.13–0.98 (m, 1H), 1.04 (s, 3H); Anal. calcd for $C_{28}H_{31}NO$: C, 84.59; H, 7.85; N, 3.52. Found: C, 84.46; H, 7.81; N, 3.37.

EXAMPLE 342

2,5-Dihydro-5-(3-propenyl)-10-methylthio-2,2,4-trimethyl-1H-[1]benzopyrano[3,4-f]quinoline To a magnetically stirred solution of Example 3B (120 mg, 0.390 mmol) in anhydrous DMF (1.0 mL) at 0° C. was added sodium hydride (17 mg of a 60% dispersion in mineral oil, 0.430 mmol). The mixture was stirred under an atmosphere of nitrogen until evolution of hydrogen had ceased (1 h). Solid dimethylthiocarbamoyl chloride (64 mg, 0.520 mmol) was then introduced in a single portion and stirring was continued at 0° C. for 30 min. The cooling bath was removed and the mixture heated at 80° C. for 45 min. The reaction mixture was then poured into 1% NaOH (10 mL) and extracted with EtOAc (2×25 mL). The combined organics portions were washed with water (3×5 mL) and with brine (3 mL) then dried (MgSO$_4$), filtered and concentrated. The resulting brown residue was purified flash chromatography (elution with 25% EtOAc/hexanes) to provide the resulting thionocarbamate (43 mg, 0.109 mmol, 28%) as a yellow solid. MS (DCI/NH$_3$) m/z 348 (M+H)$^+$.

The compound prepared above (113 mg, 0.280 mmol) was placed in an open vial and immersed in a Woods metal bath heated to 270–280° C. for 6 min. The reaction was cooled and the resulting dark brown residue was purified flash chromatography (gradient elution: 20% AE 40% EtOAc/hexanes) to provide the thermally rearranged thiocarbamate product (67 mg, 0.165 mmol, 59%) as a yellow solid. MS (DCI/NH$_3$) m/z 348 (M+H)$^+$.

To a solution of the rearranged product (500 mg, 1.26 mmol) in anhydrous toluene (70 mL) at −78° C. under N$_2$ was added dropwise Dibal-H (2.02 mL of a 1.0 M solution in heptane, 2.02 mmol) maintaining the temperature at −78° C. The resulting orange-red solution was stirred at −78° C. for 1.5 h at which time a TLC of an aliquot (quenched with satd. ammonium chloride) indicated conversion to desired product. Some lower R$^f$ material (diol resulting from over-reduction) was also observed. EtOAc (10 mL) was added to the solution at −78° C. to quench the excess DIBAL-H reagent (indicated by a color change of the solution from orange-red to light yellow), followed by addition of saturated aqueous NH$_4$Cl solution (15 mL). The reaction mixture was partitioned between EtOAc (150 mL) and aqueous Rochelle's salt (sodium potassium tartrate, 40 mL) and the resulting mixture was stirred vigorously until a clear separation of layers was observed. The layers were separated and the organic layer was washed with brine (20 mL), was dried (Na$_2$SO$_4$), and was filtered. Removal of solvent gave the lactol as a light yellow foam (512 mg) which was used without further purification.

The lactol was dissolved in MeOH (30 mL) at 23° C. and p-TsOH.H$_2$O (50 mg, 25% w/w) was added portionwise as a solid. The mixture was stirred for 14 h at 23° C. and then was quenched with saturated aqueous sodium bicarbonate (10 mL) and was extracted with EtOAc (2×50 mL). The organics portions were combined and were washed with brine (20 mL) and were dried (Na$_2$SO$_4$). Filtration and concentration provided a yellow residue which was purified by flash chromatography (elution with 5% EtOAc/CH$_2$Cl$_2$) to provide the product methylacetal (157 mg, 0.416 mmol, 33% over two steps) as a yellow foam. MS (DCI/NH$_3$) m/z 379 (M-OCH$_3$)$^+$.

The lactol prepared above and allyltrimethylsilane were processed as in Example 2 to give a C-5 allyl compound. MS (DCI/NH$_3$) m/z 421 (M+H)$^+$.

EXAMPLE 343

2,5-Dihydro-5-(3-propenyl)-10-methylthio-2,2,4-trimethyl-1H-[1]benzopyrano[3,4-f]quinoline A suspension of the thiocarbamate (249 mg, 0.590 mmol) and KOH (90 mg, 1.20 mmol) in ethylene glycol (6 mL) containing water (1.5 mL) was heated at reflux (homogeneous solution) for 1.5 h. The solution was cooled and poured onto ice (10 g). The mixture was acidified (pH 4) with 10% HCl and was then extracted with CH$_2$Cl$_2$ (2×20 mL). The extracts were dried (Na$_2$SO$_4$), were filtered, and were concentrated. The resulting residue was purified by flash chromatography (elution with 5% EtOAc/CH$_2$Cl$_2$) to provide nearly homogeneous thiophenol adduct (183 mg) as an off-yellow solid that was used immediately: $^1$H NMR (300 MHz, DMSO-d$_6$) δ 7.72 (d, J=8.0 Hz, 1H), 7.08 (dd, J=7.6, 1.1 Hz, 1H), 6.96 (t, J=7.5 Hz, 1H), 6.67 (d, J=8.1 Hz, 1H), 6.63 (dd, J=7.5, 1.2 Hz, 1H), 6.28 (br s, 1H), 5.88–5.70 (m, 2H), 5.47 (br s, 1H), 5.41 (s, 1H), 5.03 (dd, J=13.2, 1.3 Hz, 1H), 4.98 (dd, J=18.4, 1.3 Hz, 1H), 2.48–2.21 (m, 2H), 2.17 (s, 3H), 1.20 (s, 3H), 1.17 (s, 3H); MS (DC/NH$_3$) m/e 350 (M+H)$^+$.

A solution of the crude thiophenol (183 mg) in DMF (10 mL) at 0° C. was treated with cesium carbonate (50 mg, 0.153 mmol). After 10 min, a solution of iodomethane (25 mg, 0.176 mmol) in DMF (0.7 mL) was added, and the solution was stirred at 0° C. for 30 min then at 23° C. for 2 h. The mixture was diluted with 1:1 EtOAc-hexane (100 mL) and was washed with water (3×25 mL) then washed with brine (25 mL). The organic portion was dried (Na$_2$SO$_4$), was filtered, and was concentrated. The resulting residue was purified by flash chromatography (elution with 5% EtOAc/hexanes) to provide the thioether (65 mg, 0.179 mmol, 34%) as an off-yellow solid: $^1$H NMR (300 MHz, DMSO-d$_6$) δ 7.82 (d, J=8.1 Hz, 1H), 7.11 (t, J=7.6 Hz, 1H), 6.98 (br d, J=7.7 Hz, 1H), 6.72 (br d, J=7.6 Hz, 1H), 6.62 (d, J=8.0 Hz, 1H), 6.27 (br s, 1H), 5.88–5.70 (m, 2H), 5.47 (br s, 1H), 5.03 (dd, J=13.3, 1.1 Hz, 1H), 4.99 (dd, J=18.3, 1.1 Hz, 1H), 2.47 (s, 3H), 2.46–2.33 (m, 1H), 2.32–2.22 (m, 1H), 2.18 (s, 3H), 1.21 (s, 3H), 1.17 (s, 3H); MS (CI/NH$_3$) m/e 364 (M+H)$^+$.

EXAMPLE 344

(+/−)2,5-Dihydro-9-(4-acetamidobutanoyloxy)-10-methoxy-2,2,4-trimethyl-5-allyl-1H-[1]benzopyranol[3,4-f]quinoline MS (APCI) m/z 491 (M+H)$^+$; 1H NMR (200 MHz, DMSO-d$_6$) δ 7.94 (t, 1H), 7.84 (d, 1H), 6.88 (d, 1H), 6.67 (d, 1H), 6.64 (d, 1H), 6.21 (s, 1H), 5.87–5.78 (m, 2H), 5.46 (s, 1H), 5.06–4.96 (m, 2H), 2.60 (s, 2H), 2.16 (dt, 2H), 2.62 (t, 2H), 2.21–2.27 (m, 2H), 2.18 (s, 2H), 1.82 (s, 2H), 1.79 (m, 2H), 1.18 (s, 2H), 1.17 (s, 2H).

EXAMPLE 345

10-(Difluoromethoxy)-2,5-dihydro-5-phenyl-2,2,4-trimethyl-1H-[1]benzopyrano[3,4-f]quinoline Example 7 and bromodifluoromethane were processed as in Example 8A to provide the desired compound.

MS (CI/NH$_3$) m/z 420 (M+H)$^+$; $^1$H NMR (300 MHz, DMSO-d$_6$) δ 7.80 (s, J=8.8 Hz, 1H), 7.26–7.15 (m, 5H), 7.16–7.13 (m, 1H), 6.97 (t, J=8.1 Hz, 1H), 6.82 (br s, 1H), 6.74 (d, J=8.9 Hz, 1H), 6.72–6.67 (m, 1H), 6.38 (br s, 1H), 5.39 (br s, 1H), 1.82 (s, 3H), 1.24 (s, 3H), 1.15 (s, 3H); HRMS (FAB) calcd m/z for C$_{26}$H$_{23}$F$_2$NO$_2$: 419.1697 (M)$^+$. Found: 419.1714.

EXAMPLE 346

10-(Bromodifluoromethoxy)-2,5-dihydro-5-phenyl-2,2,4-trimethyl-1H-[1]benzopyrano[3,4-f]quinoline MS (ESI) m/z 498 (M+H)$^+$. $^1$H NMR (300 MHz, DMSO-d$_6$) δ 7.68 (s, J=8.8 Hz, 1H), 7.25–7.14 (m, 5H), 7.03 (t, J=8.2 Hz, 1H), 6.89–6.84 (m, 1H), 6.85 (br s, 1H), 6.83–6.79 (m, 1H), 6.74 (d, J=8.6 Hz, 1H), 6.46 (br s, 1H), 5.40 (br s, 1H), 1.81 (s, 3H), 1.25 (s, 3H), 1.15 (s, 3H); $^{13}$C NMR (125 MHz, DMSO-d$_6$) δ 152.34, 146.44, 145.97, 138.38, 133.02, 130.51, 128.61 (2), 128.07, 127.92 (2), 127.33, 126.86 (2), 119.16, 117.82, 116.68, 115.84, 115.32, 114.28, 114.12, 75.60, 49.93, 29.90, 28.72, 23.26; HRMS (FAB) calcd m/z for $C_{26}H_{22}{}^{79}BrF_2NO_2$: 497.0802 (M+H)$^+$. Found: 497.0790. HRMS (FAB) calcd m/z for $C_{26}H_{22}{}^{81}BrF_2NO_2$: 499.0782 (M+H)$^+$. Found: 499.0793.

EXAMPLE 347

10-(Bromodifluoromethoxy)-5-phenyl-2,2-dimethyl-4-methylene-2,3,4,5-tetrahydro-1H-chromeno[3,4-f]quinoline MS (ESI) m/z 498 (M+H)$^+$. $^1$H NMR (300 MHz, CDCl$_3$) δ 7.88 (s, J=8.4 Hz, 1H), 7.31–7.26 (m, 2H), 7.19–7.12 (m, 3H), 6.95 (t, J=8.1 Hz, 1H), 6.86–6.78 (m, 2H), 6.64 (br s, 1H), 6.58 (d, J=8.5 Hz, 1H), 4.94 (s, 1H), 4.61 (s, 1H), 4.17 (br s, 1H), 2.45 (br d, J=12.0 Hz, 1H), 2.19 (d, J=1.24 Hz, 1H), 1.35 (s, 3H), 1.14 (s, 3H); HRMS (FAB) calcd m/z for $C_{26}H_{22}{}^{79}BrF_2NO_2$: 497.0802 (M+H)$^+$. Found: 497.0790. HRMS (FAB) calcd m/z for $C_{26}H_{22}{}^{81}BrF_2NO_2$: 499.0782 (M+H)$^+$. Found: 499.0771.

EXAMPLE 348

2,5-Dihydro-9-hydroxy-10-methoxy-2,2,4-trimethyl-5-((2-fluorophenyl)methyl)-1H-[1]benzopyranol[3,4-f]quinoline

EXAMPLE 349

10-Methoxy-5-(5-methylisoxazol-3-yl)methyidene-2,5-dihydro-5-phenyl-2,2,4-trimethyl1H-[1]benzopyrano[3,4-f]quinoline Example 1F and the lithium anion of 3,5-dimethylisoxazole were processed as in Example 1B to provide the desired compound.

MS (DCI/NH$_3$) m/z 401 (M+H)$^+$; $^1$H NMR (300 MHz, DMSO-d$_6$) δ 8.33 (d, 1H, J=8.83 Hz), 7.7–7.5 (m, 1H), 7.22 (t, 1H, J=8.09), 7.05 (d, 1H, J=1.1 Hz), 6.85 (s, 1H), 6.79 (d, 1H, J=8.82 Hz), 5.61 (s, 1H), 5.5 (s, 1H), 3.93 (s, 3H), 2.45 (s, 3H), 1.96 (d, 3H, J=1.1 Hz), 1.20–1.30 (s, 6H).

EXAMPLE 350

10-Methoxy-5-(3-methylisoxazol-5-yl)methyidene-2,5-dihydro-5-phenyl-2,2,4-trimethyl-1H-[1]benzopyrano[3,4-f]quinoline Example 1F and the lithium anion of 3,5-dimethylisoxazole were processed as in Example 1B to provide the desired compound.

MS (DCI/NH$_3$) m/z 401 (M+H)$^+$; $^1$H NMR (300 MHz, DMSO-d$_6$), isomer 1: δ 8.38 (d, 1H, J=8.83 Hz), 7.22 (t, 1H, J=8 Hz), 7.09 (s, 1H), 6.87–6.81 (m, 2H), 6.56 (s, 1H), 5.65 (s, 1H), 5.51 (s, 1H), 3.93 (s, 3H), 2.28 (s, 3H), 1.95 (s, 3H), 1.29 (s, 3H), 1.26 (s, 3H); isomer 2: δ 8.16 (d, 1H, J=8.83 Hz), 7.18 (t, 2H, J=8 Hz), 7.06 (s, 1H), 6.80–6.76 (m, 2H), 6.46 (s, 1H), 5.90 (s, 1H), 5.21 (s, 1H), 3.91 (s, 3H), 2.08 (s, 3H), 1.84 (s, 3H), 1.26 (s, 3H), 1.12 (s, 3H).

EXAMPLE 351

10-Methoxy-5-(4,5-dimethyl-1,3-oxazol-2-yl)methyidene-2,5-dihydro-5-phenyl-2,2,4-trimethyl-1H-[1]benzopyrano[3,4-f]quinoline Example 1F and the lithium anion of 2,4,5-trimethyloxazole were processed as in Example 1B to provide the desired compound.

MS (DCI/NH$_3$) m/z 415 (M+H)$^+$; $^1$H NMR (300 MHz, DMSO-d$_6$), isomer 1: δ 8.36 (d, 1H, J=8.82 Hz), 7.24–7.20 (m, 1H), 6.82 (m, 3H), 6.25 (s, 1H), 5.49 (s, 1H), 3.92 (s, 3H), 2.31 (s, 3H), 2.09 (s, 3H), 1.28 (s, 3H), 1.2 (m, 6H); 2nd isomer δ 8.09 (d, 1H, J=8.82 Hz), 7.16 (m, 1H), 6.78–6.73 (m, 2H), 5.41 (s, 1H), 5.21 (s, 1H), 3.91 (s, 3H), 2.03 (s, 3H), 1.89 (s, 3H), 1.88 (s, 3H), 1.25–1.15 (m, 6H).

EXAMPLE 352

10-Methoxy-5-(6-chloropyridin-2-yl)methyidene-2,5-dihydro-5-phenyl-2,2,4-trimethyl-1H-[1]benzopyrano[3,4-f]quinoline Example 1F and the lithium anion of 6-chloro-2-methylpyridine were processed as in Example 1B to provide the desired compound.

MS (DCI/NH$_3$) m/z 431 (M+H)$^+$; $^1$H NMR (300 MHz, DMSO-d$_6$) δ 8.35 (d, 1H, J=4.7 Hz), 8.25 (d, 1H, J=8.1 Hz), 7.9 (t, 1H, J=7.7 Hz), 7.30 (d, 1H, J=7.7 Hz), 7.21 (d, 1H, J=8 Hz), 7.00 (d, 1H, J=8.1 Hz), 6.8 (dd, 2H, J=8.4, 2.6 Hz), 6.72 (s, 1H), 5.65 (s, 1H), 5.51 (s, 3H), 3.93 (s, 3H), 1.99 (s, 3H), 1.2 (s, 6H).

EXAMPLE 353

10-Methoxy-5-(pyridin-2-yl)methyidene-2,5-dihydro-5-phenyl-2,2,4-trimethyl-1H-[1]benzopyrano[3,4-f]quinoline Example 1F and the 4-picolinyllithium were processed as in Example 1B to provide the desired compound.

MS (DCI/NH$_3$) m/z 397 (M+H)$^+$; $^1$H NMR (300 MHz, DMSO-d$_6$), isomer 1: δ 8.52 (d, 2H, J=6.1 Hz), 8.17 (d, 1H, J=8.8 Hz), 7.2 (t, 1H, J=8.2 Hz), 6.96 (s, 1H), 6.7 (m, 3H), 6.66 (s, 2H), 5.55 (s, 1H), 4.53 (s, 1H), 3.93 (s, 3H), 1.81 (d, 3H, J=1.4 Hz), 1.27 (s, 6H); isomer 2: δ 8.32 (d, 2H, J=6.1 Hz). 8.19 (d, 1H, J=8.8 Hz), 7.17 (t, 1H, J=8.2 Hz), 6.99 (s, 1H), 6.77 (m, 3H), 6.45 (s, 2H), 5.48 (s, 1H), 5.05 (s, 1H), 3.93 (s, 3H), 1.81 (d, 3H, J=1.4 Hz), 1.27 (s, 6H).

EXAMPLE 354

10-Methoxy-5-(but-3-enylidene)-2,5-dihydro-5-phenyl-2,2,4-trimethyl-1H-[1]benzopyrano[3,4-f]quinoline Example 1F and the lithium anion of cylopropylmethylbromide were processed as in Example 1B to provide the desired compound.

MS (DCI/NH$_3$) m/z 360 (M+H)$^+$; $^1$H NMR (300 MHz, DMSO-d$_6$) δ 8.16 (d, 1H, J=8.8 Hz), 7.10 (t, 1H, J=7.7 Hz), 6.8–6.6 (m, 4H), 6.47 (s, 1H), 5.89–5.75 (m, 1H), 5.41 (s, 1H), 5.10–4.93 (m, 2H), 4.67 (t, 1H, J=7.5 Hz), 3.88 (s, 3H), 1.97 (d, 3H, J=1.3 Hz), 1.20 (s, 6H).

EXAMPLE 355

10-Methoxy-5-(1-methylpropylidene)-2,5-dihydro-5-phenyl-2,2,4-trimethyl-1H-[1]benzopyrano[3,4-f]quinoline Example 1F and the sec-butyllithium were processed as in Example 1B to provide the desired compound.

MS (DCI/NH$_3$) m/z 362 (M+H)$^+$; $^1$H NMR (300 MHz, DMSO-d$_6$) δ 8.01 (d, 1H, J=8.09 Hz), 7.09 (t, 2H, J=8.09 Hz), 6.7 (dd, 2H, J=8.5, 2.6 Hz), 6.65 (d, 1H, J=8.46 Hz), 6.37 (d, 1H, J=0.8 Hz), 5.4 (s, 1H), 3.87 (s, 3H), 1.86 (d, 3H, J=1.1 Hz), 1.48 (s, 3H), 1.33 (s, 3H), 1.08 (s, 3H), 0.9 (t, 3H, J=7.3 Hz).

EXAMPLE 356

10-Methoxy-5-(1-butylidene)-2,5-dihydro-5-phenyl-2,2,4-trimethyl-1H-[1]benzopyrano[3,4-f]quinoline Example 1F and the n-butyllithium were processed as in Example 1B to provide the desired compound.

MS (DCI/NH$_3$) m/z 362 (M+H)$^+$; $^1$H NMR (300 MHz, DMSO-d$_6$) δ 8.14 (d, 1H), 7.07 (t, 1H), 6.67 (m, 3H), 6.07 (s, 1H), 5.40 (s, 1H), 4.71 (t, 1H), 3.88 (s, 3H), 2.29 (q, 1H), 2.00 (s, 3H), 1.43–1.36 (m, 2H), 1.21 (s, 6H), 0.88 (t, 3H).

EXAMPLE 357

2,5-Dihydro-10-methoxy-2,2,4-trimethyl-3-oxide-5-phenyl-1H-[1]benzopyrano[3,4-f]quinazoline

EXAMPLE 357A

8-Amino-7-bromo-1-methoxy-6H-benzo[c]chromen-6-one

A solution of Example 1E (3.0 g, 12.0 mmol) in DMF (100 mL) was treated with N-bromosuccinimide (2.2 g, 12.0 mmol), stirred for 40 minutes, poured into 900 mL of water, stirred for 5 minutes and the resulting solid was collected by filtration and dried to give the desired compound.

EXAMPLE 357B

7-Bromo-1-methoxy-6-phenyl-6H-benzo[c]chromen-8-ylamine

Example 357A (2.0 g, 6.25 mmol) and phenyllithium were processed as in Examples 1G and 1 to provide the desired compound.

EXAMPLE 357C 1-(7-Bromo-1-methoxy-6-phenyl-6H-benzo[c]chromen-8-yl)ethan-1-one Example 357B (1.23 g, 3.22 mmol), tributyl(1-ethoxyvinyl)tin, (1.4 g, 3.86 mmol), and dichlorobis(triphenylphosphine)palladium (II) (263 mg, 0.322 mmol) in NMP (30 mL) were heated at 85° C. for 24 hours under nitrogen. The mixture was partitioned between EtOAc and saturated aqueous sodium bicarbonate and filtered through Celite. The EtoAc layer was concentrated and the residue was dissolved in acetonitrile, washed 5×20 mL g with hexanes and concentrated. The resulting residue was treated with a 1:1 volume of 1N HCl/THF, stirred for 30 minutes, poured into cold, saturated sodium bicarbonate and extracted with EtOAc (5×25 mL). The organics were washed with brine, dried (Na$_2$SO$_4$) and flash chromatographed on silica eluting with 4:1 hexane/EtOAc to give the desired compound.

EXAMPLE 357D 1-(7-Bromo-1-methoxy-6-phenyl-6H-benzo[c]chromen-8-yl)ethan-1-one Oxime A solution of Example 357C (700 mg, 2.03 mmol) and hydroxylamine hydrochloride (2.45 g, 30.4 mmol) in a mixture of EtOH (70 mL) and pyridine (70 mL) was refluxed for 8 hours, cooled and concentrated. The residue was dissolved in EtOAc, washed with water, brine, dried (Na$_2$SO$_4$) and concentrated to provide the desired compound without purifiction.

EXAMPLE 357

2,5-Dihydro-10-methoxy-2,2,4-trimethyl-3-oxide-5-phenyl-1H-[1]benzopyrano[3,4-f]quinazoline Example 357D (700 mg, 1.94 mmol), CuSO$_4$ (105 mg) and acetic acid (3 drops) were combined in acetone (30 mL) and refluxed for 8 hours. The mixture was cooled, poured into water and extracted with EtOAc (3×50 mL). The organics were combined, washed with brine, dried (Na$_2$SO$_4$) and concentrated. The residue was triturated with EtOAc (30 mL) and the yellow solid was collected by filtration to provide the desired compound.

MS (DCI/NH$_3$) m/z 401 (M+H)$^+$; $^1$H NMR (300 MHz, DMSO-d$_6$) δ 8.21 (d, 1H), 7.30 (s, 1H), 7.29–7.16 (m, 5H), 7.00–6.92 (m, 2H), 6.61 (d, 1H), 6.57 (s, 1H), 6.44 (d, 1H), 3.72 (s, 3H), 2.01 (s, 3H), 1.55 (s, 3H), 1.28 (s, 3H); HRMS calcd m/z for C$_{24}$H$_{27}$NO$_2$: 400.1787 (M$^-$)$^+$. Found: 400.1786.

EXAMPLE 358

2,5-Dihydro-10-methoxy-2,2,4-trimethyl-5-phenyl-1H-[1]benzopyrano[3,4-f]quinazoline A solution of Example 357E (80 mg, 0.2 mmol) in MeOH under 4 atmospheres of hydrogen was treated with Raney nickel and stirred for 24 hours. The mixture was filtered through Celite, concentrated and the resulting residue was flash chromatographed on silica eluting with 99:1 EtOAc/MeOH to provide the desired compound.

MS (DCI/NH$_3$) m/z 385 (M+H)$^+$; $^1$H NMR (300 MHz, DMSO-d$_6$) δ 8.22 (d, 1H), 7.26–7.15 (m, 5H), 6.93 (t, 1H), 6.79 (s, 1H), 6.76 (d, 1H), 6.73 (s, 1H), 6.57 (d, 1H), 6.44 (d, 1H), 3.81 (s, 3H), 2.00 (s, 3H), 1.36 (s, 3H), 1.21 (s, 3H). HRMS calcd m/z for C$_{25}$H$_{24}$N$_2$O$_2$: 385.1916 (M+H)$^+$. Found: 385.1930.

EXAMPLE 359

2,5-Dihydro-10-methoxy-2,2-[spiro(tetrahydro-4-pyranyl)]-4-methyl-5-ally-1H-[1]benzopyrano[3,4-f]quinoline

EXAMPLE 359A

Example 357A (1.3 g, 4.08 mmol), isopropenyltrimethyltin (3.3 g, 16.3 mmol) and dichlorobis(triphenylphosphine)palladium (II) (330 mg, 0.40 mmol) in NMP (30 mL) were heated at 85° C. for 24 hours under nitrogen. The mixture was partitioned between EtOAc and saturated aqueous potassium fluoride, stirred for 3 hours and filtered through Celite. The EtOAc layer was washed 5×50 mL with water, 5×50 mL with brine, dried (Na$_2$SO$_4$) and concentrated. Flash chromatography on silica eluting with 3:1 hexane/EtOAc provided the desired product.

EXAMPLE 359

A mixture of the 2-isopropenyl aniline (56 mg, 0.2 mmol), tetrahydro-4H-pyran-4-one (160 mg, 1.6 mmol) and iodine (25 mg, 0.1 mmol) in 5 mL of toluene in an ACE sealed tube was heated at 80° C. for 1 hour, cooled and the mixture was partitioned between EtOAc and 10% aqueous Na$_2$S$_2$O$_3$. The EtOAc layer was washed with water, brine, dried (Na$_2$SO$_4$) and concentrated. Flash chromatography on silica eluting with 3:2 hexane/EtOAc provided the desired coumarin as a bright yellow powder. This resulting coumarin was processed as in Example 2 to provide the desired compound.

MS (DCI/NH$_3$) m/z 390 (M+H)$^+$; $^1$H NMR (300 MHz, DMSO-d$_6$) δ 7.92 (d, 1H), 7.07 (t, 1H), 6.75 (d, 1H), 6.70 (d, 1H), 6.52 (d, 1H), 6.24 (s, 1H), 5.87–5.73 (m, 2H), 5.71 (s, 1H), 5.01 (dd, 1H), 4.96 dd, 1H), 3.86 (s, 3H), 3.75–3.39 (m, 4H), 2.51–2.14 (m, 2H), 2.20 (s, 3H), 1.69–1.49 (m, 4H); HRMS calcd m/z for C$_{25}$H$_{27}$NO$_3$: 389.1991 (M)$^+$. Found: 389.1974. Anal. calcd for C$_{25}$H$_{27}$NO$_3$: C, 77.07; H, 6.99; N, 3.60. Found: C, 76.92; H, 7.28; N, 3.64.

EXAMPLE 360

2,5-Dihydro-10-methoxy-2,2-[spiro(hexyl)]-5-allyl-1H-[1]benzopyrano[3,4-f]quinoline Example 357A was treated sequentially with isopropenyltributyltin and cyclohexanone as in the previous example to give the desired compound.

MS (DCI/NH$_3$) m/z 388 (M+H)$^+$; $^1$H NMR (300 MHz, DMSO-d$_6$) δ 7.95 (d, 1H), 7.06 (t, 1H), 6.74 (d, 1H), 6.70 (d, 1H), 6.52 (d, 1H), 6.05 (s, 1H), 5.85–5.72 (m, 2H), 5.58 (s, 1H), 5.02 (dd, 1H), 4.97 (dd, 1H), 3.86 (s, 3H), 2.42 (m, 1H), 2.18 (s, 3H), 2.16 (m, 1H), 1.56–1.25 (m, 10H); HRMS calcd m/z for C$_{26}$H$_{29}$NO$_2$: 387.2198 (M)$^+$. Found: 387.2196.

EXAMPLE 361

2,5-Dihydro-10-methoxy-2,2-diethyl-4-methyl-5-allyl-1H-[1]benzopyrano[3,4-f]quinoline Example 357A was treated sequentially with isopropenyltributyltin and 3 pentanone as in the previous example to give the desired compound.

MS (DCI/NH$_3$) m/z 376 (M+H)$^+$; $^1$H NMR (300 MHz, DMSO-d$_6$) δ 7.92 (d, 1H), 7.05 (t, J=8 Hz, 1H), 6.68 (d, 1H), 6.59 (d, 1H), 6.51 (d, 1H), 5.98 (s, 1H), 5.86–5.77 (m, 2H), 5.27 (s, 1H), 5.04–4.95 (m, 2H), 3.85 (s, 3H), 2.42 (m, 1H), 2.21 (s, 3H), 2.15 (m, 1H), 1.42–1.35 (m, 4H), 0.83 (t, 3H), 0.82 (t, 3H); HRMS calcd m/z for C$_{25}$H$_{29}$NO$_2$: 375.2198 (M$^-$)$^+$. Found: 375.2191. Anal. calcd for C$_{25}$H$_{29}$NO$_2$: C, 79.96; H, 7.78; N, 3.73. Found: C, 79.74; H, 7.89; N, 3.54.

EXAMPLE 362

2,5-Dihydro-10-methoxy-2,2,3,4-tetramethyl-5-allyl-1H-[1]benzopyrano[3,4-f]quinoline Example 357A was treated sequentially with 1-methyl-1-propenyltributyltin and acetone as in the previous example to give the desired compound.

MS (DCI/NH$_3$) m/z 362 (M+H)$^+$; $^1$H NMR (300 MHz, DMSO-d$_6$) δ 7.97 (d, 1H), 7.07 (t, 1H), 6.70 (d, 1H), 6.62 (d, 1H), 6.53 (d, 1H), 5.90 (s, 1H), 5.76 (m, 1H), 5.61 (dd, 1H), 5.01–4.90 (m, 2H), 3.87 (s, 3H), 2.47 (m, 1H), 2.18 (m, 1H), 2.04 (s, 3H), 1.76 (s, 3H), 1.13 (s, 3H), 1.09 (s, 3H); HRMS calcd m/z for C$_{24}$H$_{27}$NO$_2$: 361.2042 (M$^-$)$^+$. Found: 361.2055.

EXAMPLE 363

2,5-Dihydro-10-methoxy-2,2-dimethyl-4-ethyl-5-allyl-1H-[1]benzopyrano[3,4-f]quinoline Example 357A was treated sequentially with 1-methylenepropyltributyltin and acetone as in the previous example to give the desired compound.

MS (DCI/NH$_3$) m/z 362 (M+H)$^+$; $^1$H NMR (300 MHz, DMSO-d$_6$) δ 7.98 (d, 1H), 7.07 (t, 1H), 6.70 (dd, 1H), 6.63 (d, 1H), 6.53 (dd, 1H), 6.12 (bs, 1H), 5.78 (m, 1H), 5.59 (dd, 1H), 5.50 (bs, 1H), 5.03–4.92 (m, 2H), 3.86 (s, 3H), 2.54–2.41 (m, 3H), 2.11 (m, 1H), 1.20 (s, 3H), 1.10 (s, 3H), 1.03 (t, 3H); HRMS calcd m/z for C$_{24}$H$_{27}$NO$_2$: 361.2042 (M$^-$)$^+$. Found: 361.2034.

EXAMPLE 364

2,5-Dihydro-10-methoxy-2,2,3-trimethyl-5-allyl-1H-[1]benzopyrano[3,4-f]quinoline Example 357A was treated sequentially with (Z)-1-propenyltributyltin and acetone as in the previous example to give the desired compound.

MS (DCI/NH$_3$) m/z 348 (M+H)$^+$; $^1$H NMR (300 MHz, DMSO-d$_6$) δ 7.89 (d, 1H), 7.04 (t, 1H), 6.68 (d, 1H), 6.52 (d, 1H), 6.47 (d, 1H), 6.21 (s, 1H), 5.96 (s, 1H), 5.88 (m, 1H), 5.43 (dd, 1H), 5.03 (m, 1H), 4.96 (m, 1H), 3.84 (s, 3H), 2.35 (m, 1H), 2.08 (m, 1H), 1.83 (s, 3H), 1.23 (s, 6H); HRMS calcd m/z for C$_{23}$H$_{25}$NO$_2$: 347.1885 (M$^-$)$^+$. Found: 347.1879.

EXAMPLE 365

Z-5-(Benzylidenyl)-9-hydroxy-10-methoxy-2,2,4-trimethyl-1H-2,5-dihydro

MS (DCI/NH$_3$) 412 (M+H)$^+$; $^1$H NMR (300 MHz, DMSO-d$_6$), δ 8.93 (s, 1H), 8.13 (d, J=8.8 Hz, 1H), 7.63 (d, J=8.8 Hz, 2H), 7.32–7.15 (m, 3H), 6.77 (d, 1H), 6.69 (d, 1H), 6.66 (d, 1H), 6.52 (s, 1H), 5.46 (s, 1H), 5.39 (s, 1H), 3.65 (s, 3H), 1.90 (s, 3H), 1.20 (s, 6H); HRMS calcd for C$_{27}$H$_{25}$NO$_3$ is 411.1834. Found 411.1821.

EXAMPLE 366

Z-5-(2,5-Difluorobenzylidenyl)-9-hydroxy-10-methoxy-2,2,4-trimethyl-1H-2,5-dihydro-[1]benzopyrano[3,4-f]quinoline MS (DCI/NH3) m/e (M+H)+ 448. $^1$H NMR (300 MHz, DMSO-d$_6$) δ 9.06 (s, 1H), 8.29 (d, J=9 Hz, 1H), 7.96 (m, 1H), 7.24 (m, 1H), 7.11 (m, 1H), 6.86 (d, J=9 Hz, 1H), 6.82 (d, J=9 Hz, 1H), 6.78 (d, J=9 Hz, 1H), 6.72 (br s, 1H), 5.75 (s, 1H), 5.48 (s, 1H), 3.75 (s, 3H), 1.99 (s, 3H), 1.26 (br s, 6H); Anal. calcd for C$_{27}$H$_{23}$NO$_3$F$_2$: C, 72.47; H, 5.18; N, 3.13. Found: C, 72.21; H, 5.31; N, 3.09.

EXAMPLE 367

Z-5-(3-Fluorobenzylidenyl)-10-chloro-9-hydroxy-2,2,4-trimethyl-2,5-dihydro-1H-[1]benzopyrano[3,4-f]quinoline MS (DCI/NH$_3$) m/z 434 (M+H)$^+$; $^1$H NMR (300 MHz, DMSO) δ 9.86 (br s, 1H), 8.40 (d, J=8.5 Hz, 1H), 7.61 (dt, J=8.6, 1.8 Hz, 1H), 7.60–7.52 (m, 1H), 7.46–7.38 (m, 1H), 7.15–7.02 (m, 1H), 7.09 (d, J=8.4 Hz, 1H), 6.85 (d, J=8.6 Hz, 1H), 6.84 (s, 1H), 6.78 (d, J=8.6 Hz, 1H), 5.68 (s, 1H), 5.48 (br s, 1H), 1.97 (br s, 3H), 1.16 (br s, 6H); $^{13}$C NMR (125 MHz, DMSO) δ 163.8, 160.6, 149.9, 149.2, 148.2, 146.4, 132.0, 130.3, 128.1, 127.3, 126.2, 125.3, 124.5, 118.7, 117.7, 117.3, 116.1, 115.5, 114.6, 114.3, 114.0, 113.7, 62.1, 29.8, 28.2, 21.2; HRMS (FAB) calcd m/z for C$_{26}$H$_{21}$ClFNO$_2$: 433.1245 (M)$^+$. Found: 433.1237.

EXAMPLE 368

Z-10-Chloro-9-hydroxy-5-(2-picolinylidenyl)-2,2,4-trimethyl-2,5-dihydro-1H-[1]benzopyrano[3,4-f] quinoline MS (DCI/NH$_3$) m/z 417 (M+H)$^+$; $^1$H NMR (300 MHz, DMSO) δ 9.79 (br s, 1H), 8.51 (ddd, J=5.9, 1.6, 1.0 Hz, 1H), 8.43 (d, J=8.6 Hz, 1H), 8.24 (dt, J=7.8, 1.0 Hz, 1H), 7.53 (td, J=7.8, 1.7 Hz, 1H), 7.22 (ddd, J=7.7, 5.8, 1.2 Hz, 1H), 7.00 (d, J=8.5 Hz, 1H), 6.88 (d, J=8.6 Hz, 1H), 6.81 (d, J=8.5 Hz, 1H), 6.63 (br s, 1H), 5.71 (s, 1H), 5.51 (br s, 1H), 2.00 (br s, 3H), 1.28 (br s, 6H); $^{13}$C NMR (125 MHz, DMSO-d$_6$) δ 153.5, 149.7, 146.4, 145.7, 136.5, 136.1, 132.7, 128.7, 128.2, 123.0, 122.4, 121.5, 118.3, 117.7, 117.6, 116.5, 115.5, 114.8, 114.4, 114.1, 113.9, 49.5, 29.7, 28.1, 21.2; HRMS (FAB) calcd m/z for $C_{25}H_{21}ClN_2O_2$: 416.1291 (M)$^+$. Found: 416.1288.

EXAMPLE 369

Z-9-Hydroxy-10-methoxy-5-(2-picolinylidenyl)-2,2,4-trimethyl-2,5-dihydro-1H-[1]benzopyrano[3,4-f]quinoline MS (DCI/NH$_3$) m/z 413 (M+H)$^+$; $^1$H NMR (300 MHz, DMSO) δ 9.08 (br s, 1H), 8.55 (ddd, J=5.3, 1.4, 1.0 Hz, 1H), 8.32 (d, J=8.6 Hz, 1H), 8.30 (br t, J=7.7 Hz, 1H), 7.83 (td, J=7.8, 1.4 Hz, 1H), 7.21 (ddd, J=7.6, 5.3, 1.2 Hz, 1H), 6.97 (d, J=8.6 Hz, 1H), 6.86 (d, J=8.5 Hz, 1H), 6.81 (d, J=8.6 Hz, 1H), 6.73 (br s, 1H), 5.80 (s, 1H), 5.54 (br s, 1H), 3.78 (s, 3H), 2.03 (br s, 3H), 1.31 (br s, 6H); $^{13}$C NMR (125 MHz, DMSO-d$_6$) δ 158.4, 149.1, 148.2, 146.6, 139.5, 136.0, 133.1, 128.8, 125.7, 124.6, 122.9, 121.0, 119.4, 118.2, 117.3, 116.9, 115.8, 115.1, 114.7, 114.0, 111.5, 73.3, 50.2, 29.9, 28.1, 22.3; HRMS (FAB) calcd m/z for $C_{26}H_{25}N_2O_3$: 413.1865 (M+H)$^+$. Found: 413.1849. Anal. calcd for $C_{26}H_{24}N_2O_3$: C, 75.71; H, 5.86; N, 6.79. Found: C, 75.61; H, 6.05; N, 6.75.

EXAMPLE 370

9-Hydroxy-10-methoxy-5-(3,5-difluorophenyl)methylidene-2,5-dihydro-5-phenyl-2,2,4-trimethyl-1H-[1]benzopyrano[3,4-f]quinoline 1H NMR (300 MHz, DMSO-d$_6$) δ 9.05 (s, 1H), 8.24 (d, J=9 Hz, 1H), 7.41 (m, 2H), 7.07 (m, 2H), 6.85 (d, J=8 Hz, 1H), 6.80 (d, J=9 Hz, 1H), 6.76 (d, J=9 Hz, 1H), 6.70 (br s, 1H), 5.57 (s, 1H), 5.46 (s, 1H), 3.72 (s, 3H), 1.96 (s, 3H), 1.27 (br s, 6H); 12C NMR (75 MHz, DMSO-d$_6$) δ 164.0 (d), 160.8 (d), 150.1, 146.2, 146.1, 144.6, 144.4, 132.1, 128.8, 125.2, 125.0, 117.9, 117.8, 115.2, 115.0, 114.8, 112.1, 110.9, 110.8, 110.5, 101.9, 101.6, 101.2, 29.3, 49.0, 21.1 (2×C); MS (DCI/NH3) m/e (M+H)+ 448.

EXAMPLE 371

9-Hydroxy-10-methoxy-5-(3,4-difluorophenyl)methylidene-2,5-dihydro-5-phenyl-2,2,4-trimethyl-1H-[1]benzopyrano[3,4-f]quinoline $^1$H NMR (300 MHz, DMSO-d$_6$) δ 9.03 (s, 1H), 8.22 (d, J=9 Hz, 1H), 7.79 (m, 1H), 7.52 (m, 1H), 7.41 (m, 1H), 6.86 (d, J=9 Hz, 1H), 6.77 (d, J=9 Hz, 1H), 6.74 (d, J=9 Hz, 1H), 6.68 (br s, 1H), 5.53 (s, 1H), 5.45 (s, 1H), 3.33 (s, 3H), 1.95 (s, 3H), 1.27 (br s, 6H); MS (DCI/NH3) m/e (M+H)+ 448. FAB HRMS calculated for $C_{27}H_{23}NO_3F_2$.

EXAMPLE 372

(Z)9-Hydroxy-10-methoxy-5-((4-fluorophenyl)methylene)-2,2,4-trimethyl-1H-2,5-dihydro-[1]benzopyrano[3,4-f]quinoline $^1$H NMR (300 MHz, DMSO-d$_6$) δ 9.01 (s, 1H), 8.19 (d, J=9 Hz, 1H), 7.77 (d, J=9 Hz, 1H), 7.76 (d, J=9 Hz, 1H), 7.22 (d, J=9 Hz, 1H), 7.18 (d, J=9 Hz, 1H), 6.84 (d, J=8 Hz, 1H), 6.75 (d, J=9 Hz, 1H), 6.72 (d, J=9 Hz, 1H), 6.66 (s, 1H), 5.53 (s, 1H), 5.45 (s, 1H), 3.71 (s, 3H), 1.96 (s, 3H), 1.26 (s, 6H); $^{13}$C NMR (75 MHz, DMSO-d$_6$) δ 161.8, 159.4 147.4, 146.0, 145.1, 144.4, 132.0, 131.4, 130.2, 130.1, 129.0, 126.2, 125.0, 117.8, 115.4, 115.3, 115.2, 114.6, 114.5, 113.3, 111.0, 59.3, 59.2, 49.5, 21.0; . MS (DCI/NH$_3$) m/z 430 (M+H)$^+$; Anal. calcd for $C_{27}H_{24}NO_3F$: C, 75.51; H, 5.63; N, 3.26. Found: C, 75.64; H, 5.97; N, 3.03.

EXAMPLE 373

(Z)-9-Hydroxy-10-methoxy-5-([2,3-difluorophenyl]methylene)-2,2,4-trimethyl-1H-2,5-dihydro-[1]benzopyrano[3,4-f]quinoline $^1$H NMR (300 MHz, DMSO-d$_6$) δ 9.09 (s, 1H), 8.27 (d, J=9 Hz, 1H), 8.04 (d, J=9 Hz, 1H), 7.33–7.20 (m, 2H), 6.87 (d, J=9 Hz, 1H), 6.82 (d, J=9 Hz, 1H), 6.76 (s, 1H), 6.75 (d, J=9 Hz, 1H), 5.75 (s, 1H), 5.49 (s, 1H), 3.73 (s, 3H), 1.99 (s, 3H), 1.26 (s, 6H); MS (DCI/NH$_3$) m/z 448 (M+H)$^+$; Anal. calcd for $C_{27}H_{23}NO_3F_2$: C, 72.47; H, 5.18; N, 3.13. Found: C, 72.17; H, 5.03; N, 2.95.

EXAMPLE 374

Z-5-(3-Fluorobenzylidenyl)-10-methoxy-9-hydroxy-2,2,4-trimethyl-2,5-dihydro-1H-[1]benzopyrano[3,4-f]quinoline $^1$H NMR (300 MHz, DMSO-d$_6$) δ 9.04 (s, 1H), 8.22 (d, 1H), 7.62–7.37 (m, 3H), 7.10–7.02 (m, 1H), 6.86 (d, 1H), 6.78 (d, 1H), 6.73 (d, 1H), 6.70 (s, 1H), 5.56 (s, 1H), 5.46 (s, 1H), 3.72 (s, 3H), 1.96 (s, 3H), 1.27 (s, 3H). MS (DCI/NH$_3$) m/z 430 (M+H)$^+$; Anal. calcd for $C_{27}H_{24}NO_3F.0.25H_2O$: C, 75.51; H, 5.63; N, 3.26. Found: C, 74.84; H, 6.17; N, 2.91.

EXAMPLE 375 rel-(5S,3'R)-9-Hydroxy-5-[1-methoxymethyl-3-cyclohexenyl]-10-methoxy-2,2,4-trimethyl-2,5-dihydro-1H-[1]benzopyrano[3,4-f]quinoline MS (DCI/NH$_3$) m/z 452 (M+H)$^+$; $^1$H NMR (300 MHz, DMSO) δ 8.02 (d, J=8.6 Hz, 1H), 6.93 (app s, 2H), 6.68 (d, J=8.3 Hz, 1H), 6.48 (br s, 1H), 5.52 (d, J=10.3 Hz, 1H), 5.42 (br s, 1H), 5.10 (br s, 1H), 4.46 (t, J=5.5 Hz, 1H), 3.81 (s, 3H), 3.65 (br d, J=5.5 Hz, 2H), 2.26–2.16 (m, 1H), 2.08 (br s, 3H), 1.95–1.88 (m, 2H), 1.77–1.62 (m, 2H), 1.57–1.44 (m, 1H), 1.37–1.28 (m, 1H), 1.30 (s, 3H), 1.11 (s, 3H); $^{13}$C NMR (125 MHz, DMSO) δ 150.4, 146.0, 144.9, 140.7, 133.9, 132.7, 127.9, 127.0, 124.3, 119.8, 117.7, 116.7, 115.7, 115.4, 112.5, 110.7, 75.9, 65.5, 56.4, 49.6, 36.6, 29.7, 27.9, 25.9, 25.0, 24.4, 20.3; HRMS (FAB) calcd m/z for $C_{27}H_{30}ClNO_3$: 451.1915 (M)$^+$. Found: 451.1922.

EXAMPLE 376

9-Hydroxy-10-methoxy-5-ethyl-2,2,4-trimethyl-2,5-dihydro-1H-[1]benzopyrano[3,4-f]quinoline $^1$H NMR (200 MHz, DMSO-d$_6$) δ 8.70 (s, 1H), 7.90 (d, J=8 Hz, 1H), 6.61 (m, 2H), 6.51 (d, J=8 Hz, 1H), 6.16 (br s, 1H), 5.52–5.40 (m, 2H), 2.62 (s, 2H), 2.09 (s, 2H, 1.79–1.58 (m, 1H), 1.52–1.27 (m, 1H), 1.17 (s, 2H), 1.15 (s, 2H), 0.89 (t, J=7 Hz, 2H); 12C NMR 75 MHz, DMSO-d6) δ 145.8, 145.0, 142.9, 142.0, 122.5, 122.4, 127.6, 126.4, 118.0, 116.4, 116.1, 114.2, 112.5, 112.2, 75.1, 59.2, 49.7, 29.2, 28.8, 25.5, 22.8, 10.4; MS (DCI/NH3) m/e (M+H)+ 252; Anal. calcd for C22H25NO2.1/2H2O: C, 72.94; H, 7.24; N, 2.92. Found: C, 72.78; H, 7.40; N, 2.74.

EXAMPLE 377

(+/−)2,5-Dihydro-9-cyanomethoxy-10-methoxy-2,2,4-trimethyl-5-allyl-1H-[1]benzopyrano[3,4-f]quinoline $_1$H NMR (200 MHz, DMSO-d6) δ 7.92 (d, 1H), 6.95 (d, 1H), 6.66 (d, 1H), 6.62 (d, 1H), 6.26 (d, 1H), 5.86 (m, 2H), 5.45 (s, 1H) 5.12 (s, 2H), 5.00 (m, 2H), 2.69 (s, 2H), 2.42 (m, 1H), 2.26 (m, 1H), 2.17 (s, 2H), 1.18 (s, 2H), 1.17 (s, 2H).

EXAMPLE 378

2,5-Dihydro-9-(4-N,N-diethylamino-4-oxo-butanoyloxy)-10-methoxy-2,2,4-trimethyl-5-(2-propenyl)-1H-[1]benzopyrano[3,4-f]quinoline $_1$H NMR (400 MHz, DMSO-d6) δ 7.78 (d, J=8.5, 1H), 6.76 (d, J=8.9, 1H), 6.60–6.55 (m, 2H), 6.18 (d, J=1.7, 1H), 5.80–5.70 (m, 2H), 5.28 (s, 1H), 4.98–4.90 (m, 2H), 2.55 (s, 2H), 2.28–2.17 (m, 4H), 2.77–2.69 (m, 2H), 2.68–2.57 (m, 2H), 2.29 (m, 1H), 2.19 (m, 1H), 2.10 (s, 2H), 1.11 (s, 2H), 1.10 (s, 2H), 1.06 (t, J=7.2, 2H), 0.95 (t, J=7.2, 2H); 13C NMR (100 MHz, DMSO-d$_6$) δ 171.5, 169.5, 148.2, 148.0, 146.2, 128.5, 124.1, 122.5, 122.1, 127.2, 126.2, 120.8, 118.2, 117.2, 116.2, 115.0, 112.8, 112.5, 72.6,60.0, 49.8, 41.1, 26.6, 29.2, 29.0, 27.4, 22.8, 14.0, 12.1; MS (ESI/NH3) m/e 519 (M+H)+, 541 (M+Na)$^+$; Anal. Calcd for $C_{31}H_{38}N_2O_5$: C, 71.79, H, 7.28, N, 5.40. Found: C, 71.50, H, 7.28, N, 5.28.

EXAMPLE 379

2,5-Dihydro-9-(4-N-piperidino-4-oxo-butanoyloxy)-10-methoxy-2,2,4-trimethyl-5-(2-propenyl)-1H-[1]benzopyrano[3,4-f]quinoline $_1$H NMR (200 MHz, DMSO-d6) δ 7.78 (d, J=8.4, 1H), 6.76 (d, J=8.8, 1H), 6.61–6.55 (m, 2H), 6.17 (d, J=1.5, 1H), 5.82–5.68 (m, 2H), 5.28 (s, 1H), 4.99–4.89 (m, 2H), 2.55 (s, 2H), 2.27 (m, 4H), 2.74 (m, 2H), 2.61 (m, 2H), 2.41 (m, 1H), 2.18 (m, 1H), 2.10 (s, 2H), 1.51–1.16 (m, 6H), 1.11 (s, 2H), 1.10 (s, 2H); 13C NMR (75 MHz, DMSO-d6) δ 171.7, 168.9, 148.5, 148.2, 146.5, 128.7, 124.2, 122.8, 122.2, 127.5, 126.5, 121.0, 118.4, 117.5, 116.4, 115.2, 114.0, 112.8, 72.8, 60.2, 50.0, 45.9, 42.4, 26.8, 29.5, 29.2, 27.7, 26.1, 25.5, 24.2, 24.1; MS (ESI/NH3) m/e 521 (M+H)+, 552 (M+Na)$^+$; Anal. Calcd for $C_{32}H_{38}N_2O_5$: C, 72.42, H, 7.22, N, 5.28. Found: C, 72.16, H, 7.26, N, 5.09.

EXAMPLE 380

2,5-Dihydro-9-(4-N-morpholino-4-oxo-butanoyloxy)-10-methoxy-2,2,4-trimethyl-5-(2-propenyl)-1H-[1]benzopyrano[3,4-f]quinoline 1H NMR (400 MHz, DMSO-d6) δ 7.78 (d, J=8.9, 1H), 6.77 (d, J=8.5, 1H), 6.60–6.55 (m, 2H), 6.18 (s, 1H), 5.80–5.70 (m, 2H), 5.28 (s, 1H), 4.98–4.90 (m, 2H), 2.55 (s, 2H), 2.52–2.42 (m, 4H), 2.40 (m, 4H), 2.76 (m, 2H), 2.65 (m, 2H), 2.40 (m, 1H), 2.20 (m, 1H), 2.10 (s, 2H), 1.11 (s, 2H), 1.10 (s, 2H); 13C NMR (100 MHz, DMSO-d6) δ 171.4, 169.4, 148.2, 148.0, 146.2, 128.5, 124.1, 122.5, 122.1, 127.2, 126.2, 120.8, 118.2, 117.2, 116.2, 115.0, 112.8, 112.6, 72.6, 66.1, 60.0, 49.8, 45.1, 41.6, 26.6, 29.2, 29.0, 28.8, 27.2, 22.8; MS (ESI/NH3) m/e 522 (M+H)+, 555 (M+Na)+; Anal. Calcd for $C_{31}H_{36}N_2O_6$: C, 69.90, H, 6.81, N, 5.26. Found: C, 69.61, H, 6.84, N, 5.04.

EXAMPLE 381

2,5-Dihydro-9-(4-N,N-dimethylamino-4-oxo-butanoyloxy)-10-methoxy-2,2,4-trimethyl-5-(3,4,5-trifluorophenyl)-1H-[1]benzopyrano[3,4-f]quinoline $_1$H NMR (400 MHz, DMSO-d$_6$) δ 7.90 (d, J=8.5, 1H), 7.07–7.02 (m, 2H), 6.80–6.70 (m, 2H), 6.62 (m, 2H), 6.44 (s, 1H), 5.42 (d, J=1.2, 1H), 2.54 (s, 2H), 2.97 (s, 2H), 2.82 (s, 2H), 2.76–2.72 (m, 2H), 2.67–2.64 (m, 2H), 1.84 (s, 2H), 1.25 (s, 2H), 1.15 (s, 2H); $_{13}$C NMR (100 MHz, DMSO-d$_6$) δ 171.4, 170.4, 150.1 (d, J=248), 148.4, 147.9, 146.4, 128.7, 128.2 (dd, J=251, 49), 126.5, 122.2, 128.2, 127.1, 126.5, 121.0, 118.5, 117.9, 116.1, 114.8, 112.0, 112.8, 112.6, 72.7, 59.7, 49.9, 26.5, 24.9, 29.7, 28.9, 28.6, 27.6, 22.2; MS (ESI/NH$_3$) m/e 581 (M+H)$^+$, 602 (M+Na)$^+$; Anal. Calcd for $C_{32}H_{31}F_3N_2O_5$: C, 66.20; H, 5.28, N, 4.82. Found: C, 66.17, H, 5.46, N, 4.65.

EXAMPLE 382

2,5-Dihydro-9-hydroxy-10-methoxy-2,2,4-trimethyl-5-(3-5-difluorophenylmethyl)-1H-[1]benzopyrano[3,4-f]quinoline $^1$H NMR (300 MHz, DMSO-d$_6$) δ 8.81 (s, 1H), 7.95 (d, J=8 Hz, 1H), 7.10–7.03 (m, 1H), 6.78 (d, J=9 Hz, 2H), 6.63 (dd, J=9, 9 Hz, 2H), 6.41 (d, J=9 Hz, 1H), 6.22 (s, 1H), 5.91 (dd, J=10, 10 Hz, 1H), 5.40 (s, 1H), 3.69 (s, 3H), 3.06–2.98 (m, 1H), 2.90–2.84 (m, 1H), 2.19 (s, 3H), 1.15 (s, 3H), 1.12 (s, 3H); $^{13}$C NMR (75 MHz, DMSO-d$_6$) δ 163.8, 163. 160.6, 160.4, 145.9, 145.2, 144.1, 142.6, 142.4, 142.3, 133.4, 131.7, 127.4, 126.5, 117.8, 116.5, 116.2, 114.5, 113.9, 112.3, 112.2, 111.9, 102.1, 101.7, 101.4, 73.5, 59.5, 49.7, 29.1, 29.0, 24.1; HRMS calc'd for $C_{27}H_{25}O_3F_2N$: m/e 449.1803, found 449.1801; Analysis calc'd for $C_{27}H_{25}O_3F_2N0.05H_2O$: C, 70.73; H, 5.72; N, 3.05; found: C, 70.52; H, 5.79; N, 2.91.

EXAMPLE 383

2,5-Dihydro-9-hydroxy-10-chloro-2,2,4-trimethyl-5-(2-thienyl)-1H-[1]benzopyrano[3,4-f]quinoline 1H NMR δ 9.51 (s, 1H), 7.95 (d, 1H, J=8.5 Hz), 7.40 (dd, 1H, J=5.1 Hz, J=1.4 Hz), 6.82 (m, 2H), 6.71 (m, 2H), 6.61 (s, 2H), 6.26 (m, 1H), 5.40 (m, 1H), 1.92 (d, 2H, J=1.4 Hz), 1.24 (s, 2H), 1.14 (s, 2H); mass spectrum (ESI) m/z: 410 (M+1); Calcd for $C_{22}H_{20}ClNO2S$: 409.0902. Found: 409.0902.

EXAMPLE 384

2,5-Dihydro-9-hydroxy-10-methoxy-2,2,4-trimethyl-5-cyclopentyl-1H-[1]benzopyrano[3,4-f]quinoline $^1$H NMR (300 MHz, DMSO-d$_6$) δ 8.70 (s, 1H), 7.99 (d, J=8 Hz, 1H), 6.63 (d, J=9 Hz, 1H), 6.61 (d, J=9 Hz, 1H), 6.48 (d, J=8 Hz, 1H), 6.27 (br s, 1H), 5.45 (br s, 1H), 5.35 (d, J=10 Hz, 1H), 3.65 (s, 3H), 2.15 (s, 3H), 2.11–1.97 (m, 1H), 1.62–1.43 (m, 4H), 1.41–1.26 (m, 2H), 1.30 (s, 3H), 1.21–1.06 (m, 2H), 1.02 (s, 3H); MS (DCI/NH$_3$) (M+H)$^+$ 3.92.

EXAMPLE 385

2,5-Dihydro-9-hydroxy-10-methoxy-2,2,4-trimethyl-5-((2-fluorophenyl)methyl)-1H-[1]benzopyrano[3,4-f]quinoline MS (DCI/NH$_3$) m/z 418 (M+H)$^+$.

EXAMPLE 386

2,5-Dihydro-9-hydroxymethyl-10-methoxy-2,2,4-trimethyl-5-allyl-1H-[1]benzopyrano[3,4-f]quinoline MS (DCI/NH$_3$) m/z 378 (M+H)$^+$; $^1$H NMR (500 MHz, DMSO) δ 7.93 (d, J=8.2 Hz, 1H), 7.16 (d, J=8.3 Hz, 1H), 6.67 (d, J=8.1 Hz, 1H), 6.63 (d, J=8.3 Hz, 1H), 6.27 (br s, 1H), 5.87–5.75 (m, 2H), 5.44 (br s, 1H), 5.03 (br d, J=10.3 Hz, 1H), 4.98 (br d, J=15.1 Hz, 1H), 4.97–4.93 (m, 1H), 4.57–4.48 (m, 2H), 3.59 (s, 3H), 2.55–2.46 (m, 1H), 2.30–2.22 (m, 1H), 2.19 (s, 3H), 1.19 (s, 3H), 1.16 (s, 3H); $^{13}$C NMR (125 MHz, DMSO) δ 154.0, 150.2, 145.9, 134.2, 133.4, 132.1, 128.9, 127.4, 126.6, 125.9, 117.2, 116.8, 116.3, 115.6, 113.9, 112.6, 73.6, 60.0, 58.1, 49.8, 36.4, 29.4, 28.9, 23.9; HRMS (FAB) calcd m/z for $C_{24}H_{27}NO_3$: 377.1991 (M)$^+$. Found: 377.1985.

EXAMPLE 387

2,5-Dihydro-9-hydroxy-10-methoxy-2,2,4-trimethyl-5-(1-pentenyl)-1H-[1]benzopyrano[3,4-f]quinoline $^1$H NMR (300 MHz, DMSO-d$_6$) δ 8.67 (s, 1H), 7.88 (d, J=9 Hz, 1H), 6.59 (d, J=9 Hz, 2H), 6.48 (d, J=8 Hz, 1H), 6.14 (s, 1H), 5.73–5.65 (m, 1H), 5.61–5.57 (m, 1H), 5.43 (s, 1H), 4.94–4.86 (m, 2H), 3.63 (s, 3H), 2.15 (s, 3H), 1.99–1.93 (m, 2H), 1.73–1.69 (m, 1H), 1.45–1.41 (m, 3H), 1.16 (s, 6H); $^{13}$C NMR (75 MHz, DMSO-d$_6$) δ 145.7, 144.9, 143.9, 143.0, 138.4, 133.4, 133.3, 127.5, 126.4, 117.9, 116.2, 116.1, 114.7, 114.2, 113.4, 112.1, 73.5, 59.3, 49.7, 32.5, 31.7, 29.1, 28.9, 24.6, 23.8; MS calc'd for $C_{25}H_{29}O_3N$: m/e 391.2147, found 391.2153; Analysis calc'd for $C_{25}H_{29}O_3N0.50H_2O$: C, 74.97; H, 7.55; N, 3.50; found: C, 75.20; H, 7.45; N, 3.49.

EXAMPLE 388

2,5-Dihydro-9-methylcarboxylate-10-methoxy-2,2,4-trimethyl-5-allyl-1H-[1]benzopyrano[3,4-f]quinoline MS (DCI/NH$_3$) m/z 406 (M+H)$^+$; $^1$H NMR (125 MHz, DMSO) δ 7.92 (d, J=8.1 Hz, 1H), 6.48 (d, J=8.3 Hz, 1H), 6.75 (d, J=8.2 Hz, 1H), 6.65 (d, J=8.2 Hz, 1H), 6.33 (br s, 1H), 5.90–5.75 (m, 2H), 5.46 (br s, 1H), 5.04 (dd, J=10.5, 1.0 Hz, 1H), 4.98 (dd, J=15.4, 1.0 Hz, 1H), 3.82 (s, 3H), 3.67 (s, 3H), 2.54–2.42 (m, 1H), 2.38–2.27 (m, 1H), 2.18 (s, 3H), 1.19 (s, 3H), 1.16 (s, 3H); $^{13}$C NMR (300 MHz, DMSO) δ 166.1, 156.5, 154.6, 146.3, 133.9, 133.5, 131.9, 129.0, 127.2, 126.2, 119.1, 118.1, 117.4, 116.2, 114.5, 114.0, 113.0, 74.0, 60.7, 51.8, 49.8, 36.8, 29.4, 29.0, 23.8; HRMS (FAB) calcd m/z for $C_{25}H_{27}NO_4$: 405.1940 (M)$^+$. Found: 405.1939.

EXAMPLE 389

2,5-Dihydro-9-hydroxy-10-methoxy-2,2,4-trimethyl-5-allenyl-1H-[1]benzopyrano[3,4-f]quinoline $^1$H NMR (300 MHz, DMSO-d$_6$) δ 8.67 (s, 1H), 7.93 (d, J=9 Hz, 1H), 6.57 (dd, J=10, 9 Hz, 2H), 6.48 (d, J=9 Hz, 1H), 6.15–6.12 (m, 2H), 5.41 (s, 1H), 5.31 (q, J=12 Hz, 1H), 4.72–4.69 (m, 1H), 4.59–4.49 (m, 1H), 3.58 (s, 3H), 2.14 (s, 3H), 1.23 (s, 3H), 1.10 (s, 3H); MS calc'd for $C_{23}H_{23}O_3N$: m/e 361.1678, found 361.1671; Analysis calc'd for C23H23O3N0.5H2O: C, 74.58; H, 6.53; N, 3.78; found: C, 74.98; H, 6.56; N, 3.83.

EXAMPLE 390

(–)(5S,3'S)2,5-Dihydro-10-methoxy-2,2,4-trimethyl-5-(cyclopenten-3-yl)-1H-[1]benzopyrano[3,4-f]quinoline $^1$H NMR (300 MHz, DMSO-d$_6$) δ 8.05 (d, J=9 Hz, 1H), 7.09 (t, J=8 Hz, 1H), 6.72 (d, J=8 Hz, 1H), 6.66 (d, J=9 Hz, 1H), 6.58 (d, J=8 Hz, 1H), 6.19 (s, 1H), (s, 1H), 5.77 (dd, J=6,3 Hz, 1H), 5.50 (d, J=10 Hz, 1H), 5.43 (s, 1H), 5.19 (dd, J=6, 2 Hz, 1H), 3.87 (s, 3H), 2.90 (m, 1H), 2.43–2.15 (m, 2H), 2.09 (s, 3H), 1.97–1.70 (m, 2H), 1.31 (s, 3H), 1.09 (s, 3H); $^{13}$C NMR (75 MHz, DMSO-d$_6$) δ 156.2, 151.4, 145.2, 133.7, 132.5, 131.6, 130.0, 128.1, 127.2, 127.1, 117.0, 116.4, 113.4, 113.1, 110.0, 105.3, 75.9, 55.6, 49.5, 48.6, 31.6, 29.7, 27.3, 27.2, 24.2; (DCI/NH$_3$) m/z 374 (M+H)$^+$; MS (FAB HRMS) calc'd for $C_{25}H_{27}NO_2$: m/e 373.2042, found: 373.2047.

EXAMPLE 391

(–)(5S,3'S)2,5-Dihydro-10-methoxy-2,2,4-trimethyl-5-(cyclohexen-3-yl)-1H-[1]benzopyrano[3,4-f]quinoline $^1$H NMR (300 MHz, DMSO-d$_6$) δ 8.03 (d, J=9 Hz, 1H), 7.07 (t, J=8 Hz, 1H), 6.68 (d, J=8 Hz, 1H), 6.63 (d, J=9 Hz, 1H), 6.57 (d, J=8 Hz, 1H), 6.15 (s, 1H), 5.62 (m, 1H), 5.54 (m, 1H), 5.46 (s, 1H), 5.09 (m, 1H), 3.85 (s, 3H), 2.29 (m, 1H), 2.10 (s, 3H), 1.95–1.80 (m, 2H), 1.72–1.50 (m, 2H), 1.38–1.10 (m, 2H), 1.28 (s, 3H), 1.05 (s, 3H); $^{13}$C NMR (75 MHz, DMSO-d$_6$) δ 156.2, 151.0, 145.0, 133.7, 130.4, 129.1, 128.1, 127.1, 126.1, 117.9, 116.5, 113.5, 113.1, 110.1, 105.4, 75.3, 55.6, 49.5, 36.8, 29.7, 27.3, 25.5, 24.6, 24.3, 20.0; MS (DCI/NH$_3$) m/z 388 (M+H)$^+$; MS (FAB HRMS) calc'd for $C_{26}H_{29}NO_2$: m/e 387.2198, found: 387.2204. [a]$^{23}_D$=–138° (c 0.114, CHCl$_3$).

EXAMPLE 392

(–)(5S,3'R)2,5-Dihydro-10-methoxy-2,2,4-trimethyl-5-(cyclohexen-3-yl)-1H-[1]benzopyrano[3,4-f]quinoline $^1$H NMR (300 MHz, DMSO-d$_6$) δ 8.05 (d, J=9 Hz, 1H), 7.06 (t, J=8 Hz, 1H), 6.67 (d, J=8 Hz, 1H), 6.64 (d, J=9 Hz, 1H), 6.59 (d, J=8 Hz, 1H), 6.19 (s, 1H), 5.82 (m, 1H), 5.72 (m, 1H), 5.41 (s, 1H), 5.40 (d, J=10 Hz, 1H), 3.87 (s, 3H), 2.29 (m, 1H), 2.13 (s, 3H), 1.95–1.80 (m, 2H), 1.72–1.50 (m, 2H), 1.38–1.10 (m, 2H), 1.30 (s, 3H), 1.02 (s, 3H); $^{13}$C NMR (75 MHz, DMSO-d$_6$) δ 156.3, 151.4, 145.0, 133.8, 130.0, 128.3, 127.9, 127.5, 127.1, 126.9, 118.5, 116.4, 113.4, 113.0, 110.2, 105.3, 76.1, 55.6, 49.4, 37.1, 29.6, 26.8, 24.7, 23.6, 21.2; MS (DCI/NH$_3$) m/z 388 (M+H)$^+$;); MS (FAB HRMS) calc'd for $C_{26}H_{29}NO_2$: m/e 387.2198, found: 387.2206. [α]$^{23}_D$=–147° (c 0.080, CHCl$_3$).

EXAMPLE 393

(–)(5S,3'R)2,5-Dihydro-10-methoxy-2,2,4-trimethyl-5-(cyclopenten-3-yl)-1H-[1]benzopyrano[3,4-f]quinoline $^1$H NMR (300 MHz, DMSO-d$_6$) δ 8.07 (d, J=9 Hz, 1H), 7.08 (t, J=8 Hz, 1H), 6.70 (d, J=8 Hz, 1H), 6.66 (d, J=9 Hz, 1H), 6.61 (d, J=8 Hz, 1H), 6.22 (s, 1H), 5.82–5.70 (m, 2H), 5.48 (d, J=13 Hz, 1H), 5.41 (d, J=10 Hz, 1H), 3.88 (s, 3H), 2.92 (m, 1H), 2.30 (m, 1H), 2.20 (m, 1H), 2.15 (s, 3H), 1.50–1.40 (m, 2H), 1.33 (s, 3H), 1.05 (s, 3H); $_{13}$C NMR (75 MHz, DMSO-d$_6$) δ 156.3, 151.8, 145.1, 133.8, 132.0, 131.8, 130.8, 127.9, 127.0, 117.7, 117.0, 116.5, 113.4, 113.3, 112.9, 109.9, 105.2, 105.0, 76.3, 49.3, 48.4, 32.4, 31.6, 26.7, 24.6, 23.9, 23.6; MS (DCI/NH$_3$) m/z 374 (M+H)$^+$; MS (FAB HRMS) calc'd for $C_{25}H_{27}NO_2$: m/e 373.2042, found: 373.2049.

EXAMPLE 394

2,5-Dihydro-9-hydroxy-10-methoxy-2,2,4-trimethyl-5-(3(Z)-pentenyl)-1H-[1]benzopyrano[3,4-f]quinoline $^1$H NMR (300 MHz, DMSO-d$_6$) δ 8.71 (s, 1H), 7.92 (d, J=8 Hz, 1H), 6.62 (d, J=9 Hz, 1H), 6.60 (d, J=9 Hz, 1H), 6.47

(d, J=9 Hz, 1H), 6.18 (br s, 1H), 5.63 (dd, J=4.9 Hz, 1H), 5.43 (br s, 1H), 5.36 (m, 2H), 3.64 (s, 3H), 2.44–2.33 (m, 1H), 2.33–2.19 (m, 1H), 2.15 (s, 3H), 1.70 (m, 2H), 1.16 (s, 6H), 0.75 (t, J=8 Hz, 3H); MS (DCI/NH$_3$) (M+H)$^{30}$ 3.92.

EXAMPLE 395

2,5-Dihydro-9-hydroxy-10-methoxy-2,2,4-trimethyl-5-(3-acetoxyphenyl)-1H-[1]benzopyrano[3,4-f]quinoline MS (DCI/NH3) m/z 458 (M+H)+; 1H NMR (400 MHz, DMSO-d6) 8.62 (S, 1H), 7.92 (d, 1H), 7.27 (t, 1H), 7.12 (d, 1H), 6.94 (dd, 1H), 6.82 (s, 1H), 6.72 (d, 1H), 6.67 (s, 1H), 6.44 (d, 1H), 6.27 (d, 1H, 6.20 (s, 1H), 5.29 (s, 1H), 2.55 (s, 2H), 2.18 (s, 2H), 1.81 (s, 2H), 1.25 (s, 2H), 1.12 (s, 2H).

EXAMPLE 396

10-Difluoromethoxy-5-[[3-(methylthio)methoxy]phenyl]-2,2,4-trimethyl-1H-2,5-dihydro-[1]benzopyrano[3,4-f]quinoline MS (DCI/NH3) 496 (M+H)+; 1H NMR (200 MHz, DMSO-d$_6$), δ 7.80 (d, J=8.5 Hz, 1H), 7.21 (t, JH-F=56 Hz, 1H), 7.20–7.12 (m, 2H), 6.99 (t, 1H), 6.82–6.68 (m, 7H), 6.29 (d, J=1.1 Hz, 1H), 5.40 (s, 1H), 5.14 (s, 2H), 2.08 (s, 2H), 1.85 (s, 2H), 1.22 (s, 2H), 1.16 (s, 2H); HRMS calcd for C$_{28}$H$_{27}$NO2F2S is 495.1680. Found 495.1682.

EXAMPLE 397

2,5-Dihydro-7-bromo-9-hydroxy-10-chloro-2,2,4-trimethyl-5-allyl-1H-[1]benzopyrano[3,4-f]quinoline MS (DCI/NH$_3$) m/z 448 (M+H)$^+$; $^1$H NMR (300 MHz, DMSO) δ 10.03 (s, 1H), 7.90 (d, J=8.5 Hz, 1H), 7.00 (app s, 2H), 6.63 (d, J=8.4 Hz, 1H), 6.43 (br s, 1H), 5.92–5.77 (m, 2H), 5.47 (br s, 1H), 5.11–4.97 (m, 1H), 2.44–2.26 (m, 2H), 2.19 (s, 3H), 1.22 (s, 3H), 1.18 (s, 3H); $_{13}$C NMR (125 MHz, DMSO-d$_6$) δ 156.7, 150.2, 148.6, 144.0, 139.1, 136.3, 135.5, 130.8, 129.2, 124.4, 117.6, 115.9, 115.2, 114.0, 111.6, 75.9, 51.6, 48.3, 35.5, 29.8, 27.9, 24.0; HRMS (FAB) calcd m/z for C$_{22}$H$_{21}$$^{77}$BrClNO$_2$: 445.0444 (M)$^+$. Found: 445.0436. HRMS (FAB) calcd m/z for C$_{22}$H$_{21}$$^{79}$BrClNO$_2$: 447.0424 (M)$^+$. Found: 447.0413. Anal. Calcd for C$_{22}$H$_{21}$BrClNO$_2$: C, 59.15; H, 4.74; N, 3.14. Found: C, 59.31; H, 4.85; N, 3.22.

EXAMPLE 398

2,5-Dihydro-9-hydroxy-10-methoxy-2,2,4-trimethyl-5-(3-hydroxyphenyl)-1H-[1]benzopyrano[3,4-f]quinoline MS (DCI/NH3) m/z 416 (M+H)+; 1H NMR (400 MHz, DMSO-d6) 9.22 (s, 1H), 8.56 (s, 1H), 7.92 (d, 1H), 6.98 (t, 1H), 6.71 (d, 1H), 6.64 (d, 1H), 6.58 (m, 2H), 6.54 (dd, 1H), 6.44 (d, 1H), 6.22 (d, 1H), 6.22 (s, 1H), 5.27 (s, 1H), 2.56 (s, 2H), 1.82 (s, 2H), 1.24 (s, 2H), 1.12 (s, 2H).

EXAMPLE 399

2,5-Dihydro-9-methylthiomethoxy-10-methoxy-2,2,4-trimethyl-5-(3-(methylthio)methoxyphenyl)-1H-[1]benzopyrano[3,4-f]quinoline MS (DCI/NH3) m/z 526 (M+H)+1H NMR (400 MHz, DMSO-d6) 7.94 (d, 1H), 7.14 (t, 1H), 6.82–6.70 (m, 6H), 6.50 (d, 1H), 6.24 (s, 1H), 5.29 (s, 1H), 5.16 (s, 2H), 5.14 (s, 2H), 2.61 (s, 2H), 2.14 (s, 2H), 2.08 (s, 2H), 1.82 (s, 2H), 1.24 (s, 2H), 1.16 (s, 2H).

EXAMPLE 400

2,5-Dihydro-9-hydroxy-10-methoxy-2,2,4-trimethyl-5-(3-(methylthiomethoxy)phenyl)-1H-[1]benzopyrano[3,4-f]quinoline MS (DCI/NH3) m/z 476 (M+H)+; 1H NMR (400 MHz, DMSO-d6) 8.58 (s, 1H), 7.92 (d, 1H), 7.12 (t, 1H), 6.82–6.6.71 (m, 4H), 6.62 (s, 1H), 6.42 (d, 1H), 6.26 (d, 1H), 6.25 (s, 1H), 5.28 (s, 1H), 5.12 (s, 2H), 2.55 (s, 2H), 2.07 (s, 2H), 1.84 (s, 2H), 1.22 (s, 2H), 1.15 (s, 2H).

EXAMPLE 401

9-Hydroxy-10-chloro-5-(phenylmethylene)-2,2,4-trlimethyl-1H-2,5-dihydro-[1]benzopyrano[3,4-f]quinoline 1H NMR δ 9.48 (s, 1H), 7.98 (m, 1H), 7.42 (m, 1H), 7.22 (m, 5H), 7.00 (m, 1H), 6.71 (m, 1H), 6.52 (m, 1H), 6.42 (m, 1H), 5.47 (m, 0.5H), 5.12 (m, 0.5H), 1.96 (s. 2H), 1.02 (s, 2H), 0.85 (s, 2H); mass spectrum (DCl) m/z: 416 (M+1); Calcd for C$_{26}$H$_{22}$ClNO$_2$: 415.1229. Found: 415.1229.

EXAMPLE 402

2,5-Dihydro-9-hydroxy-10-methoxy-2,2,4-trimethyl-5-([2-N,N-dimethylcarbamoyloxylphenyl)-1H-[1]benzopyrano[3,4-f]quinoline MS (DCI/NH3) 504 (M+NH4)+, 487 (M+H)+; 1H NMR (400 MHz, DMSO-d$_6$) 8.59 (s, 1H), 7.92 (d, 1H), 7.22 (t, 1H), 7.09 (d, 1H), 6.91 (dd, 1H), 6.81 (t, 1H), 6.72 (d, 1H), 6.66 (d, 1H), 6.44 (d, 1H), 6.24 (d, 1H), 6.27 (s, 1H), 5.28 (s, 1H), 2.55 (s, 2H), 2.949s, 2H), 2.82 (s, 2H), 1.81 (s, 1H), 1.24 (s, 2H), 1.21 (s, 2H).

EXAMPLE 403

2,5-Dihydro-9-N,N-dimethylcarbamoyloxy-10-methoxy-2,2,4-trimethyl-5-([2-N,N-dimethylcarbamoyloxy]phenyl)-1H-[1]benzopyrano[3,4-f]quinoline MS (DCI/NH$_3$) 575 (M+MH4)+; $_1$H NMR (400 MHz, DMSO-d$_6$) 7.90 (d, 1H), 7.25 (t, 1H), 7.11 (d, 1H), 6.95 (dd, 1H), 6.85 (s, 1H), 6.79 (s, 1H), 6.75 (d, 1H), 6.71 (d, 1H), 6.52 (d, 1H), 6.49 (s, 1H), 5.41 (s, 1H), 2.52 (s, 2H), 2.02 (s, 2H), 2.94 (s, 2H), 2.89 (s, 2H), 2.85 (s, 2H), 1.84 (s, 2H), 1.25 (s, 2H), 1.15 (s, 2H).

EXAMPLE 404

2,5-Dihydro-9-hydroxy-10-chloro-2,2,4-trimethyl-5-ethyl-1H-[1]benzopyrano[3,4-f]quinoline $^1$H NMR (300 MHz, DMSO-d$_6$) δ 9.59 (s, 1H), 7.91 (d, J=8 Hz, 1H), 6.75 (s, 2H), 6.62 (d, J=8 Hz, 1H), 6.29 (d, J=2 Hz, 1H), 5.46 (m, 2H), 2.14 (s, 3H), 1.57 (m, 2H), 1.19 (s, 3H), 1.15 (s, 3H), 0.89 (t, J=7 Hz, 3H); Hi Res MS (APCI) m/e calc'd for C$_{21}$H$_{22}$NO$_2$Cl: 355.1339, found 355.1353.

EXAMPLE 405

2,5-Dihydro-9-hydroxy-10-chloro-2,2,4-trimethyl-5-isopropyl-1H-[1]benzopyrano[3,4-f]quinoline $^1$H NMR (300 MHz, DMSO-d$_6$) δ 9.57 (s, 1H), 8.02 (d, J=8 Hz, 1H), 6.76 (s, 2H), 6.65 (d, J=9 Hz, 1H), 6.45 (s, 1H), 5.45 (s, 1H), 5.32 (d, J=9 Hz, 1H), 2.17 (s, 3H), 1.70 (m, 1H), 1.30 (s, 3H), 1.02 (s, 3H), 0.92 (d, J=6 Hz, 3H), 0.67 (d, J=6 Hz, 3H); HRMS (APCI) m/e calc'd for $C_{22}H_{24}NO_2Cl$: 369.1496, found 369.1492.

EXAMPLE 406

9-Hydroxy-10-methoxy-5-(phenylmethylene)-2,2,4-trimethyl-1H-2,5-dihydro-[1]benzopyrano[3,4-f]quinoline MS (DCI/NH3) 412 (M+H)+; 1H NMR (200 MHz, DMSO-d6), δ 8.92 (s, 1H), 8.12 (d, J=8.8 Hz, 1H), 7.62 (d, J=8.8 Hz, 2H), 7.22–7.15 (m, 2H), 6.77 (d, 1H), 6.69 (d, 1H), 6.66 (d, 1H), 6.52 (s, 1H), 5.46 (s, 1H), 5.29 (s, 1H), 2.65 (s, 2H), 1.90 (s, 2H), 1.20 (s, 6H); HRMS calcd for $C_{27}H_{25}NO_2$ is 411.1824. Found 411.1821.

EXAMPLE 407

2,5-Dihydro-9-hydroxy-10-chloro-2,2,4-trimethyl-5-butyl-1H-[1]benzopyrano[3,4-f]quinoline $^1$H NMR (300 MHz, DMSO-$d_6$) δ 9.55 (br s, 1H), 7.91 (d, J=9 Hz, 1H), 6.74 (s, 2H), 6.61 (d, J=8 Hz, 1H), 6.26 (d, J=1 Hz, 1H), 5.56 (dd, J=11, 2 Hz, 1H), 5.45 (br s, 1H), 2.15 (m, 3H), 1.64 (m, 1H), 1.46 (m, 1H), 1.31 (m, 4H), 1.19 (s, 3H), 1.15 (s, 3H), 0.78 (t, J=7 Hz, 3H); MS (DCI/NH$_3$) m/e (M+H)$^+$ 384.

EXAMPLE 408

2,5-Dihydro-9-hydroxy-10-methoxy-2,2,4-trimethyl-5-(1-thiazol-2-yl)-1H-[1]benzopyrano[3,4-f]quinoline $^1$H NMR (300 MHz, DMSO-$d_6$) δ 8.72 (s, 1H), 8.02 (d, J=8 Hz, 1H), 6.88 (s, 1H), 6.70 (d, J=8 Hz, 1H), 6.68 (d, J=8 Hz, 1H), 6.61 (d, J=9 Hz, 1H), 6.54 (s, 1H), 6.20 (s, 1), 5.49 (s, 1H), 3.72 (s, 3H), 2.57 (s, 3H), 2.30 (s, 3H), 1.33 (s, 3H), 1.14 (s, 3H), $^{13}$C NMR (75 MHz, DMSO-$d_6$) δ 182.9, 182.5, 181.3, 179.8, 169.8, 167.9, 165.5, 163.8, 154.6, 154.4, 153.6, 151.7, 151.3, 150.0, 127.0, 96.8, 87.2, 67.6, 65.7, 60.3; MS (DCI/NH3) (M+H)$^+$ 322.

EXAMPLE 409

2,5-Dihydro-9-hydroxy-10-chloro-2,2,4-trimethyl-5-(2-methylpropyl)-1H-[1]benzopyrano[3,4-f]quinoline $^1$H NMR (300 MHz, DMSO-$d_6$) δ 9.59 (br s, 1H), 7.91 (d, J=9 Hz, 1H), 6.75 (d, J=8 Hz, 1H), 6.73 (d, J=8 Hz, 1H), 6.62 (d, J=8 Hz, 1H), 6.28 (d, J=2 Hz, 1H), 5.70 (dd, J=12, 2 Hz, 1H), 5.45 (br s, 1H), 2.17 (s, 3H), 1.68 (m, 2H), 1.23 (m, 2H), 1.19 (s, 3H), 1.15 (s, 3H), 0.98 (d, J=6 Hz, 3H), 0.75 (d, J=7 Hz, 3H); MS (DCI/NH$_3$) m/e (M+H)$^+$ 384.

EXAMPLE 410

2,5-Dihydro-9-hydroxymethyl-10-chloro-2,2,4-trimethyl-5-allyl-1H-[1]benzopyrano[3,4-f]quinoline MS (DCI/NH$_3$) m/z 381 (M)$^+$; $^1$H NMR (500 MHz, DMSO) δ 7.91 (d, J=8.4 Hz, 1H), 7.30 (d, J=8.5 Hz, 1H), 6.90 (d, J=8.4 Hz, 1H), 6.64 (d, J=8.5 Hz, 1H), 6.32 (br s, 1H), 5.90–5.73 (m, 2H), 5.47 (br s, 1H), 5.28 (t, J=5.1 Hz, 1H), 5.04 (dd, J=10.2, 1.1 Hz, 1H), 4.97 (dd, J=10.2, 1.1 Hz, 1H), 4.64–4.50 (m, 2H), 2.46–2.25,(m, 2H), 2.17 (br s, 3H), 1.21 (s, 3H), 1.16 (s, 3H); HRMS (FAB) calcd m/z for $C_{23}H_{24}ClNO_2$: 381.1496 (M)$^+$. Found: 381.1495.

EXAMPLE 411

2,5-Dihydro-9-hydroxy-10-chloro-2,2,4-trimethyl-5-propyl-1H-[1]benzopyrano[3,4-f]quinoline $^1$H NMR (300 MHz, DMSO-$d_6$) δ 9.55 (s, 1H), 7.90 (d, J=9 Hz, 1H), 6.74 (s, 2H), 6.60 (d, J=9 Hz, 1H), 6.26 (s, 1H), 5.59 (d, J=9 Hz, 1H), 5.45 (s, 1H), 2.15 (s, 3H), 1.65 (m, 1H), 1.38 (m, 3H), 1.19 (s, 3H), 1.15 (s, 3H), 0.82 (t, J=7 Hz, 3H); $_{13}$C NMR (75 MHz, DMSO-$d_6$) δ 148.6, 146.1, 143.6, 134.8, 133.4, 127.4, 127.0, 123.9, 116.2, 115.9, 115.9, 115.2, 113.9, 112.5, 73.9, 49.8, 33.4, 29.4, 28.8, 23.8, 18.7, 13.4; Hi Res MS (APCI) m/e calc'd for $C_{22}H_{24}NO_2Cl$: 369.1496, found 369.1504.

EXAMPLE 412

9-Hydroxy-10-methoxy-5-([3-fluorophenyl]methylene)-2,2,4-trimethyl-1H-2,5-dihydro-[1]benzopyrano[3,4-f]quinoline 1H NMR (200 MHz, DMSO-d6) δ 9.04 (s, 1H), 8.22 (d, 1H), 7.62–7.27 (m, 2H), 7.10–7.02 (m, 1H), 6.86 (d, 1H), 6.78 (d, 1H), 6.72 (d, 1H), 6.70 (s, 1H), 5.56 (s, 1H), 5.46 (s, 1H), 2.72 (s, 2H), 1.96 (s, 2H), 1.27 (s, 2H). MS (DCI/NH3) m/z 420 (M+H)+; Anal. calcd for $C_{27}H_{24}NO_2F.0.25H2O$: C, 75.51; H, 5.62; N, 2.26. Found: C, 74.84; H, 6.17; N, 2.91.

EXAMPLE 413

9-Hydroxy-10-chloro-5-([2-pyridyl]methylene)-2,2,4-trimethyl-1H-2,5-dihydro-[1]benzopyrano[3,4-f]quinoline MS (DCI/NH3) m/z 417 (M+H)+; 1H NMR (200 MHz, DMSO) δ 9.79 (br s, 1H), 8.51 (ddd, J=5.9, 1.6, 1.0 Hz, 1H), 8.42 (d, J=8.6 Hz, 1H), 8.24 (dt, J=7.8, 1.0 Hz, 1H), 7.52 (td, J=7.8, 1.7 Hz, 1H), 7.22 (ddd, J=7.7, 5.8, 1.2 Hz, 1H), 7.00 (d, J=8.5 Hz, 1H), 6.88 (d, J=8.6 Hz, 1H), 6.81 (d, J=8.5 Hz, 1H), 6.62 (br s, 1H), 5.71 (s, 1H), 5.51 (br s, 1H), 2.00 (br s, 2H), 1.28 (br s, 6H); 13C NMR (125 MHz, DMSO-d6) δ 152.5, 149.7, 146.4, 145.7, 126.5, 126.1, 122.7, 128.7, 128.2, 122.0, 122.4, 121.5, 118.2, 117.7, 117.6, 116.5, 115.5, 114.8, 114.4, 114.1, 112.9, 49.5, 29.7, 28.1, 21.2; HRMS (FAB) calcd m/z for $C_{25}H_{21}ClN_2O_2$: 416.1291 (M)+. Found: 416.1288.

EXAMPLE 414 rel-(5S)-9-Hydroxy-5-[(3S)-(1-hydroxymethyl)cyclohexen-3-yl]-10-methoxy-2,2,4-trimethyl-2,5-dihydro-1H-[1]benzopyrano[3,4-f]quinoline 1H NMR (200 MHz, DMSO-d6), δ 8.49 (s, 1H), 7.99 (d, J=8.5 Hz, 1H), 6.64 (d, J=8.5 Hz, 1H), 6.58 (d, J=8.5 Hz, 1H), 6.47 (d, J=8.5 Hz, 1H), 6.21 (br s, 1H), 5.99 (br s, 1H), 5.40 (br s, 1H), 5.26–5.21 (m, 1H), 4.81–4.72 (m, 2H), 4.02–4.02 (m, 1H), 2.61–2.58 (m, 1H), 2.52 (s, 2H), 2.00–2.95 (m, 1h), 2.21 (s, 2H), 1.61–1.40 (m, 4H), 1.22 (s, 2H), 1.28–1.24 (m, 2H), 1.04 (s, 2H); Anal. calcd for $C_{27}H_{21}NO_4$: C, 74.80; H, 7.21; N, 2.22. Found: C, 74.77; H, 7.15; N, 2.12.

EXAMPLE 415 rel-(5S)-9-Hydroxy-5-[(3S)-(1-methoxycarbonyl)cyclohexen-3-yl[-10-methoxy-2,2,4-trimethyl-2,5-dihydro-1H-[1]benzopyrano[3,4-f]quinoline MS (DCI/NH3) 462 (M+H)+; 1H NMR (200 MHz, DMSO-$d_6$), δ 8.72 (s, 1H), 8.04 (d, J=8.5 Hz, 1H), 6.90–6.87

(m, 1H), 6.67 (d, J=8.5 Hz, 1H), 6.64 (d, J=8.5 Hz, 1H), 6.52 (d, J=8.5 Hz, 1H), 6.25–6.29 (m, 1H), 5.50–5.44 (m, 2H), 4.06–4.00 (m, 1H), 2.66 (s, 2H), 2.62 (s, 2H), 2.20–2.27 (m, 1H), 2.18–2.05 (m, 1H), 2.12 (s, 2H), 1.72–1.60 (m, 2H), 1.25–1.24 (m, 2H), 1.20 (s, 2H), 1.04 (s, 2H); HRMS calcd for $C_{28}H_{21}NO_5$ is 461.2202. Found 461.2196. Anal. calcd for $C_{28}H_{21}NO_5 \cdot 0.25H2O$: C, 72.15; H, 6.81; N, 2.00. Found: C, 72.06; H, 7.06; N, 2.82.

EXAMPLE 416

2,5-Dihydro-9-hydroxy-10-methoxy-2,2,4-trimethyl-5-(3,5-dichlorophenyl)-1H-[1]benzopyrano[3,4-f]quinoline MS DCI m/z 468 (M+H)+; 1H NMR (200 MHz, DMSO), δ 8.69 (s, 1H), 7.96 (d, J=8.8 Hz, 1H), 7.44 (t, J=1.8 Hz, 1H), 7.17 (d, J=1.8 Hz, 2H), 6.76 (d, J=8.4 Hz, 1H), 6.70 (s, 1H), 6.48 (d, J=8.8 Hz, 1H), 6.28 (d, J=8.8 Hz, 1H), 6.25 (d, J=1.5 Hz, 1H), 5.41 (s, 1H), 2.57 (s, 2H), 1.82 (s, 2H), 1.25 (s, 2H), 1.14 (s, 2H); 13C NMR (200 MHz, DMSO), δ 145.9, 145.2, 142.6, 142.1, 122.7, 122.0, 128.8, 127.6, 127.2, 127.1, 126.6, 118.2, 117.9, 117.2, 114.5, 112.2, 72.7, 59.0, 49.8, 29.6, 28.2, 22.2. HRMS calcd for $C_{26}H_{23}ClFNO_3$ is 467.1066. Found 467.1064.

EXAMPLE 417

(–)(5S,3'S)2,5-Dihydro-9-hydroxy-10-chloro-2,2,4-trimethyl-5-(1-methylcyclohexen-3-yl)-1H-[1]benzopyrano[3,4-f]quinoline MS (DCI/NH$_3$) m/z 422 (M+H)+; 1H NMR (300 MHz, DMSO) δ 9.55 (s, 1H), 8.02 (d, J=8.4 Hz, 1H), 6.77 (app s, 2H), 6.68 (d, J=8.4 Hz, 1H), 6.41 (br s, 1H), 5.50–5.42 (m, 2H), 4.88 (br s, 1H), 2.23–2.15 (m, 1H), 2.07 (br s, 3H), 1.91–1.80 (m, 2H), 1.76–1.63 (m, 2H), 1.60–1.46 (m, 1H), 1.50 (br s, 3H), 1.38–1.28 (m, 1H), 1.30 (s, 3H), 1.09 (s, 3H); 13C NMR (125 MHz, DMSO) δ 148.6, 145.7, 143.7, 135.8, 133.7, 132.6, 128.2, 126.8, 123.7, 120.2, 117.7, 115.9 (2), 115.3, 114.1, 112.4, 75.6, 49.5, 36.3, 29.6, 29.3, 27.5, 25.1, 24.2, 23.7, 20.2; HRMS (FAB) calcd m/z for $C_{26}H_{28}ClNO_2$: 421.1809 (M)+. Found: 421.1810.

EXAMPLE 418

(–)(5S,3'R)2,5-Dihydro-9-hydroxy-10-chloro-2,2,4-trimethyl-5-(1-methylcyclohexen-3-[1]benzopyrano[3,4-f]quinoline MS (DCI/NH$_3$) m/z 422 (M+H)+; 1H NMR (300 MHz, DMSO) δ 9.58 (s, 1H), 8.05 (d, J=8.4 Hz, 1H), 6.79 (ABq, J=8.0 Hz, ?n$_{AB}$=14.4 Hz, 2H), 6.67 (d, J=8.3 Hz, 1H), 6.47 (br s, 1H), 5.49–5.46 (m, 2H), 5.35 (d, J=8.9 Hz, 1H), 2.28–2.15 (m, 1H), 2.12 (br s, 3H), 1.93–1.80 (m, 1H), 1.78–1.63 (m, 2H), 1.64–1.51 (m, 1H), 1.62 (br s, 3H), 1.31 (s, 3H), 1.25–1.13 (m, 2H), 1.04 (s, 3H); 13C NMR (125 MHz, DMSO) δ 148.7, 145.8, 144.2, 135.1, 134.0, 132.1, 127.9, 126.7, 123.7, 121.4, 118.0, 116.0 (2), 115.4, 114.2, 112.4, 103.4, 76.4, 49.5, 37.1, 29.5, 27.2, 24.5, 23.8 (2), 21.6; HRMS (FAB) calcd m/z for $C_{26}H_{28}ClNO_2$: 421.1809 (M)+. Found: 421.1816.

EXAMPLE 419

(+)(5R,3'S)2,5-Dihydro-9-hydroxy-10-chloro-2,2,4-trimethyl-5-(1-methylcyclohexen-3-yl)-1H-[1]benzopyrano[3,4-f]quinoline $[\alpha]_D^{25}$ + 237.8° (c=0.5, CHCl$_3$); MS (DCI/NH$_3$) m/z 422 (M+H)+; 1H NMR (300 MHz, DMSO) δ 9.58 (s, 1H), 8.05 (d, J=8.4 Hz, 1H), 6.79 (ABq, J=8.0 Hz, ?n$_{AB}$=14.4 Hz, 2H), 6.67 (d, J=8.3 Hz, 1H), 6.47 (br s, 1H), 5.49–5.46 (m, 2H), 5.35 (d, J=8.9 Hz, 1H), 2.28–2.15 (m, 1H), 2.12 (br s, 3H), 1.93–1.80 (m, 1H), 1.78–1.63 (m, 2H), 1.64–1.51 (m, 1H), 1.62 (br s, 3H), 1.31 (s, 3H), 1.25–1.13 (m, 2H), 1.04 (s, 3H); 13C NMR (125 MHz, DMSO) δ 148.7, 145.8, 144.2, 135.1, 134.0, 132.1, 127.9, 126.7, 123.7, 121.4, 118.0, 116.0 (2), 115.4, 114.2, 112.4, 103.4, 76.4, 49.5, 37.1, 29.5, 27.2, 24.5, 23.8 (2), 21.6; HRMS (FAB) calcd m/z for $C_{26}H_{28}ClNO_2$: 421.1809 (M)+. Found: 421.1806.

EXAMPLE 420

(+)(5R,3'R)2,5-Dihydro-9-hydroxy-10-chloro-2,2,4-trimethyl-5-(1-methylcyclohexen-3-)yl)-1H-[1]benzopyrano[3,4-f]quinoline $[\alpha]_D^{25}$ +147.5° (c=0.2, CHCl$_3$); MS (DCI/NH$_3$) m/z 422 (M+H)+; 1H NMR (300 MHz, DMSO) δ 9.55 (s, 1H), 8.02 (d, J=8.4 Hz, 1H), 6.77 (app s, 2H), 6.68 (d, J=8.4 Hz, 1H), 6.41 (br s, 1H), 5.50–5.42 (m, 2H), 4.88 (br s, 1H), 22.23–2.15 (m, 1H), 2.07 (br s, 3H), 1.91–1.80 (m, 2H), 1.76–1.63 (m, 2H), 1.60–1.46 (m, 1H), 1.50 (br s, 3H), 1.38–1.28 (m, 1H), 1.30 (s, 3H), 1.09 (s, 3H); 13C NMR (125 MHz, DMSO) δ 148.6, 145.7, 143.7, 135.8, 133.7, 132.6, 128.2, 126.8, 123.7, 120.2, 117.7, 115.9 (2), 115.3, 114.1, 112.4, 75.6, 49.5, 36.3, 29.6, 29.3, 27.5, 25.1, 24.2, 23.7, 20.2; HRMS (FAB) calcd m/z for $C_{26}H_{28}ClNO_2$: 421.1809 (M)+. Found: 421.1794.

EXAMPLE 421

(+/–)2,5-Dihydro-9-(4-N,N-dimethylamino-4-oxo-butanoyloxy)-10-chloro-2,2,4-trimethyl-5-allyl-1H-[1]benzopyrano[3,4-f]quinoline MS (ESI) m/z 495 (M+H)+; 1H NMR (200 MHz, DMSO-d6) δ 7.90 (d, 1H), 6.99 (d, 1H), 6.92 (d, 1H), 6.64 (d, 1H), 6.42 (s, 1H), 5.81–5.76 (m, 2H), 5.48 (s, 1H), 5.07–4.94 (m, 2H), 2.99 (s, 2H), 2.84 (s, 2H), 2.82–2.68 (m, 4H), 2.41–2.27 (m, 2H), 2.18 (s, 2H), 1.20 (s, 2H), 1.17 (s, 2H).

EXAMPLE 422

(–)2,5-Dihydro-9-hydroxy-10-chloro-2,2,4-trimethyl-5-cyclopentyl-1H-[1]benzopyrano[3,4-f]quinoline MS (DCI/NH3) m/z 296 (M+H)+; 1H NMR (400 MHz, DMSO-d$_6$) 1H NMR (200 MHz, DMSO-d6) δ 9.50 (bs, 1H), 8.04 (s, 1H), 6.77 (d, 1H), 6.72 (d, 1H), 6.65 (d, 1H), 6.42 (d, 1H), 5.50 (s, 1H), 5.42 (d, 1H) 2.18–1.08 (m, 18H).

EXAMPLE 423

2,5-Dihydro-9-(4-N,N-dimethylamino-4-oxo-butanoyloxy)-10-methoxy-2,2,4-trimethyl-5-(1-methylethyl)-1H-[1]benzopyrano[3,4-f]quinoline 1H NMR (400 MHz, DMSO-d6) δ 7.92 (d, J=8.5, 1H), 6.83 (d, J=8.5, 1H), 6.71–6.65 (m, 2H), 6.31 (d, J=1.7, 1H), 5.46 (br m, 1H), 5.37 (d, J=9.7, 1H), 3.61 (s, 3H), 3.00 (s, 3H), 2.84 (s, 3H), 2.80 (m, 2H), 2.70 (m, 2H), 2.17 (s, 3H), 1.80 (m, 1H), 1.31 (s, 3H), 1.03 (s, 3H), 0.95 (d, J=6.4, 3H), 0.65 (d, J=6.8, 3H); 13C NMR (125 MHz, DMSO-d6) δ 171.5, 170.4, 149.0, 148.0, 145.6, 138.3, 133.6, 131.0, 127.9, 125.8, 120.7, 118.2, 118.2, 115.4, 113.4, 112.1, 78.0, 60.0, 49.4, 36.4, 34.9, 30.9, 29.6, 28.9, 27.6, 27.3, 23.8, 19.4, 17.8; MS (ESI/NH3) m/e 493 (M+H)+, 515 (M+Na)+; HRMS calcd m/z for $C_{29}H_{26}N_2O_5$: 492.2624. Found: 492.2613.

EXAMPLE 424

2,5-Dihydro-9-(4-N,N-dimethylamino-4-oxo-butanoyloxy)-10-methoxy-5-(phenylmethyl)-2,2,4-trimethyl-1H-[1]benzopyrano[3,4-f]quinoline $_1$H NMR (500 MHz, DMSO-d6) δ 7.90 (d, J=8.8, 1H), 7.29–7.26 (m, 2H), 7.21 (m, 1H), 7.09 (d, J=7.0, 2H), 6.89 (d, J=8.8, 1H), 6.66 (d, J=8.8, 1H), 6.60 (d, J=8.8, 1H), 6.25 (d, J=1.8, 1H), 5.98 (dd, J=10.1, 2.5, 1H), 5.42 (s, 1H), 2.67 (s, 2H), 2.01 (s, 2H), 2.97 (m, 1H), 2.85 (s, 2H), 2.84–2.81 (m, 2H), 2.72–2.69 (m, 2H), 2.22 (s, 2H), 1.17 (s, 2H), 1.14 (s, 2H); 13C NMR (125 MHz, DMSO-d$_6$) δ 171.5, 170.4, 148.2, 148.1, 146.2, 128.4, 127.6, 122.4, 121.9, 128.9, 128.2, 127.2, 126.2, 126.2, 120.8, 118.2, 116.2, 115.2, 112.9, 112.6, 74.8, 60.1, 49.7, 28.2, 24.9, 29.2, 29.1, 28.9, 27.6, 24.2; MS (ESI/NH3) m/e 541 (M+H)+, 562 (M+Na)+; Anal. Calcd for $C_{33}H_{36}N_2O_5$: C, 72.21, H, 6.71, N, 5.18. Found: C, 72.87, H, 6.97, N, 4.90.

EXAMPLE 425

2,5-Dihydro-9-(4-N,N-dimethylamino-4-oxo-butanoyloxy)-10-methoxy-2,2,4-trimethyl-5-(2-thienyl)-1H-[1]benzopyrano[3,4-f]quinoline $^1$H NMR (500 MHz, DMSO-d6) δ 7.90 (d, J=8.4, 1H), 7.40 (dd, J=5.0, 1.3, 1H), 6.96 (s, 1H), 6.86 (m, 1H), 6.80 (m, 1H), 6.74–6.71 (m, 2H), 6.57 (d, J=8.4, 1H), 6.32 (d, J=1.8, 1H), 5.41 (s, 1H), 3.58 (s, 3H), 2.98 (s, 3H), 2.83 (s, 3H), 2.77–2.74 (m, 2H), 2.68–2.65 (m, 2H), 1.95 (d, J=1.1, 3H), 1.23 (s, 3H), 1.15 (s, 3H); 13C NMR (125 MHz, DMSO-d6) δ 171.1, 170.2, 148.6, 147.5, 146.0, 142.8, 138.4, 132.8, 130.1, 128.0, 127.2, 126.3, 126.1, 125.9, 125.8, 120.4, 118.4, 116.8, 115.8, 114.3, 112.3, 70.9, 59.5, 49.7, 36.2, 34.7, 29.5, 28.7, 28.5, 27.4, 22.8; MS (ESI/NH$_3$) m/e 533 (M+H)+, 555 (M+Na)+; Anal. Calcd for $C_{20}H_{22}N_2O_5S$: C, 67.65, H, 6.06, N, 5.26. Found: C, 67.48, H, 6.16, N, 5.07.

EXAMPLE 426

2,5-Dihydro-9-(4-N,N-dimethylaminobutanoyloxy)-10-methoxy-2,2,4-trimethyl-5-(2-propenyl)-1H-[1]benzopyrano[3,4-f]quinoline $_1$H NMR (500 MHz, DMSO-d$_6$) δ 7.85 (d, J=8.4, 1H), 6.86 (d, J=8.4, 1H), 6.68–6.61 (m, 2H), 6.25 (d, J=1.5, 1H), 5.86–5.78 (m, 2H), 5.46 (s, 1H), 5.06–4.98 (m, 2H), 2.61 (s, 2H), 2.62 (t, J=7.1, 2H), 2.47 (m, 11H), 2.22 (t, J=7.0, 2H), 2.25 (m, 1H), 2.18 (s, 2H), 2.16 (s, 6H), 1.80 (m, 2H), 1.18 (s, 2H), 1.17 (s, 2H); 13C NMR (125 MHz, DMSO-d6) δ 171.8, 148.4, 147.9, 146.2, 128.5, 124.0, 122.5, 122.1, 127.2, 126.2, 120.7, 118.2, 117.2, 116.2, 115.0, 112.8, 112.6, 72.6, 59.9, 58.0, 45.1, 26.6, 21.1, 29.2, 29.0, 22.8, 22.5; MS (ESI/NH3) m/e 477 (M+H)+; Anal. Calcd for $C_{29}H_{36}N_2O4$: C, 72.08, H, 7.61, N, 5.88. Found: C, 72.77, H, 7.74, N, 5.64.

EXAMPLE 427

9-(2-Ethoxy-2-oxo-ethylaminocarbonyl)-oxy-10-methoxy-5-(3-propenyl)-2,2,4-trimethyl-1H-2,5-dihydro-[1]benzopyrano[3,4-f]quinoline MS (DCI/NH$_3$) 510 (M+NH$_4$)+, 492 (M+H)+, 264; 1H NMR (200 MHz, DMSO-d$_6$), δ 8.21 (t, J=6.0 Hz, 1H), 7.86 (d J=8.5 Hz, 1H), 6.86 (d, J=8.5 Hz, 1H), 6.64 (d, J=8.5 Hz, 1H), 6.62 (d, J=8.5 Hz, 1H), 6.29 (d, J=1.1 Hz, 1H), 5.90–5.76 (m, 2H), 5.45 (br s, 1H), 5.04 (dd, J=10.2, 1.8 Hz, 1H), 4.99 (dd, J=17.2, 1.8 Hz, 1H), 4.12 (q, J=7.0 Hz, 2H), 2.85 (d, J=6.0 Hz, 2 Hz), 2.65 (s, 2H), 2.20–2.22 (m, 2H), 2.17 (d, J=1.1 Hz, 2H), 1.21 (t, J=7.0 Hz, 2H), 1.18 (s, 2H), 1.17 (s, 2H); Anal. calcd for $C_{28}H_{22}N_2O_6$: C, 68.28; H, 6.55; N, 5.69. Found: C, 67.97; H, 6.59; N, 5.62.

EXAMPLE 428

(+/−)2,5-Dihydro-9-(3-acetamido-propanoyloxy)-10-methoxy-2,2,4-trimethyl-5-allyl-1H-[1]benzopyrano[3,4-f]quinoline MS (APCI) m/z 477 (M+H)+; 1H NMR (200 MHz, DMSO-d6) δ 8.04 (t, 1H), 7.85 (d, 1H), 6.90 (d, 1H), 6.68 (d, 1H), 6.64 (d, 1H), 6.26 (s, 1H), 5.87–5.77 (m, 2H), 5.46 (s, 1H), 5.04 (dd, 1H), 4.98 (dd, 1H), 2.61 (s, 2H), 2.40 (q, 2H), 2.76 (t, 2H), 2.52–2.44 (m, 1H), 2.20–2.24 (m, 1H), 2.18 (s, 2H), 1.84 (s, 2H), 1.18 (s, 2H), 1.17 (s, 2H).

EXAMPLE 429

(+/−)2,5-Dihydro-9-hydroxy-10-chloro-2,2,4-trimethyl-5-benzyl-1H-[1]benzopyrano[3,4-f]quinoline MS (DCI/NH3) m/z 418 (M+H)+; 1H NMR (400 MHz, DMSO-d6) 1H NMR (200 MHz, DMSO-d$_6$) δ 9.70 (bs, 1H), 7.99 (s, 1H), 7.20–7.08 (m, 5H), 6.79 (d, 1H), 6.67 (d, 1H), 6.62 (d, 1H), 6.19 (d, 1H), 5.86 (dd, 1H), 5.44 (s, 1H) 2.98–2.84 (m, 2H), 2.22 (s, 2H), 1.19 (s, 2H), 1.17 (s, 2H).

EXAMPLE 430

9-Hydroxy-10-methoxy-5-(phenylmethylene)-2,2,4-trimethyl-1H-2,5-dihydro-[1]benzopyrano[3,4-f]quinoline (DCI/NH$_3$) 412 (M+H)$^+$; $^1$H NMR (300 MHz, DMSO-d$_6$), δ 8.93 (s, 1H), 8.13 (d, J=8.8 Hz, 1H), 7.63 (d, J=8.8 Hz, 2H), 7.32–7.15 (m, 3H), 6.77 (d, 1H), 6.69 (d, 1H), 6.66 (d, 1H), 6.52 (s, 1H), 5.46 (s, 1H), 5.39 (s, 1H), 3.65 (s, 3H), 1.90 (s, 3H), 1.20 (s, 6H); HRMS calcd for $C_{27}H_{25}NO_3$ is 411.1834, found 411.1821.

EXAMPLE 431

9-(Dimethylaminothiocarbonyl)-oxy-10-methoxy-5-(3-propenyl)-2,2,4-trimethyl-1H-2,5-dihydro-[1]benzopyrano[3,4-f]quinoline MS (DCI/NH3) 451 (M+H)+; 1H NMR (200 MHz, DMSO-d6), δ 7.84 (d J=8.8 Hz, 1H), 6.80 (d, J=8.8 Hz, 1H), 6.65 (d, J=8.8 Hz, 1H), 6.62 (d, J=8.8 Hz, 1H), 6.26 (d, J=1.7 Hz, 1H), 5.90–5.76 (m, 2H), 5.46 (br s, 1H), 5.04 (dd, J=10.2, 1.8 Hz, 1H), 4.98 (dd, J=17.2, 1.8 Hz, 1H), 2.64 (s, 2H), 2.29 (s, 2H), 2.26 (s, 2H), 2.22–2.22 (m, 2H), 2.18 (d, J=1.7 Hz, 2H), 1.18 (s, 2H), 1.16 (s, 2H); Anal. calcd for $C_{26}H_{20}N_2O_2S.0.5H_2O$: C, 67.94; H, 6.79; N, 6.09. Found: C, 68.06; H, 6.80; N, 6.12.

EXAMPLE 432

(+/−)2,5-Dihydro-9-(N-carbamoyl-2-aminoacetoxy)-10-methoxy-2,2,4-trimethyl-5-allyl-1H-[1]benzopyrano[3,4-f]quinoline MS (APCI) m/z 464 (M+H)+; $_1$H NMR (200 MHz, DMSO-d$_6$) δ 7.78 (d, 1H), 6.79 (d, 1H), 6.60 (d, 1H), 6.57 (d, 1H), 6.27 (t, 1H), 6.18 (bs, 1H), 5.80–5.70 (m, 2H), 5.67 (s, 2H), 5.28 (s, 1H), 4.97 (dd, 1H), 4.92 (dd, 1H), 4.01 (d, 2H), 2.55 (s, 2H), 2.42–2.27 (m, 1H), 2.22–2.16 (m, 1H), 2.10 (s, 2H), 1.11 (s, 2H), 1.10 (s, 2H).

EXAMPLE 433

(+/−)2,5-Dihydro-9-(4-ethoxy-4-oxo-butoxy)-10-methoxy-2,2,4-trimethyl-5-allyl-1H-[1]benzopyrano[3,4-f]quinoline 1H NMR (200 MHz, DMSO-d6) δ 7.92 (d, 1H, J=8 Hz), 6.79 (d, 1H), 6.62 (d, 1H, J=8 Hz), 6.58 (d, 1H, J=8 Hz), 6.18 (d, 1H, J=2 Hz), 5.82 (m, 1H), 5.72 (dd, 1H, J=2 Hz, J=2 Hz, J=9 Hz) 5.45 (s, 1H), 5.05–4.97 (m, 2H), 4.08 (q, 2H, J=5 Hz), 4.02–2.91 (m, 2H), 2.70 (s, 2H), 2.50 (t, 2H, J=5 Hz), 2.45 (m, 1H), 2.21 (m, 1H), 2.16 (s, 2H), 2.00 (quin, 2H, J=5 Hz), 1.19 (t, 2H, J=5 Hz), 1.17 (s, 6H).

EXAMPLE 434

(+/−)2,5-Dihydro-9-(4-oxo-pentanoyloxy)-10-methoxy-2,2,4-trimethyl-5-allyl-1H-[1]benzopyrano[3,4-f]quinoline MS (APCI) m/z 462 (M+H)+; $_1$H NMR (200 MHz, DMSO-d6) δ 7.78 (d, 1H), 6.77 (d, 1H), 6.59 (d, 1H), 6.57 (d, 1H), 6.18 (s, 1H), 5.80–5.68 (m, 2H), 5.28 (s, 1H), 4.96 (dd, 1H), 4.92 (dd, 1H), 2.54 (s, 2H), 2.79 (dd, 2H), 2.70 (dd, 2H), 2.41–2.16 (m, 2H), 2.10 (s, 2H), 2.09 (s, 2H), 1.11 (s, 2H), 1.10 (s, 2H).

EXAMPLE 435

2,5-Dihydro-9-hydroxy-10-chloro-2,2,4-trimethyl-5-(3,4,5-trifluorophenyl)-1H-[1]benzopyrano[3,4-f]quinoline $_1$H NMR δ 9.20 (s, 1H), 7.91 (d, 1H, J=8.5 Hz), 6.92 (m, 2H), 6.88 (m, 2H), 6.57 (d, 1H, J=8.5 Hz), 6.28 (m, 1H), 5.45 (m, 1H), 1.81 (s, 2H), 1.29 (s, 2H), 1.09 (s, 2H); mass spectrum (DCl) m/z: 458 (M+1); Calcd for $C_{25}H_{19}ClF_2NO_2$: 457.1056. Found: 457.1054.

EXAMPLE 436

2,5-Dihydro-9-methylthiomethoxy-10-methoxy-2,2,4-trimethyl-5-allyl-1H-[1]benzopyrano[3,4-f]quinoline MS (DCI/NH3) m/z 424 (M+H)+; 1H NMR (400 MHz, DMSO-d6) 7.92 (d, 1H), 6.88 (d, 1H), 6.62 (d, 1H), 6.60 (d, 1H), 6.20 (s, 1H), 5.81 (m, 1H), 5.74 (dd, 1H), 5.45 (s, 1H), 5.24 (s, 1H), 5.02 (d, 1H), 4.99 (d, 1H), 2.70 (s, 2H), 2.45 (m, 2H), 2.22 (s, 2H), 2.18 (s, 2H), 1.18 (s, 2H), 1.17 (s, 2H).

EXAMPLE 437

2,5-Dihydro-9-(4-N,N-diethylamino-4-oxo-pentanoyloxy)-10-methoxy-2,2,4-trimethyl-5-(2-propenyl)-1H-[1]benzopyrano[3,4-f]quinoline $^1$H NMR (400 MHz, DMSO-d6) δ 7.84 (d, J=8.5, 1H), 6.88 (d, J=8.9, 1H), 6.68–6.62 (m, 2H), 6.26 (br s, 1H), 5.85–5.77 (m, 2H), 5.45 (br s, 1H), 5.05–4.97 (m, 2H), 3.60 (s, 3H), 3.34–3.21 (m, 4H), 2.65 (t, J=7.4, 2H), 2.45–2.41 (m, 3H), 2.27 (m, 1H), 2.17 (s, 3H), 1.90 (m, 2H), 1.18 (s, 3H), 1.17 (s, 3H), 1.12 (t, J=7.0, 3H), 1.02 (t, J=7.2, 3H); 13C NMR (100 MHz, DMSO-d6) δ 171.7, 170.3, 148.4, 147.9, 146.3, 138.4, 134.0, 133.5, 132.1, 127.3, 126.1, 120.7, 118.2, 117.2, 116.2, 114.9, 113.8, 112.6, 73.6, 59.9, 49.8, 41.2, 10 36.6, 32.7, 30.9, 29.3, 29.0, 23.8, 20.4, 14.2, 13.1; MS (ESI/NH2) m/e 533 (M+H)+, 555 (M+Na)+; Anal. Calcd for $C_{22}H_{40}N_2O_5$: C, 72.15, H, 7.57, N, 5.26. Found: C, 72.16, H, 7.76, N, 5.06.

EXAMPLE 438

2,5-Dihydro-9-(4-N,N-dimethylamino-4-oxo-pentanoyloxy)-10-methoxy-2,2,4-trimethyl-5-(2-propenyl)-1H-[1]benzopyrano[3,4-f]quinoline 1H NMR (400 MHz, DMSO-d6) δ 7.77 (d, J=8.5, 1H), 6.81 (d, J=8.9, 1H), 6.61–6.56 (m, 2H), 6.19 (d, J=1.7, 1H), 5.80–5.70 (m, 2H), 5.28 (s, 1H), 4.98–4.90 (m, 2H), 2.71 (s, 2H), 2.90 (s, 2H), 2.76 (s, 2H), 2.58 (t, J=7.4, 2H), 2.28–2.25 (m, 2H), 2.20 (m, 1H), 2.10 (s, 2H), 1.84 (m, 2H), 1.11 (s, 2H), 1.10 (s, 2H); 13C NMR (100 MHz, DMSO-d6) δ 171.7, 171.2, 148.4, 147.9, 146.2, 128.4, 124.1, 122.5, 122.1, 127.2, 126.2, 120.7, 118.2, 117.2, 116.2, 114.9, 112.8, 112.6, 72.6, 59.9, 49.8, 26.6, 24.8, 22.8, 21.2, 29.2, 29.0, 22.8, 20.2; MS (ESI/NH3) m/e 505 (M+H)+, 527 (M+Na)+; Anal. Calcd for $C_{30}H_{36}N_2O_5$: C, 71.40, H, 7.19, N, 5.55. Found: C, 71.20, H, 7.19, N, 5.29.

EXAMPLE 439

2,5-Dihydro-9-(4-N-piperidino-4-oxo-pentanoyloxy)-10-methoxy-2,2,4-trimethyl-5-(2-propenyl)-1H-[1]benzopyrano[3,4-f]quinoline $_1$H NMR (400 MHz, DMSO-d6) δ 7.78 (d, J=8.9, 1H), 6.81 (d, J=8.5, 1H), 6.61–6.55 (m, 2H), 6.19 (d, J=1.7, 1H), 5.80–5.70 (m, 2H), 5.28 (s, 1H), 4.98–4.90 (m, 2H), 2.52 (s, 2H), 2.25 (m, 4H), 2.58 (t, J=7.2, 2H), 2.29–2.25 (m, 2H), 2.20 (m, 1H), 2.10 (s, 2H), 1.82 (m, 2H), 1.51 (m, 2H), 1.42 (m, 2H), 1.26 (m, 2H), 1.11 (s, 2H), 1.10 (s, 2H); 13C NMR (100 MHz, DMSO-d6) δ 171.7, 169.6, 148.4, 147.9, 146.2, 128.4, 124.0, 122.5, 122.1, 127.2, 126.1, 120.7, 118.2, 117.2, 116.2, 114.9, 112.8, 112.6, 72.6, 59.9, 49.8, 45.8, 35 41.9, 26.6, 22.8, 21.2, 29.2, 29.0, 26.0, 25.2, 24.0, 22.8, 20.4; MS (ESI/NH3) m/e 545 (M+H)+, 567 (M+Na)+; Anal. Calcd for $C_{33}H_{40}N_2O_5$: C, 72.77, H, 7.40, N, 5.14. Found: C 72.50, H 7.42, N 4.99.

EXAMPLE 440

2,5-Dihydro-9-(4-N-morpholino-4-oxo-pentanoyloxy)-10-methoxy-2,2,4-trimethyl-5-(2-propenyl)-1H-[1]benzopyrano[3,4-f]quinoline 1H NMR (400 MHz, DMSO-d6) δ 7.77 (d, J=8.5, 1H), 6.81 (d, J=8.5, 1H), 6.61–6.56 (m, 2H), 6.19 (s, 1H), 5.78–5.70 (m, 2H), 5.28 (s, 1H), 4.98–4.90 (m, 2H), 2.52 (s, 2H), 2.50 (m, 4H), 2.29 (t, J=4.7, 4H), 2.59 (t, J=7.4, 2H), 2.41–2.27 (m, 2H), 2.20 (m, 1H), 2.10 (s, 2H), 1.82 (m, 2H), 1.11 (s, 2H), 1.10 (s, 2H); 13C NMR (100 MHz, DMSO-d6) δ 171.6, 170.2, 148.4, 147.9, 146.2, 128.4, 124.0, 122.5, 122.1, 127.2, 126.1, 120.7, 118.2, 117.2, 116.2, 114.9, 112.8, 112.6, 72.6, 66.1, 60.0, 49.8, 45.2, 41.4, 26.6, 22.7, 21.0, 29.2, 29.0, 22.8, 20.2; MS (ESI/NH3) m/e 547 (M+H)+, 569 (M+Na)$^+$; Anal. Calcd for $C_{32}H_{38}N_2O_6$: C, 70.21, H, 7.01, N, 5.12. Found: C, 69.99, H, 7.06, N, 4.91.

EXAMPLE 441

(−)2,5-Dihydro-9-(4-N,N-dimethylamino-4-oxo-butanoyloxy)-10-methoxy-2,2,4-trimethyl-5(S)-(3(S)-1-cyclopenten-3-yl)-1H-[1]benzopyrano[3,4-f]quinoline MS (APCI) m/z 517 (M+H)+; 1H NMR (200 MHz, DMSO-d6) δ 7.94 (d, 1H), 6.84 (d, 1H), 6.69 (d, 1H), 6.67 (d, 1H), 6.22 (s, 1H), 5.75 (dd, 1H), 5.52 (d, 1H), 5.42 (s, 1H), 5.17 (dd, 1H), 2.62 (s, 2H), 2.99 (s, 2H), 2.90–2.85 (m, 1H), 2.84 (s, 2H), 2.80 (t, 2H), 2.68 (t, 2H), 2.29–2.21 (m, 1H), 2.25–2.12 (m, 1H), 2.08 (s, 2H), 1.92–1.74 (m, 2H), 1.20 (s, 2H), 1.08 (s, 2H).

EXAMPLE 442

10-Methoxy-9-(allylaminocarbonyl)oxy-5-(3-propenyl)-2,2,4-trimethyl-1H-2,5-dihydro-[1]benzopyrano[3,4-f]quinoline MS (DCI/NH3) 464 (M+NH4)+, 447 (M+H)+, 264. 1H NMR (200 MHz, DMSO-d6), δ 7.96 (t, J=5.9 Hz, 1H), 7.86 (d, J=8.5 Hz, 1H), 6.86 (d, J=8.5 Hz, 1H), 6.62 (d, J=8.5 Hz, 2H), 6.28 (d, J=1.5 Hz, 1H), 5.90–5.76 (m, 2H), 5.45 (br s, 1H), 5.27–4.97 (m, 4H), 2.71 (m, 1H), 2.64 (s, 2H), 2.41–2.22 (m, 2H), 2.17 (d, J=1.5 Hz, 2H), 1.18 (s, 2H), 1.17 (s, 2H); Anal. calcd for $C_{27}H_{20}N_2O_4 \cdot 0.25H_2O$: C, 71.89; H, 6.81; N, 6.21. Found: C, 72.18; H, 7.08; N, 5.98.

EXAMPLE 443

10-Methoxy-9-(cyclohexylaminocarbonyl)-oxy-5-(3-propenyl)-2,2,4-trimethyl-1H-2,5-dihydro-[1]benzopyrano[3,4-f]quinoline MS (DCI/NH3) 506 (M+NH4)+, 489 (M+H)+, 264. 1H NMR (200 MHz, DMSO-d6), δ 7.86 (d J=8.8 Hz, 1H), 7.67 (d, J=7.8 Hz, 1H), 6.84 (d, J=8.8 Hz, 1H), 6.62 (d, J=8.8 Hz, 1H), 6.61 (d, J=8.8 Hz, 1H), 6.25 (d, J=1.0 Hz, 1H), 5.90–5.76 (m, 2H), 5.45 (br s, 1H), 5.04 (dd, J=10.2, 1.8 Hz, 1H), 4.99 (dd, J=17.2, 1.8 Hz, 1H), 4.02 (br s, 1H), 2.62 (s, 2H), 2.20–2.22 (m, 2H), 2.17 (d, J=1.0 Hz, 2H), 1.86–1.52 (m, 5H), 1.21–1.22 (m, 5H), 1.18 (s, 2H), 1.17 (s, 2H); HRMS calcd for $C_{20}H_{26}N_2O_4$ is 488.2675. Found 488.2670.

EXAMPLE 444

2,5-Dihydro-9-hydroxy-10-methoxy-2,2,4-trimethyl-5-(3-thienyl)-1H-[1]benzopyrano[3,4-f]quinoline $^1$H NMR (300 MHz, DMSO-d$_6$) δ 8.57 (s, 1H), 7.91 (d, J=9 Hz, 1H), 7.35 (dd, J=5, 5 Hz, 1H), 6.99 (d, J=5 Hz, 1H), 6.92 (s, 1H), 6.68 (d, J=9 Hz, 1H), 6.64 (s, 1H), 6.44 (d, J=9 Hz, 1H), 6.34 (d, J=9 Hz, 1H), 6.21 (s, 1H), 5.38 (s, 1H), 3.57 (s, 3H), 1.87 (s, 3H), 1.23 (s, 3H), 1.13 (s, 3H); $^{13}$C NMR (125 MHz, DMSO-d$_6$) δ 183.2, 182.4, 181.4, 181.1, 170.3, 168.8, 165.3, 165.2, 164.1, 163.9, 163.5, 163.4, 162.6, 155.8, 154.7, 151.6, 149.6, 108.9, 96.6, 87.3, 67.3, 66.0, 60.6; MS (DCI/NH3) (M+H)$^+$ 406.

EXAMPLE 445

2,5-Dihydro-9-hydroxy-10-methoxy-2,2,4-trimethyl-5-(4-(fluorophenyl)methyl)-1H-[1]benzopyrano[3,4-f]quinoline $^1$H NMR (300 MHz, DMSO-d$_6$) δ 8.47 (s, 1H), 7.94 (d, J=8 Hz, 1H), 7.33–7.31 (m, 1H), 7.13–7.04 (m, 3H), 6.62 (dd, J=9, 8 Hz, 2H), 6.41 (d, J=9 Hz, 1H), 6.41 (s, 1H), 5.82 (dd, J=10, 9 Hz, 1H), 5.40 (s, 1H), 3.69 (s, 3H), 3.01–2.93 (m, 1H), 2.81–2.76 (m, 1H), 2.20 (s, 1H), 1.15 (s, 3H), 1.13 (s, 3H); $^{13}$C NMR (75 MHz, DMSO-d$_6$) δ 162.5, 159.2, 145.8, 145.1, 144.0, 142.8, 134.1, 133.4, 132.2, 130.8, 130.7, 127.4, 126.4, 117.9, 116.4, 116.2, 115.0, 114.7, 114.4, 113.8, 112.5, 74.4, 59.5, 49.7, 37.1, 29.2, 29.0, 24.3; MS calc'd for $C_{27}H_{26}O_3NF$: m/e 431.1897, found 431.1905; Analysis calc'd for $C_{27}H_{26}O_3NF0.30H_2O$: C, 74.23; H, 6.14; N, 3.21; found: C, 74.16; H, 6.44; N, 2.96.

EXAMPLE 446

10-Carbaldehyde Oxime-5-(2-propenyl)-2,5-dihydro-2,2,4-trimethyl-1H-[1]benzopyrano[3,4-f]quinoline A solution of Example 330 in ethanol (5 mL) and pyridine (0.1 mL) was treated with hydroxylamine hydrochloride, heated to reflux for 30 minutes, cooled to room temperature, and concentrated. The concentrate was dissolved in ethyl acetate (20 mL) and washed with 1M HCl. The layers were separated and the organic layer was dried (Na$_2$SO$_4$), filtered, and concentrated to provide the desired product as a white solid.

MS (DCI/NH$_3$) m/z 361 (M+H)$^+$; $^1$H NMR (300 MHz, DMSO-d$_6$), δ 8.24 (s, 1H), 7.33 (dd, J=7.7, 1 Hz, 1H), 7.16 (t, J=8 Hz, 1H), 6.94 (d, J=8 Hz, 1H), 6.92 (dd, J=7.7, 1 Hz, 1H), 6.69 (d, J=8 Hz, 1H), 6.28 (s, 1H), 5.90–5.76 (m, 2H), 5.50 (d, J=1.1 Hz, 1H), 5.04 (dd, J=10.3, 1.8 Hz, 1H), 4.96 (dd, J=17.3, 1.8 Hz, 1H), 2.47–2.41 (m, 1H), 2.34–2.27 (m, 1H), 2.19 (s, 3H), 1.22 (s, 3H), 1.17 (s, 3H); Anal. calcd for $C_{23}H_{24}N_2O_2$: C, 76.64; H, 6.71; N, 7.77. Found C, 76.42; H, 6.65; N, 7.60.

EXAMPLE 447

10-Benzyloxy-5-(2-propenyl)-2,5-dihydro-2,2,4-trimethyl-1H-[1]benzopyrano[3,4-f]quinoline A solution of Example 82 in DMF at 0° C. was treated sequentially with cesium carbonate and benzyl bromide, warmed to room temperature, stirred for 1 hour, recooled to ° C., treated with saturated NH$_4$Cl, and extracted with ethyl acetate. The extract was washed with 0.5 M HCl and brine, dried (Na$_2$SO$_4$), filtered, and concentrated. The concentrare was purified by flash chromatography on silica gel with with 10% ethyl acetate/hexanes to provide the desired product as a white foam.

MS (ESI(+)) m/z 424 (M+H)$^+$; $^1$H NMR (300 MHz, DMSO-d$_6$) δ 8.03 (d, 1H, J=8.81 Hz), 7.45 (d, 2H, J=7.3 Hz), 7.39 (t, 2H, J=7.7 Hz), 7.05 (t, 1H, J=8.06 Hz), 6.80 (d, 1H, J=8.86 Hz), 6.53 (t, 2H, J=8.8 Hz), 6.06 (s, 1H), 6.55 (m, 1H), 5.44 (s, 1H), 5.22 (q, 2H, J=41.7, 1Hz), 5.00–5.04 (m, 2H), 2.16 (s, 3H), 1.16 (s, 3H), 1.14 (s, 3H); $^{13}$C NMR (125 MHz, DMSO-d$_6$) δ 155.0, 150.9, 145.5, 137.0, 134.2, 133.5, 132.1, 128.4, 127.7, 127.5, 127.4, 127.1, 126.9, 117.1, 116.1, 115.8, 113.7, 113.0, 110.6, 107.0, 73.4, 70.1, 49.7, 36.5, 28.9, 23.9.

What is claimed is:

1. A pharmaceutical composition for use in selectively modulating the activation, repression, agonism, and antagonism effects of glucocorticoid receptors and not progesterone, androgen, estrogen, or mineralocorticoid receptors, in a mammal comprising an effective amount of a compound of the Formula I

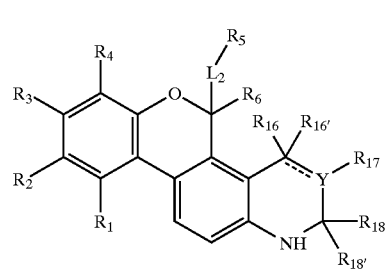

or a pharmaceutically acceptable salt thereof and a pharmaceutical carrier, where the symbol, +z,1 ═══, represents a single bond or a double bond, $R_1$ is —$L_1$—$R_A$ where $L_1$ is selected from
(1) a covalent bond,
(2) —O—,
(3) —S(O)$_t$— where t is 0, 1, or 2, (4) —C(X)—, where X is O or S,
(5) —N(R$_7$)— where R$_7$ is selected from
  (a) hydrogen,
  (b) aryl,
  (c) cycloalkyl of three to twelve carbons,
  (d) alkanoyl where the alkyl part is one to twelve carbons,
  (e) alkoxycarbonyl where the alkyl part is one to twelve carbons,
  (f) alkoxycarbonyl where the alkyl part is one to twelve carbons and is substituted by 1 or 2 aryl groups,
  (g) alkyl of one to twelve carbons,
  (h) alkyl of one to twelve carbons substituted with 1 or 2 substituents independently selected from
    (i) aryl and
    (ii) cycloalkyl of three to twelve carbons,
  (i) alkenyl of three to twelve carbons,
    provided that a carbon of a carbon-carbon double bond is not attached directly to nitrogen,
  (j) alkynyl of three to twelve carbons,
    provided that a carbon of a carbon-carbon triple bond is not attached directly to nitrogen,
(6) —N(R$_8$)C(X)N(R$_9$)— where X is O or S and R$_8$ and R$_9$ are independently selected from
  (a) hydrogen,
  (b) aryl,
  (c) cycloalkyl of three to twelve carbons,
  (d) alkyl of one to twelve carbons,
  (e) alkyl of one to twelve carbons substituted with 1 or 2 substituents independently selected from aryl or cycloalkyl of three to twelve carbons,
  (f) alkenyl of three to twelve carbons,
    provided that a carbon of a carbon-carbon double bond is not attached directly to nitrogen,
  (g) alkynyl of three to twelve carbons,
    provided that a carbon of a carbon-carbon triple bond is not attached directly to nitrogen,
(7) —X'C(X)— where X is previously defined and X' is O or S,
(8) —C(X)X'—,
(9) —X'C(X)X"— where X and X' are previously defined and X" is O or S,
  provided that when X is O, at least one of X' or X" is O,
(10) —N(R$_8$)C(X)—,
(11) —C(X)N(R$_8$)—,
(12) —N(R$_8$)C(X)X'—,
(13) —X'C(X)N(R$_8$)—,
(14) —SO$_2$N(R$_8$)—,
(15) —N(R$_8$)SO$_2$—, and
(16) —N(R$_8$)SO$_2$N(R$_9$)—
  where (6)–(16) are drawn with their right ends attached to R$_A$, and R$_A$ is selected from
(1) —OH,
(2) —OG where G is a —OH protecting group,
(3) —SH,
(4) —CO$_2$R$_{20}$ where R$_{20}$ is hydrogen or alkyl of one to twelve carbons,
(5) alkoxylcarbonyl,
(6) —CN,
(7) halo,
(8) haloalkoxy of one to twelve carbons,
(9) perfluoroalkoxy of one to twelve carbons,
(10) —CHO,
(11) —NR$_7$R$_7$' where R$_7$' is the same as defined for R$_7$,
(12) —C(X)NR$_8$R$_9$,
(13) —OSO$_2$R$_{11}$ where R$_{11}$ is selected from
  (a) aryl,
  (b) cycloalkyl of three to twelve carbons,
  (c) alkyl of one to twelve carbons,
  (d) alkyl of one to twelve carbons substituted with 1, 2, 3, or 4 halo substituents, and
  (e) perfluoroalkyl of one to twelve carbons,
    provided that when R$_A$ is (1)–(13), L$_1$ is a covalent bond,
(14) alkyl of one to twelve carbons,
(15) alkenyl of two to twelve carbons,
  provided that a carbon of a carbon-carbon double bond is not attached directly to L$_1$ when L$_1$ is other than a covalent bond,
(16) alkynyl of two to twelve carbons,
  provided that a carbon of a carbon-carbon triple bond is not attached directly to L$_1$ when L$_1$ is other than a covalent bond,
  where (14), (15), and (16) can be substituted with 1, 2, or 3 substituents independently selected from
  (a) alkoxy of one to twelve carbons,
  (b) —OH,
    provided that no two —OH groups are attached to the same carbon,
  (c) —SH,
  (d) thioalkoxy of one to twelve carbons,
    provided that no two —SH groups are attached to the same carbon,
  (e) —CN,
  (f) halo,
  (g) —CHO,
  (h) —NO$_2$,
  (i) haloalkoxy of one to twelve carbons,
  (j) perfluoroalkoxy of one to twelve carbons,
  (k) —NR$_7$R$_{R7}$,
  (l) =NNR$_7$R$_7$,
  (m) —NR$_7$NR$_7$R$_{7"}$ where R$_{7"}$ is the same as defined for R$_7$,
  (n) —CO$_2$R$_{10}$ where R$_{10}$ is selected from
    (i) hydrogen,
    (ii) aryl,
    (iii) aryl substituted with 1, 2, or 3 alkyl of one to twelve carbon substituents,
    (iv) cycloalkyl of three to twelve carbons,
    (v) alkyl of one to twelve carbons, and
    (vi) alkyl of one to twelve carbons substituted with aryl or cycloalkyl of three to twelve carbons,
  (o) —C(X)NR$_8$R$_9$,
  (p) =N—OR$_{10}$,
  (q) =NR$_{10}$,
  (r) —S(O)$_r$R$_{10}$,
  (s) —X'C(X)R$_{10}$,
  (t) (=X),
  (u) —OSO$_2$R$_{11}$, and
  (v) aryl,
(17) cycloalkyl of three to twelve carbons,
(18) cycloalkenyl of four to twelve carbons,
  provided that a carbon of a carbon-carbon double bond is not attached directly to L$_1$ when L$_1$ is other than a covalent bond,
  where (17) and (18) can be substituted with 1, 2, 3, or 4 substituents independently selected from (a) alkyl of one to twelve carbons,
(b) aryl,
(c) alkoxy of one to twelve carbons,
(d) halo,
(e) alkoxycarbonyl where the alkyl group is one to twelve carbons, and
(f) —OH,
provided that no two —OH groups are attached to the same carbon,
(19) perfluoroalkyl of one to twelve carbons,
(20) aryl, and
(21) heterocycle
where (20) and (21) can be substituted with 1, 2, 3, 4, or 5 substituents independently selected from
(a) alkyl of one to twelve carbons,
(b) alkanoyloxy where the alkyl part is one to twelve carbons,
(c) alkoxycarbonyl where the alkyl part is one to twelve carbons,
(d) alkoxy of one to twelve carbons,
(e) halo,
(f) —OH,
provided that no two —OH groups are attached to the same carbon,
(g) thioalkoxy of one to twelve carbons,
(h) perfluoroalkyl of one to twelve carbons,
(i) —NR$_7$R$_{7'}$,
(j) —CO$_2$R$_{10}$,
(k) —OSO$_2$R$_{11}$, and
(l) (=X);

R$_2$, R$_3$, and R$_4$ are independently hydrogen or R$_1$; or
R$_1$ and R$_2$ together are —X*—Y*—Z*— where X* is —O— or —CH$_2$—, Y* is —C(O)— or —(C(R$_{12}$)(R$_{13}$))$_v$— where R$_{12}$ and R$_{13}$ are independently hydrogen or alkyl of one to twelve carbons and v is 1, 2, or 3, and Z* is selected from —CH$_2$—, —CH$_2$S(O)$_t$—, —CH$_2$O—, —CH$_2$N(R$_7$)—, —N(R$_7$)—, and —O—;

L$_2$ is selected from
(1) a covalent bond,
(2) alkylene of one to twelve carbons,
(3) alkylene of one to twelve carbons substituted with 1 or 2 substituents independently selected from
(a) spiroalkyl of three to eight carbon atoms,
(b) spiroalkenyl of five or eight carbon atoms,
(c) oxo,
(d) halo, and
(e) —OH,
provided that no two —OH groups are attached to the same carbon,
(4) alkynylene of two to twelve carbons,
(5) —N(R$_7$)—,
(6) —C(X)—,
(7) —O—, and
(8) —S(O)$_t$—; and R$_5$ is selected from
(1) halo,
(2) hydrogen,
(3) —C(=NR$_7$)OR$_{10}$,
(4) —CN,
provided that when R$_5$ is (1), (2), or (3), L$_2$ is a covalent bond,
(5) alkyl of one to twelve carbons,
(6) alkynyl two to twelve carbons,
provided that a carbon of a carbon-carbon triple bond is not attached directly to L$_2$ when L$_2$ is other than a covalent bond,
(7) cycloalkyl of three to twelve carbons,
(8) heterocycle,
(9) aryl
provided that when R$_5$ is (9), L$_2$ is other than —N(R$_7$)— or —O—, and where (5)–(9) can be substituted with 1, 2, 3, 4, or 5 substituents independently selected from
(a) —OH,
provided that no two —OH groups are attached to the same carbon,
(b) —SH,
provided that no two —SH groups are attached to the same carbon,
(c) —CN,
(d) halo,
(e) —CHO,
(f) —NO$_2$,
(g) haloalkoxy of one to twelve carbons,
(h) perfluoroalkoxy of one to twelve carbons,
(i) —NR$_{8'}$R$_{9'}$ where R$_{8'}$ and R$_{9'}$ are selected from
(i) hydrogen,
(ii) alkanoyl where the alkyl part is one to twelve carbons,
(iii) alkoxycarbonyl where the alkyl part is one to twelve carbons,
(iv) alkoxycarbonyl where the alkyl part is one to twelve carbons and is substituted with 1 or 2 phenyl substituents,
(v) cycloalkyl of three to twelve carbons,
(vi) alkyl of one to twelve carbons,
(vii) alkyl of one to twelve carbons substituted with 1, 2, or 3 substituents independently selected from
alkoxy of one to twelve carbons,
cycloalkyl of three to twelve carbons,
aryl, and
alkoxycarbonyl where the alkyl group is one to twelve carbons,
(viii) alkenyl of three to twelve carbons,
provided that a carbon of a carbon-carbon double bond is not directly attached to nitrogen,
(ix) alkynyl of three to twelve carbons,
provided that a carbon of a carbon-carbon triple bond is not directly attached to nitrogen,
(x) —C(O)NR$_x$R$_y$ where R$_x$ and R$_y$ are independently selected from hydrogen and alkyl of one to twelve carbons,
(xi) alkoxy of one to twelve carbons,
(xii) aryl, and
(xiii) aryl substituted with 1, 2, 3, 4, or 5 substituents independently selected from
alkyl of one to twelve carbons,
alkanoyloxy where the alkyl part is one to twelve carbons,
alkoxycarbonyl where the alkyl part is one to twelve carbons,
alkoxy of one to twelve carbons,
halo,
—OH
provided that no two -OH groups are attached to the same carbon,
thioalkoxy of one to twelve carbons,
perfluoroalkyl of one to twelve carbons,
—NR$_7$R$_{7'}$,
—CO$_2$R$_{10}$,
—OSO$_2$R$_{11}$, and
(=X), or
R$_{8'}$ and R$_{9'}$ together with the nitrogen atom to which they are attached form a ring selected from (i) aziridine,
(ii) azetidine,
(iii) pyrrolidine,
(iv) piperidine,
(v) pyrazine,
(vi) morpholine,
(vii) phthalimide,
(viii) thiomorpholine, and
(ix) thiomorpholine sulfone
where (i)–(ix) can be substituted with 1, 2, or 3 alkyl of one to twelve carbon substituents,
(j) =$NNR_8 R_{9'}$,
(k) —$N(R_7)NR_8 R_{9'}$,
(l) —$CO_2R_8$,
(m) —$C(X)NR_8 R_{9'}$,
(n) =N—$OR_8$,
(o) =$NR_8$,
(p) —$S(O)_tR_{10}$,
(q) —X'C(X)$R_8$,
(r) (=X),
(s) —O—$(CH_2)_q$—Z—$R_{10}$ where $R_{10}$ is defined previously, q is 1, 2, or 3, and Z is O or —$S(O)_t$—,
(t) —OC(X)$NR_8 R_{9'}$,
(u) —$OSO_2R_{11}$,
(v) alkanoyloxy where the alkyl group is one to twelve carbons,
(w) —$L_BR_{30}$ where $L_B$ is selected from
  (i) a covalent bond,
  (ii) —O—,
  (iii) —$S(O)_t$—, and
  (iv) —C(X)— and
  $R_{30}$ is selected from
  (i) alkyl of one to twelve carbons,
  (ii) alkenyl of one to twelve carbons,
    provided that a carbon of a carbon-carbon double bond is not attached directly to $L_B$ when $L_B$ is other than a covalent bond,
  (iii) alkynyl of one to twelve carbons,
    provided that a carbon of a carbon-carbon triple bond is not attached directly to $L_B$ when $L_B$ is other than a covalent bond,
    where (i), (ii), and (iii) can be substituted with
      cycloalkyl of three to twelve carbons,
      —OH,
      provided that no two —OH groups are attached to the same carbon,
      halo,
      alkoxy of one to twelve carbons,
      thioalkoxy of one to twelve carbons,
      —$NR_8 R_{9'}$,
      —O—$(CH_2)_q$—Z—$R_{10}$,
      alkoxycarbonyl where the alkyl group is one to twelve carbons,
      alkanoyloxy where the alkyl group is one to twelve carbons,
      —$N(R_7)SO_2$-(alkyl of one to twelve carbons),
      —$OSO_2$-(alkyl of one to twelve carbons),
      aryl, and
      heterocycle,
  (iv) aryl,
  (v) aryl substituted with 1, 2, 3, 4, or 5 substituents independently selected from
      alkyl of one to twelve carbons,
      halo,
      —$NO_2$, and
      —OH,
      provided that no two —OH groups are attached to the same carbon,
  (vi) heterocycle, and
  (vii) heterocycle substituted with 1, 2, 3, 4, or 5 substituents independently selected from
      alkyl of one to twelve carbons,
      halo,
      —$NO_2$, and
      —OH,
      provided that no two —OH groups are attached to the same carbon,
  (x) —X'C(X)X"$R_{10}$,
  (y) —N(H)C(O)N(H)$NH_2$,
  (z) alkenyl of two carbons,
  (aa) —C(=$NR_7$)$OR_{10}$, and
  (bb) —$N(R_7)C(X)NR_8 R_{9'}$, (10)

$$\begin{array}{c} R_{20} \\ | \\ C=C \\ | \quad \backslash R_{21} \\ R_{19} \end{array}$$

where the carbon-carbon double bond is in the Z or E configuration, and $R_{19}$, $R_{20}$, and $R_{21}$ are independently selected from
(a) hydrogen,
(b) halo,
(c) alkoxycarbonyl where the alkyl group is of one to twelve carbons,
(d) alkyl of one to twelve carbons, and
(e) alkyl of one to twelve carbons substituted with
  (i) alkoxy of one to twelve carbons,
  (ii) —OH,
    provided that no two —OH groups are attached to the same carbon,
  (iii) —SH,
    provided that no two —SH groups are attached to the same carbon,
  (iv) —CN,
  (v) halo,
  (vi) —CHO,
  (vii) —$NO_2$,
  (viii) haloalkoxy of one to twelve carbons,
  (ix) perfluoroalkoxy of one to twelve carbons,
  (x) —$NR_8 R_{9'}$,
  (xi) —$NNR_8 R_{9'}$,
  (xii) —$N(R_7)NR_8 R_{9'}$,
  (xiii) —$CO_2R_{10}$,
  (xiv) —C(X)$NR_8 R_{9'}$,
  (xv) =N—$OR_{10}$,
  (xvi) =$NR_{10}$,
  (xvii) —$S(O)_tR_{10}$,
  (xviii) —X'C(X)$R_{10}$,
  (xix) (=X),
  (xx) —O—$(CH_2)_q$—Z—$R_{10}$,
  (xxi) —OC(X)$NR_8 R_{9'}$,
  (xxii) —$L_BR_{30}$,
  (xxiii) alkanoyloxy where the alkyl group is one to twelve carbons,
  (xxiv) —$OSO_2R_{11}$, and
  (xxv) —$N(R_7)C(X)NR_8 R_{9'}$, or
  $R_{20}$ and $R_{21}$ together are selected from
(a) cycloalkyl of three to twelve carbon atoms,
(b) cycloalkenyl of four to twelve carbon atoms, and (c)

(allene) where $R_{22}$ and $R_{23'}$ are independently hydrogen or alkyl of one to twelve carbons, and

(11) cycloalkenyl of four to twelve carbons
where the cycloalkenyl group or the ring formed by $R_{20}$ and $R_{21}$ together can be substituted with one or two substituents independently selected from
(a) alkoxy of one to twelve carbons,
(b) —OH,
provided that no two —OH groups are attached to the same carbon,
(c) —SH,
provided that no two —SH groups are attached to the same carbon,
(d) —CN,
(e) halo,
(f) —CHO,
(g) —NO$_2$,
(h) haloalkoxy of one to twelve carbons,
(i) perfluoroalkoxy of one to twelve carbons,
(j) —NR$_8$·R$_9'$,
(k) —NNR$_8$·R$_9'$,
(l) —N(R$_7$)NR$_8$·R$_9'$,
(m) —CO$_2$R$_{10}$,
(n) —C(X)NR$_8$·R$_9'$,
(o) =N—OR$_{10}$, (p) =NR$_{10}$, (q) —S(O)$_r$R$_{10}$,
(r) —X'C(X)R$_{10}$,
(s) (=X),
(t) —O—(CH$_2$)$_q$—Z—R$_{10}$,
(u) —OC(X)NR$_8$·R$_9'$,
(v) —L$_B$R$_{30}$,
(w) alkanoyloxy where the alkyl group is one to twelve carbons,
(x) —OSO$_2$R$_{11}$, and
(y) —N(R$_7$)C(X)NR$_8$·R$_9'$;

$R_6$ is hydrogen or alkyl of one to twelve carbon atoms; or
—L$_2$—R$_5$ and $R_6$ together are selected from
(1) =O,
(2)

where d is 1, 2, 3, or 4 and A is selected from
(a) —CH$_2$—,
(b) —O—,
(c) —S(O)$_r$, and
(d) —N(R$_7$)—, and
(3)

where the carbon-carbon double bond can be in the E or Z configuration and $R_{26}$ and $R_{26'}$ are independently selected from
(a) hydrogen,
(b) alkenyl of three to twelve carbons,
(c) aryl,
(d) heterocycle,
(e) alkyl of one to twelve carbons,
(e) cycloalkyl of three to twelve carbons,
(g) cycloalkenyl of four to twelve carbons, and
(h) cycloalkenyl of four to twelve carbons where (a)–(f) can be substituted with 1, 2, 3, 4, or 5 substituents independently selected from
(i) alkoxy of one to twelve carbons,
(ii) —OH,
provided that no two —OH groups are attached to the same carbon,
(iii) —SH,
provided that no two —SH groups are attached to the same carbon,
(iv) —CN,
(v) halo,
(vi) —CHO,
(vii) —NO$_2$,
(viii) haloalkoxy of one to twelve carbons,
(ix) perfluoroalkoxy of one to twelve carbons,
(x) —NR$_8$·R$_9'$,
(xi) =NNR$_8$·R$_9'$,
(xii) —N(R$_7$)NR$_8$·R$_9'$,
(xiii) —CO$_2$R$_{10}$,
(xiv) —C(X)NR$_8$·R$_9'$,
(xv) =N—OR$_{10}$,
(xvi) =NR$_{10}$,
(xvii) —S(O)$_r$R$_{10}$,
(xviii) —X'C(X)R$_{10}$,
(xix) (=X),
(xx) —O—(CH$_2$)$_q$—Z—R$_{10}$,
(xxi) —OC(X)NR$_8$·R$_9'$,
(xxii) —L$_B$R$_{30}$,
(xxii) alkanoyloxy where the alkyl group is one to twelve carbons,
(xxiii) —OSO$_2$R$_{11}$, and
(xxiv) —N(R$_7$)(X)NR$_8$·R$_9'$;

$R_{16}$ and $R_{16'}$ are independently hydrogen or alkyl of one to six carbons; or
$R_{16}$ and $R_{16'}$ together are =CH$_2$;
a broken line represents the optional presence of a double bond,
provided that when $R_{16}$ and $R_{16'}$ together are alkenyl of two carbons forming an exocyclic double bond, the endocyclic double bond is not present;
Y is carbon;
$R_{17}$ is hydrogen or alkyl of one to six carbons; and
$R_{18}$ and $R_{18'}$ are independently hydrogen or alkyl of one to six carbons; or
$R_{18}$ and $R_{18'}$ together are a cycloheteroalkyl ring or a cycloalkyl ring of three to eight carbons.

2. A pharmaceutical composition for use in treating inflammation, immune, autoimmune, and inflammatory diseases in a mammal by selectively modulating the activation, repression, agonism, and antagonism effects of the mammal's glucocorticoid receptors and not progesterone, androgen, estrogen, or mineralocorticoid receptors, comprising an effective amount of a compound having Formula II:

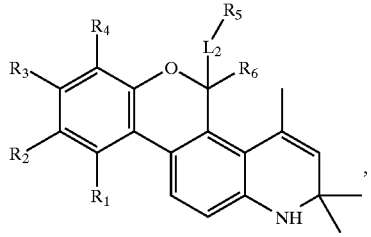

or a pharmaceutically acceptable salt, and a pharmaceutical carrier, where $R_1$, $R_2$, $R_3$, $R_4$, $R_5$, $R_6$, and $L_2$, are defined in claim 1.

3. The composition of claim 1 or 2 where $R_1$ is —$L_1$—$R_A$, $L_1$ is —O— or —S—, and $R_A$ is alkyl of one to twelve carbons optionally substituted as defined in claim 1, or $R_1$ and $R_2$ together are —X*—Y*—Z*—.

4. The composition of claim 1 or 3 selected from 2,5-dihydro-10-methoxy-2,2,4-trimethyl-5-phenyl-1H-[1]benzopyrano[3,4-f]quinoline, 2,5-dihydro-10-methoxy-2,2,4-trimethyl-5-(2-propenyl)-1H-[1]benzopyrano[3,4-f]quinoline, 10-(difluoromethoxy)-2,5-dihydro-2,2,4-trimethyl-5-(2-propenyl)-1H-[1]benzopyrano[3,4-f]quinoline, 10-ethoxy-2,5-dihydro-2,2,4-trimethyl-5-phenyl-1H-[1]benzopyrano[3,4-f]quinoline, 5-(3-bromo-5-methylphenyl)-2,5-dihydro-10-methoxy-2,2,4-trimethyl-1H-[1]benzopyrano[3,4-f]quinoline, 3-(2,5-dihydro-10-methoxy-2,2,4-trimethyl-1H-[1]benzopyrano[3,4-f]quinolin-5-yl)phenol, acetate (ester), 3-(2,5-dihydro-10-methoxy-2,2,4-trimethyl-1H-[1]benzopyrano[3,4-f]quinolin-5-yl)phenol, 2,5-dihydro-10-methoxy-2,2,4-trimethyl-5-[[3-(methylthio)methoxy]phenyl]-1H-[1]benzopyrano[3,4-f]quinoline,

[3-(2,5-dihydro-10-methoxy-2,2,4-trimethyl-1H-[1]benzopyrano[3,4-f]quinolin-5-yl)phenyl]dimethylcarbamate, 5-[3-(2-furanyl)-5-methylphenyl]-2,5-dihydro-10-methoxy-2,2,4-trimethyl1H-[1]benzopyrano[3,4-f]quinoline, 2,5-dihydro-10-methoxy-2,2,4-trimethyl-5-[3-methyl-5-(1-morpholinyl)phenyl]-1H-[1]benzopyrano[3,4-f]quinoline, 2,5-dihydro-10-methoxy-2,2,4-trimethyl-5-(phenylmethylene)-1H-[1]benzopyrano[3,4-f]quinoline, 5-(3,5-dichlorophenyl)-2,5-dihydro-10-methoxy-2,2,4-trimethyl-1H-[1]benzopyrano[3,4-f]quinoline, 5-butyl-2,5-dihydro-10-methoxy-2,2,4-trimethyl-1H-[1]benzopyrano[3,4-f]quinoline, 2,5-dihydro-10-methoxy-2,2,4-trimethyl-5-[3-(trifluoromethyl)phenyl]-1H-[1]benzopyrano[3,4-f]quinoline, 2,5-dihydro-10-methoxy-5-(4-methoxyphenyl)-2,2,4-trimethyl-1H-[1]benzopyrano[3,4-f]quinoline, 5-(3-chlorophenyl)-2,5-dihydro-10-methoxy-2,2,4-trimethyl-1H-[1]benzopyrano[3,4-f]quinoline, 2,5-dihydro-10-methoxy-2,2,4-trimethyl-5-(3-methylphenyl)-1H-[1]benzopyrano[3,4-f]quinoline, (±)-2,5-dihydro-10-methoxy-2,2,4-trimethyl-5-phenyl-1H-[1]benzopyrano[3,4-f]quinoline, (±)-2,5-dihydro-10-methoxy-2,2,4-trimethyl-5-phenyl-1H-[1]benzopyrano[3,4-f]quinoline, 5-(3,5-dimethylphenyl)-2,5-dihydro-10-methoxy-2,2,4-trimethyl-1H-[1]benzopyrano[3,4-f]quinoline, 5-(4-chlorophenyl)-2,5-dihydro-10-methoxy-2,2,4-trimethyl-1H-[1]benzopyrano[3,4-f]quinoline, 5-(3,4-dimethylphenyl)-2,5-dihydro-10-methoxy-2,2,4-trimethyl-1H-[1]benzopyrano[3,4-f]quinoline, 5-(4-fluorophenyl)-2,5-dihydro-10-methoxy-2,2,4-trimethyl-1H-[1]benzopyrano[3,4-f]quinoline, 5-[3,5-bis(trifluoromethyl)phenyl]-2,5-dihydro-10-methoxy-2,2,4-trimethyl-1H-[1]benzopyrano[3,4-f]quinoline, (−)-5-(3,5-dichlorophenyl)-2,5-dihydro-10-methoxy-2,2,4-trimethyl-1H-[1]benzopyrano[3,4-f]quinoline, (+)-5-(3,5-dichlorophenyl)-2,5-dihydro-10-methoxy-2,2,4-trimethyl-1H-[1]benzopyrano[3,4-f]quinoline, 5-(3,5-difluorophenyl)-2,5-dihydro-10-methoxy-2,2,4-trimethyl-1H-[1]benzopyrano[3,4-f]quinoline, 2,5-dihydro-10-methoxy-2,2,4,N-tetramethyl-N-phenyl-1H-[1]benzopyrano[3,4-f]quinolin-5-amine, (−)2,5-dihydro-10-methoxy-2,2,4-trimethyl-5-(2-propenyl)-1H-[1]benzopyrano[3,4-f]quinoline, (+)-2,5-dihydro-10-methoxy-2,2,4-trimethyl-5-(2-propenyl)-1H-[1]benzopyrano[3,4-f]quinoline, 2,5-dihydro-10-methoxy-2,2,4-trimethyl-1H-[1]benzopyrano[3,4-f]quinoline, 4-(2,5-dihydro-10-methoxy-2,2,4-trimethyl-1H-[1]benzopyrano[3,4-f]quinolin-5-yl)-N,N-dimethylbenzenamide, 2,5-dihydro-10-methoxy-2,2,4-trimethyl-(5-methoxy-2-thienyl)-1H-[1]benzopyrano[3,4-f]quinoline, 2,5-dihydro-10-methoxy-2,2,4-trimethyl-5-(5-propyl-2-thienyl)-1H-[1]benzopyrano[3,4-f]quinoline, 2,5-dihydro-10-methoxy-2,2,4-trimethyl-5-[4-(1-morpholinyl)phenyl]-1H-[1]benzopyrano[3,4-f]quinoline, 1-(2,5-dihydro-10-methoxy-2,2,4-trimethyl-1H-[1]benzopyrano[3,4-f]quinolin-5-yl)-3,3-dimethyl-2-butanone, 2,5-dihydro-10-methoxy-2,2,4-trimethyl-1H-[1]benzopyrano[3,4-f]quinoline-5-carbonitrile, 1-(2,5-dihydro-10-methoxy-2,2,4-trimethyl-1H-[1]benzopyrano[3,4-f]quinolin-5-yl)-2-propanone, methyl-2,5-dihydro-10-methoxy-2,2,4-trimethyl-1H-[1]benzopyrano[3,4-f]quinoline-5-acetate, 2-(2,5-dihydro-10-methoxy-2,2,4-trimethyl-1H-[1]benzopyrano[3,4-f]quinolin-5-yl)-1-phenylethanone, 5-[2-(chloromethyl)-2-propenyl]-2,5-dihydro-10-methoxy-2,2,4-trimethyl-1H-[1]benzopyrano[3,4-f]quinoline, 2,5-dihydro-10-methoxy-2,2,4-trimethyl-(-methylene-1H-[1]benzopyrano[3,4-f]quinoline-5-propanol, acetate (ester), 2,5-dihydro-10-methoxy-2,2,4-trimethyl-5-(4-methylphenyl)-1H-[1]benzopyrano[3,4-f]quinoline, 5-(3-fluoro-4-methylphenyl)-2,5-dihydro-10-methoxy-2,2,4-trimethyl-1H-[1]benzopyrano[3,4-f]quinoline, 5-(3-bromophenyl)-2,5-dihydro-10-methoxy-2,2,4-trimethyl-1H-[1]benzopyrano[3,4-f]quinoline, 2,5-dihydro-10-methoxy-2,2,4-trimethyl-5-(phenylmethyl)-1H-[1]benzopyrano[3,4-f]quinoline,
2,5-dihydro-10-methoxy-2,2,4-trimethyl-5-propyl-1H-[1]benzopyrano[3,4-f]quinoline,
5-(4-fluorophenyl)-2,5-dihydro-10-methoxy-2,2,4-trimethyl-1H-[1]benzopyrano[3,4-f]quinoline,
5-(3-fluorophenyl)-2,5-dihydro-10-methoxy-2,2,4-trimethyl-1H-[1]benzopyrano[3,4-f]quinoline,
2,5-dihydro-10-methoxy-2,2,4,5-tetramethyl-1H-[1]benzopyrano[3,4-f]quinoline,
2,5-dihydro-10-methoxy-2,2,4-trimethyl-5-(1-methylethyl)-1H-[1]benzopyrano[3,4-f]quinoline,
2,5-dihydro-10-methoxy-2,2,4-trimethyl-5-(2-methylpropyl)-1H-[1]benzopyrano[3,4-f]quinoline,
5-ethyl-2,5-dihydro-10-methoxy-2,2,4-trimethyl-1H-[1]benzopyrano[3,4-f]quinoline,
2,5-dihydro-10-methoxy-2,2,4-trimethyl-1H-[1]benzopyrano[3,4-f]quinoline-5-carboximidic acid ethyl ester,
2,5-dihydro-10-methoxy-2,2,4-trimethyl-(-methylene 1H-[1]benzopyrano[3,4-f]quinoline-5-propanol,
2,5-dihydro-10-methoxy-2,2,4,N,N-pentamethyl-1H-[1]benzopyrano[3,4-f]quinoline-5-acetamide,
2,5-dihydro-10-methoxy-2,2,4,N,N-pentamethyl-1H-[1]benzopyrano[3,4-f]quinoline-5-ethanamine,
N-cyclopropyl-2,5-dihydro-10-methoxy-2,2,4-trimethyl-1H-[1]benzopyrano[3,4-f]quinoline-5-acetamide,
2,5-dihydro-10-methoxy-2,2,4-trimethyl-5-(2-propynyl)-1H-[1]benzopyrano[3,4-f]quinoline,
5-(2,5-dihydro-10-methoxy-2,2,4-trimethyl-1H-[1]benzopyrano[3,4-f]quinolin-5-yl)-2(5H)-furanone,
5-(3-butenyl)-2,5-dihydro-10-methoxy-2,2,4-trimethyl-1H-[1]benzopyrano[3,4-f]quinoline,
2,5-dihydro-10-methoxy-2,2,4-trimethyl-1H-[1]benzopyrano[3,4-f]quinoline-5 propanol,
5-(3,5-dichlorophenyl)-10-ethoxy-2,5-dihydro-2,2,4-trimethyl-1H-[1]benzopyrano[3,4-f]quinoline,
10-(bromodifluoromethoxy)-2,5-dihyro-2,2,4-trimethyl-5-(2-propenyl)-1H-[1]benzopyrano[3,4-f]quinoline,
[3-(2,5-dihydro-10-methoxy-2,2,4-trimethyl-1H-[1]benzopyrano[3,4-f]quinolin-5-yl)phenyl]methylcarbonate,
2,5-dihydro-10-methoxy-5-(3-methoxyphenyl)-2,2,4-trimethyl-1H-[1]benzopyrano[3,4-f]quinoline,
2,5-dihydro-10-methoxy-2,2,4-trimethyl-5-[3-(2-propenyloxy)phenyl]-1H-[1]benzopyrano[3,4-f]quinoline,
2,5-dihydro-10-methoxy-2,2,4-trimethyl-5-[3-(phenylmethoxy)phenyl]-1H-[1]benzopyrano[3,4-f]quinoline,
5-[3-(cyclopropylmethoxy)phenyl]-2,5-dihydro-10-methoxy-2,2,4-trimethyl-1H-[1]benzopyrano[3,4-f]quinoline,
2,5-dihydro-10-methoxy-2,2,4-trimethyl-5-[3-[2-(1-piperidinyl)ethoxy]pheny]-1H-[1]benzopyrano[3,4-f]quinoline,
5-(3-hexyloxyphenyl)-2,5-dihydro-10-methoxy-2,2,4-trimethyl-1H-[1]benzopyrano[3,4-f]quinoline,
5-[3-(2,4-dinitrophenoxy)phenyl]-2,5-dihydro-10-methoxy-2,2,4-trimethyl-1H-[1]benzopyrano[3,4-f]quinoline,
2,5-dihydro-10-methoxy-2,2,4-trimethyl-5-[3-(2-propynyloxy)phenyl]-1H-[1]benzopyrano[3,4-f]quinoline,
3-(2,5-dihydro-10-methoxy-2,2,4-trimethyl-1H-[1]benzopyrano[3,4-f]quinolin-5-yl)phenol-4-methylbenzenesulfonate (ester),
4-(2,5-dihydro-10-methoxy-2,2,4-trimethyl-1H-[1]benzopyrano[3,4-f]quinolin-5-yl)phenolacetate (ester),
4-(2,5-dihydro-10-methoxy-2,2,4-trimethyl-1H-[1]benzopyrano [3,4-]quinolin-5-yl)phenol,
2,5-dihydro-10-methoxy-2,2,4-trimethyl-5-[[4-(methylthio)methoxy]phenyl]-1H-[1]benzopyrano[3,4-f]quinoline,
[4-(2,5-dihydro-10-methoxy-2,2,4-trimethyl-1H-[1]benzopyrano[3,4-f]quinolin-5-yl)phenyl]dimethylcarbamate,
2,5-dihydro-10-methoxy-2,2,4-trimethyl-5-[4-(phenylmethoxy)phenyl]-1H-[1]benzopyrano[3,4-f]quinoline,
2,5-dihydro-10-methoxy-2,2,4-trimethyl-5-[3-(methoxymethoxy)phenyl]-1H-[1]benzopyrano[3,4-f]quinoline,
[(2,5-dihydro-10-methoxy-2,2,4-trimethyl-1H-[1]benzopyrano[3,4-f]quinolin-5-yl)phenyl]1-morpholinecarboxylate,
2,5-dihydro-10-methoxy-2,2,4-trimethyl-5-[3-[(methylsuffinyl)methoxy]phenyl]-1H-[1]benzopyrano[3,4-f]quinoline,
O-[3-(2,5-dihydro-10-methoxy-2,2,4-trimethyl-1H-[1]benzopyrano[3,4-f]quinolin-5-yl)phenyl]ester,
2,5-dihydro-10-methoxy-2,2,4-trimethyl-5-[3-(methylthio)phenyl]-1H-[1]benzopyrano[3,4-f]quinoline,
O-[3-(2,5-dihydro-10-methoxy-2,2,4-trimethyl-1H-[1]benzopyrano[3,4-f]quinolin-5-yl)phenyl]methylcarbonothioate,
[3-(2,5-dihydro-10-methoxy-2,2,4-trimethyl]-1H-[1]benzopyrano[3,4-f]quinolin-5-yl)phenyl]trifluoromethanesulfonate,
5-[3-(4,5-dihydro-4,4-dimethyl-2-oxazolyl)phenyl]-2,5-dihydro-10-methoxy-2,2,4-trimethyl-1H-[1]benzopyrano[3,4-f]quinoline,
ethyl 3-(2,5-dihydro-10-methoxy-2,2,4-trimethyl-1H-[1]benzopyrano[3,4-f]quinolin-5-yl)benzoate,
3-(2,5-dihydro-10-methoxy-2,2,4-trimethyl-1H-[1]benzopyrano[3,4-f]quinolin-5-yl)benzoic acid,
2,5-dihydro-10-methoxy-2,2,4-trimethyl-5-[3-methyl-5-(2-propenyl)phenyl]-1H-[1]benzopyrano[3,4-4-f]quinoline,
1-[3-(2,5-dihydro-10-methoxy-2,2,4-trimethyl-1H-[1]benzopyrano[3,4-f]quinolin-5-yl)-5-methylphenyl]ethanone,
3-(2,5-dihydro-10-methoxy-2,2,4-trimethyl-1H-[1]benzopyrano[3,4-f]quinolin-5-yl)-5-trimethylbenzenemethanol,
5-[3-(2-furanyl)phenyl]-2,5-dihydro-10-methoxy-2,2,4-trimethyl-1H-[1]benzopyrano[3,4-f]quinoline,
2,5-dihydro-10-methoxy-2,2,4-trimethyl-5-[3-methyl-5-(1 H-pyrrolidin-1-yl)phenyl]-1H-[1]benzopyrano[3,4-f]quinoline,
3-(2,5-dihydro-10-methoxy-2,2,4-trimethyl-1H-[1]benzopyrano[3,4-f]quinolin-5-methyl)-5,N-dimethylbenzenamine,
3-(2,5-dihydro-10-methoxy-2,2,4-trimethyl-1H-[1]benzopyrano[3,4-f]quinolin-5-yl)-5-methyl-N-(2-propenyl)benzamide, 3-(2,5-dihydro-10-methoxy-2,2,4-trimethyl-1H-[1]benzopyrano[3,4-f]quinolin-5-yl)-N-(2-methoxyethyl)-5-methylbenzenamide, 3-(2,5-dihydro-10-methoxy-2,2,4-trimethyl-1H-[1]benzopyrano[3,4-f]quinolin-5-yl)-N-(2-propenyl)benzenamide, N'-[3-(2,5-dihydro-10-methoxy-2,2,4-trimethyl-1H-[1]benzopyrano[3,4-f]quinolin-5-yl)-5-methylphenyl]-N,N-dimethylurea, N-[3-(2,5-dihydro-10-methoxy-2,2,4-trimethyl-1H-[1]benzopyrano[3,4-f]quinolin-5-yl)phenyl]benzenemethanamide, 5-[(3,5-dichlorphenyl)methylene]-2,5-dihydro-10-methoxy-2,2,4-trimethyl-1H-[1]benzopyrano[3,4-f]quinoline, 5-[(4-chlorophenyl)methylene]-2,5-dihydro-10-methoxy-2,2,4-trimethyl-1H-[1]benzopyrano[3,4-f]quinoline, 2,5-dihydro-10-methoxy-2,2,4-trimethyl-5-[[3-(trifluoromethyl)phenyl]methylene]-1H-[1]benzopyrano[3,4-f]quinoline, 5-[(2,6-difluorophenyl)methylene]-2,5-dihydro-10-methoxy-2,2,4-trimethyl-1H-[1]benzopyrano[3,4-f]quinoline, 5-[(2-chlorophenyl)methylene]-2,5-dihydro-10-methoxy-2,2,4-trimethyl-1H-[1]benzopyrano[3,4-f]quinoline, 5-[(2,6-dichlorophenyl)methylene]-2,5-dihydro-10-methoxy-2,2,4-trimethyl-1H-[1]benzopyrano[3,4-f]quinoline, 5-[(2-fluorophenyl)methylene]-2,5-dihydro-10-methoxy-2,2,4-trimethyl-1H-[1]benzopyrano[3,4-f]quinoline, 2,5-dihydro-10-methoxy-2,2,4-trimethyl-5-[(4,5-dihydro-4,4-dimethyl-2-oxazolyl)methylene]-1H-[1]benzopyrano[3,4-f]quinoline, 2,5-dihydro-10-methoxy-2,2,4-trimethyl-5-(2-pyridinylmethylene)-1H-[1]benzopyrano[3,4-f]quinoline, 2,5-dihydro-10-methoxy-2,2,4-trimethyl-5-(2-thienyl)-1H-[1]benzopyrano[3,4-f]quinoline, 2,5-dihydro-9,10-dimethoxy-2,2,4-trimethyl-5-(2-propenyl)-1H-[1]benzopyrano[3,4-f]quinoline, 5-(2-cyclohexen-1-yl)-2,5-dihydro-9,10-dimethoxy-2,2,4-trimethyl-1H-[1]benzopyrano[3,4-f]quinoline, 2,5-dihydro-10-methoxy-5-(3-methyl-3-butenyl)-2,2,4-trimethyl-1H-[1]benzopyrano[3,4-f]quinoline, 2,5-dihydro-10-methoxy-5-(5,5-dimethyl-3-cyclohexenyl)-2,2,4-trimethyl-1H-[1]benzopyrano[3,4-f]quinoline, rel(5R,2'R)2,5-dihydro-10-methoxy-5-(2-oxo-3-tetrahydropyranyl)-2,2,4-trimethyl-1H-[1]benzopyrano[3,4-f]quinoline, anti(5R,2'S)2,5-dihydro-10-methoxy-5-(2-oxo-3-tetrahydropyranyl)-2,2,4-trimethyl-1H-[1]benzopyrano[3,4-f]quinoline, 2,5-dihydro-10-methoxy-5-(3-cyclopentenyl)-2,2,4-trimethyl-1H-[1]benzopyrano[3,4-f]quinoline, 2,5-dihydro-10-methoxy-5-(3-cyclohexenyl)-2,2,4-trimethyl-1H-[1]benzopyrano[3,4-f]quinoline, 2,5-dihydro-10-methoxy-5-(3-butenyl)-2,2,4-trimethyl-1H-[1]benzopyrano[3,4-f]quinoline, 2,5-dihydro-10-methoxy-5-(1-ethenyl-1-cyclohexyl)-2,2,4-trimethyl-1H-[1]benzopyrano[3,4-f]quinoline, 2,5-dihydro-10-methoxy-5-(4,4-dimethyl-3-cyclohexenyl)-2,2,4-trimethyl-1H-[1]benzopyrano[3,4-f]quinoline, 2,5-dihydro-10-methoxy-5-(1-methylene-2-cyclohexyl)-2,2,4-trimethyl-1H-[1]benzopyrano[3,4-f]quinoline, 2,5-dihydro-10-methoxy-5-(1-oxo-2-cyclohexyl)-2,2,4-trimethyl-1H-[1]benzopyrano[3,4-f]quinoline, 2,5-dihydro-10-methoxy-5-(3-cyclooctenyl)-2,2,4-trimethyl-1H-[1]benzopyrano[3,4-f]quinoline, 2,5-dihydro-10-methoxy-5-(3-cycloheptenyl)-2,2,4-trimethyl-1H-[1]benzopyrano[3,4-f]quinoline, 2,5-dihydro-10-methoxy-5-(1-cyclohexenylmethyl)-2,2,4-trimethyl-1H-[1]benzopyrano[3,4-f]quinoline, 2,5-dihydro-10-methoxy-5-(3,3-dimethyl-6-cyclohexenyl)-2,2,4-trimethyl-1H-[1]benzopyrano[3,4-f]quinoline, 2,5-dihydro-10-methoxy-5-(2-bromo-3-propenyl)-2,2,4-trimethyl-1H-[1]benzopyrano[3,4-f]quinoline, rel(5R,3'R)2,5-dihydro-10-methoxy-5-(1-hydroxymethyl-3-cyclohexenyl)-2,2,4-trimethyl-1H-[1]benzopyrano[3,4-f]quinoline, rel(5R,3'S)2,5-dihydro-10-methoxy-5-(1-hydroxymethyl-3-cyclohexenyl)-2,2,4-trimethyl-1H-[1]benzopyrano[3,4-f]quinoline, 2,5-dihydro-10-methoxy-5-(3-hydroxymethyl-3-cyclohexenyl)-2,2,4-trimethyl-1H-[1]benzopyrano[3,4-f]quinoline, 2,5-dihydro-10-methoxy-5-(3-indolyl)-2,2,4-trimethyl-1H-[1]benzopyrano[3,4-f]quinoline, rel(5S,3'S)2,5-dihydro-10-methoxy-5-(1-methyl-3-cyclohexenyl)-2,2,4-trimethyl-1H-[1]benzopyrano[3,4-f]quinoline, rel(5R,3'S)2,5-dihydro-10-methoxy-5-(1-methyl-3-cyclohexenyl)-2,2,4-trimethyl-1H-[1]benzopyrano[3,4-f]quinoline, (−)(5S,3'S)2,5-dihydro-10-methoxy-5-(1-methyl-3-cyclohexenyl)-2,2,4-trimethyl-1H-[1]benzopyrano[3,4-f]quinoline, (−)(5S,3'R)2,5-dihydro-10-methoxy-5-(1-hydroxymethyl-3-cyclohexenyl)-2,2,4-trimethyl-1H-[1]benzopyrano[3,4-f]quinoline, (+)(5R,3'S)2,5-dihydro-10-methoxy-5-(1-hydroxymethyl-3-cyclohexenyl)-2,2,4-trimethyl-1H-[1]benzopyrano[3,4-f]quinoline, (−)-(5S,3'R)2,5-dihydro-10-methoxy-5-(1-methyl-3-cyclohexenyl)-2,2,4-trimethyl-1H-[1]benzopyrano[3,4-f]quinoline, (+)-(5R,3'S)2,5-dihydro-10-methoxy-5-(1-methyl-3-cyclohexenyl)-2,2,4-trimethyl-1H-[1]benzopyrano[3,4-f]quinoline, 2,5-dihydro-10-methoxy-5-(1-chloromethyl-3-cyclohexenyl)-2,2,4-trimethyl-1H-[1]benzopyrano[3,4-f]quinoline, rel(5R,3'R)2,5-dihydro-10-methoxy-5-(1-methoxymethyl-3-cyclohexenyl)-2,2,4-trimethyl-1H-[1]benzopyrano[3,4-f]quinoline, rel(5R,3'R)2,5-dihydro-10-methoxy-5-(1-methylthiomethyl-3-cyclohexenyl)-2,2,4-trimethyl-1H-[1]benzopyrano[3,4-f]quinoline, rel(5R,3'S)2,5-dihydro-10-methoxy-5-(1-acetoxymethyl-3-cyclohexenyl)-2,2,4-trimethyl-1H-[1]benzopyrano[3,4-f]quinoline, rel(5R,3'R)2,5-dihydro-10-methoxy-5-(1-acetoxymethyl-3-cyclohexenyl)-2,2,4-trimethyl-1H-[1]benzopyrano[3,4-f]quinoline, rel(5R,3'R)2,5-dihydro-10-methoxy-5-(1-methoxymethyl-3-cyclohexenyl)-2,2,4-trimethyl-1H-[1]benzopyrano[3,4-f]quinoline, rel(5R,3'R)2,5-dihydro-10-methoxy-5-(1-(N,N-dimethylamino)methyl-3-cyclohexenyl)-2,2,4-trimethyl-1H-[1]benzopyrano[3,4-f]quinoline, rel(5R,3'S)2,5-dihydro-10-methoxy-5-(1-methylthiomethyl-3-cyclohexenyl)-2,2,4-trimethyl-1H-[1]benzopyrano[3,4-f]quinoline, rel(5R,3'R)2,5-dihydro-10-methoxy-5-(1-(N-morpholine)methyl-3-cyclohexenyl)-2,2,4-trimethyl-1H-[1]benzopyrano[3,4-f]quinoline, rel(5R,3'R)2,5-dihydro-10-methoxy-5-(1-(N-methyl-N-methylsulfonylamino)methyl-3-cyclohexenyl)-2,2,4-trimethyl-1H-[1]benzopyrano[3,4-f]quinoline, rel(5R,3'S)2,5-dihydro-10-methoxy-S-(1-(N,N-dimethylamino)methyl-3-cyclohexenyl)-2,2,4-trimethyl-1H-[1]benzopyrano[3,4-f]quinoline, rel(5R,3'R)2,5-dihydro-10-methoxy-5-(1-(N-methylamino)methyl-3-cyclohexenyl)-2,2,4-trimethyl-1H-[1]benzopyrano[3,4-f]quinoline, 2,5-dihydro-10-methoxy-5-(2-methyl-3-propenyl)-2,2,4-trimethyl-1H-[1]benzopyrano[3,4-f]quinoline, 2,5-dihydro-10-methoxy-5-(1,3-butadien-2-yl)-2,2,4-trimethyl-1H-[1]benzopyrano[3,4-f]quinoline, 2,5-dihydro-10-methoxy-5-(2-carbomethoxy-3-propenyl)-2,2,4-trimethyl-1H-[1]benzopyrano[3,4-f]quinoline 2,5-dihydro-10-methoxy-5-(1,2-dihydroxy-3-propyl)-2,2,4-trimethyl-1H-[1]benzopyrano[3,4-f]quinoline, 2,5-dihydro-10-methoxy-5-(1,2-epoxy-3-propenyl)-2,2,4-trimethyl-1H-[1]benzopyrano[3,4-f]quinoline, 2,5-dihydro-10-methoxy-5-(1-(N-phthalimido)-3-propyl)-2,2,4-trimethyl-1H-[1]benzopyrano[3,4-f]quinoline, 2,5-dihydro-10-methoxy-5-(1-amino-3-propyl)-2,2,4-trimethyl-1H-[1]benzopyrano[3,4-f]quinoline, 2,5-dihydro-10-methoxy-5-(1-(hydrazinocarbonylamino)-3-propyl)-2,2,4 trimethyl-1H-[1]benzopyrano[3,4-f]quinoline, (E) 2,5-dihydro-10-methoxy-5-(2-carbomethoxy-1-ethenyl)-2,2,4-trimethyl-1H-[1]benzopyrano[3,4-f]quinoline, (Z)-2,5-dihydro-10-methoxy-5-(1-propenyl)-2,2,4-trimethyl-1H-[1]benzopyrano[3,4-f]quinoline, (E) 2,5-dihydro-10-methoxy-5-(3-hydroxy-1-propenyl)-2,2,4-trimethyl-1H-[1]benzopyrano[3,4-f]quinoline, (E) 2,5-dihydro-10-methoxy-5-(3-(N,N-dimethylaminocarbonyloxy)-1-propenyl)-2,2,4-trimethyl-1H-[1]benzopyrano[3,4-f]quinoline, (E) 2,5-dihydro-10-methoxy-5-(3-methoxymethoxy-1-propenyl)-2,2,4-trimethyl-1H-[1]benzopyrano[3,4-f]quinoline, 2,5-dihydro-10-methoxy-5-(3-hydroxy-3-propenyl)-2,2,4-trimethyl-1H-[1]benzopyrano[3,4-f]quinoline, methyl 2-(2,5-dihydro-10-methoxy-2,2,4-trimethyl-1H-[1]benzopyrano[3,4-f]quinolin-5-yl)acetyl hydroxamate, 2-(2,5-dihydro-10-methoxy-2,2,4-trimethyl-1H-[1]benzopyrano[3,4-f]quinolin-5-yl)acetaldehyde, 2,5-dihydro-10-methoxy-5-(2-cyclohexylidenylethyl)-2,2,4-trimethyl-1H-[1]benzopyrano[3,4-f]quinoline 2,5-dihydro-10-methoxy-5-(2-cyclopentylidenylethyl)-2,2,4-trimethyl-1H-[1]benzopyrano[3,4-f]quinoline 2,5-dihydro-10-methoxy-5-(2-cycloheptylidenylethyl)-2,2,4-trimethyl-1H-[1]benzopyrano[3,4-f]quinoline 2,5-dihydro-10-methoxy-5-(3-methyl-2-butenyl)-2,2,4-trimethyl-1H-[1]benzopyrano[3,4-f]quinoline trans 2,5-dihydro-10-methoxy-5-(2-butenyl)-2,2,4-trimethyl-1H-[1]benzopyrano[3,4-f]quinoline trans 2,5-dihydro-10-methoxy-5-(2-penten-1-yl)-2,2,4-trimethyl-1H-[1]benzopyrano[3,4-f]quinoline 2,5-dihydro-10-methoxy-5-(1,1-difluoro-1-propen-3-yl)-2,2,4-trimethyl-1H-[1]benzopyrano[3,4-f]quinoline (E) methyl 2-(2,5-dihydro-10-methoxy-2,2,4-trimethyl-1H-[1]benzopyrano[3,4-f]quinoline, (E) 2,5-dihydro-10-methoxy-5-(4-hydroxy-2-buten-1-yl)-2,2,4-trimethyl-1H-[1]benzopyrano[3,4-f]quinoline, (E) 2,5-dihydro-10-methoxy-5-(4-(N,N-dimethylaminocarbonyloxy)-2-buten-1-yl)-2,2,4-trimethyl-1H-[1]benzopyrano[3,4-f]quinoline, (E) 2,5-dihydro-10-methoxy-5-(4-(N-methylaminocarbonyloxy)-2-buten-1-yl)-2,2,4-trimethyl-1H-[1]benzopyrano[3,4-f]quinoline, (E) 2,5-dihydro-10-methoxy-5-(2-butenyl)-2,2,4-trimethyl-1H-[1]benzopyrano[3,4-f]quinoline, 2,5-dihydro-10-methoxy-5-(2-hydroxyethyl)-2,2,4-trimethyl-1H-[1]benzopyrano[3,4-f]quinoline, 2,5-dihydro-10-methoxy-5-(2-(N-benzylcarbonyloxy)ethyl)-2,2,4-trimethyl-1H-[1]benzopyrano[3,4-f]quinoline, 2,5-dihydro-10-methoxy-5-(2-(N-morpholinocarbonyloxy)ethyl)-2,2,4-trimethyl-1H-[1]benzopyrano[3,4-f]quinoline, 2,5-dihydro-10-methoxy-5-(2-(N-(2-methoxyethyl)aminocarbonyloxy)ethyl)-2,2,4 trimethyl-1H-[1]benzopyrano[3,4-f]quinoline, 2,5-dihydro-10-methoxy-5-(2-(N-methyaminocarbonyloxyoxy)ethyl)-2,2,4-trimethyl-1H-[1]benzopyrano[3,4-f]quinoline, 2,5-dihydro-10-methoxy-5-(2-(N,N-dimethylaminocarbonyloxy)ethyl)-2,2,4-trimethyl-1H-[1]benzopyrano[3,4-f]quinoline, 2,5-dihydro-10-methoxy-5-(2-methoxymethoxyethyl)-2,2,4-trimethyl-1H-[1]benzopyrano[3,4-f]quinoline, 2,5-dihydro-10-methoxy-5-(2,2-dimethylethoxycarbonylamino)methyl)-2,2,4-trimethyl-1H-[1]benzopyrano[3,4-f]quinoline, 2,5-dihydro-10-methoxy-5-(aminomethyl)-2,2,4-trimethyl-1H-[1]benzopyrano[3,4-f]quinoline, 2,5-dihydro-10-methoxy-5-(ethoxycarbonylamino)methyl)-2,2,4-trimethyl-1H-[1]benzopyrano[3,4-f]quinoline, 2,5-dihydro-10-methoxy-5-(carboethoxy)-2,2,4-trimethyl-1H-[1]benzopyrano[3,4-f]quinoline, 2,5-dihydro-10-methoxy-5-(cyclopentyl)-2,2,4-trimethyl-1H-[1]benzopyrano[3,4-f]quinoline 2,5-dihydro-10-methoxy-5-(1-methylpropa-1,2-dienyl)-2,2,4-trimethyl-1H-[1]benzopyrano[3,4-f]quinoline, 2,5-dihydro-10-methoxy-5-(3,4,5-trifluorophenyl)-2,2,4-trimethyl-1H-[1]benzopyrano[3,4-f]quinoline, 2,5-dihydro-10-methoxy-5-(cyclohexyl)-2,2,4-trimethyl-1H-[1]benzopyrano[3,4-f]quinoline, 2,5-dihydro-10-methoxy-5-(2-pyridyl)-2,2,4-trimethyl-1H-[1]benzopyrano[3,4-f]quinoline, 2,5-dihydro-10-methoxy-5-(3-pyridyl)-2,2,4-trimethyl-1H-[1]benzopyrano[3,4-f]quinoline, 2,5-dihydro-10-methoxy-5-(4-pyridyl)-2,2,4-trimethyl-1H-[1]benzopyrano[3,4-f]quinoline, 9-10-methylenedioxy-5-phenyl-2,2,4-trimethyl-1H-2,5-dihydro-[1]benzopyrano[3,4-f]quinoline, 9-chloro-10-methoxy-5-phenyl-2,2,4-trimethyl-2,5-dihydro-1H-[1]benzopyrano[3,4-f]quinoline, 5-(3-propenyl)-9-chloro-10-difluoromethoxy-2,2,4-trimethyl-2,5-dihydro-1H-[1]benzopyrano[3,4-f]quinoline, 9-chloro-10-difluoromethoxy-5-phenyl-2,2,4-trimethyl-2,5-dihydro-1H-[1]benzopyrano[3,4-f]quinoline 8-fluoro-10-methoxy-5-phenyl-2,2,4-trimethyl-2,5-dihydro-1H-[1]benzopyrano[3,4-f]quinoline 5-(3-propenyl)-8-fluoro-10-methoxy-2,2,4-trimethyl-2,5-dihydro-1H-[1]benzopyrano[3,4-f]quinoline (10-methoxy-9-fluoro-5-(3-propenyl)-2,2,4-trimethyl-1H-2,5-dihydro-[1]benzopyrano[3,4-f]quinoline 10-methoxy-9-hydroxy-5-(3-propenyl)-2,2,4-trimethyl-1H-2,5-dihydro-[1]benzopyrano[3,4-f]quinoline (+/−)2,5-dihydro-9-hydroxy-10-methoxy-2,2,4-trimethyl-5-(3-cyclohexenyl)-1H-[1]benzopyrano[3,4-f]quinoline (+/−)2,5-dihydro-9-hydroxy-10-methoxy-2,2,4-trimethyl-5-(1-methylcyclohexen-3-yl)-1H-[1]benzopyrano[3,4-f]quinoline, (−)(5S,3'S)-9-hydroxy-5-[1-methyl-3-cyclohexenyl]-10-methoxy-2,2,4-trimethyl-2,5-dihydro-1H-[1]benzopyrano[3,4-f]quinoline, (+)(5R,3'R)-9-hydroxy-5-[1-methyl-3-cyclohexenyl]-10-methoxy-2,2,4-trimethyl-2,5-dihydro-1H-[1]benzopyrano[3,4-f]quinoline, (+)(5R,3'S)-9-hydroxy-5-[1-methyl-3-cyclohexenyl]-10-methoxy-2,2,4-trimethyl-2,5-dihydro-1H-[1]benzopyrano[3,4-f]quinoline, (−)(5S,3'R)-9-hydroxy-5-[1-methyl-3-cyclohexenyl]-10-methoxy-2,2,4-trimethyl-2,5-dihydro-1H-[1]benzopyrano[3,4-f]quinoline, rel-(5S,3'R)-9-hydroxy-5-[1-hydroxymethyl-3-cyclohexenyl]-10-methoxy-2,2,4-trimethyl-2,5-dihydro-1H-[1]benzopyrano[3,4-f]quinoline, (+/−)(5S,3'R)-2,5-dihydro-9-hydroxy-10-methoxy-2,2,4-trimethyl-5-(1-methylcyclohexen-3-yl)-1H-[1]benzopyrano[3,4-f]quinoline, rel-(5S,3'R)-9-hydroxy-5-[1-methoxymethyl-3-cyclohexenyl]-10-methoxy-2,2,4-trimethyl-2,5-dihydro-1H-[1]benzopyrano[3,4-f]quinoline, 2,5-dihydro-9-hydroxy-10-methoxy-5-propyl-2,2,4-trimethyl-1H-[1]benzopyrano[3,4-f]quinoline, (−)(5S,3'S)-2,5-dihydro-9-hydroxy-10-methoxy-2,2,4-trimethyl-5-(3-cycloheptenyl)-1H-[1]benzopyrano[3,4-f]quinoline, (−)(5S,3'R)-2,5-dihydro-9-hydroxy-10-methoxy-2,2,4-trimethyl-5-(3-cycloheptenyl)-1H-[1]benzopyrano[3,4-f]quinoline, 2,5-dihydro-9-hydroxy-10-methoxy-2,2,4-trimethyl-5-phenyl-1H-[1]benzopyrano[3,4-f]quinoline, 2,5-dihydro-9-hydroxy-10-methoxy-2,2,4-trimethyl-5-(3,5-difluorophenyl)-1H-[1]benzopyrano[3,4-f]quinoline, 2,5-dihydro-9-hydroxy-10-methoxy-2,2,4-trimethyl-5-(3,4,5-trifluorophenyl)-1H-[1]benzopyrano[3,4-f]quinoline, 5-butyl-2,5-dihydro-9-hydroxy-10-methoxy-2,2,4-trimethyl-1H-[1]benzopyrano[3,4-f]quinoline, (−)(5S,3'S)-2,5-dihydro-9-hydroxy-10-methoxy-2,2,4-trimethyl-5-(3-cyclopentenyl)-1H-[1]benzopyrano[3,4-f]quinoline, (−)(5S,3'R)-2,5-dihydro-9-hydroxy-10-methoxy-2,2,4-trimethyl-5-(3-cyclopentenyl)-1H-[1]benzopyrano[3,4-f]quinoline, 2,5-dihydro-9-hydroxy-10-methoxy-2,2,4-trimethyl-5-(3,4-difluorophenyl)-1H-[1]benzopyrano[3,4-f]quinoline, 2,5-dihydro-9-hydroxy-10-methoxy-2,2,4-trimethyl-5-(4-fluorophenyl)-1H-[1]benzopyrano[3,4-f]quinoline, 2,5-dihydro-9-hydroxy-10-methoxy-2,2,4-trimethyl-5-(3-trifluoromethylphenyl)-1H-[1]benzopyrano[3,4-f]quinoline, 2,5-dihydro-9-hydroxy-10-methoxy-2,2,4-trimethyl-5-(3-5-bistrifluoromethylphenyl)-1H-[1]benzopyrano[3,4-f]quinoline, 2,5-dihydro-9-hydroxy-10-methoxy-2,2,4-trimethyl-5-(3-trifluoromethyl-4-chlorophenyl)-1H-[1]benzopyrano[3,4-f]quinoline, 2,5-dihydro-9-hydroxy-10-methoxy-2,2,4-trimethyl-5-(2-methylpropyl)-1H-[1]benzopyrano[3,4-f]quinoline, 2,5-dihydro-9-hydroxy-10-methoxy-2,2,4-trimethyl-5-(3-fluoro-4-chlorophenyl)-1H-[1]benzopyrano[3,4-f]quinoline, 2,5-dihydro-9-hydroxy-10-methoxy-2,2,4-trimethyl-5-(3-butenyl)-1H-[1]benzopyrano[3,4-f]quinoline, 2,5-dihydro-9-hydroxy-10-methoxy-5-(phenylmethyl)-2,2,4-trimethyl-1H-[1]benzopyrano[3,4-f]quinoline, (−)(5S,3'R) 2,5-dihydro-9-hydroxy-10-methoxy-2,2,4-trimethyl-5-[1-ethyl-3-cyclohexenyl]-1H-[1]benzopyrano[3,4-f]quinoline, (−)(S)-5-cyclopentyl-2,5-dihydro-9-hydroxy-10-methoxy-2,2,4-trimethyl-1-[1]benzopyrano[3,4-f]quinoline, (+)(R)-5-cyclopentyl-2,5-dihydro-9-hydroxy-10-methoxy-2,2,4-trimethyl-1H-[1]benzopyrano[3,4-f]quinoline, 2,5-dihydro-9-hydroxy-10-methoxy-5-(3-propynyl)-2,2,4-trimethyl-1H-[1]benzopyrano[3,4-f]quinoline, 2,5-dihydro-9-hydroxy-10-methoxy-2,2,4-trimethyl-5-(2-propyl)-1H-[1]benzopyrano[3,4-f]quinoline, 2,5-dihydro-9-hydroxy-10-methoxy-2,2,4-trimethyl-5-(5-methoxy-2-thienyl)-1H-[1]benzopyrano[3,4-f]quinoline, (±)2,5-dihydro-9-hydroxy-10-methoxy-2,2,4-trimethyl-5-(2,3,4,5,6-pentafluorophenyl)-1H-[1]benzopyrano[3,4-f]quinoline, (+/−)2,5-dihydro-9-hydroxy-10-methoxy-2,2,4-trimethyl-5(S)-(3(S)-1-hydroxymethylcyclopenten-3-yl)-1H-[1]benzopyrano[3,4-f]quinoline, (+/−)2,5-dihydro-9-hydroxy-10-methoxy-2,2,4-trimethyl-5(S)-(3(S)-1-methylcarboxylatecyclopenten-3-yl-1H-[1]benzopyrano[3,4-f]quinoline, (−)(5S,3'S) 2,5-dihydro-9-hydroxy-10-methoxy-2,2,4-trimethyl-5-(3-cyclohexenyl)-1H-[1]benzopyrano[3,4-f]quinoline, (−)(5S,3'R) 2,5-dihydro-9-hydroxy-10-methoxy-2,2,4-trimethyl-5-(3-cyclohexenyl)-1H-[1]benzopyrano[3,4-f]quinoline, 2,5-dihydro-9-hydroxy-10-methoxy-2,2,4-trimethyl-5-(2-thienyl)-1H-[1]benzopyrano[3,4-f]quinoline, (+)2,5-dihydro-9-hydroxy-10-methoxy-2,2,4-trimethyl-5-(2-methylphenyl)-1H-[1]benzopyrano[3,4-f]quinoline, 2,5-dihydro-9-hydroxy-10-methoxy-2,2,4-trimethyl-5-(2-acetoxymethyl-3propenyl)-1H-[1]benzopyrano[3,4-f]quinoline, (+)(5R,3'S)2,5-dihydro-9-hydroxy-10-methoxy-2,2,4-trimethyl-5-[1-ethyl-3-cyclohexenyl]-1H-[1]benzopyrano[3,4-f]quinoline, 2,5-dihydro-9-hydroxy-10-methoxy-2,2,4-trimethyl-5-cyclohexyl-1H-[1]benzopyrano[3,4-f]quinoline, 2,5,5-trihydro-9-hydroxy-10-methoxy-2,2,4-trimethyl-1H-[1]benzopyrano[3,4-f]quinoline, 2,5-dihydro-9-hydroxy-10-methoxy-2,2,4-trimethyl-5-(2-hydroxymethyl-3-propenyl)-1H-[1]benzopyrano[3,4-f]quinoline, methyl 2-[2,5-dihydro-9-hydroxy-10-methoxy-2,2,4-trimethyl-1H-[1]benzopyrano[3,4-f]-5-quinolinyl]acetate, (Z) 2,5-dihydro-9-hydroxy-10-methoxy-2,2,4-trimethyl-5-(2-butenyl)-1H-[1]benzopyrano[3,4-f]quinoline, 2,5-dihydro-9-hydroxy-10-methoxy-2,2,4-trimethyl-5-(3-methyl-2-butenyl)-1H-[1]benzopyrano[3,4-f]quinoline, (+)(5S,3'S) 2,5-dihydro-9-hydroxy-10-methoxy-2,2,4-trimethyl-5-(3-cyclohexenyl)-1H-[1]benzopyrano[3,4-f]quinoline, (+)(5R,3'R) 2,5-dihydro-9-hydroxy-10-methoxy-2,2,4-trimethyl-5-(3-cyclohexenyl)-1H-[1]benzopyrano[3,4-f]quinoline, (+)(5R,3'S)-2,5(R)-dihydro-9-hydroxy-10-methoxy-2,2,4-trimethyl-5-(3-cyclopentenyl)-1H-[1]benzopyrano[3,4-f]quinoline, (+)(5R,3'R)-2,5(R)-dihydro-9-hydroxy-10-methoxy-2,2,4-trimethyl-5-(3-cyclopentenyl)-1H-[1]benzopyrano[3,4-f]quinoline, rel-(5S)-9-hydroxy-5-[(3R)-(1-methoxycarbonyl)cyclohexen-3-yl]-10-methoxy-2,2-trimethyl-1H-[1]benzopyrano[3,4-f]quinoline, 2,5-dihydro-9-hydroxy-10-methoxy-2,2,4-trimethyl-5-(2-methyl-3-propenyl)-1H-[1]benzopyrano[3,4-f]quinoline, 9,10-Dimethoxy-5-(3-propenyl)-2,2,4-trimethyl-1H-2,5-dihydro-[1]benzopyrano[3,4-f]quinoline, 9,10-Dimethoxy-5-[3-cyclohexenyl]-methoxy-2,2,4-trimethyl-2,5-dihydro-1H -[1]benzopyrano[3,4-f]quinoline, 10-methoxy-9-ethoxy-5-(3-propenyl)-2,2,4-trimethyl-1H-2,5-dihydro-[1]benzopyrano[3,4-f]quinoline, 10-methoxy-9-(3-propenyloxy)-5-(3-propenyl)-2,2,4-trimethy-1H-2,5-dihydro-[1]benzopyrano[3,4-f]quinoline, 10-methoxy-9-(3-propynyloxy)-5-(3-propenyl)-2,2,4-trimethyl-1H-2,5-dihydro-[1]benzopyrano[3,4-f]quinoline, 2,5-dihydro-9-acetoxy-10-methoxy-2,2,4-trimethyl-5-(2-propenyl)-1H-[1]benzopyrano[3,4-f]quinoline, 2,5-dihydro-9-(4-N,N-dimethylamino-4-oxo-butanoyloxy)-10-methoxy-2,2,4-trimethyl-5-(2-propenyl)-1H-[1]benzopyrano[3,4-f]quinoline, 7-bromo-5-[3-cyclohexenyl]-10-methoxy-2,2,4-trimethyl-2,5-dihydro-1H-[1]benzopyrano[3,4-f]quinoline, 10-methoxy-7-bromo-5-(3-propenyl)-2,2,4-trimetyl-1H-2,5-dihydro-[1]benzopyrano[3,4-f]quinoline, 7-bromo-5-[1-methyl-3-cyclohexenyl]-10-methoxy-2,2,4-trimethyl-2,5-dihydro-1H-[1]benzopyrano[3,4-f]quinoline, 10-methoxy-9-bromo-5-(3-propenyl)-2,2,4-trimethyl-1H-2,5-dihydro-[1]benzopyrano[3,4-f]quinoline, 7,9-Dibromo-10-methoxy-5-(3-propenyl)-2,2,4-trimethyl-1H-2,5-dihydro-[1]benzopyrano[3,4-f]quinoline, 7,9-Dibromo-5-[cyclohexen-3-yl]-10-methoxy-2,2,4-trimethyl-2,5-dihydro-1H-[1]benzopyrano[3,4-f]quinoline, 7,9-Dibromo-5-[1-methyl-3-cyclohexenyl]-10-methoxy-2,2,4-trimethyl-2,5-dihydro-1H-[1]benzopyrano[3,4-f]quinoline, 10-methoxy-7-(2-ethenyl)-5-(3-propenyl)-2,2,4-trimethyl-1H-2,5-dihydro-[1]benzopyrano[3,4-f]quinoline, 10-methoxy-7-methyl-5-(3-propenyl)-2,2,4-trimethyl-1H-2,5-dihydro-[1]benzopyrano[3,4-f]quinoline, 10-methoxy-7-acetyl-5-(3-propenyl)-2,2,4-trimethyl-1H-2,5-dihydro-[1]benzopyrano[3,4-f]quinoline, (+/−)2,5-dihydro-9-methyl-10-methoxy-2,2,4-trimethyl-5-(1-methylcyclohexen-3-yl)-1H-[1]benzopyrano[3,4-f]quinoline, 10-methoxy-7-methyl-9-methyl-5-(3-propenyl)-2,2,4-trimethyl-1H-2,5-dihydro-[1]benzopyrano[3,4-f]quinoline, 2,5-dihydro-10-methoxy-5-(3-(N-methyl-N-(carbomethoxymethyl)aminocarbanyloxy)phenyl)-2,2,4-trimethyl-1H-[1]benzopyrano[3,4-f]quinoline, 2,5-dihydro-10-methoxy-5-(3-(N-methyl-N-(N-methylcarbonyl)aminocarbonyloxy)phenyl)-2,2,4-trimethyl-1H-[1]benzopyrano[3,4-f]quinoline, 2,5-dihydro-10-methoxy)-5-(3-(N-methylaminocarbonyloxy)phenyl)-2,2,4-trimethyl-1H-[1]benzopyrano[3,4-f]quinoline, 2,5-dihydro-10-methoxy-5-(3-(2-hydroxyethyl)phenyl)-2,2,4-trimethyl-1H-[1]benzopyrano[3,4-f]quinoline, 2,5-dihydro-10-methoxy-5-(3-(2-methanesulfonyloxyethyl)phenyl)-2,2,4-trimethyl-1H-[1]benzopyrano[3,4-f]quinoline, 2,5-dihydro-10-methoxy-5-(3-(2-methythioethyl)phenyt)-2,2,4-trimethyl-1H-[1]benzopyrano[3,4-f]quinoline, 2,5-dihydro-10-methoxy-5-(3-(2-(N,N-dimethylaminocarbonyloxy)ethyl)phenyl)-2,2,4-trimethyl-1H-[1]benzopyrano[3,4-f]quinoline, 2,5-dihydro-10-methoxy-5-(3-(2-(N,N-dimethylamino)ethyl)phenyl)-2,2,4-trimethyl-1H-[1]benzopyrano[3,4-f]quinoline, 2,5-dihydro-10-methoxy-5-cyclopropyl-2,2,4-trimethyl-1H-[1]benzopyrano[3,4-f]quinoline, 2,5-dihydro-10-methoxy-5-ethenyl-2,2,4-trimethyl-1H-[1]benzopyrano[3,4-f]quinoline, trans 2,5-dihydro-10-methoxy-5-(2-phenylethenyl)-2,2,4-trimethyl-1H-[1]benzopyrano[3,4-f]quinoline, 2,5-dihydro-10-methoxy-5-(2-phenylethynyl)-2,2,4-trimethyl-1H-[1]benzopyrano[3,4-f]quinoline, cis 2,5-dihydro-10-methoxy-5-(2-phenylethenyl)-2,2,4-trimethyl-1H-[1]benzopyrano[3,4-f]quinoline, 2,5-dihydro-10-methoxy-5-(2-methylpropenyl)-2,2,4-trimethyl-1H-[1]benzopyrano[3,4-f]quinoline, trans 2,5-dihydro-10-methoxy-5-(1-cyclohexenyl)-2,2,4-trimethyl-1H-[1]benzopyrano[3,4-f]quinoline, 2,5-dihydro-5-(3-propenyl)-10-methylthio-2,2,4-trimethyl-1H-[1]benzopyrano[3,4-f]quinoline, (+/−)-2,5-dihydro-9-(4-acetamidobutanoyloxy)-10-methoxy-2,2,4-trimethyl-5-allyl-1H-[1]benzopyrano[3,4-f]quinoline, 10-(difluoromethoxy)-2,5-dihydro-5-phenyl-2,2,4-trimethyl-1H-[1]benzopyrano[3,4-f]quinoline, 10-(bromodifluoromethoxy)-2,5-dihydro-5-phenyl-2,2,4-trimethyl-1H-[1]benzopyrano[3,4-f]quinoline, 2,5-dihydro-9-hydroxy-10-methoxy-2,2,4-trimethyl-5-((2-fluorophenyl)methyl)-1H-[1]benzopyrano[3,4-f]quinoline, 10-methoxy-5-(5-methylisoxazol-3-yl)methyidene-2,5-dihydro-5-phenyl-2,2,4-trimethyl-1H-[1]benzopyrano[3,4-f]quinoline, 10-methoxy-5-(3-methylisoxazol-5-yl)methyidene-2,5-dihydro-5-phenyl-2,2,4-trimethyl-1H-[1]benzopyrano[3,4-f]quinoline, 10-methoxy-5-(4,5-dimethyl-1,3-oxazol-2-yl)-methyidene-2,5-dihydro-5-phenyl-2,2,4-trimethyl-1H-[1]benzopyrano[3,4-f]quinoline, 10-methoxy-5-(6-chloropyridin-2-methyidene-2,5-dihydro-5-phenyl-2,2,4-trimethyl-1H-[1]benzoyrano[3,4-f]quinoline, 10-methoxy-5-(pyridin-2-yl)methyidene-2,5-dihydro-5-phenyl-2,2,4-trimethyl-1H-[1-f]quinoline, 10-methoxy-5-(but-3-enylidene)-2,5-dihydro-5-phenyl-2,2,4-trimethyl-1H-[1-f]quinoline, 10-methoxy-5-(1-methylpropylidene)-2,5-dihydro-5-phenyl-2,2,4-trimethyl-1H-[1-f]quinoline, 10-methoxy-5-(1-butylidene)-2,5-dihydro-5-phenyl-2,2,4-trimethyl-1H-[1-f]quinoline, Z-5-(benzylidenyl)-9-hydroxy-10-methoxy-2,2,4-trimethyl-1H-2,5-dihydro-[1]benzopyrano[3,4-f]quinoline, Z-5-(2,5-difluorobenzylidenyl)-9-hydroxy-10-methoxy-2,2,4-trimethyl-1H-2,5-dihydro-[1]benzopyrano[3,4-f]quinoline, Z-9-hydroxy-10-methoxy-5-(2-picolinylidenyl)-2,2,4-trimethyl-2,5-dihydro-1H-[1]benzopyrano[3,4-f]quinoline, 9-hydroxy-10-methoxy-5-(3,5-difluorophenyl)methylidene-2,5-dihydro-5-phenyl-2,2,4-trimethyl-1H-[1]benzopyrano[3,4-f]quinoline, 9-hydroxy-10-methoxy-5-(3,4-difluorophenyl)methylidene-2,5-dihydro-5-phenyl-2,2,4-trimethyl-1H-[1]benzopyrano[3,4-f]quinoline, (Z) 9-hydroxy-10-methoxy-5-((4-fluorophenyl)methylene)-2,2,4-trimethyl-1H-2,5-dihydro-[1]benzopyrano[3,4-f]quinoline, (Z)-9-hydroxy-10-methoxy-5-([2,3-difluorophenyl]methylene)-2,2,4-trimethyl-1H-2,5-dihydro-[1]benzopyrano[3,4-f]quinoline, Z-5-(3-fluorobenzylidenyl)-10-methoxy-9-hydroxy-2,2,4-trimethyl-2,5-dihydro-1H-[1]benzopyrano[3,4-f]quinoline, 9-hydroxy-10-methoxy-5-ethyl-2,2,4-trimethyl-2,5-dihydro-1H-[1]benzopyrano[3,4-f]quinoline, (+/−) 2,5-dihydro-9-cyanomethoxy-10-methoxy-2,2,4-trimethyl-5-allyl-1H-[1]benzopyrano[3,4-f]quinoline, 2,5-dihydro-9-(4-N,N-diethylamino-4-oxo-butanoyloxy)-10-methoxy-2,2,4-trimethyl-5-(2-propenyl)-1H-[1]benzopyrano[3,4-f]quinoline, 2,5-dihydro-9-(4-N-piperidino-4-oxo-butanoyloxy)-10-methoxy-2,2,4-trimethyl-5(2-propenyl)-1H-[1]benzopyrano[3,4-f]quinoline, 2,5-dihydro-9-(4-N-morpholino4-oxo-butanoyloxy)-10-methoxy-2,2,4-trimethyl-5-(2-propenyl)-1H-[1]benzopyrano[3,4-f]quinoline, 2,5-dihydro-9-(4-N,N-dimethylamino-4-oxo-butanoyloxy)-10-methoxy-2,2,4-trimethyl-5-(3,4,5-trifluorophenyl)-1H-[1]benzopyrano[3,4-f]quinoline, 2,5-dihydro-9-hydroxy-10-methoxy-2,2,4-trimethyl-5-(3-5-difluorophenylmethyl)-1H-[1]benzopyrano[3,4-f]quinoline, 2,5-dihydro-9-hydroxy-10-methoxy-2,2,4-trimethyl-5-cyclopentyl-1H-[1]benzopyrano[3,4-f]quinoline, 2,5-dihydro-9-hydroxy-10-methoxy-2,2,4-trimethyl-5-((2-fluorophenyl)methyl)-1H-[1]benzopyrano[3,4-f]quinoline, 2,5-dihydro-9-hydroxymethyl-10-methoxy-2,2,4-trimethyl-5-allyl-1H-[1]benzopyrano[3,4-f]quinoline, 2,5-dihydro-9-hydroxy-10-methoxy-2,2,4-trimethyl-5-(1-pentenyl)-1H-[1]benzopyrano[3,4-f]quinoline 2,5-dihydro-9-methylcarboxylate-10-methoxy-2,2,4-trimethyl-5-allyl-1H-[1]benzopyrano[3,4-f]quinoline 2,5-dihydro-9-hydroxy-10-methoxy-2,2,4-trimethyl-5-allenyl-1H-[1]benzopyrano[3,4-f]quinoline (−)(5S,3'S)-2,5-dihydro-10-methoxy-2,2,4-trimethyl-5-(cyclopenten-3-yl)-1H-[1]benzopyrano[3,4-f]quinoline (−)(5S,3'S)-2,5-dihydro-10-methoxy-2,2,4-trimethyl-5-(cyclohexen-3-yl)-1H-[1]benzopyrano[3,4-f]quinoline (−)(5S,3'R)-2,5-dihydro-10-methoxy-2,2,4-trimethyl-5-(cyclohexen-3-yl)-1H-[1]benzopyrano[3,4-f]quinoline (−)(5S,3'R)-2,5-dihydro-10-methoxy-2,2,4-trimethyl-5-(cyclopenten-3-yl)-1H-[1]benzopyrano[3,4-f]quinoline 2,5-dihydro-9-hydroxy-10-methoxy-2,2,4-trimethyl-5-(3(Z)-pentenyl)-1H-[1]benzopyrano[3,4-f]quinoline 2,5-dihydro-9-hydroxy-10-methoxy-2,2,4-trimethyl-5-(3-acetoxyphenyl)-1H-[1]benzopyrano[3,4-f]quinoline 10-difluoromethoxy-5-[[3-(methylthio)methoxy]phenyl]-2,2,4-trimethyl-1H-2,5-dihydro-[1]benzopyrano[3,4-f]quinoline, 2,5-dihydro-9-hydroxy-10-methoxy-2,2,4-trimethyl-5-(3-hydroxyphenyl)-1H-[1]benzopyrano[3,4-f]quinoline, 2,5-dihydro-9-methylthiomethoxy-10-methoxy-2,2,4-trimethyl-5-(3(methylthio)methoxyphenyl)-1H-[1]benzopyrano[3,4-f]quinoline, 2,5-dihydro-9-hydroxy-10-methoxy-2,2,4-trimethyl-5-(3(methylthiomethoxy)phenyl)-1H-[1]benzopyrano[3,4-f]quinoline, 2,5-dihydro-9-N,N-dimethylcarbamoyloxy-10-methoxy-2,2,4-trimethyl-5-([2-N,N-dimethylcarbamoyloxy]phenyl)-1H-[1]benzopyrano[3,4-f]quinoline, 9-hydroxy-10-methoxy-5-(phenylmethylene)-2,2,4-trimethyl-1H-2,5-dihydro-[1]benzopyrano[3,4-f]quinoline, 9-hydroxy-10-methoxy-5-([3-fluorophenyl]methylene)-2,2,4-trimethyl-1H-2,5-dihydro-[1]benzopyrano[3,4-f]quinoline, rel-(5S)-9-hydroxy-5-[(3S)-(1-methoxycarbonyl)cyclohexen-3-yl]-10-methoxy-2,2,4-trimethyl-2,5-dihydro-1H-[1]benzopyrano[3,4-f]quinoline, 2,5-dihydro-9-hydroxy-10-methoxy-2,2,4-trimethyl-5-(3,5-dichlorophenyl)-1H-[1]benzopyrano[3,4-f]quinoline, 2,5-dihydro-9-(4-N,N-dimethylamino-4-oxo-butanoyloxy)-10-methoxy-2,2,4-trimethyl-5-(1-methylethyl)-1H-[1]benzopyrano[3,4-f]quinoline, 2,5-dihydro-9-(4-N,N-dimethylamino-4-oxo-butanoyloxy)-10-methoxy-5-(phenylmethyl)-2,2,4-trimethyl-1H-[1]benzopyrano[3,4-f]quinoline, 2,5-dihydro-9-(4-N,N-dimethylamino-4-oxo-butanoyloxy)-10-methoxy-2,2,4-trimethyl-5-(2-thienyl)-1H-[1]benzopyrano[3,4-f]quinoline, 2,5-dihydro-9-(4-N,N-dimethylaminobutanoyloxy)-10-methoxy-2,2,4-trimethyl-5-(2-propenyl)-1H-[1]benzopyrano[3,4-f]quinoline, 9-(2-ethoxy-2-oxo-ethylaminocarbonyl)-oxy-10-methoxy-5-(3-propenyl)-2,2,4-trimethyl-1H-2,5-dihydro-[1]benzopyrano[3,4-f]quinoline, (+/−)2,5-dihydro-9-(3-acetamido-propanoyloxy)-10-methoxy-2,2,4-trimethyl-5-allyl-1H-[1]benzopyrano[3,4-f]quinoline, 9-hydroxy-10-methoxy-5-(phenylmethylene)-2,2,4-trimethyl-1H-2,5-dihydro-[1]benzopyrano[3,4-f]quinoline, 9-(dimethylaminothiocarbonyl)-oxy-10-methoxy-5-(3-propenyl)-2,2,4-trimethyl-1H-2,5-dihydro-[1]benzopyrano[3,4-f]quinoline, (+/−)2,5-dihydro-9-(N-carbamoyl-2-aminoacetoxy)-10-methoxy-2,2,4-trimethyl-5 allyl-1H-[1]benzopyrano[3,4-f]quinoline, (+/−)2,5-dihydro-9-(4-ethoxy-4-oxo-butoxy)-10-methoxy-2,2,4-trimethyl-5-allyl-1H-[1]benzopyrano[3,4-f]quinoline, (+/−)2,5-dihydro-9-(4-oxo-pentanoyloxy)-10-methoxy-2,2,4-trimethyl-5-allyl-1H-[1]benzopyrano[3,4-f]quinoline, 2,5-dihydro-9-methylthiomethoxy-10-methoxy-2,2,4-trimethyl-5-allyl-1H-[1]benzopyrano[3,4-f]quinoline, 2,5-dihydro-9-(4-N,N-diethylamino-4-oxo-pentanoyloxy)-10-methoxy-2,2,4-trimethyl-5-(2-propenyl)-1H-[1]benzopyrano[3,4-f]quinoline, 2,5-dihydro-9-(4-N,N-dimethylamino-4-oxo-pentanoyloxy)-10-methoxy-2,2,4-trimethyl-5-(2-propenyl)-1H-[1]benzopyrano[3,4-f]quinoline, 2,5-dihydro-9-(4-N-pipenidino-4-oxo-pentanoyloxy)-10-methoxy-2,2,4-trimethyl-5-(2-propenyl)-1H-[1]benzopyrano[3,4-f]quinoline, 2,5-dihydro-9-(4-N-morpholino-4-oxo-pentanoyloxy)-10-methoxy-2,2,4-trimethyl-5-(2-propenyl)-1H-[1]benzopyrano[3,4-f]quinoline, (−)2,5-dihydro-9-(4-N,N-dimethylamino-4-oxo-butanoyloxy)-10-methoxy-2,2,4-trimethyl-5(S)-(3(S)-1-cyclopenten-3-yl)-1H-[1]benzopyrano[3,4-f]quinoline, 10-methoxy-9-(allylaminocarbonyl)oxy-5-(3-propenyl)-2,2,4-trimethyl-1H-2,5-dihydro-[1]benzopyrano[3,4-f]quinoline, 10-methoxy-9-(cyclohexylaminocarbonyl)-oxy-5-(3-propenyl)-2,2,4-trimethyl-1H-2,5-dihydro-[1]benzopyrano[3,4-f]quinoline, 2,5-dihydro-9-hydroxy-10-methoxy-2,2,4-trimethyl-5-(3-thienyl)-1H-[1]benzopyrano[3,4-f]quinoline, 2,5-dihydro-9-hydroxy-10-methoxy-2,2,4-trimethyl-5-(4-(fluorophenyl)methyl)-1H-[1]benzopyrano[3,4-f]quinoline, and 10-benzyloxy-5-(2-propenyl)-2,5-dihydro-2,2,4-trimethyl-1H-[1]benzopyrano[3,4-f]quinoline, rel-(5S,3'R)-9-hydroxy-10-methoxy-5-{1-hydroxymethyl-cyclohexyl}-2,2,4-trimethyl-2,5-dihydro-1H-[1]benxopyrano[3,4-f]quinoline, and 2,5-dihydro-9-hydroxy-10-methoxy-2,2,4-trimethyl-5-(1-thiazol-2-yl)-1H-[1]benzopyrano[3,4-f]quinoline.

5. The composition of claim 1 or 2 where $R_1$ is —$L_1$—$R_A$, $L_1$ is a covalent bond and $R_A$ is —$NR_7R'_7$.

6. The composition of claim 1 or 5 selected from 2,5-dihydro-2,2,4,N-tetramethyl-5-(2-propenyl)-1H-[1]benzopyrano[3,4-f]quinolin-10-amine, 5-(3,5-dichlorophenyl)-2,5-dihydro-2,2,4,N-tetramethyl-1H-[1]benzopyrano[3,4-f]quinolin-10-amine, and 5-(3,5-dichlorophenyl)-2,5-dihydro-2,2,4-trimethyl-N-(2-propenyl)-1H-[1]benzopyrano[3,4-f]quinolin-10-amine.

7. The composition of claim 1 or 2 where $R_1$ is —$L_1$—$R_A$, $L_1$ is —C(X)X'—, X and X' are —O—, and $R_A$ is alkyl of one to twelve carbons optionally substituted as defined in claim 1.

8. The composition of claim 1 or 7 selected from methyl 2,5-dihydro-2,2,4-trimethyl-5-(2-propenyl)-1H-[1]benzopyrano[3,4-f]quinoline-10-carboxylate, and methyl 2,5-dihydro-5-phenyl-2,2,4-trimethyl-1H-[1]benzopyrano[3,4-f]quinoline-10-carboxylate.

9. The composition of claim 1 or 2 where $R_1$ is —$L_1$—$R_A$, $L_1$ is —X'C(X)—, X and X' are —O—, and $R_A$ is alkyl of one to twelve carbons optionally substituted as defined in claim 1.

10. The composition of claim 1 or 9 that is 2,5-dihydro-2,2,4-trimethyl-5-phenyl-1H-[1]benzopyrano[3,4-f]quinoline-10-ol acetate (ester).

11. The composition of claim 1 or 9 where $R_1$ is —$L_1$—$R_A$, $L_1$ is a covalent bond and $R_A$ is alkyl of one to twelve carbons optionally substituted as defined in claim 1.

12. The composition of claim 1 or 11 selected from 10-ethyl-2,5-dihydro-2,2,4-trimethyl-5-phenyl-1H-[1]benzopyrano[3,4-f]quinoline, 2,5-dihydro-2,2,4,10-tetramethyl-5-phenyl-1H-[1]benzopyrano[3,4-f]quinoline, 5-(3,5-dichlorophenyl)-10-ethyl-2,5-dihydro-2,2,4-trimethyl-1H-[1]benzopyrano[3,4-f]quinoline, 2,5-dihydro-2,2,4-trimethyl-5-(2-propenyl)-1H-[1]benzopyrano[3,4-f]quinoline-10-methanol, 2,5-dihydro-10-(2-hydroxymethyl)-5-(3-propenyl)-2,2,4-trimethyl-1H-[1]benzopyrano[3,4-f]quinoline, 2,5-dihydro-10-aminomethyl-5-(3-propenyl)-2,2,4-trimethyl-1H-[1]benzopyrano[3,4-f]quinoline, 2,5-dihydro-10-methoxymethyl-5-(3-propenyl)-2,2,4-trimethyl-1H-[1)benzopyrano[3,4-f]quinoline, 2,5-dihydro-10-(hydroxymethyl)-5-phenyl-2,2,4-trimethyl-1H-[1]benzopyrano[3,4-f]quinoline, 2,5-dihydro-10-(methoxymethyl)-5-phenyl-2,2,4-trimethyl-1H-[1]benzopyrano[3,4-f]quinoline, and 10-carbaldehyde oxime-5-(2-propenyl)-2,5-dihydro-2,2,4-trimethyl-1H-[1]benzopyrano[3,4-f]quinoline.

13. The composition of claim 1 or 2 where $R_1$ is —$L_1$—$R_A$, $L_1$ is a covalent bond, and $R_A$ is alkenyl of two to twelve carbons optionally substituted as defined in claim 1.

14. The composition of claim 1 or 13 selected from 10-ethenyl-2,5-dihydro-2,2,4-trimethyl-5-(2-propenyl)-1H-[1]benzopyrano[3,4-f]quinoline, 2,5-dihydro-dihydro-10-ethenyl-5-phenyl-2,2,4-trimethyl-1H-[1]benzopyrano[3,4-f]quinoline, 2,5-dihydro-10-ethenyl-5-oxo-2,2,4-trimethyl-1H-[1]benzopyrano[3–4-f]quinoline, 5-(3-cyclohexenyl)-2,5-dihydro-10-ethenyl-2,2,4-trimethyl-1H-[1]benzopyrano[3,4-f]quinoline, 2,5-dihydro-10-ethenyl-5-[1-methyl-3-cyclohexenyl]-2,2,4-trimethyl-1H-[1]benzopyrano[3,4-f]quinoline, and 5-(3-propenyl)-9-chloro-10-ethenyl-2,2,4-trimethyl-2,5-dihydro-1H-{1}benzopyrano[3,4-f]quinoline.

15. The composition of claim 1 or 2 where $R_1$ is —$L_1$—$R_A$, $L_1$ is a covalent bond and $R_A$ is alkynyl of two to twelve carbons optionally substituted as defined in claim 1.

16. The composition of claim 1 or 2 selected from 10-ethynyl-2,5-dihydro-2,2,4-trimethyl-5-(2-propenyl)-1H-[1]benzopyrano[3,4-f]quinoline, and 2,5-dihydro-10-ethynyl-5-phenyl-2,2,4-trimethyl-1H-[1]benzopyrano[3,4-f]quinoline.

17. The composition of claim 1 or 2 where $R_1$ is —$L_1$—$R_A$, $L_1$ is a covalent bond and $R_A$ is —OH, halo, heterocycle, —CN, —$CO_2$H, or —CHO.

18. The composition of claim 1 or 17 selected from 2,5-dihydro-2,2,4-trimethyl-5-phenyl-1H-[1]benzopyrano[3,4-f]quinolin-10-ol, 5-(3,5-dichlorophenyl)-2,5-dihydro-2,2,4-trimethyl-1H-[1]benzopyrano[3,4-f]quinolin-10-ol, 2,5-dihydro-2,2,4-trimethyl-5-(2-propenyl)-1H-[1]benzopyrano[3,4-f]quinolin-10-ol, 10-chloro-9-hydroxy-5-(3-propenyl)-2,2,4-trimethyl-1H-2,5-dihydro-[1]benzopyrano[3,4-f]quinoline, 10-chloro-9-hydroxy-5-phenyl-2,2,4-trimethyl-1H-2,5-dihydro-[1]benzopyrano[3,4-f]quinoline, 0-chloro-9-hydroxy-5-(3-trifluoromethylphenyl)-2,2,4-trimethyl-1H-2,5-dihydro-[1]benzopyrano[3,4-f]quinoline, 10-chloro-9-hydroxy-5-(3,5-dimethylphenyl)-2,2,4-trimethyl-1H-2,5-dihydro-[1]benzopyrano[3,4-f]quinoline, rel-(5S,3'R)-9-hydroxy-10-methoxy-5-[1-hydroxymethyl-3-cyclohexenyl]-2,2,4-trimethyl-1H-[1]benzopyrano[3,4-f]quinoline, (−)2,5(S)-dihydro-9-hydroxy-10-chloro-2,2,4-trimethyl-5-(3S-cyclopentenyl)-1H-[1]benzopyrano[3,4-f]quinoline, (−)2,5(S)-dihydro-9-hydroxy-10-chloro-2,2,4-trimethyl-5-(3R-cyclopentenyl)-1H-[1]benzopyrano[3,4-f]quinoline, 10-chloro-9-hydroxy-5-(3,5-dichlorophenyl)-2,2,4-trimethyl-1H-2,5-dihydro-[1]benzopyrano[3,4-f]quinoline, (+)-(5R,3'S)-2,5-dihydro-9-hydroxy-10-chloro-2,2,4-trimethyl-5-(3-cyclopentenyl)-1H-[1]benzopyrano[3,4-f]quinoline, (+)-(5R,3'R)-2,5-dihydro-9-hydroxy-10-chloro-2,2,4-trimethyl-5-(3-cyclopentenyl)-1H-[1]benzopyrano[3,4-f]quinoline, 10-chloro-9-hydroxy-5-(3,4-difluorophenyl)-2,2,4-trimethyl-1H-2,5-dihydro-[1]benzopyrano[3,4-f]quinoline, 10-chloro-5-(3-propenyl)-2,2,4-trimethyl-2,5-dihydro-1H-[1]benzopyrano[3,4-f]quinoline (+/−)2,5-dihydro-10-chloro-2,2,4-trimethyl-5-phenyl-1H-[1]benzopyrano[3,4-f]quinoline 2,5-dihydro-10-(2-furanyl)-5-(3-propenyl)-2,2,4-trimethyl-1H-[1]benzopyrano[3,4-f]quinoline 2,5-dihydro-10-cyano-5-(3-propenyl)-2,2,4-trimethyl-1H-[1]benzopyrano[3,4-f]quinoline 2,5-dihydro-10-carboxy-5-(3-propenyl)-2,2,4-trimethyl-1H-[1]benzopyrano[3,4-f]quinoline 2,5-dihydro-10-formyl-5-(3-propenyl)-2,2,4-trimethyl-1H-[1]benzopyrano[3,4-f]quinoline 2,5-dihydro-10-formyl-5-phenyl-2,2,4-trimethyl-1H-[1]benzopyrano[3,4-f]quinoline, Z-5-(3-fluorobenzylidenyl)-10-chloro-9-hydroxy-2,2,4-trimethyl-2,5-dihydro-1H-[1]benzopyrano[3,4-f]quinoline, Z-10-chloro-9-hydroxy-5-(2-picolinylidenyl)-2,2,4-trimethyl-2,5-dihydro-1H-[1]benzopyrano[3,4-f]quinoline, rel-(5S,3'R)-9-hydroxy-5-[1-methoxymethyl-3-cyclohexenyl]-10-chloro-2,2,4-trimethyl-2,5-dihydro-1H-[1]benzopyrano[3,4-f]quinoline, 2,5-dihydro-9-hydroxy-10-chloro-2,2,4-trimethyl-5-(2-thienyl)-1H-[1]benzopyrano[3,4-f]quinoline, 9-hydroxy-10-chloro-5-(phenylmethylene)-2,2,4-trimethyl-1H-2,5-dihydro-[1]benzopyrano[3,4-f]quinoline, and 2,5-dihydro-9-hydroxy-10-chloro-2,2,4-trimethyl-5-(3,4,5-trifluorophenyl)-1H-[1]benzopyrano[3,4-f]quinoline, 2,5-dihydro-7-bromo-9-hydroxy-10-chloro-2,2,4-trimethyl-5-allyl-1H-[1]benzopyrano[3,4-f]quinoline, 2,5-dihydro-9-hydroxy-10-chloro-2,2,4-trimethyl-5-([2-N,N-dimethylcarbamoyloxy]phenyl)-1H-[1]benzopyrano[3,4-f]quinoline, 2,5-dihydro-9-hydroxy-10-chloro-2,2,4-trimethyl-5-ethyl-1H-[1]benzopyrano[3,4-f]quinoline, 2,5-dihydro-9-hydroxy-10-chloro-2,2,4-trimethyl-5-isopropyl-1H-[1]benzopyrano[3,4-f]quinoline, 2,5-dihydro-9-hydroxy-10-chloro-2,2,4-trimethyl-5-butyl-1H-[1]benzopyrano[3,4-f]quinoline, 2,5-dihydro-9-hydroxy-10-methoxy-2,2,4-trimethyl-5-(1-thiazol-2-yl)-1H-[1]benzopyrano[3,4-f]quinoline, 2,5-dihydro-9-hydroxy-10-chloro-2,2,4-trimethyl-5-(2-methylpropyl)-1H-[1]benzopyrano[3,4-f]quinoline, 2,5-dihydro-9-hydroxymethyl-10-chloro-2,2,4-trimethyl-5-allyl-1H-[1]benzopyrano[3,4-f]quinoline, 2,5-dihydro-9-hydroxy-10-chloro-2,2,4-trimethyl-5-propyl-1H-[1]benzopyrano[3,4-f]quinoline, 9-hydroxy-10-chloro-5-([2-pyridyl]methylene)-2,2,4-trimethyl-1H-2,5-dihydro-[1]benzopyrano[3,4-f]quinoline, rel-(5S)-9-hydroxy-5-[(3S)-(1-hydroxymethyl)cyclohexen-3-yl]-10-chloro-2,2,4-trimethyl-2,5-dihydro-1H-[1]benzopyrano[3,4-f]quinoline, (−)(5S,3'S)-2,5-dihydro-9-hydroxy-10-chloro-2,2,4-trimethyl-5-(1-methylcyclohexen-3-yl)-1H-[1]benzopyrano[3,4-f]quinoline, (−)(5S,3'R)-2,5-dihydro-9-hydroxy-10-chloro-2,2,4-trimethyl-5-(1-methylcyclohexen-3-yl)-1H-[1]benzopyrano[3,4-f]quinoline, (+)(5R,3'S)-2,5-dihydro-9-hydroxy-10-chloro-2,2,4-trimethyl-5-(1-methylcyclohexen-3-yl)-1)-1H-[1]benzopyrano[3,4-f]quinoline, (+)(5R,3'R)-2,5-dihydro-9-hydroxy-10-chloro-2,2,4-trimethyl-5-(1-methylcyclohexen-3-yl)-[1]benzopyrano[3,4-f]quinoline, (+/−)-2,5-dihydro-9-(4-N,N-dimethylamino-4-oxo-butanoyloxy)-10-chloro-2,2,4-trimethyl-5-allyl-1H-[1]benzopyrano[3,4-f]quinoline, (−)2,5-dihydro-9-hydroxy-10-chloro-2,2,4-trimethyl-5-cyclopentyl-1H-[1]benzopyrano[3,4-f]quinoline, (+/−)2,5-dihydro-9-hydroxy-10-chloro-2,2,4-trimethyl-5-benzyl-1H-[1]benzopyrano[3,4-f]quinoline, and 2,5-dihydro-2,2,4-trimethyl-5-(2-propenyl)-1H-[1] benzopyrano[3,4-f]quinloine-10-carboxylic acid.

19. The composition of claim 1 or 2 where $R_1$ is —$L_1$—$R_A$, $L_1$ is O and $R_A$ is alkenyl of three to twelve carbons optionally substituted as defined in claim 1.

20. The composition of claim 1 or 19 that is 2,5-dihydro-2,2,4-trimethyl-5-phenyl-10-(2-propenyloxy)-1H-[1]benzopyrano[3,4-f]quinoline.

21. The composition of claim 1 or 2 where $R_1$ is —$L_1$—$R_A$, $L_1$ is O and $R_A$ is alkynyl of three to twelve carbons optionally substituted in the manner set forth in claim 1.

22. The composition of claim 1 or 21 that is 2,5-dihydro-2,2,4-trimethyl-5-phenyl-10-(2-propynyloxy)-1H-[1]benzopyrano[3,4-f]quinoline.

23. The composition of claim 1 or 2 where $R_1$ is —$L_1$—$R_A$, $L_1$ is —X'C(X)X"—, X, X' and X" are O.

24. The composition of claim 1 or 23 that is 5-(3,5-dichlorophenyl)-2,5-dihydro-2,2,4-trimethyl-1H-[1]benzopyrano[3,4-f]quinolin-10-yl]-methylcarbonate.

25. The composition of claim 1 or 2 of Formula III

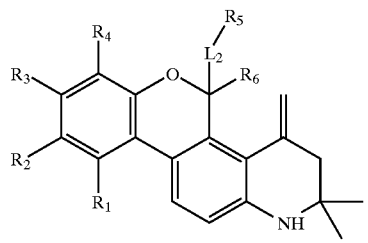

III or a pharmaceutically acceptable salt thereof, and a pharmaceutical carrier, where $R_1$, $R_2$, $R_3$, $R_4$, $R_5$, $R_6$, and $L_2$, are as defined in claim 1 or 2.

26. The composition of claim 1 or 25 where $R_1$ is —$L_1$—$R_A$, $L_1$ is —O—, and $R_A$ is alkyl of one to twelve carbons optionally substituted as in claim 1.

27. The composition of claim 1 or 26 that is 10-(bromodifluoromethoxy)-5-phenyl-2,2-dimethyl-4-methylene-2,3,4,5-tetrahydro-1H-chromeno[3,4-f] quinoline.

28. The composition of claim 1 or 2 of Formula V

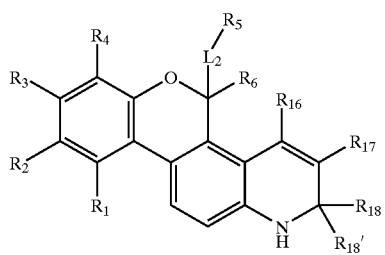

(V)

or a pharmaceutically acceptable salt thereof, and a pharmaceutical carrier, where $R_1$, $R_2$, $R_3$, $R_4$, $R_5$, $R_6$, and $L_2$, are as defined in claim 1 or 2;

$R_{16}$ and $R_{17}$ are independently hydrogen or alkyl of one to six carbons; and $R_{18}'$ and $R_{18}$, are independently hydrogen or alkyl of one to six carbons; or $R_{18}$ and $R_{18'}$ together are a cycloheteroalkyl ring or a cycloalkyl ring of three to eight carbons.

29. The composition of claim 1 or 28 where $R_1$ is —$L_1$—$R_A$, $L_1$ is —O—, and $R_A$ is alkyl of one to three carbons optionally substituted in the manner set forth in claim 1.

30. The composition of claim 1 or 29 selected from 2,5-dihydro-10-methoxy-2,2-[spiro (tetrahydro-4-pyranyl)]-4-methyl-5-allyl-1H-[1]benzopyrano[3,4-f] quinoline, 2,5-dihydro-10-methoxy-2,2-[spiro(hexyl)]-5-allyl-1H-[1]benzopyrano[3,4-f]quinoline, 2,5-dihydro-10-methoxy-2,2-diethyl-4-methyl-5-allyl-1H-[1]benzopyrano[3,4-f]quinoline, 2,5-dihydro-10-methoxy-2,2,3,4-tetramethyl-5-allyl-1H-[1]benzopyrano[3,4-f]quinoline, 2,5-dihydro-10-methoxy-2,2-dimethyl-4-ethyl-5-allyl-1H-[1]benzopyrano[3,4-f]quinoline, and 2,5-dihydro-10-methoxy-2,2,3-trimethyl-5-allyl-1H-[1]benzopyrano[3,4-f]quinoline.

31. The composition of claim 1 or 2 wherein Ri is selected from amino, $C_1$–$C_3$-alkyl, $C_2$–$C_4$-alkoxycarbonyloxy, $C_1$–$C_3$-aminoalkyl, $C_3$-alkenylamino, $C_2$–$C_4$-alkanoyloxy, $C_1$–$C_3$-alkylamine, cyano, $C_3$–$C_4$-cycloalkyl, $C_2$–$C_3$-alkenyl, $C_2$–$C_3$-alkynyl, $C_3$-alkenyloxy, $C_3$-alkynyloxy, $C_1$–$C_3$-alkoxy, $C_2$–$C_3$-alkoxycarbonyl, $C_2$–$C_4$-alkoxyalkyl, benzyl, carbaldehyde oxime, $C_1$–$C_3$-dialkylamine, carboxy, furan-2-yl, halo, hydroxyl, $C_1$–$C_3$-hydroxyalkyl, formyl, and $C_1$–$C_3$-thioalkoxy.

32. The composition of claim 1 or 2 wherein $R_1$ is methoxy.

33. The composition of claim 1 or 2 selected from 2,5-dihydro-10-methoxy-2,2,4-trimethyl-5-phenyl-1H-[1]benzopyrano[3,4-f]quinoline, 2,5-dihydro-10-methoxy-2,2,4-trimethyl-5-(2-propenyl)-1H-[1]benzopyran[3,4-f]quinoline, 2,5-dihydro-2,2,4,N-tetramethyl-5-(2-propenyl)-1H-[1]benzopyrano[3,4-f]quinolin-10-amine, methyl 2,5-dihydro-2,2,4-trimethyl-5-(2-propenyl)-1H-[1]benzopyrano[3,4-f]quinoline-10-carboxylate, 10-ethenyl-2,5-dihydro-2,2,4-trimethyl-5-(2-propenyl)-1H-[1]benzopyrano[3,4-f]quinoline, 2,5-dihydro-2,2,4-trimethyl-5-phenyl-1H-[1] benzopyrano[3,4-f]quinolin-10-ol, 10-(difluoromethoxy)-2,5-dihydro-2,2,4-trimethyl-5-(2-propenyl)-1H-[1]benzopyrano[3,4-f]quinoline, 10-ethoxy-2,5-dihydro-2,2,4-trimethyl-5-phenyl-1H-[1]benzopyrano[3,4-f]quinoline, 2,5-dihydro-2,2,4-trimethyl-5-phenyl-1H-[1] benzopyrano[3,4-f]quinoline-10-ol acetate(ester), 5-(3-bromo-5-methylphenyl)-2,5-dihydro-10-methoxy-2,2,4-trimethyl-1H-[1]benzopyrano[3,4-f]quinoline, 3-(2,5-dihydro-10-methoxy-2,2,4-trimethyl-1H-[1] benzopyrano[3,4-f]quinolin-5-yl)phenol,acetate(ester), 3-(2,5-dihydro-10-methoxy-2,2,4-trimethyl-1H-[1] benzopyrano[3,4-f]quinolin-5-yl)phenol, 2,5-dihydro-10-methoxy-2,2,4-trimethyl-5-[[3-(methylthio)methoxy]phenyl]-1H-[1]benzopyrano[3,4-f]quinoline,

[3-(2,5-dihydro-10-methoxy-2,2,4-trimethyl-1H-[1] benzopyrano[3,4-f]quinolin-5-yl)phenyl] dimethylcarbamate, 5-[3-(2-furanyl)-5-methylphenyl]-2,5-dihydro-10-methoxy-2,2,4-trimethyl-1H-[1]benzopyrano[3,4-f] quinoline, 2,5-dihydro-10-methoxy-2,2,4-trimethyl-5-[3-methyl-5-(1-morpholinyl)phenyl]-1H-[1]benzopyrano[3,4-f]quinoline, 2,5-dihydro-10-methoxy-2,2,4-trimethyl-5-(phenylmethylene)-1H-[1]benzopyrano[3,4-f]quinoline, 5-(3,5-dichlorophenyl)-2,5-dihydro-10-methoxy-2,2,4-trimethyl-1H-[1]benzopyrano[3,4-f]quinoline, 5-butyl-2,5-dihydro-10-methoxy-2,2,4-trimethyl-1H-[1]benzopyrano[3,4-f]quinoline, 2,5-dihydro-10-methoxy-2,2,4-trimethyl-5-[3-(trifluoromethyl)phenyl]-1H-[1]benzopyrano[3,4-f]quinoline, 2,5-dihydro-10-methoxy-5-(4-methoxyphenyl)-2,2,4-trimethyl-1H-[1]benzopyrano[3,4-f]quinoline, 5-(3-chlorophenyl)-2,5-dihydro-10-methoxy-2,2,4-trimethyl-1H-[1]benzopyrano[3,4-f]quinoline, 2,5-dihydro-10-methoxy-2,2,4-trimethyl-5-(3-methylphenyl)-1H-[1]benzopyrano[3,4-f]quinoline, (±)-2,5-dihydro-10-methoxy-2,2,4-trimethyl-5-phenyl-1H-[1]benzopyrano[3,4-f]quinoline, 5-(3,5-dimethylphenyl)-2,5-dihydro-10-methoxy-2,2,4-trimethyl-1H-[1]benzopyrano[3,4-f]quinoline 5-(4-chlorophenyl)-2,5-dihydro-10-methoxy-2,2,4-trimethyl-1H-[1]benzopyrano[3,4-f]quinoline 5-(3,4-dimethylphenyl)-2,5-dihydro-10-methoxy-2,2,4-trimethyl-1H-[1]benzopyrano[3,4-f]quinoline 5-(4-fluorophenyl)-2,5-dihydro-10-methoxy-2,2,4-trimethyl-1H-[1]benzopyrano[3,4-f]quinoline, 5-[3,5-bis(trifluoromethyl)phenyl]-2,5-dihydro-10-methoxy-2,2,4-trimethyl-1H-[1]benzopyrano[3,4-f]quinoline (−)-5-(3,5-dichlorophenyl)-2,5-dihydro-10-methoxy-2,2,4-trimethyl-1H-[1]benzopyrano[3,4-f]quinoline (+)-5-(3,5-dichlorophenyl)-2,5-dihydro-10-methoxy-2,2,4-trimethyl-1H-[1]benzopyrano[3,4-f]quinoline, 5-(3,5-difluorophenyl)-2,5-dihydro-10-methoxy-2,2,4-trimethyl-1H-[1]benzopyrano[3,4-f]quinoline, 2,5-dihydro-10-methoxy-2,2,4,N-tetramethyl-N-phenyl-1H-[1]benzopyrano[3,4-f]quinolin-5-amine, (−)-2,5-dihydro-10-methoxy-2,2,4-trimethyl-5-(2-propenyl)-1H-[1]benzopyrano[3,4-f]quinoline, (+)-2,5-dihydro-10-methoxy-2,2,4-trimethyl-5-(2-propenyl)-1H-[1]benzopyrano[3,4-f]quinoline, 2,5-dihydro-10-methoxy-2,2,4-trimethyl-1H-[1]benzopyrano[3,4-f]quinoline, 4-(2,5-dihydro-10-methoxy-2,2,4-trimethyl-1H-[1]benzopyrano[3,4-f]quinolin-5-yl)-N,N-dimethylbenzenamine, 2,5-dihydro-10-methoxy-2,2,4-trimethyl-5-(5-methoxy-2-thienyl)-1H-[1]benzopyrano[3,4-f]quinoline, 2,5-dihydro-10-methoxy-2,2,4-trimethyl-5-(5-propyl-2-thienyl)-1H-[1]benzopyrano[3,4-f]quinoline, 2,5-dihydro-10-methoxy-2,2,4-trimethyl-5-[4-(1-morpholinyl)phenyl]-1H-[1]benzopyrano[3,4-f]quinoline, 1-(2,5-dihydro-10-methoxy-2,2,4-trimethyl-1H-[1]benzopyrano[3,4-f]quinolin-5-yl)-3,3-dimethyl-2-butanone, 2,5-dihydro-10-methoxy-2,2,4-trimethyl-1H-[1]benzopyrano[3,4-f]quinoline-5-carbonitrile, 1-(2,5-dihydro-10-methoxy-2,2,4-trimethyl-1H-[1]benzopyrano[3,4-f]quinolin-5-yl)-2-propanone, methyl-2,5-dihydro-10-methoxy-2,2,4-trimethyl-1H-[1]benzopyrano[3,4-f]quinoline-5-acetate, 2-(2,5-dihydro-10-methoxy-2,2,4-trimethyl-1H-[1]benzopyrano[3,4-f]quinolin-5-yl)-1-phenylethanone, 5-[2-(chloromethyl)-2-propenyl]-2,5-dihydro-10-methoxy-2,2,4-trimethyl-1H-[1]benzopymno[3,4-f]quinoline, 2,5-dihydro-10-methoxy-2,2,4-trimethyl-(-methylene-1H-[1]benzopyrano[3,4-f]quinoline-5-propanol, acetate (ester), 2,5-dihydro-10-methoxy-2,2,4-trimethyl-5-(4-methylphenyl)-1H-[1]benzopyrano[3,4-f]quinoline, 5-(3-fluoro-4-methylphenyl)-2,5-dihydro-10-methoxy-2,2,4-trimethyl-1H-[1]benzopyrano[3,4-f]quinoline, 5-(3-bromophenyl)-2,5-dihydro-10-methoxy-2,2,4-trimethyl-1H-[1]benzopyrano[3,4-f]quinoline, 2,5-dihydro-10-methoxy-2,2,4-trimethyl-5-(phenylmethyl)-1H-[1]benzopyrano[3,4-f]quinoline, 2,5-dihydro-10-methoxy-2,2,4-trimethyl-5-propyl-1H-[1]benzopyrano[3,4-f]quinoline, 5-(4-fluorophenyl)-2,5-dihydro-10-methoxy-2,2,4-trimethyl-1H-[1]benzopyrano[3,4-f]quinoline, 5-(3-fluorophenyl)-2,5-dihydro-10-methoxy-2,2,4-trimethyl-1H-[1]benzopyrano[3,4-f]quinoline, 2,5-dihydro-10-methoxy-2,2,4,5-tetramethyl-1H-[1]benzopyrano[3,4-f]quinoline, 2,5-dihydro-10-methoxy-2,2,4-trimethyl-5-(1-methylethyl)-1H-[1]benzopyrano[3,4-f]quinoline, 2,5-dihydro-10-methoxy-2,2,4-trimethyl-5-(2-methylpropyl)-1H-[1]benzopyrano[3,4-f]quinoline, 5-ethyl-2,5-dihydro-10-methoxy-2,2,4-trimethyl-1H-[1]benzopyrano[3,4-f]quinoline, 2,5-dihydro-10-methoxy-2,2,4-trimethyl-1H-[1]benzopyrano[3,4-f]quinoline-5-carboximidic acid ethyl ester, 2,5-dihydro-10-methoxy-2,2,4-trimethyl-(-methylene-1H-[1]benzopyrano[3,4-f]quinoline-5-propanol, 2,5-dihydro-10-methoxy-2,2,4,N,N-pentamethyl-1H-[1]benzopyrano[3,4-f]quinoline-5-acetamide, 2,5-dihydro-10-methoxy-2,2,4,N,N-pentamethyl-1H-[1]benzopyrano[3,4-f]quinoline-5-ethanamine, N-cyclopropyl-2,5-dihydro-10-methoxy-2,2,4-trimethyl-1H-[1]benzopyrano[3,4-f]quinoline-5-acetamide, 2,5-dihydro-10-methoxy-2,2,4-trimethyl-5-(2-propynyl)-1H-[1]benzopyrano[3,4-f]quinoline, 5-(2,5-dihydro-10-methoxy-2,2,4-trimethyl-1H-[1]benzopyrano[3,4-f]quinolin-5-yl)-2,(5H)-furanone, 5-(3-butenyl)-2,5-dihdyro-10-methoxy-2,2,4-trimethyl-1H-[1]benzopyrano[3,4-f]quinoline, 2,5-dihydro-10-methoxy-2,2,4-trimethyl-1H-[1]benzopyrano[3,4-f]quinoline-5-propanol, 10-ethyl-2,5-dihydro-2,2,4-trimethyl-5-phenyl-1H-[1]benzopyrano[3,4-f]quinoline, 2,5-dihydro-2,2,4,10-tetramethyl-5-phenyl-1H-[1]benzopyrano[3,4-f]quinoline, 5-(3,5-dichlorophenyl)-10-ethyl-2,5-dihydro-2,2,4-trimethyl-1H-[1]benzopyrano [3,4-f]quinoline, 5-(3,5-dichlorophenyl)-2,5-dihydro-2,2,4,N-tetramethyl-1H-[1]benzopyrano[3,4-f]quinolin-10-amine, 5-(3,5-dichlorophenyl)-2,5-dihydro-2,2,4-trimethyl-N-(2-propenyl)-1H-[1]benzopyrano[3,4-f]quinolin-10-amine, 2,5-dihydro-2,2,4-trimethyl-5-phenyl-10-(2-propynyloxy)-1H-[1]benzopyrano[3,4-f]quinoline, 2,5-dihydro-2,2,4-trimethyl-5-phenyl-10-(2-propenyloxy)-1H-[1]benzopyrano[3,4-f]quinoline, 2,5-dihydro-2,2,4-trimethyl-5-(2-propenyl)-1H-[1]benzopyrano[3,4-f]quinoline-10-methanol, 2,5-dihydro-2,2,4-trimethyl-5-(2-propenyl)-1H-[1]benzopyrano[3,4-f]quinoline-10-carboxylic acid, 5-(3,5-dichlorophenyl)-10-ethoxy-2,5-dihydro-2,2,4-trimethyl-1H-[1]benzopyrano[3,4-f]quinoline, 5-(3,5-dichlorophenyl)-2,5-dihydro-2,2,4-trimethyl-1H-[1]benzopyrano[3,4-f]quinolin-10-ol, 5-(3,5-dichlorophenyl)-2,5-dihydro-2,2,4-trimethyl-1H-[1]benzopyrano[3,4-f]quinolin-10-yl]-methylcarbonate, 2,5-dihydro-2,2,4-trimethyl-5-(2-propenyl)-1H-[1]benzopyrano[3,4-f]quinolin-10-ol, 10-(bromodifluoromethoxy)-2,5-dihyro-2,2,4-trimethyl-5-(2-propenyl)-1H-[1]benzopyrano[3,4-f]quinoline,

[3-(2,5-dihydro-10-methoxy-2,2,4-trimethyl-1H-[1]benzopyrano[3,4-f]quinolin-5-yl)phenyl]methylcarbonate, 2,5-dihydro-10-methoxy-5-(3-methoxyphenyl)-2,2,4-trimethyl-1H-[1]benzopyrano[3,4-f]quinoline, 2,5-dihydro-10-methoxy-2,2,4-trimethyl-5-[3-(2-propenyloxy)phenyl]-1H-[1]benzopyrano[3,4-f]quinoline, 2,5-dihydro-10-methoxy-2,2,4-trimethyl-5-[3-(phenylmethoxy)phenyl]-1H-[1]benzopyrano[3,4-f]quinoline, 5-[3-(cyclopropylmethoxy)phenyl]-2,5-dihydro-10-methoxy-2,2,4-trimethyl-1H-[1]benzopyrano[3,4-f]quinoline, 2,5-dihydro-10-methoxy-2,2,4-trimethyl-5-[3-[2-(1-piperidinyl)ethoxy]pheny]-1H-[1]benzopyrano[3,4-f]quinoline, 5-(3-hexyloxyphenyl)-2,5-dihydro-10-methoxy-2,2,4-trimethyl-1H-[1]benzopyrano[3,4-f]quinoline, 5-[3-(2,4-dinitrophenoxy)phenyl]-2,5-dihydro-10-methoxy-2,2,4-trimethyl-1H-[1]benzopyrano[3,4-f]quinoline, 2,5-dihydro-10-methoxy-2,2,4-trimethyl-5-[3-(2-propynyloxy)phenyl]-1H-[1]benzopyrano[3,4-f]quinoline, 3-(2,5-dihydro-10-methoxy-2,2,4-trimethyl-1H-[1]benzopyrano[3,4-f]quinolin-5-yl)phenol 4-methylbenzenesulfonate(ester), 4-(2,5-dihydro-10-methoxy-2,2,4-trimethyl-1H-[1]benzopyrano[3,4-f]quinolin-5-yl)phenolacetate(ester), 4-(2,5-dihydro-10-methoxy-2,2,4-trimethyl-1H-[1]benzopyrano[3,4-f]quinolin-5-yl)phenol, 2,5-dihydro-10-methoxy-2,2,4-trimethyl-5-[[4-(methylthio)methoxy]phenyl]-1H-[1]benzopyrano[3,4-f]quinoline,

[4-(2,5-dihydro-10-methoxy-2,2,4-trimethyl-1H-[1]benzopyrano[3,4-f]quinolin-5-yl)phenyl]dimethycarbamate, 2,5-dihydro-10-methoxy-2,2,4-trimethyl-5-[4-(phenylmethoxy)phenyl]-1H-[1]benzopyrano[3,4-f]quinoline, 2,5-dihydro-10-methoxy-2,2,4-trimethyl-5-[3-(methoxymethoxy)phenyl]-1H-[1]benzopyrano[3,4-f]quinoline,

[(2,5-dihydro-10-methoxy-2,2,4-trimethyl-1H-[1]benzopyrano[3,4-f]quinolin-5-yl)phenyl]-1-morpholinecarboxylate, 2,5-dihydro-10-methoxy-2,2,4-trimethyl-5-[3-[(methylsulfinyl)methoxy]phenyl]-1H-[1]benzopyrano[3,4-f]quinoline, O-[3-(2,5-dihydro-10-methoxy-2,2,4-trimethyl-1H-[1]benzopyrano[3,4-f]quinolin-5-yl)phenyl]ester, 2,5-dihydro-10-methoxy-2,2,4-trimethyl-5-[3-(methylthio)phenyl]-1H-[1]benzopyrano[3,4-f]quinoline, O-[3-(2,5-dihydro-10-methoxy-2,2,4-trimethyl-1H-[1]benzopyrano[3,4-f]quinolin-5-yl)phenyl]methylcarbonothioate,

[3-(2,5-dihydro-10-methoxy-2,2,4-trimethyl]-1H-[1]benzopyrano[3,4-f]quinolin-5-yl)phenyl]trifluoromethanesulfonate, 5-[3-(4,5-dihydro-4,4-dimethyl-2-oxazolyl)phenyl]-2,5-dihydro-10-methoxy-2,2,4-trimethyl-1H-[1]benzopyrano[3,4-f]quinoline, ethyl 3-(2,5-dihydro-10-methoxy-2,2,4-trimethyl-1H-[1]benzopyrano[3,4-f]quinolin-5-yl)benzoate, 3-(2,5-dihydro-10-methoxy-2,2,4-trimethyl-1H-[1]benzopyrano[3,4-f]quinolin-5-yl)benzoic acid, 2,5-dihydro-10-methoxy-2,2,4-trimethyl-5-[3-methyl-5-(2-propenyl)phenyl]-1H-[1]benzopyrano[3,4-f]quinoline, 1-[3-(2,5-dihydro-10-methoxy-2,2,4-trimethyl-1H-[1]benzopyrano[3,4-f]quinolin-5-yl)-5-methylphenyl]ethanone, 3-(2,5-dihydro-10-methoxy-2,2,4-trimethyl-1H-[1]benzopyrano[3,4-f]quinolin-5-yl)-5-trimethylbenzenemethanol, 5-[3-(2-furanyl)phenyl]-2,5-dihydro-10-methoxy-2,2,4-trimethyl-1H-[1]benzopyrano[3,4-f]quinoline, 2,5-dihydro-10-methoxy-2,2,4-trimethyl-5-[3-methyl-5-(1H-pyrrolidin-1-yl)phenyl]-1H-[1]benzopyrano[3,4-f]quinoline, 3-(2,5-dihydro-10-methoxy-2,2,4-trimethyl-1H-[1]benzopyrano[3,4-f]quinolin-5-methyl)-5,N-dimethylbenzenamine, 3-(2,5-dihydro-10-methoxy-2,2,4-trimethyl-1H-[1]benzopyrano[3,4-f]quinolin-5-yl)-5-methyl-N-(2-propenyl)benzamide, 3-(2,5-dihydro-10-methoxy-2,2,4-trimethyl-1H-[1]benzopyrano[3,4-f]quinolin-5-yl)-N-(2-methoxyethyl)-5-methylbenzenamine, 3-(2,5-dihydro-10-methoxy-2,2,4-trimethyl-1H-[1]benzopyrano[3,4-f]quinolin-5-yl)N-(2-propenyl)benzenamine, N'-[3-(2,5-dihydro-10-methoxy-2,2,4-trimethyl-1H-[1]benzopyrano[3,4-f]quinolin-5-yl)-5-methylphenyl]-N,N-dimethylurea, N-[3-(2,5-dihydro-10-methoxy-2,2,4-trimethyl-1H-[1]benzopyrano[3,4-f]quinolin-5-yl)-phenyl]benzenemethanamine, 5-[(3,5-dichlorophenyl)methylene]-2,5-dihydro-10-methoxy-2,2,4-trimethyl-1H-[1]benzopyrano[3,4-f]quinoline, 5-[(4-chlorophenyl)methylene]-2,5-dihydro-10-methoxy-2,2,4-trimethyl-1H-[1]benzopyrano[3,4-f]quinoline, 2,5-dihydro-10-methoxy-2,2,4-trimethyl-5-[[3-(trifluoromethyl)phenyl]-methylene-1H-[1]-benzopyrano[3,4-f]quinoline, 5-[(2,6-difluorophenyl)methylene]-2,5-dihydro-10-methoxy-2,2,4-trimethyl-1H-[1]benzopyrano[3,4-f]quinoline, 5-[(2-chlorophenyl)methylene]-2,5-dihydro-10-methoxy-2,2,4-trimethyl-1H-[1]benzopyrano[3,4-f]quinoline, 5-[(2,6-dichlorophenyl)methylene]-2,5-dihydro-10-methoxy-2,2,4-trimethyl-1H-[1]benzopyrano[3,4-f]quinoline, 5-[(2-fluorophenyl)methylene]-2,5-dihydro-10-methoxy-2,2,4-trimethyl-1H-[1benzopyrano[3,4-f]quinoline, 2,5-dihydro-10-methoxy-2,2,4-trimethyl-5-[(4,5-dihydro-4,4-dimethyl-2 oxazolyl)methylene]-1H-[1]benzopyrano[3,4-f]quinoline, 2,5-dihydro-10-methoxy-2,2,4-trimethyl-5-(2-pyridinylmethylene)-1H-[1]benzopyrano[3,4-f]quinoline, 2,5-dihydro-10-methoxy-2,2,4-trimethyl-5-(2-thienyl)-1H-[1]benzopyrano[3,4-f]quinoline, 2,5-dihydro-9,10-dimethoxy-2,2,4-trimethyl-5-(2-propenyl)-1H-[1]benzopyrano[3,4-f]quinoline, 5-(2-cyclohexen-1-yl)-2,5-dihydro-9,10-dimethoxy-2,2,4-trimethyl-1H-[1]benzopyrano[3,4-f]quinoline, 2,5-dihydro-10-methoxy-5-(3-methyl-3-butenyl)-2,2,4-trimethyl-1H-[1]benzopyrano[3,4-f]quinoline, 2,5-dihydro-10-methoxy-5-(5,5-dimethyl-3-cyclohexenyl)-2,2,4-trimethyl-1H-[1]benzopyrano[3,4-f]quinoline, rel (5R,2'R)2,5-dihydro-10-methoxy-5-(2-oxo-3-tetrahydropyranyl)-2,2,4-trimethyl-1H-[1]benzopyrano[3,4-f]quinoline, anti(5R,2'S)2,5-dihydro-10-methoxy-5-(2-oxo-3-tetrahydropyranyl)-2,2,4-trimethyl-1H-[1]benzopyrano[3,4-f]quinoline, 2,5-dihydro-10-methoxy-5-(3-cyclopentenyl)-2,2,4-trimethyl-1H-[1]benzopyrano[3,4-f]quinoline, 2,5-dihydro-10-methoxy-5-(3-cyclohexenyl)-2,2,4-trimethyl-1H-[1]benzopyrano[3,4-f]quinoline, 2,5-dihydro-10-methoxy-5-(3-butenyl)-2,2,4-trimethyl-1H-[1]benzopyrano[3,4-f]quinoline, 2,5-dihydro-10-methoxy-5-(1-ethenyl-1-cyclohexyl)-2,2,4-trimethyl-1H-[1]benzopyrano[3,4-f]quinoline, 2,5-dihydro-10-methoxy-5-(4,4-dimethyl-3-cyclohexenyl)-2,2,4-trimethyl-1H-[1]benzopyrano[3,4-f]quinoline, 2,5-dihydro-10-methoxy-5-(1-methylene-2-cyclohexyl)-2,2,4-trimethyl-1H-[1]benzopyrano[3,4-f]quinoline, 2,5-dihydro-10-methoxy-5-(1-oxo-2-cyclohexyl)-2,2,4-trimethyl-1H-[1]benzopyrano[3,4-f]quinoline, 2,5-dihydro-10-methoxy-5-(3-cyclooctenyl)-2,2,4-trimethyl-1H-[1]benzopyrano[3,4-f]quinoline, 2,5-dihydro-10-methoxy-5-(3-cycloheptenyl)-2,2,4-trimethyl-1H-[1]benzopyrano[3,4-f]quinoline, 2,5-dihydro-10-methoxy-5-(1-cyclohexenylmethyl)-2,2,4-trimethyl-1H-[1]benzopyrano[3,4-f]quinoline, 2,5-dihydro-10-methoxy-5-(3,3-dimethyl-6-cyclohexenyl)-2,2,4-trimethyl-1H-[1]benzopyrano[3,4-f]quinoline, 2,5-dihydro-10-methoxy-5-(2-bromo-3-propenyl)-2,2,4-trimethyl-1H-[1]benzopyrano[3,4-f]quinoline, rel(5R,3'R)2,5-dihydro-10-methoxy-5-(1-hydroxymethyl-3-cyclohexenyl)-2,2,4-trimethyl-1H-[1]benzopyrano[3,4-f]quinoline, rel(5R,3'S) 2,5-dihydro-10-methoxy-5-(1-hydroxymethyl-3-cyclohexenyl)-2,2,4-trimethyl-1H-[1]benzopyrano[3,4-f]quinoline, 2,5-dihydro-10-methoxy-5-(3-hydroxymethyl-3-cyclohexenyl)-2,2,4-trimethyl-1H-[1]benzopyrano[3,4-f]quinoline, 2,5-dihydro-10-methoxy-5-(3-indolyl)-2,2,4-trimethyl-1H-[1]benzopyrano[3,4-f]quinoline, rel(5S,3'S)2,5-dihydro-10-methoxy-5-(1-methyl-3-cyclohexenyl)-2,2,4-trimethyl-1H-[1]benzopyrano[3,4-f]quinoline, rel(5R,3'S) 2,5-dihydro-10-methoxy-5-(1-methyl-3-cyclohexenyl)-2,2,4-trimethyl-1H-[1]benzopyrano[3,4-f]quinoline, (−)(5S,3'S) 2,5-dihydro-10-methoxy-5-(1-methyl-3-cyclohexenyl)-2,2,4-trimethyl-1H[1]benzopyrano[3,4-f]quinoline, (−)(5S,3'R)2,5-dihydro-10-methoxy-5-(1-hydroxymethyl-3-cyclohexenyl)-2,2,4-trimethyl-1H-[1]benzopyrano[3,4-f]quinoline, (+)(5R,3'S)2,5-dihydro-10-methoxy-5-(1-hydroxymethyl-3-cyclohexenyl)-2,2,4-trimethyl-1H-[1]benzopyrano[3,4-f]quinoline, (−)-(5S,3'R)2,5-dihydro-10-methoxy-5-(1-methyl-3-cyclohexenyl)-2,2,4-trimethyl-1H-[1]benzopyrano[3,4-f]quinoline, (+)-(5R,3'S)2,5-dihydro-10-methoxy-5-(1-methyl-3-cyclohexenyl)-2,2,4-trimethyl-1H-[1]benzopyrano[3,4-f]quinoline, 2,5-dihydro-10-methoxy-5-(1-chloromethyl-3-cyclohexenyl)-2,2,4-trimethyl-1H-[1]benzopyrano[3,4-f]quinoline, rel(5R,3'R)2,5-dihydro-10-methoxy-5-(1-methoxymethyl-3-cyclohexenyl)-2,2,4-trimethyl-1H-[1]benzopyrano[3,4-f]quinoline, rel(5R,3'R)2,5-dihydro-10-methoxy-5-(1-methylthiomethyl-3-cyclohexenyl)-2,2,4-trimethyl-1H-[1]benzopyrano[3,4-f]quinoline, rel(5R,3'S)2,5-dihydro-10-methoxy-5-(1-acetoxymethyl-3-cyclohexenyl)-2,2,4-trimethyl-1H-[1]benzopyrano[3,4-f]quinoline, rel(5R,3'R)2,5-dihydro-10-methoxy-5-(1-acetoxymethyl-3-cyclohexenyl)-2,2,4-trimethyl-1H-[1]benzopyrano[3,4-f]quinoline, rel(5R,3'R)2,5-dihydro-10-methoxy-5-(1-methoxymethyl-3-cyclohexenyl)-2,2,4-trimethyl-1H-[1]benzopyrano[3,4-f]quinoline, rel(5R,3'R)2,5-dihydro-10-methoxy-5-(1-(N,N-dimethylamino)methyl-3-cyclohexenyl)-2,2,4]benzopyrano[3,4-f]quinoline, rel(5R,3'S)2,5-dihydro-10-methoxy-5-(1-methylthiomethyl-3-cyclohexenyl)-2,2,4-trimethyl-[1]benzopyrano[3,4-f]quinoline, rel(5R,3'R)2,5-dihydro-10-methoxy-5-(1-(N-morpholino)methyl-3-cyclohexenyl)-2,2,4-trimethyl-1H-[1]benzopyrano[3,4-f]quinoline, rel(5R,3'R)2,5-dihydro-10-methoxy-5-(1(N-methyl-N-methylsulfonylamino)methyl-3-cyclohexenyl)-2,2,4-trimethyl-1H-[1]benzopyrano[3,4-f]quinoline, rel(5R,3'S)2,5-dihydro-10-methoxy-5-(1-(N,N-dimethylamino)methyl-3-cyclohexenyl)-2,2,4-trimethyl-1H-[1]benzopyrano[3,4-f]quinoline, rel(5R,3'R)2,5-dihydro-10-methoxy-5-(1-(N-methylamino)methyl-3-cyclohexenyl)-2,2,4-trimethyl-1H-[1]benzopyrano[3,4-f]quinoline, 2,5-dihydro-10-methoxy-5-(2-methyl-3-propenyl)-2,2,4-trimethyl-1H-[1]benzopyrano[3,4-f]quinoline, 2,5-dihydro-10-methoxy-5-(1,3-butadien-2-yl)-2,2,4-trimethyl-1H-[1]benzopyrano[3,4-f]quinoline, 2,5-dihydro-10-methoxy-5-(2-carbomethoxy-3-propenyl)-2,2,4-trimethyl-1H-[1]benzopyrano[3,4-f]quinoline, 2,5-dihydro-10-methoxy-5-(1,2-dihydroxy-3-propyl)-2,2,4-trimethyl-1H-[1]benzopyrano[3,4-f]quinoline, 2,5-dihydro-10-methoxy-5-(1,2-epoxy-3-propenyl)-2,2,4-trimethyl-1H-[1]benzopyrano[3,4-f]quinoline, 2,5-dihydro-10-methoxy-5-(1-(N-phthalimido)-3-propyl)-2,2,4-trimethyl-1H-[1]benzopyrano[3,4-f]quinoline, 2,5-dihydro-10-methoxy-5-(1-amino-3-propyl)-2,2,4-trimethyl-1H-[1]benzopyrano[3,4-f]quinoline, 2,5-dihydro-10-methoxy-5-(1-(hydrazinocarbonylamino)-3-propyl)-2,2,4-trimethyl-1H-[1]benzopyrano[3,4-f]quinoline, (E) 2,5-dihydro-10-methoxy-5-(2-carbomethoxy-1-ethenyl)-2,2,4-trimethyl-1H-[1]benzopyrano[3,4-f]quinoline, (Z)-2,5-dihydro-10-methoxy-5-(1-propenyl)-2,2,4-trimethyl-1H-[1]benzopyrano[3,4-f]quinoline, (E) 2,5-dihydro-10-methoxy-5-(3-hydroxy-1-propenyl)-2,2,4-trimethyl-1H-[1]benzopyrano[3,4-f]quinoline, (E) 2,5-dihydro-10-methoxy-5-(3-(N,N-dimethylaminocarbonyloxy)-1-propenyl)-2,2,4-trimethyl-1H-[1]benzopyrano[3,4-f]quinoline, (E) 2,5-dihydro-10-methoxy-5-(3-methoxymethoxy-1-propenyl)-2,2,4-trimethyl-1H-[1]benzopyrano[3,4-f]quinoline, 2,5-dihydro-10-methoxy-5-(3-hydroxy-3-propenyl)-2,2,4-trimethyl-1H-[1]benzopyrano[3,4-f]quinoline, methyl 2-(2,5-dihydro-10-methoxy-2,2,4-trimethyl-1H-[1]benzopyrano[3,4-f]quinolin-5-yl)acetyl hydroxamate, 2-(2,5-dihydro-10-methoxy-2,2,4-trimethyl-1H-[1]benzopyrano[3,4-f]quinolin-5-yl)acetaldehyde, 2,5-dihydro-10-methoxy-5-(2-cyclohexylidenylethyl)-2,2,4-trimethyl-1H-[1]benzopyrano[3,4-f]quinoline, 2,5-dihydro-10-methoxy-5-(2-cyclopentylidenylethyl)-2,2,4-trimethyl-1H-[1]benzopyrano[3,4-f]quinoline 2,5-dihydro-10-methoxy-5-(2-cycloheptylidenylethyl)-2,2,4-trimethyl-1H-[1]benzopyrano[3,4-f]quinoline, 2,5-dihydro-10-methoxy-5-(3-methyl-2-butenyl)-2,2,4-trimethyl-1H-[1]benzopyrano[3,4-f]quinoline, trans 2,5-dihydro-10-methoxy-5-(2-butenyl)-2,2,4-trimethyl-1H-[1]benzopyrano[3,4-f]quinoline, trans 2,5-dihydro-10-methoxy-5-(2-penten-1-yl)-2,2,4-trimethyl-1H-[1]benzopyrano[3,4-f]quinoline, 2,5-dihydro-10-methoxy-5-(1,1-difluoro-1-propen-3-yl)-2,2,4-trimethyl-1H-[1]benzopyrano[3,4-f]quinoline, (E) methyl 2-(2,5-dihydro-10-methoxy-2,2,4-trimethyl-1H-[1]benzopyrano[3,4-f]quinolin-5-yl)2-butenoate, (E) 2,5-dihydro-10-methoxy-5-(4-hydroxy-2-buten-1-yl)-2,2,4-trimethyl-1H-[1]benzopyrano[3,4-f]quinoline, (E) 2,5-dihydro-10-methoxy-5-(4-(N,N-dimethylaminocarbonyloxy)-2-buten-1-yl)-2,2,4-trimethyl-1H-[1]benzopyrano[3,4-f]quinoline, (E) 2,5-dihydro-10-methoxy-5-(4-(N-methylaminocarbonyloxy)-2-buten-1-yl)-2,2,4-trimethyl-1H-[1]benzopyrano[3,4-f]quinoline, (E) 2,5-dihydro-10-methoxy-5-(2-butenyl)-2,2,4-trimethyl-1H-[1]benzopyrano[3,4-f]quinoline, 2,5-dihydro-10-methoxy-5-(2-hydroxyethyl)-2,2,4-trimethyl-1H-[1]benzopyrano[3,4-f]quinoline, 2,5-dihydro-10-methoxy-5-(2-(N-benzylcarbonyloxy)ethyl)-2,2,4-trimethyl-1H-[1]benzopyrano[3,4-f]quinoline, 2,5,-dihydro-10-methoxy-5-(2-(N-morpholinocarbonyloxy)ethyl)-2,2,4-trimethyl-1H-[1]benzopyrano[3,4-f]quinoline, 2,5-dihydro-10-methoxy-5-(2-(N-(2-methoxyethyl)aminocarbonyloxy)ethyl)-2,2,4-trimethyl-1H-[1]benzopyrano[3,4-f]quinoline, 2,5-dihydro-10-methoxy-5-(2-(N-methylaminocarbonyloxyoxy)ethyl)-2,2,4-trimethyl-1H-[1]benzopyrano[3,4-f]quinoline, 2,5-dihydro-10-methoxy-5-(2-(N,N-dimethylaminocarbonyloxy)ethyl)-2,2,4-trimethyl-1H-[1]benzopyrano[3,4-f]quinoline, 2,5-dihydro-10-methoxy-5-(2-methoxymethoxyethyl)-2,2,4-trimethyl-1H-[1]benzopyrano[3,4-f]quinoline, 2,5-dihydro-10-methoxy-5-(2,2-dimethylethoxycarbonylamino)methyl)-2,2,4-trimethyl-1H-[1]benzopyrano[3,4-f]quinoline, 2,5-dihydro-10-methoxy-5-(aminomethyl)-2,2,4-trimethyl-1H-[1]benzopyrano-[3,4-f]quinoline, 2,5-dihydro-10-methoxy-5-(ethoxycarbonylamino)methyl)-2,2,4-trimethyl-1H-[1]benzopyrano[3,4-f]quinoline, 2,5-dihydro-10-methoxy-5-(carboethoxy)-2,2,4-trimethyl-1H-[1]benzopyrano[3,4-f]quinoline, 2,5-dihydro-10-methoxy-5-(cyclopentyl)-2,2,4-trimethyl-1H-[1]benzopyrano[3,4-f]quinoline, 2,5-dihydro-10-methoxy-5-(1-methylpropa-1,2-dienyl)-2,2,4-trimethyl-1H-[1]benzopyrano[3,4-f]quinoline, 2,5-dihydro-10-methoxy-5-(3,4,5-trifluorophenyl)-2,2,4-trimethyl-1H-[1]benzopyrano[3,4-f]quinoline, 2,5-dihydro-10-methoxy-5-(cyclohexyl)-2,2,4-trimethyl-1H-[1]benzopyrano[3,4-f]quinoline, 2,5-dihydro-10-methoxy-5-(2-pyridyl)-2,2,4-trimethyl-1H-[1]benzopyrano[3,4-f]quinoline, 2,5-dihydro-10-methoxy-5-(3-pyridyl)-2,2,4-trimethyl-1H-[1]benzopyrano[3,4-f]quinoline, 2,5-dihydro-10-methoxy-5-(4-pyridyl)-2,2,4-trimethyl-1H-[1]benzopyrano[3,4-f]quinoline, (10-chloro-9-hydroxy-5-(3-propenyl)-2,2,4-trimethyl-1H-2,5-dihydro-[1]benzopyrano-[1]benzopyrano[3,4-f]quinoline, 10-chloro-9-hydroxy-5-phenyl-2,2,4-trimethyl-1H-2,5-dihydro-[1]benzopyrano[3,4-f]quinoline, 10-chloro-9-hydroxy-5-(3-trifluoromethylphenyl)-2,2,4-trimethyl-1H-2,5-dihydro-[1]benzopyrano[3,4-f]quinoline, 10-chloro-9-hydroxy-5-(3,5-dimethylphenyl)-2,2,4-trimethyl-1H-2,5-dihydro-[1]benzopyrano[3,4-f]quinoline, rel-(5S,3'R)-9-hydroxy-10-methoxy-5-[1-hydroxymethyl-3-cyclohexenyl]-2,2,4-trimethyl-1H-[1]benzopyrano[3,4-f]quinoline, (−)2,5(S)-dihydro-9-hydroxy-10-chloro-2,2,4-trimethyl-5-(3S-cyclopentenyl)-1H-[1]benzopyrano[3,4-f]quinoline, (−)2,5(S)-dihydro-9-hydroxy-10-chloro-2,2,4-trimethyl-5-(3R-cyclopentenyl)-1H-[1]benzopyrano[3,4-f]quinoline, 10-chloro-9-hydroxy-5-(3,5-dichlorophenyl)-2,2,4-trimethyl-1H-2,5-dihydro-[1]benzopyrano[3,4-f]quinoline, (+)-(5R,3'S) 2,5-dihydro-9-hydroxy-10-chloro-2,2,4-trimethyl-5-(3-cyclopentenyl)-1H-[1]benzopyrano[3,4-f]quinoline, (+)-(5R,3'R)-2,5-dihydro-9-hydroxy-10-chloro-2,2,4-trimethyl-5-(3-cyclopentenyl)-1H-[1]benzopyrano[3,4-f]quinoline, 10-chloro-9-hydroxy-5-(3,4-difluorophenyl)-2,2,4-trimethyl-1H-2,5-dihydro-[1]benzopyrano[3,4-f]quinoline, 9-10-methylenedioxy-5-phenyl-2,2,4-trimethyl-1H-2,5-dihydro-[1]benzopyrano[3,4-f]quinoline, 5-(3-propenyl)-9-chloro-10-ethenyl-2,2,4-trimethyl-2,5-dihydro-1H-[1]benzopyrano[3,4-f]quinoline, 9-chloro-10-methoxy-5-phenyl-2,2,4-trimethyl-2,5-dihydro-1H-[1]benzopyrano[3,4-f]quinoline, 5-(3-propenyl)-9-chloro-10-difluoromethoxy-2,2,4-trimethyl-2,5-dihydro-1H-[1]benzopyrano[3,4-f]quinoline, 9-chloro-10-difluoromethoxy-5-phenyl-2,2,4-trimethyl-2,5-dihydro-1H-[1]benzopyrano[3,4-f]quinoline, 8-fluoro-10-methoxy-5-phenyl-2,2,4-trimethyl-2,5-dihydro-1H-[1]benzopyrano[3,4-f]quinoline, 5-(3-propenyl)-8-fluoro-10-methoxy-2,2,4-trimethyl-2,5-dihydro-1H-[1]benzopyrano[3,4-f]quinoline, (10-methoxy-9-fluoro-5-(3-propenyl)-2,2,4-trimethyl-1H-2,5-dihydro-[1]benzopyrano[3,4-f]quinoline, 10-methoxy-9-hydroxy-5-(3-propenyl)-2,2,4-trimethyl-1H-2,5-dihydro-[1]benzopyrano[3,4-f]quinoline, (+/−)2,5-dihydro-9-hydroxy-10-methoxy-2,2,4-trimethyl-5-(3-cyclohexenyl)-1H-[1]benzopyrano[3,4-f]quinoline, (+/−)2,5-dihydro-9-hydroxy-10-methoxy-2,2,4-trimethyl-5-(1-methylcyclohexen-3-yl)-1H-[1]benzopyrano[3,4-f]quinoline, (−)(5S,3'S)-9-hydroxy-5-[1-methyl-3-cyclohexenyl]-10-methoxy-2,2,4-trimethyl-2,5-dihydro-1H-[1]benzopyrano[3,4-f]quinoline, (+)(5R,3'R)-9-hydroxy-5-[1-methyl-3-cyclohexenyl]-10-methoxy-2,2,4-trimethyl-2,5-dihydro-1H-[1]benzopyrano[3,4-f]quinoline, (+)(5R,3'S)-9-hydroxy-5-[1-methyl-3-cyclohexenyl]-10-methoxy-2,2,4-trimethyl-2,5-dihydro-1H-[1]benzopyrano[3,4-f]quinoline, (−)(5S,3'R)-9-hydroxy-5-[1-methyl-3-cyclohexenyl]-10-methoxy-2,2,4-trimethyl-2,5-dihydro-1H-[1]benzopyrano[3,4-f]quinoline, rel-(5S,3'R)-9-hydroxy-5-[1-hydroxymethyl-3-cyclohexenyl]-10-methoxy-2,2,4-trimethyl-2,5-dihydro-1H-[1]benzopyrano[3,4-f]quinoline, (+/−)(5S,3'R)2,5-dihydro-9-hydroxy-10-methoxy-2,2,4-trimethyl-5-(1-methylcyclohexen-3-yl)-1H-[1]benzopyrano[3,4-f]quinoline, rel-(5S,3'R)-9-hydroxy-5-[1-methoxymethyl-3-cyclohexenyl]-10-methoxy-2,2,4-trimethyl-2,5-dihydro-1H-[1]benzopyrano[3,4-f]quinoline, 2,5-dihydro-9-hydroxy-10-methoxy-5-propyl-2,2,4-trimethyl-1H-[1]benzopyrano[3,4-f]quinoline, (−)(5S,3'S)-2,5-dihydro-9-hydroxy-10-methoxy-2,2,4-trimethyl-5-(3-cycloheptenyl)-1H-[1]benzopyrano[3,4-f]quinoline, (−)(5S,3'R)2,5-dihydro-9-hydroxy-10-methoxy-2,2,4-trimethyl-5-(3-cycloheptenyl)-1H-[1]benzopyrano[3,4-f]quinoline, 2,5-dihydro-9-hydroxy-10-methoxy-2,2,4-trimethyl-5-phenyl-1H-[1]benzopyrano[3,4-f]quinoline, 2,5-dihydro-9-hydroxy-10-methoxy-2,2,4-trimethyl-5-(3,5-difluorophenyl)-1H-[1]benzopyrano[3,4-f]quinoline, 2,5-dihydro-9-hydroxy-10-methoxy-2,2,4-trimethyl-5-(3,4,5-trifluorophenyl)-1H-[1]benzopyrano[3,4-f]quinoline, 5-butyl-2,5-dihydro-9-hydroxy-10-methoxy-2,2,4-trimethyl-1H-[1]benzopyrano[3,4-f]quinoline, (−)(5S,3'S)2,5-dihydro-9-hydroxy-10-methoxy-2,2,4-trimethyl-5-(3-cyclopentenyl)-1H-[1]benzopyrano[3,4-f]quinoline, (−)(5S,3'R)2,5-dihydro-9-hydroxy-10-methoxy-2,2,4-trimethyl-5-(3-cyclopentenyl)-1H-[1]benzopyrano[3,4-f]quinoline, 2,5-dihydro-9-hydroxy-10-methoxy-2,2,4-trimethyl-5-(3,4-difluorophenyl)-1H-[1]benzopyrano[3,4-f]quinoline, 2,5-dihydro-9-hydroxy-10-methoxy-2,2,4-trimethyl-5-(4-fluorophenyl)-1H-[1]benzopyrano[3,4-f]quinoline, 2,5-dihydro-9-hydroxy-10-methoxy-2,2,4-trimethyl-5-(3-trifluoromethylphenyl)-1H-[1]benzopyrano[3,4-f]quinoline, 2,5-dihydro-9-hydroxy-10-methoxy-2,2,4-trimethyl-5-(3–5-bistrifluoromethylphenyl)-1H-[1]benzopyrano[3,4-f]quinoline, 2,5-dihydro-9-hydroxy-10-methoxy-2,2,4-trimethyl-5-(3-trifluoromethyl-4-chlorophenyl)-1H-[1]benzopyrano[3,4-f]quinoline, 2,5-dihydro-9-hydroxy-10-methoxy-2,2,4-trimethyl-5-(2-methylpropyl)-1H-[1]benzopyrano[3,4-f]quinoline, 2,5-dihydro-9-hydroxy-10-methoxy-2,2,4-trimethyl-5-(3-fluoro-4-chlorophenyl)-1H-[1]benzopyrano[3,4-f]quinoline, 2,5-dihydro-9-hydroxy-10-methoxy-2,2,4-trimethyl-5-(3-butenyl)-1H-[1]benzopyrano[3,4-f]quinoline, 2,5-dihydro-9-hydroxy-10-methoxy-5-(phenylmethyl)-2,2,4-trimethyl-1H-[1]benzopyrano[3,4-f]quinoline, (−)(5S,3'R)2,5-dihydro-9-hydroxy-10-methoxy-2,2,4-trimethyl-5-[1-ethyl-3-cyclohexenyl]-1H-[1]benzopyrano[3,4-f]quinoline, (−)(S)5-cyclopentyl-2,5-dihydro-9-hydroxy-10-methoxy-2,2,4-trimethyl-1H-[1]benzopyrano[3,4-f]quinoline, (+)(R)5-cyclopentyl-2,5-dihydro-9-hydroxy-10-methoxy-2,2,4-trimethyl-1H-[1]benzopyrano[3,4-f]quinoline, 2,5-dihydro-9-hydroxy-10-methoxy-5-(3-propynyl)-2,2,4-trimethyl-1H-[1]benzopyrano[3,4-f]quinoline, 2,5-dihydro-9-hydroxy-10-methoxy-2,2,4-trimethyl-5-(2-propyl)-1H-[1]benzopyrano[3,4-f]quinoline, 2,5-dihydro-9-hydroxy-10-methoxy-2,2,4-trimethyl-5-(5-methoxy-2-thienyl)-1H-[1]benzopyrano[3,4-f]quinoline, (±)2,5-dihydro-9-hydroxy-10-methoxy-2,2,4-trimethyl-5-(2,3,4,5,6-pentafluorophenyl)-1H-[1]benzopyrano[3,4-f]quinoline, (+/−)2,5-dihydro-9-hydroxy-10-methoxy-2,2,4-trimethyl-5(S)-(3(S)-1-hydroxymethylcyclopenten-1yl)-1H-[1]benzopyrano[3,4-f]quinoline, (+/−)2,5-dihydro-9-hydroxy-10-methoxy-2,2,4-trimethyl-5(S)-(3(S)-1-methylcarboxylatecyclopenten-3-yl)-1H-[1]benzopyrano[3,4-f]quinoline, (−)(5S,3'S)2,5-dihydro-9-hydroxy-10-methoxy-2,2,4-trimethyl-5-(3-cyclohexenyl)-1H-[1]benzopyrano,[3,4-f]quinoline, (−)(5S,3'R)2,5-dihydro-9-hydroxy-10-methoxy-2,2,4-trimethyl-5-(3-cyclohexenyl)-1H-[1]benzopyrano[3,4-f]quinoline, 2,5-dihydro-9-hydroxy-10-methoxy-2,2,4-trimethyl-5-(2-thienyl)-1H-[1]benzopyrano[3,4-f]quinoline, (±)2,5-dihydro-9-hydroxy-10-methoxy-2,2,4-trimethyl-5-(2-methylphenyl)-1H-[1]benzopyrano[3,4-f]quinoline, 2,5-dihydro-9-hydroxy-10-methoxy-2,2,4-trimethyl-5-(2-acetoxymethyl-3-propenyl)-1H-[1]benzopyrano[3,4-f]quinoline, (+)(5R,3'S)2,5-dihydro-9-hydroxy-10-methoxy-2,2,4-trimethyl-5-[1-ethyl-3-cyclohexenyl]-1H-[1]benzopyrano[3,4-f]quinoline, 2,5-dihydro-9-hydroxy-10-methoxy-2,2,4-trimethyl-5-cyclohexyl-1H-[1]benzopyrano[3,4-f]quinoline, 2,5,5-trihydro-9-hydroxy-10-methoxy-2,2,4-trimethyl-1H-[1]benzopyrano[3,4-f]quinoline, 2,5-dihydro-9-hydroxy-10-methoxy-2,2,4-trimethyl-5-(2-hydroxymethyl-3-propenyl)-1H-[1]benzopyrano[3,4-f]quinoline, methyl 2-[2,5-dihydro-9-hydroxy-10-methoxy-2,2,4-trimethyl-1H-[1]benzopyrano[3,4-f]-5-quinolinyl]acetate, (Z) 2,5-dihydro-9-hydroxy-10-methoxy-2,2,4-trimethyl-5-(2-butenyl)-1H-[1]benzopyrano[3,4-f]quinoline, 2,5-dihydro-9-hydroxy-10-methoxy-2,2,4-trimethyl-5-(3-methyl-2-butenyl)-1H-[1]benzopyrano[3,4-f]quinoline, (+)(5S,3'S) 2,5-dihydro-9-hydroxy-10-methoxy-2,2,4-trimethyl-5-(3-cyclohexenyl)-1H-[1]benzopyrano[3,4-f]quinoline, (+)(5R,3'R) 2,5-dihydro-9-hydroxy-10-methoxy-2,2,4-trimethyl-5-(3-cyclohexenyl)-1H-[1]benzopyrano[3,4-f]quinoline, (+)(5R,3'S) 2,5(R)-dihydro-9-hydroxy-10-methoxy-2,2,4-trimethyl-5-(3-cyclopentenyl)-1H-[1]benzopyrano[3,4-f]quinoline, (+)(5R,3'R) 2,5(R)-dihydro-9-hydroxy-10-methoxy-2,2,4-trimethyl-5-(3-cyclopentenyl)-1H-[1]benzopyrano[3,4-f]quinoline, rel-(5S)-9-hydroxy-5-[(3R)-(1-methoxycarbonyl)cyclohexen-3-yl]-10-methoxy-2,2,4-trimethyl-2,5-dihydro-1H-[1]benzopyrano[3,4-f]quinoline, 2,5-dihydro-9-hydroxy-10-methoxy-2,2,4-trimethyl-5-(2-methyl-3-propenyl)-1H-[1]benzopyrano[3,4-f]quinoline, 9,10-Dimethoxy-5-(3-propenyl)-2,2,4-trimethyl-1H-2,5-dihydro-[1]benzopyrano[3,4-f]quinoline, 9,10-Dimethoxy-5-[3-cyclohexenyl]-methoxy-2,2,4-trimethyl-2,5-dihydro-1H-[1]benzopyrano[3,4-f]quinoline, 10-methoxy-9-ethoxy-5-(3-propenyl)-2,2,4-trimethyl-1H-2,5-dihydro-[1]benzopyrano[3,4-f]quinoline, 10-methoxy-9-(3-propenyloxy)-5-(3-propenyl)-2,2,4-trimethyl-1H-2,5-dihydro-[1]benzopyrano[3,4-f]quinoline, 10-methoxy-9-(3-propynyloxy)-5-(3-propenyl)-2,2,4-trimethyl-1H-2,5-dihydro-[1]benzopyrano[3,4-f]quinoline, 2,5-dihydro-9-acetoxy-10-methoxy-2,2,4-trimethyl-5-(2-propenyl)-1H-[1]benzopyrano[3,4-f]quinoline, 2,5-dihydro-9-(4-N,N-dimethylamino-4-oxo-butanoyloxy)-10-methoxy-2,2,4-trimethyl-5-(2-propenyl-1H-[1]benzopyrano[3,4-f]quinoline, 7-bromo-5-[3-cyclohexenyl]-10-methoxy-2,2,4-trimethyl-2,5-dihydro-1H-[1]benzopyrano[3,4-f]quinoline, 10-methoxy-7-bromo-5-(3-propenyl)-2,2,4-trimethyl-1H-2,5-dihydro-[1]benzopyrano[3,4-f]quinoline, 7-bromo-5-[1-methyl-3-cyclohexenyl]-10-methoxy-2,2,4-trimethyl-2,5-dihydro-1H-[1]benzopyrano[3,4-f]quinoline, 10-methoxy-9-bromo-5-(3-propenyl)-2,2,4-trimethyl-1H-2,5-dihydro-[1]benzopyrano[3,4-f]quinoline, 7,9-Dibromo-10-methoxy-5-(3-propenyl)-2,2,4-trimethyl-1H-2,5-dihydro-[1]benzopyrano[3,4-f]quinoline, 7,9-Dibromo-5-[cyclohexen-3-yl]-10-methoxy-2,2,4-trimethyl-2,5-dihydro-1H-[1]benzopyrano[3,4-f]quinoline, 7,9-Dibromo-5-[1-methyl-3-cyclohexenyl]-10-methoxy-2,2,4-trimethyl-2,5-dihydro-1H-[1]benzopyrano[3,4-f]quinoline, 10-methoxy-7-(2-ethenyl)-5-(3-propenyl)-2,2,4-trimethyl-1H-2,5-dihydro-[1]benzopyrano[3,4-f]quinoline, 10-methoxy-7-methyl-5-(3-propenyl)-2,2,4-trimethyl-1H-2,5-dihydro-[1]benzopyrano[3,4-f]quinoline, 10-methoxy-7-acetyl-5-(3-propenyl)-2,2,4-trimethyl-1H-2,5-dihydro-[1]benzopyrano[3,4-F]quinoline, (+/−)2,5-dihydro-9-methyl-10-methoxy-2,2,4-trimethyl-5-(1-methylcyclohexen-3-yl)-1H-[1]benzopyrano[3,4-f]quinoline, 10-methoxy-7-methyl-9-methyl-5-(3-propenyl)-2,2,4-trimethyl-1H-2,5-dihydro-[1]benzopyrano[3,4-f]quinoline, 10-chloro-5-(3-propenyl)-2,2,4-trimethyl-2,5-dihydro-1H-[1]benzopyrano[3,4-f]quinoline, (+/−)2,5-dihydro-10-chloro-2,2,4-trimethyl-5-phenyl-1H-[1]benzopyrano[3,4-f]quinoline, 2,5-dihydro-10-methoxy-5-(3-(N-methyl-N-(carbomethoxymethyl)aminocarbonyloxy)phenyl)-2,2,4-trimethyl-1H-[1]benzopyrano[3,4-f]quinoline, 2,5-dihydro-10-methoxy-5-(3-(N-methyl-N-(N-methylcarbonyl)aminocarbonyloxy)phenyl)-2,2,4-trimethyl-1H-[1]benzopyrano[3,4-f]quinoline, 2,5-dihydro-10-methoxy-5-(3-(N-methylaminocarbonyloxy)phenyl)-2,2,4-trimethyl-1H-[1]benzopyrano[3,4-f]quinoline, 2,5-dihydro-10-methoxy-5-(3-(2-hydroxyethyl)phenyl)-2,2,4-trimethyl-1H-[1]benzopyrano[3,4-f]quinoline, 2,5-dihydro-10-methoxy-5-(3-(2-methanesulfonyloxyethyl)phenyl)-2,2,4-trimethyl-1H-[1]benzopyrano[3,4-f]quinoline, 2,5-dihydro-10-methoxy-5-(3-(2-methythioethyl)phenyl)-2,2,4-trimethyl-1H-[1]benzopyrano[3,4-f]quinoline, 2,5-dihydro-10-methoxy-5-(3-(2-(N,N-dimethylaminocarbonyloxy)ethyl)phenyl)-2,2,4-trimethyl-1H-[1]benzopyrano[3,4-f]quinoline, 2,5-dihydro-10-methoxy-5-(3-(2-(N,N-dimethylamino)ethyl)phenyl)-2,2,4-trimethyl-1H-[1]benzopyrano[3,4-f]quinoline, 2,5-dihydro-10-methoxy-5-cyclopropyl-2,2,4-trimethyl-1H-[1]benzopyrano[3,4-f]quinoline,
2,5-dihydro-10-methoxy-5-ethenyl-2,2,4-trimethyl-1H-[1]benzopyrano[3,4-f]quinoline,
trans 2,5-dihydro-10-methoxy-5-(2-phenylethenyl)-2,2,4-trimethyl-1H-[1]benzopyrano[3,4-f]quinoline,
2,5-dihydro-10-methoxy-5-(2-phenylethynyl)-2,2,4-trimethyl-1H-[1]benzopyrano[3,4-f]quinoline,
cis 2,5-dihydro-10-methoxy-5-(2-phenylethenyl)-2,2,4-trimethyl-1H-[1]benzopyrano[3,4-f]quinoline,
2,5-dihydro-10-methoxy-5-(2-methylpropenyl)-2,2,4-trimethyl-1H-[1]benzopyrano[3,4-f]quinoline,
trans 2,5-dihydro-10-methoxy-5-(1-cyclohexenyl)-2,2,4-trimethyl-1H-[1]benzopyrano[3,4-f]quinoline,
2,5-dihydro-10-(2-furanyl)-5-(3-propenyl)-2,2,4-trimethyl-1H-[1]benzopyrano[3,4-f]quinoline,
2,5-dihydro-10-cyano-5-(3-propenyl)-2,2,4-trimethyl-1H-[1]benzopyrano[3,4-f]quinoline,
2,5-dihydro-10-carboxy-5-(3-propenyl)-2,2,4-trimethyl-1H-[1]benzopyrano[3,4-f]quinoline,
2,5-dihydro-10-(2-hydroxymethyl)-5-(3-propenyl)-2,2,4-trimethyl-1H-[1]benzopyrano[3,4-f]quinoline,
2,5-dihydro-10-formyl-5-(3-propenyl)-2,2,4-trimethyl-1H-[1]benzopyrano[3,4-f]quinoline,
2,5-dihydro-10-aminomethyl-5-(3-propenyl)-2,2,4-trimethyl-1H-[1]benzopyrano[3,4-f]quinoline,
2,5-dihydro-10-methoxymethyl-5-(3-propenyl)-2,2,4-trimethyl-1H-[1]benzopyrano[3,4-f]quinoline,
2,5-dihydro-10-ethenyl-5-phenyl-2,2,4-trimethyl-1H-[1]benzopyrano[3,4-f]quinoline,
2,5-dihydro-10-ethynyl-5-phenyl-2,2,4-trimethyl-1H-[1]benzopyrano[3,4-f]quinoline,
methyl 2,5-dihydro-5-phenyl-2,2,4-trimethyl-1H-[1]benzopyrano[3,4-f]quinoline-10-carboxylate,
2,5-dihydro-10-(hydroxymethyl)-5-phenyl-2,2,4-trimethyl-1H-[1]benzopyrano[3,4-f]quinoline,
2,5-dihydro-10-formyl-5-phenyl-2,2,4-trimethyl-1H-[1]benzopyrano[3,4-f]quinoline,
2,5-dihydro-10-(methoxymethyl)-5-phenyl-2,2,4-trimethyl-1H-[1]benzopyrano[3,4-f]quinoline,
2,5-dihydro-10-ethenyl-5-oxo-2,2,4-trimethyl-1H-[1]benzopyrano[3,4-f]quinoline,
5-(3-cyclohexenyl)-2,5-dihydro-10-ethenyl-2,2,4-trimethyl-1H-[1]benzopyrano[3,4-f]quinoline,
2,5-dihydro-10-ethenyl-5-[1-methyl-3-cyclohexenyl]-2,2,4-trimethyl-1H-[1]benzopyrano[3,4-f]quinoline,
2,5-dihydro-5-(3-propenyl)-10-methylthio-2,2,4-trimethyl-1H-[1]benzopyrano[3,4-f]quinoline,
2,5-dihydro-5-(3-propenyl)-10-methylthio-2,2,4-trimethyl-1H-[1]benzopyrano[3,4-f]quinoline,
(+/−)2,5-dihydro-9-(4-acetamidobutanoyloxy)-10-methoxy-2,2,4-trimethyl-5-allyl-1H-[1]benzopyrano[3,4-f]quinoline,
10-(difluoromethoxy)-2,5-dihydro-5-phenyl-2,2,4-trimethyl-1H-[1]benzopyrano[3,4-f]quinoline,
10-(bromodifluoromethoxy)-2,5-dihydro-5-phenyl-2,2,4-trimethyl-1H-[1]benzopyrano[3,4-f]quinoline,
10-(bromodifluoromethoxy)-5-phenyl-2,2-dimethyl-4-methylene-2,3,4,5-tetrahydro-1H-chromeno[3,4-f]quinoline,
2,5-dihydro-9-hydroxy-10-methoxy-2,2,4-trimethyl-5-((2-fluorophenyl)methyl)-1H-[1]benzopyrano[3,4-f]quinoline,
10-methoxy-5-(5-methylisoxazol-3-yl)methyidene-2,5-dihydro-5-phenyl-2,2,4-trimethyl-1H-[1]benzopyrano[3,4-f]quinoline,
10-methoxy-5-(3-methylisoxazol-5-yl)methyidene-2,5-dihydro-5-phenyl-2,2,4-trimethyl-1H-[1]benzopyrano[3,4-f]quinoline,
10-methoxy-5-(4,5-dimethyl-1,3-oxazol-2-yl)methyidene-2,5-dihydro-5-phenyl-2,2,4-trimethy-1H-[1]benzopyrano[3,4-f]quinoline,
10-methoxy-5-(6-chloropyridin-2-yl)methyidene-2,5-dihydro-5-phenyl-2,2,4-trimethyl-1H-[1]benzopyrano[3,4-f]quinoline,
10-methoxy-5-(pyridin-2-yl)methyidene-2,5-dihydro-5-phenyl-2,2,4-trimethyl-1H-[1]benzopyrano[3,4-f]quinoline,
10-methoxy-5-(but-3-enylidene)-2,5-dihydro-5-phenyl-2,2,4-trimethyl-1H-[1]benzopyrano[3,4-f]quinoline,
10-methoxy-5-(1-methylpropylidene)-2,5-dihydro-5-phenyl-2,2,4-trimethyl-1H-[1]benzopyrano[3,4-f]quinoline,
10-methoxy-5-(1-butylidene)-2,5-dihydro-5-phenyl-2,2,4-trimethyl-1H-[1]benzopyrano[3,4-f]quinoline,
2,5-dihydro-10-methoxy-2,2,4-trimethyl-3-oxide-5-phenyl-1H-[1]benzopyrano[3,4-f]quinoline,
2,5-dihydro-10-methoxy-2,2,4-trimethyl-5-phenyl-1H-[1]benzopyrano[3,4-f]quinoline,
2,5-dihydro-10-methoxy-2,2-[spiro(tetrahydro-4-pyranyl)]-4-methyl-5-allyl-1H-[1]benzopyrano[3,4-f]quinoline,
2,5-dihydro-10-methoxy-2,2-[spiro(hexyl)]-5-allyl-1H-[1]benzopyrano[3,4-f]quinoline,
2,5-dihydro-10-methoxy-2,2-diethyl-4-methyl-5-allyl-1H-[1]benzopyrano[3,4-f]quinoline,
2,5-dihydro-10-methoxy-2,2,3,4-tetramethyl-5-allyl-1H-[1]benzopyrano[3,4-f]quinoline,
2,5-dihydro-10-methoxy-2,2-dimethyl-4-ethyl-5-allyl-1H-[1]benzopyrano[3,4-f]quinoline,
2,5-dihydro-10-methoxy-2,2,3-trimethyl-5-allyl-1H-[1]benzopyrano[3,4-f]quinoline,
Z-5-(benzylidenyl)-9-hydroxy-10-methoxy-2,2,4-trimethyl-1H-2,5-dihydro-[1]benzopyrano[3,4-f]quinoline,
Z-5-(2,5-difluorobenzylidenyl)-9-hydroxy-10-methoxy-2,2,4-trimethyl-1H-2,5-dihydro-[1]benzopyrano[3,4-f]quinoline,
Z-5-(3-fluorobenzylidenyl)-10-chloro-9-hydroxy-2,2,4-trimethyl-2,5-dihydro-1H-[1]benzopyrano[3,4-f]quinoline,
Z-10-chloro-9-hydroxy-5-(2-picolinylidenyl)-2,2,4-trimethyl-2,5-dihydro-1H-[1]benzopyrano[3,4-f]quinoline,
Z-9-hydroxy-10-methoxy-5-(2-picolinylidenyl)-2,2,4-trimethyl-2,5-dihydro-1H-[1]benzopyrano[3,4-f]quinoline,
9-hydroxy-10-methoxy-5-(3,5-difluorophenyl)methylidene-2,5-dihydro-5-phenyl-2,2,4-trimethyl-1H-[1]benzopyrano[3,4-f]quinoline,
9-hydroxy-10-methoxy-5-(3,4-difluorophenyl)methylidene-2,5-dihydro-5-phenyl-2,2,4-trimethyl-1H-[1]benzopyrano[3,4-f]quinoline,
(Z) 9-hydroxy-10-methoxy-5-((4-fluorophenyl)methylene)-2,2,4-trimethyl-1H-2,5-dihydro-[1]benzopyrano[3,4-f]quinoline, (Z)-9-hydroxy-10-methoxy-5-([2,3-difluorophenyl]-methylene)-2,2,4-trimethyl-1H-2,5-dihydro-[1]benzopyrano[3,4-f]quinoline, Z-5-(3-fluorobenzylidenyl)-10-methoxy-9-hydroxy-2,2,4-trimethyl-2,5-dihydro-1H-[1]benzopyrano[3,4-f]quinoline, rel-(5S,3'R)-9-hydroxy-5-[1-methoxymethyl-3-cyclohexenyl]-10-chloro-2,2,4-trimethyl-2,5-dihydro-1H-[1]benzopyrano[3,4-f]quinoline, 9-hydroxy-10-methoxy-5-ethyl-2,2,4-trimethyl-2,5-dihydro-1H-[1]benzopyrano[3,4-f]quinoline, (+/−)2,5-dihydro-9-cyanomethoxy-10-methoxy-2,2,4-trimethyl-5-allyl-1H-[1]benzopyrano[3,4-f]quinoline, 2,5-dihydro-9-(4-N,N-diethylamino-4-oxo-butanoyloxy)-10-methoxy-2,2,4-trimethyl-5(2-propenyl)-1H-[1]benzopyrano[3,4-f]quinoline, 2,5-dihydro-9-(4-N-piperidino-4-oxo-butanoyloxy)-10-methoxy-2,2,4-trimethyl-5-(2-propenyl)-1H-[1]benzopyrano[3,4-f]quinoline, 2,5-dihydro-9-(4-N-morpholino-4-oxo-butanoyloxy)-10-methoxy-2,2,4-trimethyl-5-(2-propenyl)-1H-[1]benzopyrano[3,4-f]quinoline, 2,5-dihydro-9-(4-N,N-dimethylamino-4-oxo-butanoyloxy)-10-methoxy-2,2,4-trimethyl-5-(3,4,5-trifluorophenyl)-1H-[1]benzopyrano[3,4-f]quinoline, 2,5-dihydro-9-hydroxy-10-methoxy-2,2,4-trimethyl-5-(3-5-difluorophenylmethyl)-1H-[1]benzopyrano[3,4-f]quinoline, 2,5-dihydro-9-hydroxy-10-chloro-2,2,4-trimethyl-5-(2-thienyl)-1H-[1]benzopyrano[3,4-f]quinoline, 2,5-dihydro-9-hydroxy-10-methoxy-2,2,4-trimethyl-5-cyclopentyl-1H-[1]benzopyrano[3,4-f]quinoline, 2,5-dihydro-9-hydroxy-10-methoxy-2,2,4-trimethyl-5-((2-fluorophenyl)methyl)-1H-[1]benzopyrano[3,4-f]quinoline, 2,5-dihydro-9-hydroxymethyl-10-methoxy-2,2,4-trimethyl-5-allyl-1H-[1]benzopyrano[3,4-f]quinoline, 2,5-dihydro-9-hydroxy-10-methoxy-2,2,4-trimethyl-5-(1-pentenyl)-1H-[1]benzopyrano[3,4-f]quinoline, 2,5-dihydro-9-methylcarboxylate-10-methoxy-2,2,4-trimethyl-5-allyl-1H-[1]benzopyrano[3,4-f]quinoline, 2,5-dihydro-9-hydroxy-10-methoxy-2,2,4-trimethyl-5-allenyl-1H-[1]benzopyrano[3,4-f]quinoline, (−)(5S,3'S) 2,5-dihydro-10-methoxy-2,2,4-trimethyl-5-(cyclopenten-3-yl)-1H-[1]benzopyrano[3,4-f]quinoline, (−)(5S,3'S)2,5-dihydro-10-methoxy-2,2,4-trimethyl-5-(cyclohexen-3-yl)-1H-[1]benzopyrano[3,4-f]quinoline, (−)(5S,3'R)2,5-dihydro-10-methoxy-2,2,4-trimethyl-5-(cyclohexen-3-yl)-1H-[1]benzopyrano[3,4-f]quinoline, (−)(5S,3'R)2,5-dihydro-10-methoxy-2,2,4-trimethyl-5-(cyclopenten-3-yl)-1H-[1]benzopyrano[3,4-f]quinoline, 2,5-dihydro-9-hydroxy-10-methoxy-2,2,4-trimethyl-5-(3(Z)-pentenyl)-1H-[1]benzopyrano[3,4-f]quinoline, 2,5-dihydro-9-hydroxy-10-methoxy-2,2,4-trimethyl-5-(3-acetoxyphenyl)-1H-[1]benzopyrano[3,4-f]quinoline, 10-difluoromethoxy-5-[[3-(methylthio)methoxy]phenyl]-2,2,4-trimethyl-1H-2,5-dihydro-[1]benzopyrano[3,4-f]quinoline, 2,5-dihydro-7-bromo-9-hydroxy-10-chloro-2,2,4-trimethyl-5-allyl-1H-[1]benzopyrano[3,4-f]quinoline, 2,5-dihydro-9-hydroxy-10-methoxy-2,2,4-trimethyl-5-(3-hydroxyphenyl)-1H-[1]benzopyrano[3,4-f]quinoline, 2,5-dihydro-9-methylthiomethoxy-10-methoxy-2,2,4-trimethyl-5-(3(methylthio)methoxyphenyl)-1H-[1]benzopyrano[3,4-f]quinoline, 2,5-dihydro-9-hydroxy-10-methoxy~2,2,4-trimethyl-5-(3-(methylthiomethoxy)phenyl-1H-[1]benzopyrano[3,4-f]quinoline, 9-hydroxy-10-chloro-5-(phenylmethylene)-2,2,4-trimethyl-1H-2,5-dihydro-[1]benzopyrano[3,4-f]quinoline, 2,5-dihydro-9-hydroxy-10-chloro-2,2,4-trimethyl-5-([2-N,N-dimethylcarbamoyloxy]phenyl)-1H-[1]benzopyrano[3,4-f]quinoline, 2,5-dihydro-9-N,N-dimethylcarbamoyloxy-10-methoxy-2,2,4-trimethyl-5-([2-N,N-dimethylcarbamoyloxy]phenyl)-1H-[1]benzopyrano[3,4-f]quinoline, 2,5-dihydro-9-hydroxy-10-chloro-2,2,4-trimethyl-5-ethyl-1H-[1]benzopyrano[3,4-f]quinoline, 2,5-dihydro-9-hydroxy-10-chloro-2,2,4-trimethyl-5-isopropyl-1H-[1]benzopyrano[3,4-f]quinoline, 9-hydroxy-10-methoxy-5-(phenylmethylene)-2,2,4-trimethyl-1H-2,5-dihydro-[1]benzopyrano[3,4-f]quinoline, 2,5-dihydro-9-hydroxy-10-chloro-2,2,4-trimethyl-5-butyl-1H-[1]benzopyrano[3,4-f]quinoline, 2,5-dihydro-9-hydroxy-10-chloro-2,2,4-trimethyl-5-(1-thiazol-2-yl)-1H-[1]benzopyrano[3,4-f]quinoline, 2,5-dihydro-9-hydroxy-10-chloro-2,2,4-trimethyl-5-(2-methylpropyl)-1H-[1]benzopyrano[3,4-f]quinoline, 2,5-dihydro-9-hydroxymethyl-10-chloro-2,2,4-trimethyl-5-allyl-1H-[1]benzopyrano[3,4-f]quinoline, 2,5-dihydro-9-hydroxy-10-chloro-2,2,4-trimethyl-5-propyl-1H-[1]benzopyrano[3,4-f]quinoline, 9-hydroxy-10-methoxy-5-([3-fluorophenyl]-methylene)-2,2,4-trimethyl-1H-2,5-dihydro-[1]benzopyrano[3,4-f]quinoline, 9-hydroxy-10-chloro-5-([2-pyridyl]-methylene)-2,2,4-trimethyl-1H-2,5-dihydro-[1]benzopyrano[3,4-f]quinoline, rel-(5S)-9-hydroxy-5-[(3S)-(1-hydroxymethyl)cyclohexen-3-yl]-10-chloro-2,2,4-trimethyl-2,5-dihydro-1H-[1]benzopyrano[3,4-f]quinoline, rel-(5S)-9-hydroxy-5-[(3S)-(1-methoxycarbonyl)cyclohexen-3-yl]-10-methoxy-2,2,4-trimethyl-2,5-dihydro-1H-[1]benzopyrano[3,4-f]quinoline, 2,5-dihydro-9-hydroxy-10-methoxy-2,2,4-trimethyl-5-(3,5-dichlorophenyl)-1H-[1]benzopyrano[3,4-f]quinoline, (−)(5S,3'S)2,5-dihydro-9-hydroxy-10-chloro-2,2,4-trimethyl-5-(1-methylcyclohexen-3-yl)-1H-[1]benzopyrano[3,4-f]quinoline, (−)(5S,3'R)2,5-dihydro-9-hydroxy-10-chloro-2,2,4-trimethyl-5-(1-methylcyclohexen-3-yl)-1H-[1]benzopyrano[3,4-f]quinoline, (+)(5R,3'S)2,5-dihydro-9-hydroxy-10-chloro-2,2,4-trimethyl-5-(1-methylcyclohexen-3-yl)-1H-[1]benzopyrano[3,4-f]quinoline, (+)(5R,3'R)2,5-dihydro-9-hydroxy-10-chloro-2,2,4-trimethyl-5-(1-methylcyclohexen-3-yl)-1H-[1]benzopyrano[3,4-f]quinoline, (+/−)2,5-dihydro-9-(4-N,N-dimethylamino-4-oxo-butanoyloxy)-10-chloro-2,2,4-trimethyl-5-allyl-1H-[1]benzopyrano[3,4-f]quinoline, (−)2,5-dihydro-9-hydroxy-10-chloro-2,2,4-trimethyl-5-cyclopentyl-1H-[1]benzopyrano[3,4-f]quinoline, 2,5-dihydro-9-(4-N,N-dimethylamino-4-oxo-butanoyloxy)-10-methoxy-2,2,4-trimethyl-5(1-methylethyl)-1H-[1]benzopyrano[3,4-f]quinoline, 2,5-dihydro-9-(4-N,N-dimethylamino-4-oxo-butanoyloxy)-10-methoxy-5(phenylmethyl)-2,2,4-trimethyl-1H-[1]benzopyrano[3,4-f]quinoline, 2,5-dihydro-9-(4-N,N-dimethylamino-4-oxo-butanoyloxy)-10-methoxy-2,2,4-trimethyl-5(2-thienyl)-1H-[1]benzopyrano[3,4-f]quinoline, 2,5-dihydro-9-(4-N,N-dimethylaminobutanoyloxy)-10-methoxy-2,2,4-trimethyl-5-(2 propenyl)-1H-[1]benzopyrano[3,4-f]quinoline, 9-(2-ethoxy-2-oxo-ethylaminocarbonyl)-oxy-10-methoxy-5-(3-propenyl)-2,2,4-trimethyl-1H-2,5-dihydro-[1]benzopyrano[3,4-f]quinoline, (+/−)2,5-dihydro-9-(3-acetamido-propanoyloxy)-10-methoxy-2,2,4-trimethyl-5-allyl-1H-[1]benzopyrano[3,4-f]quinoline, (+/−)2,5-dihydro-9-hydroxy-10-chloro-2,2,4-trimethyl-5-benzyl-1H-[1]benzopyrano[3,4-f]quinoline, 9-hydroxy-10-methoxy-5-(phenylmethylene)-2,2,4-trimethyl-1H-2,5-dihydro-[1]benzopyrano[3,4-f]quinoline, 9-(dimethylaminothiocarbonyl)-oxy-10-methoxy-5-(3-propenyl)-2,2,4-trimethyl-1H-2,5-dihydro-[1]benzopyrano[3,4-f]quinoline, (+/−)2,5-dihydro-9-(N-carbamoyl-2-aminoacetoxy)-10-methoxy-2,2,4-trimethyl-5-allyl-1H-[1]benzopyrano[3,4-f]quinoline, (+/−)2,5-dihydro-9-(4-ethoxy-4-oxo-butoxy)-10-methoxy-2,2,4-trimethyl-5-allyl-1H-[1]benzopyrano[3,4-f]quinoline, (+/−)2,5-dihydro-9-(4-oxo-pentanoyloxy)-10-methoxy-2,2,4-trimethyl-5-allyl-1H-[1]benzopyrano[3,4-f]quinoline, 2,5-dihydro-9-hydroxy-10-chloro-2,2,4-trimethyl-5-(3,4,5-trifluorophenyl)-1H-[1]benzopyrano[3,4-f]quinoline, 2,5-dihydro-9-methylthiomethoxy-10-methoxy-2,2,4-trimethyl-5-allyl-1H-[1]benzopyrano[3,4-f]quinoline, 2,5-dihydro-9-(4-N,N-diethylamino-4-oxo-pentanoyloxy)-10-methoxy-2,2,4-trimethyl-5(2-propenyl-1H-[1]benzopyrano[3,4-f]quinoline, 2,5-dihydro-9-(4-N,N-dimethylamino-4-oxo-pentanoyloxy)-10-methoxy-2,2,4-trimethyl-5-(2-propeny-1H-[1]benzopyrano[3,4-f]quinoline, 2,5-dihydro-9-(4-N-piperidino-4-oxo-pentanoyloxy)-10-methoxy-2,2,4-trimethyl-5-(2-propenyl)-1H-[1]benzopyrano[3,4-f]quinoline, 2,5-dihydro-9-(4-N-morpholino-4-oxo-pentanoyloxy)-10-methoxy-2,2,4-trimethyl-5-(2-propenyl)-1H-[1]benzopyrano[3,4-f]quinoline, (−)2,5-dihydro-9-(4-N,N-dimethylamino-4-oxo-butanoyloxy)-10-methoxy-2,2,4-trimethyl-5(S)-(3(S)-1-cyclopenten-3-yl)-1H-[1]benzopyrano[3,4-f]quinoline, 10-methoxy-9-(allylaminocarbonyl)oxy-5-(3-propenyl)-2,2,4-trimethyl-1H-2,5-dihydro-[1]benzopyrano[3,4-f]quinoline, 10-methoxy-9-(cyclohexylaminocarbonyl)-oxy-5-(3-propenyl)-2,2,4-trimethyl-1H-2,5-dihydro-[1]benzopyrano[3,4-f]quinoline, 2,5-dihydro-9-hydroxy-10-methoxy-2,2,4-trimethyl-5-(3-thienyl)-1H-[1]benzopyrano[3,4-f]quinoline, 2,5-dihydro-9-hydroxy-10-methoxy-2,2,4-trimethyl-5-(4-(fluorophenyl)methyl)-1H-[1]benzopyrano[3,4-f]quinoline, 10-carbaldehyde oxime-5-(2-propenyl)-2,5-dihydro-2,2,4-trimethyl-1H-[1]benzopyrano[3,4-f]quinoline, and 10-benzyloxy-5-(2-propenyl)-2,5-dihydro-2,2,4-trimethyl-1H-[1]benzopyrano[3,4-f]quinoline.

34. A method of selectively modulating the activation, repression, agonism, and antagonism effects of the glucocorticoid receptor in a mammal comprising administering an effective amount of a composition of any of claims 1 to 33.

35. A method of treating inflammation or immune, autoimmune or inflammatory diseases in a mammal comprising administering an effective amount of a composition of any of claims 1 to 33.

* * * * *

UNITED STATES PATENT AND TRADEMARK OFFICE
CERTIFICATE OF CORRECTION

PATENT NO. : 6,506,766 B1
DATED : January 14, 2003
INVENTOR(S) : Michael J. coghlan et al.

It is certified that error appears in the above-identified patent and that said Letters Patent is hereby corrected as shown below:

Title page,
Item [75], Inventers, replace "Redwood City, CA" with -- Gurnee, IL --, and replace "Guilford, CT" with -- Grayslake, IL --.

Column 190,
Line 61, replace "delete" with -- +Z,1 --.

Column 194,
Line 26, replace "I" with -- 1 --.

Column 195,
Lines 35 and 39, replace "*B*" in the words "LB when LB" with -- B --.

Column 197,
Lines 1-5 Formula (c) should read

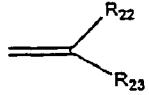

Line 28, replace "(k)-NNR$_8$R$_9$" with -- (k) =NNR$_{8'}$R$_{9'}$ --.

Column 198,
Line 38, replace "-LBR$_{30}$," with -- -LBR$_{30}$,"-- --.

Column 200,
Line 36, replace "-(5-methoxy-2-" with -- -5-(-methoxy-2-thienyl) --.

Column 202,
Line 26, replace "[(methylsuffinyl)" with -- [(methylsufinyl) --.
Line 48, replace "[3,4-4f]" with -- [3,4-f] --.

Column 203,
Line 50, replace "rel" with -- *rel* --.
Line 53, replace "anti" with -- *anti* --.

UNITED STATES PATENT AND TRADEMARK OFFICE
CERTIFICATE OF CORRECTION

PATENT NO.    : 6,506,766 B1
DATED         : January 14, 2003
INVENTOR(S)   : Michael J. coghlan et al.

It is certified that error appears in the above-identified patent and that said Letters Patent is hereby corrected as shown below:

Column 204,
Lines 16, 19, 28, 31, 52, 55, 58, 61 and 64, replace "rel" with -- *rel* --.

Column 205,
Lines 1, 4, 7 10 and 16, replace "rel" with -- *rel* --.
Line 13, replace "rel(5R,3'S)2,5-dihydro–10-methoxy)-S-" with -- rel(5R,3'S)2,%-dihdro-10-methoxy-5- --.

Column 207,
Lines 38 and 44, replace "rel" with -- *rel* --.

Column 208,
Line 33, replace "(+)(R)-5-" with -- (+)(R) 5- --.

Column 211,
Line 17, replace "(6-chloropyridin-2-methyidene-" with -- (6-chloropyridin-2-yl) methyidene --.
Line 26, replace "-1H-[1]quinoline," with -- 1H-[1]benzopyrano[3,4-f]quinoline --.

Column 212,
Line 33 and 35, after the word "quinoline", put a -- . --.
Line 44, replace "(3(methylthio)" with -- (3-(methylthio) --.

Column 215,
Line 29, replace "0-chloro-" with -- 10-chloro --.
Line 36, replace "trimethyl-1H-[1]" with -- trimethyl-2,5-dihydro-1H-[1] --.

Column 216,
Line 11, replace "rel" with -- *rel* --.
Line 21, replace the "," after the word "quinoline" with a period -- . --.
Line 58, replace "-3-yl)-[1]" with -- -3-yl)-H-[1] --.
Line 60, replace "(+/-)-2,5" with -- (+/-)2,5 --.

Column 220,
Line 51, replace "yl)-2,(5H)" with -- yl)-2(5H) --.

UNITED STATES PATENT AND TRADEMARK OFFICE
CERTIFICATE OF CORRECTION

PATENT NO.     : 6,506,766 B1
DATED          : January 14, 2003
INVENTOR(S)    : Michael J. coghlan et al.

It is certified that error appears in the above-identified patent and that said Letters Patent is hereby corrected as shown below:

Column 223,
Lines 30, 33 and 65, replace "rel" with -- *rel* --.

Column 224,
Lines 9, 34, 37, 40, 43, 46 49, 52, 55, 58, 62 and 65, replace "rel" with -- *rel* --.
Line 50, replace "-2,2,4]bebzopyrano" with -- -2,4-trimethyl-1H-[benzopyrano --.
Line 53, replace "trimethyl-[1]benzopyrano" with -- trimethyl-1H-[1]benzopyrano --.

Column 226,
Line 59, replace "rel" with -- *rel* --.
Line 60, replace "trimethyl-1H-[1]" with -- trimethyl-2,5-dihydro-1H-[1] --.

Column 227,
Lines 53 and 59, replace "rel" with -- *rel* --.

Column 228,
Line 64, replace "-ly)-1H-" with -- -3-yl)-1H- --.

Column 233,
Line 7, replace "rel" with -- *rel* --.

Signed and Sealed this

Sixteenth Day of September, 2003

JAMES E. ROGAN
*Director of the United States Patent and Trademark Office*